United States Patent
Tully et al.

(10) Patent No.: US 9,150,568 B2
(45) Date of Patent: Oct. 6, 2015

(54) COMPOSITIONS AND METHODS FOR MODULATING FXR

(75) Inventors: David C. Tully, Emeryville, CA (US); Paul Vincent Rucker, Carlsbad, CA (US); Phillip B. Alper, San Diego, CA (US); Daniel Mutnick, San Diego, CA (US); Donatella Chianelli, San Diego, CA (US)

(73) Assignee: NOVARTIS AG, Basel (CH)

( * ) Notice: Subject to any disclaimer, the term of this patent is extended or adjusted under 35 U.S.C. 154(b) by 63 days.

(21) Appl. No.: 13/993,138

(22) PCT Filed: Nov. 30, 2011

(86) PCT No.: PCT/US2011/062724
§ 371 (c)(1),
(2), (4) Date: Jun. 11, 2013

(87) PCT Pub. No.: WO2012/087519
PCT Pub. Date: Jun. 28, 2012

(65) Prior Publication Data
US 2013/0331349 A1    Dec. 12, 2013

Related U.S. Application Data

(60) Provisional application No. 61/425,189, filed on Dec. 20, 2010, provisional application No. 61/554,297, filed on Nov. 1, 2011.

(51) Int. Cl.
| | |
|---|---|
| *C07D 451/06* | (2006.01) |
| *C07D 519/00* | (2006.01) |
| *C07H 17/00* | (2006.01) |
| *A61K 45/06* | (2006.01) |
| *A61K 31/46* | (2006.01) |
| *A61K 31/506* | (2006.01) |
| *A61K 31/497* | (2006.01) |
| *A61K 31/501* | (2006.01) |
| *A61K 31/4709* | (2006.01) |
| *A61K 31/5025* | (2006.01) |
| *A61K 31/706* | (2006.01) |
| *C07D 471/04* | (2006.01) |
| *C07D 487/04* | (2006.01) |

(52) U.S. Cl.
CPC ............ *C07D 451/06* (2013.01); *A61K 31/46* (2013.01); *A61K 31/4709* (2013.01); *A61K 31/497* (2013.01); *A61K 31/501* (2013.01); *A61K 31/506* (2013.01); *A61K 31/5025* (2013.01); *A61K 31/706* (2013.01); *A61K 45/06* (2013.01); *C07D 471/04* (2013.01); *C07D 487/04* (2013.01); *C07D 519/00* (2013.01); *C07H 17/00* (2013.01)

(58) Field of Classification Search
CPC ...... C07D 45/06; C07D 519/00; C07H 17/00; A61K 45/06; A61K 31/46; A61K 31/506; A61K 31/497; A61K 31/501; A61K 31/4709; A61K 31/5025; A61K 31/706
USPC ................. 514/32, 248, 252.04, 255.05, 300; 536/17.4; 544/238, 331; 546/125, 126, 546/15
See application file for complete search history.

(56) References Cited

U.S. PATENT DOCUMENTS

| | | |
|---|---|---|
| 7,319,109 B2 | 1/2008 | Boggs |
| 2013/0261108 A1 | 10/2013 | Mutnick |

FOREIGN PATENT DOCUMENTS

| | | |
|---|---|---|
| WO | WO2004048349 A1 | 6/2004 |
| WO | 2007092751 A2 | 8/2007 |
| WO | WO2007092751 A3 | 8/2007 |
| WO | WO2007140174 A3 | 12/2007 |
| WO | WO2009012125 | 1/2009 |
| WO | WO2009/055331 A2 | 3/2009 |
| WO | WO2011053688 | 5/2011 |
| WO | 2012087521 A1 | 6/2012 |
| WO | WO2012087521 A1 | 6/2012 |

OTHER PUBLICATIONS

Glossary of medical education terms, Institute of International Medical Education. http://www.iime.org/glossary.htm Accessed in Mar. 2013.*
American Academy of Pediatrics Clinical Practice Guideline. Management of Hyperbilirubinemia in the Newborn Infant 35 or More Weeks of Gestation. Pediatrics 114:297-316, 2004.*

* cited by examiner

*Primary Examiner* — Mark Shibuya
*Assistant Examiner* — Yih-Horng Shiao
(74) *Attorney, Agent, or Firm* — Emily Tongco Wu; Genomics Institute of the Novartis Research Foundation

(57) ABSTRACT

The present invention relates to compounds of Formula (I), a stereoisomer, enantiomer, a pharmaceutically acceptable salt or an amino acid conjugate thereof; wherein variables are as defined herein; and their pharmaceutical compositions, which are useful as modulators of the activity of Farnesiod X receptors (FXR).

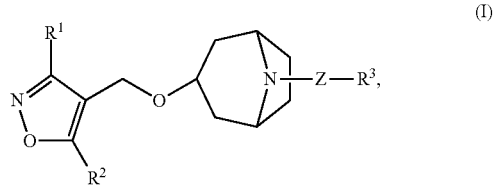

29 Claims, No Drawings

COMPOSITIONS AND METHODS FOR MODULATING FXR

CROSS-REFERENCE TO RELATED APPLICATIONS

This application is a 371 U.S. national phase application of international application number PCT/US2011/062724 filed 30 Nov. 2011, which application claims the benefit of U.S. provisional patent application No. 61/554,297 filed 1 Nov. 2011; and of U.S. provisional Ser. No. 61/425,189 filed 20 Dec. 2010; each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Aug. 6, 2013, is named 54466 sequence_ST25.txt and is 773 bytes in size.

TECHNICAL FIELD

The present invention relates to compositions and methods for modulating the activity of farnesoid X receptors (FXRs).

BACKGROUND

The farnesoid X receptor (FXR) is a member of the nuclear hormone receptor superfamily and is primarily expressed in the liver, kidney and intestine (see, e.g., Seol et al. (1995) Mol. Endocrinol. 9:72-85 and Forman et al. (1995) Cell 81:687-693). It functions as a heterodimer with the retinoid X receptor (RXR) and binds to response elements in the promoters of target genes to regulate gene transcription. The FXR-RXR heterodimer binds with highest affinity to an inverted repeat-1 (IR-1) response element, in which consensus receptor-binding hexamers are separated by one nucleotide. FXR is part of an interrelated process, in that FXR is activated by bile acids (the end product of cholesterol metabolism) (see, e.g., Makishima et al. (1999) Science 284: 1362-1365, Parks et al. (1999) Science 284:1365-1368, Wang et al. (1999) Mol. Cell. 3:543-553), which serve to inhibit cholesterol catabolism. See also, Urizar et al. (2000) J. Biol. Chem. 275:39313-39317.

FXR is a key regulator of cholesterol homeostasis, triglyceride synthesis and lipogenesis. (Crawley, Expert Opinion Ther. Patents (2010), 20(8): 1047-1057). In addition to the treatment of dyslipidemia, multiple indications for FXR have been described, including treatment of liver disease, diabetes, vitamin D-related diseases, drug-induced side effects and hepatitis. (Crawley, supra). While advances have been made in the development of novel FXR agonists, significant room for improvement remains. It is the object of the present invention to provide novel compounds that are agonists or partial agonists of FXR exhibiting physicochemical, in vitro and/or in vivo ADME (adsorption, distribution, metabolism and excretion) properties superior to known agonists of FXR and/or superior pharmacokinetics in vivo.

DISCLOSURE OF THE INVENTION

The present invention relates to compositions and methods for modulating the activity of farnesoid X receptors (FXRs). In one aspect, the present invention relates to compounds which act as agonists or partial agonists of FXR.

In a first embodiment, the compounds of the invention are defined by Formula (I):

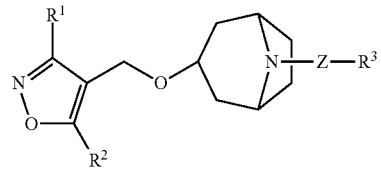

(I)

or a stereoisomer, enantiomer, a pharmaceutically acceptable salt or an amino acid conjugate thereof;

Z is phenylene, $C_{5-7}$ cycloalkylene o(5-10 membered monocyclic or bicyclic heteroaryl containing 1-2 heteroatoms selected from N, O and S; each of which is optionally substituted with 1-2 $R^6$ radicals selected from halogen, $C_{1-6}$ alkyl, halo$C_{1-6}$ alkyl, $C_{1-6}$ alkoxy, halo$C_{1-6}$ alkoxy, or cyclopropyl;

$R^1$ is phenyl, pyridyl, bicyclo[3.1.0]hexanyl, spiro[2.3] hexanyl, bicyclo[3.1.1]heptanyl, spiro[2.5]octanyl, bicyclo[4.1.0]heptanyl, bicyclo[3.1.0]hexan-6-yl, spiro [2.3]hexan-5-yl, bicyclo[3.1.1]heptan-3-yl, spiro[2.5] octan-4-yl, bicyclo[4.1.0]heptan-3-yl, cyclohexyl or cyclopentyl, each of which is optionally substituted with 1-3 $R^{1a}$; or $R^1$ is cyclopropyl optionally substituted with 1-2 $R^{1a}$ or phenyl;

$R^{1a}$ is halogen, $C_{1-6}$ alkyl, halo$C_{1-6}$ alkyl, $C_{1-6}$ alkoxy, halo$C_{1-6}$ alkoxy or cyclopropyl;

$R^2$ is $C_{1-3}$ alkyl, halo$C_{1-3}$ alkyl or cyclopropyl optionally substituted with $C_{1-3}$ alkyl or halo$C_{1-3}$ alkyl;

$R^3$ is —X—$CO_2R^4$, hydroxy$C_{1-6}$ alkyl, $CONR^4R^5$, CONR $(CR_2)_{1-4}CO_2R^4$, $CONR(CR_2)_{1-4}SO_3R^5$ or tetrazolyl; wherein X is a bond, $C_{1-2}$ alkylene or cyclopropyl; and R, $R^4$ and $R^5$ are independently hydrogen or $C_{1-6}$ alkyl.

In a second embodiment, the compounds of the invention are defined by Formula (I) wherein $R^2$ is cyclopropyl.

In a third embodiment, the compounds of the invention are defined by Formula (I) in any of the first or second embodiments, wherein Z is phenylene, pyridylene, pyrimidinylene, pyrazinylene, pyridazinylene, thiazolylene, benzothiazolyl, benzo[d]isothiazolyl, imidazo[1,2-a]pyridinyl, quinolinyl, 1H-indolyl, pyrrolo[1,2-b]pyridazinyl, benzofuranyl, benzo [b]thiophenyl, 1H-indazolyl, benzo[d]isoxazolyl, quinazolinyl, 1H-pyrrolo[3,2-c]pyridinyl, pyrazolo[1,5-a]pyrimidinyl, imidazo[1,2-b]pyridazinyl, pyrazolo[1,5-a]pyridinyl; each of which is optionally substituted with 1-2 $R^6$ radicals selected from halogen, $C_{1-6}$ alkyl, halo$C_{1-6}$ alkyl, $C_{1-6}$ alkoxy, halo$C_{1-6}$ alkoxy, or cyclopropyl.

In a fourth embodiment, the compounds of the invention are selected from the group consisting of:

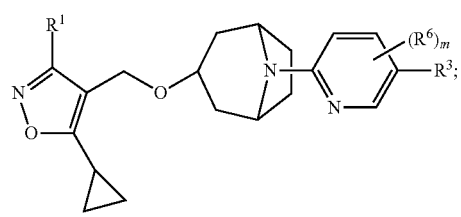

I-A

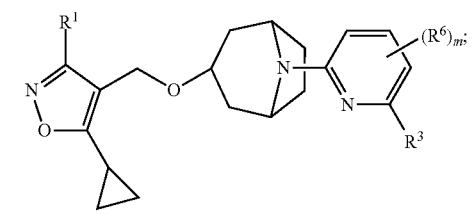
I-B
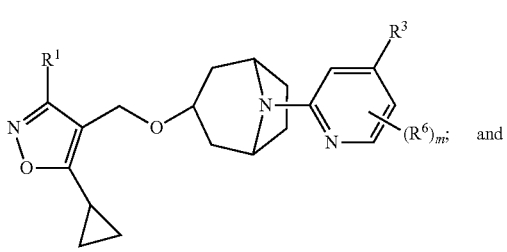
I-C
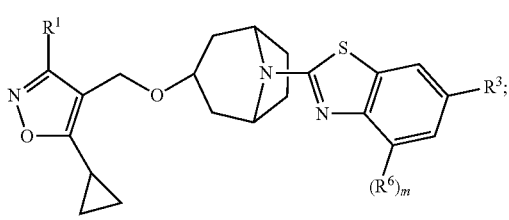
I-D
or a stereoisomer, enantiomer, a pharmaceutically acceptable salt or an amino acid conjugate thereof; m is 0-1; and R, R³ and R⁶ are as defined in Formula (I).
In a fifth embodiment, the compounds of the invention are selected from the group consisting of:
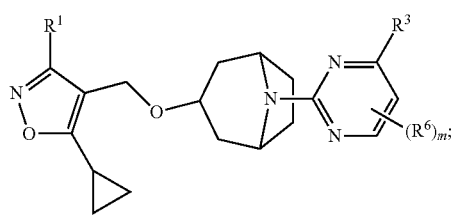
I-E
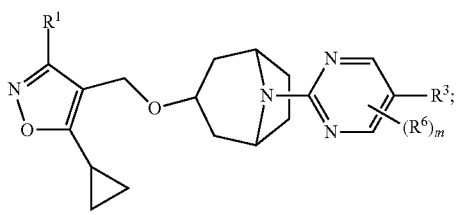
I-F
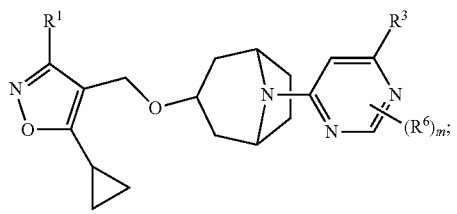
I-G
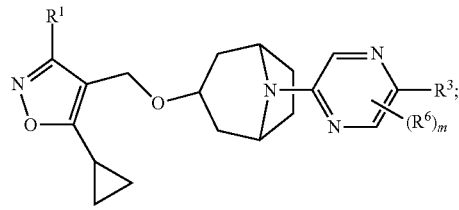
I-H
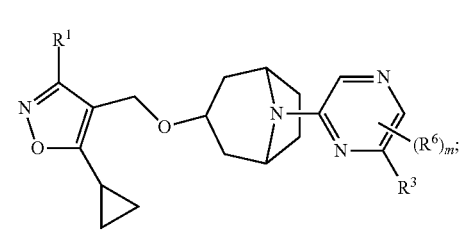
I-I
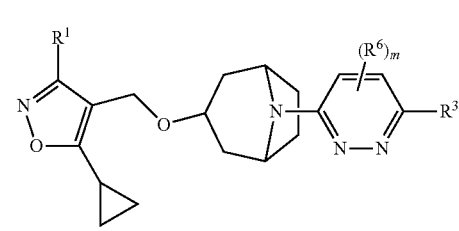
I-J
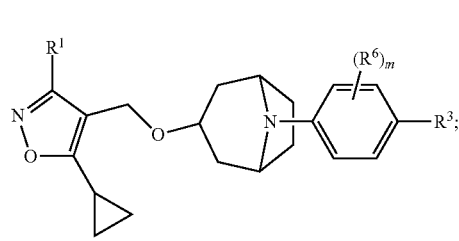
I-K
I-L
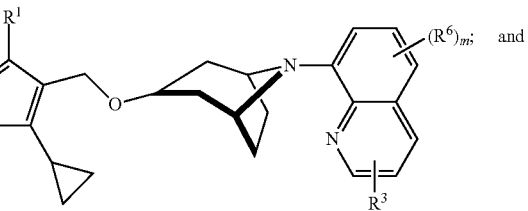
I-M
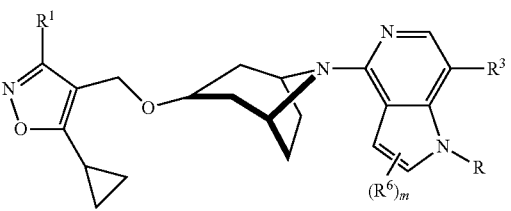
I-N or a stereoisomer, enantiomer, a pharmaceutically acceptable salt or an amino acid conjugate thereof; m is 0-1; and R, $R^3$ and $R^6$ are as defined in Formula (I).

In a sixth embodiment, the compounds of the invention are selected from the group consisting of:

I-O
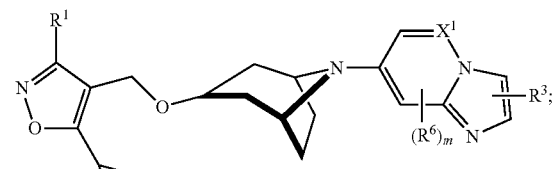

I-P
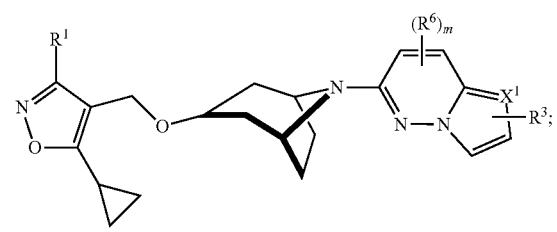

I-Q
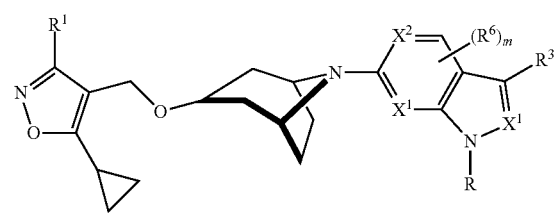

I-R
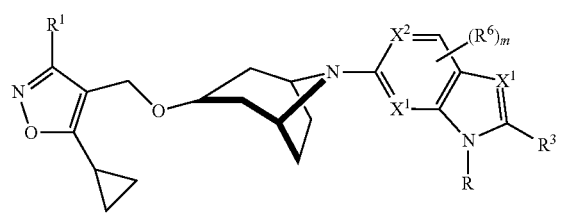

I-S
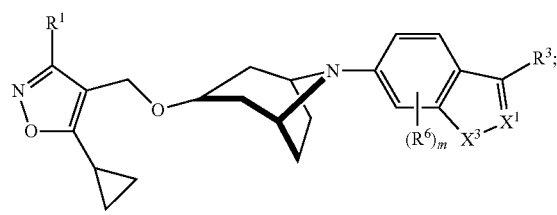

I-T
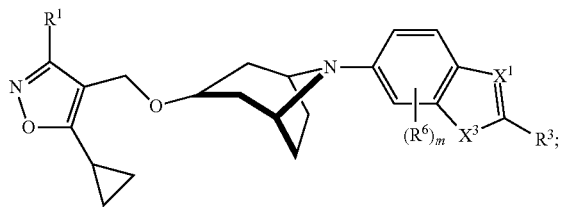

-continued

I-U
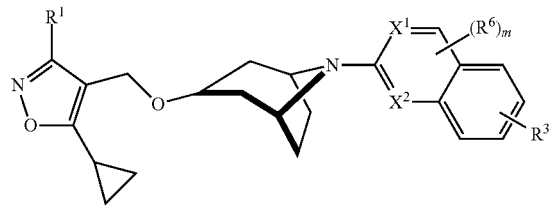

I-V
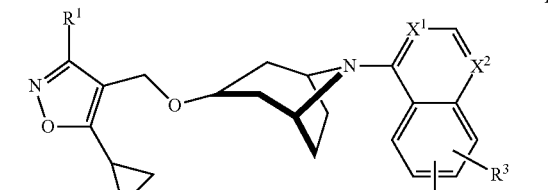

I-W
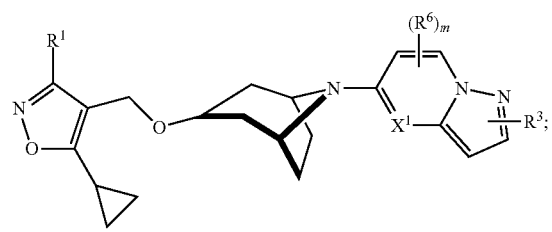

I-X and
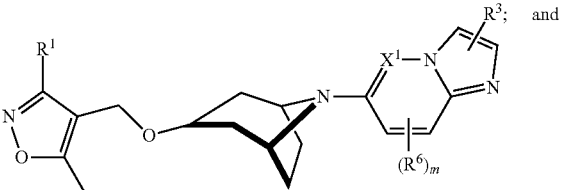

I-Y
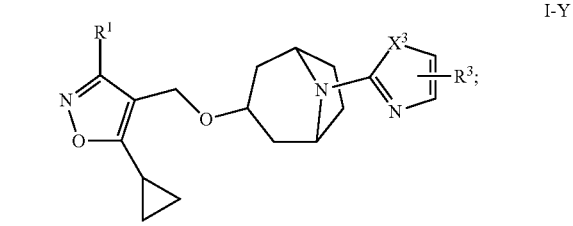

or a stereoisomer, enantiomer, a pharmaceutically acceptable salt or an amino acid conjugate thereof, wherein:

$X^1$ and $X^2$ are independently N, CH or $CR^6$;

$X^3$ is O or S;

$R^6$ may be attached to any position in the ring;

m is 0-1; and R, $R^3$ and $R^6$ are as defined in Formula (I).

In a seventh embodiment, the compounds of the invention are defined by Formula (I) and (IA)-(IY) in any of the above embodiments, wherein $R^1$ is phenyl substituted with 1-3 $R^{1a}$; and $R^{1a}$ is halogen, $C_{1-6}$ alkyl, halo$C_{1-6}$ alkyl, $C_{1-6}$alkoxy, halo$C_{1-6}$ alkoxy.

In an eighth embodiment, the compounds of the invention are defined by Formula (I) and (IA)-(IY) in any of the above embodiments, wherein $R^3$ is —X—$CO_2R^4$; X is a bond and $R^4$ is hydrogen or $C_{1-6}$ alkyl.

In a ninth embodiment, the compounds of the invention are defined by Formula (I) and (IA)-(IY) in any of the above embodiments, wherein R⁶ is methyl, methoxy, fluoro or trifluoromethoxy.

Specific compounds of the invention are selected from the group consisting of:

methyl 2-[3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylate;

methyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylate;

2-[3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid;

methyl 2-[3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazole-6-carboxylate;

methyl 2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazole-6-carboxylate;

2-[3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazole-6-carboxylic acid;

2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazole-6-carboxylic acid;

Methyl 2-(3((5-cyclopropyl-3-(2-(trifluoromethoxy)phenyl)isoxazol-4-yl)methoxy)-8-azabicyclo[3.2.1]octan-8-yl]-4-methoxybenzo[d]thiazole-6-carboxylate;

2-[3-({5-cyclopropyl-3-[2-(trifluoromethoxy)phenyl]-1,2-oxazol-4-yl}methoxy)-8-azabicyclo[3.2.1]octan-8-yl]-4-methoxy-1,3-benzothiazole-6-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-methoxy-1,3-benzothiazole-6-carboxylic acid;

methyl 2-(3-((5-cyclopropyl-3-(2-(trifluoromethyl)phenyl)isoxazol-4-yl)methoxy)-8-azabicyclo[3.2.1]octan-8-yl)-4-methoxybenzo[d]thiazole-6-carboxylate;

2-[3-({5-cyclopropyl-3-[2-(trifluoromethyl)phenyl]-1,2-oxazol-4-yl}methoxy)-8-azabicyclo[3.2.1]octan-8-yl]-4-methoxy-1,3-benzothiazole-6-carboxylic acid;

2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-methoxy-1,3-benzothiazole-6-carboxylic acid;

ethyl 2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylate;

ethyl 2-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylate;

2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylic acid;

2-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylic acid;

2-{2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazol-6-yl]propan-2-ol;

2-{2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazol-6-yl]propan-2-ol;

2-[3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxamide;

2-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxamide;

6-[3-({5-cyclopropyl-3-[2-(trifluoromethoxy)phenyl]-1,2-oxazol-4-yl}methoxy)-8-azabicyclo[3.2.1]octan-8-yl]pyridine-3-carboxamide;

6-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-3-carboxamide;

2-[3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxamide;

2-(1R,3r,5S)-3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxamide;

ethyl 2-[3-({5-cyclopropyl-3-[2-(trifluoromethyl)phenyl]-1,2-oxazol-4-yl}methoxy)-8-azabicyclo[3.2.1]octan-8-yl]-1,3-benzothiazole-6-carboxylate;

ethyl 2-(1R,3r,5S)-3-({5-cyclopropyl-3-[2-(trifluoromethyl)phenyl]-1,2-oxazol-4-yl}methoxy)-8-azabicyclo[3.2.1]octan-8-yl]-1,3-benzothiazole-6-carboxylate;

2-[3-({5-cyclopropyl-3-[2-(trifluoromethyl)phenyl]-1,2-oxazol-4-yl}methoxy)-8-azabicyclo[3.2.1]octan-8-yl]-1,3-benzothiazole-6-carboxylic acid;

2-(1R,3r,5S)-3-({5-cyclopropyl-3-[2-(trifluoromethyl)phenyl]-1,2-oxazol-4-yl}methoxy)-8-azabicyclo[3.2.1]octan-8-yl]-1,3-benzothiazole-6-carboxylic acid;

ethyl 2-[3-({5-cyclopropyl-3-[2-(difluoromethoxy)phenyl]-1,2-oxazol-4-yl}methoxy)-8-azabicyclo[3.2.1]octan-8-yl]-1,3-benzothiazole-6-carboxylate;

ethyl 2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-1,3-benzothiazole-6-carboxylate;

2-[3-({5-cyclopropyl-3-[2-(difluoromethoxy)phenyl]-1,2-oxazol-4-yl}methoxy)-8-azabicyclo[3.2.1]octan-8-yl]-1,3-benzothiazole-6-carboxylic acid;

2-(1R,3r,5S)-3-({5-cyclopropyl-3-[2-(difluoromethoxy)phenyl]-1,2-oxazol-4-yl}methoxy)-8-azabicyclo[3.2.1]octan-8-yl]-1,3-benzothiazole-6-carboxylic acid;

methyl 2-[3-({5-cyclopropyl-3-[2-(difluoromethoxy)phenyl]-1,2-oxazol-4-yl}methoxy)-8-azabicyclo[3.2.1]octan-8-yl]-4-fluoro-1,3-benzothiazole-6-carboxylate;

methyl 2-(1R,3r,5S)-3-({5-cyclopropyl-3-[2-(difluoromethoxy)phenyl]-1,2-oxazol-4-yl}methoxy)-8-azabicyclo[3.2.1]octan-8-yl]-4-fluoro-1,3-benzothiazole-6-carboxylate;

2-[3-({5-cyclopropyl-3-[2-(difluoromethoxy)phenyl]-1,2-oxazol-4-yl}methoxy)-8-azabicyclo[3.2.1]octan-8-yl]-4-fluoro-1,3-benzothiazole-6-carboxylic acid;

2-(1R,3r,5S)-3-({5-cyclopropyl-3-[2-(difluoromethoxy)phenyl]-1,2-oxazol-4-yl}methoxy)-8-azabicyclo[3.2.1]octan-8-yl]-4-fluoro-1,3-benzothiazole-6-carboxylic acid;

2-[3-({5-cyclopropyl-3-[2-(difluoromethoxy)phenyl]-1,2-oxazol-4-yl}methoxy)-8-azabicyclo[3.2.1]octan-8-yl]-4-methoxy-1,3-benzothiazole-6-carboxylic acid;

2-(1R,3r,5S)-3-({5-cyclopropyl-3-[2-(difluoromethoxy)phenyl]-1,2-oxazol-4-yl}methoxy)-8-azabicyclo[3.2.1]octan-8-yl]-4-methoxy-1,3-benzothiazole-6-carboxylic acid;

ethyl 2-[3-{[5-cyclopropyl-3-(2,6-difluorophenyl)-1,2-oxazol-4-yl]methoxy}-8-azabicyclo[3.2.1]octan-8-yl]-1,3-benzothiazole-6-carboxylate;
ethyl 2-(1R,3r,5S)-3-{[5-cyclopropyl-3-(2,6-difluorophenyl)-1,2-oxazol-4-yl]methoxy}-8-azabicyclo[3.2.1]octan-8-yl]-1,3-benzothiazole-6-carboxylate;
2-[3-{[5-cyclopropyl-3-(2,6-difluorophenyl)-1,2-oxazol-4-yl]methoxy}-8-azabicyclo[3.2.1]octan-8-yl]-1,3-benzothiazole-6-carboxylic acid;
2-(1R,3r,5S)-3-{[5-cyclopropyl-3-(2,6-difluorophenyl)-1,2-oxazol-4-yl]methoxy}-8-azabicyclo[3.2.1]octan-8-yl]-1,3-benzothiazole-6-carboxylic acid;
methyl 2-[3-{[5-cyclopropyl-3-(2,6-difluorophenyl)-1,2-oxazol-4-yl]methoxy}-8-azabicyclo[3.2.1]octan-8-yl]-4-methoxy-1,3-benzothiazole-6-carboxylate;
methyl 2-[(1R,3r,5S)-3-{[5-cyclopropyl-3-(2,6-difluorophenyl)-1,2-oxazol-4-yl]methoxy}-8-azabicyclo[3.2.1]octan-8-yl]-4methoxy-1,3-benzothiazole-6-carboxylate;
2-[3-{[5-cyclopropyl-3-(2,6-difluorophenyl)-1,2-oxazol-4-yl]methoxy}-8-azabicyclo[3.2.1]octan-8-yl]-4-methoxy-1,3-benzothiazole-6-carboxylic acid;
2-[(1R,3r,5S)-3-{[5-cyclopropyl-3-(2,6-difluorophenyl)-1,2-oxazol-4-yl]methoxy}-8-azabicyclo[3.2.1]octan-8-yl]-4-methoxy-1,3-benzothiazole-6-carboxylic acid;
methyl 2-[3-{[5-cyclopropyl-3-(2,6-difluorophenyl)-1,2-oxazol-4-yl]methoxy}-8-azabicyclo[3.2.1]octan-8-yl]-4-fluoro-1,3-benzothiazole-6-carboxylate;
methyl 2-[(1R,3r,5S)-3-{[5-cyclopropyl-3-(2,6-difluorophenyl)-1,2-oxazol-4-yl]methoxyl-8-azabicyclo[3.2.1]octan-8-yl]-4-fluoro-1,3-benzothiazole-6-carboxylate;
2-[3-{[5-cyclopropyl-3-(2,6-difluorophenyl)-1,2-oxazol-4-yl]methoxy}-8-azabicyclo[3.2.1]octan-8-yl]-4-fluoro-1,3-benzothiazole-6-carboxylic acid;
2-[(1R,3r,5S)-3-{[5-cyclopropyl-3-(2,6-difluorophenyl)-1,2-oxazol-4-yl]methoxy}-8-azabicyclo[3.2.1]octan-8-yl]-4-fluoro-1,3-benzothiazole-6-carboxylic acid;
Ethyl 2-(3 4(5-cyclopropyl-3-((trans)-2-(trifluoromethyl)cyclohexyl)isoxazol-4-yl)methoxy)-8-azabicyclo[3.2.1]octan-8-yl)benzo[d]thiazole-6-carboxylate;
2-[3-({[5-cyclopropyl-3-[2-(trifluoromethyl)cyclohexyl]-1,2-oxazol-4-yl]methoxy)-8-azabicyclo[3.2.1]octan-8-yl]-1,3-benzothiazole-6-carboxylic acid;
2-[(1R,3r,5S)-3-({[5-cyclopropyl-3-(1S,2S)-2-(trifluoromethyl)cyclohexyl]-1,2-oxazol-4-yl]methoxy)-8-azabicyclo[3.2.1]octan-8-yl]-1,3-benzothiazole-6-carboxylic acid;
2-[3-({[5-cyclopropyl-3-[2-(trifluoromethyl)cyclohexyl]-1,2-oxazol-4-yl]methoxy)-8-azabicyclo[3.2.1]octan-8-yl]-4-fluoro-1,3-benzothiazole-6-carboxylic acid;
2-[(1R,3r,5S)-3-({[5-cyclopropyl-3-(1S,2S)-2-(trifluoromethyl)cyclohexyl]-1,2-oxazol-4-yl]methoxy)-8-azabicyclo[3.2.1]octan-8-yl]-4-fluoro-1,3-benzothiazole-6-carboxylic acid;
2-[3-({[5-cyclopropyl-3-[2-(trifluoromethyl)cyclohexyl]-1,2-oxazol-4-yl]methoxy)-8-azabicyclo[3.2.1]octan-8-yl]-4-methoxy-1,3-benzothiazole-6-carboxylic acid;
2-[(1R,3r,5S)-3-({[5-cyclopropyl-3-(1S,2S)-2-(trifluoromethyl)cyclohexyl]-1,2-oxazol-4-yl]methoxy)-8-azabicyclo[3.2.1]octan-8-yl]-4-methoxy-1,3-benzothiazole-6-carboxylic acid;
2-[3-{[5-cyclopropyl-3-(4,4-dimethylcyclohexyl)-1,2-oxazol-4-yl]methoxy}-8-azabicyclo[3.2.1]octan-8-yl]-1,3-benzothiazole-6-carboxylic acid;
2-[(1R,3r,5S)-3-{[5-cyclopropyl-3-(4,4-dimethylcyclohexyl)-1,2-oxazol-4-yl]methoxyl-8-azabicyclo[3.2.1]octan-8-yl]-1,3-benzothiazole-6-carboxylic acid;
2-[3-{[5-cyclopropyl-3-(4,4-dimethylcyclohexyl)-1,2-oxazol-4-yl]methoxy}-8-azabicyclo[3.2.1]octan-8-yl]-4-fluoro-1,3-benzothiazole-6-carboxylic acid;
2-(1R,3r,5S)-3-{[5-cyclopropyl-3-(4,4-dimethylcyclohexyl)-1,2-oxazol-4-yl]methoxyl-8-azabicyclo[3.2.1]octan-8-yl]-4- fluoro-1,3-benzothiazole-6-carboxylic acid;
methyl 5-(3 ((5-cyclopropyl-3-(2-(trifluoromethyl)cyclohexyl)isoxazol-4-yl)methoxy)-8-azabicyclo[3.2.1]octan-8-yl)pyrazine-2-carboxylate;
methyl 5-(1R,3r,5S)-(3-5-cyclopropyl-41S,2S)-2-(trifluoromethyl)cyclohexyl)isoxazol-4-yl)methoxy)-8-azabicyclo[3.2.1]octan-8-yl)1pyrazine-2-carboxylate;
5-[3-({5-cyclopropyl-3-[2-(trifluoromethyl)cyclohexyl]-1,2-oxazol-4-yl]methoxy)-8-azabicyclo[3.2.1]octan-8-yl]pyrazine-2-carboxylic acid;
5-(1R,3r,5S)-3-({5-cyclopropyl-3-[(1S,2 5)-2-(trifluoromethyl)cyclohexyl]-1,2-oxazol-4-yl]methoxy)-8-azabicyclo[3.2.1]octan-8-yl]pyrazine-2-carboxylic acid;
methyl 2-(3-((5-cyclopropyl-3-(2-(trifluoromethyl)cyclohexyl)isoxazol-4-yl)methoxy)-8-azabicyclo[3.2.1]octan-8-yl)-4-methylpyrimidine-5-carboxylate;
methyl 2-(1R,3r,5S)-(3-5-cyclopropyl-3-4 1S,2S)-2-(trifluoromethyl)cyclohexyl)isoxazol-4-yl)methoxy)-8-azabicyclo[3.2.1]octan-8-yl)1-4-methylpyrimidine-5-carboxylate;
2-[3-({5-cyclopropyl-3-[2-(trifluoromethyl)cyclohexyl]-1,2-oxazol-4-yl]methoxy)-8-azabicyclo[3.2.1]octan-8-yl)-6-methylpyrimidine-4-carboxylic acid;
2-(1R,3r,5S)-3-[({5-cyclopropyl-3-[(1S,2 5)-2-(trifluoromethyl)cyclohexyl]-1,2-oxazol-4-yl]methoxy)-8-azabicyclo[3.2.1]octan-8-yl]-6-methylpyrimidine-4-carboxylic acid;
methyl 2-(3-((3-cyclohexyl-5-cyclopropylisoxazol-4-yl)methoxy)-8-azabicyclo[3.2.1]octan-8-yl)-6-methylpyrimidine-4-carboxylate;
2(3-cyclohexyl-5-cyclopropylisoxazol-4-yl)methoxy}-8-azabicyclo[3.2.1]octan-8-yl)-6-methylpyrimidine-4-carboxylic acid;
2-[3-[(3-cyclohexyl-5-cyclopropyl-1,2-oxazol-4-yl)methoxy]-8-azabicyclo[3.2.1]octan-8-yl]-4-fluoro-1,3-benzothiazole-6-carboxylic acid;
2-(1R,3r,5S)-3-[(3-cyclohexyl-5-cyclopropyl-1,2-oxazol-4-yl)methoxyl-8-azabicyclo[3.2.1]octan-8-yl]-4-fluoro-1,3-benzothiazole-6-carboxylic acid;
2-[3-[(3-cyclohexyl-5-cyclopropyl-1,2-oxazol-4-yl)methoxy]-8-azabicyclo[3.2.1]octan-8-yl]-4-methoxy-1,3-benzothiazole-6-carboxylic acid
2-(1R,3r,5S)-3-(3-cyclohexyl-5-cyclopropyl-1,2-oxazol-4-yl)methoxy]-8-azabicyclo[3.2.1]octan-8-yl]-4-methoxy-1,3-benzothiazole-6-carboxylic acid
Ethyl 2-(3-((5-cyclopropyl-3-(2-phenylcyclopropyl)isoxazol-4-yl)methoxy)-8-azabicyclo[3.2.1]octan-8-yl)benzo[d]thiazole-6-carboxylate;
2-[3-({5-cyclopropyl-3-[2-phenylcyclopropyl]-1,2-oxazol-4-yl}methoxy)-8-azabicyclo[3.2.1]octan-8-yl]-1,3-benzothiazole-6-carboxylic acid;
2-[(1R,3r,5S)-3-({5-cyclopropyl-3-[(1S,2S)-2-phenylcyclopropyl]-1,2-oxazol-4-yl]methoxy)-8-azabicyclo[3.2.1]octan-8-yl]-1,3-benzothiazole-6-carboxylic acid;
2-[3-({5-cyclopropyl-3-[2-(trifluoromethyl)cyclopropyl]-1,2-oxazol-4-yl]methoxy)-8-azabicyclo[3.2.1]octan-8-yl]-4-fluoro-1,3-benzothiazole-6-carboxylic acid;
2-[(1R,3r,5S)-3-({5-cyclopropyl-3-[(1S,2S)-2-(trifluoromethyl)cyclopropyl]-1,2-oxazol-4-yl]methoxy)-8-azabicyclo[3.2.1]octan-8-yl]-4-fluoro-1,3-benzothiazole-6-carboxylic acid;

2-[3-({5-cyclopropyl-3-[2-methylcyclopropyl]-1,2-oxazol-4-yl}methoxy)-8-azabicyclo[3.2.1]octan-8-yl]-4-fluoro-1,3-benzothiazole-6-carboxylic acid;
2-[(1R,3r,5S)-3-({5-cyclopropyl-3-[(1S,2S)-2-methylcyclopropyl]-1,2-oxazol-4-yl}methoxy)-8-azabicyclo[3.2.1]octan-8-yl]-4-fluoro-1,3-benzothiazole-6-carboxylic acid;
2-[3-[(3,5-dicyclopropyl-1,2-oxazol-4-yl)methoxy]-8-azabicyclo[3.2.1]octan-8-yl]-4-fluoro-1,3-benzothiazole-6-carboxylic acid;
2-[(1R,3r,5S)-3-[(3,5-dicyclopropyl-1,2-oxazol-4-yl)methoxy]-8-azabicyclo[3.2.1]octan-8-yl]-4-fluoro-1,3-benzothiazole-6-carboxylic acid;
2-[3-[(3,5-dicyclopropyl-1,2-oxazol-4-yl)methoxy]-8-azabicyclo[3.2.1]octan-8-yl]-4-methoxy-1,3-benzothiazole-6-carboxylic acid;
2-[(1R,3r,5S)-3-[(3,5-dicyclopropyl-1,2-oxazol-4-yl)methoxy]-8-azabicyclo[3.2.1]octan-8-yl]-4-methoxy-1,3-benzothiazole-6-carboxylic acid;
Ethyl 2-(3-((5-cyclopropyl-3-(spiro[2.5]octan-6-yl)isoxazol-4-yl)methoxy)-8-azabicyclo[3.2.1]octan-8-yl)benzo[d]thiazole-6-carboxylate;
2-[3-[(5-cyclopropyl-3-{spiro[2.5]octan-6-yl}-1,2-oxazol-4-yl)methoxyl-8-azabicyclo[3.2.1]octan-8-yl]-1,3-benzothiazole-6-carboxylic acid;
2-[(1R,3r,5S)-3-[(5-cyclopropyl-3-{spiro[2.5]octan-6-yl}-1,2-oxazol-4-yl)methoxyl-8-azabicyclo[3.2.1]octan-8-yl]-1,3-benzothiazole-6-carboxylic acid;
Methyl 2-(3-((5-cyclopropyl-3-(spiro[2.5]octan-6-yl)isoxazol-4-yl)methoxy)-8-azabicyclo[3.2.1]octan-8-yl)-4-fluorobenzo[d]thiazole-6-carboxylate;
2-[3-[(5-cyclopropyl-3-{spiro[2.5]octan-6-yl}-1,2-oxazol-4-yl)methoxy}-8-azabicyclo[3.2.1]octan-8-yl]-4-fluoro-1,3-benzothiazole-6-carboxylic acid;
2-[(1R,3r,5S)-3-[(5-cyclopropyl-3-{spiro[2.5]octan-6-yl}-1,2-oxazol-4-yl)methoxyl-8-azabicyclo[3.2.1]octan-8-yl]1-4-fluoro-1,3-benzothiazole-6-carboxylic acid;
Methyl 2-(3-((5-cyclopropyl-3-(spiro[2.5]octan-6-yl)isoxazol-4-yl)methoxy)-8-azabicyclo[3.2.1]octan-8-yl)-4-methoxybenzo[d]thiazole-6-carboxylate;
2-[3-[(5-cyclopropyl-3-{spiro[2.5]octan-6-yl}-1,2-oxazol-4-yl)methoxyl-8-azabicyclo[3.2.1]octan-8-yl]-4-methoxy-1,3-benzothiazole-6-carboxylic acid;
2-[(1R,3r,5S)-3-[(5-cyclopropyl-3-{spiro[2.5]octan-6-yl}-1,2-oxazol-4-yl)methoxyl-8-azabicyclo[3.2.1]octan-8-yl]-4-methoxy-1,3-benzothiazole-6-carboxylic acid;
2-[3-[(5-cyclopropyl-3-{spiro[2.5]octan-6-}-1,2-oxazol-4-yl)methoxyl-8-azabicyclo[3.2.1]octan-8-yl]-6-methylpyrimidine-4-carboxylic acid;
2-[(1R,3r,5S)-3-[(5-cyclopropyl-3-{spiro[2.5]octan-6-yl}-1,2-oxazol-4-yl)methoxyl-8-azabicyclo[3.2.1]octan-8-yl]-6-methylpyrimidine-4-arboxylic acid;
2-({2-[3-({5-cyclopropyl-3-[2-(trifluoromethoxy)phenyl]-1,2-oxazol-4-yl]methoxy)-8-azabicyclo[3.2.1]octan-8-yl]-1,3-benzothiazol-6-yl}formamido)acetic acid;
2-({2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazol-6-yl}formamido)acetic acid;
2-({2-[3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)acetic acid;
2-({2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)acetic acid;
2-({6-[3-({5-cyclopropyl-3-[2-(trifluoromethoxy)phenyl]-1,2-oxazol-4-yl}methoxy)-8-azabicyclo[3.2.1]octan-8-yl]pyridin-3-yl}formamido)acetic acid;
2-({6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridin-3-yl}formamido)acetic acid;
2-({2-[3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazol-6-yl}formamido)acetic acid;
2-({2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazol-6-yl}formamido)acetic acid;
2-({2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazol-6-yl}formamido)ethane-1-sulfonic acid;
2-({2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazol-6-yl]formamido)ethane-1-sulfonic acid;
2-({2-[3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)ethane-1-sulfonic acid;
2-({2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl]formamido)ethane-1-sulfonic acid;
2-({2-[3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazol-6-yl}formamido)ethane-1-sulfonic acid;
2-({2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazol-6-yl}formamido)ethane-1-sulfonic acid;
2-({6-[3-({5-cyclopropyl-3-[2-(trifluoromethoxy)phenyl]-1,2-oxazol-4-yl}methoxy)-8-azabicyclo[3.2.1]octan-8-yl]pyridin-3-yl}formamido)ethane-1-sulfonic acid;
2-({6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridin-3-yl]formamido)ethane-1-sulfonic acid;
methyl 5-bromo-6-[3-({5-cyclopropyl-3-[2-(trifluoromethoxy)phenyl]-1,2-oxazol-4-yl}methoxy)-8-azabicyclo[3.2.1]octan-8-yl]pyridine-3-carboxylate;
methyl 5-bromo-6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-3-carboxylate;
Methyl 5-cyclopropyl-6-(3-((5-cyclopropyl-3-(2-(trifluoromethoxy)phenyl)isoxazol-4-yl)methoxy)-8-azabicyclo[3.2.1]octan-8-yl)nicotinate;
Methyl 5-cyclopropyl-6-((1R,3r,5S)-3-((5-cyclopropyl-3-(2-(trifluoromethoxy)phenyl)isoxazol-4-yl)methoxy)-8-azabicyclo[3.2.1]octan-8-yl)nicotinate;
5-cyclopropyl-6-[3-({5-cyclopropyl-3-[2-(trifluoromethoxy)phenyl]-1,2-oxazol-4-yl}methoxy)-8-azabicyclo[3.2.1]octan-8-yl]pyridine-3-carboxylic acid;
5-cyclopropyl-6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-3-carboxylic acid;
methyl 6-[3-({5-cyclopropyl-3-[2-(trifluoromethoxy)phenyl]-1,2-oxazol-4-yl}methoxy)-8-azabicyclo[3.2.1]octan-8-yl]pyridine-3-carboxylate;

methyl 6-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-3-carboxylate;
6-[3-({5-cyclopropyl-3-[2-(trifluoromethoxy)phenyl]-1,2-oxazol-4-yl}methoxy)-8-azabicyclo[3.2.1]octan-8-yl]pyridine-3-carboxylic acid;
6-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-3-carboxylic acid;
methyl 2-[3-({5-cyclopropyl-3-[2-(trifluoromethoxy)phenyl]-1,2-oxazol-4-yl}methoxy)-8-azabicyclo[3.2.1]octan-8-yl]pyrimidine-5-carboxylate;
methyl 2-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrimidine-5-carboxylate;
2-[3-({5-cyclopropyl-3-[2-(trifluoromethoxy)phenyl]-1,2-oxazol-4-yl}methoxy)-8-azabicyclo[3.2.1]octan-8-yl]pyrimidine-5-carboxylic acid;
2-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrimidine-5-carboxylic acid;
methyl 5-[3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylate;
methyl 5-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylate;
5-[3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylic acid;
5-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylic acid;
methyl 6-[3-({5-cyclopropyl-3-[2-(trifluoromethyl)phenyl]-1,2-oxazol-4-yl}methoxy)-8-azabicyclo[3.2.1]octan-8-yl]pyridine-3-carboxylate;
methyl 6-(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-3-carboxylate;
6-[3-({5-cyclopropyl-3-[2-(trifluoromethyl)phenyl]-1,2-oxazol-4-yl}methoxy)-8-azabicyclo[3.2.1]octan-8-yl]pyridine-3-carboxylic acid;
6-(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-3-carboxylic acid;
methyl 2-[3-({5-cyclopropyl-3-[2-(trifluoromethoxy)phenyl]-1,2-oxazol-4-yl}methoxy)-8-azabicyclo[3.2.1]octan-8-yl]-6-methylpyrimidine-4-carboxylate;
methyl 2-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]1-6-methylpyrimidine-4-carboxylate;
2-[3-({5-cyclopropyl-3-[2-(trifluoromethoxy)phenyl]-1,2-oxazol-4-yl}methoxy)-8-azabicyclo[3.2.1]octan-8-yl]-6-methylpyrimidine-4-carboxylic acid;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-6-methylpyrimidine-4-carboxylic acid;
methyl 2-(3-((5-cyclopropyl-3-(2-(trifluoromethyl)phenyl)isoxazol-4-yl)methoxy)-8-azabicyclo[3.2.1]octan-8-yl)-6-methylpyrimidine-4-carboxylate;
2-[3-({5-cyclopropyl-3-[2-(trifluoromethyl)phenyl]-1,2-oxazol-4-yl}methoxy)-8-azabicyclo[3.2.1]octan-8-yl]-6-methylpyrimidine-4-carboxylic acid;
2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-6-methylpyrimidine-4-carboxylic acid;

methyl 2-{6-[3-({5-cyclopropyl-3-[2-(trifluoromethoxy)phenyl]-1,2-oxazol-4-yl}methoxy)-8-azabicyclo[3.2.1]octan-8-yl]pyridin-3-yl}acetate;
methyl 2-{6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridin-3-yl}acetate;
2-{6-[3-({5-cyclopropyl-3-[2-(trifluoromethoxy)phenyl]-1,2-oxazol-4-yl}methoxy)-8-azabicyclo[3.2.1]octan-8-yl]pyridin-3-yl}acetic acid;
2-{6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridin-3-yl}acetic acid;
methyl 2-[3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyrimidine-5-carboxylate;
methyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyrimidine-5-carboxylate;
2-[3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyrimidine-5-carboxylic acid;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyrimidine-5-carboxylic acid;
methyl 6-[3-(5-cyclopropyl-3-[2-(trifluoromethoxy)phenyl]-1,2-oxazol-4-yl]methoxy)-8-azabicyclo[3.2.1]octan-8-yl]-4-(trifluoromethyl)pyridine-3-carboxylate;
methyl 6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyridine-3-carboxylate;
6-[3-(5-cyclopropyl-3-[2-(trifluoromethoxy)phenyl]-1,2-oxazol-4-yl]methoxy)-8-azabicyclo[3.2.1]octan-8-yl]-4-(trifluoromethyl)pyridine-3-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyridine-3-carboxylic acid;
methyl 6-[3-({5-cyclopropyl-3-[2-(trifluoromethoxy)phenyl]-1,2-oxazol-4-yl]methoxy)-8-azabicyclo[3.2.1]octan-8-yl]-4-methylpyridine-3-carboxylate;
methyl 6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-methylpyridine-3-carboxylate;
6-[3-({5-cyclopropyl-3-[2-(trifluoromethoxy)phenyl]-1,2-oxazol-4-yl}methoxy)-8-azabicyclo[3.2.1]octan-8-yl]-4-methylpyridine-3-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-methylpyridine-3-carboxylic acid;
methyl 6-[3-({5-cyclopropyl-3-[2-(trifluoromethoxy)phenyl]-1,2-oxazol-4-yl]methoxy)-8-azabicyclo[3.2.1]octan-8-yl]-5-methylpyridine-3-carboxylate;
methyl 6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-5-methylpyridine-3-carboxylate;
6-[3-({5-cyclopropyl-3-[2-(trifluoromethoxy)phenyl]-1,2-oxazol-4-yl}methoxy)-8-azabicyclo[3.2.1]octan-8-yl]-5-methylpyridine-3-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-5-methylpyridine-3-carboxylic acid;
methyl 6-[3-({5-cyclopropyl-3-[2-(trifluoromethoxy)phenyl]-1,2-oxazol-4-yl]methoxy)-8-azabicyclo[3.2.1]octan-8-yl]pyrazine-2-carboxylate;

methyl 6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylate;

6-[3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylic acid;

methyl 2-[3-({5-cyclopropyl-3-[2-(trifluoromethoxy)phenyl]-1,2-oxazol-4-yl}methoxy)-8-azabicyclo[3.2.1]octan-8-yl]pyrimidine-4-carboxylate;

methyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrimidine-4-carboxylate;

2-[3-({5-cyclopropyl-3-[2-(trifluoromethoxy)phenyl]-1,2-oxazol-4-yl}methoxy)-8-azabicyclo[3.2.1]octan-8-yl]pyrimidine-4-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrimidine-4-carboxylic acid;

methyl 6-[3-({5-cyclopropyl-3-[2-(trifluoromethoxy)phenyl]-1,2-oxazol-4-yl}methoxy)-8-azabicyclo[3.2.1]octan-8-yl]pyridine-2-carboxylate;

methyl 6-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-2-carboxylate;

6-[3-({5-cyclopropyl-3-[2-(trifluoromethoxy)phenyl]-1,2-oxazol-4-yl}methoxy)-8-azabicyclo[3.2.1]octan-8-yl]pyridine-2-carboxylic acid;

6-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-2-carboxylic acid;

methyl 2-[3-({5-cyclopropyl-3-[2-(trifluoromethyl)phenyl]-1,2-oxazol-4-yl}methoxy)-8-azabicyclo[3.2.1]octan-8-yl]pyridine-4-carboxylate;

methyl 2-(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-4-carboxylate;

2-[3-({5-cyclopropyl-3-[2-(trifluoromethyl)phenyl]-1,2-oxazol-4-yl}methoxy)-8-azabicyclo[3.2.1]octan-8-yl]pyridine-4-carboxylic acid;

2-(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-4-carboxylic acid;

methyl 6-[3-({5-cyclopropyl-3-[2-(trifluoromethyl)phenyl]-1,2-oxazol-4-yl}methoxy)-8-azabicyclo[3.2.1]octan-8-yl]-2-methylpyridine-4-carboxylate;

methyl 6-(1R,3r,5S)-3-({5-cyclopropyl-3-[2-(trifluoromethyl)phenyl]-1,2-oxazol-4-yl}methoxy)-8-azabicyclo[3.2.1]octan-8-yl]-2-methylpyridine-4-carboxylate;

2-[3-({5-cyclopropyl-3-[2-(trifluoromethyl)phenyl]-1,2-oxazol-4-yl}methoxy)-8-azabicyclo[3.2.1]octan-8-yl]-6-methylpyridine-4-carboxylic acid;

2-(1R,3r,5S)-3-({5-cyclopropyl-3-[2-(trifluoromethyl)phenyl]-1,2-oxazol-4-yl}methoxy)-8-azabicyclo[3.2.1]octan-8-yl]-6-methylpyridine-4-carboxylic acid;

methyl 2-[3-({5-cyclopropyl-3-[2-(trifluoromethyl)phenyl]-1,2-oxazol-4-yl}methoxy)-8-azabicyclo[3.2.1]octan-8-yl]pryimidine-5-carboxylate;

methyl 2-(1R,3r,5S)-3-({5-cyclopropyl-3-[2-(trifluoromethyl)phenyl]-1,2-oxazol-4-yl}methoxy)-8-azabicyclo[3.2.1]octan-8-yl]pryimidine-5-carboxylate;

2-[3-({5-cyclopropyl-3-[2-(trifluoromethyl)phenyl]-1,2-oxazol-4-yl}methoxy)-8-azabicyclo[3.2.1]octan-8-yl]pryimidine-5-carboxylic acid;

2-(1R,3r,5S)-3-({5-cyclopropyl-3-[2-(trifluoromethyl)phenyl]-1,2-oxazol-4-yl}methoxy)-8-azabicyclo[3.2.1]octan-8-yl]pryimidine-5-carboxylic acid;

methyl 5-[3-({5-cyclopropyl-3-[2-(trifluoromethyl)phenyl]-1,2-oxazol-4-yl}methoxy)-8-azabicyclo[3.2.1]octan-8-yl]pyrazine-2-carboxylate;

methyl 5-(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyrazine-2-carboxylate;

5-[3-({5-cyclopropyl-3-[2-(trifluoromethyl)phenyl]-1,2-oxazol-4-yl}methoxy)-8-azabicyclo[3.2.1]octan-8-yl]pyrazine-2-carboxylic acid;

5-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyrazine-2-carboxylic acid;

methyl 6-[3-{5-cyclopropyl-3-[2-(trifluoromethyl)phenyl]-1,2-oxazol-4-yl]methoxy)-8-azabicyclo[3.2.1]octan-8-yl]-4-(trifluoromethyl)pyridine-3-carboxylate;

methyl 6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-(trifluoromethyl)pyridine-3-carboxylate;

6-[3-({5-cyclopropyl-3-[2-(trifluoromethyl)phenyl]-1,2-oxazol-4-yl]methoxy)-8-azabicyclo[3.2.1]octan-8-yl]-4-(trifluoromethyl)pyridine-3-carboxylic acid;

6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-(trifluoromethyl)pyridine-3-carboxylic acid;

methyl 2-[3-({5-cyclopropyl-3-[2-(trifluoromethyl)phenyl]-1,2-oxazol-4-yl]methoxy)-8-azabicyclo[3.2.1]octan-8-yl]pryimidine-4-carboxylate;

methyl 2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pryimidine-4-carboxylate;

2-[3-({5-cyclopropyl-3-[2-(trifluoromethyl)phenyl]-1,2-oxazol-4-yl]methoxy)-8-azabicyclo[3.2.1]octan-8-yl]pryimidine-4-carboxylic acid;

2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pryimidine-4-carboxylic acid;

methyl 6-[3-{5-cyclopropyl-3-[2-(trifluoromethyl)phenyl]-1,2-oxazol-4-yl]methoxy)-8-azabicyclo[3.2.1]octan-8-yl]pyridine-2-carboxylate;

methyl 6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-2-carboxylate;

6-[3-({5-cyclopropyl-3-[2-(trifluoromethyl)phenyl]-1,2-oxazol-4-yl]methoxy)-8-azabicyclo[3.2.1]octan-8-yl]pyridine-2-carboxylic acid;

6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-2-carboxylic acid;

methyl 6-[3-{5-cyclopropyl-3-[2-(difluoromethoxy)phenyl]-1,2-oxazol-4-yl]methoxy)-8-azabicyclo[3.2.1]octan-8-yl]-4-(trifluoromethyl)pyridine-3-carboxylate;

methyl 6-[(1R,3r,5S)-3-({5-cyclopropyl-3-[2-(difluoromethoxy)phenyl]-1,2-oxazol-4-yl]methoxy)-8-azabicyclo[3.2.1]octan-8-yl]-4-(trifluoromethyl)pyridine-3-carboxylate;

6-[3-({5-cyclopropyl-3-[2-(difluoromethoxy)phenyl]-1,2-oxazol-4-yl]methoxy)-8-azabicyclo[3.2.1]octan-8-yl]-4-(trifluoromethyl)pyridine-3-carboxylic acid;

6-(1R,3r,5S)-3-({5-cyclopropyl-3-[2-(difluoromethoxy)phenyl]-1,2-oxazol-4-yl}methoxy)-8-azabicyclo[3.2.1]octan-8-yl]-4-(trifluoromethyl)pyridine-3-carboxylic acid;

methyl 2-[3-({5-cyclopropyl-3-[2-(difluoromethoxy)phenyl]-1,2-oxazol-4-yl}methoxy)-8-azabicyclo[3.2.1]octan-8-yl]pryimidine-4-carboxylate;

methyl 2-(1R,3r,5S)-3-({5-cyclopropyl-3-[2-(difluoromethoxy)phenyl]-1,2-oxazol-4-yl}methoxy)-8-azabicyclo[3.2.1]octan-8-yl]pryimidine-4-carboxylate;

2-[3-({5-cyclopropyl-3-[2-(difluoromethoxy)phenyl]-1,2-oxazol-4-yl}methoxy)-8-azabicyclo[3.2.1]octan-8-yl]pryimidine-4-carboxylic acid;

2-(1R,3r,5S)-3-({5-cyclopropyl-3-[2-(difluoromethoxy)phenyl]-1,2-oxazol-4-yl}methoxy)-8-azabicyclo[3.2.1]octan-8-yl]pryimidine-4-carboxylic acid;

methyl 6-[3-{5-cyclopropyl-3-[2-(difluoromethoxy)phenyl]-1,2-oxazol-4-yl}methoxy)-8-azabicyclo[3.2.1]octan-8-yl]pyridine-2-carboxylate;

methyl 6-(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyridine-2-carboxylate;

methyl 6-[3-({5-cyclopropyl-3-[2-(difluoromethoxy)phenyl]-1,2-oxazol-4-yl}methoxy)-8-azabicyclo[3.2.1]octan-8-yl]-4-methylpyridine-3-carboxylate;

methyl 6-(1R,3r,5S)-3-({5-cyclopropyl-3-[2-(difluoromethoxy)phenyl]-1,2-oxazol-4-yl}methoxy)-8-azabicyclo[3.2.1]octan-8-yl]-4-methylpyridine-3-carboxylate;

6-[3-({5-cyclopropyl-3-[2-(difluoromethoxy)phenyl]-1,2-oxazol-4-yl}methoxy)-8-azabicyclo[3.2.1]octan-8-yl]-4-methylpyridine-3-carboxylic acid;

6-(1R,3r,5S)-3-({5-cyclopropyl-3-[2-(difluoromethoxy)phenyl]-1,2-oxazol-4-yl}methoxy)-8-azabicyclo[3.2.1]octan-8-yl]-4-methylpyridine-3-carboxylic acid;

methyl 2-[3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxylate;

methyl 2-(1R,3r,5S)-3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxylate;

methyl 4-chloro-6-[3-({5-cyclopropyl-3-[2-(difluoromethoxy)phenyl]-1,2-oxazol-4-yl}methoxy)-8-azabicyclo[3.2.1]octan-8-yl]pyridine-3-carboxylate;

methyl 4-chloro-6-(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyridine-3-carboxylate;

4-chloro-6-[3-({5-cyclopropyl-3-[2-(difluoromethoxy)phenyl]-1,2-oxazol-4-yl}methoxy)-8-azabicyclo[3.2.1]octan-8-yl]pyridine-3-carboxylic acid;

4-chloro-6-(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyridine-3-carboxylic acid;

methyl 6-[3-({5-cyclopropyl-3-[2-(difluoromethoxy)phenyl]-1,2-oxazol-4-yl}methoxy)-8-azabicyclo[3.2.1]octan-8-yl]-5-methylpyridine-3-carboxylate;

methyl 6-[(1R,5S)-3-({5-cyclopropyl-3-[2-(difluoromethoxy)phenyl]-1,2-oxazol-4-yl}methoxy)-8-azabicyclo[3.2.1]octan-8-yl]-5-methylpyridine-3-carboxylate;

6-[3-({5-cyclopropyl-3-[2-(difluoromethoxy)phenyl]-1,2-oxazol-4-yl}methoxy)-8-azabicyclo[3.2.1]octan-8-yl]-5-methylpyridine-3-carboxylic acid;

6-[(1R,5S)-3-({5-cyclopropyl-3-[2-(difluoromethoxy)phenyl]-1,2-oxazol-4-yl}methoxy)-8-azabicyclo[3.2.1]octan-8-yl]-5-methylpyridine-3-carboxylic acid;

2-[3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxylic acid;

2-[(1R,5S)-3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxylic acid;

methyl 6-[3-({5-cyclopropyl-3-[2-(difluoromethoxy)phenyl]-1,2-oxazol-4-yl}methoxy)-8-azabicyclo[3.2.1]octan-8-yl]pyridazine-3-carboxylate;

methyl 6-[(1R,5S)-3-({5-cyclopropyl-3-[2-(difluoromethoxy)phenyl]-1,2-oxazol-4-yl}methoxy)-8-azabicyclo[3.2.1]octan-8-yl]pyridazine-3-carboxylate;

6-[3-({5-cyclopropyl-3-[2-(difluoromethoxy)phenyl]-1,2-oxazol-4-yl}methoxy)-8-azabicyclo[3.2.1]octan-8-yl]pyridazine-3-carboxylic acid;

6-[(1R,5S)-3-({5-cyclopropyl-3-[2-(difluoromethoxy)phenyl]-1,2-oxazol-4-yl}methoxy)-8-azabicyclo[3.2.1]octan-8-yl]pyridazine-3-carboxylic acid;

methyl 2-[3-({5-cyclopropyl-3-[2-(difluoromethoxy)phenyl]-1,2-oxazol-4-yl}methoxy)-8-azabicyclo[3.2.1]octan-8-yl]pyrimidine-5-carboxylate;

methyl 2-[(1R,5S)-3-({5-cyclopropyl-3-[2-(difluoromethoxy)phenyl]-1,2-oxazol-4-yl}methoxy)-8-azabicyclo[3.2.1]octan-8-yl]pyrimidine-5-carboxylate;

2-[3-({5-cyclopropyl-3-[2-(difluoromethoxy)phenyl]-1,2-oxazol-4-yl}methoxy)-8-azabicyclo[3.2.1]octan-8-yl]pyrimidine-5-carboxylic acid;

2-[(1R,5S)-3-({5-cyclopropyl-3-[2-(difluoromethoxy)phenyl]-1,2-oxazol-4-yl}methoxy)-8-azabicyclo[3.2.1]octan-8-yl]pyrimidine-5-carboxylic acid;

methyl 5-[3-({5-cyclopropyl-3-[2-(difluoromethoxy)phenyl]-1,2-oxazol-4-yl}methoxy)-8-azabicyclo[3.2.1]octan-8-yl]pyrazine-2-carboxylate;

methyl 5-[(1R,5S)-3-({5-cyclopropyl-3-[2-(difluoromethoxy)phenyl]-1,2-oxazol-4-yl}methoxy)-8-azabicyclo[3.2.1]octan-8-yl]pyrazine-2-carboxylate;

5-[3-({5-cyclopropyl-3-[2-(difluoromethoxy)phenyl]-1,2-oxazol-4-yl}methoxy)-8-azabicyclo[3.2.1]octan-8-yl]pyrazine-2-carboxylic acid;

5-[(1R,5S)-3-({5-cyclopropyl-3-[2-(difluoromethoxy)phenyl]-1,2-oxazol-4-yl}methoxy)-8-azabicyclo[3.2.1]octan-8-yl]pyrazine-2-carboxylic acid;

6-[3-({5-cyclopropyl-3-[2-(difluoromethoxy)phenyl]-1,2-oxazol-4-yl}methoxy)-8-azabicyclo[3.2.1]octan-8-yl]pyridine-3-carboxylic acid;

6-[(1R,5S)-3-({5-cyclopropyl-3-[2-(difluoromethoxy)phenyl]-1,2-oxazol-4-yl}methoxy)-8-azabicyclo[3.2.1]octan-8-yl]pyridine-3-carboxylic acid;

methyl 6-[3-{[5-cyclopropyl-3-(2,6-difluorophenyl)-1,2-oxazol-4-yl]methoxy}-8-azabicyclo[3.2.1]octan-8-yl]pyridine-3-carboxylate;

methyl 6-[(1R,5S)-3-{[5-cyclopropyl-3-(2,6-difluorophenyl)-1,2-oxazol-4-yl]methoxy}-8-azabicyclo[3.2.1]octan-8-yl]pyridine-3-carboxylate;

6-[3-{[5-cyclopropyl-3-(2,6-difluorophenyl)-1,2-oxazol-4-yl]methoxy}-8-azabicyclo[3.2.1]octan-8-yl]pyridine-3-carboxylic acid;

6-[(1R,5S)-3-{[5-cyclopropyl-3-(2,6-difluorophenyl)-1,2-oxazol-4-yl]methoxy}-8-azabicyclo[3.2.1]octan-8-yl]pyridine-3-carboxylic acid;

methyl 2-[3-{[5-cyclopropyl-3-(2,6-difluorophenyl)-1,2-oxazol-4-yl]methoxy}-8-azabicyclo[3.2.1]octan-8-yl]pyrimidine-5-carboxylate;

methyl 2-[(1R,5S)-3-{[5-cyclopropyl-3-(2,6-difluorophenyl)-1,2-oxazol-4-yl]methoxy}-8-azabicyclo[3.2.1]octan-8-yl]pyrimidine-5-carboxylate;

2-[3-{[5-cyclopropyl-3-(2,6-difluorophenyl)-1,2-oxazol-4-yl]methoxy}-8-azabicyclo[3.2.1]octan-8-yl]pyrimidine-5-carboxylic acid;

2-[(1R,5S)-3-{[5-cyclopropyl-3-(2,6-difluorophenyl)-1,2-oxazol-4-yl]methoxy}-8-azabicyclo[3.2.1]octan-8-yl]pyrimidine-5-carboxylic acid;

methyl 5-[3-{[5-cyclopropyl-3-(2,6-difluorophenyl)-1,2-oxazol-4-yl]methoxy}-8-azabicyclo[3.2.1]octan-8-yl]pyrazine-2-carboxylate;
methyl 5-[(1R,5S)-3-{[5-cyclopropyl-3-(2,6-difluorophenyl)-1,2-oxazol-4-yl]methoxy}-8-azabicyclo[3.2.1]octan-8-yl]pyrazine-2-carboxylate;
5-[3-{[5-cyclopropyl-3-(2,6-difluorophenyl)-1,2-oxazol-4-yl]methoxy}-8-azabicyclo[3.2.1]octan-8-yl]pyrazine-2-carboxylic acid;
5-[(1R,5S)-3-{[5-cyclopropyl-3-(2,6-difluorophenyl)-1,2-oxazol-4-yl]methoxy}-8-azabicyclo[3.2.1]octan-8-yl]pyrazine-2-carboxylic acid;
methyl 6-[3-{[5-cyclopropyl-3-(2,6-difluorophenyl)-1,2-oxazol-4-yl]methoxy}-8-azabicyclo[3.2.1]octan-8-yl]-4-(trifluoromethyl)pyridine-3-carboxylate;
methyl 6-[(1R,5S)-3-{[5-cyclopropyl-3-(2,6-difluorophenyl)-1,2-oxazol-4-yl]methoxy}-8-azabicyclo[3.2.1]octan-8-yl]-4-(trifluoromethyl)pyridine-3-carboxylate;
6-[3-({[5-cyclopropyl-3-(2,6-difluorophenyl)-1,2-oxazol-4-yl}methoxy)-8-azabicyclo[3.2.1]octan-8-yl]-4-(trifluoromethyl)pyridine-3-carboxylic acid;
6-(1R,3r,5S)-3-({[5-cyclopropyl-3-(2,6-difluorophenyl)-1,2-oxazol-4-yl]methoxy}-8-azabicyclo[3.2.1]octan-8-yl]-4-(trifluoromethyl)pyridine-3-carboxylic acid;
methyl 5-cyclopropyl-6-[3-{[5-cyclopropyl-3-(2,6-difluorophenyl)-1,2-oxazol-4-yl]methoxy)-8-azabicyclo[3.2.1]octan-8-yl]pyridine-3-carboxylate;
methyl 5-cyclopropyl-6-(1R,3r,5S)-3-{[5-cyclopropyl-3-(2,6-difluorophenyl)-1,2-oxazol-4-yl]methoxy}-8-azabicyclo[3.2.1]octan-8-yl]pyridine-3-carboxylate;
5-cyclopropyl-6-[3-{[5-cyclopropyl-3-(2,6-difluorophenyl)-1,2-oxazol-4-yl]methoxy)-8-azabicyclo[3.2.1]octan-8-yl]pyridine-3-carboxylic acid;
5-cyclopropyl-6-](1R,3r,5S)-3-{[5-cyclopropyl-3-(2,6-difluorophenyl)-1,2-oxazol-4-yl]methoxy}-8-azabicyclo[3.2.1]octan-8-yl]pyridine-3-carboxylic acid;
methyl 2-[3-{[5-cyclopropyl-3-(2,6-difluorophenyl)-1,2-oxazol-4-yl]methoxy}-8-azabicyclo[3.2.1]octan-8-yl]-6-methylpyrimidine-4-carboxylate;
methyl 2-(1R,3r,5S)-3-{[5-cyclopropyl-3-(2,6-difluorophenyl)-1,2-oxazol-4-yl]methoxy}-8-azabicyclo[3.2.1]octan-8-yl]-6-methylpyrimidine-4-carboxylate;
2-[3-{[5-cyclopropyl-3-(2,6-difluorophenyl)-1,2-oxazol-4-yl]methoxy}-8-azabicyclo[3.2.1]octan-8-yl]-6-methylpyrimidine-4-carboxylic acid;
2-(1R,3r,5S)-3-{[5-cyclopropyl-3-(2,6-difluorophenyl)-1,2-oxazol-4-yl]methoxy}-8-azabicyclo[3.2.1]octan-8-yl]-6-methylpyrimidine-4-carboxylic acid;
methyl 2-chloro-6-[3-{[5-cyclopropyl-3-(2,6-difluorophenyl)-1,2-oxazol-4-yl]methoxy}-8-azabicyclo[3.2.1]octan-8-yl]pryimidine-4-carboxylate;
methyl 2-chloro-6-(1R,3r,5S)-3-{[5-cyclopropyl-3-(2,6-difluorophenyl)-1,2-oxazol-4-yl]methoxy}-8-azabicyclo[3.2.1]octan-8-yl]pryimidine-4-carboxylate;
methyl 6-chloro-2-[3-{[5-cyclopropyl-3-(2,6-difluorophenyl)-1,2-oxazol-4-yl]methoxy}-8-azabicyclo[3.2.1]octan-8-yl]pryimidine-4-carboxylate;
methyl 6-chloro-2-[(1R,3r,5S)-3-{[5-cyclopropyl-3-(2,6-difluorophenyl)-1,2-oxazol-4-yl]methoxy}-8-azabicyclo[3.2.1]octan-8-yl]pryimidine-4-carboxylate;
methyl 5-bromo-6-[3-{[5-cyclopropyl-3-(2,6-difluorophenyl)-1,2-oxazol-4-yl]methoxy }-8-azabicyclo[3.2.1]octan-8-yl]pyridine-3-carboxylate;
methyl 5-bromo-6-[(1R,3r,5S)-3-{[5-cyclopropyl-3-(2,6-difluorophenyl)-1,2-oxazol-4-yl]methoxy}-8-azabicyclo[3.2.1]octan-8-yl]pyridine-3-carboxylate;
methyl 4-[3-({5-cyclopropyl-3-[2-(trifluoromethoxy)phenyl]-1,2-oxazol-4-yl}methoxy)-8-azabicyclo[3.2.1]octan-8-yl]-3-fluorobenzoate;
methyl 4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-3-fluorobenzoate;
4-[3-({5-cyclopropyl-3-[2-(trifluoromethoxy)phenyl]-1,2-oxazol-4-yl}methoxy)-8-azabicyclo[3.2.1]octan-8-yl]-3-fluorobenzoic acid;
4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-3-fluorobenzoic acid;
methyl 4-[3-({5-cyclopropyl-3-[2-(trifluoromethoxy)phenyl]-1,2-oxazol-4-yl}methoxy)-8-azabicyclo[3.2.1]octan-8-yl]-3,5-difluorobenzoate;
methyl 4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-3,5-difluorobenzoate;
4-[3-({5-cyclopropyl-3-[2-(trifluoromethoxy)phenyl]-1,2-oxazol-4-yl}methoxy)-8-azabicyclo[3.2.1]octan-8-yl]-3,5-difluorobenzoic acid;
4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-3,5-difluorobenzoic acid;
methyl 4-[3-({5-cyclopropyl-3-[2-(difluoromethoxy)phenyl]-1,2-oxazol-4-yl}methoxy)-8-azabicyclo[3.2.1]octan-8-yl]-3,5-difluorobenzoate;
methyl 4-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-3,5-difluorobenzoate;
4-[3-({5-cyclopropyl-3-[2-(difluoromethoxy)phenyl]-1,2-oxazol-4-yl}methoxy)-8-azabicyclo[3.2.1]octan-8-yl]-3,5-difluorobenzoic acid;
4-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-3,5-difluorobenzoic acid;
methyl 4-[3-({5-cyclopropyl-3-[2-(trifluoromethyl)phenyl]-1,2-oxazol-4-yl}methoxy)-8-azabicyclo[3.2.1]octan-8-yl]-3,5-difluorobenzoate;
methyl 4-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-3,5-difluorobenzoate;
4-[3-({5-cyclopropyl-3-[2-(trifluoromethyl)phenyl]-1,2-oxazol-4-yl}methoxy)-8-azabicyclo[3.2.1]octan-8-yl]-3,5-difluorobenzoic acid;
4-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-3,5-difluorobenzoic acid;
methyl 4-[3-{[5-cyclopropyl-3-(2,6-difluorophenyl)-1,2-oxazol-4-yl]methoxy}-8-azabicyclo[3.2.1]octan-8-yl]-3-fluorobenzoate;
methyl 4-[(1R,3r,5S)-3-{[5-cyclopropyl-3-(2,6-difluorophenyl)-1,2-oxazol-4-yl]methoxy}-8-azabicyclo[3.2.1]octan-8-yl]-3-fluorobenzoate;
4-[3-{[5-cyclopropyl-3-(2,6-difluorophenyl)-1,2-oxazol-4-yl]methoxy}-8-azabicyclo[3.2.1]octan-8-yl]-3-fluorobenzoic acid;
4-[(1R,3r,5S)-3-{[5-cyclopropyl-3-(2,6-difluorophenyl)-1,2-oxazol-4-yl]methoxy}-8-azabicyclo[3.2.1]octan-8-yl]-3-fluorobenzoic acid;
methyl 4-[3-{[5-cyclopropyl-3-(2,6-difluorophenyl)-1,2-oxazol-4-yl]methoxy}-8-azabicyclo[3.2.1]octan-8-yl]-3,5-difluorobenzoate;
methyl 4-[(1R,3r,5S)-3-{[5-cyclopropyl-3-(2,6-difluorophenyl)-1,2-oxazol-4-yl]methoxy}-8-azabicyclo[3.2.1]octan-8-yl]-3,5-difluorobenzoate;

4-[3-{[5-cyclopropyl-3-(2,6-difluorophenyl)-1,2-oxazol-4-yl]methoxy}-8-azabicyclo[3.2.1]octan-8-yl]-3,5-difluorobenzoic acid;

4-[(1R,3r,5S)-3-{[5-cyclopropyl-3-(2,6-difluorophenyl)-1,2-oxazol-4-yl]methoxy}-8-azabicyclo[3.2.1]octan-8-yl]-3,5-difluorobenzoic acid;

methyl 4-[3-({5-cyclopropyl-3-[2-(trifluoromethyl)phenyl]-1,2-oxazol-4-yl}methoxy)-8-azabicyclo[3.2.1]octan-8-yl]-3-fluorobenzoate;

methyl 4-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-3-fluorobenzoate;

4-[3-({5-cyclopropyl-3-[2-(trifluoromethyl)phenyl]-1,2-oxazol-4-yl}methoxy)-8-azabicyclo[3.2.1]octan-8-yl]-3-fluorobenzoic acid;

4-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-3-fluorobenzoic acid;

methyl 4-[3-({5-cyclopropyl-3-[2-(difluoromethoxy)phenyl]-1,2-oxazol-4-yl}methoxy)-8-azabicyclo[3.2.1]octan-8-yl]-3-fluorobenzoate;

methyl 4-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-3-fluorobenzoate;

4-[3-({5-cyclopropyl-3-[2-(difluoromethoxy)phenyl]-1,2-oxazol-4-yl}methoxy)-8-azabicyclo[3.2.1]octan-8-yl]-3-fluorobenzoic acid;

4-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-3-fluorobenzoic acid;

4-(3-((5-cyclopropyl-3-(2-(difluoromethoxy)phenyl)isoxazol-4-yl)methoxy)-8-azabicyclo[3.2.1]octan-8-yl)-3-fluorobenzonitrile;

3-({5-cyclopropyl-3-[2-(difluoromethoxy)phenyl]-1,2-oxazol-4-yl}methoxy)-8-[2-fluoro-4-(5H-1,2,3,4-tetrazol-5-yl)phenyl]-8-azabicyclo[3.2.1]octane;

(1R,3r,5S)-3-({5-cyclopropyl-3-[2-(difluoromethoxy)phenyl]-1,2-oxazol-4-yl}methoxy)-8-[2-fluoro-4-(5H-1,2,3,4-tetrazol-5-yl)phenyl]-8-azabicyclo[3.2.1]octane;

4-[3-({5-cyclopropyl-3-[2-(difluoromethoxy)phenyl]-1,2-oxazol-4-yl}methoxy)-8-azabicyclo[3.2.1]octan-8-yl]-3-fluorobenzamide;

4-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-3-fluorobenzamide;

methyl 6-(3-((5-cyclopropyl-3-(2-(trifluoromethoxy)phenyl)isoxazol-4-yl)methoxy)-8-azabicyclo[3.2.1]octan-8-yl)benzo[d]isothiazole-3-carboxylate;

6-[3-({5-cyclopropyl-3-[2-(trifluoromethoxy)phenyl]-1,2-oxazol-4-yl}methoxy)-8-azabicyclo[3.2.1]octan-8-yl]-1,2-benzothiazole-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,2-benzothiazole-3-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-1,2-benzothiazole-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,2-benzothiazole-3-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]imidazo[1,2-a]pyridine-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]imidazo[1,2-a]pyridine-3-carboxylic acid;

7-[3-({5-cyclopropyl-3-[2-(trifluoromethoxy)phenyl]-1,2-oxazol-4-yl}methoxy)-8-azabicyclo[3.2.1]octan-8-yl]quinoline-3-carboxylic acid;

7-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]quinoline-3-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-1-methyl-1H-indole-2-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-methyl-1H-indole-2-carboxylic acid;

2-[3-({5-cyclopropyl-3-[2-(trifluoromethoxy)phenyl]-1,2-oxazol-4-yl}methoxy)-8-azabicyclo[3.2.1]octan-8-yl]pyrrolo[1,2-b]pyridazine-6-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrrolo[1,2-b]pyridazine-6-carboxylic acid;

4-[3-({5-cyclopropyl-3-[2-(trifluoromethoxy)phenyl]-1,2-oxazol-4-yl}methoxy)-8-azabicyclo[3.2.1]octan-8-yl]benzoic acid;

4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]benzoic acid;

1-{4-[3-({5-cyclopropyl-3-[2-(trifluoromethoxy)phenyl]-1,2-oxazol-4-yl}methoxy)-8-azabicyclo[3.2.1]octan-8-yl]phenyl}cyclopropane-1-carboxylic acid;

1-{4-[(1R,5S)-3-({5-cyclopropyl-3-[2-(trifluoromethoxy)phenyl]-1,2-oxazol-4-yl}methoxy)-8-azabicyclo[3.2.1]octan-8-yl]phenyl}cyclopropane-1-carboxylic acid;

5-[3-{[5-cyclopropyl-3-(2-cyclopropylphenyl)-1,2-oxazol-4-yl]methoxy}-8-azabicyclo[3.2.1]octan-8-yl]-4-methyl-1-benzofuran-2-carboxylic acid;

5-[(1R,5S)-3-{[5-cyclopropyl-3-(2-cyclopropylphenyl)-1,2-oxazol-4-yl]methoxy}-8-azabicyclo[3.2.1]octan-8-yl]-4-methyl-1-benzofuran-2-carboxylic acid;

5-[3-{[3-(2-chlorophenyl)-5-cyclopropyl-1,2-oxazol-4-yl]methoxy}-8-azabicyclo[3.2.1]octan-8-yl]-4-methyl-1-benzofuran-2-carboxylic acid;

5-[(1R,5S)-3-{[3-(2-chlorophenyl)-5-cyclopropyl-1,2-oxazol-4-yl]methoxy}-8-azabicyclo[3.2.1]octan-8-yl]-4-methyl-1-benzofuran-2-carboxylic acid;

5-[3-{[5-cyclopropyl-3-(2,6-difluorophenyl)-1,2-oxazol-4-yl]methoxy}-8-azabicyclo[3.2.1]octan-8-yl]-4-methyl-1-benzofuran-2-carboxylic acid;

5-[(1R,5S)-3-{[5-cyclopropyl-3-(2,6-difluorophenyl)-1,2-oxazol-4-yl]methoxy}-8-azabicyclo[3.2.1]octan-8-yl]-4-methyl-1-benzofuran-2-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]-4-methyl-1-benzofuran-2-carboxylic acid;

5-[(1R,5S)-3-({5-cyclopropyl-3-[2-(trifluoromethoxy)phenyl]-1,2-oxazol-4-yl}methoxy)-8-azabicyclo[3.2.1]octan-8-yl]-4-methyl-1-benzofuran-2-carboxylic acid;

5-[3-({5-cyclopropyl-3-[2-(trifluoromethyl)phenyl]-1,2-oxazol-4-yl}methoxy)-8-azabicyclo[3.2.1]octan-8-yl]-4-methyl-1-benzofuran-2-carboxylic acid;

5-[(1R,5S)-3-({5-cyclopropyl-3-[2-(trifluoromethyl)phenyl]-1,2-oxazol-4-yl}methoxy)-8-azabicyclo[3.2.1]octan-8-yl]-4-methyl-1-benzofuran-2-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]-1-benzothiophene-2-carboxylic acid;

5-[(1R,5S)-3-({5-cyclopropyl-3-[2-(trifluoromethoxy)phenyl]-1,2-oxazol-4-yl}methoxy)-8-azabicyclo[3.2.1]octan-8-yl]-1-benzothiophene-2-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]-1-benzofuran-2-carboxylic acid;

5-[(1R,5S)-3-({5-cyclopropyl-3-[2-(trifluoromethoxy)phenyl]-1,2-oxazol-4-yl}methoxy)-8-azabicyclo[3.2.1]octan-8-yl]-1-benzofuran-2-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-1-benzofuran-2-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-benzofuran-2-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]-1-methyl-1H-indazole-3-carboxylic acid;

5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-methyl-1H-indazole-3-carboxylic acid;

8-[3-({5-cyclopropyl-3-[2-(trifluoromethoxy)phenyl]-1,2-oxazol-4-yl}methoxy)-8-azabicyclo[3.2.1]octan-8-yl]quinoline-3-carboxylic acid;

8-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]quinoline-3-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-1,2-benzoxazole-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,2-benzoxazole-3-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]-1-methyl-1H-indole-2-carboxylic acid;

5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-methyl-1H-indole-2-carboxylic acid;

5-[3-({5-cyclopropyl-3-[2-(trifluoromethyl)phenyl]-1,2-oxazol-4-yl}methoxy)-8-azabicyclo[3.2.1]octan-8-yl]-1-benzofuran-2-carboxylic acid;

5-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-1-benzofuran-2-carboxylic acid;

6-[3-({5-cyclopropyl-3-[2-(trifluoromethyl)phenyl]-1,2-oxazol-4-yl}methoxy)-8-azabicyclo[3.2.1]octan-8-yl]-1,2-benzothiazole-3-carboxylic acid;

6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-1,2-benzothiazole-3-carboxylic acid;

6-[3-{[5-cyclopropyl-3-(2-cyclopropylphenyl)-1,2-oxazol-4-yl]methoxy}-8-azabicyclo[3.2.1]octan-8-yl]-1,2-benzothiazole-3-carboxylic acid;

6-[(1R,3r,5S)-3-{[5-cyclopropyl-3-(2-cyclopropylphenyl)-1,2-oxazol-4-yl]methoxy}-8-azabicyclo[3.2.1]octan-8-yl]-1,2-benzothiazole-3-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-5-fluoro-1,2-benzothiazole-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-5-fluoro-1,2-benzothiazole-3-carboxylic acid;

7-[3-({5-cyclopropyl-3-[2-(trifluoromethoxy)phenyl]-1,2-oxazol-4-yl}methoxy)-8-azabicyclo[3.2.1]octan-8-yl]imidazo[1,2-a]pyridine-2-carboxylic acid;

7-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]imidazo[1,2-a]pyridine-2-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-1-methyl-1H-indazole-3-carboxylic acid;

6-(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-methyl-1H-indazole-3-carboxylic acid;

2-[3-({3-[bicyclo[3.1.0]hexan-6-yl]-5-cyclopropyl-1,2-oxazol-4-yl}methoxy)-8-azabicyclo[3.2.1]octan-8-yl]-4-fluoro-1,3-benzothiazole-6-carboxylic acid;

2-(1R,3r,5S)-3-({3-(1R,5S)-bicyclo[3.1.0]hexan-6-yl]-5-cyclopropyl-1,2-oxazol-4-yl}methoxy)-8-azabicyclo[3.2.1]octan-8-yl]-4-fluoro-1,3-benzothiazole-6-carboxylic acid;

2-[3-({5-cyclopropyl-3-[1-methylbicyclo[3.1.0]hexan-6-yl]-1,2-oxazol-4-yl}methoxy)-8-azabicyclo[3.2.1]octan-8-yl]-4-fluoro-1,3-benzothiazole-6-carboxylic acid;

2-(1R,3r,5S)-3-({5-cyclopropyl-3-(1R,5R,6S)-1-methylbicyclo[3.1.0]hexan-6-yl]-1,2-oxazol-4-yl}methoxy)-8-azabicyclo[3.2.1]octan-8-yl]-4-fluoro-1,3-benzothiazole-6-carboxylic acid;

2-[3-[(3-cyclopentyl-5-cyclopropyl-1,2-oxazol-4-yl)methoxy]-8-azabicyclo[3.2.1]octan-8-yl]-4-fluoro-1,3-benzothiazole-6-carboxylic acid;

2-[(1R,3r,5S)-3-[(3-cyclopentyl-5-cyclopropyl-1,2-oxazol-4-yl)methoxy]-8-azabicyclo[3.2.1]octan-8-yl]-4-fluoro-1,3-benzothiazole-6-carboxylic acid;

2-[3-[(5-cyclopropyl-3-{spiro[2.3]hexan-5-yl}-1,2-oxazol-4-yl)methoxy]-8-azabicyclo[3.2.1]octan-8-yl]-4-fluoro-1,3-benzothiazole-6-carboxylic acid;

2-(1R,3r,5S)-3-[(5-cyclopropyl-3-{spiro[2.3]hexan-5-yl}-1,2-oxazol-4-yl)methoxy]-8-azabicyclo[3.2.1]octan-8-yl]-4-fluoro-1,3-benzothiazole-6-carboxylic acid;

2-[3-({5-cyclopropyl-3-[2,6,6-trimethylbicyclo[3.1.1]heptan-3-yl]-1,2-oxazol-4-yl}methoxy)-8-azabicyclo[3.2.1]octan-8-yl]-4-fluoro-1,3-benzothiazole-6-carboxylic acid;

2-(1R,3r,5S)-3-({5-cyclopropyl-3-(1R,2S,3S,5S)-2,6,6-trimethylbicyclo[3.1.1]heptan-3-yl]-1,2-oxazol-4-yl}methoxy)-8-azabicyclo[3.2.1]octan-8-yl]-4-fluoro-1,3-benzothiazole-6-carboxylic acid;

2-[3-[(5-cyclopropyl-3-{spiro[2.5]octan-4-yl}-1,2-oxazol-4-yl)methoxy]-8-azabicyclo[3.2.1]octan-8-yl]-4-fluoro-1,3-benzothiazole-6-carboxylic acid;

2-(1R,3r,5S)-3-[(5-cyclopropyl-3-{spiro[2.5]octan-4-yl}-1,2-oxazol-4-yl)methoxy]-8-azabicyclo[3.2.1]octan-8-yl]-4-fluoro-1,3-benzothiazole-6-carboxylic acid;

2-[3-({3-[bicyclo[4.1.0]heptan-3-yl]-5-cyclopropyl-1,2-oxazol-4-yl]methoxy)-8-azabicyclo[3.2.1]octan-8-yl]-4-fluoro-1,3-benzothiazole-6-carboxylic acid;

2-[(1R,3r,5S)-3-(1 3-[(1S,3S,6S)-bicyclo[4.1.0]heptan-3-yl]-5-cyclopropyl-1,2-oxazol-4-yl}methoxy)-8-azabicyclo[3.2.1]octan-8-yl]-4-fluoro-1,3-benzothiazole-6-carboxylic acid;

2-[3-{[5-cyclopropyl-3-(2-methylphenyl)-1,2-oxazol-4-yl]methoxy}-8-azabicyclo[3.2.1]octan-8-yl]-4-fluoro-1,3-benzothiazole-6-carboxylic acid;

2-(1R,3r,5S)-3-{[5-cyclopropyl-3-(2-methylphenyl)-1,2-oxazol-4-yl]methoxy}-8-azabicyclo[3.2.1]octan-8-yl]-4-fluoro-1,3-benzothiazole-6-carboxylic acid;

6-[3-{[5-cyclopropyl-3-(2-methylphenyl)-1,2-oxazol-4-yl]methoxy}-8-azabicyclo[3.2.1]octan-8-yl]pyridine-3-carboxylic acid;

6-(1R,3r,5S)-3-{[5-cyclopropyl-3-(2-methylphenyl)-1,2-oxazol-4-yl]methoxy}-8-azabicyclo[3.2.1]octan-8-yl]pyridine-3-carboxylic acid;

2-[3-{[5-cyclopropyl-3-(2-methylphenyl)-1,2-oxazol-4-yl]methoxy}-8-azabicyclo[3.2.1]octan-8-yl]-6-methylpyrimidine-4-carboxylic acid;

2-(1R,3r,5S)-3-{[5-cyclopropyl-3-(2-methylphenyl)-1,2-oxazol-4-yl]methoxy}-8-azabicyclo[3.2.1]octan-8-yl]-6-methylpyrimidine-4-carboxylic acid;

2-[3-{[5-cyclopropyl-3-(2-methylphenyl)-1,2-oxazol-4-yl]methoxy}-8-azabicyclo[3.2.1]octan-8-yl]-1,3-benzothiazole-6-carboxylic acid;

2-(1R,3r,5S)-3-{[5-cyclopropyl-3-(2-methylphenyl)-1,2-oxazol-4-yl]methoxy}-8-azabicyclo[3.2.1]octan-8-yl]-1,3-benzothiazole-6-carboxylic acid;

2-[3-{[5-cyclopropyl-3-(2-methylphenyl)-1,2-oxazol-4-yl]methoxy}-8-azabicyclo[3.2.1]octan-8-yl]-4-methoxy-1,3-benzothiazole-6-carboxylic acid;

2-(1R,3r,5S)-3-{[5-cyclopropyl-3-(2-methylphenyl)-1,2-oxazol-4-yl]methoxy}-8-azabicyclo[3.2.1]octan-8-yl]-4-methoxy-1,3-benzothiazole-6-carboxylic acid;

2-[3-{[5-cyclopropyl-3-(4-fluorophenyl)-1,2-oxazol-4-yl]methoxy}-8-azabicyclo[3.2.1]octan-8-yl]-1,3-benzothiazole-6-carboxylic acid;

2-(1R,3r,5S)-3-{[5-cyclopropyl-3-(4-fluorophenyl)-1,2-oxazol-4-yl]methoxy}-8-azabicyclo[3.2.1]octan-8-yl]-1,3-benzothiazole-6-carboxylic acid;

2-[3-{[5-cyclopropyl-3-(4-fluorophenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(4-fluorophenyl)-1,2-oxazol-4-yl]methoxy}-8-azabicyclo[3.2.1]octan-8-yl]-4-methoxy-1,3-benzothiazole-6-carboxylic acid;

2-[3-{[5-cyclopropyl-3-(3-fluorophenyl)-1,2-oxazol-4-yl]methoxy}-8-azabicyclo[3.2.1]octan-8-yl]-4-methoxy-1,3-benzothiazole-6-carboxylic acid;

2-(1R,3r,5S)-3-{[5-cyclopropyl-3-(3-fluorophenyl)-1,2-oxazol-4-yl]methoxy}-8-azabicyclo[3.2.1]octan-8-yl]-4-methoxy-1,3-benzothiazole-6-carboxylic acid;

6-[3-{[5-cyclopropyl-3-(3-fluorophenyl)-1,2-oxazol-4-yl]methoxy}-8-azabicyclo[3.2.1]octan-8-yl]pyridine-3-carboxylic acid;

6-(1R,3r,5S)-3-{[5-cyclopropyl-3-(3-fluorophenyl)-1,2-oxazol-4-yl]methoxy}-8-azabicyclo[3.2.1]octan-8-yl]pyridine-3-carboxylic acid;

2-[3-{[5-cyclopropyl-3-(3-fluorophenyl)-1,2-oxazol-4-yl]methoxy}-8-azabicyclo[3.2.1]octan-8-yl]-6-methylpyrimidine-4-carboxylic acid;

2-(1R,3r,5S)-3-{[5-cyclopropyl-3-(3-fluorophenyl)-1,2-oxazol-4-yl]methoxy}-8-azabicyclo[3.2.1]octan-8-yl]-6-methylpyrimidine-4-carboxylic acid;

2-[3-{[5-cyclopropyl-3-(2-fluoro-6-methylphenyl)-1,2-oxazol-4-yl]methoxy}-8-azabicyclo[3.2.1]octan-8-yl]-4-methoxy-1,3-benzothiazole-6-carboxylic acid;

2-(1R,3r,5S)-3-{[5-cyclopropyl-3-(2-fluoro-6-methylphenyl)-1,2-oxazol-4-yl]methoxy}-8-azabicyclo[3.2.1]octan-8-yl]-4-methoxy-1,3-benzothiazole-6-carboxylic acid;

6-[3-{[5-cyclopropyl-3-(2-fluoro-6-methylphenyl)-1,2-oxazol-4-yl]methoxy}-8-azabicyclo[3.2.1]octan-8-yl]pyridine-3-carboxylic acid;

6-(1R,3r,5S)-3-{[5-cyclopropyl-3-(2-fluoro-6-methylphenyl)-1,2-oxazol-4-yl]methoxy}-8-azabicyclo[3.2.1]octan-8-yl]pyridine-3-carboxylic acid;

2-[3-{[5-cyclopropyl-3-(2-fluoro-6-methylphenyl)-1,2-oxazol-4-yl]methoxy}-8-azabicyclo[3.2.1]octan-8-yl]-6-methylpyrimidine-4-carboxylic acid;

2-(1R,3r,5S)-3-{[5-cyclopropyl-3-(2-fluoro-6-methylphenyl)-1,2-oxazol-4-yl]methoxy}-8-azabicyclo[3.2.1]octan-8-yl]-6-methylpyrimidine-4-carboxylic acid;

2-[3-{[5-cyclopropyl-3-(2,6-dimethylphenyl)-1,2-oxazol-4-yl]methoxy}-8-azabicyclo[3.2.1]octan-8-yl]-4-methoxy-1,3-benzothiazole-6-carboxylic acid;

2-(1R,3r,5S)-3-{[5-cyclopropyl-3-(2,6-dimethylphenyl)-1,2-oxazol-4-yl]methoxy}-8-azabicyclo[3.2.1]octan-8-yl]-4-methoxy-1,3-benzothiazole-6-carboxylic acid;

6-[3-{[5-cyclopropyl-3-(2,6-dimethylphenyl)-1,2-oxazol-4-yl]methoxy}-8-azabicyclo[3.2.1]octan-8-yl]pyridine-3-carboxylic acid;

6-(1R,3r,5S)-3-{[5-cyclopropyl-3-(2,6-dimethylphenyl)-1,2-oxazol-4-yl]methoxy}-8-azabicyclo[3.2.1]octan-8-yl]pyridine-3-carboxylic acid;

2-[3-{[5-cyclopropyl-3-(2,6-dimethylphenyl)-1,2-oxazol-4-yl]methoxy}-8-azabicyclo[3.2.1]octan-8-yl]-6-methylpyrimidine-4-carboxylic acid;

2-(1R,3r,5S)-3-{[5-cyclopropyl-3-(2,6-dimethylphenyl)-1,2-oxazol-4-yl]methoxy}-8-azabicyclo[3.2.1]octan-8-yl]-6-methylpyrimidine-4-carboxylic acid;

2-[3-{[3-(2-chloro-6-fluorophenyl)-5-cyclopropyl-1,2-oxazol-4-yl]methoxy}-8-azabicyclo[3.2.1]octan-8-yl]-4-rnethoxy-1,3-benzothiazole-6-carboxylic acid;

2-(1R,3r,5S)-3-{[3-(2-chloro-6-fluorophenyl)-5-cyclopropyl-1,2-oxazol-4-yl]methoxy)-8-azabicyclo[3.2.1]octan-8-yl]-4-rnethoxy-1,3-benzothiazole-6-carboxylic acid;

6-[3-{[3-(2-chloro-6-fluorophenyl)-5-cyclopropyl-1,2-oxazol-4-yl]methoxy}-8-azabicyclo[3.2.1]octan-8-yl]pyridine-3-carboxylic acid;

6-(1R,3r,5S)-3-{[3-(2-chloro-6-fluorophenyl)-5-cyclopropyl-1,2-oxazol-4-yl]methoxy}-8-azabicyclo[3.2.1]octan-8-yl]pyridine-3-carboxylic acid;

2-[3-{[3-(2-chloro-6-fluorophenyl)-5-cyclopropyl-1,2-oxazol-4-yl]methoxy}-8-azabicyclo[3.2.1]octan-8-yl]-6-methylpyrimidine-4-carboxylic acid;

2-(1R,3r,5S)-3-{[3-(2-chloro-6-fluorophenyl)-5-cyclopropyl-1,2-oxazol-4-yl]methoxy}-8-azabicyclo[3.2.1]octan-8-yl]-6-methylpyrimidine-4-carboxylic acid;

2-[3-{[3-(2-chlorophenyl)-5-cyclopropyl-1,2-oxazol-4-yl]methoxy}-8-azabicyclo[3.2.1]octan-8-yl]-4-rnethoxy-1,3-benzothiazole-6-carboxylic acid;

2-(1R,3r,5S)-3-{[3-(2-chlorophenyl)-5-cyclopropyl-1,2-oxazol-4-yl]methoxy}-8-azabicyclo[3.2.1]octan-8-yl]-4-rnethoxy-1,3-benzothiazole-6-carboxylic acid;

6-[3-{[3-(2-chlorophenyl)-5-cyclopropyl-1,2-oxazol-4-yl]methoxy}-8-azabicyclo[3.2.1]octan-8-yl]pyridine-3-carboxylic acid;

6-(1R,3r,5S)-3-{[3-(2-chlorophenyl)-5-cyclopropyl-1,2-oxazol-4-yl]methoxy}-8-azabicyclo[3.2.1]octan-8-yl]pyridine-3-carboxylic acid;

2-[3-{[3-(2-chlorophenyl)-5-cyclopropyl-1,2-oxazol-4-yl]methoxy}-8-azabicyclo[3.2.1]octan-8-yl]-6-methylpyrimidine-4-carboxylic acid;

2-(1R,3r,5S)-3-{[3-(2-chlorophenyl)-5-cyclopropyl-1,2-oxazol-4-yl]methoxy}-8-azabicyclo[3.2.1]octan-8-yl]-6-methylpyrimidine-4-carboxylic acid;

2-[3-{[5-cyclopropyl-3-(2-cyclopropylphenyl)-1,2-oxazol-4-yl]methoxy}-8-azabicyclo[3.2.1]octan-8-yl]-4-fluoro-1,3-benzothiazole-6-carboxylic acid;

2-(1R,3r,5S)-3-{[5-cyclopropyl-3-(2-cyclopropylphenyl)-1,2-oxazol-4-yl]methoxy}-8-azabicyclo[3.2.1]octan-8-yl]-4-fluoro-1,3-benzothiazole-6-carboxylic acid;

6-[3-{[5-cyclopropyl-3-(2-cyclopropylphenyl)-1,2-oxazol-4-yl]methoxy}-8-azabicyclo[3.2.1]octan-8-yl]pyridine-3-carboxylic acid;

6-(1R,3r,5S)-3-{[5-cyclopropyl-3-(2-cyclopropylphenyl)-1,2-oxazol-4-yl]methoxy}-8-azabicyclo[3.2.1]octan-8-yl]pyridine-3-carboxylic acid;

6-[3-{[5-cyclopropyl-3-(2,6-difluorophenyl)-1,2-oxazol-4-yl]methoxy}-8-azabicyclo[3.2.1]octan-8-yl]-5-methylpyridine-3-carboxylic acid;

6-[(1R,3r,5S)-3-{[5-cyclopropyl-3-(2,6-difluorophenyl)-1,2-oxazol-4-yl]methoxy}-8-azabicyclo[3.2.1]octan-8-yl]-5-methylpyridine-3-carboxylic acid;

6-3-{[5-cyclopropyl-3-(2,6-difluorophenyl)-1,2-oxazol-4-yl]methoxy}-8-azabicyclo[3.2.1]octan-8-yl]-4-methylpyridine-3-carboxylic acid;

6-[(1R,3r,5S)-3-{[5-cyclopropyl-3-(2,6-difluorophenyl)-1,2-oxazol-4-yl]methoxy}-8-azabicyclo[3.2.1]octan-8-yl]-4-methylpyridine-3-carboxylic acid;

6-[3-({5-cyclopropyl-3-[2-(difluoromethoxy)phenyl]-1,2-oxazol-4-yl}methoxy)-8-azabicyclo[3.2.1]octan-8-yl]pyridine-2-carboxylic acid;

6-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyridine-2-carboxylic acid;

methyl 2-[3-({5-cyclopropyl-3-[2-(trifluoromethoxy)phenyl]-1,2-oxazol-4-yl}methoxy)-8-azabicyclo[3.2.1]octan-8-yl]-4-methyl-1,3-benzothiazole-6-carboxylate;

methyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-methyl-1,3-benzothiazole-6-carboxylate;

2-[3-({5-cyclopropyl-3-[2-(trifluoromethoxy)phenyl]-1,2-oxazol-4-yl}methoxy)-8-azabicyclo[3.2.1]octan-8-yl]-4-methyl-1,3-benzothiazole-6-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-methyl-1,3-benzothiazole-6-carboxylic acid;

methyl 2-[3-({5-cyclopropyl-3-[2-(trifluoromethyl)phenyl]-1,2-oxazol-4-yl}methoxy)-8-azabicyclo[3.2.1]octan-8-yl]-4-methyl-1,3-benzothiazole-6-carboxylate;

methyl 2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-methyl-1,3-benzothiazole-6-carboxylate;

2-[3-({5-cyclopropyl-3-[2-(trifluoromethyl)phenyl]-1,2-oxazol-4-yl}methoxy)-8-azabicyclo[3.2.1]octan-8-yl]-4-methyl-1,3-benzothiazole-6-carboxylic acid;

2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-methyl-1,3-benzothiazole-6-carboxylic acid;

methyl 2-[3-{[5-cyclopropyl-3-(2,6-difluorophenyl)-1,2-oxazol-4-yl]methoxy}-8-azabicyclo[3.2.1]octan-8-yl]-4-methyl-1,3-benzothiazole-6-carboxylate;

methyl 2-[(1R,3r,5S)-3-{[5-cyclopropyl-3-(2,6-difluorophenyl)-1,2-oxazol-4-yl]methoxy}-8-azabicyclo[3.2.1]octan-8-yl]-4-methyl-1,3-benzothiazole-6-carboxylate;

2-[3-{[5-cyclopropyl-3-(2,6-difluorophenyl)-1,2-oxazol-4-yl]methoxy}-8-azabicyclo[3.2.1]octan-8-yl]-4-methyl-1,3-benzothiazole-6-carboxylic acid;

2-[(1R,3r,5S)-3-{[5-cyclopropyl-3-(2,6-difluorophenyl)-1,2-oxazol-4-yl]methoxy}-8-azabicyclo[3.2.1]octan-8-yl]-4-methyl-1,3-benzothiazole-6-carboxylic acid;

2-[3-{[5-cyclopropyl-3-(2-fluorophenyl)-1,2-oxazol-4-yl]methoxy}-8-azabicyclo[3.2.1]octan-8-yl]-4-methyl-1,3-benzothiazole-6-carboxylic acid;

2-(1R,3r,5S)-3-{[5-cyclopropyl-3-(2-fluorophenyl)-1,2-oxazol-4-yl]methoxy}-8-azabicyclo[3.2.1]octan-8-yl]-4-methyl-1,3-benzothiazole-6-carboxylic acid;

2-[3-{[5-cyclopropyl-3-(4-fluorophenyl)-1,2-oxazol-4-yl]methoxy}-8-azabicyclo[3.2.1]octan-8-yl]-4-methyl-1,3-benzothiazole-6-carboxylic acid;

2-(1R,3r,5S)-3-{[5-cyclopropyl-3-(4-fluorophenyl)-1,2-oxazol-4-yl]methoxy}-8-azabicyclo[3.2.1]octan-8-yl]-4-methyl-1,3-benzothiazole-6-carboxylic acid;

2-[3-{[5-cyclopropyl-3-(2-methylphenyl)-1,2-oxazol-4-yl]methoxy}-8-azabicyclo[3.2.1]octan-8-yl]-4-methyl-1,3-benzothiazole-6-carboxylic acid;

2-(1R,3r,5S)-3-{[5-cyclopropyl-3-(2-methylphenyl)-1,2-oxazol-4-yl]methoxy}-8-azabicyclo[3.2.1]octan-8-yl]-4-methyl-1,3-benzothiazole-6-carboxylic acid;

methyl 2-[3-{[5-cyclopropyl-3-(2-methylphenyl)-1,2-oxazol-4-yl]methoxy}-8-azabicyclo[3.2.1]octan-8-yl]-4-methyl-1,3-benzothiazole-6-carboxylate;

methyl 2-[(1R,3r,5S)-3-{[5-cyclopropyl-3-(2-methylphenyl)-1,2-oxazol-4-yl]methoxy}-8-azabicyclo[3.2.1]octan-8-yl]-4-methyl-1,3-benzothiazole-6-carboxylate;

2-[3-{[5-cyclopropyl-3-(2,4-difluorophenyl)-1,2-oxazol-4-yl]methoxy}-8-azabicyclo[3.2.1]octan-8-yl]-4-methyl-1,3-benzothiazole-6-carboxylic acid;

2-(1R,3r,5S)-3-{[5-cyclopropyl-3-(2,4-difluorophenyl)-1,2-oxazol-4-yl]methoxy}-8-azabicyclo[3.2.1]octan-8-yl]-4-methyl-1,3-benzothiazole-6-carboxylic acid;

methyl 4-bromo-2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylate;

methyl 4-bromo-2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylate;

4-bromo-2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylic acid;

4-bromo-2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylic acid;

6-cyclopropyl-2-[3-({5-cyclopropyl-3-[2-(difluoromethoxy)phenyl]-1,2-oxazol-4-yl}methoxy)-8-azabicyclo[3.2.1]octan-8-yl]pryimidine-4-carboxylic acid;

6-cyclopropyl-2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pryimidine-4-carboxylic acid;

6-cyclopropyl-2-[3-({5-cyclopropyl-3-[2-(trifluoromethoxy)phenyl]-1,2-oxazol-4-yl}methoxy)-8-azabicyclo[3.2.1]octan-8-yl]pryimidine-4-carboxylic acid;

6-cyclopropyl-2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pryimidine-4-carboxylic acid;

6-cyclopropyl-2-[3-{5-cyclopropyl-3-[2-(trifluoromethyl)phenyl]-1,2-oxazol-4-yl}methoxy)-8-azabicyclo[3.2.1]octan-8-yl]pryimidine-4-carboxylic acid;

6-cyclopropyl-2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pryimidine-4-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-2-methylpyridine-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-2-methylpyridine-3-carboxylic acid;

6-[3-({5-cyclopropyl-3-[2-(trifluoromethyl)phenyl]-1,2-oxazol-4-yl}methoxy)-8-azabicyclo[3.2.1]octan-8-yl]-2-methylpyridine-3-carboxylic acid;

6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-2-methylpyridine-3-carboxylic acid;

6-[3-{[5-cyclopropyl-3-(2-methylphenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(2-methylphenyl)-1,2-oxazol-4-yl]methoxy}-8-azabicyclo[3.2.1]octan-8-yl]-2-methylpyridine-3-carboxylic acid;

6-[3-{[5-cyclopropyl-3-(2,6-difluorophenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(2,6-difluorophenyl)-1,2-oxazol-4-yl]methoxy}-8-azabicyclo[3.2.1]octan-8-yl]-2-methylpyridine-3-carboxylic acid;

6-[3-{[5-cyclopropyl-3-(2-fluorophenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(2-fluorophenyl)-1,2-oxazol-4-yl]methoxy}-8-azabicyclo[3.2.1]octan-8-yl]-2-methylpyridine-3-carboxylic acid;

6-[3-{[5-cyclopropyl-3-(2,6-dimethylphenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(2,6-dimethylphenyl)-1,2-oxazol-4-yl]methoxy}-8-azabicyclo[3.2.1]octan-8-yl]-2-methylpyridine-3-carboxylic acid;

6-[3-{[5-cyclopropyl-3-(3-fluorophenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(3-fluorophenyl)-1,2-oxazol-4-yl]methoxy}-8-azabicyclo[3.2.1]octan-8-yl]-2-methylpyridine-3-carboxylic acid;

6-[3-{[5-cyclopropyl-3-(2-fluoro-6-methylphenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(2-fluoro-6-methylphenyl)-1,2-oxazol-4-yl]methoxy}-8-azabicyclo[3.2.1]octan-8-yl]-2-methylpyridine-3-carboxylic acid;

6-[3-{[3-(2-chloro-6-fluorophenyl)-5-cyclopropyl-1,2-oxazol-4-yl]methoxy}-8-azabicyclo[3.2.1]octan-8-yl]-2-methylpyridine-3-carboxylic acid;

6-[(1R,3r,5S)-3-{[3-(2-chloro-6-fluorophenyl)-5-cyclopropyl-1,2-oxazol-4-yl]methoxy}-8-azabicyclo[3.2.1]octan-8-yl]-2-methylpyridine-3-carboxylic acid;

2-[3-({5-cyclopropyl-3-[2-(trifluoromethoxy)phenyl]-1,2-oxazol-4-yl}methoxy)-8-azabicyclo[3.2.1]octan-8-yl]quinoline-6-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]quinoline-6-carboxylic acid;

2-[3-({5-cyclopropyl-3-[2-(trifluoromethyl)phenyl]-1,2-oxazol-4-yl}methoxy)-8-azabicyclo[3.2.1]octan-8-yl]quinoline-6-carboxylic acid;

2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]quinoline-6-carboxylic acid;

2-[3-({5-cyclopropyl-3-[2-(trifluoromethoxy)phenyl]-1,2-oxazol-4-yl}methoxy)-8-azabicyclo[3.2.1]octan-8-yl]quinoline-5-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]quinoline-5-carboxylic acid;

4-[3-({5-cyclopropyl-3-[2-(trifluoromethoxy)phenyl]-1,2-oxazol-4-yl}methoxy)-8-azabicyclo[3.2.1]octan-8-yl]quinazoline-7-carboxylic acid;

4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]quinazoline-7-carboxylic acid;

6-[3-({5-cyclopropyl-3-[2-(trifluoromethyl)phenyl]-1,2-oxazol-4-yl}methoxy)-8-azabicyclo[3.2.1]octan-8-yl]-4-methylpyridine-2-carboxylic acid;

6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-methylpyridine-2-carboxylic acid;

4-[3-({5-cyclopropyl-3-[2-(trifluoromethoxy)phenyl]-1,2-oxazol-4-yl}methoxy)-8-azabicyclo[3.2.1]octan-8-yl]-1-methyl-1H-pyrrolo[3,2-c]pyridine-7-carboxylic acid;

4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-methyl-1H-pyrrolo[3,2-c]pyridine-7-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]pyrazolo[1,5-a]pyrimidine-3-carboxylic acid;

5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazolo[1,5-a]pyrimidine-3-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]imidazo[1,2-b]pyridazine-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]imidazo[1,2-b]pyridazine-3-carboxylic acid;

2-[3-{[5-cyclopropyl-3-(2,4-difluorophenyl)-1,2-oxazol-4-yl]methoxy}-8-azabicyclo[3.2.1]octan-8-yl]-1,3-benzothiazole-6-carboxylic acid;

2-[(1R,3r,5S)-3-{[5-cyclopropyl-3-(2,4-difluorophenyl)-1,2-oxazol-4-yl]methoxy}-8-azabicyclo[3.2.1]octan-8-yl]-1,3-benzothiazole-6-carboxylic acid;

2-[3-{[5-cyclopropyl-3-(2,4-difluorophenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(2,4-difluorophenyl)-1,2-oxazol-4-yl]methoxy}-8-azabicyclo[3.2.1]octan-8-yl]-4-methoxy-1,3-benzothiazole-6-carboxylic acid;

6-[3-{[5-cyclopropyl-3-(2,4-difluorophenyl)-1,2-oxazol-4-yl]methoxy}-8-azabicyclo[3.2.1]octan-8-yl]pyridine-3-carboxylic acid;

6-[(1R,3r,5S)-3-{[5-cyclopropyl-3-(2,4-difluorophenyl)-1,2-oxazol-4-yl]methoxy}-8-azabicyclo[3.2.1]octan-8-yl]pyridine-3-carboxylic acid;

2-[3-{[5-cyclopropyl-3-(2,3-difluorophenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(2,3-difluorophenyl)-1,2-oxazol-4-yl]methoxy}-8-azabicyclo[3.2.1]octan-8-yl]-4-methoxy-1,3-benzothiazole-6-carboxylic acid;

6-[3-{[5-cyclopropyl-3-(2,3-difluorophenyl)-1,2-oxazol-4-yl]methoxy}-8-azabicyclo[3.2.1]octan-8-yl]pyridine-3-carboxylic acid;

6-[(1R,3r,5S)-3-{[5-cyclopropyl-3-(2,3-difluorophenyl)-1,2-oxazol-4-yl]methoxy}-8-azabicyclo[3.2.1]octan-8-yl]pyridine-3-carboxylic acid;

2-[3-{[5-cyclopropyl-3-(2,3-difluorophenyl)-1,2-oxazol-4-yl]methoxy}-8-azabicyclo[3.2.1]octan-8-yl]-6-methylpyrimidine-4-carboxylic acid;

2-[(1R,3r,5S)-3-{[5-cyclopropyl-3-(2,3-difluorophenyl)-1,2-oxazol-4-yl]methoxy}-8-azabicyclo[3.2.1]octan-8-yl]-6-methylpyrimidine-4-carboxylic acid;

2-[3-{[5-cyclopropyl-3-(2-fluorophenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(2-fluorophenyl)-1,2-oxazol-4-yl]methoxy}-8-azabicyclo[3.2.1]octan-8-yl]-4-methoxy-1,3-benzothiazole-6-carboxylic acid;

2-[3-{[5-cyclopropyl-3-(2-fluorophenyl)-1,2-oxazol-4-yl]methoxy}-8-azabicyclo[3.2.1]octan-8-yl]-6-methylpyrimidine-4-carboxylic acid;

2-[(1R,3r,5S)-3-{[5-cyclopropyl-3-(2-fluorophenyl)-1,2-oxazol-4-yl]methoxy}-8-azabicyclo[3.2.1]octan-8-yl]-6-methylpyrimidine-4-carboxylic acid;
6-[3-{[5-cyclopropyl-3-(2-fluorophenyl)-1,2-oxazol-4-yl]methoxy}-8-azabicyclo[3.2.1]octan-8-yl]pyridine-3-carboxylic acid;
6-(1R,3r,5S)-3-{[5-cyclopropyl-3-(2-fluorophenyl)-1,2-oxazol-4-yl]methoxy}-8-azabicyclo[3.2.1]octan-8-yl]pyridine-3-carboxylic acid;
2-[3-{[5-cyclopropyl-3-(2,6-dichlorophenyl)-1,2-oxazol-4-yl]methoxy}-8-azabicyclo[3.2.1]octan-8-yl]-1,3-benzothiazole-6-carboxylic acid;
2-[(1R,3r,5S)-3-{[5-cyclopropyl-3-(2,6-dichlorophenyl)-1,2-oxazol-4-yl]methoxy}-8-azabicyclo[3.2.1]octan-8-yl]-1,3-benzothiazole-6-carboxylic acid;
2-[3-{[5-cyclopropyl-3-(2,6-dichlorophenyl)-1,2-oxazol-4-yl]methoxy}-8-azabicyclo[3.2.1]octan-8-yl]-4-methoxy-1,3-benzothiazole-6-carboxylic acid;
2-[(1R,3r,5S)-3-{[5-cyclopropyl-3-(2,6-dichlorophenyl)-1,2-oxazol-4-yl]methoxy}-8-azabicyclo[3.2.1]octan-8-yl]-4-methoxy-1,3-benzothiazole-6-carboxylic acid;
6-[3-{[5-cyclopropyl-3-(2,6-dichlorophenyl)-1,2-oxazol-4-yl]methoxy}-8-azabicyclo[3.2.1]octan-8-yl]pyridine-3-carboxylic acid;
6-[(1R,3r,5S)-3-{[5-cyclopropyl-3-(2,6-dichlorophenyl)-1,2-oxazol-4-yl]methoxy}-8-azabicyclo[3.2.1]octan-8-yl]pyridine-3-carboxylic acid;
6-[3-{5-cyclopropyl-3-[2-(trifluoromethyl)pyridin-3-yl]-1,2-oxazol-4-yl}methoxy)-8-azabicyclo[3.2.1]octan-8-yl]pyridine-3-carboxylic acid;
6-[(1R,3r,5S)-3-({5-cyclopropyl-3-[2-(trifluoromethyl)pyridin-3-yl]-1,2-oxazol-4-yl}methoxy)-8-azabicyclo[3.2.1]octan-8-yl]pyridine-3-carboxylic acid;
2-[3-({5-cyclopropyl-3-[2-(trifluoromethoxy)phenyl]-1,2-oxazol-4-yl}methoxy)-8-azabicyclo[3.2.1]octan-8-yl]-1,3-thiazole-4-carboxylic acid;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-thiazole-4-carboxylic acid;
2-[3-({5-cyclopropyl-3-[2-(trifluoromethoxy)phenyl]-1,2-oxazol-4-yl}methoxy)-8-azabicyclo[3.2.1]octan-8-yl]-1,3-thiazole-5-carboxylic acid;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-thiazole-5-carboxylic acid;
2-[3-({5-cyclopropyl-3-[2-(trifluoromethyl)phenyl]-1,2-oxazol-4-yl}methoxy)-8-azabicyclo[3.2.1]octan-8-yl]-1,3-thiazole-5-carboxylic acid;
2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-1,3-thiazole-5-carboxylic acid;
6-[3-({5-cyclopropyl-3-[2-(trifluoromethoxy)phenyl]-1,2-oxazol-4-yl}methoxy)-8-azabicyclo[3.2.1]octan-8-yl]imidazo[1,2-b]pyridazine-2-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]imidazo[1,2-b]pyridazine-2-carboxylic acid;
6-[3-({5-cyclopropyl-3-[2-(trifluoromethyl)phenyl]-1,2-oxazol-4-yl}methoxy)-8-azabicyclo[3.2.1]octan-8-yl]imidazo[1,2-b]pyridazine-2-carboxylic acid;
6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]imidazo[1,2-b]pyridazine-2-carboxylic acid;
5-[3-({5-cyclopropyl-3-[2-(trifluoromethyl)phenyl]-1,2-oxazol-4-yl}methoxy)-8-azabicyclo[3.2.1]octan-8-yl]pyrazolo[1,5-a]pyrimidine-2-carboxylic acid;
5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazolo[1,5-a]pyrimidine-2-carboxylic acid;
5-[3-({5-cyclopropyl-3-[2-(trifluoromethyl)phenyl]-1,2-oxazol-4-yl}methoxy)-8-azabicyclo[3.2.1]octan-8-yl]pyrazolo[1,5-a]pyrimidine-2-carboxylic acid;
5-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyrazolo[1,5-a]pyrimidine-2-carboxylic acid;
6-[3-{[5-cyclopropyl-3-(2,6-difluorophenyl)-1,2-oxazol-4-yl]methoxy}-8-azabicyclo[3.2.1]octan-8-yl]imidazo[[1,2-b]pyridazine-2-carboxylic acid;
6-[(1R,3r,5S)-3-{[5-cyclopropyl-3-(2,6-difluorophenyl)-1,2-oxazol-4-yl]methoxy}-8-azabicyclo[3.2.1]octan-8-yl]imidazo[[1,2-b]pyridazine-2-carboxylic acid;
6-[3-{[5-cyclopropyl-3-(2-fluoro-6-methylphenyl)-1,2-oxazol-4-yl]methoxy}-8-azabicyclo[3.2.1]octan-8-yl]imidazo[[1,2-b]pyridazine-2-carboxylic acid;
6-[(1R,3r,5S)-3-{[5-cyclopropyl-3-(2-fluoro-6-methylphenyl)-1,2-oxazol-4-yl]methoxy}-8-azabicyclo[3.2.1]octan-8-yl]imidazo[1,2-b]pyridazine-2-carboxylic acid;
7-[3-({5-cyclopropyl-3-[2-(trifluoromethoxy)phenyl]-1,2-oxazol-4-yl}methoxy)-8-azabicyclo[3.2.1]octan-8-yl]imidazo[[1,2-a]pyridine-3-carboxylic acid;
7-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]imidazo[1,2-a]pyridine-3-carboxylic acid;
5-[3-({5-cyclopropyl-3-[2-(trifluoromethoxy)phenyl]-1,2-oxazol-4-yl}methoxy)-8-azabicyclo[3.2.1]octan-8-yl]pyrazolo[1,5-a]pyridine-3-carboxylic acid;
5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazolo[1,5-a]pyridine-3-carboxylic acid;
6-((2-(3-((5-cyclopropyl-3-(2-(trifluoromethyl)phenyl)isoxazol-4-yl)methoxy)-8-azabicyclo[3.2.1]octan-8-yl)-4-fluorobenzo[d]thiazole-6-carbonyl)oxy)-3,4,5-trihydroxytetrahydro-2H-pyran-2-carboxylic acid;
(2S,3S,4S,5R,6S)-6-((2-((1R,3S,5S)-3-((5-cyclopropyl-3-(2-(trifluoromethyl)phenyl)isoxazol-4-yl)methoxy)-8-azabicyclo[3.2.1]octan-8-yl)-4-fluorobenzo[d]thiazole-6-carbonyl)oxy)-3,4,5-trihydroxytetrahydro-2H-pyran-2-carboxylic acid;
6-((2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carbonyl)oxy)-3,4,5-trihydroxytetrahydro-2H-pyran-2-carboxylic acid;
(2S,3S,4S,5R,6S)-6-((2-((1R,3S,5S)-3-(5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carbonyl)oxy)-3,4,5-trihydroxytetrahydro-2H-pyran-2-carboxylic acid;
6-((6-(3-((5-cyclopropyl-3-(2-(trifluoromethoxy)phenyl)isoxazol-4-yl)methoxy)-8-azabicyclo[3.2.1]octan-8-yl)nicotinoyl)oxy)-3,4,5-trihydroxytetrahydro-2H-pyran-2-carboxylic acid; and
(2S,3S,4S,5R,6S)-6-((6-((1R,3S,5S)-3-((5-cyclopropyl-3-(2-(trifluoromethoxy)phenyl)isoxazol-4-yl)methoxy)-8-azabicyclo[3.2.1]octan-8-yl)nicotinoyl)oxy)-3,4,5-trihydroxytetrahydro-2H-pyran-2-carboxylic acid; or
a stereoisomer, enantiomer, a pharmaceutically acceptable salt or an amino acid conjugate thereof.

In one embodiment, the invention provides a glycine conjugate of a compound of the invention. In another embodiment, the invention provides a taurine conjugate of a compound of the invention. In yet another embodiment, the invention provides an acyl glucuronide conjugate of a compound of the invention.

The present invention also provides a compound having Formula (III)

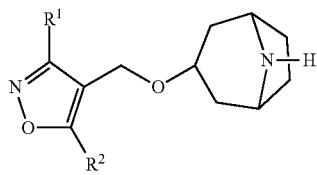

wherein $R^1$ and $R^2$ are as defined in Formula (I); or a pharmaceutically acceptable salt thereof. In one embodiment, $R^2$ in Formula (III) is cyclopropyl.

Furthermore, the present invention provides a process for preparing a compound of Formula (I), comprising reacting a compound of Formula (III) with a compound of Y—Z—$R^3$;
 wherein Y is a leaving group (such as chloro or bromo); and $R^1$, $R^2$, $R^3$ and Z are as defined in Formula (I);
 and optionally, converting a compound of Formula (I), wherein the substituents have the meaning as defined in Formula (I), into another compound of Formula (I) as defined in Formula (I); and
 recovering the resulting compound of Formula (I) in free form or as a salt; and optionally converting the compound of Formula (I) obtained in free form into a desired salt, or an obtained salt into the free form.

Definitions

For purposes of interpreting this specification, the following definitions will apply and whenever appropriate, terms used in the singular will also include the plural and vice versa.

As used herein, "$C_{1-6}$alkyl" denotes a an alkyl radical having from 1 up to 6, particularly up to 4 carbon atoms, the radicals being either linear or branched with single or multiple branching; for example, butyl, such as n-butyl, sec-butyl, isobutyl, tert-butyl; propyl, such as n-propyl or isopropyl; ethyl or methyl; more particularly, methyl, propyl or tert-butyl. "$C_{1-3}$ alkyl" refers to an alkyl radical as defined herein, containing one to three carbon atoms.

As used herein, the term "alkylene" refers to divalent alkyl group as defined herein above having a specified number of carbon atoms. Representative examples of alkylene include, but are not limited to, methylene, ethylene, n-propylene, iso-propylene, n-butylene, sec-butylene, iso-butylene, tert-butylene, and the like.

As used herein, "$C_{3-8}$ cycloalkyl" refers to saturated or unsaturated monocyclic or bicyclic hydrocarbon groups of 3-8 carbon atoms (including spirocyclic rings). Furthermore, the term "$C_{3-8}$ cycloalkyl" as used herein may encompass monovalent and divalent cycloalkyls, which will be apparent to those skilled in the art. Exemplary monocyclic hydrocarbon groups include, but are not limited to, cyclopropyl, cyclobutyl, cyclopentyl, cyclopentenyl, cyclohexyl, cyclohexenyl and the like, and monovalent or divalent forms thereof. Exemplary bicyclic hydrocarbon groups include but are not limited to bicyclo[2.1.1]hexyl, bicyclo[2.2.1]heptyl, 6,6-dimethylbicyclo[3.1.1]heptyl, 2,6,6-trimethylbicyclo[3.1.1]heptyl, bicyclo[2.2.2]octyl, bicyclo[3.1.0]hexanyl, bicyclo[3.1.0]hexan-6-yl, spiro[2.3]hexanyl, spiro[2.3]hexan-5-yl, spiro[2.5]octanyl, bicyclo[3.1.1]heptanyl, bicyclo[3.1.1]heptan-3-yl, bicyclo[4.1.0]heptanyl, bicyclo[4.1.0]heptan-3-yl and the like, and monocyclic or divalent forms thereof. Exemplary spirocyclic rings include but are not limited to spiro[2.5]octan-6-yl and the like, and monocyclic or divalent forms thereof.

As used herein, "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together; and may encompass monovalent and divalent aryls, which will be apparent to those skilled in the art. Non-limiting examples include phenyl, phenylene, naphthyl, naphthylene, tetrahydronaphthyl or tetrahydronaphthylene.

As used herein, "heteroaryl" refers to a 5-14 membered monocyclic- or bicyclic- or tricyclic-aromatic ring system having 1 to 8 heteroatoms. Typically, the heteroaryl is a 5-10 membered ring system (e.g., 5-7 membered monocycle or an 8-10 membered bicycle) or a 5-7 membered ring system. Furthermore, the term "heteroaryl" as used herein may encompass monovalent or divalent heteroaryls, which will be apparent to those skilled in the art. Typical monocyclic heteroaryl groups include 2-o(3-thienyl, 2-o(3-furyl, 2- o(3-pyrrolyl, 2-, 4-, o(5-imidazolyl, 3-, 4-, o(5-pyrazolyl, 2-, 4-, o(5-thiazolyl, 3-, 4-, o(5-isothiazolyl, 2-, 4-,o(5-oxazolyl, 3-, 4-, o(5-isoxazolyl, 3-o(5-1,2,4-triazolyl, 4-o(5-1,2,3-triazolyl, tetrazolyl, 2-, 3-, o(4-pyridyl, 3-o(4-pyridazinyl, 3-, 4-, o(5-pyrazinyl, 2-pyrazinyl, 2-, 4-, o(5-pyrimidinyl, and monovalent or divalent forms thereof. Typical bicyclic heteroaryl groups include benzofuranyl, benzo[d]isothiazolyl, benzo[d]isoxazolyl, benzothiazolyl, benzo[b]thiophenyl, imidazo[1,2-a]pyridinyl, imidazo[1,2-b]pyridazinyl, 1H-indolyl, 1H-indazolyl, pyrazolo[1,5-a]pyridinyl, pyrrolo[1,2-b]pyridazinyl, 1H-pyrrolo[3,2-c]pyridinyl, pyrazolo[1,5-a]pyrimidinyl, quinazolinyl and the like, and monovalent or divalent forms thereof.

As used herein, "$C_{1-6}$ alkoxy" refers to $C_{1-6}$ alkyl-O—, and is particularly methoxy, ethoxy, isopropyloxy, or tert-butoxy.

As used herein, "hydroxy$C_{1-6}$ alkyl" refers to $C_{1-6}$ alkyl-OH, wherein $C_{1-6}$ alkyl is as defined above. The hydroxy group may be attached to the alkyl radical on any carbon within the alkyl radical, and is particularly hydroxymethyl, 2-hydroxyethyl o(2-hydroxy-2-propyl.

As used herein, "halogen" or "halo" refers to fluoro, chloro, bromo, and iodo; and more particularly, fluoro or chloro.

As used herein, "halo$C_{1-6}$ alkyl" refers to an alkyl radical, as defined above, that is substituted by one or more halo radicals, as defined above, and is particularly fluoro$Cl_{1-6}$ alkyl, more particularly trifluoromethyl.

As used herein, "halo$C_{1-6}$alkoxy" refers to an alkoxy radical, as defined above, that is substituted by one or more halo radicals, as defined above, and is particularly fluoro$C_{1-6}$ alkoxy, more particularly, trifluoromethoxy or difluoromethoxy.

As used herein, a "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

As used herein, the term "amino acid conjugate" refers to conjugates of the compound of Formula I, (I-A) to (I-Y), (I'), II, and (II-A)-(II-K) with any suitable amino acid. Preferably, such suitable amino acid conjugates of the compound of Formula I, (I-A) to (I-Y), (I'), II, and (II-A)-(II-K) will have the added advantage of enhanced integrity in bile or intestinal fluids. Suitable amino acids include but are not limited to glycine, taurine and acyl glucuronide. Thus, the present invention encompasses the glycine, taurine and acylglucuronide conjugates of the compound of Formula I, (I-A) to (I-Y), (I'), II, and (II-A)-(II-K).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term "therapeutically effective amount" refers to an amount of the compound of Formula I, (I-A) to (I-Y), (I'), II, and (II-A)-(II-K) which is sufficient to achieve the stated effect. Accordingly, a therapeutical effective amount of a compound of Formula I, (I-A) to (I-Y), (I'), II, and (II-A)-(II-K) used in for the treatment of a condition mediated by FXR will be an amount sufficient for the treatment of the condition mediated by FXR.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "dyslipidemia" refers to an abnormality in, or abnormal amounts of lipids and lipoproteins in the blood and the disease states resulting, caused by, exacerbated by, or adjunct to such abnormality (see, Dorland's Illustrated Medical Dictionary, 29th edition, W.B. Saunders Publishing Company, New York, N.Y.). Disease states encompassed within the definition of dyslipidemia as used herein include hyperlipidemia, hypertriglyceremia, low plasma HDL, high plasma LDL, high plasma VLDL, liver cholestasis, and hypercholesterolemia.

As used herein, the phrase "diseases related to dyslipidemia" as used herein refers to diseases including but not limited to atherosclerosis, thrombosis, coronary artery disease, stroke, and hypertension. Diseases related to dyslipidemia also include metabolic diseases such as obesity, diabetes, insulin resistance, and complications thereof.

As used herein, the term "cholestasis" refers to any condition in which the flow of bile from the liver is blocked, and may be intrahepatic (i.e., occurring inside the liver) or extrahepatic (i.e., occurring outside the liver).

As used herein, "liver fibrosis" includes liver fibrosis due to any cause, including but not limited to virally-induced liver fibrosis such as that due to hepatitis B and C; exposure to alcohol (alcoholic liver disease), pharmaceutical compounds, oxidative stress, cancer radiation therapy or industrial chemicals; and diseases such as primary biliary cirrhosis, fatty liver, obesity, non-alcoholic steatohepatitis, cystic fibrosis, hemochromatosis, and auto-immune hepatitis.

"FXR agonist" as used herein refers to an agent that directly binds to and upregulates the activity of FXR.

As used herein, the term "a," "an," "the" and similar terms used in the context of the present invention (especially in the context of the claims) are to be construed to cover both the singular and plural unless otherwise indicated herein or clearly contradicted by the context.

The chemical naming protocol and structure diagrams used herein employ and rely on the chemical naming features as utilized by the ChemDraw program (available from CambridgeSoft Corp., Cambridge, Mass.). In particular, compound structures and names were derived using Chemdraw Ultra (Version 10.0) and/or ChemAxon Name Generator (JChem Version 5.3.1.0).

MODES OF CARRYING OUT THE INVENTION

The present invention relates to compositions and methods for FXR. Various embodiments of the invention are described herein. It will be recognized that features specified in each embodiment may be combined with other specified features to provide further embodiments.

In one aspect, compounds of the invention are defined by Formula (I):

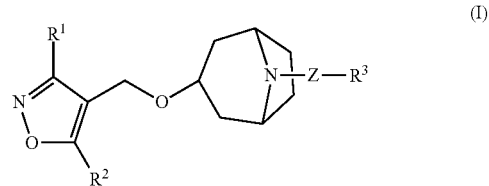

(I)

or a stereoisomer, enantiomer, a pharmaceutically acceptable salt or an amino acid conjugate thereof;

Z is phenylene, $C_{5-7}$ cycloalkylene o(5-10 membered monocyclic or bicyclic heteroaryl containing 1-2 heteroatoms selected from N, O and S; each of which is optionally substituted with 1-2 $R^6$ radicals selected from halogen, $C_{1-6}$ alkyl, halo$C_{1-6}$ alkyl, $C_{1-6}$ alkoxy, halo$C_{1-6}$ alkoxy, or cyclopropyl;

$R^1$ is phenyl, pyridyl, bicyclo[3.1.0]hexanyl, spiro[2.3]hexanyl, bicyclo[3.1.1]heptanyl, spiro[2.5]octanyl, bicyclo[4.1.0]heptanyl, bicyclo[3.1.0]hexan-6-yl, spiro[2.3]hexan-5-yl, bicyclo[3.1.1]heptan-3-yl, spiro[2.5]octan-4-yl, bicyclo[4.1.0]heptan-3-yl, cyclohexyl or cyclopentyl, each of which is optionally substituted with 1-3 $R^{1a}$; or $R^1$ is cyclopropyl optionally substituted with 1-2 $R^{1a}$ or phenyl;

$R^{1a}$ is halogen, $C_{1-6}$ alkyl, halo$C_{1-6}$ alkyl, $C_{1-6}$ alkoxy, halo$C_{1-6}$ alkoxy or cyclopropyl;

$R^2$ is $C_{1-3}$ alkyl, halo$C_{1-3}$ alkyl or cyclopropyl optionally substituted with $C_{1-3}$ alkyl or halo$C_{1-3}$ alkyl;

$R^3$ is —X—$CO_2R^4$, hydroxy$C_{1-6}$ alkyl, $CONR^4R^5$, $CONR(CR_2)_{1-4}CO_2R^4$, $CONR(CR_2)_{1-4}SO_3R^5$ or tetrazolyl; wherein X is a bond, $C_{1-2}$ alkylene or cyclopropyl; and R, $R^4$ and $R^5$ are independently hydrogen or $C_{1-6}$ alkyl.

In one embodiment, the compounds of the invention are selected from the group consisting of:

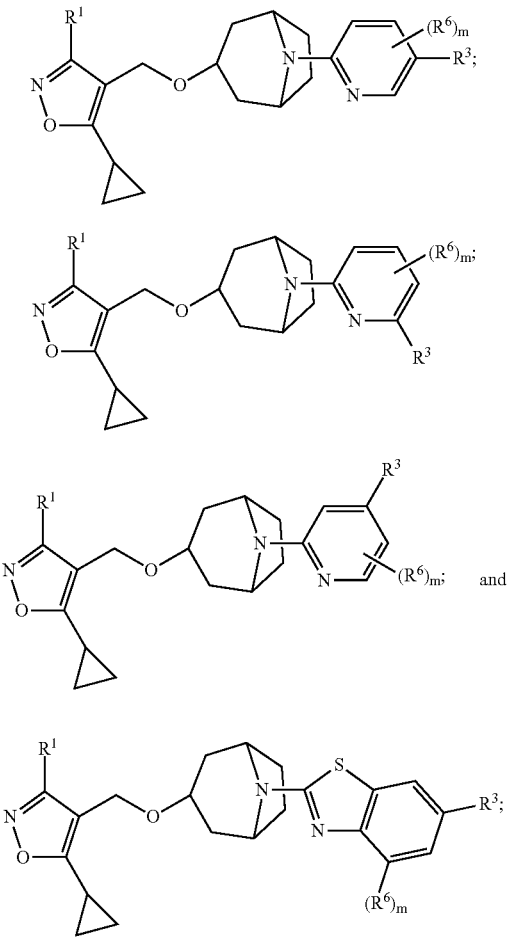

I-A

I-B

I-C

I-D or a stereoisomer, enantiomer, a pharmaceutically acceptable salt or an amino acid conjugate thereof; m is 0-1; and R, $R^3$ and $R^6$ are as defined in Formula (I).

In another embodiment, the compounds of the invention are selected from the group consisting of:

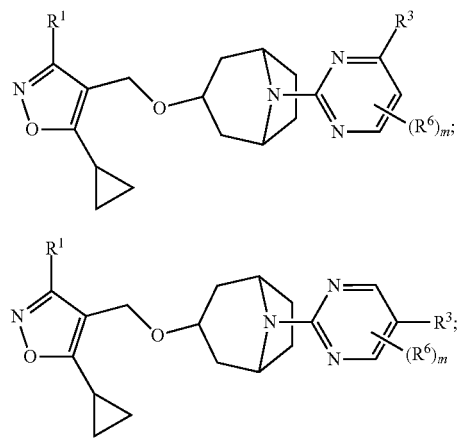

I-E

I-F

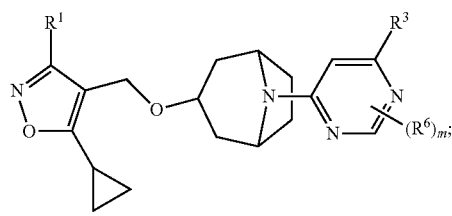

I-G

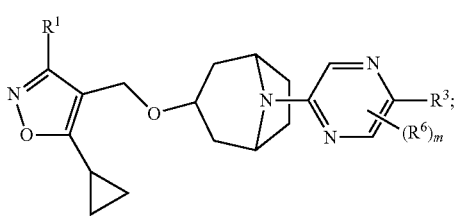

I-H

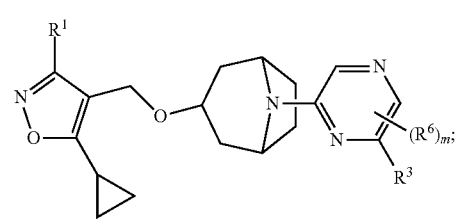

I-I

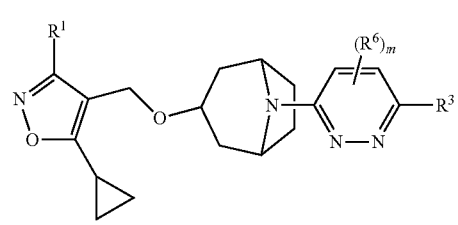

I-J

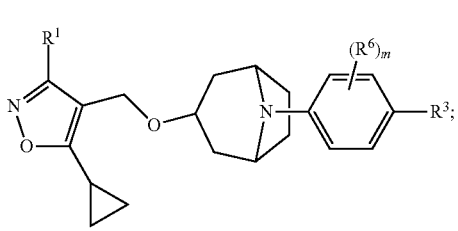

I-K

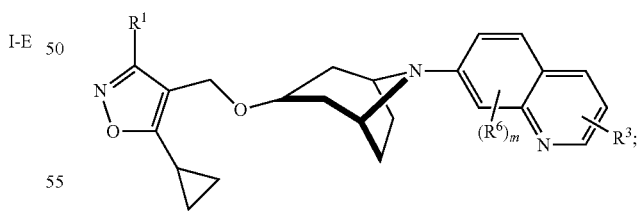

I-L

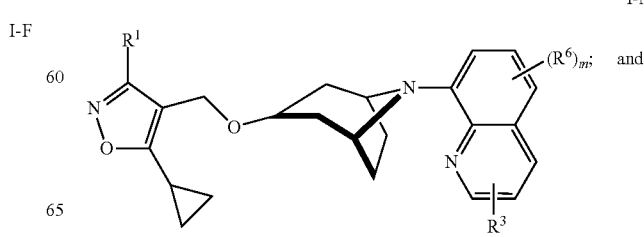

I-M

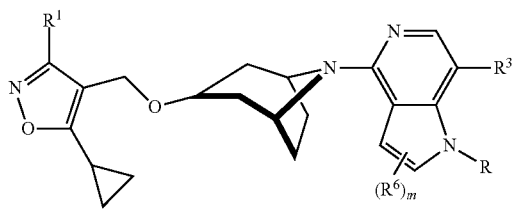
I-N

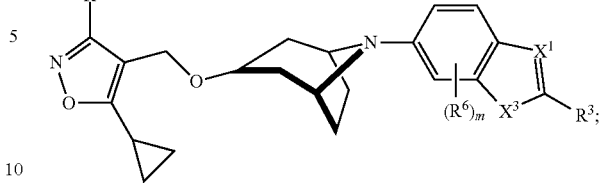
I-T or a stereoisomer, enantiomer, a pharmaceutically acceptable salt or an amino acid conjugate thereof; m is 0-1; and R, $R^3$ and $R^6$ are as defined in Formula (I).

In yet another embodiment, the compounds of the invention are selected from the group consisting of:

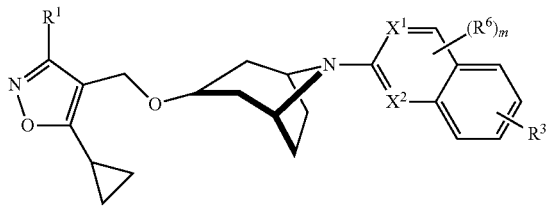
I-U

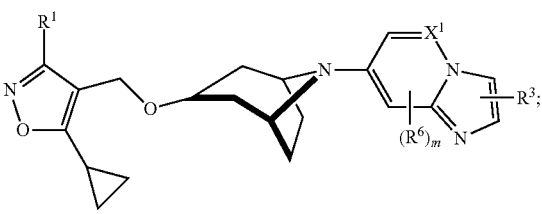
I-O

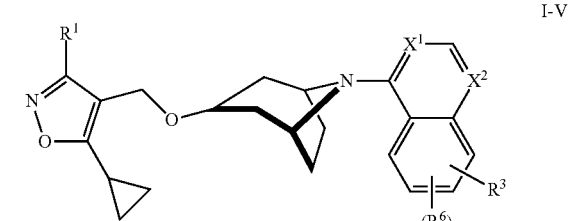
I-V

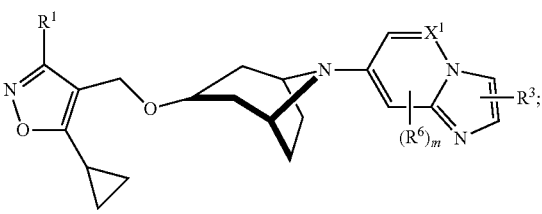
I-P

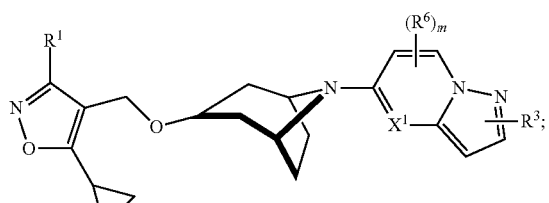
I-W

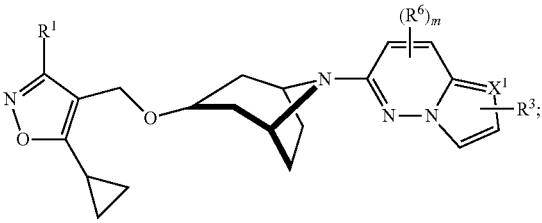
I-Q

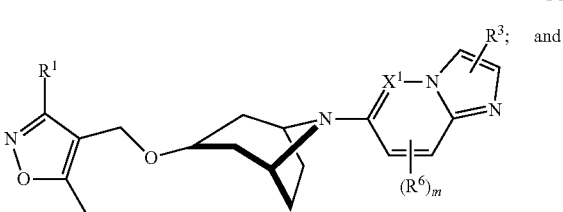
I-X

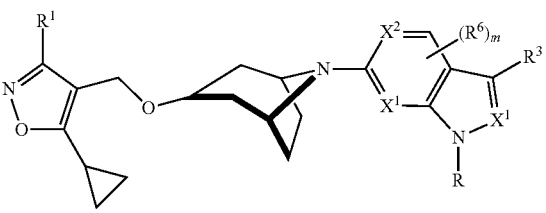
I-R

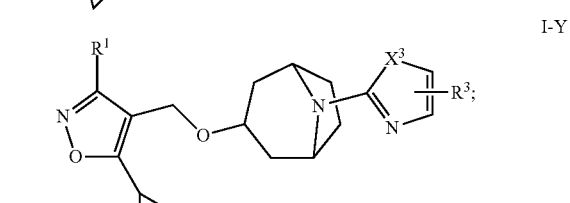

and

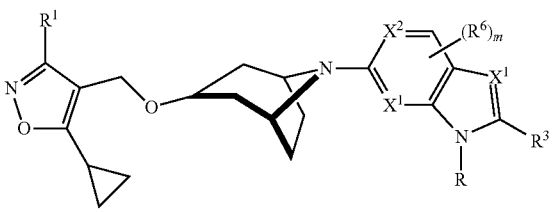
I-S

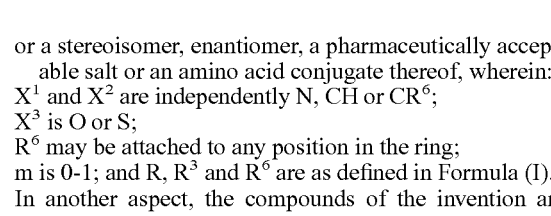
I-Y

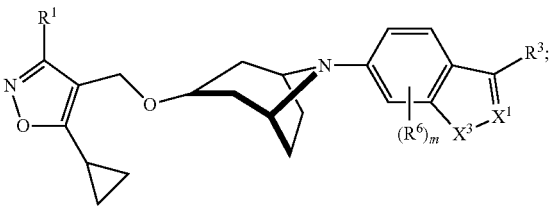

or a stereoisomer, enantiomer, a pharmaceutically acceptable salt or an amino acid conjugate thereof, wherein:
$X^1$ and $X^2$ are independently N, CH or $CR^6$;
$X^3$ is O or S;
$R^6$ may be attached to any position in the ring;
m is 0-1; and R, $R^3$ and $R^6$ are as defined in Formula (I).

In another aspect, the compounds of the invention are defined by Formula (I'):

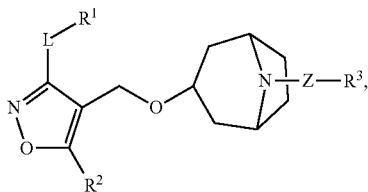
(I)

wherein L is a bond, $C_{1-4}$ alkylene or $C_{1-4}$alkylene-O—;
Z is phenyl, $C_{5-7}$ cycloalkyl o(5-10 membered monocyclic or bicyclic heteroaryl containing 1-2 heteroatoms selected from N, O and S; each of which is optionally substituted with 1-2 $R^6$ radicals selected from halogen, $C_{1-6}$ alkyl, halo$C_{1-6}$ alkyl, $C_{1-6}$ alkoxy, halo$C_{1-6}$ alkoxy, cyclopropyl or $NR^4R^5$;
$R^1$ is phenyl substituted with 1-3 $R^{1a}$; or $R^1$ is $C_{3-8}$ cycloalkyl optionally substituted with 1-3 $R^{1a}$ or phenyl;
$R^{1a}$ is halogen, $C_{1-6}$ alkyl, halo$C_{1-6}$ alkyl, $C_{1-6}$ alkoxy or halo$C_{1-6}$ alkoxy;
$R^2$ is $C_{1-3}$ alkyl, halo$C_{1-3}$ alkyl or cyclopropyl optionally substituted with $C_{1-3}$ alkyl or halo$C_{1-3}$ alkyl;
$R^3$ is —X—$CO_2R^4$, hydroxy$C_{1-6}$ alkyl, $CONR^4R^5$, $CONR(CR_2)_{1-4}CO_2R^4$, $CONR(CR_2)_{1-4}SO_3R^5$, cyano, tetrazolyl or $SO_2NR^4R^5$; wherein X is a bond or $C_{1-2}$ alkylene; and
$R^4$ and $R^5$ are independently hydrogen or $C_{1-6}$ alkyl; or
a stereoisomer, enantiomer, a pharmaceutically acceptable salt or an amino acid conjugate thereof.

In one embodiment, the compounds of the invention are defined by Formula (I'), wherein L is a bond, —$CH_2$—or —$CH_2$—O—; and more particularly, wherein L is a bond.

In another embodiment, the compounds of the invention are defined by Formula II:

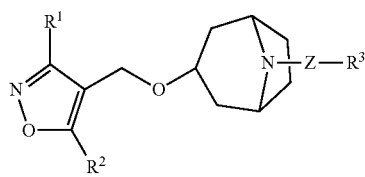
II wherein Z is phenyl, pyridyl, pyrimidinyl, pyrazinyl, pyridazinyl, benzothiazolyl or benzo[d]isothiazolyl; each of which is optionally substituted with 1-2 $R^6$ radicals selected from halogen, $C_{1-6}$ alkyl, halo$C_{1-6}$ alkyl, $C_{1-6}$ alkoxy, halo$C_{1-6}$ alkoxy, cyclopropyl or $NR^4R^5$;
$R^1$ is phenyl substituted with 1-3 $R^{1a}$; or $R^1$ is $C_{3-8}$ cycloalkyl optionally substituted with 1-3 $R^{1a}$ or phenyl;
$R^{1a}$ is halogen, $C_{1-6}$ alkyl, halo$C_{1-6}$ alkyl, $C_{1-6}$ alkoxy or halo$C_{1-6}$ alkoxy;
$R^2$ is $C_{1-3}$ alkyl, halo$C_{1-3}$ alkyl or cyclopropyl optionally substituted with $C_{1-3}$ alkyl or halo$C_{1-3}$ alkyl;
$R^3$ is $CO_2R^4$, hydroxy$C_{1-6}$ alkyl, $CONR^4R^5$, $CONR(CR_2)_{1-4}CO_2R^4$, $CONR(CR_2)_{1-4}SO_3R^5$ or tetrazolyl; and
$R^4$ and $R^5$ are independently hydrogen or $C_{1-6}$ alkyl; or
a stereoisomer, enantiomer, a pharmaceutically acceptable salt or an amino acid conjugate thereof.

In yet another embodiment, the compounds of the invention are selected from the group consisting of:

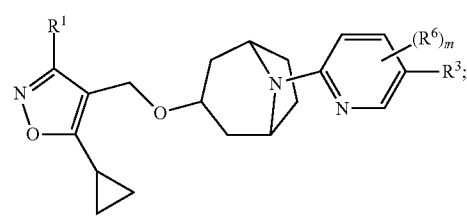
II-A

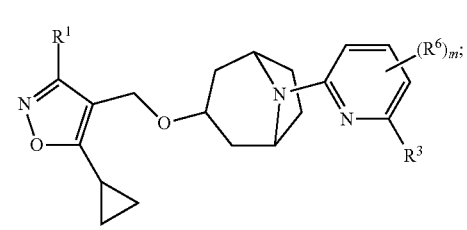
II-B

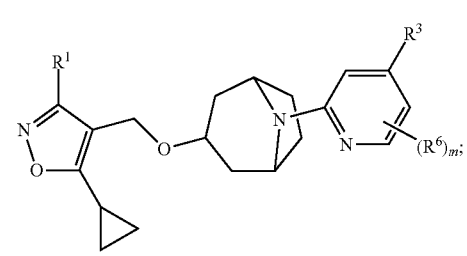
II-C

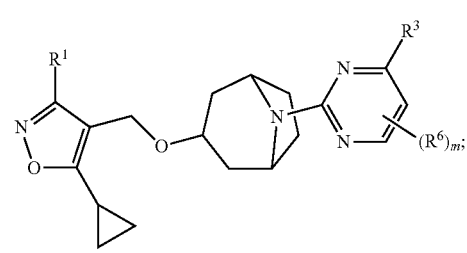
II-D

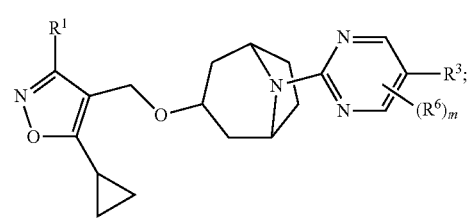
II-E

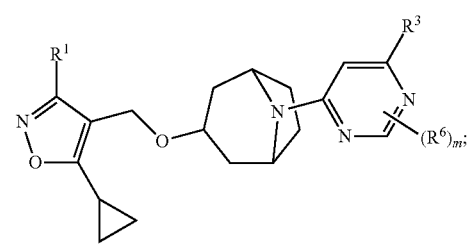
II-F

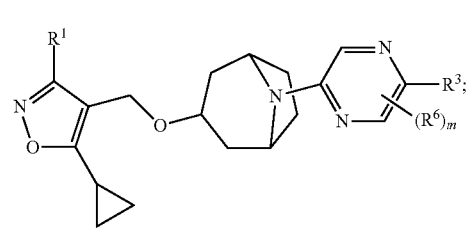
II-G

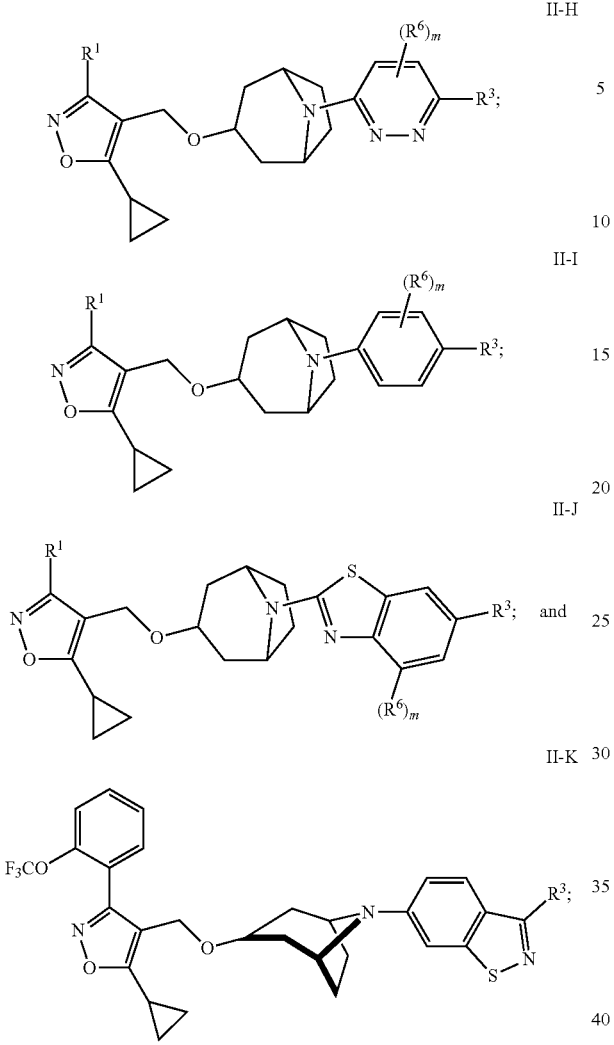

wherein $R^1$ is phenyl substituted with 1-3 $R^{1a}$; or $R^1$ is $C_{3-8}$cycloalkyl optionally substituted with 1-3 $R^{1a}$ or phenyl;
$R^{1a}$ is halogen, $C_{1-6}$ alkyl, haloC$_{1-6}$ alkyl, $C_{1-6}$ alkoxy or haloC$_{1-6}$ alkoxy;
$R^3$ is CO$_2$R$^4$, hydroxyC$_{1-6}$ alkyl, CONR$^4$R$^5$, CONR(CR$_2$)$_{1-4}$CO$_2$R$^4$, CONR(CR$_2$)$_{1-4}$SO$_3$R$^5$ or tetrazolyl;
$R^4$ and $R^5$ are independently hydrogen or $C_{1-6}$ alkyl;
$R^6$ is halogen, $C_{1-6}$ alkyl, haloC$_{1-6}$ alkyl, $C_{1-6}$ alkoxy or haloC$_{1-6}$ alkoxy;
m is 0-1; or
a stereoisomer, enantiomer, a pharmaceutically acceptable salt or an amino acid conjugate thereof.

In other embodiments, the invention provides a compound of Formula I, I-A, I-B, I-C, I-D, I-E, I-F, I-G, I-H, I-I, I-J, I-K, I-L, I-M, I-N, I-O, I-P, I-Q, I-R, I-S, I-T, I-U, I-V, I-W, I-X, I-Y, (I'), II, II-A, II-B, II-C, II-D, II-E, II-F, II-G, II-H, II-I, II-J or II-K (collectively, Formula I, (I-A) to (I-Y), (I'), II, and (II-A)-(II-K)), wherein a substituent is defined, collectively or in any combination or sub-combination, as follows:

a) Z is phenyl, pyridyl, pyrimidinyl, pyrazinyl, pyridazinyl, benzothiazolyl or benzo[d]-isothiazolyl; each of which is optionally substituted with 1-2 R$^6$ radicals; and more particularly, Z is pyridyl, pyrimidinyl, pyrazinyl or benzothiazolyl, each of which is optionally substituted with 1-2 R$^6$ radicals;

b) R$^1$ is phenyl substituted with 1-3 R$^{1a}$; or R$^1$ is C$_{3-8}$ cycloalkyl optionally substituted with 1-3 R$^{1a}$ or phenyl; particularly, R$^1$ is phenyl, spiro[2.5]octan-6-yl, bicyclo[3.1.0]hexan-6-yl, spiro[2.3]hexan-5-yl, bicyclo[3.1.1]heptan-3-yl, bicyclo[4.1.0]heptan-3-yl, cyclohexyl, cyclopentyl or norbonyl, each of which is optionally substituted with 1-3 R$^{1a}$; or R$^1$ is cyclopropyl optionally substituted with 1-2 R$^{1a}$ or phenyl; and more particularly, R$^1$ is phenyl or spiro[2.5]octan-6-yl, each of which is optionally substituted with 1-2 R$^{1a}$;

c) R$^{1a}$ is halogen, C$_{1-6}$ alkyl, haloC$_{1-6}$ alkyl, C$_{1-6}$ alkoxy or haloC$_{1-6}$ alkoxy; particularly R$^{1a}$ is fluoro, methyl, trifluoromethyl, trifluoromethoxy, difluoromethoxy or methoxy;

d) R$^2$ is C$_{1-3}$ alkyl, haloC$_{1-3}$ alkyl or cyclopropyl optionally substituted with C$_{1-3}$ alkyl or haloC$_{1-3}$ alkyl; and more particularly, R$^2$ is cyclopropyl;

e) R$^3$ is —X—CO$_2$R$^4$, hydroxyC$_{1-6}$ alkyl, CONR$^4$R$^5$, CONR(CR$_2$)$_{1-4}$CO$_2$R$^4$, CONR(CR$_2$)$_{1-4}$SO$_3$R$^5$, cyano, tetrazolyl or SO$_2$NR$^4$R$^5$; particularly, R$^3$ is —X—CO$_2$R$^4$, CONR(CR$_2$)CO$_2$R$^4$, CONR(CR$_2$)$_2$SO$_3$R$^5$; and more particularly, R$^3$ is —X—CO$_2$R$^4$; X is a bond and each R$^4$ and R$^5$ are independently hydrogen or C$_{1-6}$ alkyl;

f) R$^6$ is selected halogen, C$_{1-6}$ alkyl, haloC$_{1-6}$ alkyl, C$_{1-6}$ alkoxy, haloC$_{1-6}$ alkoxy, cyclopropyl or NR$^4$R$^5$ wherein R$^4$ and R$^5$ are independently hydrogen or C$_{1-6}$ alkyl; particularly, R$^6$ is selected from halo (particularly fluoro, chloro, bromo), C$_{1-6}$ alkyl (particularly methyl), haloC$_{1-6}$ alkyl (particularly trifluoromethyl), C$_{1-6}$ alkoxy (particularly methoxy) or haloC$_{1-6}$ alkoxy (particularly trifluoromethoxy); and more particularly, R$^6$ is methyl, methoxy, fluoro or trifluoromethoxy; and g) m is 0-2; and more particularly, m is 0-1.

In another aspect, the present invention provides pharmaceutical compositions comprising a compound having Formula I, (I-A) to (I-Y), (I'), II, and (II-A)-(II-K), and a pharmaceutically acceptable carrier. The present invention also provides a pharmaceutical composition comprising a compound of Formula I, (I-A) to (I-Y), (I'), II, and (II-A)-(II-K) for use in the treatment of a condition mediated by FXR.

The compounds of Formula I, (I-A) to (I-Y), (I'), II, and (II-A)-(II-K), and their pharmaceutically acceptable salts exhibit valuable pharmacological properties when tested in vitro in cell-free kinase assays and in cellular assays, and are therefore useful as pharmaceuticals. In particular, the compounds of the invention are agonists of Farnesoid X receptors (FXRs), and are useful as pharmaceuticals to treat FXR-mediated conditions such as cholestasis, intrahepatic cholestasis, estrogen-induced cholestasis, drug-induced cholestasis, cholestasis of pregnancy, parenteral nutrition-associated cholestasis, primary biliary cirrhosis (PBC), primary sclerosing cholangitis (PSC), progressive familiar cholestasis (PFIC), non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, liver fibrosis, dyslipidemia, atherosclerosis, diabetes, diabetic nephropathy, colitis, newborn jaundice, prevention of kernicterus, veno-occlusive disease, portal hypertension, metabolic syndrome, hypercholesterolemia, intestinal bacterial overgrowth, erectile dysfunction, progressive fibrosis of the liver caused by any of the diseases above or by infectious hepatitis, or other FXR-mediated conditions leading to extrahepatic cholestasis. The compounds of the invention are also useful for lowering total cholesterol, lowering LDL cholesterol, lowering VLDL cholesterol, raising HDL levels, and/or lowering triglyceride levels.

In one aspect, the invention provides methods for modulating FXR in a cell, comprising contacting the cell with an effective amount of a compound of Formula I, (I-A) to (I-Y), (I'), II, and (II-A)-(II-K), or a pharmaceutical composition thereof.

In another aspect, the invention provides methods to treat, ameliorate or prevent a FXR-mediated disorder in a subject suffering there from, comprising administering to the subject a therapeutically effective amount of a compound of Formula I, (I-A) to (I-Y), (I'), II, and (II-A)-(II-K), or a pharmaceutical composition thereof, and optionally in combination with a second therapeutic agent. The present invention also provides for the use of a compound of Formula I, (I-A) to (I-Y), (I'), II, and (II-A)-(II-K), and optionally in combination with a second therapeutic agent, in the manufacture of a medicament for treating a FXR-mediated disorder such as cholestasis, intrahepatic cholestasis, estrogen-induced cholestasis, drug-induced cholestasis, cholestasis of pregnancy, parenteral nutrition-associated cholestasis, primary biliary cirrhosis (PBC), primary sclerosing cholangitis (PSC), progressive familiar cholestasis (PFIC), non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, liver fibrosis, dyslipidemia, atherosclerosis, diabetes, diabetic nephropathy, colitis, newborn jaundice, prevention of kernicterus, veno-occlusive disease, portal hypertension, metabolic syndrome, hypercholesterolemia, intestinal bacterial overgrowth, or erectile dysfunction.

In yet another aspect, the present invention provides a combination comprising a therapeutically effective amount of a compound of Formula I, (I-A) to (I-Y), (I'), II, and (II-A)-(II-K), and a second therapeutic agent being useful in the treatment of cholestasis, intrahepatic cholestasis, estrogen-induced cholestasis, drug-induced cholestasis, cholestasis of pregnancy, parenteral nutrition-associated cholestasis, primary biliary cirrhosis (PBC), primary sclerosing cholangitis (PSC), progressive familiar cholestasis (PFIC), non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, liver fibrosis, dyslipidemia, atherosclerosis, diabetes, diabetic nephropathy, colitis, newborn jaundice, prevention of kernicterus, venocclusive disease, portal hypertension, metabolic syndrome, hypercholesterolemia, intestinal bacterial overgrowth, or erectile dysfunction.

Unless specified otherwise, the term "compounds of the present invention"refers to compounds of Formula I, (I-A) to (I-Y), (I'), II, and (II-A)-(II-K), prodrugs thereof, salts of the compound and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates).

Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any formula given herein is also intended to represent unlabeled forms as well as isotopically labeled forms of the compounds. Lsotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}$, C, $^{14}C$, $^{15}N$, $^{18}F$, $^{31}P$, $^{32}P$, $^{35}S$, $^{36}Cl$ and $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula I, (I-A) to (I-Y), (I'), II, and (II-A)-(II-K). The concentration of such a heavier isotope, specifically deuterium, may be defined by the isotopic enrichment factor. The term "isotopic enrichment factor"as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of Formula I, (I-A) to (I-Y), (I'), II, and (II-A)-(II-K) can generally be prepared by conventional techniques known to those skilled in the art or by processes analogous to those described in the accompanying Examples and Processes using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d^6$-acetone, $d^6$-DMSO.

Compounds of the invention, i.e. compounds of Formula I, (I-A) to (I-Y), (I'), II, and (II-A)-(II-K) that contain groups capable of acting as donors and/or acceptors for hydrogen bonds may be capable of forming co-crystals with suitable co-crystal formers. These co-crystals may be prepared from compounds of Formula I, (I-A) to (I-Y), (I'), II, and (II-A)-(II-K) by known co-crystal forming procedures. Such procedures include grinding, heating, co-subliming, co-melting, or contacting in solution compounds of Formula I, (I-A) to (I-Y), (I'), II, and (II-A)-(II-K) with the co-crystal former under crystallization conditions and isolating co-crystals thereby formed. Suitable co-crystal formers include those described in WO 2004/078163. Hence the invention further provides co-crystals comprising a compound of Formula I, (I-A) to (I-Y), (I'), II, and (II-A)-(II-K).

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. Any resulting mixtures of isomers can be separated on the basis of the physicochemical differences of the constituents, into the pure or substantially pure geometric or optical isomers, diastereomers, racemates, for example, by chromatography and/or fractional crystallization. Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Pharmacology and Utility

The compounds of Formula I, (I-A) to (I-Y), (I'), II, and (II-A)-(II-K) in free form or in salt form, exhibit valuable pharmacological properties, e.g. FXR modulating properties, e.g. as indicated in in vitro and/or in vivo tests as provided in the next sections, and are therefore indicated for therapy in treating a disorder which may be treated by modulating FXR, such as those described below.

FXR regulates a complex pattern of response genes in the liver that have impact on diverse physiological processes. FXR represses the induction of Cyp7A1 via the upregulation of mRNA encoding SHP, a further nuclear receptor that is dominant repressive over LRH-1. Parallel to the repression of bile acid synthesis via SHP, FXR induces a range of so-called ABC (for ATP-binding cassette) transporters that are responsible for the export of toxic bile acids from the hepatocyte cytosol into the canaliculi, the small bile duct ramifications where the bile originates. This hepatoprotective function of FXR became first apparent with the analysis of FXR knockout mice where under- or overexpression of several ABC-transporters in the liver was shown (Sinai et al., Cell 2000, 102(6), 731-744). Further detailed analysis revealed that the major bile salt excretory pump BSEP or ABCB 11, as well as the key enzyme which mediates lipid transfer from lipoproteins to phospholipids, PLTP, and the two key canalicular membrane transporters for phospholipids, MRP-2 (ABCC4) and MDR-3 (ABCB4), are direct targets for ligand-directed transcriptional activation by FXR. The fact that FXR seems to be the major metabolite sensor and regulator for the synthesis, export and re-circulation of bile acids suggested the use of FXR ligands to induce bile flow and change bile acid composition towards a more hydrophilic composition.

With the development of the first synthetic FXR ligand GW4064 as a tool compound (Maloney et al., J. Med. Chem. 2000, 43(16), 2971-2974; Willson et al., Med. Res. Rev. 2001, 21(6) 513-22), and the development of the semisynthetic artificial bile acid ligand 6-alpha-ethyl-CDCA, the effects of superstimulation of FXR by potent agonists could be analyzed. It was shown that both ligands induce bile flow in bile duct ligated animals. In addition to choleretic effects, hepatoprotective effects could also be demonstrated (Pellicciari et al., J. Med. Chem. 2002, 45(17), 3569-3572; Liu et al., J. Clin. Invest. 2003, 112(11), 1678-1687). This hepatoprotective effect was further narrowed down to an anti-fibrotic effect that results from the repression of Tissue Inhibitors of Matrix-Metalloproteinases, TIMP-1 and 2, the induction of collagen-deposit resolving Matrix-Metalloproteinase 2 (MMP-2) in hepatic stellate cells and the subsequent reduction of alpha-collagen mRNA and Transforming growth factor beta (TGF-beta) mRNA which are both pro-fibrotic factors by FXR agonists (Fiorucci et al., Gastroenterology 2004, 127(5), 1497-1512; Fiorucci et al., Pharmacol. Exp. Ther. 2005, 314(2), 584-595).

The anti-fibrotic activity of FXR is at least partially mediated by the induction of PPARγ, a further nuclear receptor, with which anti-fibrotic activity is associated (Fiorucci et al., J. Pharmacol. Exp. Ther. 2005, 315(1), 58-68; Galli et al., Gastroenterology 2002, 122(7), 1924-1940; Pineda Torra et al., Mol. Endocrinol. 2003, 17(2), 259-272). Furthermore, anti-cholestatic activity was demonstrated in bile-duct ligated animal models as well as in animal models of estrogen-induced cholestasis (Fiorucci et al., J. Pharmacol. Exp. Ther. 2005, 313(2), 604-612).

Genetic studies demonstrate that in hereditary forms of cholestasis (Progressive Familiar Intrahepatic Cholestasis=PFIC, Type 1-IV), either nuclear localization of FXR itself is reduced as a consequence of a mutation in the FIC1 gene (in PFIC Type I, also called Byler's Disease) (Chen et al., Gastroenterology. 2004, 126(3), 756-64; Alvarez et al., Hum. Mol. Genet. 2004; 13(20), 2451-60) or levels of the FXR target gene encoding MDR-3 phospholipid export pump are reduced (in PFIC Type III). Taken together, there is a growing body of evidence that FXR binding compounds will demonstrate substantial clinical utility in the therapeutic regimen of chronic cholestatic conditions such as Primary Biliary Cirrhosis (PBC) or Primary Sclerosing Cholangitis (PSC) (reviewed in: Rizzo et al., Curr. Drug Targets Immune Endocr. Metabol. Disord. 2005, 5(3), 289-303; Zollner, Mol. Pharm. 2006, 3(3), 231-51, Cai et al., Expert Opin. Ther. Targets 2006, 10(3), 409-421).

Furthermore, FXR seems to be involved in the regulation of many diverse physiological processes which are relevant in the etiology and for the treatment of diseases as diverse as cholesterol gallstones, metabolic disorders such as Type II Diabetes, dyslipidemias or obesity, chronic inflammatory diseases such as Inflammatory Bowel Diseases or chronic intrahepatic forms of cholestasis and many others diseases (Claudel et al., Arterioscler. Thromb. Vase. Biol. 2005, 25(10), 2020-2030; Westin et al., Mini Rev. Med. Chem. 2005, 5(8), 719-727).

Cholesterol gallstones form due to low solubility of cholesterol that is actively pumped out of the liver cell into the lumen of the canaliculi. The relative percentage of the three major components, bile acids, phospholipids and free cholesterol, determines the formation of mixed micelles and hence apparent solubility of free cholesterol in the bile. FXR polymorphisms map as quantitative trait loci as one factor contributing to gallstone disease (Wittenburg, Gastroenterology 2003, 125(3), 868-881). Using the synthetic FXR tool compound GW4064, it could be demonstrated that activation of FXR leads to an improvement of the Cholesterol Saturation Index (CSI) and directly to an abolishment of gallstone formation in C57L gallstone susceptible mice, whereas drug treatment in FXR knockout mice shows no effect on gallstone formation (Moschetta et al., Nature Medicine 2004, 10(12), 1352-1358). These results qualify FXR as a good target for the development of small molecule agonists that can be used to prevent cholesterol gallstone formation or to prevent reformation of gallstones after surgical removal or Shockwave lithotripsy (discussed in: S. Doggrell "New targets in and potential treatments for cholesterol gallstone disease"Curr. Opin. Investig. Drugs 2006, 7(4), 344-348).

FXR has also been shown to be a key regulator of serum triglycerides (Maloney et al., J. Med. Chem. 2000, 43(16), 2971-2974; Willson et al., Med. Res. Rev. 2001, 21(6), 513-22). Recent reports indicate that activation of FXR by synthetic agonists leads to significant reduction of serum triglycerides, mainly in the form of reduced VLDL, but also to reduced total serum cholesterol (Kast et al., Mol. Endocrinol. 2001, 15(10), 1720-1728; Urizar et al., Science 2002, 296 (5573), 1703-1706; Lambert et al., J. Biol. Chem. 2003, 278, 2563-2570; Watanabe et al., J. Clin. Invest. 2004, 113(10), 1408-1418; Figge et al., J. Biol. Chem. 2004, 279(4), 2790-2799; Bilz et al., Am. J. Physiol. Endocrinol. Metab. 2006, 290(4), E716-22).

However, the lowering of serum triglycerides is not a stand alone effect. Treatment of db/db or ob/ob mice with synthetic FXR agonist GW4064 resulted in marked and combined reduction of serum triglycerides, total cholesterol, free fatty acids, ketone bodies such as 3-OH Butyrate. Moreover, FXR activation engages with the intracellular insulin signaling pathway in hepatocytes, resulting in reduced output of glucose from liver gluconeogenesis but concomitant increase in liver glycogen. Insulin sensitivity as well as glucose tolerance were positively impacted by FXR treatment (Stayrook et al., Endocrinology 2005, 146(3), 984-91; Zhang et al., Proc. Natl. Acad. Sci. USA 2006, 103(4), 1006-1011; Cariou et al., J. Biol. Chem. 2006, 281, 11039-11049; Ma et al., J. Clin. Invest. 2006, 116(4), 1102-1109; Duran-Sandoval et al., Biochimie 2005, 87(1), 93-98).

An effect on reduction of body weight was also recently observed in mice overfed with a high lipid diet (Lihong et al., American Diabetes Association (ADA) 66th annual scientific sessions, June 2006, Abstract Numbe(856-P). This weight loss effect might result from FXR's induction of FGF-19, a fibroblast growth factor that is known to lead to weight loss and athletic phenotype (Holt et al., Genes Dev. 2003, 17(13), 1581-1591; Tomlinson et al., Endocrinology 2002, 143(5), 1741-1747). Taken together, FXR binding compounds are thought to be good candidates for the treatment of Type II Diabetes because of their insulin sensitization, glycogenogenic, and lipid lowering effects.

In one embodiment, said compounds and pharmaceutical compositions are used for the preparation of a medicament for the treatment of chronic intrahepatic and some forms of extrahepatic cholestatic conditions, such as primary biliary cirrhosis (PBC), primary sclerosing cholangitis (PSC), progressive familiar cholestasis (PFIC), alcohol-induced cirrhosis and associated cholestasis, or liver fibrosis resulting from chronic cholestatic conditions or acute intraheptic cholestatic conditions such as estrogen or drug induced cholestasis.

In another embodiment, the compounds according to the invention and pharmaceutical compositions comprising said compounds are used in the treatment of Type II Diabetes which can be overcome by FXR-mediated upregulation of systemic insulin sensitivity and intracellular insulin signalling in liver, increased peripheral glucose uptake and metabolisation, increased glycogen storage in liver, decreased output of glucose into serum from liver-borne gluconeogenesis.

The invention also relates to a compound of Formula I, (I-A) to (I-Y), (I'), II, and (II-A)-(II-K), or to a pharmaceutical composition comprising said compound, for the treatment of gastrointestinal conditions with a reduced uptake of dietary fat and fat-soluble dietary vitamins which can be overcome by increased intestinal levels of bile acids and phospholipids.

In another embodiment, the compounds according to the invention are useful for beneficially altering lipid profiles, including but not limited to lowering total cholesterol levels, lowering LDL cholesterol levels, lowering VLDL cholesterol levels, raising HDL cholesterol levels, and/or lowering triglyceride levels. Thus, the present invention provides a method for treating FXR mediated conditions such as dyslipidemia and diseases related to dyslipidemia comprising administering a therapeutically effective amount of a compound of the present invention to a subject in need thereof.

In a further embodiment, said compound or pharmaceutical composition is used for treating a disease selected from the group consisting of lipid and lipoprotein disorders such as hypercholesterolemia, hypertriglyceridemia, and atherosclerosis as a clinically manifest condition which can be ameliorated by FXR's beneficial effect on raising HDL cholesterol, lowering serum triglycerides, increasing conversion of liver cholesterol into bile acids and increased clearance and metabolic conversion of VLDL and other lipoproteins in the liver.

In one further embodiment, said compound and pharmaceutical composition are used for the preparation of a medicament where the combined lipid lowering, anti-cholestatic and anti-fibrotic effects of FXR-targeted medicaments can be exploited for the treatment of liver steatosis and associated syndromes such as non-alcoholic steatohepatitis ("NASH"), or for the treatment of cholestatic and fibrotic effects that are associated with alcohol-induced cirrhosis, or with viral-borne forms of hepatitis.

In conjunction with the hypolipidemic effects, it was also shown that loss of functional FXR leads to increased atherosclerosis in ApoE knockout mice (Hanniman et al., J. Lipid Res. 2005, 46(12), 2595-2604). Therefore, FXR agonists might have clinical utility as anti-atherosclerotic and cardioprotective drugs. The downregulation of Endothelin-1 in Vascular Smooth Muscle Cells might also contribute to such beneficial therapeutic effects (He et al., Circ. Res. 2006, 98(2), 192-9).

The invention also relates to a compound according to Formula I, (I-A) to (I-Y), (I'), II, and (II-A)-(II-K), or a pharmaceutical composition comprising said compound, for preventive and posttraumatic treatment of cardiovascular disorders such as acute myocardial infarction, acute stroke, or thrombosis which occur as an endpoint of chronic obstructive atherosclerosis. In a few selected publications, the effects of FXR and FXR agonists on proliferation of cancer and non-malignant cells and apoptosis have been assessed. From these preliminary results it seems as if FXR agonists might also influence apoptosis in cancer cell lines (Niesor et al., Curr. Pharm. Des. 2001, 7(4), 231-59) and in Vascular Smooth Muscle Cells (VSMCs) (Bishop-Bailey et al., Proc. Natl. Acad. Sci. USA. 2004, 101(10), 3668-3673).

Furthermore, FXR seems to be expressed in metastasizing breast cancer cells and in colon cancer (Silva, J. Lipid Res. 2006, 47(4), 724-733; De Gottardi et al., Dig. Dis. Sci. 2004, 49(6), 982-989). Other publications that focus primarily on FXR's effect on metabolism draw a line to intracellular signaling from FXR via the Forkhead/Wingless (FOXO) family of transcriptional modulators to the Phosphatidylinositol-trisphosphat (PI3)-Kinase/Akt signal transduction pathway (Duran-Sandoval et al., J. Biol. Chem. 2005, 280(33), 29971-29979; Zhang et al., Proc. Natl. Acad. Sci. USA. 2006, 103 (4), 1006-1011) that is similarly employed by insulin intracellular signaling as well as neoplastically transformed cells. Thus, FXR may also be a potential target for the treatment of proliferative diseases, especially metastasizing cancer forms that overexpress FXR or those where the FOXO/PI3-Kinase/Akt Pathway is responsible for driving proliferation. Therefore, the compounds according to Formula I, (I-A) to (I-Y), (I'), II, and (II-A)-(II-K), or pharmaceutical composition comprising said compounds are suitable for treating non-malignant hyperproliferative disorders such as increased neointima formation after balloon vessel dilatation and stent application due to increased proliferation of vascular smooth muscle cells (VSMCs) or Bening Prostate Hyperplasia (BPH), a pre-neoplastic form of hyperproliferation, other forms of scar tissue formation and fibrotisation which can be overcome by e.g. FXR-mediated intervention into the PI-3Kinase/AKT/mTOR intracellular signalling pathway, reduction in Matrix-Metalloproteinase activity and alpha-Collagen deposition.

In a further embodiment, said compounds and pharmaceutical compositions are used for the treatment of malignant hyperproliferative disorders such as cancer (e.g. certain forms of breast or prostate cancer) where interference with PI-3-Kinase/AKT/mTOR signalling and/or induction of p27kip and/or induction of apoptosis will have a beneficial impact.

FXR seems also to be involved in the control of antibacterial defense in the intestine (Inagaki et al., Proc. Natl. Acad. Sci. USA. 2006, 103(10), 3920-3905) although an exact mechanism is not provided. From these published data, however, one can conclude that treatment with FXR agonists might have a beneficial impact in the therapy of Inflammatory Bowel Disorders (IBD), in particular those forms where the upper (ileal) part of the intestine is affected (e.g. ileal Crohn's disease) because this seems to be the site of action of FXR's control on bacterial growth. In IBD, the desensitization of the adaptive immune response is somehow impaired in the intestinal immune system. Bacterial overgrowth might then be the causative trigger towards establishment of a chronic inflammatory response. Hence, dampening of bacterial growth by FXR-borne mechanisms might be a key mechanism to prevent acute inflammatory episodes. Thus, the invention also relates to a compound according to formula (I) or a pharmaceutical composition comprising said compound for treating a disease related to Inflammatory Bowel Diseases such as Crohn's disease or Colitis ulcerosa. FXR-mediated restoration of intestinal barrier function and reduction in non-commensal bacterial load is believed to be helpful in reducing the exposure of bacterial antigens to the intestinal immune system and can therefore reduce inflammatory responses.

The invention further relates to a compound or pharmaceutical composition for the treatment of obesity and associated disorders such as metabolic syndrome (combined conditions of dyslipidemias, diabetes and abnormally high body-mass index) which can be overcome by FXR-mediated lowering of serum triglycerides, blood glucose and increased insulin sensitivity and FXR-mediated weight loss.

In one embodiment, said compound or pharmaceutical composition is for treating persistent infections by intracellular bacteria or parasitic protozoae such as *Mycobacterium* spec. (Treatment of Tuberculosis or Lepra), *Listeria monocytogenes* (Treatment of Listeriosis), *Leishmania* spec. (Leishmaniosis), *Trypanosoma* spec. (Chagas Disease; Trypanosomiasis; Sleeping Sickness).

In a further embodiment, the compounds or pharmaceutical composition of the present invention are useful in the preparation of a medicament for treating clinical complications of Type I and Type II Diabetes. Examples of such complications include Diabetic Nephropathy, Diabetic Retinopathy, Diabetic Neuropathies, Peripheral Arterial Occlusive Disease (PAOD). Other clinical complications of Diabetes are also encompassed by the present invention.

Furthermore, conditions and diseases which result from chronic fatty and fibrotic degeneration of organs due to enforced lipid and specifically triglyceride accumulation and subsequent activation of profibrotic pathways may also be treated by applying the compounds or pharmaceutical composition of the present invention. Such conditions and diseases encompass Non-Alcoholic Steatohepatitis (NASH) and chronic cholestatic conditions in the liver, Glomerulosclerosis and Diabetic Nephropathy in the kidney, Macula Degeneration and Diabetic Retinopathy in the eye and Neurodegenerative diseases such as Alzheimer's Disease in the brain or Diabetic Neuropathies in the peripheral nervous system.

Administration and Pharmaceutical Compositions

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein, a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of Formula I, (I-A) to (I-Y), (I'), II, and (II-A)-(II-K) and at least one other therapeutic agent as a combined preparation for simultaneous, separate or sequential use in therapy. In one embodiment, the therapy is the treatment of a disease or condition mediated by FXR. Products provided as a combined preparation include a composition comprising a compound of Formula I, (I-A) to (I-Y), (I'), II, and (II-A)-(II-K), and the other therapeutic agent(s) together in the same pharmaceutical composition, or the compound of Formula I, (I-A) to (I-Y), (I'), II, and (II-A)-(II-K) and the other therapeutic agent(s) in separate form, e.g. in the form of a kit.

In one embodiment, the invention provides a pharmaceutical composition comprising a compound of Formula I, (I-A) to (I-Y), (I'), II, and (II-A)-(II-K), and another therapeutic agent(s). It is contemplated that the invention provides a pharmaceutical composition comprising a compound of Formula I, (I-A) to (I-Y), (I'), II, and (II-A)-(II-K) in combination with a naturally occurring non-toxic bile acid, such as ursodeoxycholic acid, as an aid in preventing possible depletion of fat-soluble vitamins secondary to treatment with an FXR agonist. Accordingly, the compounds of the invention may be administered concurrently with the naturally occurring non-toxic bile acid, either as separate entities or as a single formulation comprising a compound of Formula I, (I-A) to (I-Y), (I'), II, and (II-A)-(II-K) and naturally occurring bile acid.

Optionally, the pharmaceutical composition may comprise a pharmaceutically acceptable excipient, as described above.

In one embodiment, the invention provides a kit comprising two or more separate pharmaceutical compositions, at least one of which contains a compound of Formula I, (I-A) to (I-Y), (I'), II, and (II-A)-(II-K). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of Formula I, (I-A) to (I-Y), (I'), II, and (II-A)-(II-K) for treating a disease or condition mediated by FXR, wherein the medicament is prepared for administration with another therapeutic agent. The invention also provides the use of another therapeutic agent for treating a disease or condition mediated by FXR, wherein the medicament is administered with a compound of Formula I, (I-A) to (I-Y), (I'), II, and (II-A)-(II-K).

The invention also provides a compound of Formula I, (I-A) to (I-Y), (I'), II, and (II-A)-(II-K) for use in a method of treating a disease or condition mediated by FXR, wherein the compound of Formula I, (I-A) to (I-Y), (I'), II, and (II-A)-(II-K) is prepared for administration with another therapeutic agent. The invention also provides another therapeutic agent for use in a method of treating a disease or condition mediated by FXR, wherein the other therapeutic agent is prepared for administration with a compound of Formula I, (I-A) to (I-Y), (I'), II, and (II-A)-(II-K). The invention also provides a compound of Formula I, (I-A) to (I-Y), (I'), II, and (II-A)-(II-K) for use in a method of treating a disease or condition mediated by FXR, wherein the compound of Formula I, (I-A) to (I-Y), (I'), II, and (II-A)-(II-K) is administered with another therapeutic agent. The invention also provides another therapeutic agent for use in a method of treating a disease or condition mediated by FXR, wherein the other therapeutic agent is administered with a compound of Formula I, (I-A) to (I-Y), (I'), II, and (II-A)-(II-K).

The invention also provides the use of a Formula I, (I-A) to (I-Y), (I'), II, and (II-A)—(II-K) for treating a disease or condition mediated by FXR, wherein the patient has previously (e.g. within 24 hours) been treated with another therapeutic agent. The invention also provides the use of another therapeutic agent for treating a disease or condition mediated by FXR, wherein the patient has previously (e.g. within 24 hours) been treated with a compound of Formula I, (I-A) to (I-Y), (I'), II, and (II-A)-(II-K).

In one embodiment, the other therapeutic agent is useful in the treatment of dyslipidemia, cholestasis, estrogen-induced cholestasis, drug-induced cholestasis, primary biliary cirrhosis (PBC), primary sclerosing cholangitis (PSC), progressive familiar cholestasis (PFIC), alcohol-induced cirrhosis, cystic fibrosis, cholelithiasis, liver fibrosis, atherosclerosis or diabetes, particularly type II diabetes.

Processes for Making Compounds of the Invention

Typically, the compounds of Formula I, (I-A) to (I-Y), and (II-A)-(II-K) can be prepared according to any one of Schemes I, II and III, provided infra.

The present invention also provides a process for the production of a compound of Formula I, comprising reacting a compound of Formula III:

57

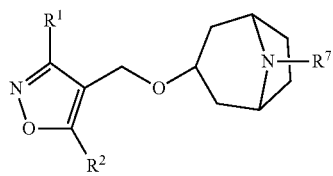

III with a compound of Formula Y-Z-R³;
wherein Y is a leaving group;
R¹, R² and Z are as defined in Formula I;
R³ is —X—CO₂R⁴ wherein X is a bond or methylene;
R⁴ is $C_{1-6}$ alkyl; and R⁷ is H or a protecting group; and
optionally, converting a compound of Formula I, wherein the substituents have the meaning as defined, into another compound of Formula I as defined; and
recovering the resulting compound of Formula I in free form or as a salt; and optionally converting the compound of Formula I obtained in free form into a desired salt, or an obtained salt into the free form.

Each reaction step can be carried out in a manner known to those skilled in the art. For example, a reaction can be carried in the presence of a suitable solvent or diluent or of mixture thereof. A reaction can also be carried, if needed, in the presence of an acid or a base, with cooling or heating, for example in a temperature range from approximately −30°C. to approximately 150°C. In particular examples, a reaction is carried in a temperature range from approximately 0°C. to 100°C., and more particularly, in a temperature range from room temperature to approximately 80°C., in an open or closed reaction vessel and/or in the atmosphere of an inert gas, for example nitrogen.

In one embodiment, the compounds of Formula I, (I-A) to (I-Y), and (II-A)-(II-K) can be prepared following the procedures in Scheme 1:

Scheme 1

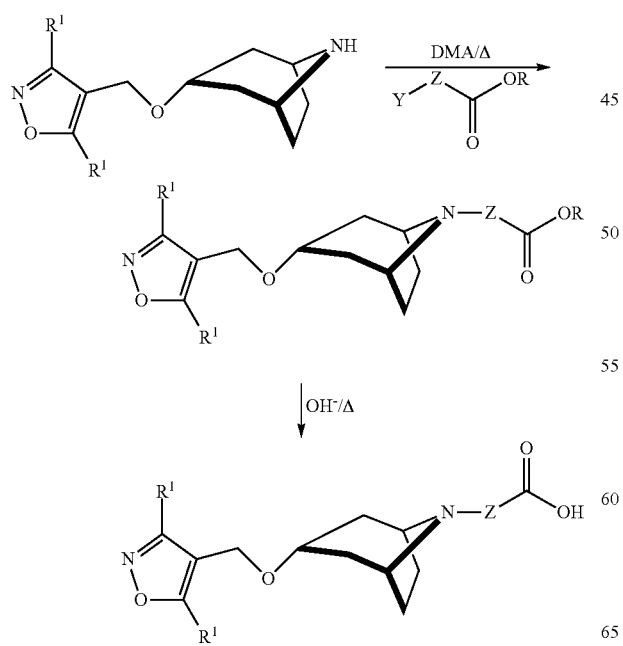

58 wherein R¹, R² and Z are as defined in Formula I; R is $C_{1-6}$ alkyl; and Y is a leaving group.

In another embodiment, the compounds of Formula I, (I-A) to (I-Y), and (II-A)-(II-K) can be prepared following the procedures in Scheme 2:

Scheme 2

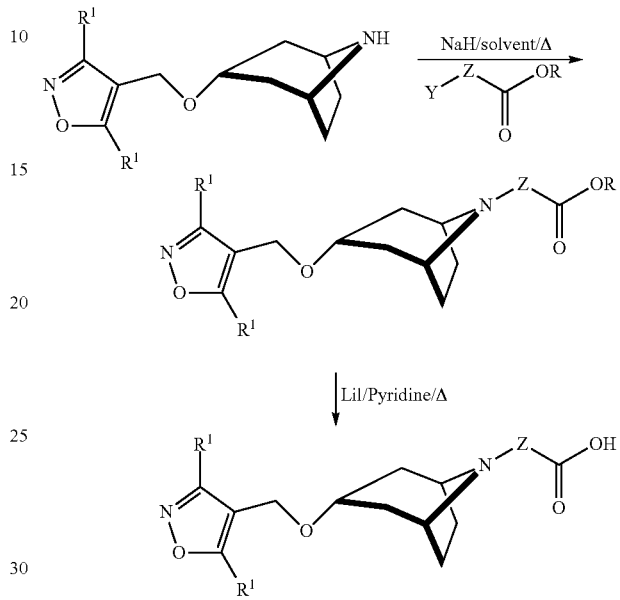

wherein R¹, R² and Z are as defined in Formula I; R is $C_{1-6}$ alkyl; and Y is a leaving group.

In yet another embodiment, the compounds of Formula I, (I-A) to (I-Y), II, and (II-A)-(II-K) can be prepared following the procedures in Scheme 3:

Scheme 3

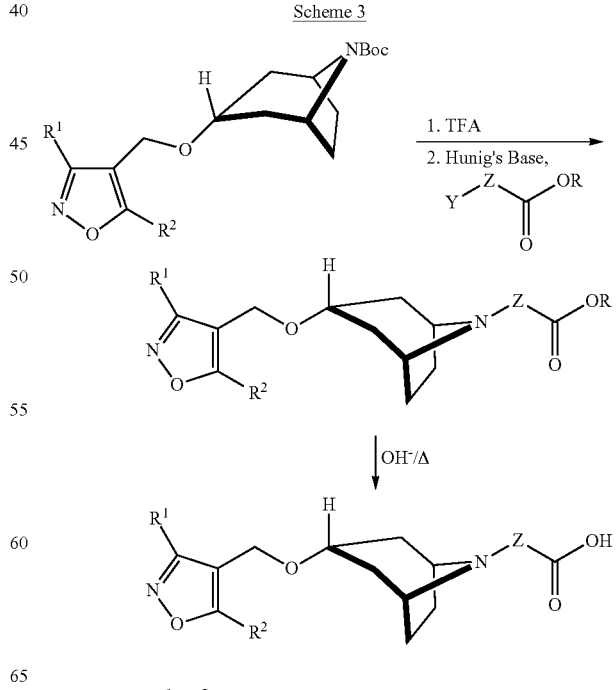

wherein R¹, R² and Z are as defined in Formula I; R is $C_{1-6}$ alkyl; and Y is a leaving group.

The invention also relates to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ. Compounds of the invention and intermediates can also be converted into each other according to methods generally known to those skilled in the art. Intermediates and final products can be worked up and/or purified according to standard methods, e.g. using chromatographic methods, distribution methods, (re-) crystallization, and the like.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie"(Methods of Organic Chemistry), Houben Weyl, 4th edition, Volume 15/I, Georg Thieme Verlag, Stuttgart 1974, in H.-D. Jakubke and H. Jeschkeit, "Aminosaiuren, Peptide, Proteine"(Amino acids, Peptides, Proteins), Verlag Chemie, Weinheim, Deerfield Beach, and Basel 1982, and in Jochen Lehmann, "Chemie der Kohlenhydrate: Monosaccharide und Derivate"(Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps mentioned herein before and hereinafter can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100°C. to about 190°C., including, for example, from approximately −80°C. to approximately 150°C., for example at from −80 to −60°C., at room temperature, at from −20 to 40°C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers. Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or(1-or(2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds of the present invention are either obtained in the free form, as a salt thereof, or as prodrug derivatives thereof. When both a basic group and an acid group are present in the same molecule, the compounds of the present invention may also form internal salts, e.g., zwitterionic molecules. In many cases, the compounds of the present invention are capable of forming acid and/or base salts by virtue of the presence of amino and/or carboxyl groups or groups similar thereto. As used herein, the terms "salt"or "salts"refers to an acid addition or base addition salt of a compound of the invention. "Salts"include in particular "pharmaceutical acceptable salts". The term "pharmaceutically acceptable salts"refers to salts that retain the biological effectiveness and properties of the compounds of this invention and, which typically are not biologically or otherwise undesirable.

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers. Salts can be converted into the free compounds in accordance with methods known to those skilled in the art. Metal and ammonium salts can be converted, for example, by treatment with suitable acids, and acid addition salts, for example, by treatment with a suitable basic agent.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate, trifluoroacetate and tris(hydroxymethyl)aminomethane salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See The Practice of Medicinal Chemistry, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, may also be obtained in the form of hydrates, or their crystals may, for example, include the solvent used for crystallization. Different crystalline forms may be present. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the present invention, including salts, hydrates and solvates thereof, may inherently or by design form polymorphs.

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80°C.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

PREPARATION OF INTERMEDIATES

Intermediate 1

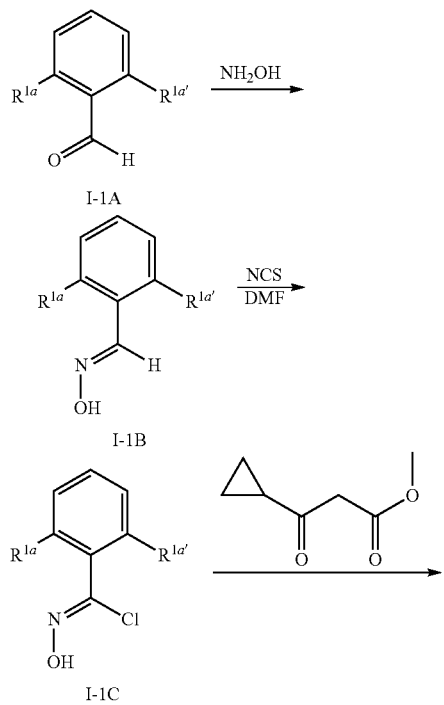

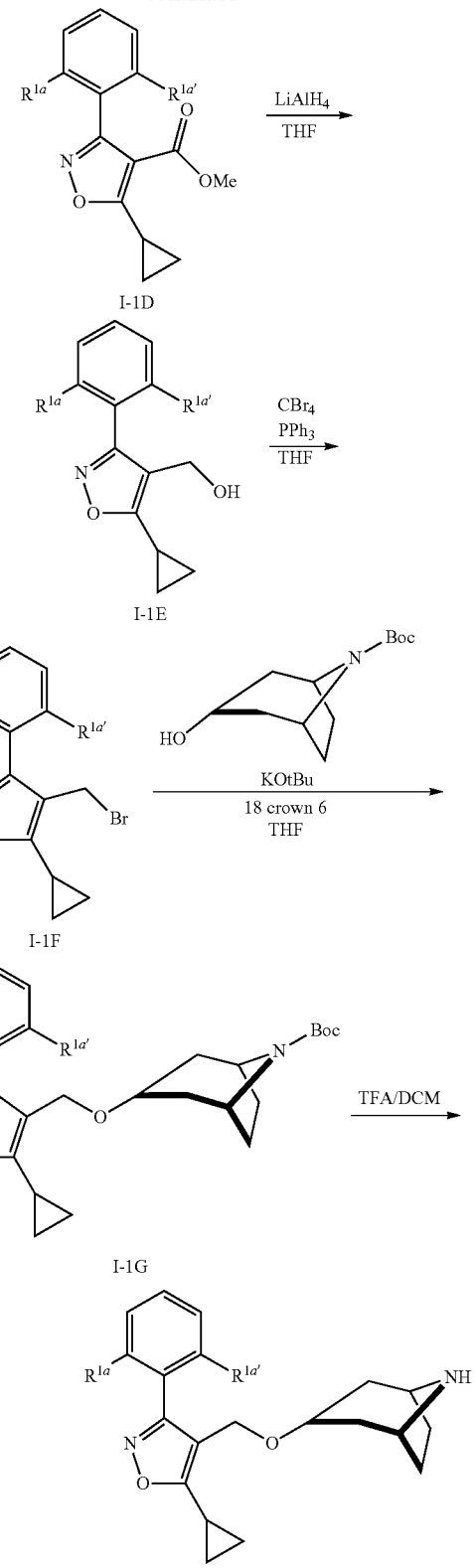

$R^{1a} = OCF_3$; $R^{1a'} = H$ (I-1H)
$R^{1a} = CF_3$; $R^{1a'} = H$ (I-1I)
$R^{1a} = OCHF_2$; $R^{1a'} = H$ (I-1J)
$R^{1a}$, $R^{1a'}$ = fluoro (I-1K)

2-(Trifluoromethoxy)Benzaldehyde oxime (I-1B). To a solution of sodium hydroxide (7 g, 175.00 mmol, 1.19 equiv) in water (120 mL) was added a stirred solution of $NH_2OH \cdot HCl$ (11.8 g, 169.78 mmol, 1.15 equiv) in water (120 mL) at 0°C. The resulting solution was stirred fo(10 min at 0°C. Then a solution of 2-(trifluoromethoxy)benzaldehyde (28 g, 147.29 mmol, 1.00 equiv) in ethanol (120 mL) was added. The resulting solution was allowed to stir for an additional 1 h at room temperature. The resulting solution was diluted with 500 ml of $H_2O$, extracted with 2×700 mL of ethyl acetate and the organic layers were combined, washed with 2×300 mL of brine, dried over anhydrous sodium sulfate and concentrated under vacuum to give (E)-2-(trifluoromethoxy) benzaldehyde oxime as an off-white crystalline solid.

N-hydroxy-2-(trifluoromethoxy)benzimidoyl chloride (I-1C). NCS (22 g, 166.04 mmol, 1.12 equiv) was slowly added to a stirred solution of (E)-2-(trifluoromethoxy)benzaldehyde oxime (30 g, 146.27 mmol, 1.00 equiv) in N,N-dimethylformamide (300 mL) keeping the internal temperature below 25°C. The reaction mixture was stirred fo(1 h at room temperature. The resulting solution was diluted with water (300 mL) and extracted with ethyl acetate (2×500 mL). The organic layers were combined, washed with brine (5×300 mL), dried over anhydrous sodium sulfate, and concentrated under vacuum to give (Z)-2-(trifluoromethoxy)benzoyl chloride oxime as a light yellow crystalline solid.

Methyl 5-cyclopropyl-3-(2-(trifluoromethoxy)phenyl) isoxazole-4-carboxylate (I-1D). Potassium carbonate (11 g, 79.7 mmol, 1.09 equiv) was suspended in THF (100 mL) and the mixture was stirred. A solution of methyl 3-cyclopropyl-3-oxopropanoate (11 g, 77.5 mmol, 1.06 equiv) in 50 ml THF was added to the above stirred mixture and stirred fo(30 min at −10°C. To this reaction mixture was added a solution of (Z)-2-(trifluoromethoxy)benzoyl chloride oxime (17.6 g, 73.3 mmol, 1.00 equiv) in THF (50 mL) at −5°C. and then allowed to stir fo(6 h at 35°C. The reaction mixture was diluted with 200 mL of $H_2O$, extracted with ethyl acetate (2×300 mL). The organic layer was washed with brine (2×200 mL), dried over anhydrous sodium sulfate, concentrated under vacuum, and then purified by silica gel column chromatography using ethyl acetate/petroleum ether (1:100-1:20) eluent to afford methyl 5-cyclopropyl-3-(2-(trifluoromethoxy)phenyl)isoxazole-4-carboxylate as a white solid.

(5-Cyclopropyl-3-(2-(trifluoromethoxy)phenyl)isoxazol-4-yl)-methanol (I-1E). A 250-mL round-bottom flask was purged with nitrogen and a suspension of $LiAlH_4$ (2.5 g, 65.8 mmol, 2.87 equiv) in tetrahydrofuran (50 mL) was added. This was followed by the addition of a solution of methyl 5-cyclopropyl-3-(2-(trifluoromethoxy)phenyl)isoxazole-4-carboxylate (7.5 g, 22.9 mmol, 1.00 equiv) in tetrahydrofuran (50 mL) dropwise at −10°C. The resulting reaction mixture was stirred fo(30 min at −10°C. When the reaction was complete, it was quenched by the addition of 3 mL of ethyl acetate, followed by 3 mL of water and $O_1$ mL of 15% aqueous NaOH, all whilst maintaining a vigorous stirring. The resulting white precipitate was filtered through celite®, and the filter cake was washed with 200 mL of ethyl acetate. The filtrate was washed with brine (2×100 mL), dried over anhydrous sodium sulfate, and concentrated under vacuum. This resulted in 7 g of (5-cyclopropyl-3-(2-(trifluoromethoxy)phenyl)isoxazol-4-yl)methanol as yellow oil. ($^1$H-NM(300 MHz, $CDCl_3$) δ 7.56 (m, 2H), 7.41 (m, 2H), 4.50 (s, 2H), 2.20 (m, 1H), 1.72 (s, 1H, —OH) 1.11-1.28 (m, 4H).

4-(Bromomethyl)-5-cyclopropyl-3-(2-(trifluoromethoxy)-phenyl)isoxazole (I-1F). Into a 100 mL round bottom flask was placed (5-cyclopropyl-3-(2-(trifluoromethoxy)phenyl)isoxazol-4-yl)-methanol (4 g, 13.3 mmol), triphenylphosphine (5.6 g, 20 mmol, 1.5 equiv) and dichloromethane (40 mL). The mixture was stirred until completely dissolved, and then slowly cannulated dropwise into a stirring solution of carbon tetrabromide (6.6 g, 20 mmol, 1.5 eq) in dichloromethane (20 ml). The mixture was stirred for one hour and the solvent was then evaporated in vacuo. The crude residue was purified by silica gel chromatography using a 0-50% gradient of ethyl acetate/hexane. The desired product was obtained as a colorless oil. MS m/z 361.9/363.9 (M+1, $Br_{79}/Br_{81}$ isotope pattern).

tert-Butyl 3-((5-cyclopropyl-3-(2-(trifluoromethoxy)phenyl)isoxazol-4-yl)methoxy)-8-azabicyclo[3.2.1]octane-8-carboxylate (I-1G). A 250-mL flask was purged with nitrogen and then charged with N-Boc-nortropine (2.9 g, 12.8 mmol), 18-Crown-6 (3.4 g, 12.8 mmol), and anhydrous tetrahydrofuran (80 mL). Potassium tert-butoxide (2.9 g, 25.6 mmol) was added in small portions, and the mixture was stirred vigorously under nitrogen fo(1 h. 4-(bromomethyl)-5-cyclopropyl-3-(2-(trifluoromethoxy)-phenyl)isoxazole (4.18 g, 11.6 mmol) was dissolved in anhydrous tetrahydrofuran (20 mL) and added dropwise, and the reaction mixture was stirred overnight under a positive nitrogen pressure. The solvent was removed in vacuo and the mixture diluted with water (100 mL) and ethyl acetate (100 mL). The organic layer was separated, dried with anhydrous $MgSO_4$, and evaporated in vacuo. The crude residue was purified by silica gel chromatography using a gradient of 0-100% ethyl acetate/hexanes to yield the desired product as yellow oil. MS m/z 509.2 (M+1).

4-((8-azabicyclo[3.2.1]octan-3-yloxy)methyl)-5-cyclopropl-3-(2-(trifluoromethoxy)phenyl)isoxazole (I-1H). tert-butyl-3-((5-cyclopropyl-3-(2-(trifluoromethoxy)phenyl)isoxazol-4-yl)methoxy)-8-azabicyclo[3.2.1]octane-8-carboxylate was dissolved in 30 mL of a 20% solution of trifluoroacetic acid in dichloromethane. The solution was stirred fo(1 h at room temperature and the solvent was evaporated. The residue was dissolved in ethyl acetate (125 mL), washed with a saturated solution of sodium bicarbonate (100 mL), the organic layer was dried with anhydrous $MgSO_4$ and evaporated in vacuo. The crude residue was purified by silica gel chromatography using a gradient of 0-20% ethanol/dichloromethane to afford the desired product as a colorless oil. MS m/z 409.2 (M+1)

$^1$H NMR (DMSOd$_6$, 400 MHz); δ 8.51 (br s, 1H, NH), 7.72-7.68 (m, 1H), 7.64 (dd, J=7.6, 1.8 Hz, 1H), 7.58-7.52 (m, 2H), 4.33 (s, 2H), 3.81 (bs, 2H), 3.55 (t, J=4.5 Hz, 1H), 2.36-2.33 (m, 1H), 1.98 (app dt, J=14.8, 4.0 Hz, 2H), 1.91-1.76 (m, 6H), 1.14-1.07 (m, 4H).

4-((8-azabicyclo[3.2.1]octan-3-yloxy)methyl)-5-cyclopropyl-3-(2-(trifluoromethyl)phenyl)isoxazole (I-1I) was prepared following the same procedures. MS m/z 393.2 (M+1); $^1$H NMR (DMSOd$_6$, 400 MHz); δ 8.51 (br s, 1H, NH), 7.92 (d, J=8.0, 1.8 Hz, 1H), 7.81 (app t, J=7.1 Hz, 1H), 7.78 (app t, J=7.1 Hz, 1H), 7.58 (d, J=7.3 Hz, 1H), 4.24 (s, 2H), 3.81 (bs, 2H), 3.52 (t, J=3.7 Hz, 1H), 2.36-2.33 (m, 1H), 1.92 (app dt, J=14.8, 4.0 Hz, 2H), 1.81-1.69 (m, 6H), 1.14-1.09 (m, 4H).

4-((8-azabicyclo[3.2.1]octan-3-yloxy)methyl)-5-cyclopropyl-3-(2-(difluoromethoxy)phenyl)isoxazole (I-1J) was prepared following the same procedures. MS m/z 391.3 (M+1); $^1$H NMR (CDCl$_3$, 400 MHz); δ 9.10 (br s, 1H, NH), 7.32 (app t, J=8.4 Hz, 2H), 7.26 (app d, J=8.4 Hz, 2H), 6.44 (t, J=74 Hz, 1H, CHF$_2$), 4.32 (s, 2H), 3.82 (bs, 2H), 3.56 (t, J=4.0 Hz, 1H), 2.32 (app dt, J=15.2, 4.6 Hz, 2H), 2.08-2.04 (m, 1H), 1.98-1.89 (m, 4H), 1.78 (app br d, J=15.9 Hz, 2H), 1.26-1.20 (m, 2H), 1.14-1.09 (m, 2H).

4-((8-azabicyclo[3.2.1]octan-3-yloxy)methyl)-5-cyclopropyl-3-(2,6-difluorophenyl)isoxazole (I-1K) was prepared following the same procedures. MS m/z 361.2 (M+1); $^1$H NMR (CDCl$_3$, 400 MHz); δ 9.18 (br s, 1H, NH), 7.48-7.40 (m, 1H), 7.06-6.99 (m, 2H), 4.31 (s, 2H), 3.82 (bs, 2H), 3.59 (t, J=4.7 Hz, 1H), 2.16 (app dt, J=15.9, 4.0 Hz, 2H), 2.09-2.02 (m, 1H), 1.98-1.92 (m, 4H), 1.76 (app br d, J=15.2 Hz, 2H), 1.26-1.19 (m, 2H), 1.15-1.09 (m, 2H).

Intermediate 2

Methyl 2-chloro-4-methoxybenzothiazole-6-carboxylate (I-2)

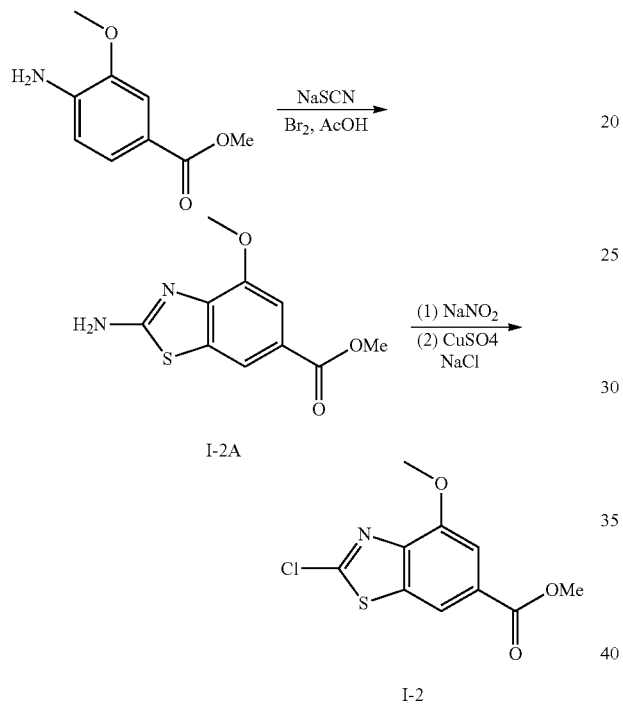

I-2A

I-2

Methyl 2-amino-4-methoxybenzo[d]thiazole-6-carboxylate (I-2A). A solution of NaSCN (27 g, 333.33 mmol, 4.00 equiv) in AcOH (50 mL) was prepared in a three-necked, round-bottomed 100-mL flask. A solution of methyl 4-amino-3-methoxybenzoate (15 g, 82.87 mmol, 1.00 equiv) in AcOH (50 mL) was added dropwise at 0°C., followed by the addition of a solution of Br$_2$ (12 g, 75.00 mmol, 1.10 equiv) in AcOH (20 mL) dropwise at 0°C. The resulting solution was stirred fo(4 h at room temperature, after which point it was then diluted with 200 mL of water. The pH of the solution was adjusted to pH=8 with sodium carbonate. The solids were collected by filtration and dried in a warm oven under reduced pressure to give methyl 2-amino-4-methoxybenzo[d]thiazole-6-carboxylate as a yellow solid.

Methyl 2-chloro-4-methoxybenzo[d]thiazole-6-carboxylate (I-2). A 1000-mL 3-necked round-bottom flask was charged with a solution of methyl 2-amino-4-methoxybenzo[d]thiazole-6-carboxylate (5 g, 21.01 mmol, 1.00 equiv) and H$_3$PO$_4$ (40 mL). To this is added of a solution of NaNO$_2$ (4.5 g, 65.22 mmol, 3.00 equiv) in water (10 mL) dropwise at 0°C. The resulting solution was stirred fo(1 h at 0°C. A solution of CuSO$_4$ (10 g, 62.50 mmol, 5.00 equiv) in water (10 mL) was then added dropwise at 0°C., followed by a solution of NaCl (18.5 g, 318.97 mmol, 15.00 equiv) in water (10 mL) dropwise at 0°C. The resulting solution was stirred fo(1 h at room temperature, and then diluted with 100 mL of water. The aqueous solution was extracted with dichloromethane (2×50 mL) and the combined organic layer was concentrated under vacuum. The residue was purified by silica gel chromatography eluting with ethyl acetate/petroleum ether (3:1) to give methyl 2-chloro-4-methoxybenzo[d]thiazole-6-carboxylate as a white solid. (ES, m/z): Calc'd for C$_{10}$H$_8$ClNO$_3$S [M+1]$^+$=258, found 258. $^1$H-NMR (CDCl$_3$, ppm): 3.98(s, 1H), 4.10(s, 1H), 7.28(s, 1H), 7.60(d, 1H, J=1.2), 8.12(d, 1H, J=1.2).

Intermediate 3

Methyl 2-bromo-4-fluorobenzothiazole-6-carboxylate (I-3)

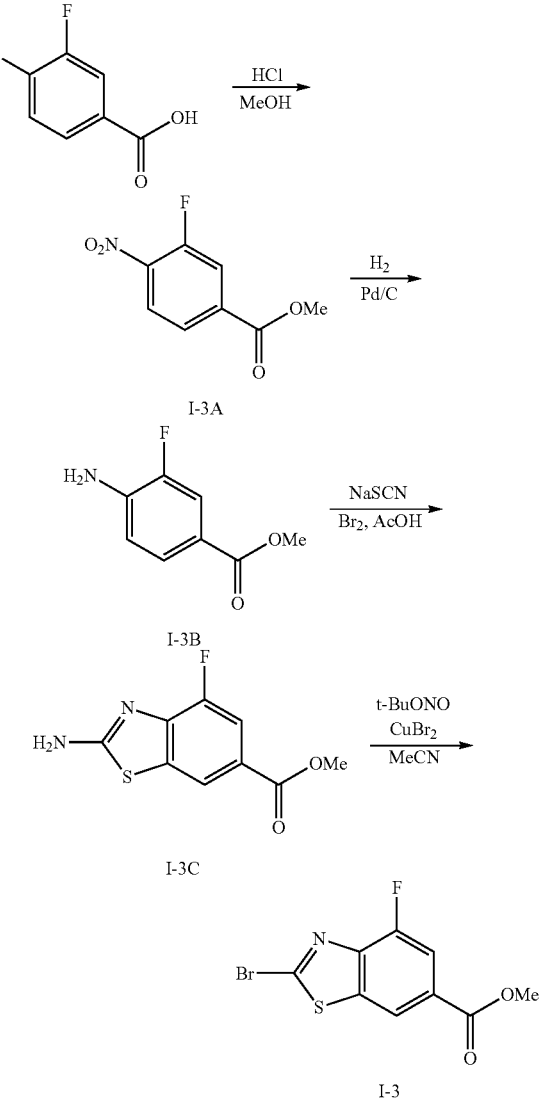

I-3A

I-3B

I-3C

I-3

Methyl 3-fluoro-4-nitrobenzoate (I-3A). Into a 2-L round-bottom flask was placed a solution of 3-fluoro-4-nitrobenzoic acid (100 g, 540.54 mmol, 1.00 equiv) and HCl (50 mL) in methanol (800 mL). The resulting solution was refluxed fo(16 h. The resulting solution was diluted with 1000 mL of EtOAc. The pH of the solution was adjusted to neutral with saturated potassium bicarbonate solution. The resulting mixture was washed with brine (2×500 mL), dried over anhydrous sodium sulfate and concentrated under vacuum to give methyl 3-fluoro-4-nitrobenzoate as a pale yellow solid.

Methyl 4-amino-3-fluorobenzoate (I-3B). Into a 2000-mL round-bottom flask maintained with a nitrogen atmosphere, was placed a solution of methyl 3-fluoro-4-nitrobenzoate (98 g, 492.46 mmol, 1.00 equiv) in ethyl acetate:methanol=1:1 (1000 mL). Then Pd/C (10 g, 10 wt %, Degussa type) was added. The flask was fitted with a balloon of hydrogen, and the heterogeneous reaction mixture was stirred fo(16 h under a hydrogen atmosphere at 30°C. The catalyst solids were filtered off and the filtrate was concentrated under vacuum to give the deisred product methyl 4-amino-3-fluorobenzoate.

Methyl 2-amino-4-fluorobenzo[d]thiazole-6-carboxylate (I-3C). Into a 1000-mL round-bottom flask, was placed a solution of methyl 4-amino-3-fluorobenzoate (45 g, 266.27 mmol, 1.00 equiv) and NaSCN (86 g, 1.06 mol, 3.99 equiv) in AcOH (350 mL). This was followed by the addition of a solution of $Br_2$ (42 g, 262.50 mmol, 0.99 equiv) in AcOH (150 mL) dropwise at 0°C. fo(1 h. The resulting solution was stirred fo(48 h at 30°C., after which point the solids were filtered. The resulting solution was diluted with $H_2O$ and the pH was adjusted to pH=8-9 with ammonium hydroxide. The resulting precipitate was collected by filtration to give the desired product methyl 2-amino-4-fluorobenzo[d]thiazole-6-carboxylate as a yellow solid.

Methyl 2-bromo-4-fluorobenzo[d]thiazole-6-carboxylate (I-3). Into a 2000-mL 3-necked round-bottom flask, was placed a suspension of $CuBr_2$ (61 g, 272.32 mmol, 1.54 equiv) in acetonitrile (800 mL). This was followed by the addition of t-BuONO (48 mL) at 0°C. dropwise over the course of 10 min. To this solution was added methyl 2-amino-4-fluorobenzo[d]thiazole-6-carboxylate (40 g, 176.99 mmol, 1.00 equiv), and the reaction mixture was stirred at 30°C. fo(48 h. The reaction mixture was then diluted with EtOAc (1 L), and the organic layer was washed with water (3×400 mL) and brine (3×400 mL), dried over anhydrous sodium sulfate, and concentrated under vacuum. The crude residue was applied onto a silica gel column eluting with ethyl acetate/petroleum ether (1:100~1:5) to give methyl 2-bromo-4-fluorobenzo[d]thiazole-6-carboxylate as a white solid. LCMS (m/z): Calc'd for $C_9H_5BrFNO_2S$ [M+1]+=290, found 290. $^1$H-NMR: ($CDCl_3$, ppm): 8.22 (d, 1H, J=0.9 Hz), 7.86 (dd, 1H, J=1.2, 9.6 Hz), 3.99 (s, 3H).

Intermediate 4

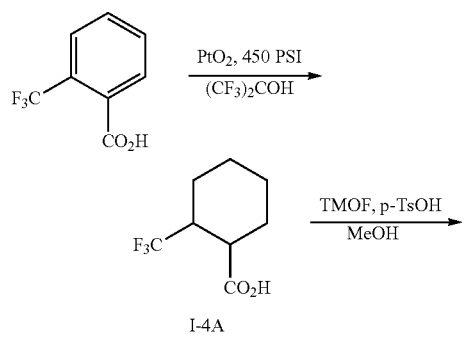

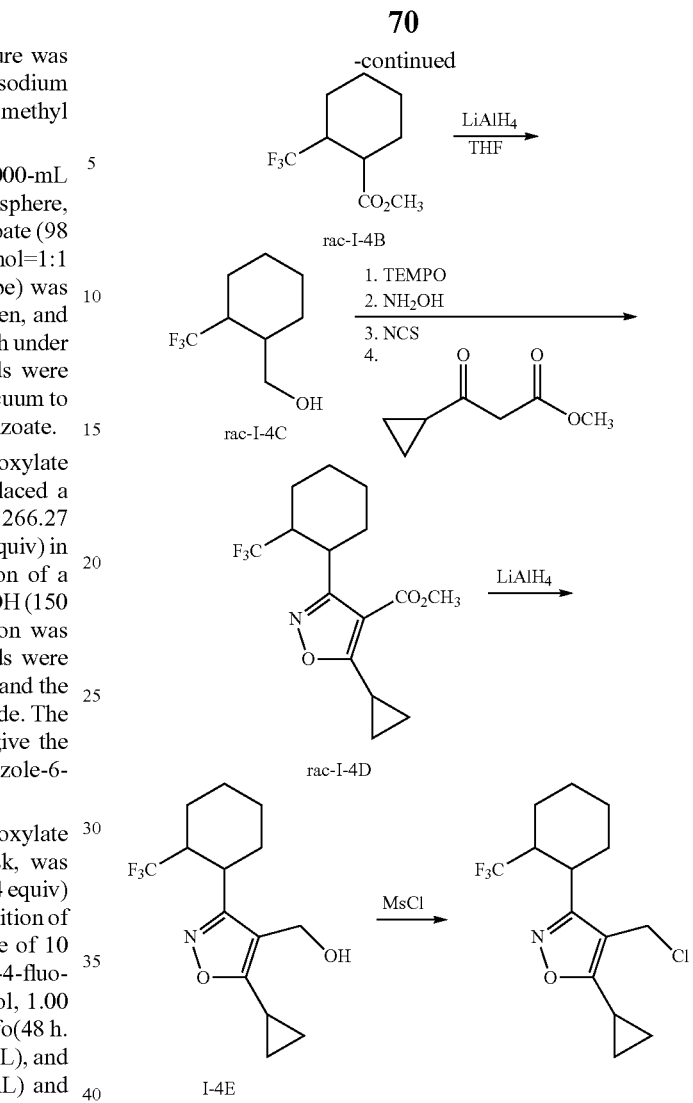

(trans)-methyl 2-(trifluoromethyl)cyclohexanecarboxylate (rac-I-4B). A solution of 2-(trifluoromethyl)cyclohexanecarboxylic acid (I-4A, JP 63051354 A 19880304, 42 g, 214 mmol) acid in methanol (150 mL) was treated with trimethyl orthoformate (39 mL, 358 mmol) followed by p-TsOH (3.7 g, 21.4 mmol) and refluxed fo(48 hours. The reaction was then cooled to rt, concentrated, diluted with EtOAc and washed with saturated $NaHCO_3$ and brine. Organics were dried ($MgSO_4$), filtered, concentrated, and distilled (50-52°C., 0.1 Torr) to give the title trans compound as a clear oil. $^1$H NMR (400 MHz, $CDCl_3$) δ 3.67 (s, 3H), 2.89 (dd, J=4.7, 4.7 Hz, 1H), 2.38 (m, 1H), 2.06(m, 1H), 1.95 (m, 1H), 1.81 (m, 2H), 1.71 (m, 1H), 1.59 (m, 1H), 1.47 (m, 1H), 1.34 (m, 1H), MS m/z 211.1 (M+1).

(trans)-2-(trifluoromethyl)cyclohexyl)methanol (rac-I-4C). A cold (0°C.) solution of rac-I-4B (35 g, 166 mmol) in THF (250 mL) was stirred with the slow addition of lithium aluminum hydride in THF (1M solution, 250 mL), and then stirred fo(1 hour. The reaction was cooled to 0°C., stirred, and treated with the dropwise addition of 1N HCl (25 mL). An additional volume of 1N HCl (500 mL) was added until the salts of the reaction had dissolved. The reaction was then extracted with $Et_2O$ and the organic phase collected, dried ($MgSO_4$), filtered, concentrated, and distilled (73-76°C., 0.1 mm Hg) to give the desired alcohol. $^1$H NMR (400 MHz, CDCl₃) δ 3.78 (m, 1H), 3.67 (m, 1H), 2.34 (m, 1H), 2.13 (m, 1H), 1.90 (m, 1H), 1.75 (m, 1H), 1.63 (m, 3H), 1.50 (m, 2H), 1.39 (m, 2H), MS m/z 165.1 (M−H₂O).

Methyl 5-cyclopropyl-3-((trans)-2-(trifluoromethyl)cyclohexyl)-isoxazole-4-carboxylate (rac-I-4D). A cold (0°C.) solution of rac-4-C (28.3 g, 155 mmol) and trichloroisocyanuric acid (37.9 g, 163 mmol) in CH₂Cl₂ (310 mL) was treated with TEMPO (242 mg, 1.55 mmol) and the reaction stirred fo(2 h. The reaction was then washed with a solution of saturated Na₂CO₃ (100 mL) followed by 1 M HCl (50 mL), dried over MgSO₄, filtered, evaporated and redissolved in ethanol (15 mL). This solution was then cooled to 0°C. and treated with 50% (aq) hydroxylamine (11.4 mL) and allowed to warm to room temperature and stir overnight. The volatiles were removed in vacuo and extracted with EtOAc. Organics were collected, dried (MgSO₄), filtered, and concentrated. The crude oxime (27.5 g, 141 mmol) was dissolved in DMF (200 mL) and treated with the portionwise addition of N-chlorosuccinimide (21.1 g, 157 mmol). The reaction slowly warmed to rt and stirred fo(1 hour. The reaction was treated with saturated NaCl (aq.) and extracted with Et₂O. Organics were collected, dried (MgSO₄), filtered, concentrated and chromatographed (SiO₂, linear gradient, 0-80% EtOAc in Hex) to afford the chloro-oxime which was dissolved in methanol (5 mL).

In another flask, a cold (0°C.) solution of methyl 3-cyclopropyl-3-oxopropanoate (23.7 g, 170 mmol) in methanol (35 mL) was treated with sodium methoxide (25% wt. solution in methanol, 30 mL). After stirring fo(20 minutes, the reaction was treated with the dropwise addition of the chloro-oxime already in methanol. The reaction warmed to rt and stirred fo(30 min. The reaction was concentrated in vacuo and diluted with EtOAc. The organics were washed with saturated NaCl (aq) and saturated NaHCO₃ (aq.). Organics were collected, dried (MgSO₄), filtered, concentrated, and chromatographed (SiO₂, linear gradient, 0-80%, EtOAc in Hexanes) to give the desired ester as an oil.

(5-cyclopropyl-3-((trans)-2-(trifluoromethyl)cyclohexyl) isoxazol-4-yl)methanol (I-4E). A cold (0°C.) solution of the rac-4-D (5.1 g, 20.5 mmol) in THF (70 mL) was treated with the dropwise addition of lithium aluminum hydride (26.6 mL, 1M solution in THF). Afte(2 hr of stirring, the reaction was cooled to 0°C. and treated with the dropwise addition of 1N HCl (aq.) until a solution persisted. The reaction was then extracted with EtOAc. The organic phase was dried (MgSO₄), filtered, concentrated, and chromatographed (SiO₂, linear gradient, 0-80%, EtOAc in hexanes) to give a racemic mixture of the title compound which was resolved using a 4.6× 100 mm ChiralPak AD-H column eluting at 30°C. with a 85% CO₂/15% MeOH solvent system. The peak eluting at 1.82 minutes was collected. ¹H NMR (400 MHz, CDCl₃) δ 4.52 (m, 2H), 3.52 (m, 1H), 2.45 (m, 1H), 2.17 (m, 1H), 2.02 (m, 1H), 1.97-1.66 (m, 5H), 1.52 (m, 1H), 1.42 (m, 1H), 1.35 (m, 1H), 1.14 (m, 2H), 1.05 (m, 2H), MS m/z 290.1 (M+1).

4-(chloromethyl)-5-cyclopropyl-3-((trans)-2-(trifluoromethyl)cyclohexyl)isoxazole (I-4). A cold (0°C.) solution of (5-cyclopropyl-3-((1S,2S)-2-(trifluoromethyl)cyclohexyl) isoxazol-4-yl)methanol (1.8 g, 6.2 mmol) dichloromethane was treated with Hunig's base (953 μL, 6.8 mmol) followed by methane sulfonyl chloride (508 L, 6.5 mmol). Afte(6 hr of stirring, the reaction was treated with H₂O and phases separated. The organic phase was collected, dried (MgSO₄), filtered, concentrated, and chromatographed (SiO₂, linear gradient, 0-80% EtOAc in Hex) to give the title compound. ¹H NMR (400 MHz, CDCl₃) δ 4.48 (dd, J=36.5, 12.6 Hz, 2H), 3.48 (m, 1H), 2.44 (m, 1H), 2.15 (ddd, J=25.5, 12.8, 3.6 Hz, 1H), 2.04-1.87 (m, 4H), 1.82-1.68 (m, 2H), 1.55 (m, 1H), 1.35 (m, 1H), 1.14 (m, 2H), 1.09 (m, 2H), MS m/z 308.1 (M+1).

Intermediate 5

4-(chloromethyl)-5-cyclopropyl-3-((trans)-2-(trifluoromethyl)cyclopropyl)isoxazole (rac-5)

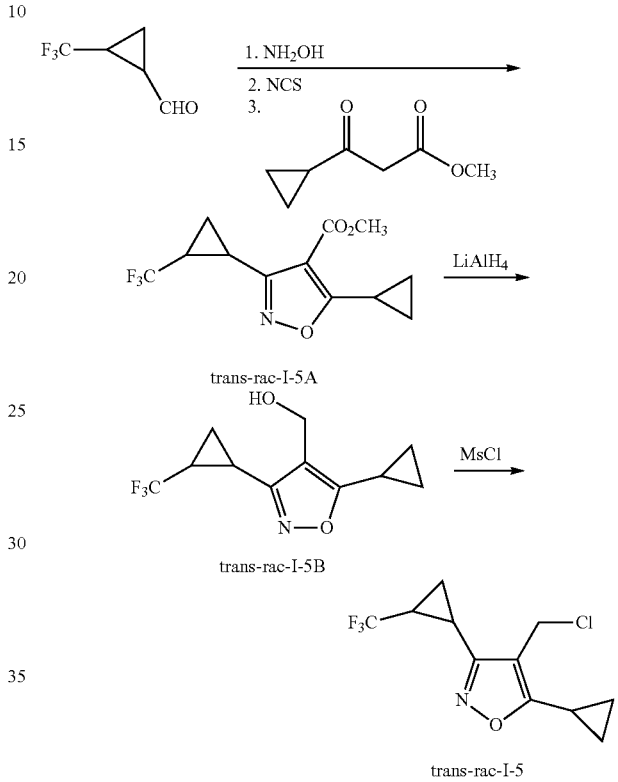

Methyl 5-cyclopropyl-3-((trans)-2-(trifluoromethyl)cyclopropyl)isoxazole-4-carboxylate (rac-I-5A). A cold (0°C.) solution of (1S,2S)-2-(trifluoromethyl)-cyclopropanecarbaldehyde (J. Chem. Soc., Perkin Trans. 2, 1984, 1907-1915; 2.0 g, 14.5 mmol) in ethanol (5 mL) was treated with 50% (aq) hydroxylamine (1.3 mL) and allowed to warm to rt and stir overnight. The volatiles were removed in vacuo and extracted with EtOAc. Organics were collected, dried (MgSO₄), filtered, and concentrated. The crude oxime (1.0 g, 6.5 mmol) was dissolved in DMF (11.3 mL) and treated with the portionwise addition of N-chlorosuccinimide (980 mg, 7.3 mmol). The reaction slowly warmed to rt and stirred fo(1 hour. The reaction was treated with saturated NaCl (aq.) and extracted with Et₂O. Organics were collected, dried (MgSO₄), filtered and concentrated to afford the crude chloro-oxime which was dissolved in methanol (5 mL).

In another flask, a cold (0°C.) solution of methyl 3-cyclopropyl-3-oxopropanoate (930 mg, 6.5 mmol) in methanol (15 mL) was treated with sodium methoxide (25% wt. solution in methanol, 1.55 mL). After stirring fo(15 minutes, the reaction was treated with the dropwise addition of the chloro-oxime already in methanol. The reaction warmed to rt and stirred for an additional 30 min. The reaction was concentrated in vacuo and diluted with EtOAc. The organics were washed with saturated NaCl (aq) and saturated NaHCO₃ (aq.). Organics were collected, dried (MgSO₄), filtered, concentrated, and chromatographed (SiO₂, linear gradient, 0-80%, EtOAc in Hexanes) to give the desired ester as an oil. $^1$H NMR (400 MHz, CDCl$_3$) δ 3.89 (s, 3H), 2.79 (m, 2H), 2.11 (m, 1H), 1.42 (m, 2H), 1.22 (m, 4H), MS m/z 276.1 (M+1).

(5-cyclopropyl-3-((trans)-2-(trifluoromethyl)-cyclopropyl)isoxazol-4-yl)methanol (rac-I-5B). A cold (0°C.) solution of methyl 5-cyclopropyl-3-((trans)-2-(trifluoromethyl) cyclopropyl)isoxazole-4-carboxylate (193 mg, 0.7 mmol) in THF (2.3 mL) was treated with the dropwise addition of lithium aluminum hydride (1.4 mL, 1M solution in THF). Afte(2 hr of stirring, the reaction was cooled to 0°C. and treated with the dropwise addition of 1N HCl (aq.) until a solution persisted. The reaction was then extracted with EtOAc. The organic phase was dried (MgSO$_4$), filtered, concentrated, and chromatographed (SiO$_2$, linear gradient, 0-80%, EtOAc in hexanes) to give the title compound. $^1$H NMR (400 MHz, CDCl$_3$) δ 4.63 (d, J=4.5 Hz, 2H), 2.31 (m, 1H), 2.14 (m, 1H), 2.01 (m, 1H), 1.67 (dd, J=5.1, 4.9 Hz, 1H), 1.42 (m, 2H), 1.10 (m, 2H), 1.05 (m, 2H), MS m/z 248.1 (M+1).

4-(chloromethyl)-5-cyclopropyl-3-((trans)-2-(trifluoromethyl)cyclopropyl)isoxazole (rac-I-5). A solution of (5-cyclopropyl-3-((trans)-2-(trifluoromethyl)-cyclopropyl)isoxazol-4-yl)methanol_(136 mg, 0.55 mmol) in dichloromethane (2 mL) was treated with triethylamine (230 μL) followed by methane sulfonyl chloride (45 μL, 0.58 mmol). Afte(2 hr of stirring, the rxn was treated with H$_2$O and phases separated. The organic phase was collected, dried (MgSO$_4$), filtered, concentrated, and chromatographed (SiO$_2$, linear gradient, 0-80% EtOAc in Hex) to afford the title compound. MS m/z 266.1 (M+1).

Intermediate 6

4-(chloromethyl)-5-cyclopropyl-3-(2-phenylcyclopropyl)isoxazole (rac-I-6)

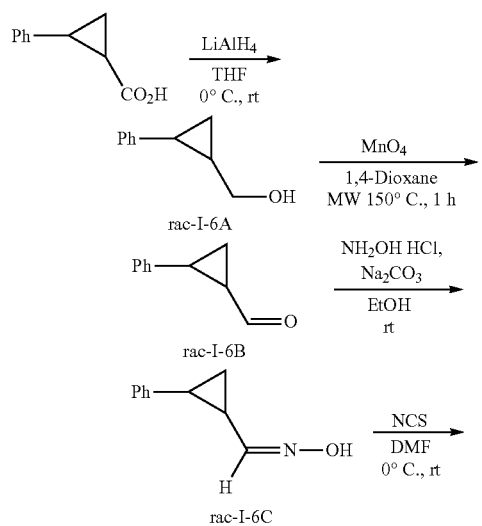

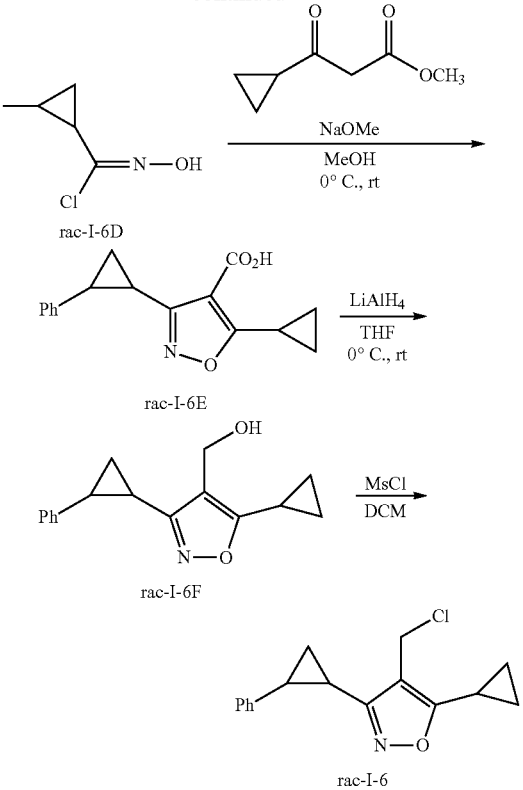

trans-2-phenylcyclopropyl)methanol (rac-I-6A). To a solution of commercialy available trans-ethyl phenylcyclopropanecarboxylic acid (3.0 g, 18.5 mmol) in anhydrous THF (27 mL) and cooled to 0°C., lithium aluminum hydride (24 mL, of a 1 M solution in THF) was added dropwise. After stirring fo(14 h at rt, the reaction mixture was cooled to 0°C. and then quenched by the dropwise addition of H$_2$O (1.6 mL), 15% NaOH (1.6 mL), H$_2$O (2.4 mL) followed by Na$_2$SO$_4$ and filtered under vacuum to afford trans-2-phenylcyclopropyl) methanol which was used without purification. $^1$H NMR (400 MHz, DMSO) δ 7.22-720 (m, 2H), 7.12-7.08 (1H), 7.06-7.04 (m, 2H), 4.61 (t, J=8.0 Hz, 1H), 3.48-3.42 (m, 1H), 3.37-3.31 (m, 1H), 2.11 (m, 1H), 1.79-1.74 (m, 1H), 1.29-1.21 (m, 1H), 0.88-0.79 (m, 2H). MS m/z 149.2 (M+1).

trans-2-Phenylcyclopropanecarbaldehyde (rac-I-6B). To a solutionof trans-2-phenylcyclopropyl)methanol rac-I-6A (1.5 g, 10.1 mmol) in 1,4-dioxane (20 mL) MnO$_4$ (4.4 g, 50.1 mmol) was added. The dark mixture was heated at 150°C. fo(0.5 h under microwave irradiation. The reaction mixture was filtered through CELITE® and washed with EtOAc. The filtrate was collected, washed with water and brine, dried over sodium sulfate, filtered and concentrated to afford trans-2-Phenylcyclopropanecarbaldehyde as brown oil (0.89 g) which was used without further purification in the next step. $^1$H NMR (400 MHz, DMSO) δ 9.09 (d, J=5.6 Hz, 1H), 7.31-7.27 (m, 2H), 7.21-7.18 (m, 3H), 2.27-2.65 (m, 1H), 2.14-2.08 (m, 1H), 1.73-1.68 (m, 1H), 1.60-1.55 (m, 1H). MS m/z 147.2 (M+1).

trans-2-Phenylcyclopropanecarbaldehyde oxime (rac-I-6C). A solution of trans-2-phenylcyclopropanecarbaldehyde rac-I-6B (0.89 g, 6.1 mmol) in EtOH (12 mL) and cooled to 0°C. was treated with hydroxylamine hydrochloride (0.43 g, 6.1 mmol) and Na$_2$CO$_3$. The reaction mixture was allowed to warm to rt and stir fo(12 h. The volatiles were removed in vacuo and extracted with EtOAc. The organics were collected, dried over Na₂SO₄ filtered, and concentrated to afford trans-2-Phenylcyclopropanecarbaldehyde oxime which was used without further purification.

trans-N-hydroxy-2-phenylcyclopropanecarbimidoyl chloride (rac-I-6D). To a solution of the crude trans-2-phenylcyclopropanecarbaldehyde oxime rac-I-6C (04 g, 2.51 mmol) in DMF (5 mL) and cooled at 0°C. N-chlorosuccinimide (0.37 g, 2.7 mmol) was added portionwise. The reaction mixture was slowly warmed to rt and stirred fo(14 h. The reaction was quenched with saturated NaCl (aq.) and extracted with Et₂O. The organics were collected, washed with water, brine, dried over Na₂SO₄, filtered, and concentrated under vacuum. The crude was purified by column chromatography on silica gel with hexane-EtOAc (5 to 20% gradient as eluant) to yield trans-N-hydroxy-2-phenylcyclopropanecarbimidoyl chloride.

5-cyclopropyl-3-(2-phenylcyclopropyl)isoxazole-4-carboxylic acid (rac-I-6E). A solution of methyl 3-cyclopropyl-3-oxopropanoate (0.36 mL, 2.9 mmol) in methanol (8 mL) was cooled to 0°C. and treated with sodium methoxide (0.76 mL of a 25% wt. solution in MeOH). After stirring fo(20 minutes, trans-N-hydroxy-2-phenylcyclopropanecarbimidoyl chloride rac-I-6D (0.57 g, 2.9 mmol) in methanol (0.5 mL) was added dropwise. The reaction mixture was warmed to rt and stirred fo(1 h. The reaction was concentrated in vacuo, diluted with water and extracted with dichloromethane. The aqueous was acidified with 6N HCl to pH=5 and extracted again with dichloromethane. The organics were washed with brine dried over Na₂SO₄, filtered, concentrated to yield 5-cyclopropyl-3-(2-phenylcyclopropyl)isoxazole-4-carboxylic acid as clear oil which was directly used in the next step without further purification. MS m/z 270.1 (M+1).

(5-cyclopropyl-3-2-phenylcyclopropyl)isoxazol-4-yl)methanol (rac-I-6F). To a solution of 5-cyclopropyl-3-(2-phenylcyclopropyl)isoxazole-4-carboxylic acid rac-I-6E (0.49 g, 1.82 mmol) in THF and cooled to 0°C. lithium aluminum hydride (4.5 mL, of a 1M solution in THF) was added dropwise. After stirring fo(12 h at rt, the reaction mixture was cooled back to 0°C. and quenched by dropwise addition of H₂O (0.5 mL), 15% NaOH (0.5 mL), H₂O (1 mL) followed by Na₂SO₄ and filtered through CELITE® under vacuum. The crude was purified by column chromatography on silica gel with DCM-EtOAc 0 to 5% gradient as eluent to give (5-cyclopropyl-3-(2-phenylcyclopropyl)isoxazol-4-yl)methanol. $^1$H NMR (400 MHz, DMSO) δ 7.31-727 (m, 2H), 7.21-7.17 (m, 3H), 5.00 (t, J=5.2 Hz, 1H), 4.42-4.33 (m, 2H), 2.39-2.35 (m, 1H), 2.23-2.13 (m, 2H), 1.57-1.52 (m, 1H), 1.46-1.42 (m, 1H), 1.05-1.04 (m, 2H), 0.95-0.91 (M, 2H). MS m/z 256.1 (M+1).

4-(chloromethyl)-5-cyclopropyl-3-(2-phenylcyclopropyl) isoxazole (rac-I-6). To a solution of rac-I-6F (0.16 g, 0.63 mmol) in dichloromethane (6 mL) and triethylamine (0.12 mL, 0.81 mmol) and cooled to 0°C. methane sulfonyl chloride (0.06 mL, 0.81 mmol) was added. After stirring fo(6 h the reaction was diluted with water and the organic were extracted with DCM. The organic layer was washed with water, brine, dried over Na₂SO₄, filtered, concentrated to yield 4-(chloromethyl)-5-cyclopropyl-3-(2-phenylcyclopropyl)isoxazole as clear oil. $^1$H NMR (400 MHz, DMSO) δ 7.32-718 (m, 5H), 4.82 (s, 1H), 2.41-2.36(m, 1H), 2.31-2.23 (m, 2H), 1.58-1.53 (m, 1H), 1.51-1.46 (m, 1H), 1.21-1.07 (m, 2H), 1.01-0.97(m, 2H). MS m/z 273.1 (M+1).

Intermediate 7

4-(chloromethyl)-5-cyclopropyl-3-(spiro[2.5]octan-6-yl)isoxazole (I-7)

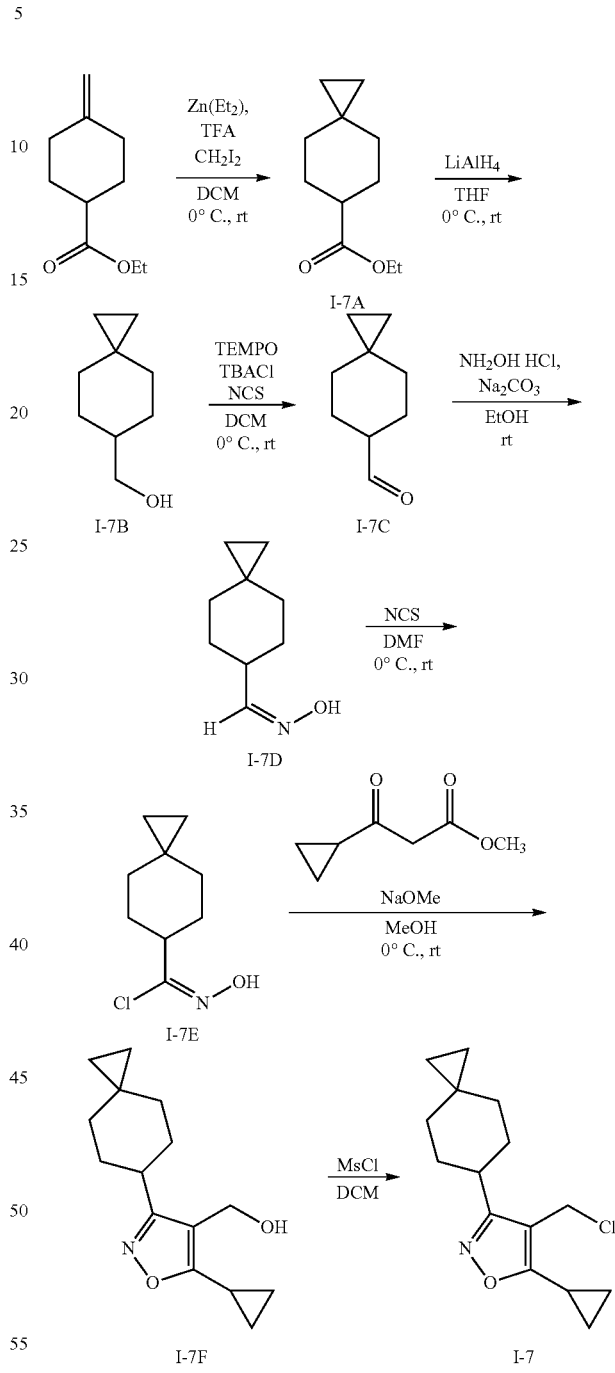

Ethyl spiro[2.5]octane-6-carboxylate (I-7A). To a solution of diethyl zinc (35 mL, of a 1M solution in hexane) in DCM (30 mL) cooled to 0°C., a solution of TFA (2.7 mL, 35.0 mmol) in DCM (12 mL) was added dropwise. After stirring the reaction mixture at 0°C. fo(1 h, CH₂I₂ (2.8 mL, 35.0 mmol) in DCM (12 mL) was slowly added and the mixture was stirred for an additional 40 min. After this time, ethyl 4-methylenecyclohexanecarboxylate (2.36 g, 14.0 mmol) in DCM (5 mL) was dropwise added to the flask and the reaction mixture was stirred for an additional 2 h. The reaction mixture was then diluted with DCM and washed with saturated aqueous NH₄Cl. The organic layer was collected, washed with brine, dried over Na₂SO₄, filtered, concentrated to yield an oil residue that was passed through a short silica gel column to afford ethyl spiro[2.5]octane-6-carboxylate. ¹H NMR (400 MHz, CDCl₃) δ 4.13 (q, J=7.2 Hz, 2H), 2.31 (m, 1H), 1.90-1.86 (m, 2H), 1.67-1.61 (m, 4H), 1.24 (t, H=7.2 Hz, 3H), 0.95-0.95 (m, 2H), 0.29-0.18 (m, 4H). MS m/z 183 (M+1).

spiro[2.5]octan-6-ylmethanol (I-7B). Spiro[2.5]octan-6-ylmethanol was prepared using the analogous protocol as previously described for the preparation of the alcohol I-6A. ¹H NMR (400 MHz, DMSO) δ 4.38 (t, J=5.2 Hz, 1H), 3.23 (dd, J=6.4 and 5.2 Hz, 2H), 1.69-1.59 (m, 4H), 1.35-1.32 (m, 1H), 1.06-1.05 (m, 2H), 0.87-0.84 (m, 2H), 0.25-0.22 (m, 2H), 0.13-0.11 (m, 2H). MS m/z 141 (M+1).

spiro[2.5]octane-6-carbaldehyde (I-7C). To a solution of spiro[2.5]octan-6-ylmethanol (1.83 g, 13 mmo) in dichloromethane (60 mL) was added NaHCO₃ (30 mL of a 0.5 M aqueous solution) and K₂CO₃ (30 mL of a 0.05M aqueous solution) and tehn cooled to 0°C. TEMPO (0.203 g, 1.3 mmol), TBACl (0.361 g, 1.3 mmol), and NCS (0.36 g, 1.3 mmol) were added successively, and the reaction mixture was stirred at rt fo(4 h. Using a separation funnel the organic layer was collected and then washed with brine, dried over Na₂SO₄. The organics were concentrated in vacuo and the crude residue was purified by column chromatography on silica gel with a gradient of 20 to 60% hexane-DCM as eluant to afford the desired product spiro[2.5]octane-6-carbaldehyde. ¹H NMR (400 MHz, CDCl₃) δ 9.66 (d, J=0.8 Hz, 1H), 2.30 (m, 1H), 1.91-1.88 (m, 2H), 1.67-1.48 (m, 4H), 1.09-104 (m, 2H), 0.31-0.29 (m, 2H), 0.22-0.20 (m, 2H). MS m/z 139.0 (M+1).

Spiro[2.5]octane-6-carbaldehyde oxime (I-7D), N-hydroxyspiro[2.5]octane-6-carbimidoyl chloride (I-7E), (5-cyclopropyl-3-(spiro[2.5]octan-6-yl)isoxazol-4-yl)methanol (I-7F) were prepared following similar protocols described previously for the preparation of I-6C, I-6D and I-6E, respectively, and used in the next step without purification. 4-(Chloromethyl)-5-cyclopropyl-3-(spiro[2.5]octan-6-yl)isoxazole was prepared by according to the analogous procedure as previously described for the preparation of Intermediate 6. ¹H NMR (400 MHz, DMDO) δ 4.79 (s, 2H), 2.81-2.74 (m, 1H), 2.32-2.25 (m, 1H), 1.91-1.87 (m, 2H), 1.83-1.77 (m, H), 1.64-1.55 (m, 2H), 1.10-1.06 (m, 2H), 1.00-0.95 (m, 4H), 0.32-0.2 (m, 4H).

Intermediate 8

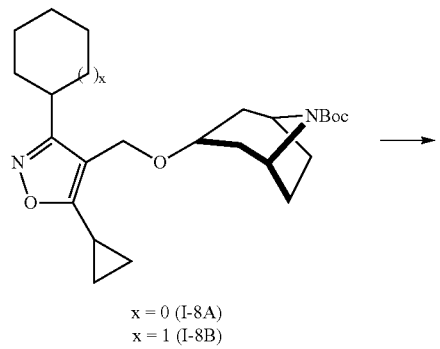

x = 0 (I-8A)
x = 1 (I-8B)

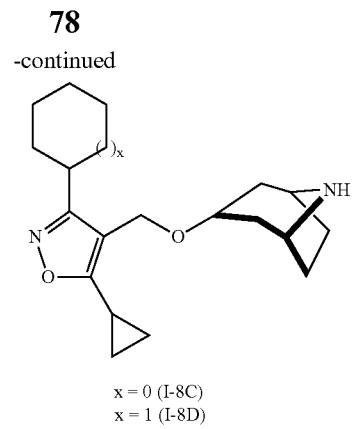

x = 0 (I-8C)
x = 1 (I-8D)

Intermediates I-8A[MS m/z 375.2 (M-ᵗBu+1)]; I-8B[MS m/z 361.2 (M-ᵗBu+1)]; I-8C and I-8D were prepared from corresponding cyclopentanecarbaldehyde or yclohexanecarbaldehyde using the analogous procedures as were described for the preparation of Intermediate 1.

Intermediate 9

4-(chloromethyl)-5-cyclopropyl-3-(4,4-dimethylcyclohexyl)isoxazole

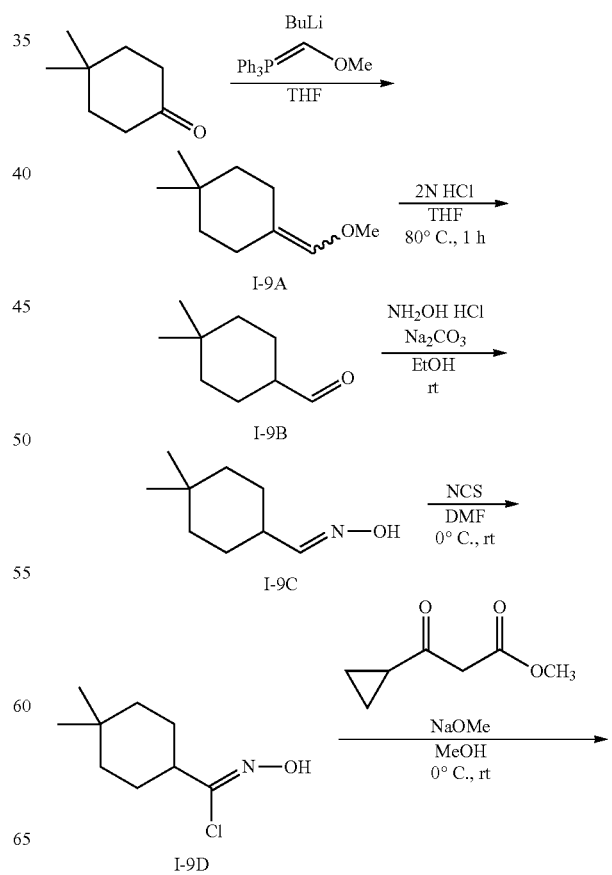

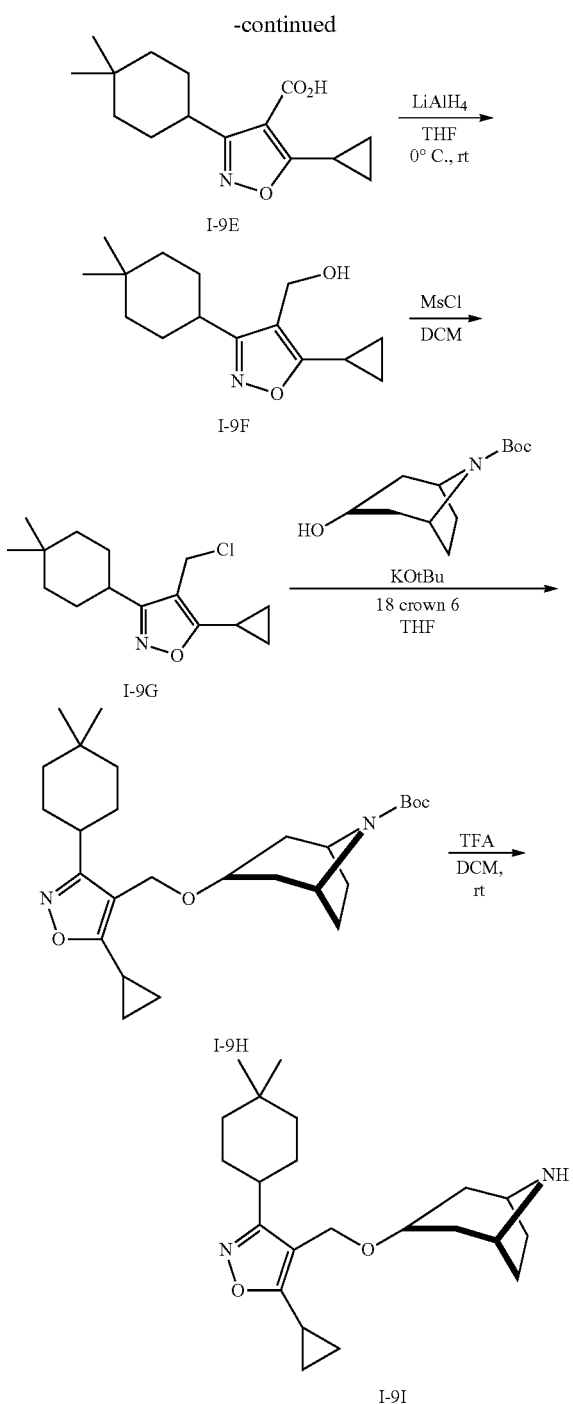

4-(methoxymethylene)-1,1-dimethylcyclohexane (I-9A). An oven-dried 500 mL one-necked round bottomed flask was charged with (methoxymethyl)triphenylphosphonium bromide (22.4 g, 65.4 mmol) and dry THF (40 mL) and then cooled to −78°C. To this solution was added n-BuLi (2.8 M in hexane, 23.3 mL, 65.4 mmol) ove(10 min by syringe. The resultant red ylide solution was then warmed to rt, stirred fo(3 hours, and cooled to −78°C. To this ylide solution was added 4-dimethyl-cyclohexanone (5.5 g, 43.6 mmol) in dry THF (5 mL) via syringe ove(10 min. After being stirred fo(1 hour at −78°C., the reaction mixture was warmed to rt slowly and stirred fo(10 hours. After that the reaction mixture was cooled to 0°C., quenched with aq. NaHCO₃ (60 mL), and extracted with ether (3×60 mL). The organic layer was washed with brine (60 mL) and dried over sodium sulfate, filtered, and concentrated. The residue was purified by silica chromatography using hexane-Et₂βisocratic 20% as eluant to give the title compound as clear oil. $^1$H NMR (400 MHz, CDCl₃) δ 5.75 (bs, 1H), 3.75 (s, 3H), 2.18 (ddd, J=12.8, 6.4, 1.2 Hz, 2H), 1.95 (ddd, J=12.8, 6.4, 1.2 Hz, 2H), 1.27 (ddd, J=12.8, 6.8, 2.0 Hz, 4H), 0.91 (s, 6H). No ionization by LCMS.

4,4-Dimethylcyclohexanecarbaldehyde (I-9B). A solution of flask 4-(methoxymethylene)-1,1-dimethylcyclohexane (2.3 g, 14.9 mmol) in a 4:1 THF/2N HCl mixture (100 mL) was refluxed fo(1 hour. The volatile was removed in vacuo and the residue was cooled to 0°C. and neutralized with 1N NaOH and extracted with Et₂O (3×60 mL). The organic layer was washed with water (50 mL), brine (60 mL) and dried over sodium sulfate, filtered, and concentrated. The residue was purified by chromatography with hexane-DCM 10% linear gradient as eluant to give the title compound as clear oil. $^1$H NMR (400 MHz, CDCl₃) δ 9.64 (d, J=1.6 Hz, 1H), 2.19-2.12 (m, 1H), 1.79-1.72 (m, 2H), 1.59-1.40 (m, 5H), 1.25-1.18 (m, 1H), 0.92 (s, 3H), 0.87 (s, 3H). No ionization by LCMS.

4,4-Dimethylcyclohexanecarbaldehyde oxime (I-9C) was prepared by reaction of 4,4-dimethylcyclohexanecarbaldehyde and hydroxylamine hydrochloride by following the same protocol as described for I-6C. MS m/z 156.1 (M+1).

N-Hydroxy-4,4-dimethylcyclohexanecarbimidoyl chloride (I-9D) was prepared by reaction of 4,4-dimethylcyclohexanecarbaldehyde oxime and N-chloro succinimide following the same protocol as described for I-6B. MS m/z 190.1 (M+1).

5-cyclopropyl-3-(4,4-dimethylcyclohexyl)isoxazole-4-carboxylic acid (I-9E) Was prepared by reaction of N-hydroxy-4,4-dimethylcyclohexanecarbimidoyl chloride and methyl 3-cyclopropyl-3-oxopropanoate following the same protocol as described for I-6E. MS m/z 264.1 (M+1).

(5-cyclopropyl-3-(4,4-dimethylcyclohexyl)isoxazol-4-yl) methanol (I-9F) was prepared by reaction of methyl 5-cyclopropyl-3-(4,4-dimethylcyclohexyl)isoxazole-4-carboxylate and LiAlH₄ following the same protocol as described for I-6F. $^1$H NMR (400 MHz, CDCl₃) δ 4.56 (s, 3H), 2.65 (m, 1H), 2.05-1.99 (m, 1H), 1.81-1.75 (m, 4H), 1.52-1.48 (m, 2H), 1.33-1.28 (m, 2H), 1.14-1.10 (m, 2H), 1.04-1.01 (m, 2H), 0.95 (s, 3H), 0.94 (s, 3H). MS m/z 250.1 (M+1).

4-(chloromethyl)-5-cyclopropyl-3-(4,4-dimethylcyclohexyl)isoxazole (I-9G) was prepared by following the analogous procedure as previously described for intermediate 1-6. $^1$H NMR (400 MHz, CDCl₃) δ 4.50 (s, 2H), 2.62-2.54 (m, 1H), 2.02-1.95 (m, 1H), 1.83-1.72 (m, 4H), 1.52-1.49 (m, 2H), 1.31 (ddd, J=25.2, 17.6, 5.6 Hz, 2H), 1.16-1.04 (m, 2H), 1.03-1.04 (m, 1H), 0.96 (s, 3H), 0.95 (s, 3H). MS m/z 268.1 (M+1).

tert-Butyl 3-((5-cyclopropyl-3-(4,4-dimethylcyclohexyl) isoxazol-4-yl)methoxy)-8-azabicyclo[3.2.1]octane-8-carboxylate (I-9H) was prepared by following the analogous procedure as previously described for example 13. MS m/z 403.2 (M−56+1).

4-((8-Azabicyclo[3.2.1]octan-3-yloxy)methyl)-5-cyclopropyl-3-(4,4-dimethylcyclohexyl)isoxazole (I-9I) was prepared by following the analogous procedure as previously described for Example 13. MS m/z 359.2 (M+1).

Intermediate 10

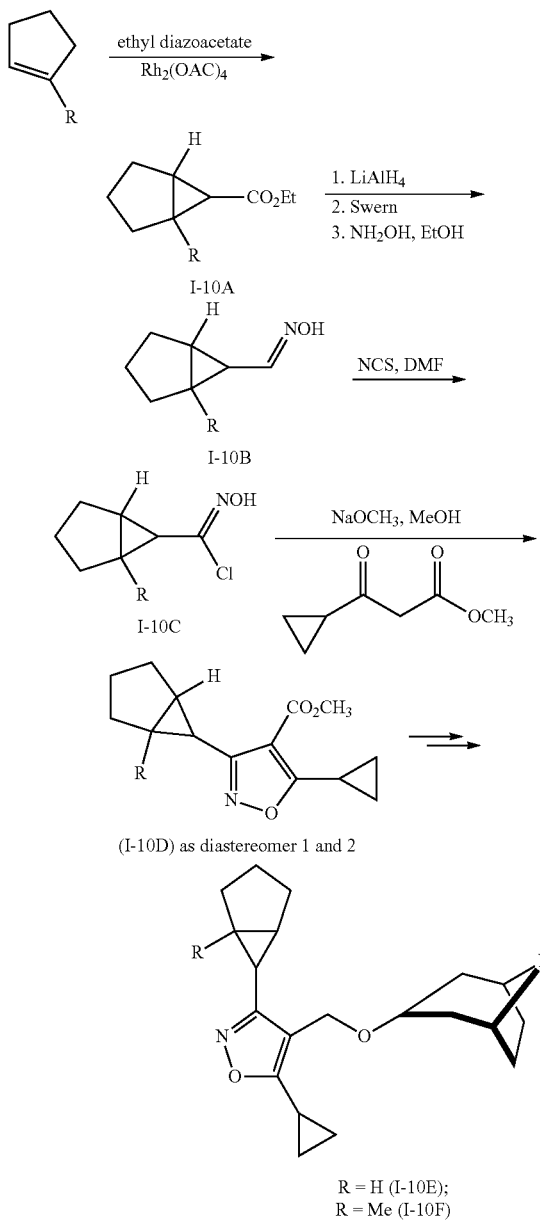

(I-10D) as diastereomer 1 and 2

R = H (I-10E);
R = Me (I-10F)

Ethyl bicyclo[3.1.0]hexane-6-carboxylate (I-10A). A solution of cyclopentene (5.0 g, 0.073 mol) and Rh$_2$(OAc)$_2$ (23.8 mg, 0.073 mmol) in dichloromethane (23 mL) was treated with the dropwise addition of ethyl diazoacetate (7.6 mL, 0.073 mol) in dichloromethane (23 mL) ove(5 hours via syringe pump. Reaction stirred fo(30 min and was then passed through a basic Alumina plug (dichloromethane as the elutant) to remove any catalyst. Reaction was concentrated in vacuo and chromatographed (SiO$_2$, linear gradient, 0-60% EtOAc in Hexanes to give the desired compound as a mixture of diastereomers. MS m/z 155.3 (M+1).

Bicyclo[3.1.0]hexane-6-carbaldehyde oxime (I-10B). A cold (0°C.) solution of the I-10A (5.2 g, 0.034 mol) in THF (113 mL) was treated with the dropwise addition of lithium aluminum hydride (44 mL, 1M solution in Et$_2$O). Afte(1 hr the reaction was recooled to 0°C. and treated with the dropwise addition of 1N HCl (aq.) until a solution persisted. The reaction was then extracted with EtOAc. The organic phase was collected, dried (MgSO$_4$), filtered, and concentrated. The crude liquid was distilled (62-67°C. at 0.1 mmHg) to give the desired material as a mixture of diastereomers.

A cold (−78°C.) solution of oxalyl chloride (2.6 mL, 0.031 mol) in dichloromethane (70 mL) was treated with the dropwise addition of DMSO (3.4 mL, 0.047 mol) in dichloromethane (15 mL). Afte(2 minutes, the alcohol from above (3.1 g, 0.028 mol) in 30 mL of dichloromethane was introduced. Afte(15 minutes, triethylamine (19.3 mL) was introduced dropwise. The reaction was then warmed to room temperature and diluted with dichloromethane and water. The organic phase was collected, washed with 1N HCl (aq.), water, saturated Na$_2$CO$_3$ (aq.), water, and brine. The organic phase was then dried (MgSO$_4$), filtered, concentrated, and diluted with ethanol (10 mL). The ethanolic solution was cooled to 0°C. and treated with 50% hydroxylamine (aq.) (2.2 mL). The reaction warmed to room temperature and stirred overnight. The reaction was concentrated in vacuo, diluted with EtOAc, and then washed with water, dried (MgSO$_4$), filtered and concentrated. MS m/z 126.2 (M+1).

N-hydroxybicyclo[3.1.0]hexane-6-carbimidoyl chloride (I-10C). A cold (0°C.) solution of I-10B (2.9 g, 0.022 mol) in DMF (25 mL) was treated with the portionwise addition of NCS (3.4 g, 0.026 mmol). The reaction slowly warmed to room temperature and stirred for an additional hour. The reaction was treated with sat'd NaCl (aq.) and extracted with Et$_2$O. The organics were dried (MgSO$_4$), filtered, and concentrated. Crude material was taken forward without further purification. MS m/z 160.1 (M+1).

Methyl 3-(bicyclo[3.1.0]hexan-6-yl)-5-cyclopropylisoxazole-4-carboxylate (I-10D). A cold (0°C.) solution of methyl 3-cyclopropyl-3-oxopropanoate (4.2 g, 0.030 mol) in methanol (100 mL) was treated with the dropwise addition of sodium methoxide in methanol (6.2 mL, 25 wt %). Afte(10 min., Intermediate I-10C (3.7 g, 0.023 mol) was introduced. The reaction stirred fo(1 hour and was then concentrated in vacuo, diluted with water and extracted with EtOAc. The organic phase was washed with sat'd NaHCO$_3$ (aq) and then dried (MgSO$_4$), filtered, and concentrated. The crude residue was purified and isomers separated by column chromatography (SiO$_2$, linear gradient, 0-15% EtOAc in Hexanes) to afford the desired products. First eluting peak (400 MHz, CDCl$_3$): δ 3.87 (s, 3H), 2.75 (m, 1H), 2.16 (dd, J=3.4, 3.2 Hz, 1H), 1.91 (m, 2H), 1.84 (m, 2H), 1.77 (m, 2H), 1.64 (m, 1H), 1.26 (m, 1H), 1.20 (m, 2H), 1.13 (m, 2H); second eluting peak (400 MHz, CDCl$_3$): 3.85 (s, 3H), 2.78 (m, 1H), 1.84-1.72 (m, 7H), 1.42 (m, 1H), 1.22 (m, 2H), 1.14 (m, 2H), 0.37 (m, 1H); MS m/z 248.1 (M+1).

tert-butyl 3-((3-(bicyclo[3.1.0]hexan-6-yl)-5-cyclopropylisoxazol-4-yl)methoxy)-8-azabicyclo[3.2.1]octane-8-carboxylate (I-10E) was prepared following analogous procedures in Intermediate 9. MS m/z 373.2 (M-$^t$Bu+1)).

tert-butyl 3-((5-cyclopropyl-3-(1-methylbicyclo[3.1.0] hexan-6-yl)isoxazol-4-yl)methoxy)-8-azabicyclo[3.2.1]octane-8-carboxylate (I-10OF) was prepared following analogous procedures in Intermediate 9. MS m/z 387.3 (M-$^t$Bu+1)).

Intermediate 11

4-(chloromethyl)-5-cyclopropyl-3-(spiro[2.5]octan-4-yl)isoxazole

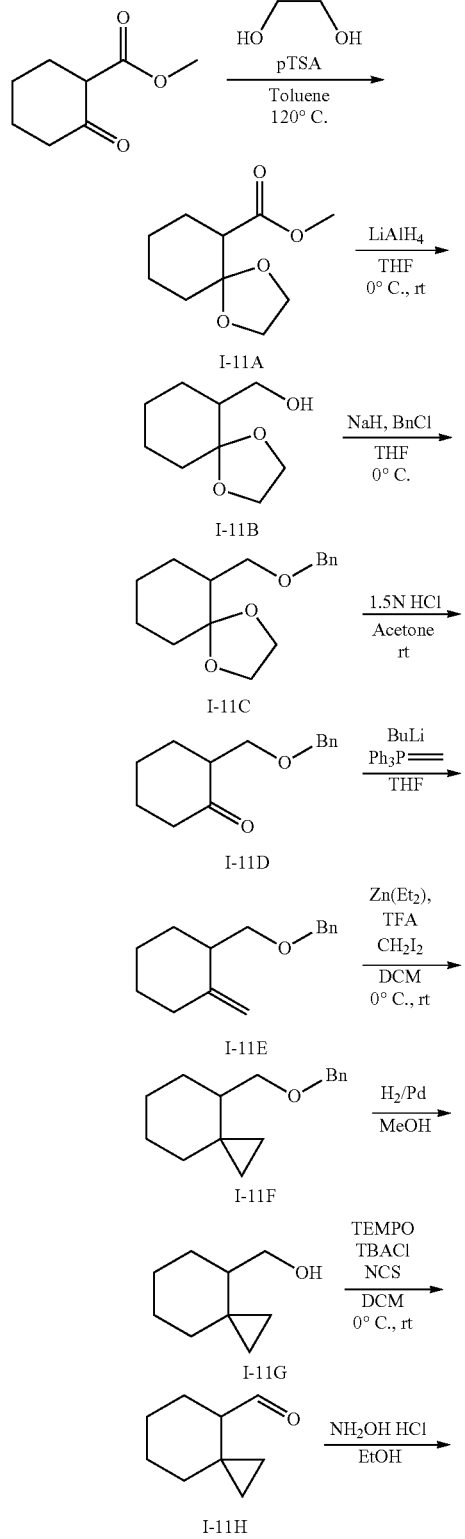

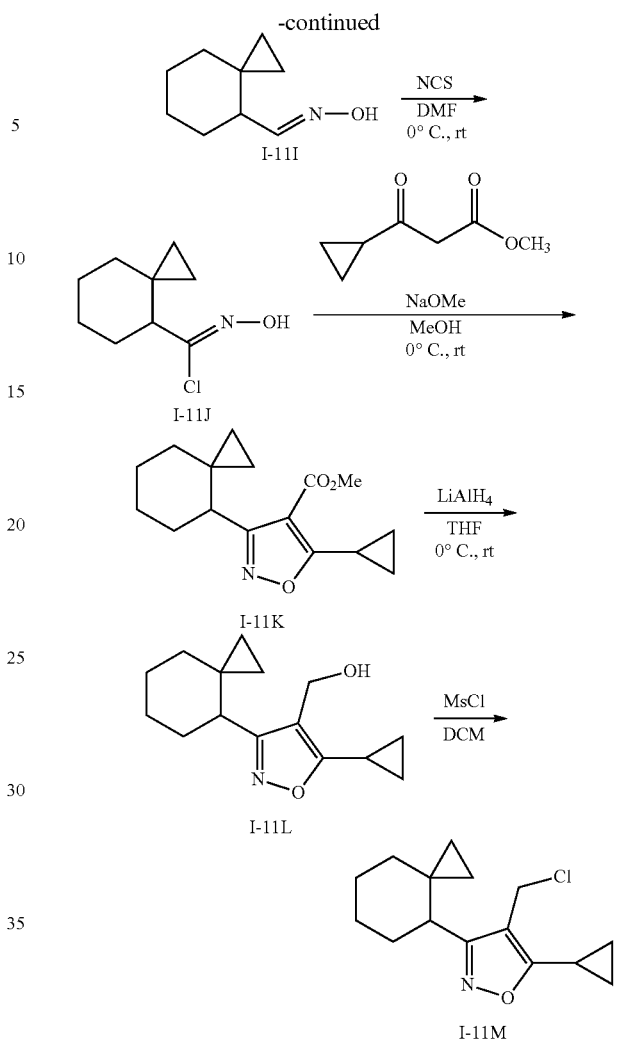

Methyl 1,4-dioxaspiro[4.5]decane-6-carboxylate (I-11A). To a solution of 2-oxocyclohexanecarboxylate (10.7 g, 68.5 mmol) in anhydrous toluene (80 mL) was added ethylene glycol (38.2 mL, 685 mmol) and pTSA (3.5 g, 20.55 mmol) and the reaction mixture was heated to 120°C. fo(18 hours. The mixture was then cooled to 0°C. and carefully quenched with aq. sodium carbonate. The volatile was separated and he aqueous was extracted with ether (3×50 mL). The combined organic layer was washed with sodium carbonate (2×50 mL), brine (60 mL), dried over sodium sulfate, filtered, and concentrated. The residue was purified by chromatography with hexane-EtOAc 10% linear gradient as eluant to give the title compound as clear oil. MS m/z 201.1 (M+1).

1,4-dioxaspiro[4.5]decan-6-ylmethanol (I-11B). To a solution of methyl 1,4-dioxaspiro[4.5]decane-6-carboxylate (3.87 g, 19.3 mmol) in THF (40 mL) and cooled to 0°C. LiAlH$_4$ was added dropwise and stirred for 5 hours. The reaction was quenched by subsequent dropwise addition of water (1.3 mL) 15% NaOH (1.3 mL) and water (2.6 mL) and filtered thru a CELITE® pad. Concentration of the filtrate afforded the title compound as clear oil that was carried to the next step without further purification. MS m/z 173.1 (M+1).

6-((Benzyloxy)methyl)-1,4-dioxaspiro[4.5]decane (I-11C). A solution of 1,4-dioxaspiro[4.5]decan-6-ylmethanol (2.3 g, 13.3 mmol) in THF (20 mL) and cooled in an ice bath, was treated with a NaH (0.48 g, 20.0 mmol). The reaction mixture was stirred for 1 hour and then benzyl bromide (2.4 mL, 20 mmol) in THF (5 mL) was added dropwise. The reaction was stirred at rt for 5 hours and then diluted with ethyl acetate (100 mL). The organic layer was washed with water, brine and dried over sodium sulfate and concentarted. Purification by silica chromatography using hexane-Et$_2$O 20% linear gradient afforded the title compound as pale yellow solid. MS m/z 263.2 (M+1).

2-((Benzyloxy)methyl)cyclohexanone (I-11D). A solution of 6-((Benzyloxy)methyl)-1,4-dioxaspiro[4.5]decane (2.4 g 9.1 mmol) in acetone (40 mL) was treated with 1.5N HCl (18 mL) and stirred at rt for 5 hours. The reaction mixture was neutralized with aqueous sodium carbonate and the volatile removed in vacuo. The residue was extracted with Et$_2$O (3×50 mL) and the combined organic layer were washed with water (30 mL), brine (30 mL) and dried over sodium sulfate and concentrated to yield the desired product as pale yellow oil that was used in the next step without further purification. MS m/z 219.1 (M+1).

(((2-Methylenecyclohexyl)methoxy)methyl)benzene (I-11E). An oven-dried 250 mL one-necked round bottomed flask was charged with methyltriphenylphosphonium bromide (4.3 g, 12.3 mmol) and dry THF (20 mL) and then cooled to −78° C. To this solution was added n-BuLi (2.8 M in hexane, 4.3 mL, 12.3 mmol) over 10 min by syringe. The resultant red ylide solution was then warmed to rt, stirred for 3 hours, and cooled to −78° C. To this ylide solution was added 2-((benzyloxy)methyl)cyclohexanone (1.8 g, 8.6 mmol) in dry THF (5 mL) via syringe over 10 min. After being stirred for 1 hour at −78° C., the reaction mixture was warmed to rt slowly and stirred for 10 hours. After that the reaction mixture was cooled to 0° C., quenched with aq. NaHCO$_3$ (60 mL), and extracted with ether (3×60 mL). The organic layer was washed with brine (60 mL) and dried over sodium sulfate, filtered, and concentrated. The residue was chromatographed with hexane-Et$_2$O isocratic 10% as eluant to give the title compound as clear oil. MS m/z 217.1 (M+1).

4-((Benzyloxy)methyl)spiro[2.5]octane (I-11F). This intermediate was prepared from (((2-methylenecyclohexyl)methoxy)methyl)benzene by using the same protocol as described for ethyl spiro[2.5]octane-6-carboxylate (I-7A). $^1$H NMR (400 MHz, CDCl$_3$) δ 7.35-7.31 (m, 4H), 7.29 (m, 1H) 4.49 (q, J=12.4 Hz, 2H), 3.52 (t, J=9.2 Hz, 1H), 3.41 (dd, J=9.2, 5.2 Hz, 1H), 1.72-1.67 (m, 1H), 1.49-1.43 (m, 4H), 1.33-1.26 (m, 1H), 0.88-0.85 (m, 1H), 0.37-0.31 (m, 2H), 0.19-0.14 (m, 2H). MS m/z 231.1 (M+1).

Spiro[2.5]octan-4-ylmethanol (I-11G). To a solution of 4-((benzyloxy)methyl)spiro[2,5]-octane (0.42 g, 1.8 mmol) in a 5:1 MeOH-EtOAc (12 mL) Pd/C (0.05 g, 5 wt %, 50% wet Degussa type) was added. The flask was fitted with a balloon of hydrogen, and the heterogeneous reaction mixture was stirred for 2 hours under a hydrogen atmosphere at rt. The catalyst solids were filtered off and the filtrate was concentrated under vacuum to give the desired product spyri[2.5]octan-4-ylmethanol as clear oil. $^1$H NMR (400 MHz, CDCl$_3$) δ 3.74-3.62 (m, 2H), 3.48 (d, J=5.2 Hz, 2H), 1.65-1.59 (m, 2H), 1.51-1.43 (m, 3H), 1.27-1.24 (m, 1H), 1.12-1.11 (m, 1H), 0.96-0.95 (m, 1H), 0.41-0.37 (m, 1H), 0.29-0.17 (m, 3H). MS m/z 123.1 (M−17+1).

Spiro[2.5]octane-4-carbaldehyde (I-11H) was prepared by following the same protocol as described for I-7B. $^1$H NMR (400 MHz, CDCl$_3$) δ 9.80 (s, 1H), 2.08-2.04 (m, 1H), 1.67-2.56 (m, 4H), 1.48-1.34 (m, 4H), 0.95-0.92 (m, 1H), 0.62-0.57 (m, 1H), 0.51-0.46 (m, 1), 0.35-0.32 (m, 2H). MS m/z 139.1 (M+1).

Spiro[2.5]octane-4-carbaldehyde oxime (I-11I) was prepared by reaction of spiro[2.5]octane-4-carbaldehyde and hydroxylamine following the same procol as described for I-6c. MS m/z 154.1 (M+1).

N-hydroxyspiro[2.5]octane-4-carbimidoyl chloride (I-11J) was prepared by reaction of spiro[2.5]octane-4-carbaldehyde oxime and N-chloro-succinimide following the same protocol as described for I-6B. MS m/z 188.0 (M+1).

5-Cyclopropyl-3-(spiro[2.5]octan-4-yl)isoxazole-4-carboxylic acid (I-11K) was prepared from N-hydroxyspiro[2.5] octane-4-carbimidoyl chloride and methyl 3-cyclopropyl-3-oxopropanoate following the same protocol as described for I-6E. MS m/z 262.1 (M+1).

(5-Cyclopropyl-3-(spiro[2.5]octan-4-yl)isoxazol-4-yl) methanol (I-11L) was prepared by reaction of 5-cyclopropyl-3-(spiro[2.5]octan-4-yl)isoxazole-4-carboxylic acid and LiAlH$_4$ following the same protocol as described for I-6F. MS m/z 248.1 (M+1).

4-(Chloromethyl)-5-cyclopropyl-3-(spiro[2.5]octan-4-yl) isoxazole (I-11M) was prepared by reaction of 5-cyclopropyl-3-(spiro[2.5]octan-4-yl)isoxazol-4-yl)methanol and methansulphonyl chloride following the same protocol as described for I-6G. MS m/z 266.1 (M+1).

Intermediate 12

3-(bicyclo[4.1.0]heptan-3-yl)-4-(chloromethyl)-5-cyclopropylisoxazole

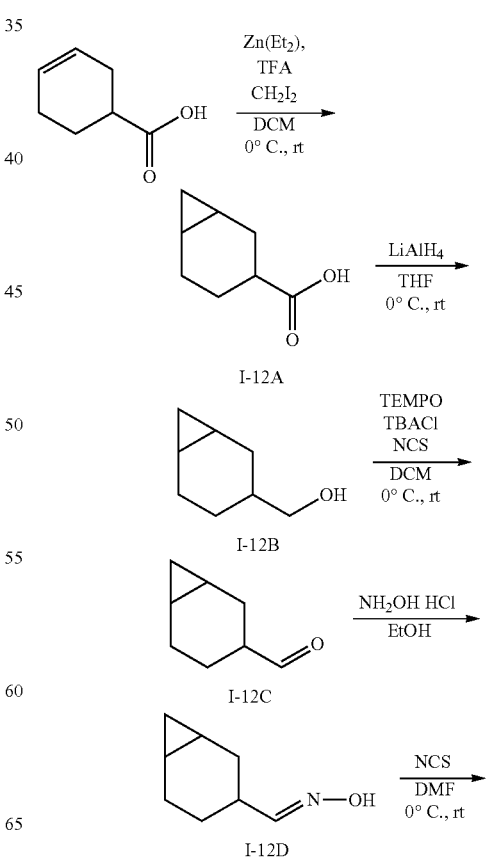

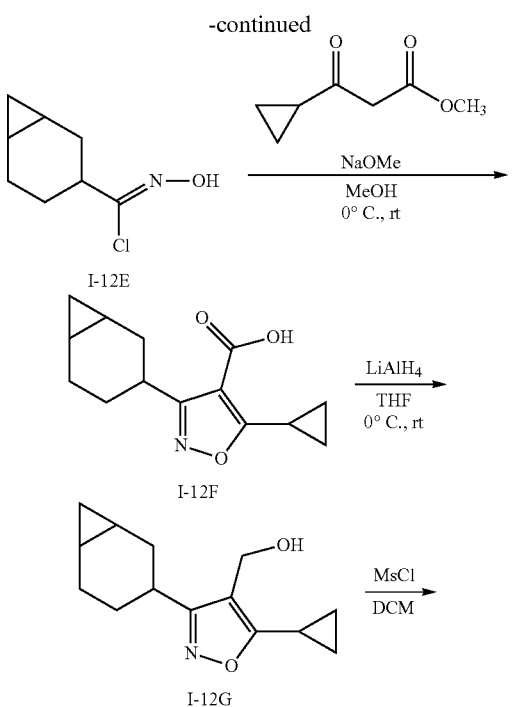

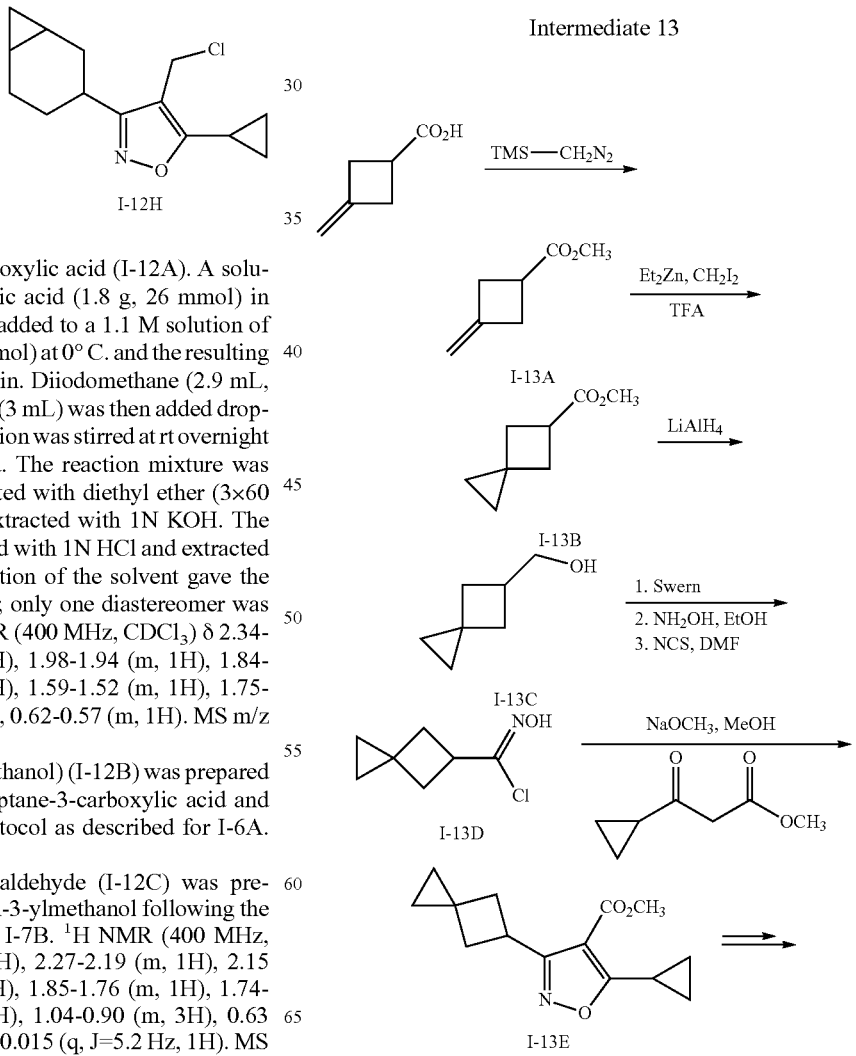

Bicyclo[4.1.0]heptane-3-carbaldehyde oxime (I-12D) was prepared by reaction of bicyclo[4.1.0]heptane-3-carbaldehyde and hydroxylamine following the same procol as described for I-6c. MS m/z 140.1 (M+1).

N-Hydroxybicyclo[4.1.0]heptane-3-carbimidoyl chloride (I-12E) was prepared by reaction of bicyclo[4.1.0]heptane-3-carbaldehyde oxime and N-chloro-succinimide following the same protocol as described for I-6B. MS m/z 174.0 (M+1).

3-(Bicyclo[4.1.0]heptan-3-yl)-5-cyclopropylisoxazole-4-carboxylic acid (I-12F) was prepared from N-hydroxybicyclo[4.1.0]heptane-3-carbimidoyl chloride and methyl 3-cyclopropyl-3-oxopropanoate following the same protocol as described for I-6E. MS m/z 248.1 (M+1).

(3-(Bicyclo[4.1.0]heptan-3-yl)-5-cyclopropylisoxazol-4-yl)methanol (I-12G) was prepared by reaction of 3-(bicyclo[4.1.0]heptan-3-yl)-5-cyclopropylisoxazole-4-carboxylic acid LiAlH$_4$ following the same protocol as described for I-6G. MS m/z 234.1 (M+1).

4-(Chloromethyl)-5-cyclopropyl-3-(spiro[2.5]octan-4-yl)isoxazole (I-12H) was prepared by reaction of 3-(bicyclo[4.1.0]heptan-3-yl)-5-cyclopropylisoxazol-4-yl)methanol and methansulphonyl chloride following the same protocol as described for I-6G. MS m/z 252.1 (M+1).

Intermediate 13

Bicyclo[4.1.0]heptane-3-carboxylic acid (I-12A). A solution of cyclohex-3-enecarboxylic acid (1.8 g, 26 mmol) in dichloro methane (20 mL) was added to a 1.1 M solution of Et,Zn in toluene (26 mL, 28.5 mmol) at 0° C. and the resulting suspension was stirred for 15 min. Diiodomethane (2.9 mL, 25.6 mmol) in dichloromethane (3 mL) was then added dropwise and the pale yellow suspension was stirred at rt overnight as a white precipitate appeared. The reaction mixture was poured into 1N HCl and extracted with diethyl ether (3×60 mL). The organic phase was extracted with 1N KOH. The aqueous phase was then acidified with 1N HCl and extracted with dichloromethane. Evaporation of the solvent gave the title compound as a white solid; only one diastereomer was detectable by $^1$H NMR. $^1$H NMR (400 MHz, CDCl$_3$) δ 2.34-2.26 (m, 1H), 2.21-2.13 (m, 1H), 1.98-1.94 (m, 1H), 1.84-1.78 (m, 1H), 1.76-1.70 (m, 1H), 1.59-1.52 (m, 1H), 1.75-1.07 (m, 1H), 0.93-0.88 (m, 2H), 0.62-0.57 (m, 1H). MS m/z 141.2 (M+1).

Bicyclo[4.1.0]heptan-3-ylmethanol) (I-12B) was prepared by reaction of bicyclo[4.1.0]heptane-3-carboxylic acid and LiAlH$_4$ following the same protocol as described for I-6A. MS m/z 248.1 (M+1).

Bicyclo[4.1.0]heptane-3-carbaldehyde (I-12C) was prepared from bicyclo[4.1.0]heptan-3-ylmethanol following the same protocol as described for I-7B. $^1$H NMR (400 MHz, CDCl$_3$) δ 9.57 (d, J=1.6 Hz, 1H), 2.27-2.19 (m, 1H), 2.15 (2.07 (m, 1H), 2.01-1.96 (m 2H), 1.85-1.76 (m, 1H), 1.74-1.68 (m, 1H), 1.53-2.46 (m, 1H), 1.04-0.90 (m, 3H), 0.63 (ddd, J=18.0, 8.8, 4.8 Hz, 1H), −0.015 (q, J=5.2 Hz, 1H). MS m/z 125.1 (M+1).

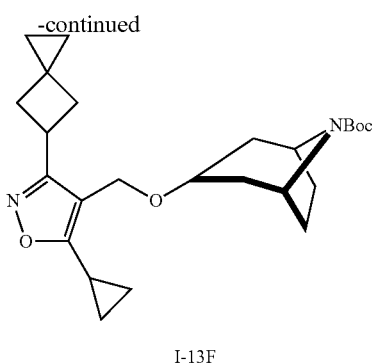

I-13F

Methyl 3-methylenecyclobutanecarboxylate (I-13A). A cold (0° C.) solution of 3-methylenecyclobutanecarboxylic acid (WO2007/063391, 6.07 g, 54.1 mmol) in dichloromethane (180 mL) and methanol (18 mL) was treated with the dropwise addition of (trimethylsilyl)diazomethane (28.4 mL, 2.0 M in Hexanes). After 30 min, 1 mL of conc. HOAc was added and the reaction concentrated in vacuo. (400 MHz, CDCl$_3$) δ 4.78 (m, 2H), 3.67 (s, 3H), 3.10 (m, 1H), 2.98 (m, 2H), 2.88 (m, 2H); MS m/z 127.1 (M+1).

Methyl spiro[2.3]hexane-5-carboxylate (I-13B). A cold (0° C.) solution of diethyl zinc (79.3 mL, 1.0 M in Hexanes) in dichloromethane (66 mL) was treated with the dropwise addition of TFA (6.11 mL, 79.3 mL) in dichloromethane (27 mL). After 1 hour of stirring, diiodomethane (6.39 mL, 79.3 mmol) in dichloromethane (27 mL) was then introduced. After 40 min, I-13A (4.00 g, 31.7 mmol) dichloromethane (10 mL) was added dropwise. The reaction was left to stir for 2 hours and then quenched with sat'd NH$_4$Cl (aq.). Phases were separated and the organic phase collected, dried (MgSO$_4$), filtered, concentrated, and distilled (42-44° C., 0.1 mmHg) to afford the desired spirocycle. (400 MHz, CDCl$_3$) δ 3.69 (s, 3H), 3.28 (m, 1H), 2.49 (m, 2H), 2.22 (m, 2H), 0.43 (m, 4H); MS m/z 141.1 (M+1).

Spiro[2.3]hexan-5-ylmethanol (I-13C). A cold (0° C.) solution of 1-13B (2.00 g, 14.3 mmol) in THF (48 mL) was treated with the dropwise addition of lithium aluminum hydride (18.6 mL, 1.0 M solution in THF). After 2 hr of stirring, the reaction was cooled to 0° C. and treated with the dropwise addition of 1N HCl (aq.) until a solution persisted. The reaction was then extracted with EtOAc. The organic phase was dried (MgSO$_4$), filtered, concentrated, and distilled (51-52° C., 0.1 mm Hg) to give the desired material. (400 MHz, CDCl$_3$) δ 3.69 (d, J=7.1 Hz, 2H), 2.58 (m, 1H), 2.15 (m, 2H), 1.83 (m, 2H), 1.73 (s, 1H), 0.38 (m, 4H); MS m/z 113.2 (M+1).

N-hydroxyspiro[2.3]hexane-5-carbimidoyl chloride (I-13D). A cold (−78° C.) solution of oxalyl chloride (0.58 mL, 6.7 mmol) in dichloromethane (13 mL) was treated with the dropwise addition of DMSO (0.74 mL) in dichloromethane (4 mL). After 2 minutes, I-13C (684 mg, 6.10 mmol) in dichloromethane (8 mL) was introduced. After 15 minutes, triethylamine (4.25 mL) was introduced dropwise. The reaction was then warmed to room temperature and diluted with dichloromethane and water. The organic phase was collected and washed with 1N HCl (aq.), water, saturated Na$_2$CO$_3$ (aq.), water, and brine. The organic phase was dried (MgSO$_4$), filtered, and concentrated. The crude material was taken upon in ethanol (10 mL) and treated with 50% hydroxylamine (0.56 mL). After overnight stirring, the reaction was concentrated in vacuo. This residue was diluted with DMF (3.5 mL) and cooled to 0° C. NCS (0.91 g, 6.8 mmol) was introduced and the reaction slowly warmed to room temperature and stirred for 2 hours. The reaction was treated with saturated NaCl (aq.) and extracted with Et$_2$O. Organics were washed with brine and then dried (MgSO$_4$), filtered, and concentrated. MS m/z 160.1 (M+1).

Methyl 5-cyclopropyl-3-(spiro[2.3]hexan-5-yl)isoxazole-4-carboxylate (I-13E): A cold (0° C.) solution of methyl 3-cyclopropyl-3-oxopropanoate (1.13 g, 7.93 mmol) in methanol (26 mL) was treated with the dropwise addition of sodium methoxide in methanol (1.65 mL, 25% wt). After 10 min., I-13D (0.97 g, 6.1 mmol) was introduced. The reaction stirred for 1 hour and was concentrated in vacuo. The residue was diluted with water and extracted with EtOAc. The organic phase was washed with sat'd NaHCO$_3$ (aq) and then dried (MgSO$_4$), filtered, and concentrated. The crude residue was purified by column chromatography (SiO$_2$, linear gradient, 0-10% EtOAc in hexanes) to afford the desired spirocycle. (400 MHz, CDCl$_3$) δ 3.96 (m, 1H), 3.84 (s, 3H), 2.80 (m, 1H), 2.57 (m, 2H), 2.38 (m, 2H), 1.26 (m, 2H), 1.16 (m, 2H), 0.51 (m, 2H), 0.39 (m, 2H); MS m/z 248.2 (M+1).

tert-butyl 3-((5-cyclopropyl-3-(spiro[2.3]hexan-5-yl)isoxazol-4-yl)methoxy)-8-azabicyclo[3.2.1]octane-8-carboxylate (I-13F) was prepared following the same procedures in Intermediate 1. MS m/z 373.3 (M-$^t$Bu+1).

Intermediate 14 tert-butyl 3-((5-cyclopropyl-3-(2,6,6-trimethylbicyclo[3.1.1]heptan-3-yl)isoxazol-4-yl)methoxy)-8-azabicyclo[3.2.1]octane-8-carboxylate

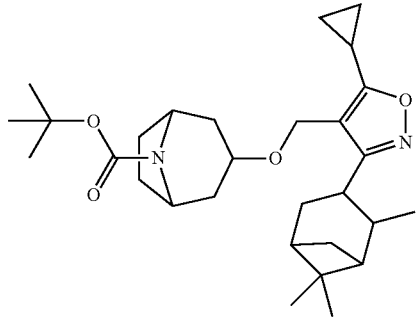 [SMILES: CC1C(c2noc(C3CC3)c2COC2CC3CCC(C2)N3C(=O)OC(C)(C)C)CC2CC1C2(C)C]

tert-butyl 3-((5-cyclopropyl-3-(2,6,6-trimethylbicyclo[3.1.1]heptan-3-yl)isoxazol-4-yl)methoxy)-8-azabicyclo[3.2.1]octane-8-carboxylate was prepared from the commercially available 2,6,6-trimethylbicyclo[3.1.1]heptane-3-carboxylic acid following analogous procedures in Intermediate 13. MS m/z 429.3 (M-$^t$Bu+1).

Intermediate 15

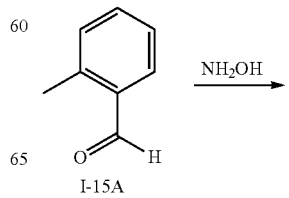

I-15A

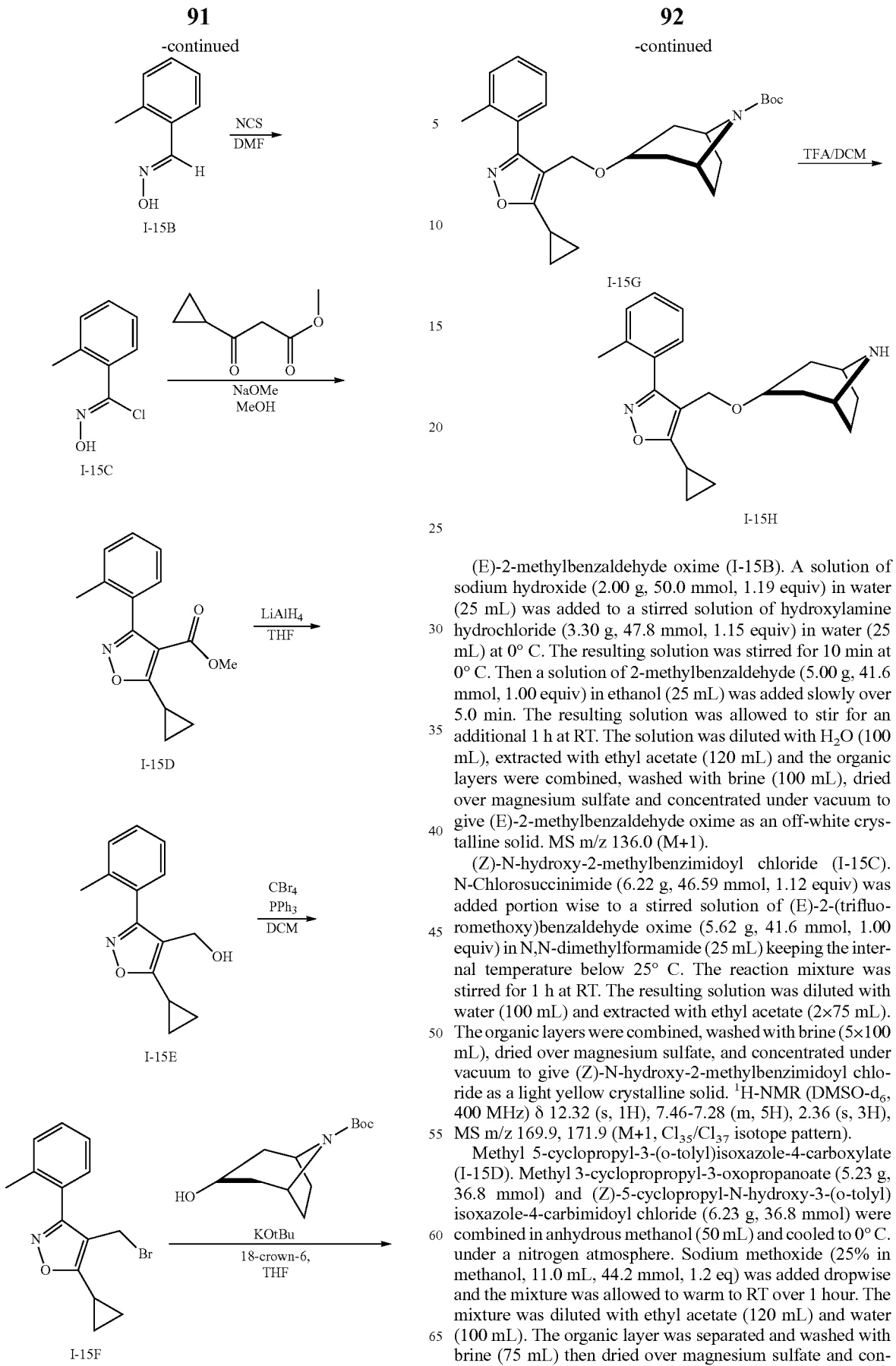

(E)-2-methylbenzaldehyde oxime (I-15B). A solution of sodium hydroxide (2.00 g, 50.0 mmol, 1.19 equiv) in water (25 mL) was added to a stirred solution of hydroxylamine hydrochloride (3.30 g, 47.8 mmol, 1.15 equiv) in water (25 mL) at 0° C. The resulting solution was stirred for 10 min at 0° C. Then a solution of 2-methylbenzaldehyde (5.00 g, 41.6 mmol, 1.00 equiv) in ethanol (25 mL) was added slowly over 5.0 min. The resulting solution was allowed to stir for an additional 1 h at RT. The solution was diluted with $H_2O$ (100 mL), extracted with ethyl acetate (120 mL) and the organic layers were combined, washed with brine (100 mL), dried over magnesium sulfate and concentrated under vacuum to give (E)-2-methylbenzaldehyde oxime as an off-white crystalline solid. MS m/z 136.0 (M+1).

(Z)-N-hydroxy-2-methylbenzimidoyl chloride (I-15C). N-Chlorosuccinimide (6.22 g, 46.59 mmol, 1.12 equiv) was added portion wise to a stirred solution of (E)-2-(trifluoromethoxy)benzaldehyde oxime (5.62 g, 41.6 mmol, 1.00 equiv) in N,N-dimethylformamide (25 mL) keeping the internal temperature below 25° C. The reaction mixture was stirred for 1 h at RT. The resulting solution was diluted with water (100 mL) and extracted with ethyl acetate (2×75 mL). The organic layers were combined, washed with brine (5×100 mL), dried over magnesium sulfate, and concentrated under vacuum to give (Z)-N-hydroxy-2-methylbenzimidoyl chloride as a light yellow crystalline solid. $^1$H-NMR (DMSO-$d_6$, 400 MHz) δ 12.32 (s, 1H), 7.46-7.28 (m, 5H), 2.36 (s, 3H), MS m/z 169.9, 171.9 (M+1, $Cl_{35}/Cl_{37}$ isotope pattern).

Methyl 5-cyclopropyl-3-(o-tolyl)isoxazole-4-carboxylate (I-15D). Methyl 3-cyclopropropyl-3-oxopropanoate (5.23 g, 36.8 mmol) and (Z)-5-cyclopropyl-N-hydroxy-3-(o-tolyl)isoxazole-4-carbimidoyl chloride (6.23 g, 36.8 mmol) were combined in anhydrous methanol (50 mL) and cooled to 0° C. under a nitrogen atmosphere. Sodium methoxide (25% in methanol, 11.0 mL, 44.2 mmol, 1.2 eq) was added dropwise and the mixture was allowed to warm to RT over 1 hour. The mixture was diluted with ethyl acetate (120 mL) and water (100 mL). The organic layer was separated and washed with brine (75 mL) then dried over magnesium sulfate and concentrated under vacuum. The oil was purified by column chromatography (SiO₂, linear gradient, 0-100% ethyl acetate in hexanes) to afford the desired product. MS m/z 258.0 (M+1).

(5-Cyclopropyl-3-(o-tolyl)isoxazol-4-yl)methanol (I-15-E). Lithium aluminum hydride (1M in tetrahydrofuran, 29 mL, 29 mmol, 2.5 eq) was added to a dry three-necked flask filled with nitrogen and cooled to 0° C. Methyl 5-cyclopropyl-3-(o-tolyl)isoxazole-4-carboxylate (3.02 g, 11.7 mmol) was dissolved in tetrahydrofuran (40 mL) and added dropwise to the flask, ensuring that the internal temperature remained below −10° C. The mixture was stirred for an hour, then ethyl acetate (1.3 mL) was added dropwise, keeping the temperature below 0° C. followed by water (1.3 mL), taking care that the mixture was vigorously stirring at all times. Sodium hydroxide solution (3.9 mL, 15% solution by weight) was added dropwise and the mixture stirred vigorously for a further 30 minutes, warming up to RT. The mixture was filtered through a CELITE® pad, which was washed with ethyl acetate (120 mL). The organics were washed with water (100 mL) and brine (75 mL) then dried over magnesium sulfate and concentrated under vacuum and purified by column chromatography (SiO₂, linear gradient, 0-100% ethyl acetate in hexanes) to afford the desired product. ¹H-NMR (MeOH-d₄, 400 MHz) δ 7.41-7.26 (m, 4H), 4.36 (s, 2H), 2.34-2.27 (m, 1H), 2.26 (s, 3H), 1.19-1.15 (m, 4H), MS m/z 230.0 (M+1).

4-(Bromomethyl)-5-cyclopropyl-3-(o-tolyl)isoxazole (I-15F). Into a 100 mL round bottom flask was placed (5-cyclopropyl-3-(o-tolyl)isoxazol-4-yl)methanol (1.86 g, 8.11 mmol), triphenylphosphine (3.50 g, 12.2 mmol, 1.5 equiv) and dichloromethane (50 mL). The mixture was stirred until completely dissolved, and then slowly cannulated dropwise into a stirring solution of carbon tetrabromide (4.00 g, 12.2 mmol, 1.5 eq) in dichloromethane (20 mL). The solution was stirred for one hour and the solvent was then evaporated in vacuo. The crude residue was purified by silica gel chromatography using a 0-50% gradient of ethyl acetate/hexanes. The desired product was obtained as a yellow oil. MS m/z 292.0/294.0 (M+1, Br₇₉/Br₈₁ isotope pattern).

tert-Butyl 3-((5-cyclopropyl-3-(o-tolyl)isoxazol-4-yl)methoxy)-8-azabicyclo[3.2.1]octane-8-carboxylate (I-15G). A flask was purged with nitrogen and then charged with N-Boc-nortropine (1.64 g, 7.20 mmol), 18-crown-6 (1.59 g, 6.00 mmol), and anhydrous tetrahydrofuran (60 mL). Potassium tert-butoxide (1.34 g, 12.0 mmol) was added portionwise, and the mixture was stirred vigorously under nitrogen for 1 hour. 4-(Bromomethyl)-5-cyclopropyl-3-(o-tolyl)isoxazole (1.75 g, 6.00 mmol) in tetrahydrofuran (20 mL, anhydrous) was added dropwise, and the reaction mixture was stirred for 1 hour under nitrogen. The solvent was reduced in vacuo and the mixture diluted with water (100 mL) and ethyl acetate (100 mL). The organic layer was separated, dried over magnesium sulfate, and evaporated in vacuo. The crude residue was purified by silica gel chromatography using a gradient of 0-100% ethyl acetate/hexanes to yield the desired product as a yellow oil. MS m/z 439.2 (M+1).

4-((8-azabicyclo[3.2.1]octan-3-yloxy)methyl)-5-cyclopropyl-3-(o-tolyl)isoxazole (I-15H). The previous amine, tert-Butyl 3-((5-cyclopropyl-3-(o-tolyl)isoxazol-4-yl)methoxy)-8-azabicyclo[3.2.1]octane-8-carboxylate (1.60 g, 3.65 mmol) was dissolved in trifluoroacetic acid in dichloromethane (30 mL, 20% solution) at RT. The solution was stirred for 1 hour at RT and the solvent was evaporated. The residue was dissolved in ethyl acetate (125 mL), washed with a saturated solution of sodium bicarbonate (100 mL), the organic layer was dried with magnesium sulfate and evaporated in vacuo. The crude residue was purified by silica gel chromatography using a gradient of 0-20% ethanol/dichloromethane to afford the desired product as a colorless oil. ¹H-NMR (DMSO-d₆, 400 MHz) δ 8.44 (bs, 1H), 7.43-7.34 (m, 2H), 7.32-7.28 (m, 2H), 4.21 (s, 2H), 3.83 (bs, 2H), 3.55 (t, J=4.0 Hz, 1H), 2.35-2.28 (m, 1H), 2.20 (s, 3Hc-1.70 (m, 8H), 1.16-1.06 (m, 4H). MS m/z 339.2 (M+1).

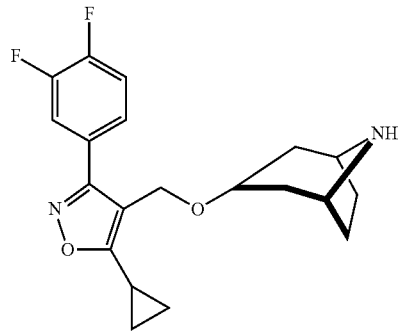

I-15I

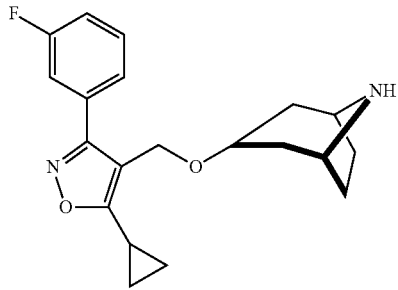

I-15J

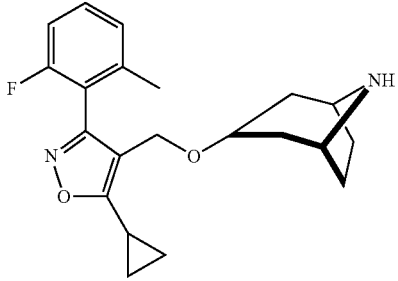

I-15K

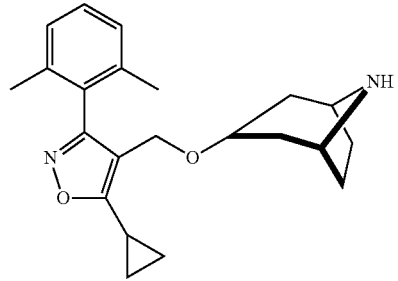

I-15L

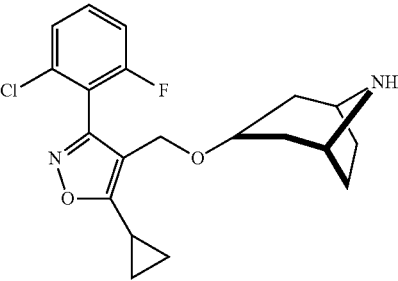

I-15M

-continued

I-15N
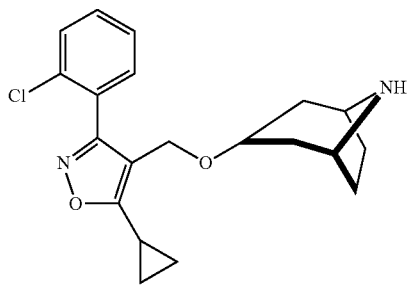

I-15O
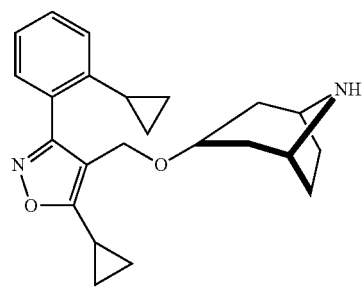

I-15P
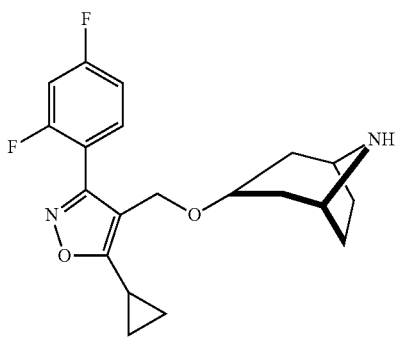

I-15Q
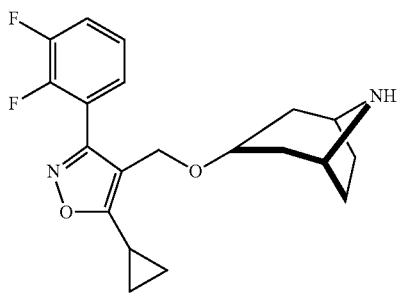

I-15R
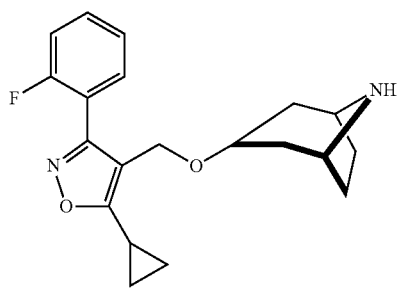

4-((8-Azabicyclo[3.2.1]octan-3-yloxy)methyl)-5-cyclopropyl-3-(3,4-difluorophenyl)isoxazole (I-15I) was prepared from 3,4-difluorobenzaldehyde according to the same procedures as described for (I-15H). MS m/z 343.1 (M+1).

4-((8-Azabicyclo[3.2.1]octan-3-yloxy)methyl)-5-cyclopropyl-3-(3-fluorophenyl)isoxazole (I-15J) was prepared from 3-fluorobenzaldehyde according to the same procedures as described for (I-15H). MS m/z 343.1 (M+1).

4-((8-Azabicyclo[3.2.1]octan-3-yloxy)methyl)-5-cyclopropyl-3-(2-fluoro-6-methylphenyl)isoxazole (I-15K) was prepared from 2-fluoro-6-methyl-benzaldehyde according to the same procedures as described for (I-15H). NMR (DMSO-$d_6$, 400 MHz) δ 8.54 (bs, 1H), 7.49-7.43 (m, 1H), 7.24-7.16 (m, 2H), 4.20 (s, 2H), 3.81 (bs, 2H), 3.52 (t, J=4.0 Hz, 1H), 2.37-2.30 (m, 1H), 2.14 (s, 3H), 1.95-1.66 (m, 8H), 1.20-1.06 (m, 4H). MS m/z 357.2 (M+1).

4-((8-Azabicyclo[3.2.1]octan-3-yloxy)methyl)-5-cyclopropyl-3-(2,6-dimethylphenyl)isoxazole (I-15L) was prepared from 2,6-dimethylbenzaldehyde according to the same procedures as described for (I-15H). MS m/z 353.2 (M+1).

4-((8-Azabicyclo[3.2.1]octan-3-yloxy)methyl)-3-(2-chloro-6-fluorophenyl)-5-cyclopropylisoxazole (I-15M) was prepared from 2-chloro-6-fluorobenzaldehyde according to the same procedures as described for (I-15H). MS m/z 377.1, 379.1 (M+1, $Cl_{35}/Cl_{37}$ isotope pattern).

4-((8-azabicyclo[3.2.1]octan-3-yloxy)methyl)-3-(2-chlorophenyl)-5-cyclopropylisoxazole (I-15N) was prepared from 2-cyclopropylbenzaldehyde according to the same procedures as described for (I-15H). MS m/z 359.1 (M+1).

4-((8-azabicyclo[3.2.1]octan-3-yloxy)methyl)-5-cyclopropyl-3-(2-cyclopropylphenyl)isoxazole (I-15O) was prepared from 2-chlorobenzaldehyde according to the same procedures as described for (I-15H). MS m/z 365.2 (M+1).

4-((8-azabicyclo[3.2.1]octan-3-yloxy)methyl)-5-cyclopropyl-3-(2,4-difluorophenyl)isoxazole (I-15P) was prepared from 2,4-difluorobenzaldehyde according to the same procedures as described for (I-15H). MS m/z 361.2 (M+1).

4-((8-azabicyclo[3.2.1]octan-3-yloxy)methyl)-5-cyclopropyl-3-(2,3-difluorophenyl)isoxazole (I-15Q) was prepared from 2,3-difluorobenzaldehyde according to the same procedures as described for (I-15H). MS m/z 361.2 (M+1).

4-((8-azabicyclo[3.2.1]octan-3-yloxy)methyl)-5-cyclopropyl-3-(2-fluorophenyl)isoxazole (I-15R) was prepared from 2-fluorobenzaldehyde according to the same procedures as described for (I-15H). MS m/z 343.2 (M+1).

Intermediate 16

Methyl 2-bromo-4-methyl-benzothiazole-6-carboxylate (I-16B)

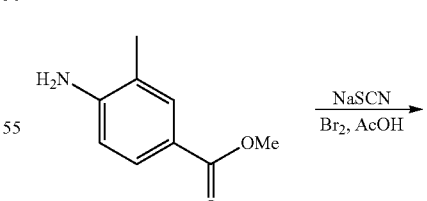

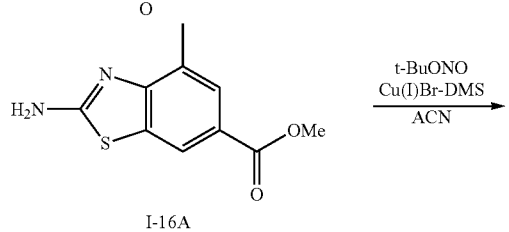

I-16A

Intermediate 17

7-bromo-imidazo[1,2-a]pyridine-3-carboxylic acid (I-17B)

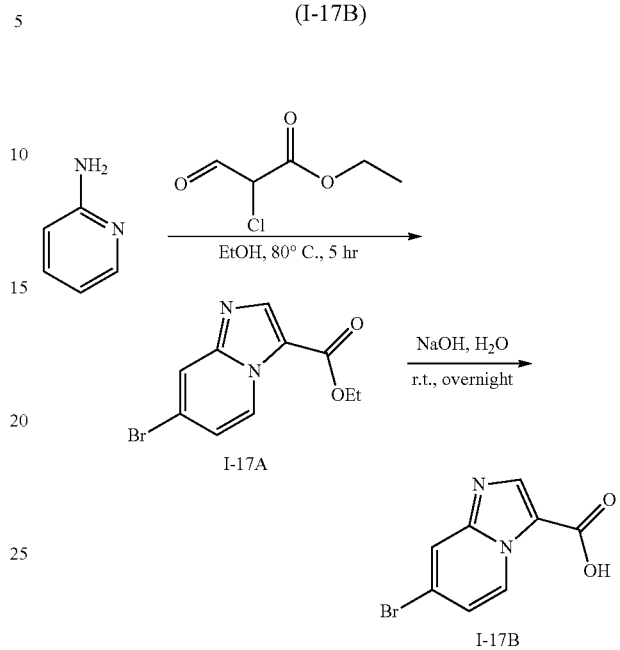

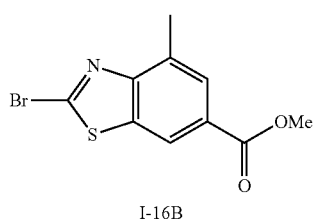

I-16B

Methyl 2-amino-4-methyl-benzothiazole-6-carboxylate (I-16A). Into a 500-mL round-bottom flask was placed a solution of methyl 4-amino-3-methylbenzoate (4.00 g, 24.2 mmol, 1.00 equiv) and NaSCN (7.00 g, 86.4 mol, 3.57 equiv) in AcOH (90 mL) that was cooled to 0° C. This was followed by the addition of a solution of $Br_2$ (3.9 g, 25 mmol, 1.0 equiv) in AcOH (25 mL) dropwise, maintaining at 0° C. over 20 min. The resulting solution was allowed to warm to RT on its own accord (over approximately 10 min.) and stirred for 48 hrs at RT. At this time, the solids of the reaction were filtered out. The resulting solution was diluted with 100 mL $H_2O$. The pH value of the solution was adjusted to 8-9 with ammonia (using Whatman PH strip paper to monitor PH adjustment) which furnished an immediate precipitation. The solids were collected by filtration and washed once with ice cold MeOH (50 mL) to afford as a yellow solid. MS m/z 223.0 (M+11). $^1H$ NMR (400 MHz, MeOH-$d_4$) δ 8.17 (app d, J=1.0 Hz, 1H), 8.03 (br s, 2H, $NH_2$), 7.68 (s, 1H), 3.82 (s, 3H), 2.42 (s, 3H).

Methyl 2-bromo-4-methyl-benzo[d]thiazole-6-carboxylate (I-16B). Into a 40 mL reaction vessel equipped with a septum, stir bar, and nitrogen line, was placed solid copper (I) bromide-DMS complex (824 mgs, 4.00 mmol) that was diluted with dry acetonitrile (8 mL). The resulting dark suspension was cooled to 0° C. with an ice bath. Next was added 90% commercial stock solution of tBuONO (tertbutyl nitrite, 1.0 mL, at 90% weight by weight furnishes a calculated material delivery of 7.6 mmoles) in a dropwise fashion over 5 min. Next was added a slurry of methyl 2-amino-4-methyl-benzothiazole-6-carboxylate (627 mg, 2.81 mmol) in acetonitrile (3 mL) via pipet, over 2 min. to prevent any possible exothermic event. The bath was pulled and the reaction was allowed to warm to RT. After 3 hrs the reaction was heated to 45° C. for 45 min. No starting material could be seen at this time as monitored by LCMS analysis against a standard solution. Next the reaction was cooled to RT, filtered to remove undesired solids, and the resulting mother liquor was then added to water (20 mL) as a rapidly stirred solution. The resulting solid was collected. MS m/z 285.9/287.9 (M+1, $Br_{79}/Br_{81}$ isotope pattern). $^1H$ NMR (400 MHz, DMSO-$d_6$): δ 8.62 (app d, J=1.0 Hz, 1H), 7.93 (app dd, J=1.5, 1.0 Hz, 1H), 3.94 (s, 3H), 2.80 (s, 3H).

Ethyl 7-bromoimidazo[1,2-a]pyridine-3-carboxylate (I-17A). A solution of ethyl 2-chloro-3-oxopropanoate (245 g, 1.64 mol) and added 4-bromopyridin-2-amine (94 g, 546 mmol) in ethanol (2 L) was heated to 80° C. for 5 h, and then concentrated under vacuum. The residue was applied to silica gel column (EA/PE, 1/2) for purification to give ethyl 7-bromoimidazo[1,2-a]pyridine-3-carboxylate as white solid.

7-bromo-imidazo[1,2-a]pyridine-3-carboxylic acid (I-17B). To a solution of ethyl 7-bromoimidazo[1,2-a]pyridine-3-carboxylate (67 g, 250 mmol) in methanol (500 mL), sodium hydroxide (2N, 249 ml, 500 mmol) was added. The resulting solution was stirred overnight at room temperature. The pH of the solution was adjusted to pH=6 with HCl (2N). The solids were collected by filtration to afford 7-bromo-imidazo[1,2-a]pyridine-3-carboxylic acid as white solid. MS [M+H]+ 241/243. $^1$H-NMR: (DMSO-$d_6$, 300 MHz): 13.3 (br, 1H), 9.19 (dd, J=7.5, 0.9 Hz, 1H), 8.25 (s, 1H), 8.15 (d, J=1.5 Hz, 1H), 7.39 (dd, J=7.5, 1.8 Hz, 1H).

Intermediate 18

Ethyl 6-bromoH-imidazo[1,2-a]pyridine-3-carboxylate (I-18B)

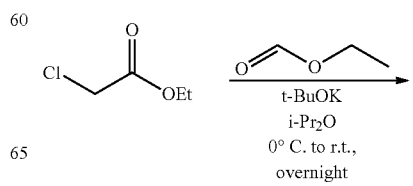

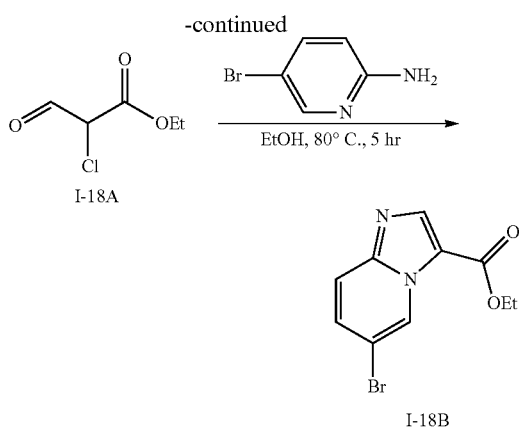

Ethyl 2-chloro-3-oxopropanoate (I-18A). A mixture of ethyl formate (385 g, 5.20 mol) and ethyl chloroacetate (640 g, 5.20 mol) was added to a suspension of potassium t-butoxide (583 g, 5.2 mol) in diisopropyl ether (5 L) at 0° C., and the resulting mixture was stirred for 24 h at room temperature. Then the pH of the solution was adjusted to pH=6 with concentrated sulfuric acid. The solid was filtered and the filtrate was concentrated under reduced pressure to afford ethyl 2-chloro-3-oxopropanoate (18-A) as oil.

Ethyl 6-bromoH-imidazo[1,2-a]pyridine-3-carboxylate (I-18B). A solution of ethyl 2-chloro-3-oxopropanoate (261 g, 1.74 mol) 5-bromopyridin-2-amine (100 g, 581 mmol) in ethanol (2L) was heated to 80° C. for 5 h and concentrated under vacuum. The residue was applied to silica gel column (EA/PE, ½) for purification to afford ethyl 6-bromoH-imidazo[1,2-a]pyridine-3-carboxylate as white solid.

Intermediate 19

Methyl 2,4-dayroom-benzothiazole-6-carboxylate (I-19B)

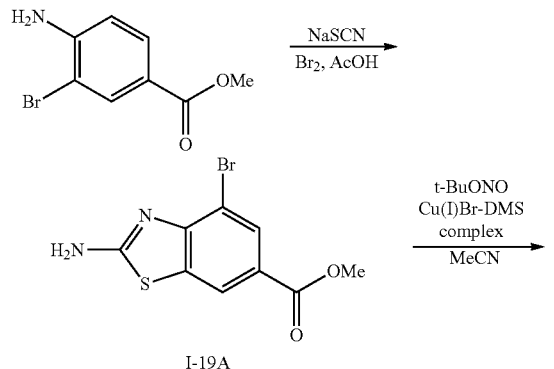

Methyl 2-amino-4-bromo-benzothiazole-6-carboxylate (I-19A). Into a 50-mL round-bottom flask, was placed a solution of methyl 4-amino-3-bromobenzoate (500 mg, 2.17 mmol, 1.00 equiv) and AcOH (9 mL) that was cooled to 0° C. This was followed by the addition of a solution of Br$_2$ (500 mg, 3.12 mmol, 1.44 equiv) in AcOH (2 mL) dropwise at 0° C. over 20 min. The resulting solution was allowed to warm to RT on its own accord (over 10 min.) once the addition event was complete. Next, the RT reaction was warmed gently to 45° C. for 35 min until near complete formation of the in situ intermediate did-bromo species (M+H with a double Br mass spectrum pattern, m/z 308/310/312; ratio 1:2:1). To the reaction was next added NaSCN (500 mg, 6.17 mol, 2.84 equiv) in AcOH (9 mL). The reaction after 4 hrs was heated to 60° C. for 24 hrs. At this time, an additional portion of NaSCN (500 mg, 6.17 mol, 2.84 equiv) in AcOH (9 mL) was added and the reaction was maintained at 60° C. for 12 hrs longer. At this time, the reaction was cooled to RT and filtration of all undesired solids was done, with a MeOH wash (10 mL) of the filter pad to ensure all liquor was extracted. The resulting liquor was then diluted was then concentrated under vacuum and reduced to a final volume of 20 mL which was subjected to reverse phase C-18 chromatography (30 to 100% acetonitrile:water, 0.05% TFA modified). Concentration of chromatographic fractions was followed by removal of any possible residual TFA using an SPE polymer supported acid capture cartridge (PLHCO$_3$ MP, part no PL3540-C603-Varian) with MeOH (6 mL) as mobilizing agent. Upon concentration of the final eluent, product was obtained as a light brown solid. MS m/z 286.9/288.9 (M+1, Br$_{79}$/Br$_{81}$ isotope pattern). $^1$H-NMR (400 MHz, MeOH-d$_4$): δ 8.38 (br s, 2H, NH$_2$), 7.96 (app d, J=0.90 Hz, 1H), 7.92 (app d, J=0.90 Hz, 1H), 3.84 (s, 3H).

Methyl 2,4-dayroom-benzothiazole-6-carboxylate (I-19B). Into a 40 mL reaction vessel equipped with a septum, stir bar, and nitrogen line, was placed solid copper (I) bromide-DMS complex (70.0 mg, 0.341 mmol) that was diluted with dry acetonitrile (2 mL). The resulting dark suspension was cooled to 0° C. with an ice bath. Next was added 90% commercial stock solution of t-BuONO (tert-butyl nitrite, 0.070 mL, at 90% weight by weight furnishes a calculated material delivery of 0.53 mmoles) in a dropwise fashion over 5 min. Next was added a slurry of methyl 2-amino-4-bromo-benzothiazole-6-carboxylate (50 mg, 0.175 mmol) in acetonitrile (1 mL) via pipet, over 2 min. to prevent any possible exothermic event. The bath was pulled and the reaction was allowed to warm to RT. After 3 hrs, no starting material could be observed as monitored by LCMS analysis against a standard solution. Next the reaction was diluted with water (4 mL) and extracted with ethyl acetate (20 mL). The organic extract was further washed with brine (1 mL) and then dried over sodium sulfate to furnish a solid that was used without further purification. MS m/z major observable: 249.9/251.9/253.9 (M+1, Br$_{79}$/Br$_{81}$ isotope pattern for compound bearing two Br atoms.

Intermediate 20

Methyl 6-cyclopropyl-2-(methylsulfonyl)pyrimidine-4-carboxylate (I-20B)

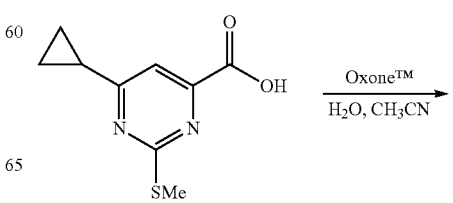

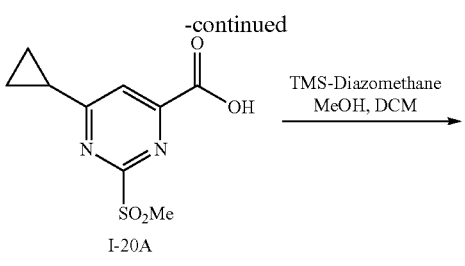

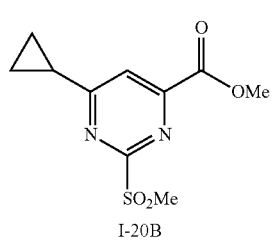

6-cyclopropyl-2-(methylsulfonyl)pyrimidine-4-carboxylic acid (I-20A). Into a 40 mL vessel was added 6-cyclopropyl-2-(methylthio)pyrimidine-4-carboxylic acid_(commerically available, Enamine Ltd, catalog number EN300-422464, 250 mg, 1.19 mmol) and acetonitrile (12.5 mL). This resulting solution was then added dropwise at RT over 5 min. to a separate 40 mL reaction vessel that was charged with a rapidly stirred suspension of Oxone™ (using Aldrich supplied Oxone which is a multicomponent triple salt mixture containing potassium monopersulfate, 2 KHSO$_5$.KHSO$_4$.K$_2$SO$_4$, 2.50 g, 4.10 mmol) and water (15 mL). Upon complete addition of the methyl thiopyrimidine, the resulting suspension was heated to 65° C. for 20 min. and subsequently cooled to RT. The resulting yellow suspension was extracted with ethyl acetate (4×100 mL) and the organic extracts were dried over magnesium sulfate, filtered and concentrated to furnish the methyl sulfonyl pyrimidine as a residue that was used directly in the next step without isolation. MS m/z 243.1 (M+1).

Methyl 6-cyclopropyl-2-(methylsulfonyl)pyrimidine-4-carboxylate (I-20B). A suspension of 6-cyclopropyl-2-(methylsulfonyl)pyrimidine-4-carboxylic acid (200 mg, 0.82 mmol) in dichloromethane (2 mL) and methanol (0.5 mL) was cooled to 0° C. Trimethylsilyl diazomethane (2.0 M in diethyl ether, 1.0 mL, 2.0 mmol) was added dropwise as not to increase the internal temperature of the reaction. Upon complete addition the suspension became a yellow colored solution that was allowed to warm to RT and maintained for 1 h at that temperature. At this time, acetic acid was added dropwise until the mixture was colorless (c.a. 2 drops, 12 M) and the resulting solution was concentrated under vacuum to a residue. The resulting oily yellow solid was dissolved in sparing ice cold acetonitrile (0.5 mL) and allowed to precipitate to furnish an off white waxy solid. MS m/z 257.1 (M+1). $^1$H NMR (400 MHz, DMSO-d$_6$): δ 8.22 (s, 1H), 3.81 (s, 3H), 3.28 (s, 3H), 2.40-2.36 (m, 1H), 1.20-1.15 (m, 2H), 1.12-1.06 (m, 2H).

Intermediate 21

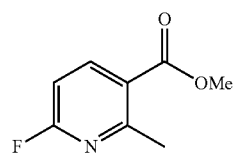

Methyl-6-fluoro-2-methylnicotinate (I-21) was prepared from commercially available 6-fluoro-2-methylnicotinic acid using the analogous procedure previously described for the preparation of Intermediate I-20b.

Intermediate 22

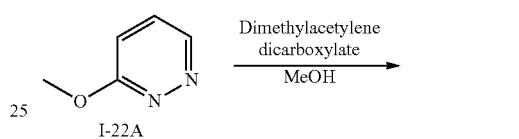

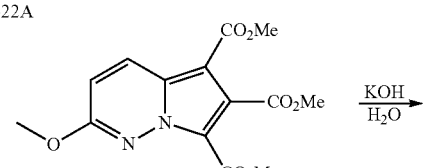

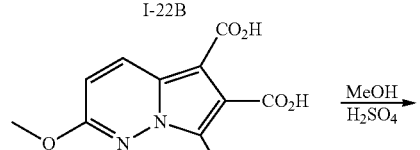

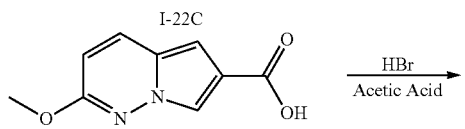

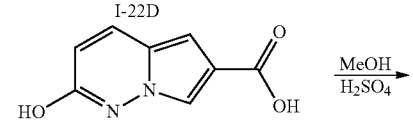

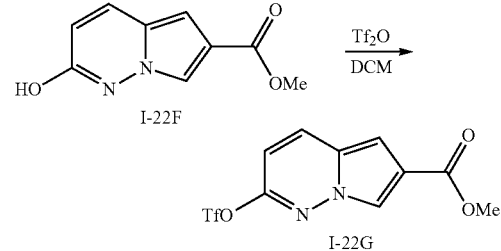

Trimethyl 2-methoxypyrrolo[1,2-b]pyridazine-5,6,7-tricarboxylate (I-22B). Commercially available 3-methoxypyridazine (3.00 g, 27.3 mmol) was dissolved in methanol (60 mL) and cooled to 0° C. Dimethylacetylene dicarboxylate (4.00 mL, 32.8 mmol, 1.2 eq) was added dropwise while the reaction was rapidly stirred. The mixture was maintained at -20° C. for two days. A pale yellow solid formed during this time that was recovered by filtration and washed with cold methanol (2 mL) to furnish an off white solid. MS m/z 323.1 (M+1).

2-Methoxypyrrolo[1,2-b]pyridazine-6-carboxylic acid (I-22D). Trimethyl 2-methoxypyrrolo[1,2-b]pyridazine-5,6, 7-tricarboxylate (1.84 g, 5.72 mmol) was suspended in a solution of potassium hydroxide (1.60 g, 28.6 mmol, 5 eq) in water (5 mL) and the mixture was heated to 60° C. for 1 h during which time all solids dissolved into a yellow solution. The solution was acidified with concentrated HCl (12 N, 5 mL) until pH=1 was achieved, and the mixture was heated to 90° C. overnight. The mixture was then cooled to RT and a dark solid was recovered by filtration. MS m/z 193.1 (M+1).

2-Hydroxypyrrolo[1,2-b]pyridazine-6-carboxylic acid (I-22E). 2-Methoxypyrrolo[1,2-b]pyridazine-6-carboxylic acid (1.06 g, 5.50 mmol) was suspended in HBr (10 mL, 33% solution in acetic acid) and heated to 50° C. for 2 hrs. The solvent was evaporated in vacuo and used directly (500 mgs). An analytical standard was prepared using reverse phase HPLC with a gradient of acetonitrile/water and 0.05% TFA as modifier. MS m/z 179.1 (M+1). $^1$H NMR (DMSO-$d_6$, 400 MHz) δ 12.29 (bs, 1H), 11.60 (bs, 1H), 7.89-7.86 (m, 2H), 6.76 (d, J=2.0 Hz, 1H), 6.36 (d, J=9.6 Hz, 1H).

Methyl 2-hydroxypyrrolo[1,2-b]pyridazine-6-carboxylate (I-22F). The semi-crude material from above, 2-Hydroxypyrrolo[1,2-b]pyridazine-6-carboxylic acid (100 mg, 0.56 mmol) was dissolved in methanol (5 mL) and concentrated sulfuric acid (2 drops). The solution was heated to 80° C. for 4 hours, and then the solvent evaporated in vacuo. The crude material was used directly in the next step. MS m/z 193.1 (M+1).

Methyl 2-(((trifluoromethyl)sulfonyl)oxy)pyrrolo[1,2-b] pyridazine-6-carboxylate (I-22G). Methyl 2-hydroxypyrrolo [1,2-b]pyridazine-6-carboxylate (50 mg, 0.26 mmol) and diisopropylethylamine (0.13 mL, 0.78 mmol, 3 eq) were combined in dichloromethane (5 mL) and cooled to 0° C. Triflic anhydride (0.09 mL, 0.52 mmol, 2 eq) was added and the mixture stirred for 30 minutes then diluted with dichloromethane (10 mL) and sodium bicarbonate solution (5 mL). The organics were separated and dried, then evaporated in vacuo. The product was purified by flash chromatography (0-100% ethyl acetate/hexanes) to yield a pale brown solid. MS m/z 325.0 (M+1).

Intermediate 23

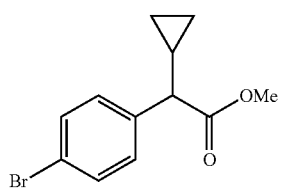 [SMILES: COC(=O)C(c1ccc(Br)cc1)C1CC1]

Methyl 1-(4-bromophenyl)cyclopropanecarboxylate (I-23) was prepared from commercially available 1-(4-bromophenyl)cyclopropanecarboxylic acid using the analogous esterification protocol previously described for the preparation of Intermediate I-20b. MS m/z 255.1/257.1 (M+1, Br$_{79}$/Br$_{81}$ isotope pattern). $^1$H-NMR (MeOH-$d_4$, 400 MHz) δ 7.42 (d, J=9.4 Hz, 2H), 7.33 (d, J=9.4 Hz, 2H), 3.62 (s, 3H), 1.58-1.52 (m, 2H), 1.21-1.17 (m, 2H).

Intermediate 24

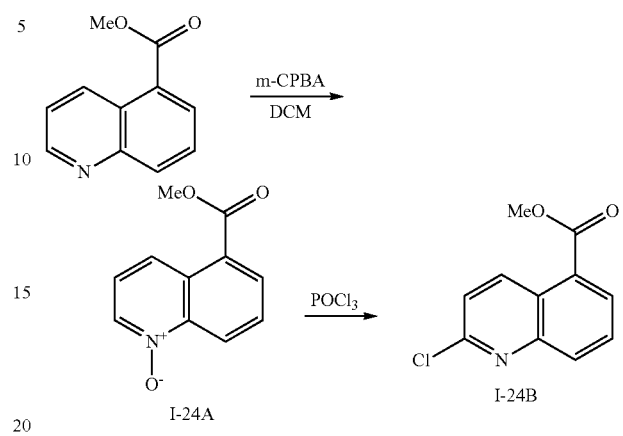

5-(methoxycarbonyl)quinoline 1-oxide (I-24A). Into a 50-mL round-bottom flask, was placed a solution of methyl quinoline-5-carboxylate (94 mg, 0.50 mmol) and methylene chloride (2 mL) that was cooled to 0° C. This was followed by the addition of a solid m-CPBA (commercial 65%, using 200 mg gives calculated effective reagent at 0.70 mmol) in a portionwise fashion. The resulting suspension was allowed to warm to RT on its own accord and maintained for 20 min. At this time the reaction was diluted with MeOH (2 mL), filtered to remove undesired solids, and then purified directly by reverse phase chromatography using 30% acetonitrile/water eluent system to furnish the desired as a white solid. MS m/z 204.0 (M+1). $^1$H NMR (400 MHz, MeOH-$d_4$): δ 9.20 (d, J=8.8 Hz, 1H), 8.89 (d, J=8.8 Hz, 1H), 8.63 (d, J=6.4 Hz, 1H), 8.40 (d, J=6.4 Hz, 1H), 7.92 (app t, J=8.6 Hz, 1H). 7.60 (dd, J=8.8, 7.5 Hz, 1H), 4.12 (s, 3H).

Methyl 2,4-dayroom-benzothiazole-6-carboxylate (I-24B). Into a 2 mL reaction vessel equipped with a septum, stir bar, and nitrogen line, was placed 5-(methoxycarbonyl) quinoline 1-oxide (70.0 mg, 0.345 mmol) and POCl$_3$. The resulting reddish solution was heated to 80° C. for 10 min., allowed to cool to RT, and was directly concentrated to a solid residue in vacuo (1 mm Hg) at 50° C. The resulting solid was rinsed with ice cold acetonitrile (0.5 mL) to furnish an off white soli. MS m/z 222.0/224.0 (M+1, Cl$_{35}$/Cl$_{37}$ isotope pattern). $^1$H NMR (400 MHz, MeOH-$d_4$): δ 9.24 (dd, J=8.8, 0.9 Hz, 1H), 8.22 (dd, J=7.2, 1.2 Hz, 1H), 8.11 (d, J=8.4 Hz, 1H), 7.71 (dd, J=8.4, 7.6 Hz, 1H), 7.41 (d, J=8.8 Hz, 1H), 3.96 (s, 3H).

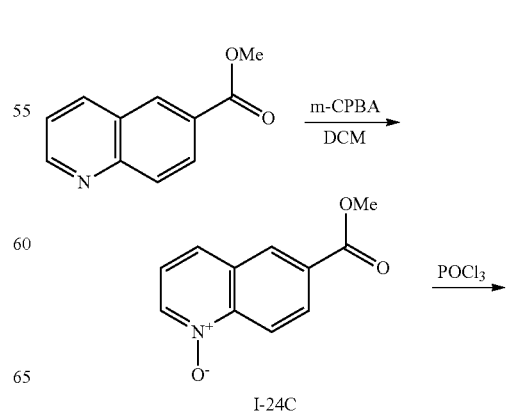

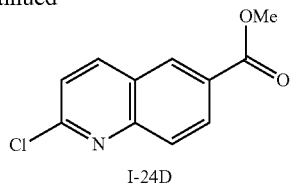

Methyl 2-chloroquinoline-6-carboxylate (I-24D) was prepared from methyl quinoline-6-carboxylate according to the analogous procedure described above for the preparation of Intermediate I-24B.

Intermediate 25

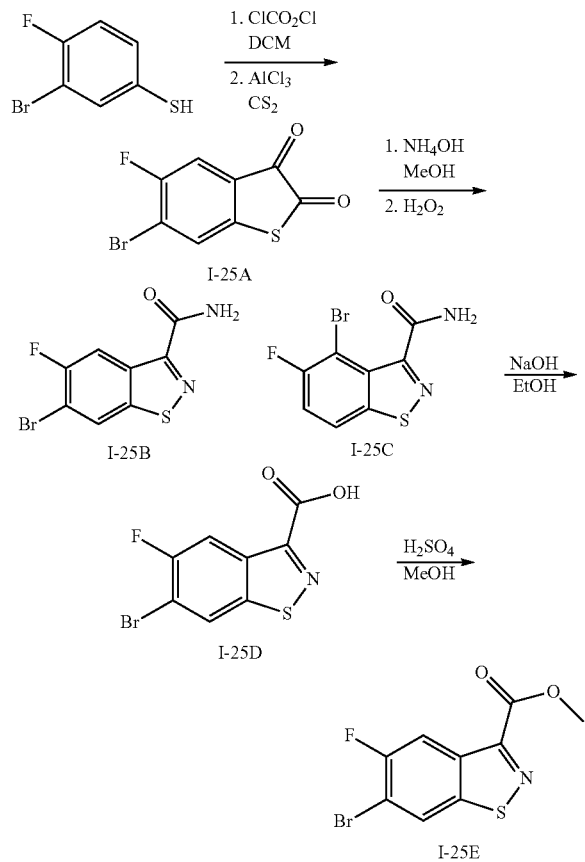

6-bromo-5-fluorobenzo[b]thiophene-2,3-dione (I-25A). A solution of commercially available 3-bromo-4-fluorobenzenethiol (1 g, 4.8 mmol) in dry dichloromethane (3 mL) was added dropwise to neat oxalyl chloride (2.1 mL, 24.1 mmol) at room temperature. Once the addition was complete, the yellow reaction mixture was heated at reflux for 14 hours. The volatiles were removed in vacuo to afford a yellow semi-solid residue that was suspended in dry carbon disulfide (2 mL) and added very slowly to a suspension of aluminum chloride (2.1 g, 21.6 mmol) in dry carbon disulfide (2 mL) at room temperature. Once the addition was complete, the reaction mixture was heated to 45° C. for 3 hours. After this time, the reaction was cooled back to room temperature and very slowly poured into ice water (10 mL), the solid that precipitated was filtered and dried in vacuo to yield 6-bromo-5-fluorobenzo[b]thiophene-2,3-dione as red-orange solid. MS m/z 260.8 and 262.9 (M+1; $Br_{79}/Br_{81}$ isotope pattern.

6-bromo-5-fluorobenzo[d]isothiazole-3-carboxamide (I-25B). To a solution of 6-bromo-5-fluorobenzo[b]thiophene-2,3-dione (I-25A) (0.3 g, 1.1 mmol) in methanol (2 mL) cooled to 10° C. ammonium hydroxide (3 mL, 26.4 mmol, of a 28% aqueous solution) was added dropwise and the reaction mixture stirred for 14 hours at room temperature. After this time, the reaction flask was cooled back to 10° C. and hydrogen peroxide (0.3 mL of a 30% aqueous solution) was added dropwise and the resulting suspension was stirred for 1 hour. The solid was removed by filtration, washed with water and dried in vacuo to afford 6-bromo-5-fluorobenzo[d]isothiazole-3-carboxamide (I-25B) and 4-bromo-5-fluorobenzo[d]isothiazole-3-carboxamide (I-25C) in a 1:1 mixture which was carried to the next step without further purification. MS 274.9 and 276.9 (M+1; $Br_{79}/Br_{81}$ isotope pattern).

6-Bromo-5-fluorobenzo[d]isothiazole-3-carboxylic acid (I-25D). A suspension of 6-bromo-5-fluorobenzo[d]isothiazole-3-carboxamide (I-25B) and 4-bromo-5-fluorobenzo[d]isothiazole-3-carboxamide (I-25C) (93 mg, 0.34 mmol) in ethanol (1.5 ml) and 6N sodium hydroxide (0.22 mL, 1.35 mmol) was refluxed for 3 hours. The reaction mixture was cooled to room temperature, diluted with water (2 mL) and acidified with 2N HCl. The solid was removed by filtration, washed with water and dried in vacuo to afford 6-bromo-5-fluorobenzo[d]isothiazole-3-carboxylic (I-25D). $^1$H-NMR (400 MHz, DMSO) δ 8.69 (d, J=6.4 Hz, 1H), 8.49 (d, J=9.6 Hz, 1H). MS 275.9 and 277.9 (M+1; $Br_{79}/Br_{81}$ isotope pattern).

Methyl 6-bromo-5-fluorobenzo[d]isothiazole-3-carboxylate (I-25E). 6-Bromo-5-fluorobenzo[d]isothiazole-3-carboxylic acid (I-25D) (57 mg, 0.21 mmol) was suspended in dry methanol (5 mL) and $H_2SO_4$ (0.2 mL) and refluxed for 3 hours. After this time the reaction was cooled to room temperature and diluted with water (3 mL) and neutralized with 5% aquesou $Na_2CO_3$ and extracted with ethyl acetate. The organic layer was washed with brine, dried over sodium sulfate and concentrated in vacuo to yield methyl 6-bromo-5-fluorobenzo[d]isothiazole-3-carboxylate (I-25E). MS 289.9 and 291.9 (M+1; $Br_{79}/Br_{81}$ isotope pattern).

Intermediate 26

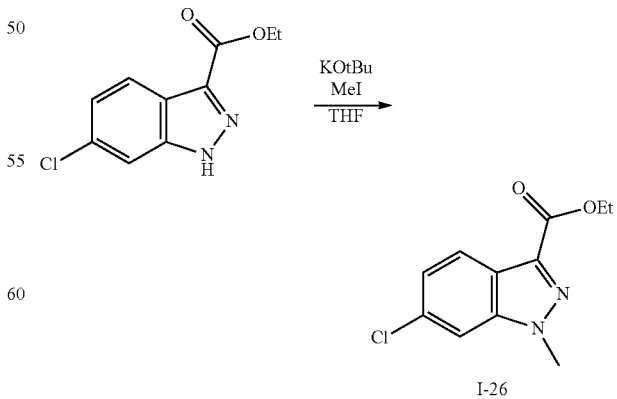

Ethyl 6-bromo-1-methyl-1H-indazole-3-carboxylate (I-26). A solution of potassium tert-butoxide (0.46 g, 4.1 mmol) in dry tetrahydrofuran (5 mL) was added drowise to a solution of ethyl 6-chloro-1-methyl-1H-indazole-3-carboxylate (0.9 g, 3.3 mmol) in tetrahydrofuran (15 mL) and cooled to 0° C. The reaction mixture was stirred for 15 min and then a solution of iodomethane (10 mL, 4.45 mmol) in tetrahydrofuran (8 mL) was added dropwise. The reaction was stirred for 2 hr at room temperature, and then diluted with water (100 mL) and extracted with ethyl acetate (3×50 mL). The combined organic layers were washed with water, brine, and dried over sodium sulfate. The removal of the volatile in vacuo furnished a yellow solid that by trituration with diethyl ether afforded ethyl 6-chloro-1-methyl-1H-indazole-3-carboxylate (I-26) as an off white solid. $^1$H-NMR (400 MHz, CDCl$_3$) δ 8.06 (d, J=8.4 Hz, 1H), 7.65 (m, 1H), 7.41 (dd, J=8.8 and 1.6 Hz, 1H), 4.51 (q, J=7.2 Hz, 2H), 4.14 (s, 3H), 1.48 (t, J=7.2 Hz, 3H). MS m/z 283.0 and 285.0 ((M+1; Br$_{79}$/Br$_{81}$ isotope pattern).

Intermediate 27

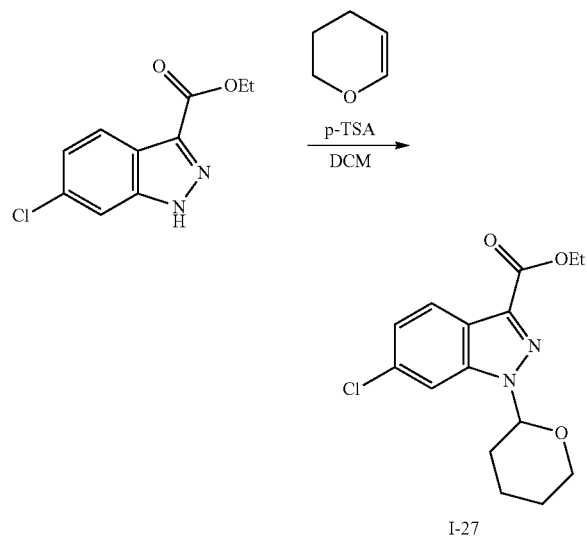

I-27

Ethyl 6-bromo-1-(tetrahydro-2H-pyran-2-yl)-1H-indazole-3-carboxylate (I-27). To a suspesion of ethyl 6-chloro-1-methyl-1H-indazole-3-carboxylate (0.43 g, 1.6 mmol) in dry dichloromethane (10 mL) was added p-toluensulfonic acid (27 mg, 0.16 mmol) follwed by neat 2,3 dihydropyranyl (0.28 mL, 3.2 mmol) dropwise. The reaction mixture was stirred for 30 min, and then diluted with dichloromethane (30 mL). The organic layer was washed with 5% Na$_2$CO$_3$, water, brine, and then dried over sodium sulfate. Removal of the solvent in vacuo afforded a yellow residue which was triturated with a 9:1 hexane-ethyl acetate mixture to furnish ethyl 6-chloro-1-(tetrahydro-2H-pyran-2-yl)-1H-indazole-3-carboxylate (I-27) as an off-white powder. $^1$H-NMR (400 MHz, CDCl$_3$) δ 8.09 (dd, J=8.4 and 0.4 Hz, 1H), 7.92 (dd, J=1.6 and 0.8 Hz, 1H), 7.44 (dd, J=8.8 and 1.6 Hz, 1H), 5.81 (dd, J=9.6 and 2.8 Hz, 1H), 4.54 (q, J=7.2 Hz, 2H), 4-10-4.14 (m, 1H), 3.80-3.74 (m, 1H), 2.51-2.48 (m, 1H), 2.17-2.10 (m, 2H), 1.81-1.68 (m, 3H), 1.49 (t, J=7.2 Hz, 3H). MS m/z 353.0 and 355.1 (M+1; Br$_{79}$/Br$_{81}$ isotope pattern.

Intermediate 28

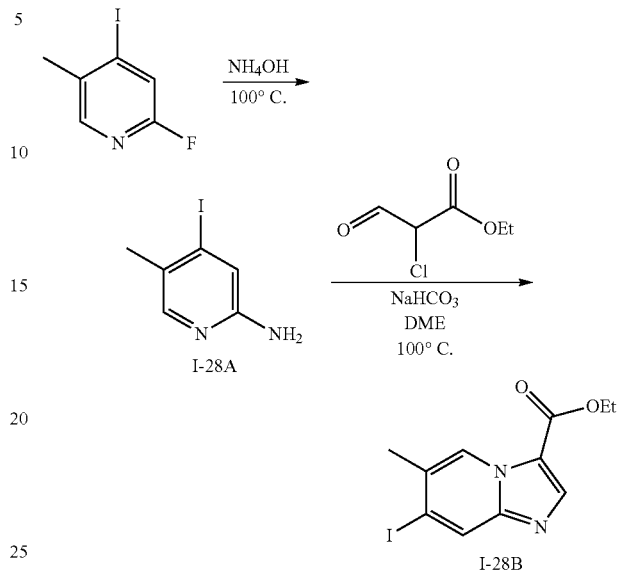

4-Iodo-5-methylpyridin-2-amine (I-28A). In a 500 mL sealed tube 2-fluoro-4-iodo-5-methylpyridine (4.0 g, 16.81 mmol) in 12N ammonium hydroxide (300 mL) was heated to 110° C. for 72 hours. Upon cooling to room temperature a white solid separated. The solid was collected, washed with water and dried in vacuo to afford 4-iodo-5-methylpyridin-2-amine (I-28A) as an off-white solid which was carried on to the next step without purification. $^1$H-NMR (400 MHz, CDCl$_3$) δ 7.82 (s, 1H), 7.04 (s, 1H), 4.27 (bs, 2H), 2.24 (s, 3H). MS m/z 235.0 (M+1).

Ethyl 7-iodo-6-methylimidazo[1,2-a]pyridine-3-carboxylate (I-28B). To a suspension of 4-iodo-5-methylpyridin-2-amine (I-28A) (1.55 g. 6.6 mmol), sodium bicarbonate (0.67 g, 7.9 mmol) in dry dimethoxyethane (10 mL) at room temperature, ethyl 2-chloro-3-oxopropanoate (1 g, 6.41 mmol) in dimethoxyethane (1 mL) was added dropwise. The reaction mixture was heated to 100° C. for 1 h and then cooled to room temperature and diluted with dichloromethane (50 mL). The organic layer was washed with water, brine, dried over sodium sulfate and concentrated in vacuo. The brown crude oil was purified by silica gel chromatography with a gradient of 0-15% ethyl acetate/hexanes to yield ethyl 7-iodo-6-methylimidazo[1,2-a]pyridine-3-carboxylate (I-28B) as light tan solid. $^1$H-NMR (400 MHz, DMSO) δ 9.11 (s, 1H), 8.41 (s, 1H), 8.22 (s, 1H), 4.36 (q, J=7.2 Hz, 2H), 2.42 (s, 3H), 1.37 (t, J=7.2 Hz, 3H). MS m/z 331.0 (M+1).

Intermediate 29

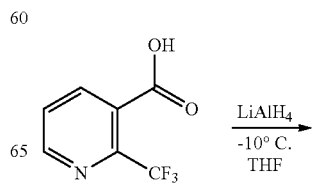

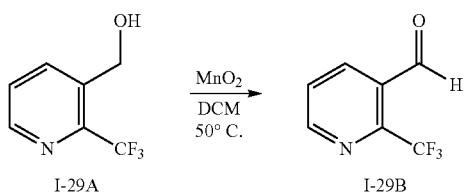

(2-(2-(Trifluoromethyl)pyridin-3-yl)methanol (I-29A). A solution of 2-(trifluoromethyl)nicotinic acid (5 g, 26.2 mml) in dry tetrahydrofuran (50 mL) was cooled to −10° C. and then treated with LiAlH₄ (39 mL, of a 1M solution in THF) by very slow addition. The reaction mixture was stirred at room temperature for 14 hours. The reaction was then cooled to −10° C. and quenched with a very slow dropwise addition of water (2 mL) and 6N HCl (1.2 mL). The reaction mixture was further diluted with water and extracted with dietyl ether (3×100 mL). The organics were combined and washed with brine, dried over sodium sulfate and concentrated in vacuo. The crude oily residue was purified by silica gel chromatography with a gradient of 0-10% ethyl acetate-dichloromethane to yield (2-(trifluoromethyl)pyridin-3-yl)methanol (I-29A) as pale yellow oil. ¹H-NMR (400 MHz, CDCl₃) δ 8.61 (d, J=4.8 Hz, 1H), 8.15 (dd, J=8.0, and 0.8 Hz, 1H), 7.55 (dd, J=8.0 and 4.4 Hz, 1H), 4.95 (d, J=6.0 Hz, 2H), 2.02 (t, J=6.0 Hz, 1H). MS m/z 178.0 (M+1).

2-(Trifluoromethyl)nicotinaldehyde (I-29B). MnO₂ (6.10 g, 70.6 mmol) was added portionwise to a solution of the above (2-(trifluoromethyl)pyridin-3-yl)methanol (I-29A) (2.5 g, 14.1 mmol) in dry dichloromethane (300 mL), and the resulting suspension was heated to 50° C. for 72 hours. After this time the mixture was filtered through Celite® and the filtrate concentrate in vacuo to afford a brown oil. This crude oil was purified by silica gel chromatography using a gradient of 0-30% ethyl acetate-hexane to furnish 2-(trifluoromethyl) nicotinaldehyde (I-29B) as clear oil. ¹H-NMR (400 MHz, CDCl₃) δ 10.4 (m, 1H), 8.89 (dd, J=4.8 and 1.2 Hz, 1H), 8.45 (dd, J=8.0, and 1.6 Hz, 1H), 7.70 (dd, J=8.0 and 4.8 Hz, 1H). MS m/z 176.0 (M+1).

Intermediate I-30

I-30

4-((8-azabicyclo[3.2.1]octan-3-yloxy)methyl)-5-cyclopropyl-3-(2-(trifluoromethyl)pyridin-3-yl)isoxazole (I-30) was prepared from Intermediate 1-29 according to the procedures described previously for the preparation of Intermediates I-15.

EXAMPLE 1

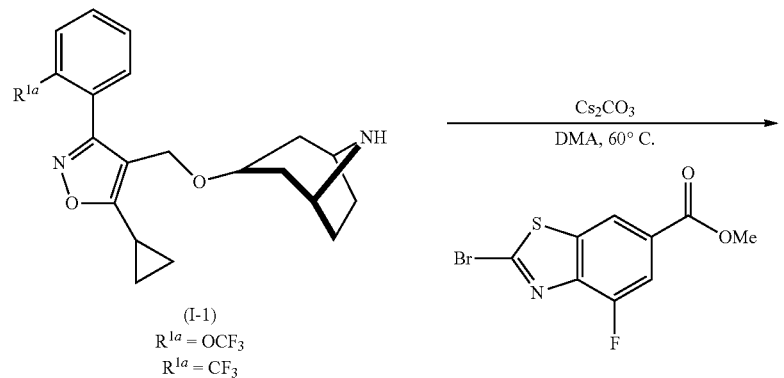

(I-1)
R¹ᵃ = OCF₃
R¹ᵃ = CF₃

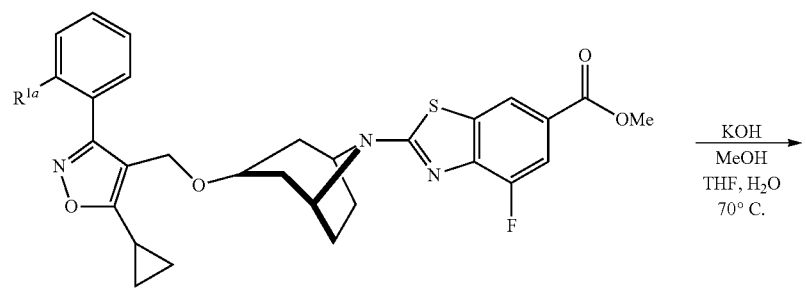

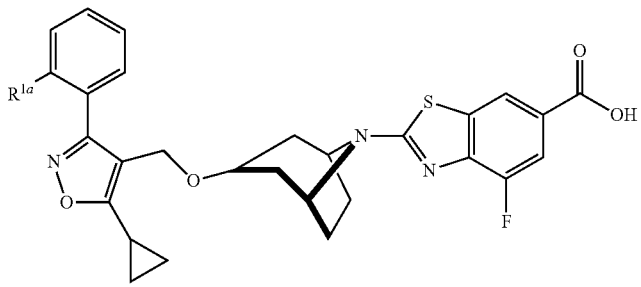

1B
R$^{1a}$ = OCF$_3$ (1-1A, 1-1B)
R$^{1a}$ = CF$_3$ (1-2A, 1-2B)

Methyl 2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carboxylate (I-1A). Into a 25-mL round-bottom flask equipped with a stir bar was added sequentially 4-((8-azabicyclo[3.2.1]octan-3-yloxy)methyl)-5-cyclopropyl-3-(2-(trifluoromethoxy)phenyl)isoxazole (I-1H) (0.525 g, 1.29 mmol), 3.6 mL of N,N-dimethylacetamide, cesium carbonate (1.08 g, 3.31 mmol), and methyl 2-bromo-4-fluorobenzo[d]thiazole-6-carboxylate (1.12 g, 3.87 mmoles). After stirring the resulting slurry at room temperature for 10 minutes, the mixture was then warmed to 60° C. and stirred for 1 h. The reaction slurry was allowed to cool to RT, and was diluted with 200 mL of ethyl acetate and washed with water (3×30 mL). The organic extracts were concentrated under vacuum and directly purified using normal phase silica gel chromatography (40 g silica column) with a 15 min gradient of 10% to 60% ethyl acetate/hexanes. Desired fractions were concentrated in vacuo, and the resulting residue crystallized upon standing to give the desired product as a white crystalline solid.

2-[3-({5-cyclopropyl]-3-[2-(trifluoromethoxy)phenyl-1,2-oxazol-4-yl}methoxy)-8-azabicyclo[3.2.1]octan-8-yl]-4-fluoro-1,3-benzothiazole-6-carboxylic acid (I-1B). To a 25-mL round-bottom flask equipped with a stir bar was added sequentially methyl 2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carboxylate (0.55 g, 0.89 mmol), 4.0 mL of THF, 2.0 mL of MeOH, and 3 N aqueous KOH solution (1 mL, 3 mmol). The resulting homogenous solution was stirred for 1 hour at 70° C., cooled to RT, and then quenched with AcOH (roughly 0.2 mL of glacial acetic, 3 mmoles) until pH=6 was achieved (Whatman class pH strip paper). At this time the reaction was diluted with ethyl acetate (40 mL) and washed with water (3×5 mL). The ethyl acetate fraction was concentrated under vacuum to give to an oily residue. To the resulting oil was then added 6 mL of MeOH. The oil quickly dissolved, then immediately began to crystallize. Upon standing for 2.5 hrs the mother liquor was withdrawn and crystals washed (3×2 mL of ice cold MeOH). The crystals were dried via vacuum (10 mm Hg pressure at 45° C. overnight) and then recrystallized from acetonitrile, filtered, and dried under vacuum to give the desired product 2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carboxylic acid.

2-[3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazole-6-carboxylic acid (I-2B). Examples 1-2A and the corresponding acid 1-2B can be prepared following the same procedures, from the reaction of intermediate 4-((8-azabicyclo[3.2.1]octan-3-yloxy)methyl)-5-cyclopropyl-3-(2-(trifluoromethyl)phenyl)isoxazole.

| Ex | | Physical Data MS (m/z), $^1$H NMR |
|---|---|---|
| 1-1A | (structure) | MS m/z 618.2 (M + 1); $^1$H NMR (DMSO D$_6$, 400 MHz) δ 8.13 (d, J = 1.6 Hz, 1H), 7.67-7.59 (m, 3H), 7.54-7.50 (m, 2H), 4.41 (s, 2H), 4.31 (bs, 2H), 3.90 (s, 3H), 3.60 (t, J = 4.8 Hz, 1H), 2.31-2.25 (m, 1H), 2.10 (app dt, J = 14.8, 4 Hz, 2H), 2.02-1.91 (m, 4H), 1.83 (app d, J = 14.8 Hz, 2H), 1.19-1.15 (m, 4H). |

| Ex | | Physical Data MS (m/z), $^1$H NMR |
|---|---|---|
| 1-1B | 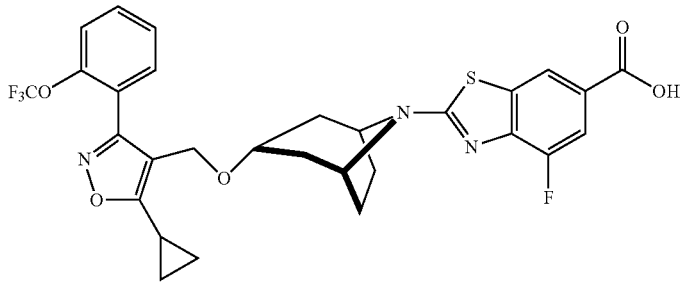 | Elemental Analysis ($C_{30}H_{29}F_4N_3O_6S$): C 56.69, H 4.60, N 6.61; Found: C 56.79, H 4.61, N 6.65. MS m/z 604.2 (M + 1); $^1$H NMR (MeOD, 400 MHz) δ 8.03 (d, J = 1.6 Hz, 1H), 7.57-7.53 (m, 2H), 7.49 (dd, J = 8.1, 1.8 Hz, 2H), 7.41 (app t, J = 7.6, 1H), 4.31 (s, 2H), 4.22 (broad s, 2H), 3.50 (t, J = 4.4 Hz, 1H), 2.22-2.15 (m, 1H), 2.00 (app dt, J = 14.8, 4.0 Hz, 2H), 1.91-1.81 (m, 4H), 1.75 (d, J = 14.4 Hz, 2H), 1.10-1.05 (m, 4H). |
| 1-2A | 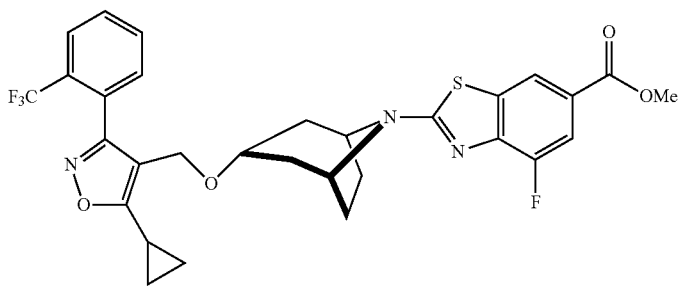 | MS m/z 602.3 (M + 1); $^1$H NMR (DMSOd$_6$, 400 MHz) δ 8.26 (d, J = 1.6 Hz, 1H), 7.92 (d, J = 8 Hz, 1H), 7.84-7.74 (m, 2H), 7.63-7.60 (m, 2H), 4.26 (bs, 4H), 3.84 (s, 3H), 3.52 (t, J = 4 Hz, 1H), 2.39-2.31 (m, 1H), 2.01-1.94 (m, 2H), 1.85-1.74 (m, 6H), 1.18-1.06 (m, 4H). |
| 1-2B | 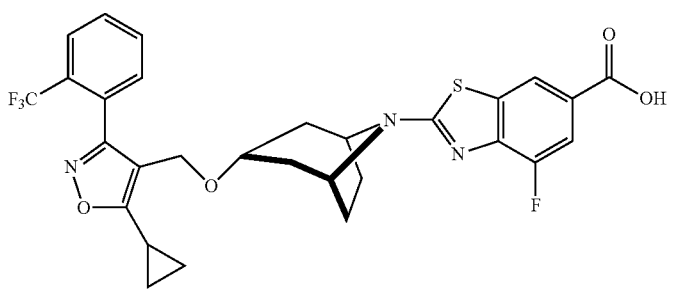 | MS m/z 588.1 (M + 1); $^1$H NMR (DMSOd$_6$, 400 MHz) δ 8.21 (d, J = 1.6 Hz, 1H), 7.89 (d, J = 7.2 Hz, 1H), 7.84-7.74 (m, 2H), 7.62-7.56 (m, 2H), 4.26 (bs, 4H), 3.52 (t, J = 4 Hz, 1H), 2.39-2.31 (m, 1H), 2.00-1.96 (m, 2H), 1.85-1.73 (m, 6H), 1.19-1.07 (m, 4H). |
EXAMPLE 2
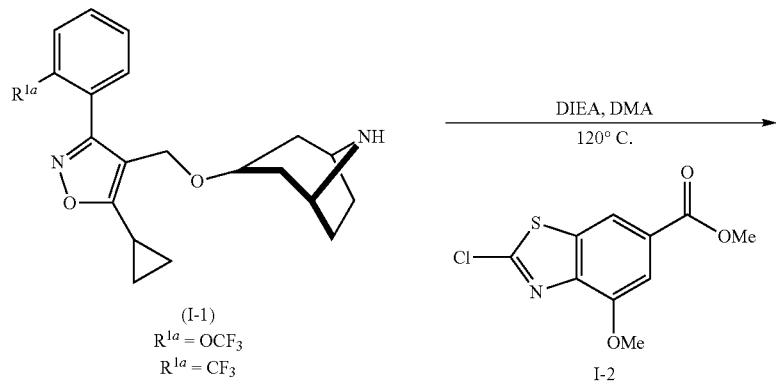

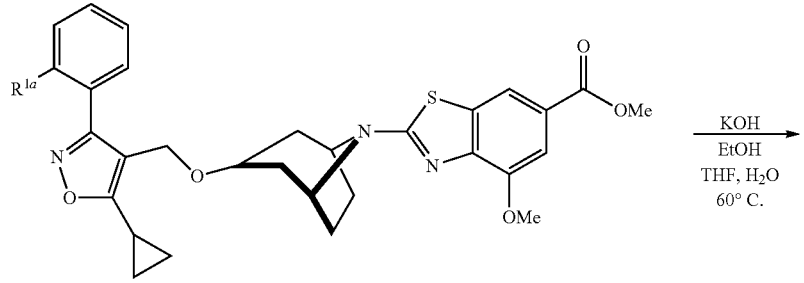

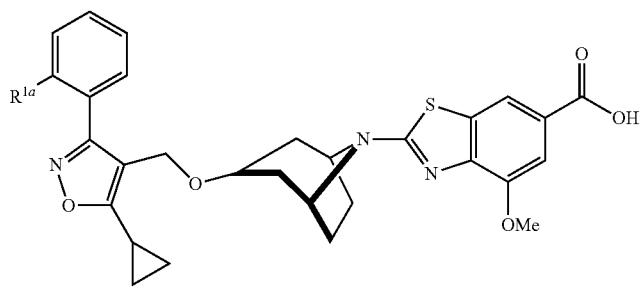

R<sup>1a</sup> = OCF₃ (2-1A, 2-1B)
R<sup>1a</sup> = CF₃ (2-2A, 2-2B)

Methyl 2-(3-((5-cyclopropyl-3-(2-(trifluoromethoxy)phenyl)isoxazol-4-yl)methoxy)-8-azabicyclo[3.2.1]octan-8-yl)-4-methoxybenzo[d]thiazole-6-carboxylate (2-1A). The ester, methyl 2-chloro-4-methoxybenzo[d]thiazole-6-carboxylate (124 mg, 0.48 mmol) and 4-((8-azabicyclo[3.2.1]octan-3-yloxy)methyl)-5-cyclopropyl-3-(2-(trifluoromethoxy)phenyl)isoxazole (200 mg, 0.48 mmol) and diisopropylethylamine (0.1 mL, 0.7 mmol) were sequentially dissolved in dimethylacetamide (1 mL) and heated to 120° C. overnight. The reaction mixture was allowed to cool to room temperature and then diluted with ethyl acetate and aqueous saturated sodium bicarbonate solution. The organics were separated, the aqueous layer was subjected to a further wash with ethyl acetate, and the organics were combined and dried (MgSO₄) then evaporated in vacuo. The product was purified by silica gel chromatography with a gradient of 0-100% ethyl acetate/hexanes to furnish 161 mg of a clear oil that was used directly in the following transformation without further manipulation.

2-(3-((5-cyclopropyl-3-(2-(trifluoromethoxy)phenyl)isoxazol-4-yl)methoxy)-8-azabicyclo[3.2.1]octan-8-yl)-4-methoxybenzo[d]thiazole-6-carboxylic acid (2-2B). The ester, methyl 2-(3-((5-cyclopropyl-3-(2-(trifluoromethoxy)phenyl)isoxazol-4-yl)methoxy)-8-azabicyclo[3.2.1]octan-8-yl)-4-methoxybenzo[d]thiazole-6-carboxylate (161 mg, 0.26 mmol) was dissolved in tetrahydrofuran (1 mL) and ethanol (1 mL) and subjected to an aqueous solution of potassium hydroxide (100 mg, 2.5 mmol in 2 mL water). The mixture was heated to 60° C. for 2 hr and then the solvent was removed in vacuo. The mixture was diluted with 5% aqueous citric acid and extracted with ethyl acetate (2×100 mL). The organics were dried (MgSO₄) then evaporated in vacuo. The product was purified by flash silica chromatography with a gradient of 0-100% ethyl acetate/hexanes to give 2-(3-((5-cyclopropyl-3-(2-(trifluoromethoxy)phenyl)isoxazol-4-yl)methoxy)-8-azabicyclo[3.2.1]octan-8-yl)-4-methoxybenzo[d]thiazole-6-carboxylic acid.

Examples 2-2A and the corresponding acid 2-2B can be prepared following the same procedures, from the reaction of intermediate 4-((8-azabicyclo[3.2.1]octan-3-yloxy)methyl)-5-cyclopropyl-3-(2-(trifluoromethyl)phenyl)isoxazole, which was prepared following the procedures for the preparation of Intermediate 1.

| Ex | | Physical Data MS (m/z), ¹H NMR |
|---|---|---|
| 2-1A | [structure] | MS m/z 630.1 (M + 1) |

| Ex | | Physical Data MS (m/z), ¹H NMR |
|---|---|---|
| 2-1B | 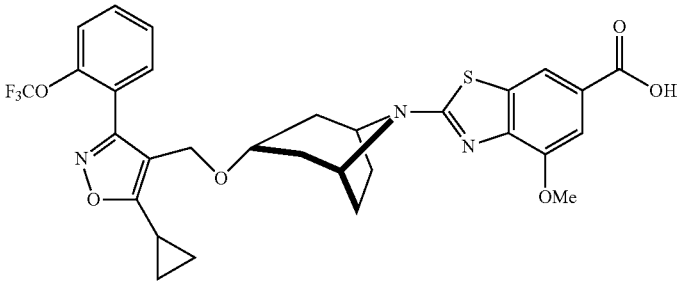 | MS m/z 616.1 (M + 1); ¹H NMR (MeOD, 400 MHz) δ 8.77 (s, 2H), 7.66-7.58 (m, 2H), 7.51 (app t, J = 8.0 Hz, 2H), 4.63 (bs, 2H), 4.40 (s, 2H), 3.55 (t, J = 4.4 Hz, 1H), 2.31-2.24 (m, 1H), 1.99-1.88 (m, 4H), 1.86-1.81 (m, 2H), 1.76 (d, J = 14.0 Hz, 2H), 1.19-1.15 (m, 4H). |
| 2-2B | 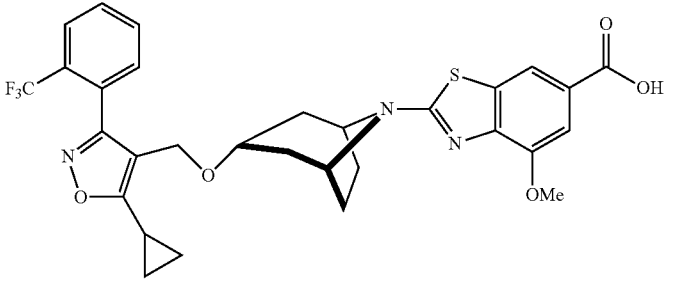 | MS m/z 600.1 (M + 1); ¹H NMR (DMSOd₆, 400 MHz) δ 7.90 (d, J = 1.2 Hz, 1H), 7.86 (d, J = 7.6 Hz, 1H), 7.73 (dt, J = 24, 7.6 Hz, 2H), 7.54 (d, J = 7.2 Hz, 1H), 7.30 (d, J = 1.6 Hz, 1H), 4.18 (s, 2H), 4.11 (bs, 2H), 3.81 (s, 3H), 3.43 (t, J = 4.4 Hz, 1H), 2.30-2.23 (m, 1H), 1.92-1.87 (m, 2H), 1.76-1.72 (m, 3H), 1.67 (t, J = 13.6 Hz, 3H), 1.10-0.99 (m, 4H). |

EXAMPLE 3

The following compounds were prepared from 4-((8-azabicyclo[3.2.1]octan-3-yloxy)methyl)-5-cyclopropyl-3-(2-(trifluoromethoxy)phenyl)isoxazole (I-1) and commercially available ethyl 2-chlorobenzo[d]thiazole-6-carboxylate according to the procedures described for the preparation of Example 1 or 2.

| Ex | | Physical Data MS (m/z), ¹H NMR |
|---|---|---|
| 3A | 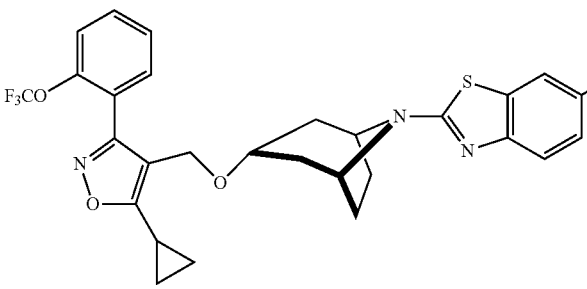 | MS m/z 614.2 (M + 1); ¹H NMR (DMSOd₆, 400 MHz) δ 8.37 (d, J = 1.6 Hz, 1H), 7.85 (dd, J = 8.8, 2 Hz, 1H), 7.71-7.63 (m, 2H), 7.59-7.53 (m, 2H), 7.47 (d, J = 8.4 Hz, 1H), 4.34 (s, 2H), 4.29 (app q J = 7.2 Hz, 2H), 4.22 (s, 2H), 3.56 (t, J = 4.4 Hz, 1H), 2.39-2.32 (m, 1H), 1.98 (dt, J = 14.8, 4 Hz, 2H), 1.85-1.80 (m, 4H), 1.74 (d, J = 14.4 Hz, 2H), 1.32 (t, J = 7.2 Hz, 3H), 1.17-1.06 (m, 4H). |
| 3B | 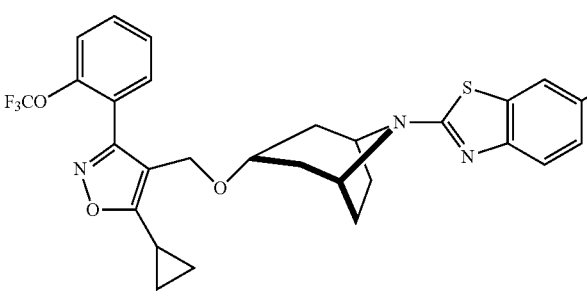 | MS m/z 586.2 (M + 1) ¹H NMR (DMSOd₆, 400 MHz); δ 8.30 (d, J = 1.6 Hz, 1H), 7.81 (dd, J = 8.4, 1.8 Hz, 1H), 7.71-7.62 (m, 2H), 7.60-7.53 (m, 2H), 7.42 (d, J = 8.4 Hz, 1H), 4.33 (s, 2H), 4.19 (bs, 2H), 3.54 (t, J = 4.4 Hz, 1H), 2.39-2.31 (m, 1H), 1.98 (dt, J = 14.8, 4 Hz, 2H), 1.86-1.77 (m, 4H), 1.73 (app d, J = 16.4 Hz, 2H), 1.17-1.04 (m, 4H). |

EXAMPLE 4

2-(2-(3-((5-cyclopropyl-3-(2-(trifluoromethoxy)phenyl)isoxazol-4-yl)methoxy)-8-azabicyclo[3.2.1]octan-8-yl)benzo[d]thiazol-6-yl)propan-2-ol

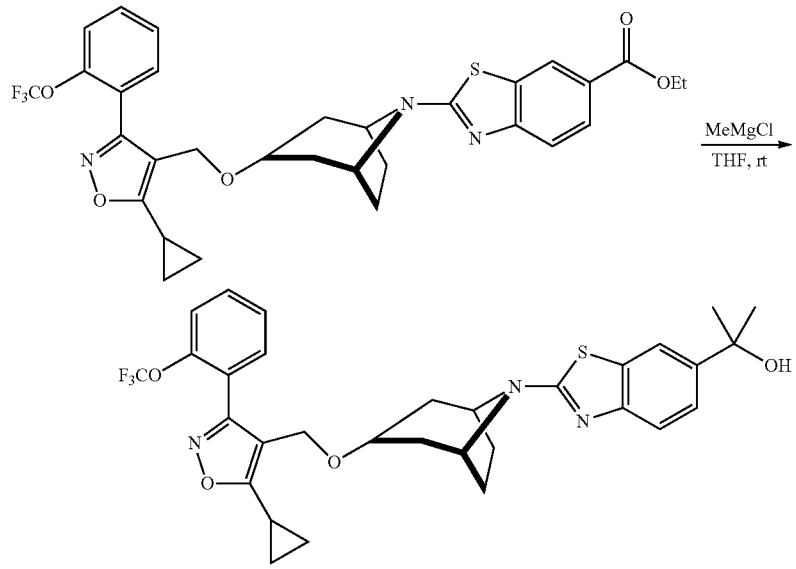

The ethyl ester Example 3-A, ethyl 2-(3-((5-cyclopropyl-3-(2-(trifluoromethoxy)phenyl)isoxazol-4-yl)methoxy)-8-azabicyclo[3.2.1]octan-8-yl)benzo[d]thiazole-6-carboxylate (20 mg, 0.033 mmol) was dissolved in THF (1.0 mL), and at RT was charged with a solution of methyl magnesium chloride (0.4 mL, 3.0 M THF, 1.2 mmol) in a dropwise fashion over a few minutes slowly enough so as not to allow the internal temperature of the reaction to exceed 30° C. After 1 hr the reaction was cooled to 0° C. and treated with MeOH (3 mL) in a dropwise fashion (rapid evolution of gas, internal temperature did not exceed 10° C.). The reaction was allowed to warm on its own accord to RT and diluted with ethyl acetate (9 mL) and the cloudy suspension was washed with 2×1 mL of 1 N HCl. The organic extracts were dried in vacuo and the resulting residue was purified using mass-directed reverse phase HPLC using gradient of 30 to 90% acetonitrile/water with 0.05% TFA as modifier. The resulting product was cold vacuum concentrated and free based using an SPE polymer support cartridge and MeOH (2 mL) mobilizing solvent (product SPE PLHCO$_3$ MP part no PL3540-C603). All resulting methanol effluent was concentrated to furnish the title compound as a white powder.

| Ex | | Physical Data MS (m/z), $^1$H NMR |
|---|---|---|
| 4 | ![structure] | MS m/z 600.2 (M + 1); $^1$H NMR (D$_4$-MeOH, 400 MHz) δ 7.98 (dd, J = 8.8, 2.0 Hz, 1H), 7.88 (d, J = 1.6 Hz, 1H), 7.64-7.58 (m, 2H), 7.52 (app t, J = 8.4 Hz, 1H), 7.41-7.36 (m, 2H), 4.52 (s, 2H), 4.31 (br s, 2H), 3.62 (t, J = 4.4 Hz, 1H), 2.39-2.32 (m, 1H), 2.09 (t, J = 4.4 Hz, 1H), 2.06 (t, J = 4.4 Hz, 1H), 2.02-1.96 (m, 4H), 1.82 (d, J = 14.4 Hz, 2H), 1.60 (br s, 6H), 1.21-1.15 (m, 4H). |

EXAMPLE 5

The previously described Example 1-1B,2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carboxylic acid (20 mg, 0.033 mmol), was suspended in methylene chloride (0.6 mL), cooled to 0° C. and treated with N,N-diisopropylethylamine (aprox. 10 uL, 0.07 mmol) and oxalyl chloride (10 uL, 0.10 mmol). After 20 minutes the reaction was concentrated in vacuo to a reddish colored residue, suspended in THF (0.5 mL) and then treated with 10 N ammonium hydroxide. After 1 hr of stirring, the reaction was diluted with ethyl acetate (1 mL), and water washed (2×0.5 mL). The resulting organic extract were concentrated to dryness, re-diluted with MeOH (2 mL), and directly purified using mass-directed reverse phase HPLC, using gradient of 30 to 90% acetonitrile/water, and 0.05% TFA as modifier. All product fractions were cold vacuum concentrated and free-based using an SPE polymer support cartridge and MeOH (2 mL) mobilizing solvent (product SPE PLHCO₃ MP part no PL3540-C603). All resulting methanol effluent was concentrated to furnish the title compound as a white powder, 14 mg (70%). MS m/z 603.1 (M+1).

Examples 5-2 and 5-3 were prepared following analogous procedures.

EXAMPLE 6

Intermediates 4-((8-azabicyclo[3.2.1]octan-3-yloxy)methyl)-5-cyclopropyl-3-(2-(trifluoromethyl)phenyl)isoxazole, 4-((8-azabicyclo[3.2.1]octan-3-yloxy)methyl)-5-cyclopropyl-3-(2-(difluoromethoxy)phenyl)isoxazole or 4-((8-azabicyclo[3.2.1]octan-3-yloxy)methyl)-5-cyclopropyl-3-(2,6-difluorophenyl)isoxazole were prepared as described

| Ex | | Physical Data MS (m/z), ¹H NMR |
|---|---|---|
| 5-1 | 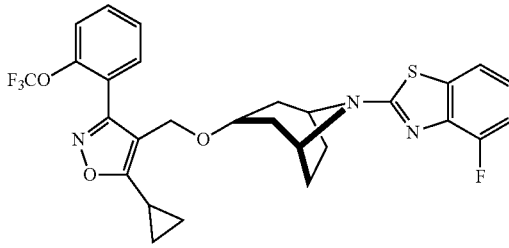 | MS m/z 603.1 (M + 1); ¹H NMR (DMSO-D₆, 400 MHz) δ 8.04 (app d, J = 11.2 Hz, 1H), 7.92 (d, J = 1.6 Hz, 1H), 7.84 (d, J = 8.1 Hz, 1H), 7.75 (d, J = 8.2 Hz, 1H), 7.70-7.65 (m, 2H), 7.03 (br s, 1H), 6.96 (br s, 1H), 3.95 (br s, 2H), 3.80 (s, 2H), 3.00 (t, J = 4.4 Hz, 1H), 2.80-2.55 (m, 9H), 1.50-1.33 (m, 4H). |
| 5-2 | 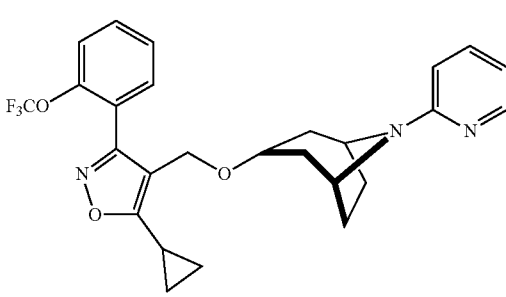 | MS m/z 529.2 (M + 1); ¹H NMR (MeOH-d₄, 400 MHz) δ 8.38 (d, J = 2.0 Hz, 1H), 8.27 (dd, J = 9.6, 1.9 Hz, 1H), 7.74 (app dt, J = 8.0, 2.0 Hz, 1H), 7.61 (app d, J = 8.0 Hz, 1H), 7.57-7.52 (m, 2H), 7.21 (dd, J = 8.4, 2.0 Hz, 1H), 4.49 (br s, 2H), 4.39 (s, 2H), 3.61 (app t, J = 4.4 Hz, 1H), 2.17-2.12 (m, 1H), 2.06-1.93 (m, 8H), 1.18 -1.12 (m, 4H). NH₂ of the amide is detectable by NMR in DMSO-d₆, appearing between 7.50 and 7.20 ppm, depending on residual water content. |
| 5-3 | 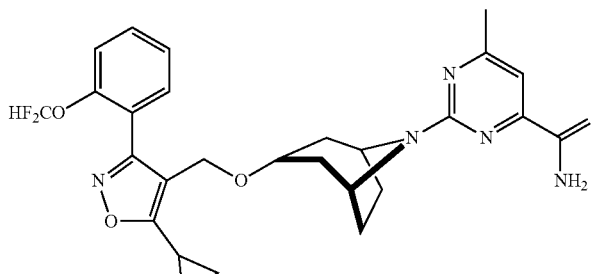 | MS m/z 526.2 (M + 1) | previously for the preparation of Intermediate 1. The following compounds were then prepared from the corresponding amine intermediates and corresponding benzothiazoles according to the procedures described previously for the preparation of Examples 1 or 2.

| Ex | | Physical Data MS (m/z), ¹H NMR |
|---|---|---|
| 6-1A | [structure] | MS m/z 598.2 (M + 1) |
| 6-1B | [structure] | MS m/z 570.1 (M + 1); ¹H NMR (DMSOd₆, 400 MHz) δ 8.23 (d, J = 1.2 Hz, 1H), 7.85 (app d, J = 7.6 Hz, 1H), 7.77-7.74 (m, 2H), 7.68 (app t, J = 7.2 Hz, 1H), 7.54 (d, J = 7.2 Hz, 1H), 7.35 (d, J = 8.4 Hz, 1H), 4.18 (s, 2H), 4.12 (bs, 2H), 3.44 (t, J = 4.4 Hz, 1H), 2.30-2.24 (m, 1H), 1.91 (dt, J = 14.8, 3.6 Hz, 2H), 1.80-1.63 (m, 6H), 1.01-0.99 (m, 4H). |
| 6-2A | [structure] | MS m/z 596.2 (M + 1) |
| 6-2B | [structure] | MS m/z 568.2 (M + 1); ¹H NMR (DMSOd₆, 400 MHz) δ 8.22 (d, J = 2 Hz, 1H), 7.74 (dd, J = 8.4, 1.6 Hz, 1H), 7.56-7.52 (m, 1H), 7.44 (dd, J = 7.8, 1.8 Hz, 1H), 7.30 (d, J = 8 Hz, 2H), 7.35 (dd, J = 11.5, 3.4 Hz, 1H), 7.18 (t, J = 73 Hz, 1H), 4.26 (s, 2H), 4.11 (bs, 2H), 3.46 (t, J = 4.4 Hz, 1H), 2.30-2.23 (m, 1H), 1.90 (dt, J = 15.2, 4 Hz, 2H), 1.77-1.74 (m, 4H), 1.64 (d, J = 14.4 Hz, 2H), 1.08-0.98 (m, 4H). |
| 6-3A | [structure] | MS m/z 600.2 (M + 1), |

| Ex | | Physical Data MS (m/z), $^1$H NMR |
|---|---|---|
| 6-3B | 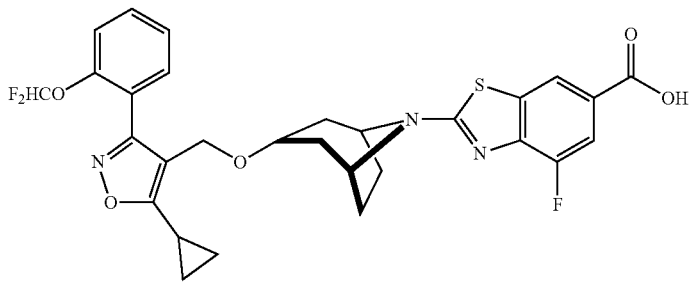 | MS m/z 586.1 (M + 1). |
| 6-4 | 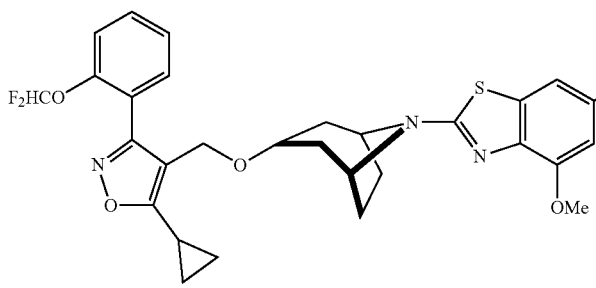 | MS m/z 598.1 (M + 1); $^1$H NMR (DMSOd$_6$, 400 MHz) δ 7.98 (d, J = 1.6 Hz, 1H), 7.61 (td, J = 6.6, 1.6 Hz, 1H), 7.51 (d, J = 8.1, 1.6 Hz, 1H), 7.40-7.36 (m, 3H), 7.25 (t, J = 73 Hz, 1H), 4.33 (s, 2H), 4.18 (bs, 2H), 3.89 (s, 3H), 3.52 (t, J = 4.4 Hz, 1H), 2.37-2.30 (m, 1H), 2.00-1.95 (m, 2H), 1.81-1.77 (m, 4H), 1.71 (d, J = 14.4, 2H), 1.15-1.05 (m, 4H). |
| 6-5A | 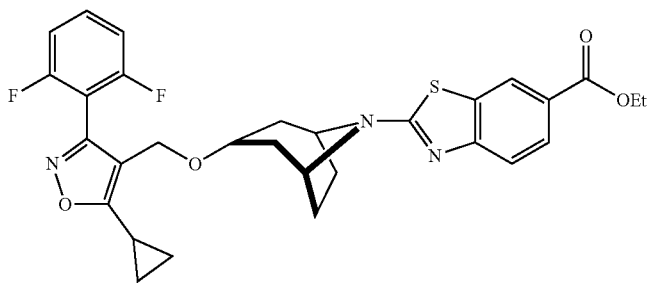 | MS m/z 566.2 (M + 1) |
| 6-5B | 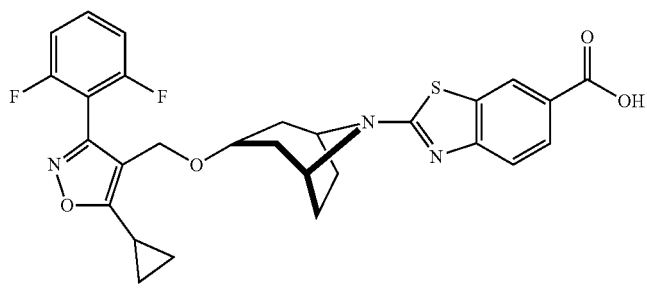 | MS m/z 538.1 (M + 1) |
| 6-6A | 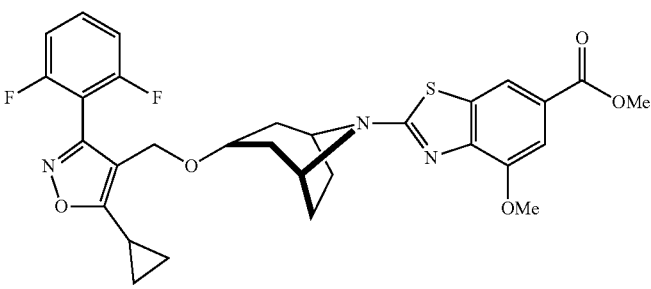 | MS m/z 582.2 (M + 1) |

| Ex | | Physical Data MS (m/z), ¹H NMR |
|---|---|---|
| 6-6B | | MS m/z 568.1 (M + 1); ¹H NMR (MeOD, 400 MHz) δ 7.91 (d, J = 1.6 Hz, 1H), 7.64-7.56 (m, 1H), 7.31-7.22 (m, 3H), 4.26 (s, 2H), 4.11 (bs, 2H), 3.82 (s, 3H), 3.46 (t, J = 4 Hz, 1H), 2.33-2.25 (m, 1H), 1.93-1.88 (m, 2H), 1.76-1.66 (m, 4H), 1.60 (d, J = 14.4 Hz, 2H), 1.10-1.00 (m, 4H). |
| 6-7A | | MS m/z 570.2 (M + 1) |
| 6-7B | | MS m/z 556.1 (M + 1) |
EXAMPLE 7
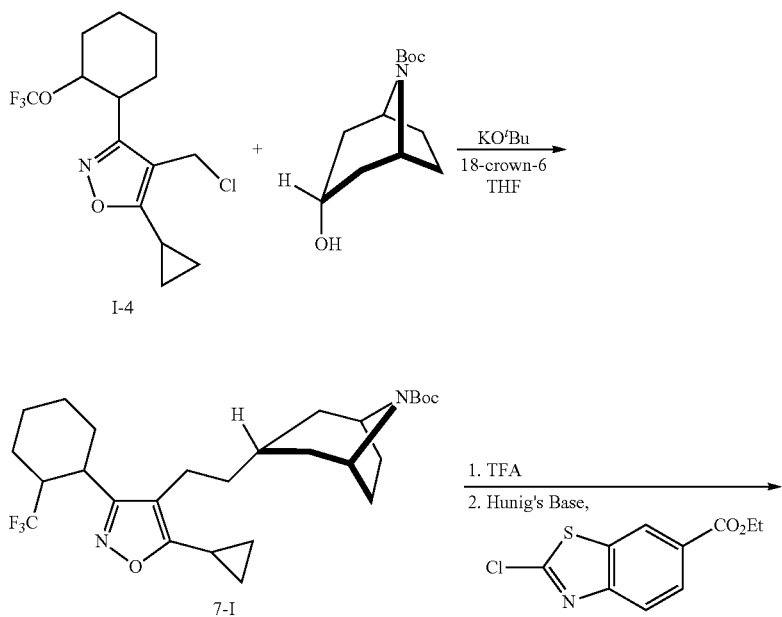

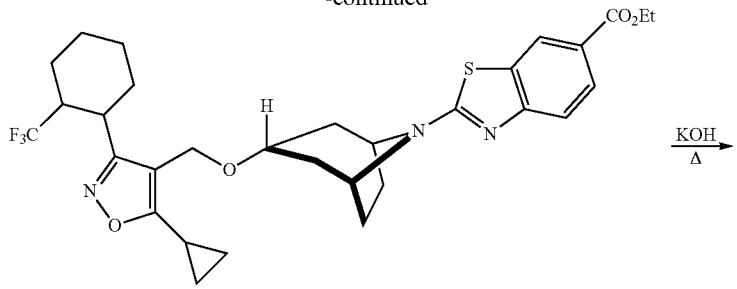

7A

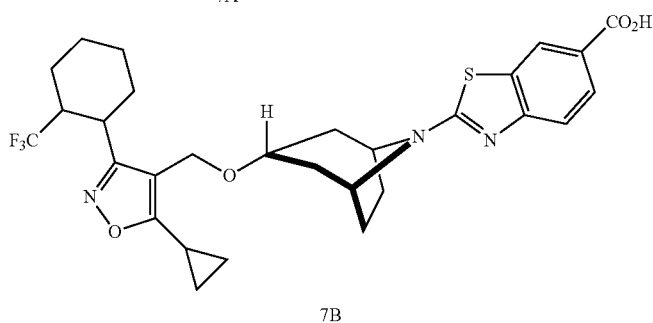

7B tert-butyl 3-((5-cyclopropyl-3-((trans)-2-(trifluoromethyl)cyclohexyl)isoxazol-4-yl)methoxy)-8-azabicyclo[3.2.1]octane-8-carboxylate (7-I). A solution of N-Boc-nortropine (579 mg, 2.55 mmol) and 18-crown-6 (808 mg, 3.06 mmol) in THF (8.5 mL) was treated with potassium tert-butoxide (343 mg, 3.06 mmol) and stirred for 10 minutes. A solution of 4-(chloromethyl)-5-cyclopropyl-3-((trans)-2-(trifluoromethyl)cyclohexyl)isoxazole (784 mg, 2.55 mmol) in THF was added. The resulting mixture was stirred at rt for 2 hours and then poured into water and extracted with EtOAc. Organics were collected, dried (MgSO$_4$), filtered, concentrated and chromatographed (SiO$_2$, linear gradient, 0-60% EtOAc in Hexanes) to give the title compound. $^1$H NMR (400 MHz, CDCl$_3$) δ 4.28 (m, 2H), 4.19 (m, 1H), 4.11 (m, 1H), 3.66 (dd, J=4.8, 4.7 Hz, 1H), 3.47 (dd, J=7.6, 3.7 Hz, 1H), 2.42 (m, 1H), 2.19 (ddd, J=25.2, 12.5, 3.4 Hz, 1H), 2.00-1.77 (m, 13H), 1.69 (m, 1H), 1.52 (m, 1H), 1.46 (s, 9H), 1.35 (m, 1H), 1.12 (m, 2H), 1.03 (m, 2H)$_4$; MS m/z 443.2 (M-$^t$Bu+1).

Ethyl 2-(3-((5-cyclopropyl-3-((trans)-2-(trifluoromethyl)cyclohexyl)isoxazol-4-yl)methoxy)-8-azabicyclo[3.2.1]octan-8-yl)benzo[d]thiazole-6-carboxylate (7A). A solution of tert-butyl 3-((5-cyclopropyl-3-((trans)-2-(trifluoromethyl)cyclohexyl)isoxazol-4-yl)methoxy)-8-azabicyclo[3.2.1]octane-8-carboxylate (67 mg, 0.13 mmol) in dichloromethane (1 mL) was treated with TFA (500 µL) and stirred for 1 hr at rt. The reaction was concentrated in vacuo and then diluted with NMP (1 mL) and then treated with Hunig's base (110 µL, 0.67 mmol) followed by ethyl 2-chlorobenzo[d]thiazole-6-carboxylate (33 mg, 0.13 mmol). After heating overnight at 120° C., the reaction was poured into water and extracted with EtOAc. The organic phase was collected, dried (MgSO$_4$), filtered, and concentrated. The crude residue was purified by chromatography (SiO$_2$, linear gradient, 0-60%, EtOAc in Hexanes) to give the title compound.

2-(3-((5-cyclopropyl-3-((trans)-2-(trifluoromethyl)cyclohexyl)isoxazol-4-yl)methoxy)-8-azabicyclo[3.2.1]octan-8-yl)benzo[d]thiazole-6-carboxylic acid (7B). A solution of ethyl 2-(3-((5-cyclopropyl-3-((trans)-2-(trifluoromethyl)cyclohexyl)isoxazol-4-yl)methoxy)-8-azabicyclo[3.2.1]octan-8-yl)benzo[d]thiazole-6-carboxylate (16 mg, 0.03 mmol) in ethanol (1 mL) was treated with potassium hydroxide (4.5 mg, 0.08 mmol) and heated to 60° C. for 2 hours. The reaction cooled RT, was concentrated in vacuo and then treated with 10% citric acid (aq.) and extracted with EtOAc. Organics were collected and concentrated. The crude material was purified via mass-directed reverse phase HPLC.

| Ex | Physical Data MS (m/z), $^1$H NMR |
|---|---|
| 7A | 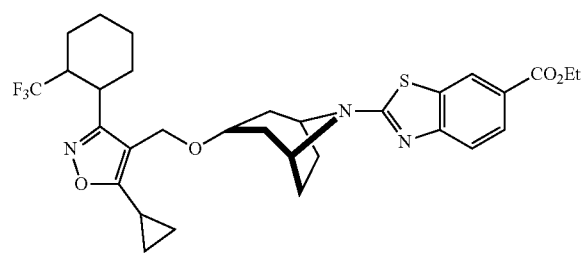 MS m/z 604.2 (M + 1). |

| Ex | | Physical Data MS (m/z), ¹H NMR |
|---|---|---|
| 7B | 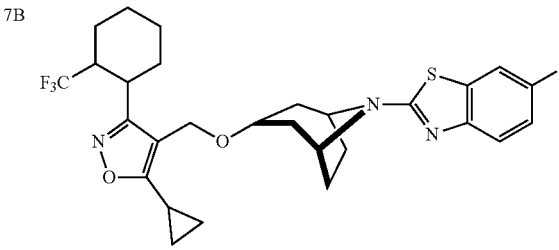 | MS m/z 576.3 (M + 1); ¹H NMR (MeOD, 400 MHz) δ 8.32 (d, J =1.6 Hz, 1H), 7.96 (dd, J = 8.5, 1.7 Hz, 1H), 7.47 (d, J = 8.5 Hz, 1H), 4.41 (dd, J = 33.5, 12.0 Hz, 2H), 4.40 (m, 2H), 3.74 (m, 1H), 3.55 (m, 1H), 2.64 (m, 1H), 2.30-2.12 (m, 6H), 2.09-2.03 (m, 4H), 1.91-1.74 (m, 5H), 1.52 (m, 1H), 1.45 (m, 1H), 1.07 (m, 4H). |

EXAMPLE 8

The following compounds were prepared from tert-butyl 3-((5-cyclopropyl-3-(2-(trifluoromethyl)cyclohexyl)isoxazol-4-yl)methoxy)-8-azabicyclo[3.2.1]octane-8-carboxylate, tert-butyl 3-((5-cyclopropyl-3-(4,4-dimethylcyclohexyl)isoxazol-4-yl)methoxy)-8-azabicyclo[3.2.1]octane-8-carboxylate or tert-butyl 3-((3-cyclohexyl-5-cyclopropylisoxazol-4-yl)methoxy)-8-azabicyclo[3.2.1]octane-8-carboxylate and the corresponding benzothiazole, pyrimidyl and pyrazine derivatives following the analogous procedures described for the preparation of Example 7.

| Ex | | Physical Data MS (m/z), ¹H NMR |
|---|---|---|
| 8-1 | 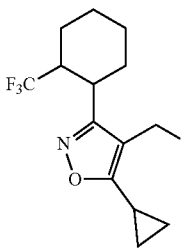 | MS m/z 594.3 (M + 1); ¹H NMR (CDCl₃, 400 MHz) δ 8.13 (d, J = 1.5 Hz, 1H), 7.75 (dd, J = 11.2, 1.5 Hz, 1H), 4.38-4.30 (m, 4H), 3.88 (m, 1H), 3.67 (m, 1H), 3.48 (m, 1H), 2.44 (m, 1H), 2.22 (m, 5H), 2.09 (m, 2H), 2.02-1.91 (m, 4H), 1.81 (m, 2H), 1.70 (m, 1H), 1.53 (m, 1H), 1.36 (m, 1H), 1.13 (m, 2H), 1.05 (m, 2H). |
| 8-2 | 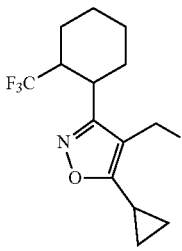 | MS m/z 606.3 (M + 1); ¹H NMR (MeOD, 400 MHz) δ 7.98 (d, J = 1.4 Hz, 1H), 7.52 (d, J = 1.4 Hz, 1H), 4.41 (m, 4H), 4.00 (s, 3H), 3.73 (m, 1H), 3.55 (m, 1H), 2.63 (m, 1H), 2.29-2.12 (m, 7H), 2.11-2.01 (m, 5H), 1.91-1.75 (m, 5H), 1.55-1.43 (m, 2H), 1.09 (m, 4H). |
| 8-3 | 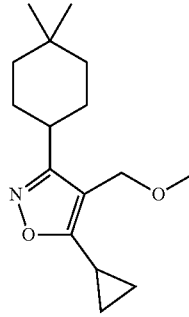 | MS m/z 536.3 (M + 1); ¹H NMR (400 MHz, DMSO) δ 12.7 (s, 1H), 8.35 (d, J = 2.0 Hz, 1H), 7.83 (d, J = 8.4, 2.0 Hz, 1H), 7.46 (d, J = 8.4 Hz, 1H), 4.36 (m, 4H), 3.71 (m, 1H), 2.64 (m, 1H), 2.23-2.16 (m, 1H), 2.13-2.09 (m, 5H), 2.02-1.95 (m, 5H), 1.76-1.72 (m, 2H), 1.68-1.58 (m, 2H), 1.46-1.42 (m, 2H), 1.26 (ddd, J = 26.0, 13.2, 4.0 Hz, 2H), 1.04-1.00 (m, 2H), 0.94-0.92 (m, 8H). MS m/z 536.1 (M + 1). |

-continued
| Ex | | Physical Data MS (m/z), ¹H NMR |
|---|---|---|
| 8-4 | 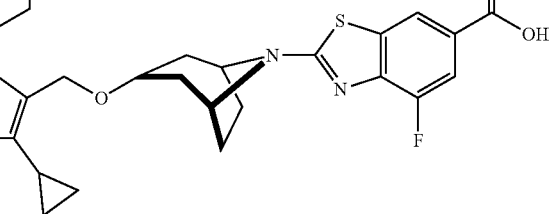 | MS m/z 554.3 (M + 1); |
| 8-5A | 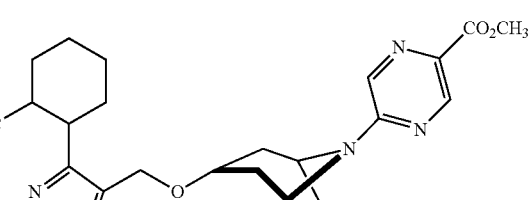 CO₂CH₃ | MS m/z 535.3 (M + 1) |
| 8-5B | 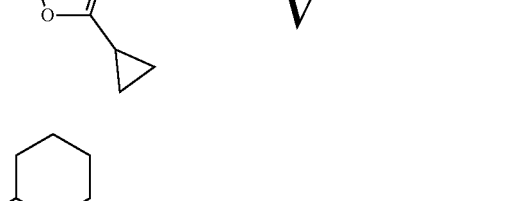 | MS m/z 521.3 (M + 1); 1H-NMR (400 MHz, d₄-MeOD) δ 8.72 (s, 1H), 8.09 (s, 1H), 4.66 (s, 2H), 4.39 (dd, J = 33.5, 12.0 Hz, 2H), 3.67 (m, 1H), 3.55 (m, 1H), 2.64 (m, 1H), 2.27 (m, 2H), 2.16 (m, 2H), 2.02 (m, 6H), 1.83 (m, 5H), 1.50 (m, 2H), 1.07 (m, 4H); MS m/z 521.3 (M + 1) |
| 8-6A | 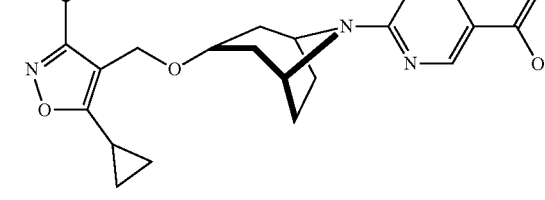 | MS m/z 549.3 (M + 1) |
| 8-6B | 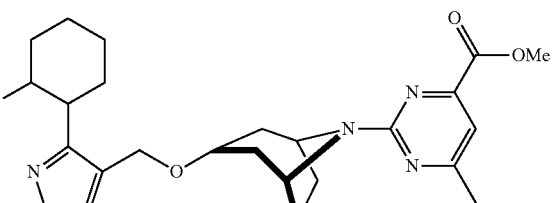 | MS m/z 535.3 (M + 1); 1H-NMR (400 MHz, d₄-MeOD) δ 6.95 (s, 1H), 4.78 (s, 1H), 4.38 (dd, J = 35.5, 12.0 Hz, 2H), 3.66 (m, 1H), 3.56 (m, 1H), 2.64 (m, 1H), 2.37 (s, 3H), 2.16 (m, 4H), 2.06 (m, 2H), 1.96-1.75 (m, 9H), 1.55-1.43 (m, 2H), 1.06 (m, 4H); MS m/z 535.3 (M + 1) |

-continued

| Ex | | Physical Data MS (m/z), ¹H NMR |
|---|---|---|
| 8-7A | 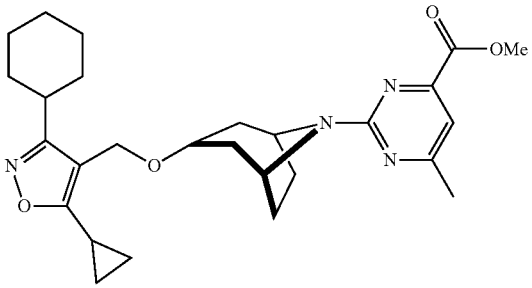 | MS m/z 481.3 (M + 1) |
| 8-7B | 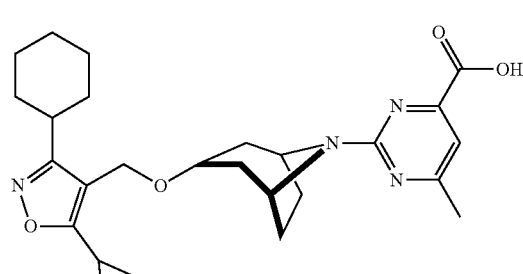 | MS m/z 538.3 (M + 1); 1H-NMR (400 MHz, d₄-MeOD) δ 6.99 (s, 1H), 4.79 (s, 2H), 4.40 (s, 2H), 3.70 (m, 1H), 2.76 (tt, J = 11.7, 3.2 Hz, 1H), 2.39 (s, 3H), 2.20 (m, 2H), 2.15 (m, 1H), 2.09 (m, 2H), 1.98 (m, 6H), 1.86 (m, 2H), 1.77 (m, 1H), 1.59-1.29 (m, 5H), 1.10-1.02 (m, 4H); MS m/z 467.3 (M + 1 |

EXAMPLE 9

The following examples may be prepared from Intermediate 8 tert-butyl 3-((3-cyclohexyl-5-cyclopropylisoxazol-4-yl)methoxy)-8-azabicyclo[3.2.1]octane-8-carboxylate and the corresponding benzothiazole following the analogous procedures described for the preparation of Example 7.

| Ex | | Physical Data MS (m/z), ¹H NMR |
|---|---|---|
| 9-1 | 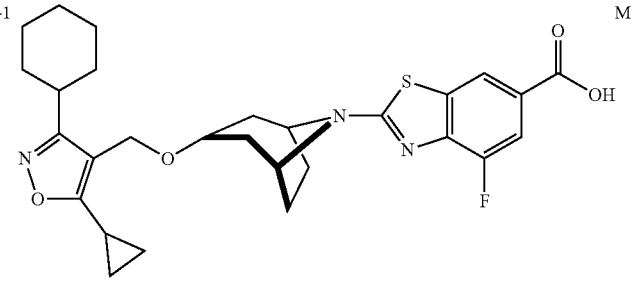 | MS m/z 526.3 (M + 1) |
| 9-2 | 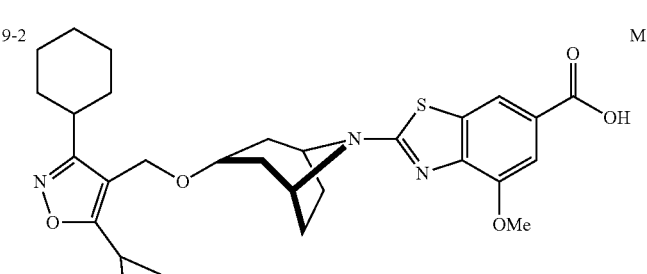 | MS m/z 538.3 (M + 1) |

EXAMPLE 10

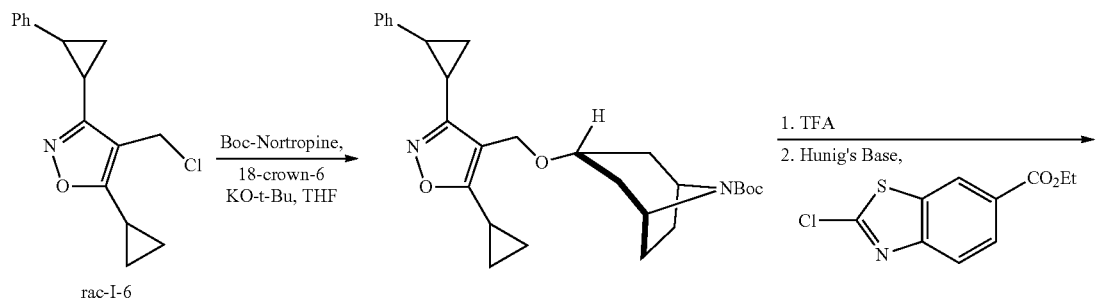

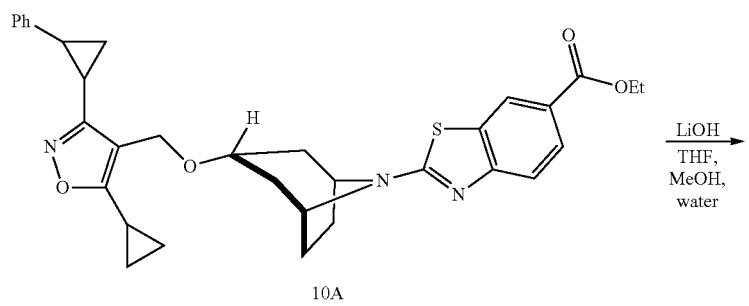

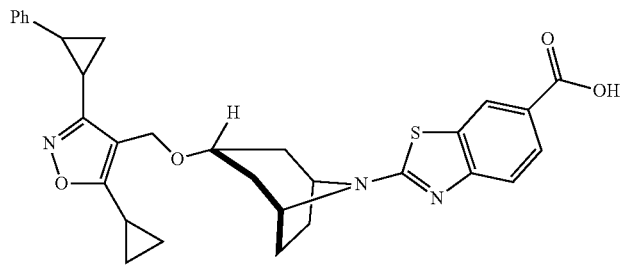

tert-butyl 3-((5-cyclopropyl-3-(2-phenylcyclopropyl)isoxazol-4-yl)methoxy)-8-azabicyclo[3.2.1]octane-8-carboxylate. A solution of N-Boc-nortropine (80 mg, 0.35 mmol) and 18-crown-6 (125 mg, 0.5 mmol) in THF (2.5 mL) was cooled to 0° C., treated with potassium tert-butoxide (59 mg, 0.53 mmol) and stirred for 10 min. A solution of 4-(chloromethyl)-5-cyclopropyl-3-(2-phenylcyclopropyl)isoxazole (80 mg, 0.29 mmol) in THF (0.5 mL) was added and the resulting mixture stirred at rt for 2 h and then poured into water and extracted with EtOAc. The organic layer was collected, washed with brine, dried over $Na_2SO_4$, filtered, concentrated to yield tert-butyl 3-((5-cyclopropyl-3-(2-phenylcyclopropyl)isoxazol-4-yl)methoxy)-8-azabicyclo[3.2.1]octane-8-carboxylate. MS m/z 409.1 (M−56+1).

Ethyl 2-(3-((5-cyclopropyl-3-(2-phenylcyclopropyl)isoxazol-4-yl)methoxy)-8-azabicyclo[3.2.1]octan-8-yl)benzo[d]thiazole-6-carboxylate (10A) was prepared from tert-butyl 3-((5-cyclopropyl-3-(2-phenylcyclopropyl)isoxazol-4-yl) methoxy)-8-azabicyclo[3.2.1]octane-8-carboxylate and ethyl 2-chlorobenzothiazole-6-carboxylate following the procedure described in the preparation of Example 7. The crude product was purified by silica gel column chromatography with hexane-EtOAc 20% isocratic as eluant to yield the title compound.

2-(3-((5-cyclopropyl-3-(2-phenylcyclopropyl)isoxazol-4-yl)methoxy)-8-azabicyclo[3.2.1]octan-8-yl)benzo[d]thiazole-6-carboxylic acid (10B). A suspension of ethyl 2-(3-((5-cyclopropyl-3-(2-phenylcyclopropyl)isoxazol-4-yl) methoxy)-8-azabicyclo[3.2.1]octan-8-yl)benzo[d]thiazole-6-carboxylate (0.03 g, 0.05 mmol) in THF:MeOH:$H_2O$=3:2:1 solution (0.6 mL) was treated with 6N LiOH (0.05 mL) at rt for 14 h. The volatiles were removed in vacuo, the residue diluted with water (1 mL), and 6N HCl was added to adjust pH to 2. The solids were collected by filtration and dried under vacuum to afford 2-(3-((5-cyclopropyl-3-(2-phenylcyclopropyl)isoxazol-4-yl)methoxy)-8-azabicyclo[3.2.1]octan-8-yl)benzo[d]thiazole-6 carboxylic acid as hydrochloride salt.

| Ex | | Physical Data MS (m/z), ¹H NMR |
|---|---|---|
| 10A | [structure: 3-(1-phenylcyclopropyl)-5-cyclopropyl-isoxazol-4-yl-methoxy tropane benzothiazole-6-carboxylic acid ethyl ester] | MS m/z 571.1 (M + 1). |
| 10B | [structure: 3-(1-phenylcyclopropyl)-5-cyclopropyl-isoxazol-4-yl-methoxy tropane benzothiazole-6-carboxylic acid] | MS m/z 542.0 (M + 1). ¹H NMR (400 MHz, D₄MeOH) δ 8.35 (d, J = 1.6 Hz, 1H), 8.84 (dd, J = 8.4 and 1.6 Hz, 1H), 7.46 (d, J = 8.4 Hz, 1H), 7.29 (m, 2H), 7.20-7.16 (m, 3H), 4.19 (bs, 2H), 2.35-2.30 (m, 2H), 2.23-2.17 (m, 3H), 2.01-1.93 (m, 6H), 1.86-1.78 (bm, 6H), 1.63-1.59 (m, 1H), 1.49-1.48 (m, 1H), 1.06-1.03 (m, 3H), 0.97-0.93 (m, 2H). |

EXAMPLE 11

The following compound was prepared from 4-(chloromethyl)-5-cyclopropyl-3-(2-(trifluoromethyl)cyclopropyl)isoxazole (rac-9) and the corresponding benzothiazole following the analogous procedures described for the preparation of Example 7.

| Ex | | Physical Data MS (m/z), ¹H NMR |
|---|---|---|
| 11 | [structure: 3-(2-(trifluoromethyl)cyclopropyl)-5-cyclopropyl-isoxazol-4-yl-methoxy tropane 4-fluoro-benzothiazole-6-carboxylic acid] | MS m/z 552.2 (M + 1); ¹H NMR (MeOD, 400 MHz) δ 8.13 (s, 1H), 7.66 (dd, J = 11.6, 0.9 Hz, 1H), 4.51 (s, 2H), 4.44 (m, 1H), 3.78 (m, 1H), 2.40 (m, 1H), 2.32-2.21 (m, 5H), 2.20-2.13 (m, 1H), 2.12-2.07 (m, 5H), 1.42 (m, 2H), 1.10 (m, 2H), 1.04 (m, 2H). |

EXAMPLE 12

The following compounds may be prepared from 4-(chloromethyl)-5-cyclopropyl-3-(2-methylcyclopropyl)isoxazole or 4-(chloromethyl)-5-cyclopropyl-3-(cyclopropyl)isoxazole and the corresponding benzothiazole following the analogous procedures described for the preparation of Example 7.

| Ex | | Physical Data MS (m/z), ¹H NMR |
|---|---|---|
| 12-1 | [structure: 3-(2-methylcyclopropyl)-5-cyclopropyl-isoxazol-4-yl-methoxy tropane 4-fluoro-benzothiazole-6-carboxylic acid] | MS m/z 498.2 (M + 1) |

| Ex | | Physical Data MS (m/z), ¹H NMR |
|---|---|---|
| 12-2 | 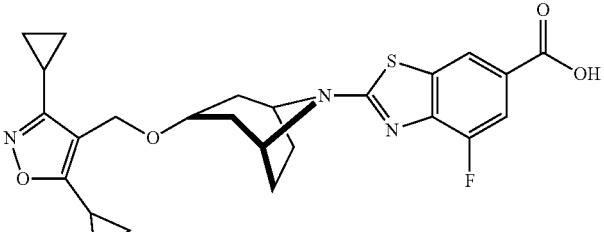 | MS m/z 484.2 (M + 1) |
| 12-3 | 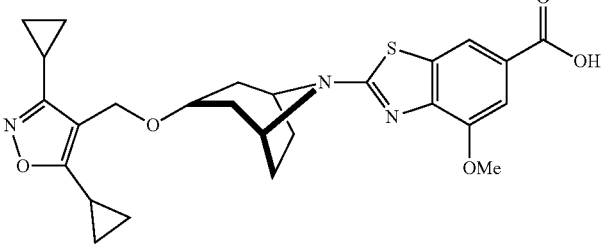 | MS m/z 496.2 (M + 1) |

EXAMPLE 13

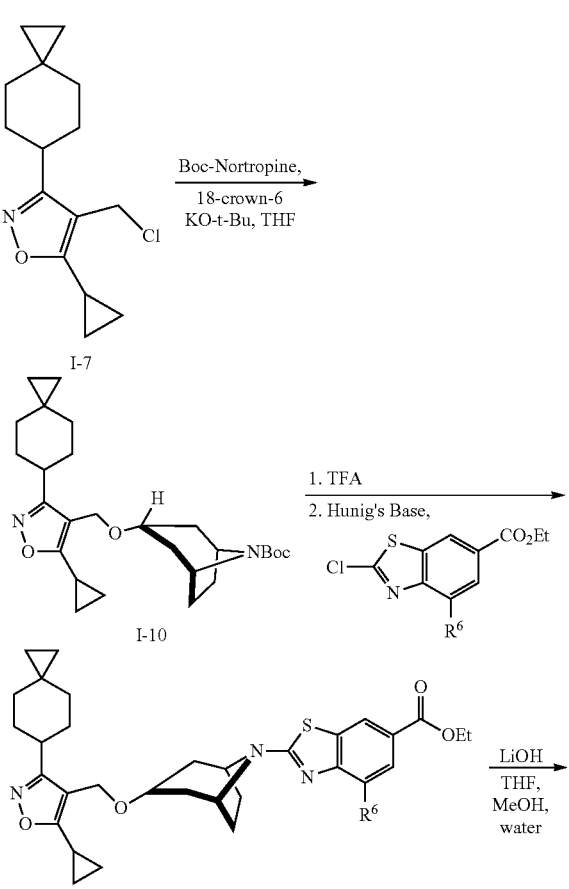

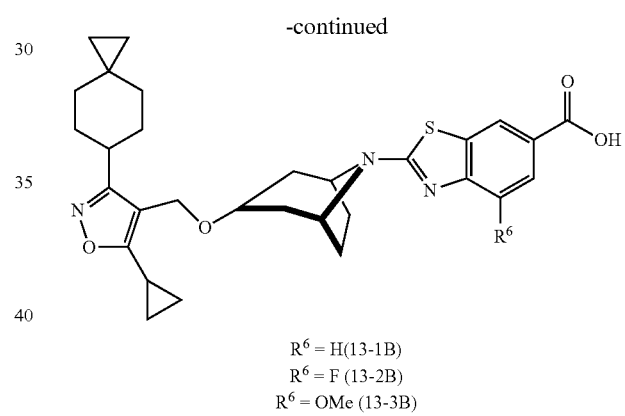

R⁶ = H (13-1B)
R⁶ = F (13-2B)
R⁶ = OMe (13-3B)

tert-Butyl 3-((5-cyclopropyl-3-(spiro[2.5]octan-6-yl)isoxazol-4-yl)methoxy)-8-azabicyclo[3.2.1]octane-8-carboxylate (I-10) was prepared following the same procedure as described for 7-I (Example 7) and was used without purification in the next step. MS m/z 401.0 (M−56+1).

Ethyl 2-(3-((5-cyclopropyl-3-(spiro[2.5]octan-6-yl)isoxazol-4-yl)methoxy)-8-azabicyclo[3.2.1]octan-8-yl)benzo[d]thiazole-6-carboxylate (13-1A) was prepared using the same procedure as described for 7A in Example 7. The crude was purified by column chromatography on silica gel with hexane-EtOAc 20% isocratic as eluant.

Ethyl 2-(3-((5-cyclopropyl-3-(spiro[2.5]octan-6-yl)isoxazol-4-yl)methoxy)-8-azabicyclo[3.2.1]octan-8-yl)benzo[d]thiazole-6-carboxylate (13-1B) was hydrolyzed using the same protocol as described for Example 7. The crude residue was diluted with water (1 mL) and 6N HCl was added until pH=6. The solid formed was collected by filtration to afford a white powder.

Examples 13-2A and 13-3A and their corresponding acids 13-2B and 13-3B were prepared following the same procedures, from the reaction of tert-Butyl 3-((5-cyclopropyl-3-(spiro[2.5]octan-6-yl)isoxazol-4-yl)methoxy)-8-azabicyclo[3.2.1]octane-8-carboxylate (I-10) and the corresponding benzothiazole.

| Ex | | Physical Data MS (m/z), ¹H NMR |
|---|---|---|
| 13-1A | | MS m/z 562.0 (M + 1). |
| 13-1B | | MS m/z 534.1 (M + 1). ¹H NMR (400 MHz, DMSO) δ 8.33 (d, J = 1.2 Hz, 1H), 7.84 (dd, J = 8.4 and 1.6 Hz, 1H), 7.46 (d, J = 8.4 Hz, 1H), 4.37 (m, 3H), 3.72 (m, 1H), 2.22-2.19 (m, 2H), 2.14-2.10 (m, 4H), 2.00-1.96 (m, 4H), 1.90-1.86 (m, 2H), 1.78-1.74 (m, 2H), 1.66-1.60 (m, 2H), 1.04-0.93 (m, 8H), 0.3-0.2 (m, 4H). |
| 13-2A | | ¹H NMR (400 MHz, DMSO) δ 8.28 (d, J = 1.2 Hz, 1H), 7.64 (dd, J = 11.2 and 1.6 Hz, 1H), 4.38 (bs, 3H), 3.84 (s, 3H), 3.73 (m, 1H), 2.76-2.71 (m, 1H), 2.23-2.21 (m, 1H), 2.15-2.10 (m, 4H), 2.03-1.99 (m, 4H), 1.90-1.86 (m, 2H), 1.81-1.74 (m, 2H), 1.67-1.58 (m, 2H), 1.04-0.93 (m, 7H), 0.32-0.20 (m, 4H). MS m/z 566.0 (M + 1). |
| 13-2B | | ¹H NMR (400 MHz, DMSO) δ 8.22 (s, 1H), 7.58 (d, J = 11.2 Hz, 1H), 4.38 (bs, 3H), 3.84-3.73 (bs, 1H), 2.77-2.71 (m, 1H), 2.23-2.19 (m, 1H), 2.15-2.10 (m, 5H), 2.02-1.93 (m, 4H), 1.89-1.86 (m, 2H), 1.77-1.74 (m, 2H), 1.66-1.60 (m, 2H), 1.04-0.95 (m, 6H), 0.30-0.21 (m, 4H). MS m/z 552.2 (M + 1). |
| 13-3A | | MS m/z 578.0 (M + 1) |

| Ex | Physical Data MS (m/z), ¹H NMR |
|---|---|
| 13-3B 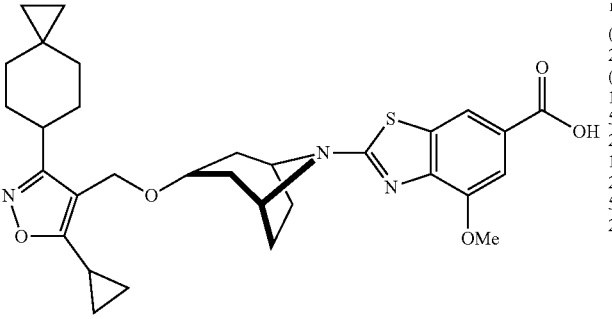 | ¹H NMR (400 MHz, DMSO) δ 7.94 (s, 1H), 7.39 (d, J = 1.2 Hz, 1H), 4.37 (s, 2H), 4.29, s, 1H), 3.83 (s, 3H), 3.73 (appt. J = 4.4 Hz, 1H), 2.77-2.71 (m, 1H), 2.24-2.17 (m, 1H), 2.13-2.10 (m, 5H), 2.01-1.95 (m, 4H), 1.90-1.86 (m, 2H), 1.78 (dt, J = 12.4 and 2.4 Hz, 2H), 1.63 (ddd, J = 25.2, 12.4, and 3.2 Hz, 2H), 1.04-1.02 (m, 2H), 0.95-0.94 (m, 5H), 0.32-0.29 (m, 2H), 0.21-0.20 (m, 2H). MS m/z 564.2 (M + 1). |

EXAMPLE 14

The following examples were prepared from tert-Butyl 3-((5-cyclopropyl-3-(spiro[2.5]octan-6-yl)isoxazol-4-yl)methoxy)-8-azabicyclo[3.2.1]octane-8-carboxylate (I-15) and the corresponding benzothiazole, pyridyl or pyrimidyl derivatives following the analogous procedures described for the preparation of Example 13.

| | Physical Data MS (m/z), ¹H NMR |
|---|---|
| 14 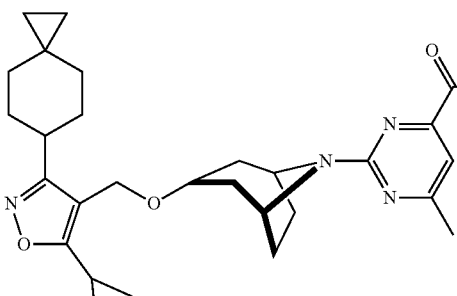 | ¹H NMR (400 MHz, CDCl3) δ 7.12 (s, 1H), 4.76-4.64 (bs, 2H), 4.34 (d, J = 2.4 Hz, 2H), 3.6 (bs 1H), 2.44 (s, 3H), 2.35-2.33 (m, 1H), 2.08-2.04 (m, 1H), 2.22-2.19 (m, 2H), 2.01-1.93 (m, 9H), 1.85-1.79 (m, 2H), 1.25-1.24 (m, 3H), 1.12-1.10 (m, 2H), 1.04-1.00 (m, 4H), 0.34-0.23 (m, 2H). MS m/z 493.2 (M + 1). |

EXAMPLE 15

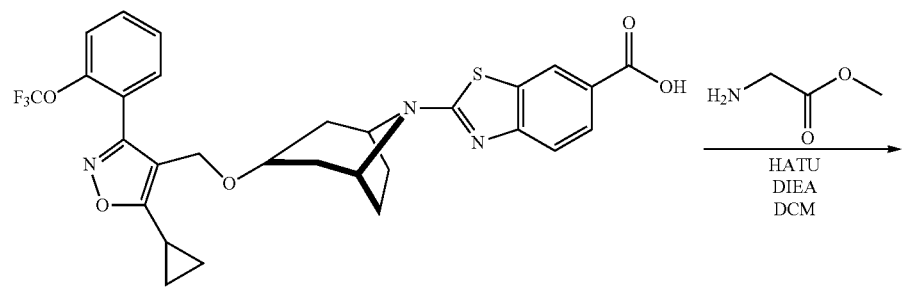

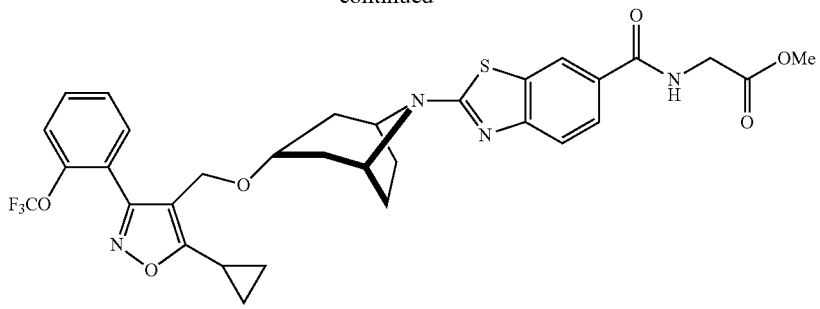

15-1A

↓ LiOH
Dioxane
H₂O

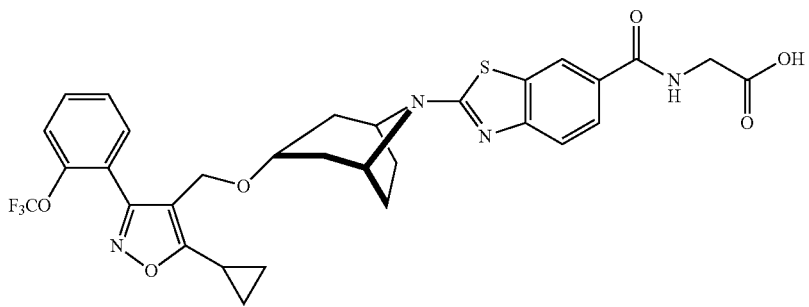

15-1B

Methyl 2-(2-(3-((5-cyclopropyl-3-(2-(trifluoromethoxy)phenyl)isoxazol-4-yl)methoxy)-8-azabicyclo[3.2.1]octan-8-yl)benzo[d]thiazole-6-carboxamido)acetate (15-1A). 2-(3-((5-cyclopropyl-3-(2-(trifluoromethoxy)phenyl)isoxazol-4-yl)methoxy)-8-azabicyclo[3.2.1]octan-8-yl)benzo[d]thiazole-6-carboxylic acid (34 mg, 0.06 mmol) was combined with glycine methyl ester hydrochloride (8 mg, 0.06 mmol), O-(7-Azabenzotriazol-1-yl)-N,N,N',N'-tetramethyluronium hexafluorophosphate (25 mg, 0.065 mmol), diisopropylethylacetate (0.05 ml) and dichloromethane (2 mL). The mixture was stirred for 1 hour, then the solvent was removed in vacuo. The residue was suspended in ethyl acetate (15 mL) and washed with sodium bicarbonate solution (5 mL). The organics were combined and dried (MgSO₄) then evaporated in vacuo. The product was purified by flash silica chromatography with 0-100% ethyl acetate in hexanes and used directly in the next procedure.

2-(2-(3-((5-cyclopropyl-3-(2-(trifluoromethoxy)phenyl)isoxazol-4-yl)methoxy)-8-azabicyclo[3.2.1]octan-8-yl)benzo[d]thiazole-6-carboxamido)acetic acid (15-1B). Methyl 2-(2-(3-((5-cyclopropyl-3-(2-(trifluoromethoxy)phenyl)isoxazol-4-yl)methoxy)-8-azabicyclo[3.2.1]octan-8-yl)benzo[d]thiazole-6-carboxamido)acetate was subjected to a solution of 4N LiOH in water (2 mL) and dioxane (2 ml) and stirred for 2 hours. The solvent was reduced in vacuo and the mixture diluted with 5% citric acid (10 ml) and extracted with ethyl acetate (2×8 mL). The organics were combined and dried (MgSO₄) then evaporated in vacuo. The product was purified with flash silica chromatography with methanol/dichloromethane with a 0-40% gradient to give the title compound as a white solid.

| Ex | | Physical Data MS (m/z), 1H NMR |
|---|---|---|
| 15-1B | 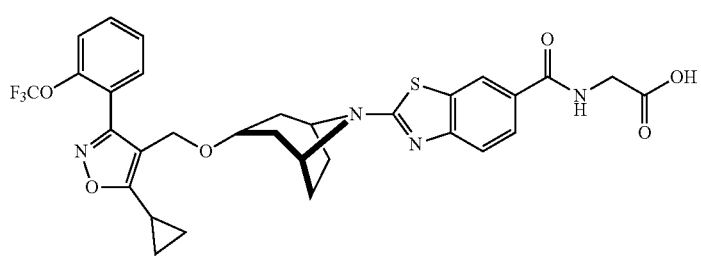 | MS m/z 643.2 (M + 1); ¹H NMR (MeOD, 400 MHz) δ 8.07 (d, J = 1.6 Hz, 1H), 7.71 (dd, J = 8.4, 1.6 Hz, 1H), 7.57-7.48 (m, 2H), 7.41 (app t, J = 7.6 Hz, 2H), 7.35 (d, J = 8.4 Hz, 1H), 4.31 (s, 2H), 4.16 (bs, 2H), 3.95 (s, 2H), 3.50 (t, J = 4.4 Hz, 1H), 2.21-2.15 (m, 1H), 2.00 (dt, J = 14.8, 4 Hz, 2H), 1.91-1.81 (m, 4H), 1.72 (d, J = 14.8 Hz, 2H), 1.09-1.05 (m, 4H). |

| Ex | | Physical Data MS (m/z), 1H NMR |
|---|---|---|
| 15-2 | 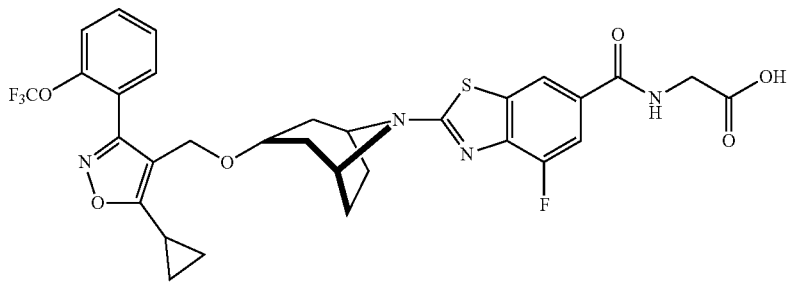 | MS m/z 661.2 (M + 1) |
| 15-3 | | MS m/z 587.2 (M + 1); ¹H NMR (MeOH-d₄, 400 MHz) δ 8.35 (d, J = 2.0 Hz, 1H), 8.29 (d, J = 9.6, 3.0 Hz, 1H), 7.64 (app dt, J = 7.6, 2.0 Hz, 1H), 7.59 (app dd, J = 8.4, 2.0 Hz, 1H), 7.54-7.48 (m, 2H), 7.28 (d, J = 9.6 Hz, 1H), 4.56 (br s, 2H), 4.44 (s, 2H), 4.18 (s, 2H), 3.61 (app t, J = 4.4 Hz, 1H), 2.29-2.27 (m, 1H), 2.06-1.89 (m, 8H), 1.19-1.15 (m, 4H). |
| 15-4 | 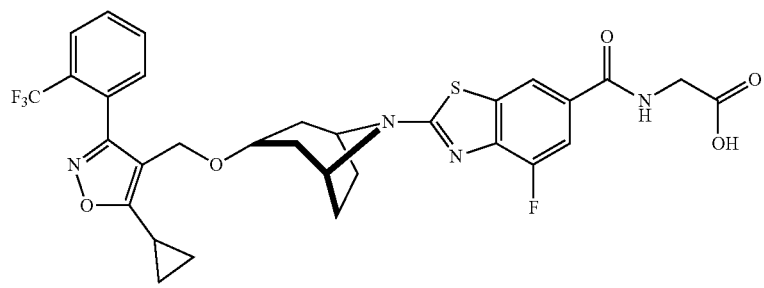 | MS m/z 645.1 (M + 1); |
EXAMPLE 16
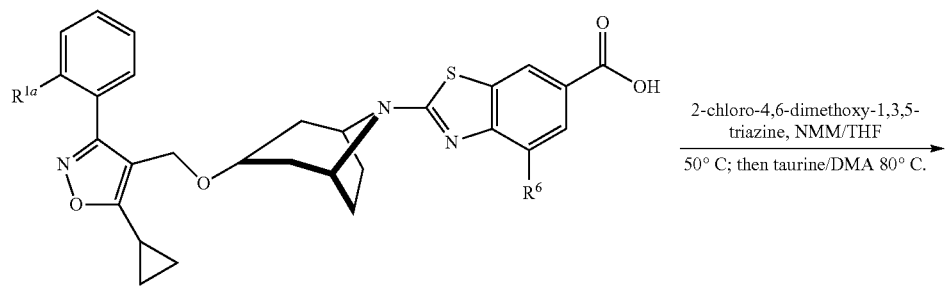
2-chloro-4,6-dimethoxy-1,3,5-triazine, NMM/THF
50° C; then taurine/DMA 80° C.

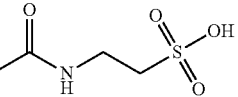
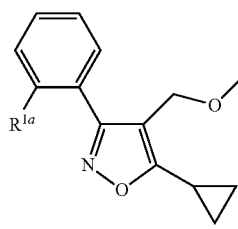

R$^{1a}$ = OCF$_3$; R$^6$ = H (16-1)
R$^{1a}$ = OCF3; R$^6$ = F (16-2)
R$^{1a}$ = CF$_3$; R$^6$ = F(16-3)

2-(2-(3-((5-cyclopropyl-3-(2-(trifluoromethoxy)phenyl)isoxazol-4-yl)methoxy)-8-azabicyclo[3.2.1]octan-8-yl)benzo[d]thiazole-6-carboxamido)ethanesulfonic acid (16-1) Charged to a resealable and pressure tolerable vessel were added the following in sequential order: the acid, 2-(3-((5-cyclopropyl-3-(2-(trifluoromethoxy)phenyl)isoxazol-4-yl)methoxy)-8-azabicyclo[3.2.1]octan-8-yl)benzo[d]thiazole-6-carboxylic acid (58.3 mg, 0.1 mmol), tetrahydrofuran (1.0 mL), N-methyl morpholine (approximately 0.1 mL, 0.7 mmol). The suspension was stirred at RT for a few minutes until complete dissolution of the starting acid. Next was added 2-chloro-4,6-dimethoxy-1,3,5-triazine (27 mg, 0.15 mmol) and the resulting solution was stirred at 50° C. for 20 minutes until a fine white precipitate formed. This precipitate was physically agitated to ensure that all materials were thoroughly mixed. Next the taurine (50 mg, 0.40 mmol) was added as a dimethyl acetamide (4 mL) suspension. The resulting suspension was sealed in the vessel and heated to 80° C. for 2 hours. The mixture was then cooled to RT. The mixture was diluted with ethyl acetate 20 mL and water washed (2×3 mL). The organics were dried under vacuum to a residue, the resulting residue was diluted with 3 mL of MeOH, and the liquid was directly purified using mass-directed reverse phase HPLC using gradient of 20 to 70% acetonitrile/water with ammonium acetate (0.05%) as modifier. The resulting product was cold vacuum concentrated to give the title compound as a white powder.

Examples 16-2 and 16-3 were prepared following the same procedures.

| Ex | | Physical Data MS (m/z), $^1$H NMR |
|---|---|---|
| 16-1 | 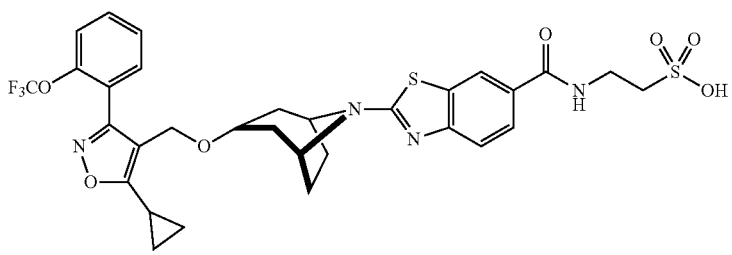 | MS m/z 693.2 (M + 1); $^1$H NMR (MeOD, 400 MHz) δ 8.27 (d, J = 1.6 Hz, 1H), 8.00 (dd, J = 8.4, 1.9 Hz, 1H), 7.65-7.53 (m, 2H), 7.42 (app t, J = 7.8 Hz, 2H), 7.35 (d, J = 8.4 Hz, 1H), 4.42 (br s, 4H), 3.81 (t, J = 6.4 Hz, 2H), 3.11 (t, J = 6.4 Hz, 2H), 2.18-1.93 (m, 8H), 1.72 (d, J = 14.8 Hz, 2H), 1.29-1.15 (m, 4H). |
| 16-2 | 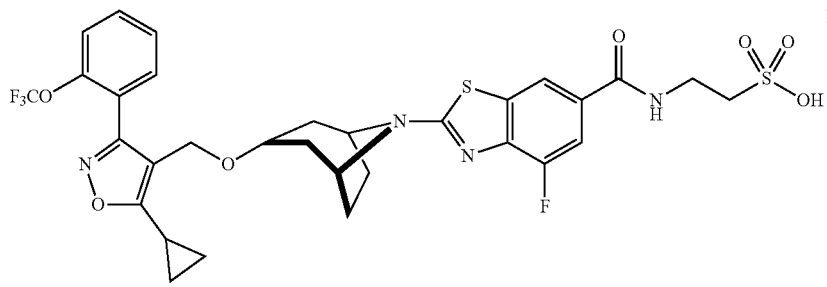 | MS m/z 711.2 (M + 1); |

| Ex | Physical Data MS (m/z), ¹H NMR |
|---|---|
| 16-3 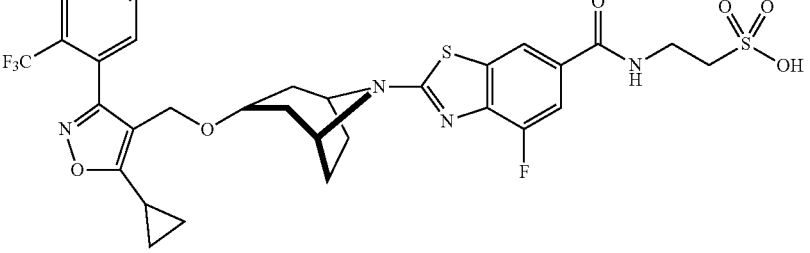 | MS m/z 695.3 (M + 1); |
| 16-4 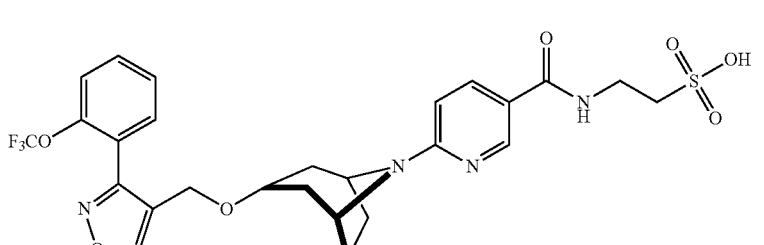 | MS m/z 637.2 (M + 1); ¹H NMR (MeOH-d₄, 400 MHz) δ 8.30 (d, J = 2.0 Hz, 1H), 8.26 (d, J = 9.6 Hz, 1H), 7.66 (app dt, J = 7.6, 2.0 Hz, 1H), 7.61 (app dd, J = 8.4, 2.0 Hz, 1H), 7.54-7.49 (m, 2H), 7.25 (d, J = 9.4, 1.8 Hz, 1H), 4.55 (br s, 2H), 4.49 (s, 2H), 3.78 (t, J = 8.4 Hz, 2H), 3.60 (app t, J = 4.4 Hz, 1H), 3.07 (t, J = 8.4 Hz, 2H), 2.27-2.21 (m, 1H), 2.08-1.93 (m, 8H), 1.21-1.16 (m, 4H). |
EXAMPLE 17
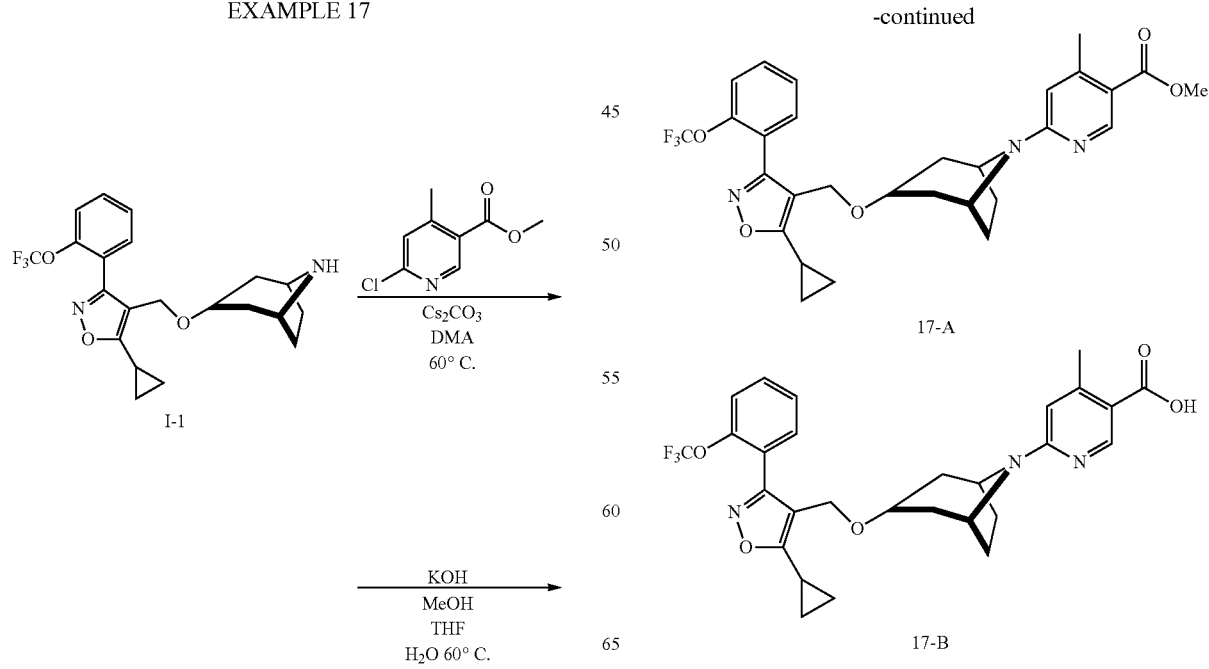

Methyl 2-(3((5-cyclopropyl-3-(2-(trifluoromethoxy)phenyl)isoxazol-4-yl)methoxy)-8-azabicyclo[3.2.1]octan-8-yl)-4-methylpyridine-6-carboxylate acid (17A). The amine, 4-((8-azabicyclo[3.2.1]octan-3-yloxy)methyl)-5-cyclopropyl-3-(2-(trifluoromethoxy)phenyl)-isoxazole (125 mg, 0.31 mmol), dimethylacetamide (1.5 mL), methyl 6-chloro-4-methylnicotinate (157 mg, 0.93 mmol), and cesium carbonate (303 mg, 0.93 mmol) were combined sequentially and heated to 60° C. for 2 hours. The mixture was diluted with water and extracted with ethyl acetate (2×10 mL). The organics were dried (MgSO₄) then evaporated in vacuo. The product was purified by flash silica chromatography with a gradient of 0-100% ethyl acetate/hexanes to furnish the desired compound as a clear oil.

2-(3((5-cyclopropyl-3-(2-(trifluoromethoxy)phenyl)isoxazol-4-yl)methoxy)-8-azabicyclo[3.2.1]octan-8-yl)-4-methylpyridine-6-carboxylate acid (17B). The preceding ester, methyl 2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carboxylate was dissolved in tetrahydrofuran (2 mL) and methanol (2 mL) and subjected to an aqueous solution of potassium hydroxide (1N aqueous solution, 2 mL, 2.0 mmoles). The mixture was heated to 60° C. for 2 hours then the solvent reduced in vacuo. The mixture was diluted with 5% citric acid in water (8 mL) and extracted with ethyl acetate (2×8 mL). The organics were dried (MgSO₄) then evaporated in vacuo. The product was purified using silica flash chromatography with a gradient of 0-100% ethyl acetate/hexanes to give the title compound as a white solid.

| Ex | | Physical Data MS (m/z), ¹H NMR |
|---|---|---|
| 17A | 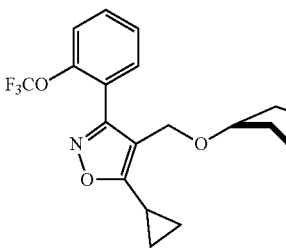 | MS m/z 558.2 (M + 1); δ ¹H NMR (DMSO D₆, 400 MHz) 8.55 (s, 1H), 7.70-7.61 (m, 2H), 7.75-7.52 (m, 2H), 6.54 (s, 1H), 4.41 (bs, 2H), 4.32 (s, 2H), 3.73 (s, 3H), 3.46 (t, J = 4.0 Hz, 1H), 2.42 (s, 3H), 2.36-2.30 (m, 1H), 1.83-1.71 (m, 6H), 1.60 (d, J = 14.4 Hz, 2H), 1.19-1.03 (m, 4H). |
| 17B | 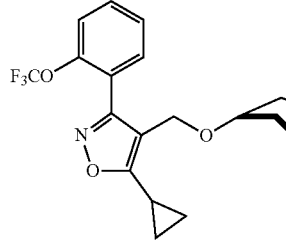 | MS m/z 544.1 (M + 1). δ ¹H NMR (DMSO D₆, 400 MHz) 12.24 (s, 1H), 8.56 (s, 1H), 7.70-7.63 (m, 2H), 7.57-7.52 (m, 2H), 6.52 (s, 1H), 4.41 (bs, 2H), 4.32 (s, 2H), 3.47 (t, J = 4.4 Hz, 1H), 2.43 (s, 3H), 2.37-2.30 (m, 1H), 1.83-1.71 (m, 6H), 1.60 (d, J = 14.4 Hz, 2H), 1.15-1.06 (m, 4H). |

EXAMPLE 18

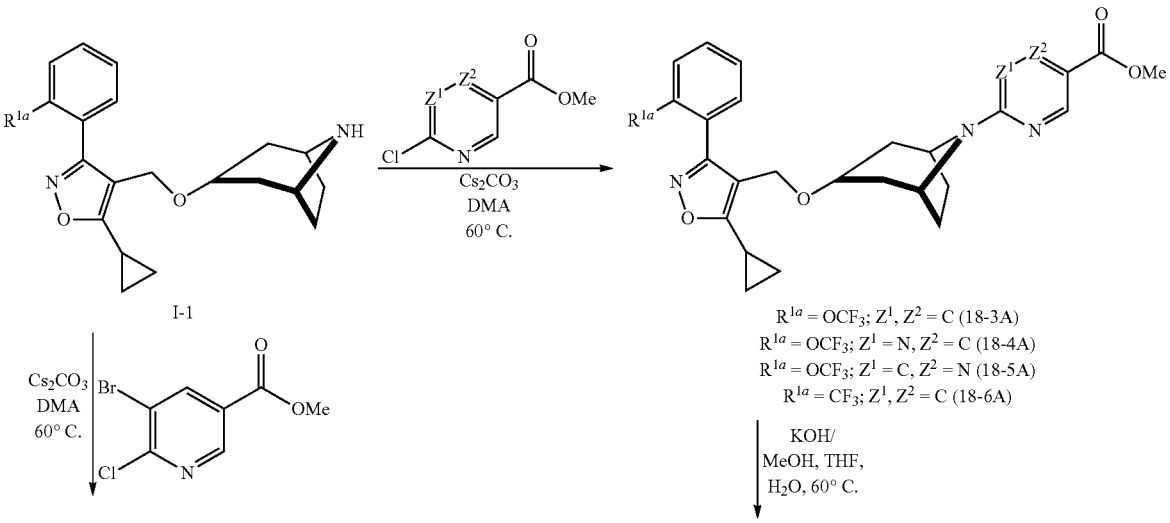

R¹ᵃ = OCF₃; Z¹, Z² = C (18-3A)
R¹ᵃ = OCF₃; Z¹ = N, Z² = C (18-4A)
R¹ᵃ = OCF₃; Z¹ = C, Z² = N (18-5A)
R¹ᵃ = CF₃; Z¹, Z² = C (18-6A)

KOH/ MeOH, THF, H₂O, 60° C.

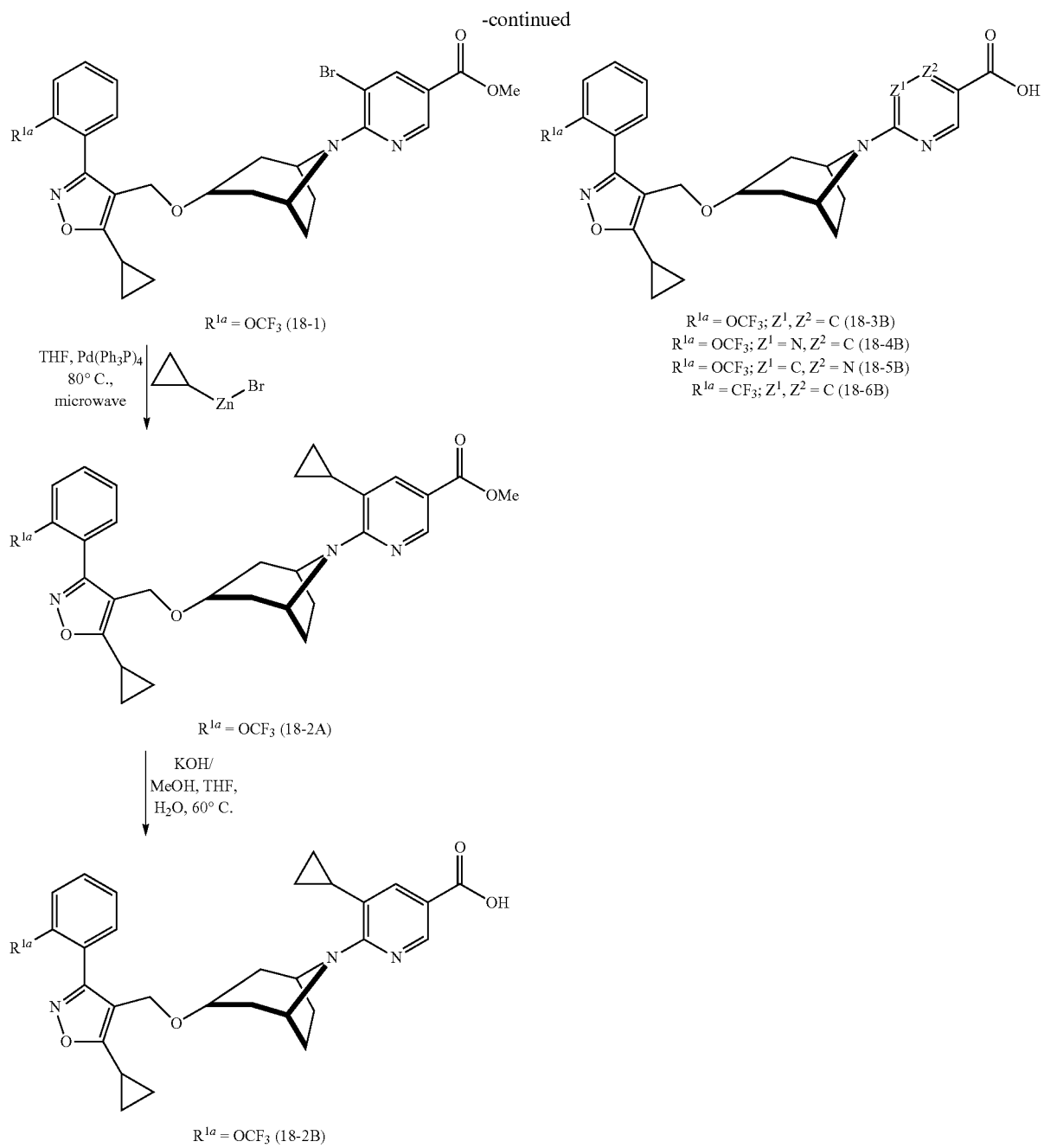

Methyl 5-bromo-6-((1S,3R)-3-((5-cyclopropyl-3-(2-(trifluoromethoxy)phenyl)isoxazol-4-yl)methoxy)-8-azabicyclo[3.2.1]octan-8-yl)nicotinate (18-1). The amine, 4-((8-azabicyclo[3.2.1]octan-3-yloxy)methyl)-5-cyclopropyl-3-(2-(trifluoromethoxy)phenyl)isoxazole (83 mg, 0.20 mmol), N,N-dimethylacetamide (0.6 mL), methyl 5-bromo-6-chloronicotinate (75 mg, 0.3 mmol), and cesium carbonate (108 mg, 0.33 mmol) were combined sequentially and heated to 60° C. for about 3 hours. The mixture was diluted with ethyl acetate 20 mL and water washed (2×3 mL). The organics were dried under vacuum to a residue and submitted to flash silica with a gradient of 0-100% ethyl acetate/hexanes to give the title compound as a clear dense oil. MS m/z 622.2/624 (M+1, Br$_{79}$/Br$_{81}$ isotope pattern).

Methyl 5-cyclopropyl-6-((1S,3R)-3-((5-cyclopropyl-3-(2-(trifluoromethoxy)phenyl)isoxazol-4-yl)methoxy)-8-azabicyclo[3.2.1]octan-8-yl)nicotinate (18-2A). The ester above, methyl 5-bromo-6-((1S,3R)-3-((5-cyclopropyl-3-(2-(trifluoromethoxy)phenyl)isoxazol-4-yl)methoxy)-8-azabicyclo[3.2.1]octan-8-yl)nicotinate (80 mg, 0.13 mmoles) was charged to a 8 mL microwave vessel and dissolved in anhydrous tetrahydrofuran (0.5 mL) under a positive pressure of Ar, and treated with Pd(PPh$_3$)$_4$, (45 mg, 0.039 mmol, Strem Cat. No 46-2150. Lot code A2890118). The resulting slurry was then treated with a solution of cyclopropyl zinc bromide (THF, 0.5 M, 4 mL, 2 mmoles, Rieke Organozinc Reagents of Lincoln Nebr., Cat no 2259 lot JEB10-17). The resulting slurry was degassed with Ar (approx. flow rate 1 cc, at 1 min purge time). The reaction was then subjected to microwave conditions (35 minutes in a CEM Discover Instrument system, 10 W energy maximum, with stirring). After the microwave event was complete and the reaction cooled, the reaction was concentrated to dryness and re-suspended in ethyl acetate (4 mL) and loaded on normal phase silica chromatography using 10-100% ethyl acetate/hexanes to give the title compound as a clear viscous oil.

5-cyclopropyl-6-((1S,3R)-3-((5-cyclopropyl-3-(2-(trifluoromethoxy)phenyl)isoxazol-4-yl)methoxy)-8-azabicyclo[3.2.1]octan-8-yl)nicotinic acid (18-2B). The ester above, methyl 5-cyclopropyl-6-((1S,3R)-3-((5-cyclopropyl-3-(2-(trifluoromethoxy)phenyl)isoxazol-4-yl)methoxy)-8-azabicyclo[3.2.1]octan-8-yl)nicotinate (60 mg, 0.103 mmoles) was dissolved in tetrahydrofuran (0.5 mL) and methanol (0.5 mL) and subjected to an aqueous solution of potassium hydroxide (6 N aqueous solution, 0.5 mL, 3.0 mmoles). The mixture was heated to 70° C. for 2 hours and then cooled to RT. The pH of the solution was adjusted to pH=6 using aqueous AcOH (0.5 mL of 6M). The mixture was diluted with ethyl acetate (20 mL), extracted and water washed (3×1 mL). The organics were dried ($MgSO_4$) then evaporated in vacuo. The product crystallized upon concentration of the ethyl acetate mother liquor, was washed with sparing ice cold ethyl acetate/hexanes (1:1) (0.5 mL) and the white solid dried to give the title compound.

6-[(1R,5S)-3-({5-cyclopropyl-3-[2-(trifluoromethoxy)phenyl]-1,2-oxazol-4-yl}methoxy)-8-azabicyclo[3.2.1]octan-8-yl]pyridine-3-carboxylic acid (18-3B) and 6-[(1R,5S)-3-({5-cyclopropyl-3-[2-(trifluoromethyl)phenyl]-1,2-oxazol-4-yl}methoxy)-8-azabicyclo[3.2.1]octan-8-yl]pyridine-3-carboxylic acid (18-6B) were prepared from Examples 18-3A and 18-6B, from the reaction of 4-((8-azabicyclo[3.2.1]octan-3-yloxy)methyl)-5-cyclopropyl-3-(2-(trifluoromethoxy)phenyl)isoxazole (I-1) or 4-((8-azabicyclo[3.2.1]octan-3-yloxy)methyl)-5-cyclopropyl-3-(2-(trifluoromethyl)phenyl)isoxazole and the corresponding pyridyl derivative.

Examples 18-4A and 18-5A and their corresponding acids 18-4B and 18-6B were prepared from the following the same procedures, from the reaction of 4-((8-azabicyclo[3.2.1]octan-3-yloxy)methyl)-5-cyclopropyl-3-(2-(trifluoromethoxy)phenyl)isoxazole (I-1) and the corresponding pyrimidinyl or pyrazinyl derivatives.

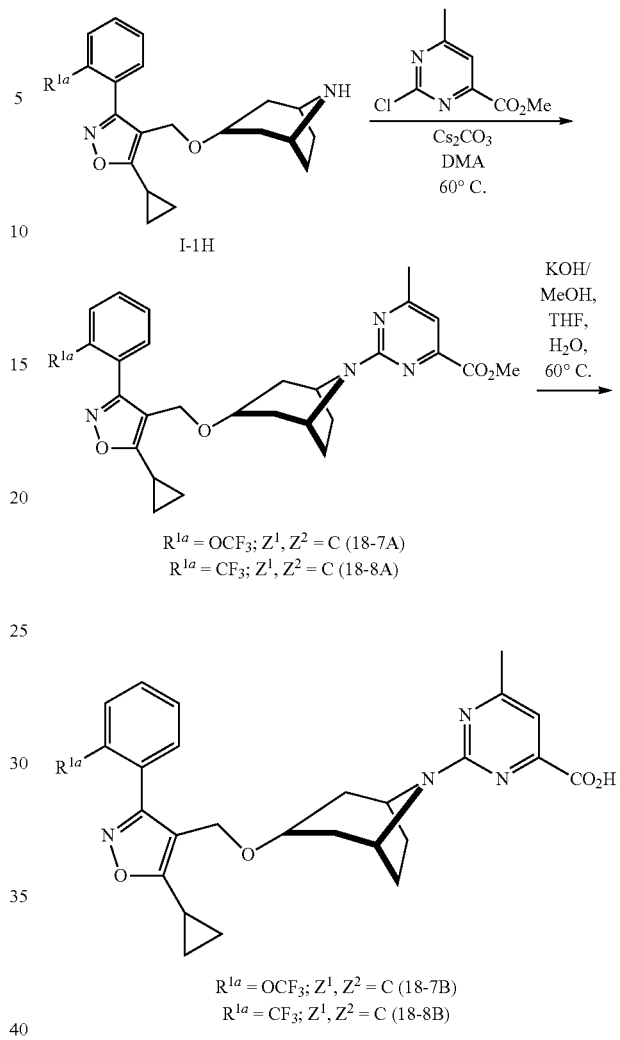

Examples 18-7A and 18-8A and their corresponding acids 18-7B and 18-8B were prepared following the same procedures, from the reaction of 4-((8-azabicyclo[3.2.1]octan-3-yloxy)methyl)-5-cyclopropyl-3-(2-(trifluoromethoxy)phenyl)isoxazole (I-1) or 4-((8-azabicyclo[3.2.1]octan-3-yloxy)methyl)-5-cyclopropyl-3-(2-(trifluoromethyl)phenyl)isoxazole and the corresponding pyrimidinyl derivatives.

| Ex | | Physical Data MS (m/z), $^1$H NMR |
|---|---|---|
| 18-1 | (structure) | MS m/z 622.2/624 (M + 1, $Br_{79}/Br_{81}$ isotope pattern) |

| Ex | | Physical Data MS (m/z), ¹H NMR |
|---|---|---|
| 18-2A | 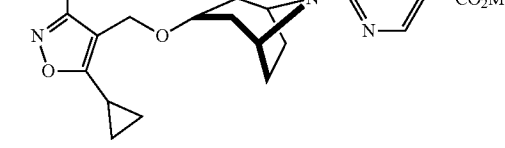 | MS m/z 584.2 (M + 1). |
| 18-2B | | MS m/z 570.2 (M + 1); ¹H NMR (D₄-MeOH, 400 MHz) δ 8.34 (d, J = 1.9 Hz, 1H), 8.03 (s, 1H), 7.68-7.58 (m, 2H), 7.51 (app dt, J = 8.2, 0.9 Hz, 2H), 4.81 (br s, 2H, partly obscured by water resonance in D₄-MeOH), 4.40 (s, 2H), 3.60 (app t, J = 4.9 Hz, 1H), 2.34-2.27 (m, 1H), 2.10 (app t, J = 4.0 Hz, 1H), 2.07 (app t, J = 4.8 Hz, 1H), 2.08-1.80 (m, 7H), 1.21-1.14 (m, 4H), 1.07 (app q, J = 6.5, 2H), 0.78 (app q, J = 6.2, 2H). |
| 18-3A | 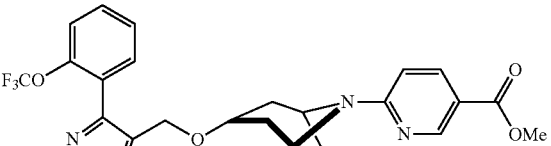 | MS m/z 544.2 (M + 1) |
| 18-3B | | MS m/z 530.2 (M + 1); ¹H NMR (MeOD, 400 MHz) δ 8.64 (d, J = 2 Hz, 1H), 7.98 (dd, J = 8.8, 2.4 Hz, 1H), 7.66-7.58 (m, 2H), 7.52-7.48 (m, 2H), 6.64 (d, J = 9.2 Hz, 1H), 4.43 (bs, 2H), 4.38 (s, 2H), 3.52 (t, J = 4.4 Hz, 1H), 2.31-2.24 (m, 1H), 1.97-1.82 (m, 6H), 1.71 (d, J = 14.4 Hz, 2H), 1.18-1.14 (m, 4H). |
| 18-4A | 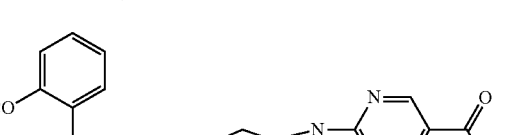 | MS m/z 545.2 (M + 1), |
| 18-4B |  | MS m/z 531.1 (M + 1), |

| Ex | | Physical Data MS (m/z), ¹H NMR |
|---|---|---|
| 18-5A | | MS m/z 545.2 (M + 1), |
| 18-5B | | MS m/z 531.2 (M + 1); ¹H NMR (DMSOd₆, 400 MHz) δ 8.51 (s, 1H), 8.01 (s, 1H), 7.64-7.56 (m, 2H), 7.51-7.46 (m, 2H), 4.41 (bs, 2H), 4.26 (s, 2H), 3.40 (t, J = 4 Hz, 1H), 2.31-2.24 (m, 1H), 1.75-1.67 (m, 6H), 1.57 (d, J = 14.8 Hz, 2H), 1.09-0.97 (m, 4H). |
| 18-6A | | MS m/z 528.2 (M + 1) |
| 18-6B | | MS m/z 514.2 (M + 1); ¹H NMR (MeOD, 400 MHz) δ 8.54 (d, J = 2 Hz, 1H), 7.88 (dd, J = 8.8, 2.4 Hz, 1H), 7.79-7.76 (m, 1H), 7.67-7.59 (m, 2H), 7.44 (d, J = 7.2 Hz, 1H), 6.55 (d, J = 8.8 Hz, 1H), 4.34 (bs, 2H), 4.17 (s, 2H), 3.39-3.37 (m, 1H), 2.21-2.12 (m, 1H), 1.90-1.74 (m, 6H), 1.63 (d, J = 14.8 Hz, 2H), 1.08-1.04 (m, 4H). |
| 18-7A | | MS m/z 559.2 (M + 1), |
| 18-7B | | MS m/z 545.2 (M + 1); ¹H NMR (MeOD, 400 MHz) δ 7.65-7.59 (m, 2H), 7.52-7.48 (m, 2H), 6.91 (s, 1H), 4.66 (bs, 2H), 4.37 (s, 2H), 3.52 (t, J = 4.8 Hz, 1H), 2.35 (s, 3H), 2.32-2.24 (m, 1H), 1.96-1.87 (m, 4H), 1.84-1.77 (m, 2H), 1.69 (d, J = 14.4 Hz, 2H), 1.18-1.14 (m, 4H). |

| Ex | Physical Data MS (m/z), ¹H NMR |
|---|---|
| 18-8A | MS m/z 515.3 (M + 1); |
| 18-8B | MS m/z 529.3 (M + 1); ¹H NMR (DMSO D$_6$, 400 MHz) δ 7.92 (d, J = 7.6 Hz, 1H), 7.83-7.73 (m, 2H), 7.60 (d, J = 7.6 Hz, 1H), 6.94 (s, 1H), 4.50 (bs, 2H), 4.23 (bs, 2H), 3.47-3.40 (m, 1H), 2.38-2.29 (m, 4H), 1.81-1.61 (m, 8H), 1.16-1.04 (m, 4H). |

EXAMPLE 19

The following examples are prepared from 4-((8-azabicyclo[3.2.1]octan-3-yloxy)methyl)-5-cyclopropyl-3-(2-(trifluoromethoxy)phenyl)isoxazole (I-1) and the corresponding pyridyl, pyrimidinyl or pyrazinyl derivatives according to the procedure described for the preparation of Example 18.

| Ex | Physical Data MS (m/z), ¹H NMR |
|---|---|
| 19-1A | MS m/z 558.2 (M + 1) |
| 19-1B | MS m/z 544.2 (M + 1) |

| Ex | | Physical Data MS (m/z), ¹H NMR |
|---|---|---|
| 19-2A | 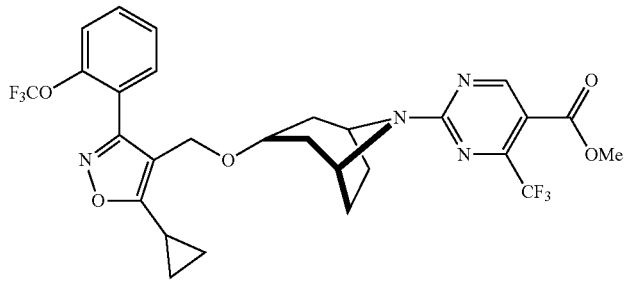 | MS m/z 613.2 (M + 1), |
| 19-2B | 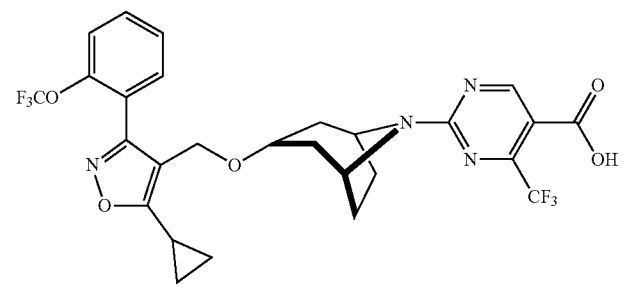 | MS m/z 599.2 (M + 1); ¹H NMR (MeOD, 400 MHz) δ 8.70 (s, 1H), 7.64-7.56 (m, 2H), 7.51-7.46 (m, 2H), 4.44 (bs, 2H), 4.26 (s, 2H), 3.44 (t, J = 4 Hz, 1H), 2.31-2.24 (m, 1H), 1.78-1.62 (m, 8H), 1.09-0.99 (m, 4H). |
| 19-3A | 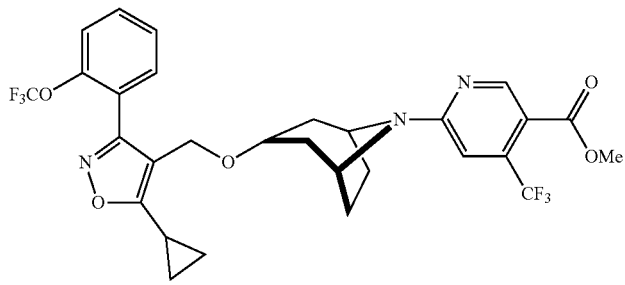 | MS m/z 612.2 (M + 1), |
| 19-3B | 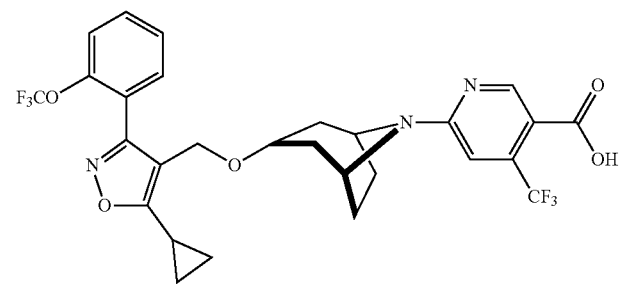 | MS m/z 598.2 (M + 1); ¹H NMR (DMSOd₆, 400 MHz) δ 8.66 (s, 1H), 7.69-7.62 (m, 2H), 7.57-7.51 (m, 2H), 6.92 (s, 1H), 4.53 (bs, 2H), 4.32 (s, 2H), 3.50-3.47 (m, 1H), 2.37-2.27 (m, 1H), 1.84-1.70 (m, 6H), 1.65 (d, J = 14.4 Hz, 2H), 1.15-1.05 (m, 4H). |
| 19-4A | 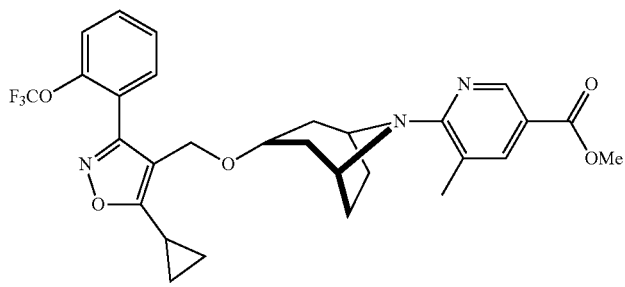 | MS m/z 558.2 (M + 1), 1H NMR (MeOD, 400 MHz) δ 8.55 (s, 1H), 7.70-7.61 (m, 2H), 7.75-7.52 (m, 2H), 6.54 (s, 1H), 4.41 (bs, 2H), 4.32 (s, 2H), 3.73 (s, 3H), 3.46 (t, J = 4 Hz, 1H), 2.42 (s, 3H), 2.36-2.30 (m, 1H), 1.83-1.71 (m, 6H), 1.60 (d, J = 14.4 Hz, 2H), 1.19-1.03 (m, 4H). |

| Ex | | Physical Data MS (m/z), ¹H NMR |
|---|---|---|
| 19-4B | 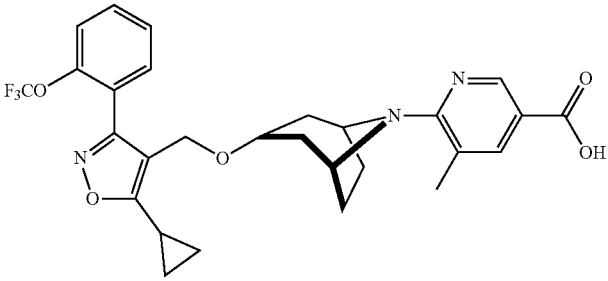 | MS m/z 544.3 (M + 1), |
| 19-5A | 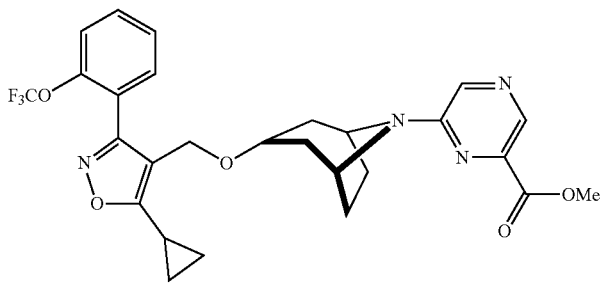 | MS m/z 545.3 (M + 1), |
| 19-5B | 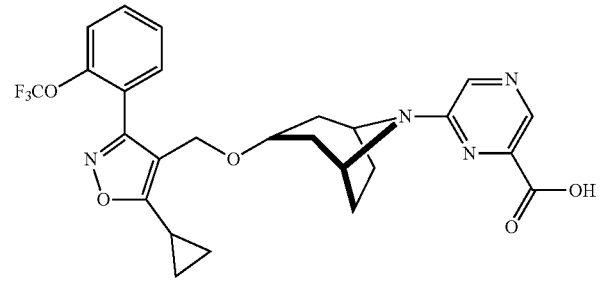 | MS m/z 531.2 (M + 1), |
| 19-6A | 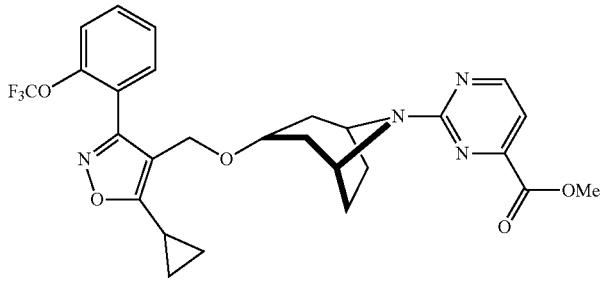 | MS m/z 545.2 (M + 1), |
| 19-6B | 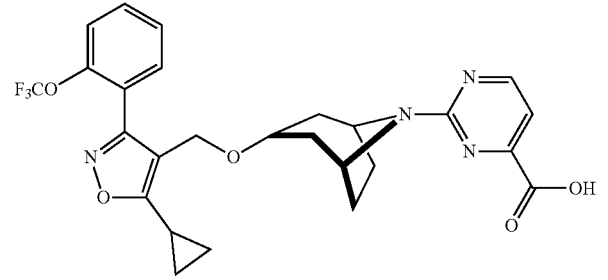 | MS m/z 531.2 (M + 1), |

| Ex | Physical Data MS (m/z), $^1$H NMR |
|---|---|
| 19-7A 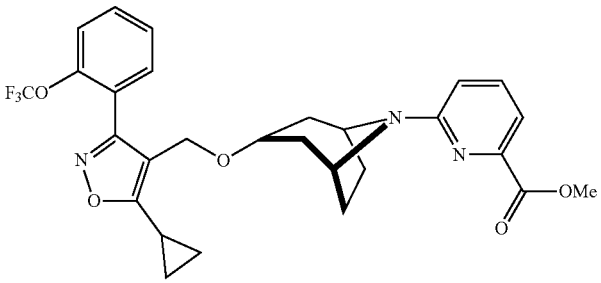 | MS m/z 544.2 (M + 1); $^1$H NMR (DMSOd$_6$, 400 MHz) δ 7.70-7.52 (m, 5H), 7.21 (d, J = 7.2 Hz, 1H), 6.90 (d, J = 8.4 Hz, 1H), 4.37 (bs, 2H), 4.32 (s, 2H), 3.81 (s, 3H), 3.45 (t, J = 8.4 Hz, 1H), 2.37-2.30 (m, 1H), 1.82-1.65 (m, 6H), 1.58 (d, 14.4 Hz, 2H), 1.17-1.04 (m, 4H). |
| 19-7B 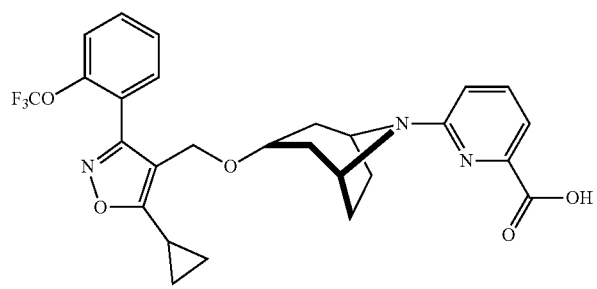 | MS m/z 530.2 (M + 1); $^1$H NMR (MeOD, 400 MHz) δ 7.56-7.58 (m, 3H), 7.50 (app t, J = 8 Hz, 2H), 7.28 (d, J = 8.4 Hz, 1H), 6.86 (d, J = 6.8 Hz, 1H), 4.49 (bs, 2H), 4.38 (s, 2H), 3.50 (t, J = 4.4 Hz, 1H), 2.30-2.24 (m, 1H), 2.00-1.89 (m, 4H), 1.89-1.81 (m, 2H), 1.70 (d, J = 14.4 Hz, 2H), 1.18-1.14 (m, 4H). |
EXAMPLE 20
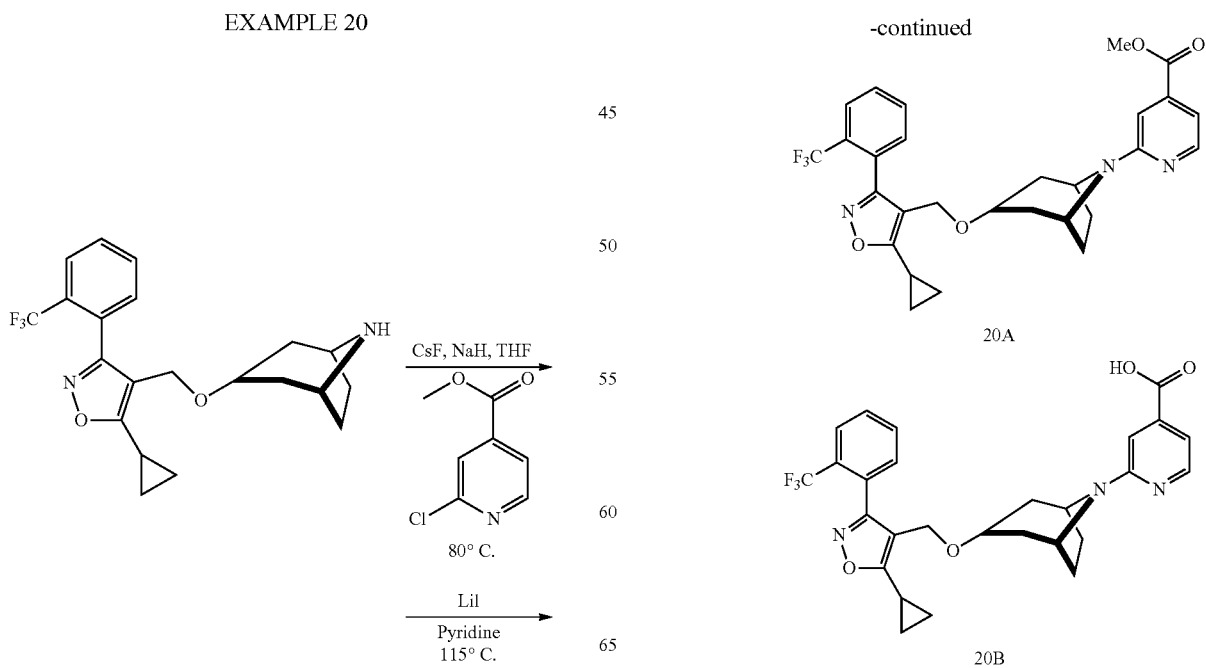

Methyl 2-(3-((5-cyclopropyl-3-(2-(trifluoromethoxy)phenyl)isoxazol-4-yl)methoxy)-8-azabicyclo[3.2.1]octan-8-yl)isonicotinate (20A). The amine, 4-((8-azabicyclo[3.2.1]octan-3-yloxy)methyl)-5-cyclopropyl-3-(2-(trifluoromethyl)phenyl)isoxazole (40 mg, 0.102 mmol) was added to 10 mL re-sealable pressure capable vessel and charged with 0.6 mL of dry THF and the oil was allowed to fully dissolve with gentle heating (40° C., 5 minutes). After the solution cooled to RT, the solution was treated with 75 mg of 60% w/w NaH-min oil (effective amount 45 mg, 1.9 mmol). A color change to yellow was observed and the solution bubbled dramatically. After 1 min, an additional 0.4 mL of anhydrous THF was added. The solution was heated to 50° C. for 3 minutes at which time methyl 2-chloroisonicotinate (60 mg, 0.35 mmoles) and CsF (51 mg, 0.33 mmol) were added sequentially. The reaction was maintained vented for 4 minutes until most bubbling stopped. Reaction was sealed and heated to 80° C. with rapid stirring of resulting dense slurry. After 3 hrs reaction was allowed to cool to RT and vented. The resulting slurry was diluted with 3 mL of MeOH and liquid was purified using reverse phase chromatography C-18 supported, using an instrument equipped with a mass trigger collection device and a gradient of 30 to 90% acetonitrile/water that was TFA modified (0.05%). The resulting product was cold vacuum concentrated and free based using an SPE polymer support cartridge and MeOH (5 mL) mobilizing solvent (product SPE PLHCO$_3$ MP part no PL3540-C603). All resulting methanol effluent was concentrated to furnish the free based intermediate ester as a viscous oil.

2-(3-((5-cyclopropyl-3-(2-(trifluoromethyl)phenyl)isoxazol-4-yl)methox)-8-azabicyclo[3.2.1]octan-8-yl)isonicotinic acid (20B). The ester above, methyl 2-(3-((5-cyclopropyl-3-(2-(trifluoromethoxy)phenyl)isoxazol-4-yl)methoxy)-8-azabicyclo[3.2.1]octan-8-yl)isonicotinate (10.5 mg, 0.02 mmol), was dissolved in anhydrous pyridine (2 mL), and treated with LiI (65 mg, 0.5 mmoles). The suspension was stirred for 10 min. at RT and was heated to 115° C. for 14 hours. The reaction was cooled and treated with 0.3 mL of AcOH, diluted with water (1 mL), and ethyl acetate extracted (3×10 mL). The resulting organic extracts were concentrated to dryness, re-diluted with MeOH (2 mL), and directly purified using mass-directed reverse phase chromatography under a gradient of 30 to 90% acetonitrile/water that was ammonium acetate modified (0.05%). All product fractions were cold vacuum concentrated to furnish the desired carboxylic acid product as a white solid.

| Ex | | Physical Data<br>MS (m/z), $^1$H NMR |
|---|---|---|
| 20A | 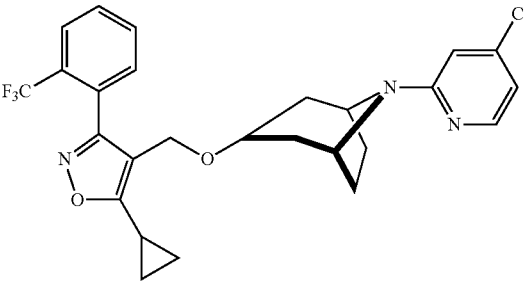 | MS m/z 528.2 (M + 1); $^1$H NMR (D$_4$-MeOH, 400 MHz) δ 8.26 (br dd, J = 6.0, 0.8 Hz, 1H), 7.92 (d, J = 7.2 Hz, 1H), 7.76 (app dq, J = 16.0, 7.2 Hz, 2H), 7.54 (d, J = 7.2, 0.9 Hz, 1H), 6.92 (dd, J = 6.4, 1.8 Hz, 1H), 6.83 (br s, 1H), 4.62 (br s, 1H), 4.25 (app q$_{ab}$, J = 12.0 Hz, 2H), 3.92 (s, 3H), 3.83 (s, 1H), 3.63 (app t, J = 4.1 Hz, 1H), 2.31-2.20 (m, 1H), 1.98-1.74 (m, 6H), 1.63 (br app d, J = 14.7 Hz, 2H), 1.15-1.09 (m, 4H). |
| 20B | 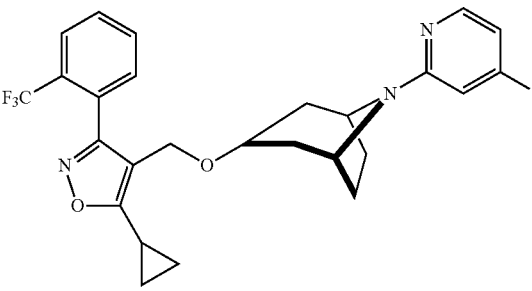 | MS m/z 514.1 (M + 1); $^1$H NMR (D$_4$-MeOH, 400 MHz) δ 7.82 (dd, J = 8.3, 0.9 Hz, 1H), 7.69 (app dq, J = 9.2, 4.5 Hz, 2H), 7.50 (d, J = 5.1 Hz, 1H), 7.49 (d, J = 7.2 Hz, 1H), 6.55 (app dd, J = 2.5, 1.0 Hz, 1H), 6.35 (dd, J = 8.2, 1.7 Hz, 1H) 4.51 (s, 1H), 4.24 (app dd, J = 15.5, 11.2 Hz, 2H), 3.89 (br s, 1H), 3.59 (app t, J = 4.4 Hz, 1H), 2.28-2.16 (m, 1H), 2.15-1.67 (m, 8H), 1.15-1.09 (m, 4H). |

EXAMPLE 21

The following examples were prepared from 4-((8-azabicyclo[3.2.1]octan-3-yloxy)methyl)-5-cyclopropyl-3-(2-(trifluoromethyl)phenyl)isoxazole and the corresponding pyridyl, pyrimidinyl or pyrazinyl derivatives according to the procedure described for the preparation of Example 18.

| Ex | | Physical Data MS (m/z), $^1$H NMR |
|---|---|---|
| 21-1A | 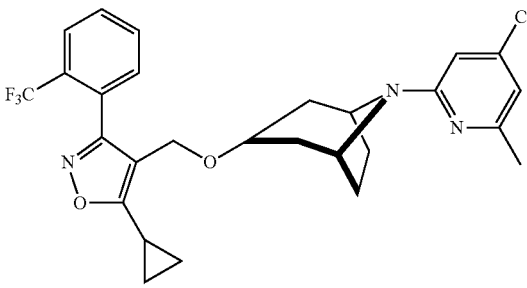 | MS m/z 542.2 (M + 1) |
| 21-1B | 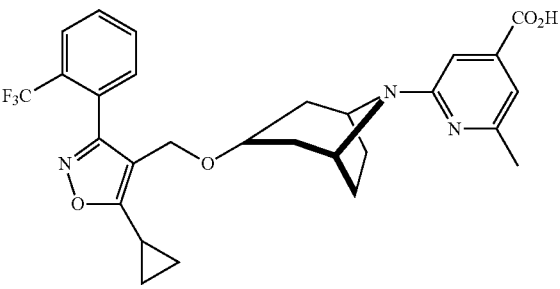 | MS m/z 528.2 (M + 1) |
| 21-2A | 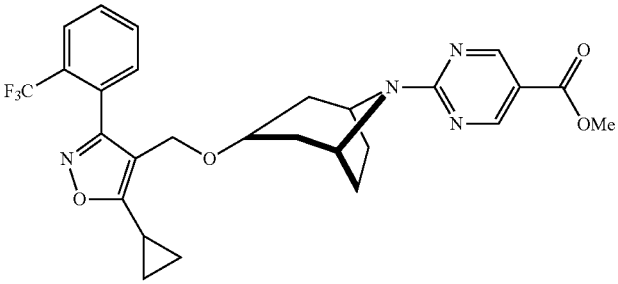 | MS m/z 529.3 (M + 1) |
| 21-2B | 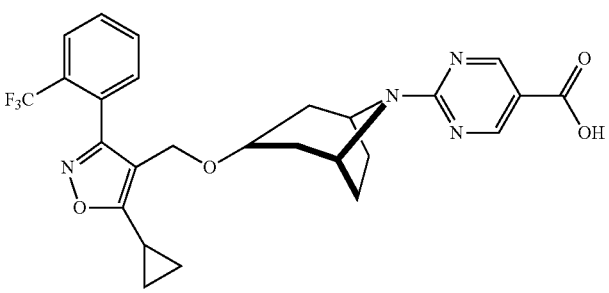 | MS m/z 515.2 (M + 1); $^1$H NMR (MeOD, 400 MHz) δ 8.68 (s, 2H), 7.78 (d, J = 7.6 Hz, 1H), 7.68-7.58 (m, 2H), 7.45 (d, J = 7.2 Hz, 1H), 4.54 (bs, 2H), 4.18 (s, 2H), 3.42 (t, J = 4.4 Hz, 1H), 2.21-2.14 (m, 1H), 1.90-1.67 (m, 8H), 1.09-1.05 (m, 4H). |
| 21-3A | 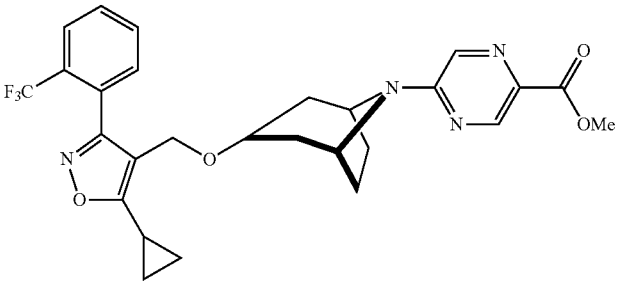 | MS m/z 529.2 (M + 1) |

| Ex | | Physical Data MS (m/z), ¹H NMR |
|---|---|---|
| 21-3B | 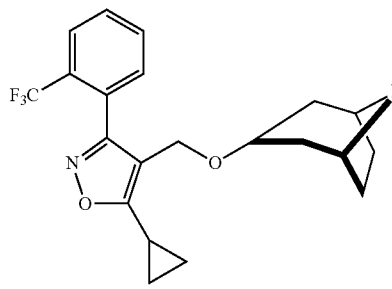 | MS m/z 515.2 (M + 1); ¹H NMR (MeOD, 400 MHz) δ 8.57 (d, J = 0.8 Hz, 1H), 7.91 (s, 1H), 7.77 (app d, J = 7.6 Hz, 1H), 7.67-7.59 (m, 2H), 7.44 (d, J = 7.2 Hz, 1H), 4.42 (bs, 2H), 4.17 (s, 2H), 3.40-3.38 (m, 1H), 2.20-2.13 (m, 1H), 1.92-1.85 (m, 2H), 1.85-1.73 (m, 4H), 1.67 (d, J = 14.8 Hz, 2H), 1.08-1.05 (m, 4H). |
| 21-4A | 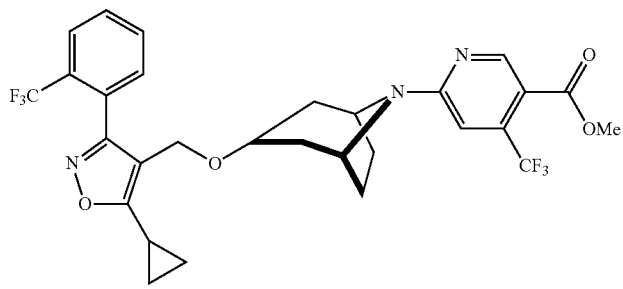 | MS m/z 596.2 (M + 1) |
| 21-4B | 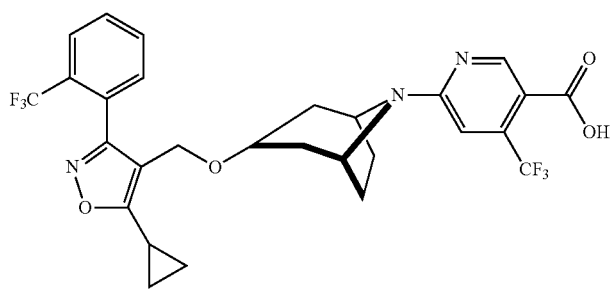 | MS m/z 582.2 (M + 1) |
| 21-5A | 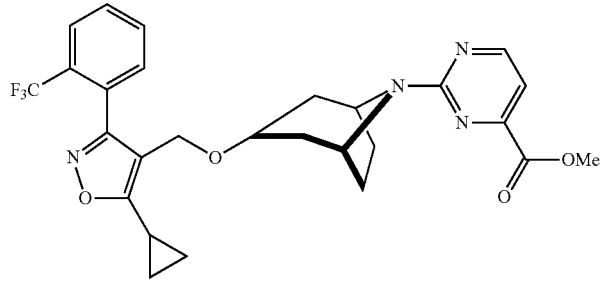 | MS m/z 529.2 (M + 1) |
| 21-5B | 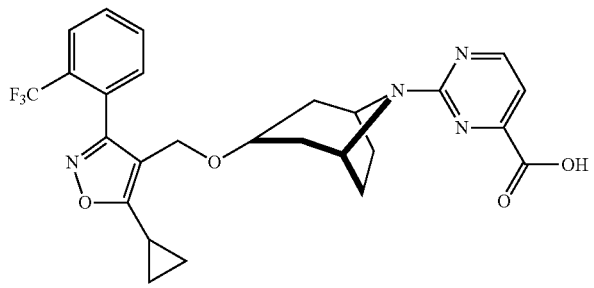 | MS m/z 515.3 (M + 1); ¹H NMR (MeOD, 400 MHz) δ 8.42 (d, J = 4.8 Hz, 1H), 7.87 (app d, J = 7.6 Hz, 1H), 7.79-7.67 (m, 2H), 7.54 (d, J = 7.2 Hz, 1H), 7.04 (d, J = 5.2 Hz, 1H), 4.64 (bs, 2H), 4.26 (s, 2H), 3.50-3.48 (m, 1H), 2.30-2.23 (m, 1H), 1.97-1.81 (m, 6H), 1.73 (d, J = 14.8 Hz, 2H), 1.19-1.15 (m, 4H). |

| Ex | Physical Data MS (m/z), ¹H NMR |
|---|---|
| 21-6A | MS m/z 528.2 (M + 1) |
| 21-6B | MS m/z 514.2 (M + 1) |

EXAMPLE 22

The following examples are prepared from 4-((8-azabicyclo[3.2.1]octan-3-yloxy)methyl)-5-cyclopropyl-3-(2-(difluoromethoxy)phenyl)isoxazole or 4-((8-azabicyclo[3.2.1]octan-3-yloxy)methyl)-5-cyclopropyl-3-(2,6-difluorophenyl) and the corresponding pyridyl, pyrimidinyl or pyrazinyl derivatives according to the procedure described for the preparation of Example 18.

| Ex | Physical Data MS (m/z), ¹H NMR |
|---|---|
| 22-1A | MS m/z 594.3 (M + 1) |
| 22-1B | MS m/z 580.1 (M + 1), |

| Ex | Physical Data MS (m/z), ¹H NMR |
|---|---|
| 22-2A 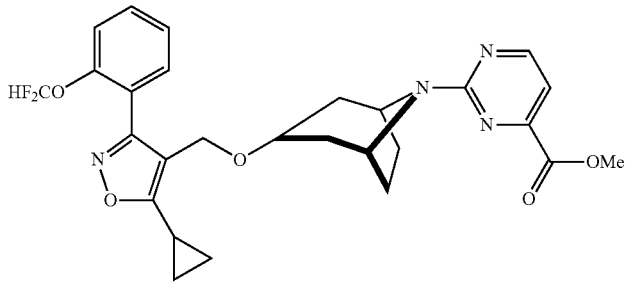 | MS m/z 527.2 (M + 1), |
| 22-2B 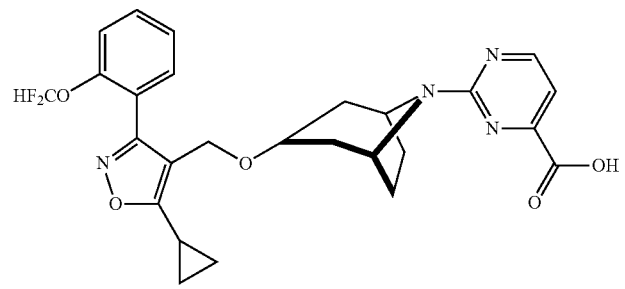 | MS m/z 513.2 (M + 1); ¹H NMR (MeOD, 400 MHz) δ 8.38 (d, J = 4.8 Hz, 1H), 7.60-7.51 (m, 2H), 7.39-7.34 (m, 2H), 7.01 (d, J = 1.2 Hz, 1H), 6.83 (t, J = 74, 1H), 4.63 (bs, 2H), 4.40 (s, 2H), 3.52 (t, J = 4.8 Hz, 1H), 2.31-2.24 (m, 1H), 1.94-1.90 (m, 4H), 1.82-1.77 (m, 2H), 1.71 (d, J = 14.4 Hz, 2H), 1.18-1.14 (m, 4H). |
| 22-3 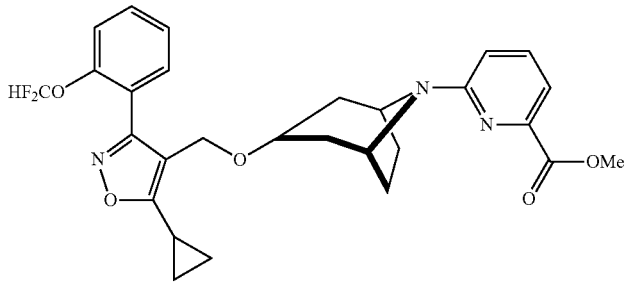 | MS m/z 526.2 (M + 1); ¹H NMR (DMSOd₆, 400 MHz) δ 7.64-7.57 (m, 2H), 7.52-7.48 (m, 1H), 7.43-7.05 (m, 4H), 6.89 (d, J = 8.4 Hz, 1H), 4.36 (bs, 2H), 4.31 (s, 2H), 3.81 (s, 3H), 3.43 (t, J = 4.4 Hz, 1H), 2.36-2.28 (m, 1H), 1.81-1.54 (m, 8H), 1.15-1.04 (m, 4H). |
| 22-4A 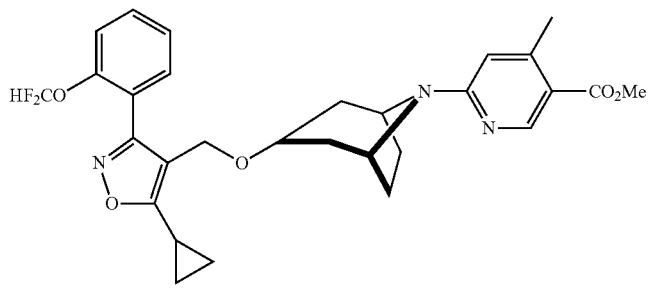 | MS m/z 540.2 (M + 1) |
| 22-4B 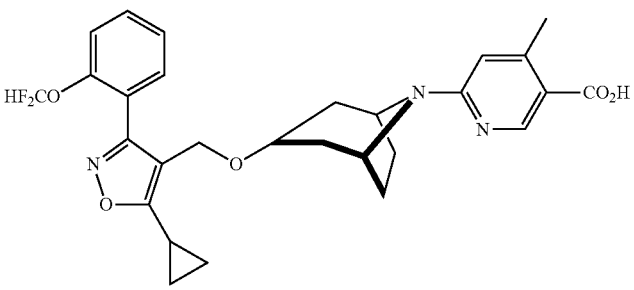 | MS m/z 526.2 (M + 1); ¹H NMR (D₄-MeOH, 400 MHz) δ 8.60 (s, 1H), 7.56 (dt, J = 7.4, 1.8 Hz, 1H), 7.51 (dd, J = 10.5, 1.5 Hz, 1H), 7.38-7.33 (m, 2H), 6.82 (t, J = 76.5 Hz, 1H), 6.44 (s, 1H), 4.41 (br s, 2H), 4.39 (bs, 2H), 3.51 (t, J = 4.0 Hz, 1H), 2.30 (s, 3H), 2.29-2.22 (m, 1H), 1.97-1.77 (m, 6H), 1.72 (app br d, J = 14.5 Hz, 2H), 1.18-1.11 (m, 4H). |

-continued
| Ex | | Physical Data MS (m/z), ¹H NMR |
|---|---|---|
| 22-5 | 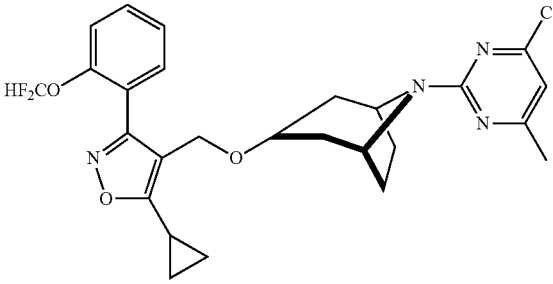 | MS m/z 541.2 (M + 1) |
| 22-6A | 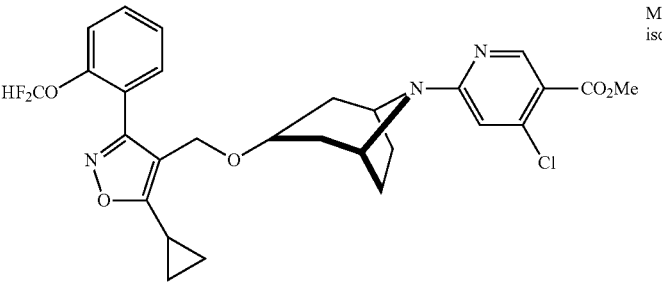 | MS m/z 560.2/562.2 (M + 1, $Cl_{35}/Cl_{37}$ isotope pattern) |
| 22-6B | 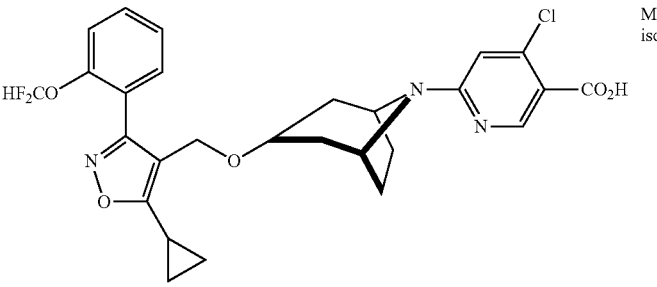 | MS m/z 547.1/549.1 (M + 1, $Cl_{35}/Cl_{37}$ isotope pattern) |
| 22-7A | 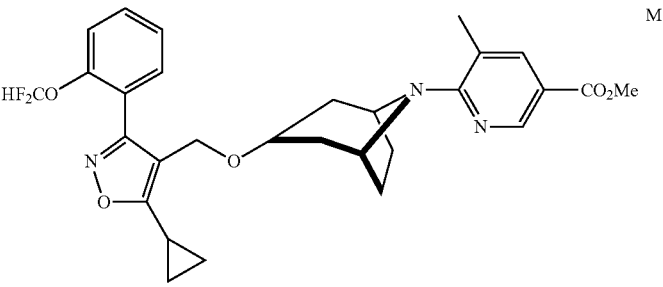 | MS m/z 540.2 (M + 1) |
| 22-7B | 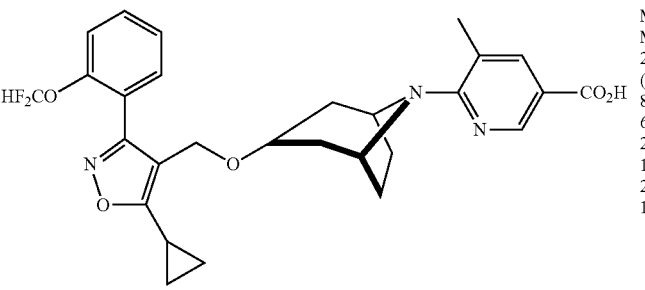 | MS m/z 526.2 (M + 1); ¹H NMR (D$_4$-MeOH, 400 MHz) δ 8.53 (d, J = 2.2 Hz, 1H), 7.83 (d, J = 2.0 Hz, 1H), 7.57 (dt, J = 7.8, 2.1 Hz, 1H), 7.51 (dd, J = 8.0, 1.6 Hz, 1H); 7.40-7.34 (m, 2H), 6.68 (t, J = 72.0 Hz, 1H), 4.45 (s, 2H), 4.38 (bs, 2H), 3.64 (t, J = 4.6 Hz, 1H), 2.39-2.34 (m, 1H), 2.38 (s, 3H), 2.08-1.98 (m, 2H), 1.89-1.84 (m, 2H), 1.80-1.73 (m, 4H), 1.18-1.13 (m, 4H). |

| Ex | | Physical Data MS (m/z), ¹H NMR |
|---|---|---|
| 22-8 | 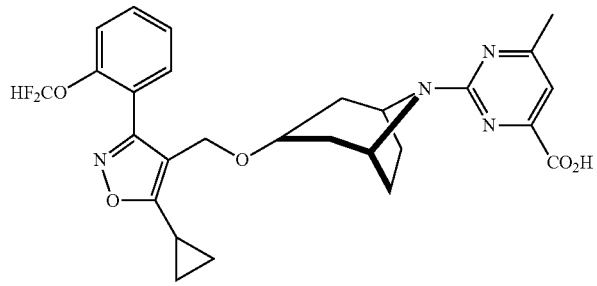 | MS m/z 527.2 (M + 1) |
| 22-9A | 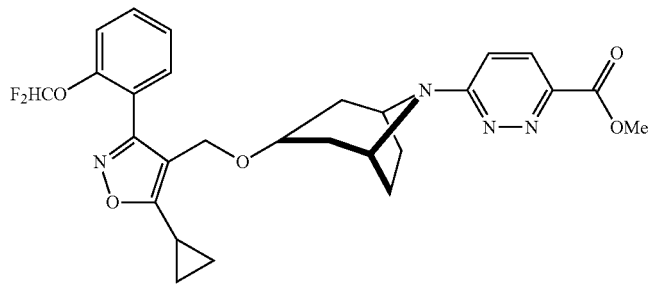 | MS m/z 527.2 (M + 1), |
| 22-9B | 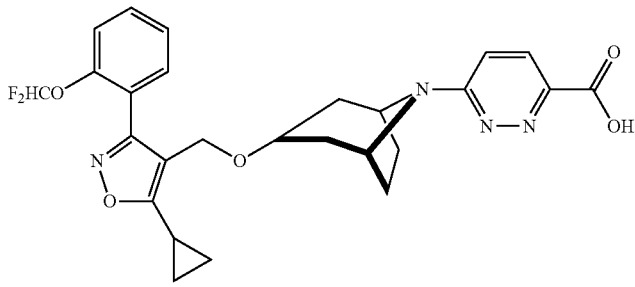 | MS m/z 513.2 (M + 1), |
| 22-10A | 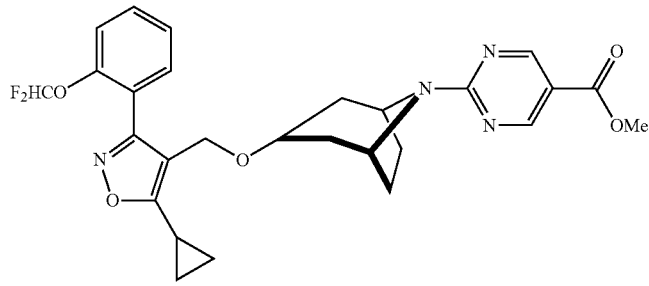 | MS m/z 527.2 (M + 1), |
| 22-10B | 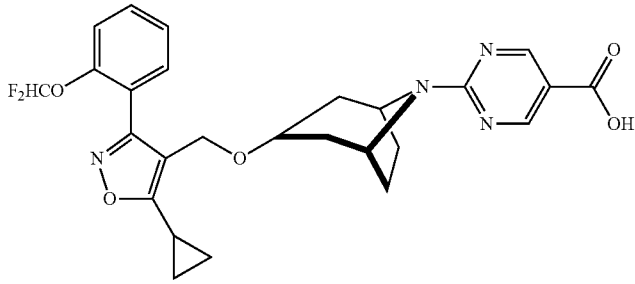 | MS m/z 513.2 (M + 1), |

| Ex | | Physical Data MS (m/z), ¹H NMR |
|---|---|---|
| 22-11A | 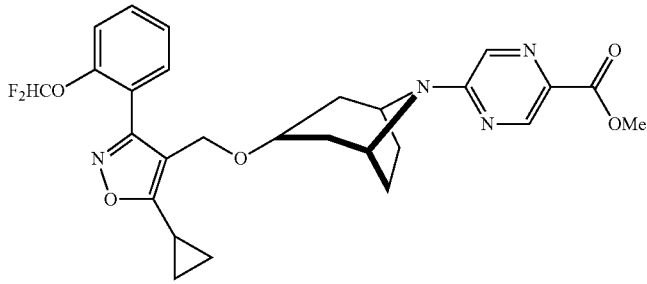 | MS m/z 527.2 (M + 1), |
| 22-11B | 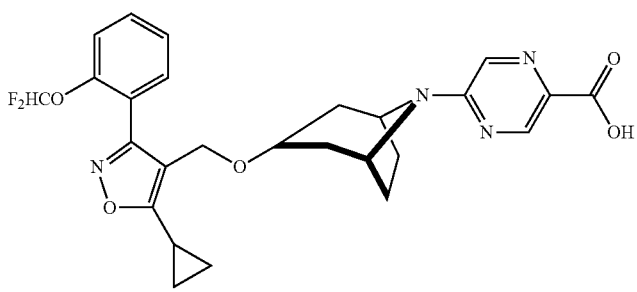 | MS m/z 513.2 (M + 1), |
| 22-12 | 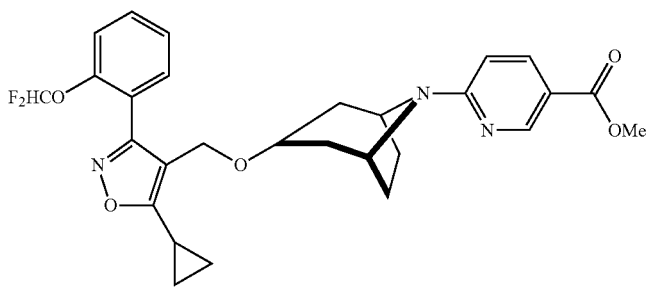 | MS m/z 512.2 (M + 1), |
| 22-13A | 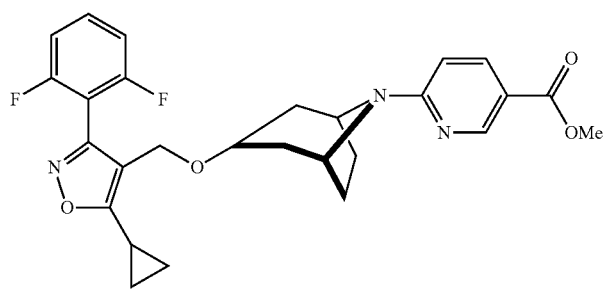 | MS m/z 496.2 (M + 1), |
| 22-13B | 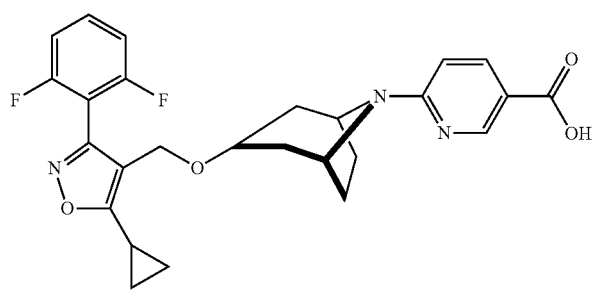 | MS m/z 482.2 (M + 1); 1H NMR (MeOD, 400 MHz) δ 8.64 (d, J = 2.4 Hz, 1H), 7.98 (dd, J = 9.2, 2.4 Hz, 1H), 7.62-7.55 (m, 1H), 7.19-7.13 (m, 2H), 6.65 (d, J = 9.2 Hz, 1H, 4.43 (bs, 2H), 4.37 (s, 2H), 3.50 (t, J = 4.8 Hz, 1H), 2.30-2.24 (m, 1H), 1.96-1.81 (m, 6H), 1.70 (d, J = 14.4 Hz, 2H), 1.19-1.15 (m, 4H). |

| Ex | | Physical Data MS (m/z), $^1$H NMR |
|---|---|---|
| 22-14A | 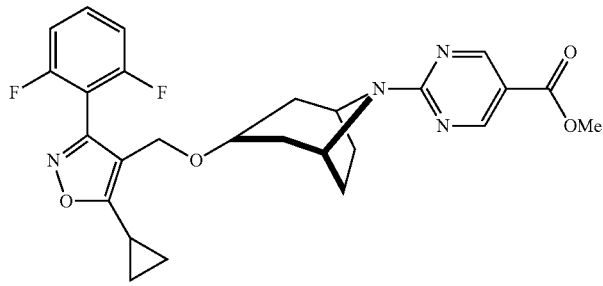 | MS m/z 497.2 (M + 1), |
| 22-14B | 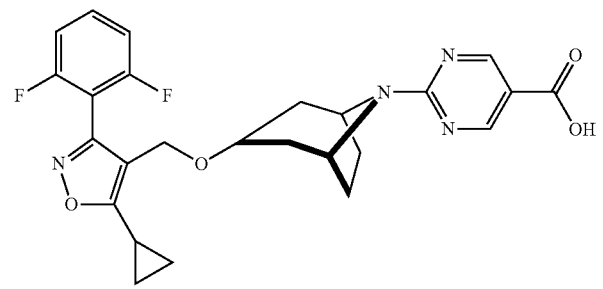 | MS m/z 483.2 (M + 1); $^1$H NMR (MeOD, 400 MHz) δ 8.77 (s, 2H), 7.63-7.55 (m, 1H), 7.19-7.14 (m, 2H), 4.60 (bs, 2H), 4.37 (s, 2H), 3.53 (t, J = 4.4 Hz, 1H), 2.31-2.24 (m, 1H), 1.94-1.78 (m, 6H), 1.73 (d, J = 14.4 Hz, 2H), 1.19-1.16 (m, 4H). |
| 22-15A | 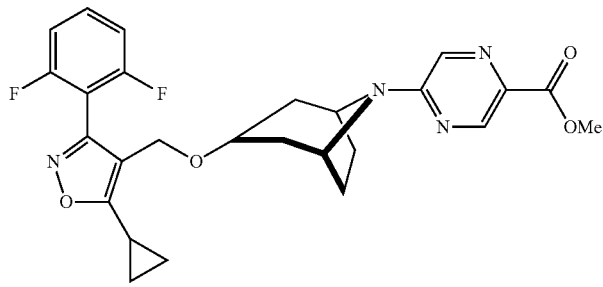 | MS m/z 497.2 (M + 1), |
| 22-15B | 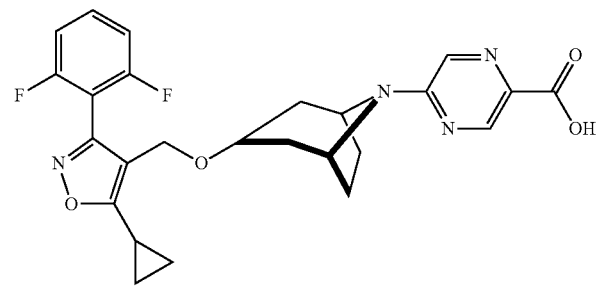 | MS m/z 483.2 (M + 1); $^1$H NMR (MeOD, 400 MHz) δ 8.38 (d, J = 0.8 Hz, 1H), 8.01 (s, 1H), 7.63-7.55 (m, 1H), 7.19-7.13 (m, 2H), 4.51 (bs, 2H), 4.37 (s, 2H), 3.51 (t, J = 4.4 Hz, 1H), 2.31-2.24 (m, 1H), 1.99-1.81 (m, 6H), 1.73 (d, J = 14.4 Hz, 2H), 1.19-1.14 (m, 4H). |
| 22-16A | 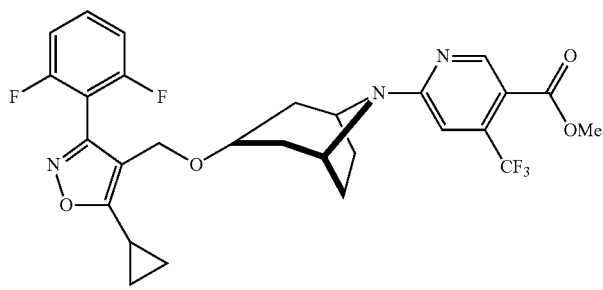 | MS m/z 564.2 (M + 1), |

| Ex | Physical Data MS (m/z), ¹H NMR |
|---|---|
| 22-16B 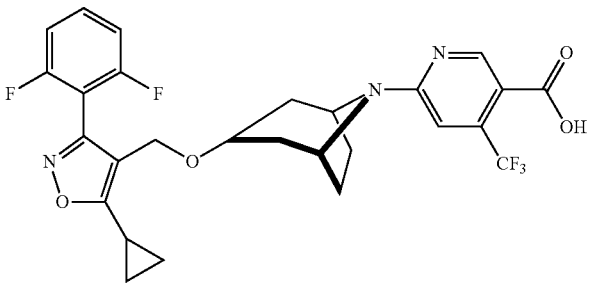 | MS m/z 550.2 (M + 1), |
| 22-17A 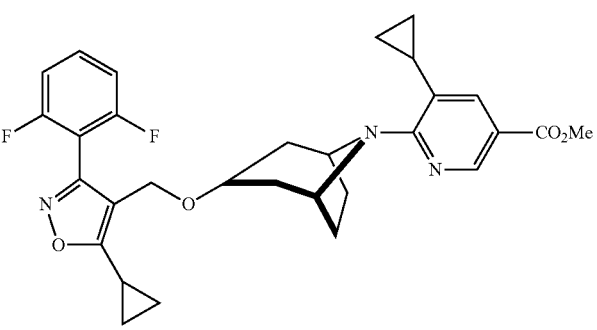 | MS m/z 536.2 (M + 1); ¹H NMR (D$_4$-MeOH, 400 MHz) δ 8.42 (d, J = 1.9 Hz, 1H), 7.79 (d, J = 2.0 Hz, 1H), 7.61 (app dt, J = 7.4, 6.2 Hz, 1H), 7.11-7.02 (m, 2H), 4.72 (br s, 2H), 4.40 (s, 2H), 3.85 (s, 3H), 3.40 (app t, J = 4.9 Hz, 1H), 2.27-2.18 (m, 1H), 2.07 (app t, J = 3.5 Hz, 1H), 2.04 (app t, J = 3.9 Hz, 1H), 1.96-1.74 (m, 7H), 1.23-1.20 (m, 4H), 1.07-1.02 (m, 2H), 0.74-0.71 (m, 2H). |
| 22-17B 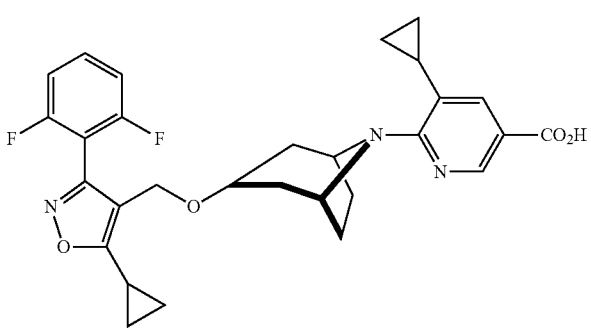 | MS m/z 522.2 (M + 1); ¹H NMR (D$_4$-MeOH, 400 MHz) δ 8.56 (d, J = 1.9 Hz, 1H), 7.80 (d, J = 2.0 Hz, 1H), 7.63 (app dt, J = 7.2, 6.5 Hz, 1H), 7.21-7.05 (m, 2H), 4.68 (br s, 2H), 4.38 (s, 2H), 3.63 (app t, J = 4.9 Hz, 1H), 2.37-2.28 (m, 1H), 2.09 (app t, J = 3.5 Hz, 1H), 2.06 (app t, J = 3.9 Hz, 1H), 1.96-1.74 (m, 7H), 1.25-1.20 (m, 4H), 1.06-1.00 (m, 2H), 0.74-0.71 (m, 2H). |
| 22-18A 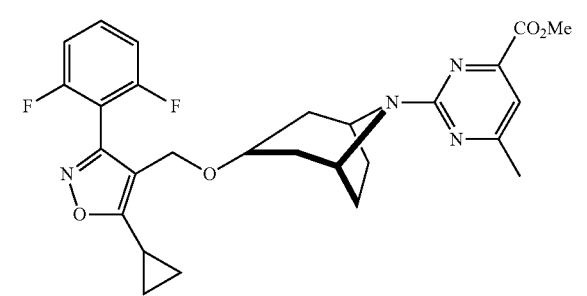 | MS m/z 511.2 (M + 1) |

| Ex | | Physical Data MS (m/z), ¹H NMR |
|---|---|---|
| 22-18B | | MS m/z 497.2 (M + 1) |
| 22-19 | | MS m/z 531.2/533.2 (M + 1, $Cl_{35}/Cl_{37}$ isotope pattern) |
| 22-20 | | MS m/z 531.2/533.2 (M + 1, $Cl_{35}/Cl_{37}$ isotope pattern) |
| 22-21 | | MS m/z 574.2/576.2 (M + 1, $Br_{79}/Br_{81}$ isotope pattern) |

EXAMPLE 23

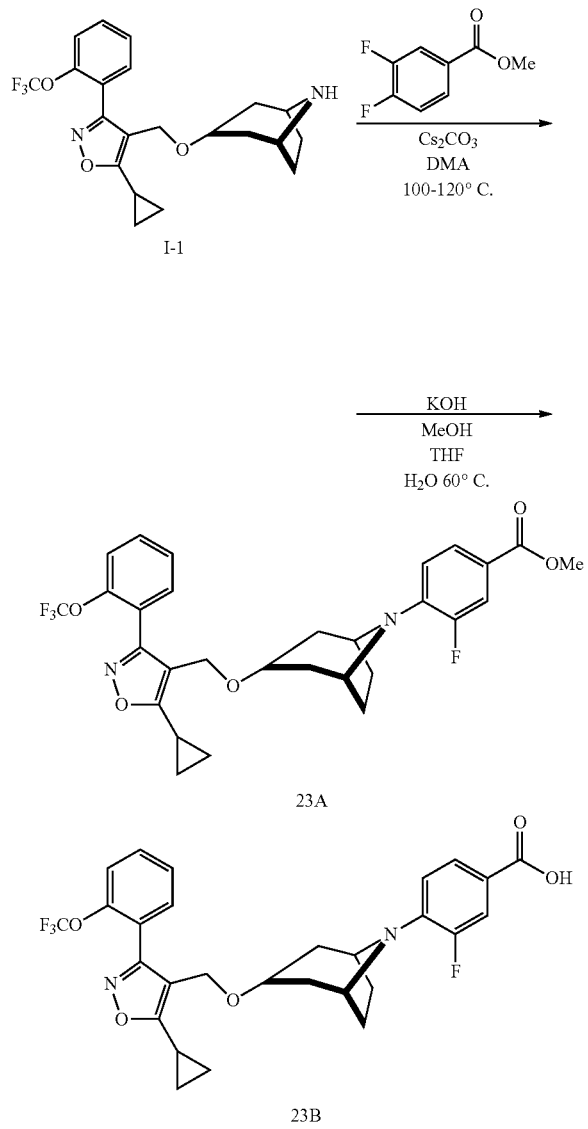

Methyl 4-(3-((5-cyclopropyl-3-(2-(trifluoromethoxy)phenyl)isoxazol-4-yl)methoxy)-8-azabicyclo[3.2.1]octan-8-yl)-3-fluorobenzoate (23A). The amine, 4-((8-azabicyclo[3.2.1]octan-3-yloxy)methyl)-5-cyclopropyl-3-(2-(trifluoromethoxy)phenyl)isoxazole (41.5 mg, 0.102 mmol), dimethylacetamide (0.6 mL), methyl 3,4 difluorobenzoate (510 mg, 3.0 mmol), and cesium carbonate (108 mg, 0.33 mmol) were combined sequentially and heated to 100° C. for about 20 minutes and then 120° C. for approximately 1 hour. The mixture was diluted with ethyl acetate 20 mL and water washed (2×3 mL). The organics were dried under vacuum to a residue, the resulting residue was diluted with 3 mL of MeOH, and the liquid was directly purified using mass directed reverse phase HPLC under a gradient of 30 to 90% acetonitrile/water that was TFA modified (0.05%). The resulting product was cold vacuum concentrated and free based using an SPE polymer support cartridge and MeOH (5 mL) mobilizing solvent (product SPE PLHCO₃ MP part no PL3540-C603). All resulting methanol effluent was concentrated to give the free based intermediate ester as a dense oil.

4-(3-((5-cyclopropyl-3-(2-(trifluoromethoxy)phenyl)isoxazol-4-yl)methoxy)-8-azabicyclo[3.2.1]octan-8-yl)-3-fluorobenzoic acid (23B). The ester above, methyl 4-(3-((5-cyclopropyl-3-(2-(trifluoromethoxy)phenyl)isoxazol-4-yl)methoxy)-8-azabicyclo[3.2.1]octan-8-yl)-3-fluorobenzoate (24 mg, 0.043 mmoles) was dissolved in tetrahydrofuran (0.5 mL) and methanol (0.5 mL) and subjected to an aqueous solution of potassium hydroxide (6 N aqueous solution, 0.5 mL, 3.0 mmoles). The mixture was heated to 70° C. for 2 hours and then cooled to RT. The pH of the solution was adjusted to 6 using aqueous HCl (0.5 mL of 6N). The mixture was diluted with ethyl acetate (20 mL), extracted and water washed (3×1 mL). The organics were dried (MgSO₄) then evaporated in vacuo. The product crystallized upon concentration of the ethyl acetate mother liquor, was washed with sparing ice cold ethyl acetate (0.5 mL), and the white solid dried to give the title compound.

| Ex | | Physical Data MS (m/z), $^1$H NMR |
|---|---|---|
| 23A | 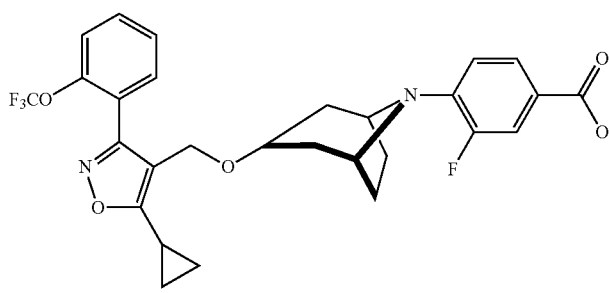 | MS m/z 561.2 (M + 1)); $^1$H NMR (D₄-MeOH, 400 MHz) δ 7.69-7.46 (m, 6H), 6.91 (t, J = 9.0 Hz, 1H), 4.38 (br s, 2H), 4.28 (s, 2H), 3.84 (s, 3H), 3.51 (app t, J = 4.6 Hz, 1H), 2.33-2.21 (m, 1H), 2.00-1.76 (m, 6H), 1.68 (br app d, J = 13.9 Hz, 2H), 1.19-1.14 (m, 4H). |

| Ex | | Physical Data MS (m/z), ¹H NMR |
|---|---|---|
| 23B | 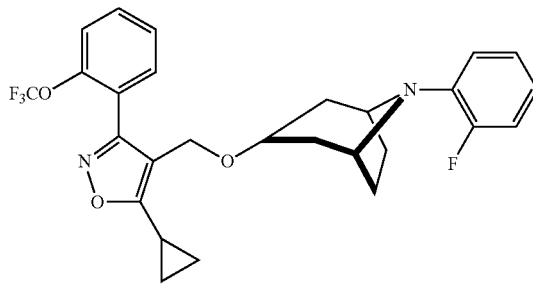 | MS m/z 547.2 (M + 1). ¹H NMR (D₄-MeOH, 400 MHz) δ 7.60-7.56 (m, 2H), 7.51 (d, J = 12.0 Hz, 1H), 7.47 (t, J = 7.1 Hz, 1H), 7.34 (app t, J = 7.8 Hz, 2H), 6.67 (t, J = 7.8 Hz, 1H), 4.27 (s, 2H), 4.18 (br s, 2H), 3.42 (app t, J = 3.6 Hz, 1H), 2.07-2.00 (m, 1H), 1.94-1.72 (m, 6H), 1.56 (br app d, J = 15.1 Hz, 2H), 1.21-1.14 (m, 4H). |

EXAMPLE 24

The following examples are prepared from 4-((8-azabicyclo[3.2.1]octan-3-yloxy)methyl)-5-cyclopropyl-3-(2-(trifluoromethoxy)phenyl)isoxazole (I-1) and the corresponding fluorinated methylbenzoate according to the procedure described for the preparation of example 23.

| Ex | | Physical Data MS (m/z), ¹H NMR |
|---|---|---|
| 24-1A | 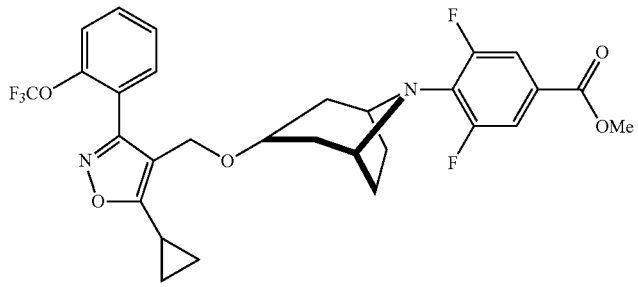 | MS m/z 579.2 (M + 1) |
| 24-1B | 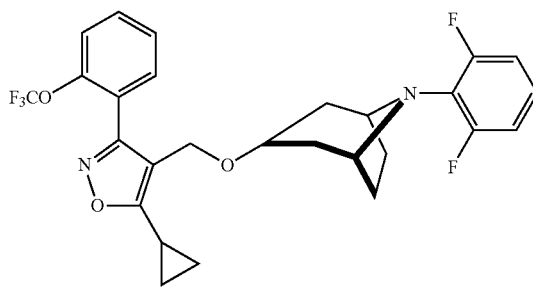 | MS m/z 565.3 (M + 1); ¹H NMR (D₄-MeOH, 400 MHz) δ 7.70-7.60 (m, 2H), 7.51 (app dt, J = 7.6, 0.9 Hz, 2H) 7.39 (app br d, J = 10.0 Hz, 2H), 4.39 (s, 2H), 4.12 (br s, 2H), 3.58 (app t, J = 5.1 Hz, 1H), 2.31-2.24 (m, 1H), 2.06 (app t, J = 4.8 Hz, 1H), 2.00 (app t, J = 4.8 Hz, 1H), 1.92-1.68 (m, 6H), 1.20-1.13 (m, 4H). |

EXAMPLE 25

The following examples are prepared from 4-((8-azabicyclo[3.2.1]octan-3-yloxy)methyl)-5-cyclopropyl-3-(2-(difluoromethoxy)phenyl)isoxazole, 4-((8-azabicyclo[3.2.1]octan-3-yloxy)methyl)-5-cyclopropyl-3-(2-(trifluoromethyl) phenyl)isoxazole, and 4-((8-azabicyclo[3.2.1]octan-3-yloxy)methyl)-5-cyclopropyl-3-(2,6-difluorophenyl) isoxazole, and the corresponding fluorinated methylbenzoate according to the procedure described for the preparation of Example 23.

| Ex | Physical Data MS (m/z), ¹H NMR |
|---|---|
| 25-1A 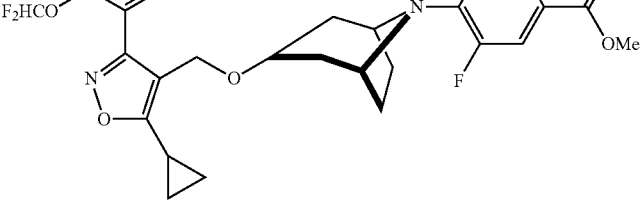 | MS m/z 561.2 (M + 1), |
| 25-1B 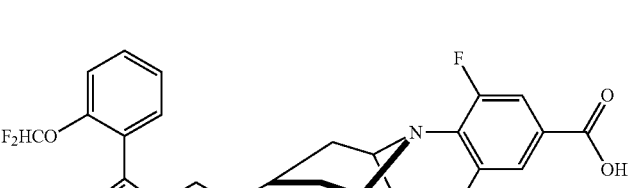 | MS m/z 547.2 (M + 1) |
| 25-2A  | MS m/z 563.2 (M + 1) |
| 25-2B 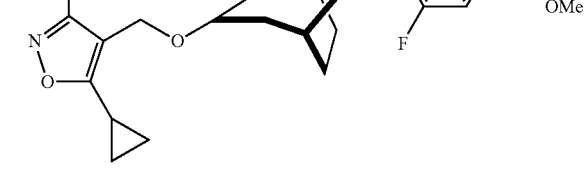 | MS m/z 549.2 (M + 1); ¹H NMR (D₄-MeOH, 400 MHz) δ 7.87 (dd, J = 8.2, 0.9 Hz, 1H), 7.74 (app dq, J = 12.0, 7.5 Hz, 2H), 7.53 (d, J = 7.1 Hz, 1H), 7.47-7.36 (m, 2H), 4.25 (s, 2H), 4.15 (br s, 2H), 3.54 (app t, J = 4.8 Hz, 1H), 2.30-2.22 (m, 1H), 2.03 (app t, J = 4.3 Hz, 1H), 1.99 (app t, J = 4.5 Hz, 1H), 1.93-1.72 (m, 6H), 1.19-1.13 (m, 4H). |
| 25-3A 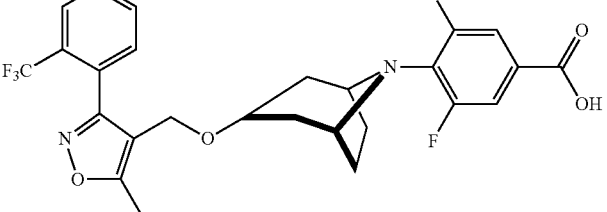 | MS m/z 513.2 (M + 1), |

| Ex | | Physical Data MS (m/z), $^1$H NMR |
|---|---|---|
| 25-3B | 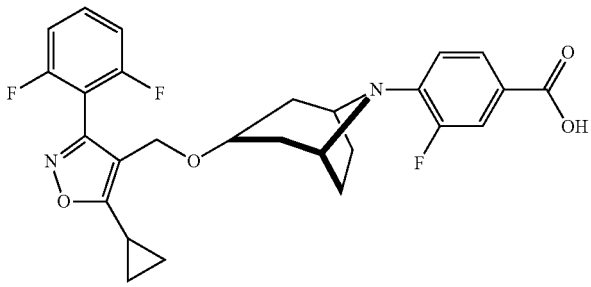 | MS m/z 499.2 (M + 1), |
| 25-4A | 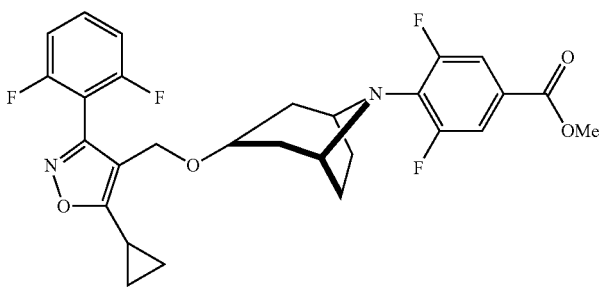 | MS m/z 513.2 (M + 1), |
| 25-4B | 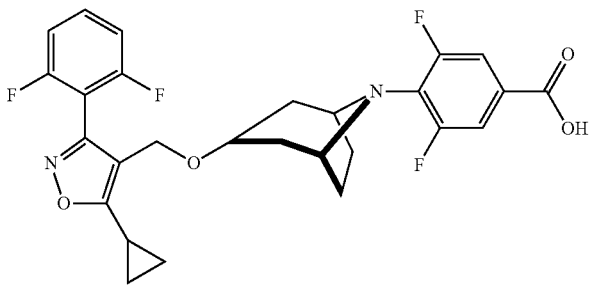 | MS m/z 517.2 (M + 1), |
| 25-5A | 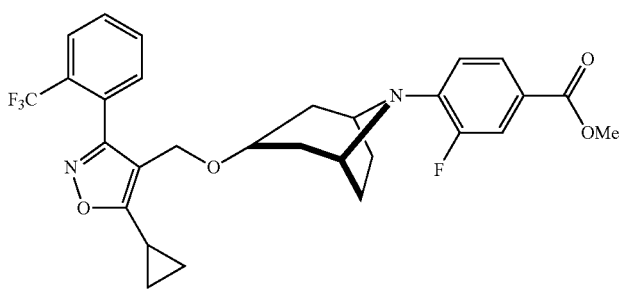 | MS m/z 545.2 (M + 1); $^1$H NMR (D$_4$-MeOH, 400 MHz) δ 7.89 (br d, J = 7.5 Hz, 1H), 7.74 (app dq, J = 11.3, 7.2 Hz, 2H), 7.66 (d, J = 7.0, 1.9 Hz, 1H), 7.58-7.51 (m, 2H), 6.90 (t, J = 8.9, 1H), 4.29 (br s, 2H), 4.25 (s, 2H), 3.83 (s, 3H), 3.47 (app t, J = 4.1 Hz, 1H), 2.31-2.20 (m, 1H), 1.98-1.77 (m, 6H), 1.67 (br app d, J = 14.7 Hz, 2H), 1.21-1.15 (m, 4H). |
| 25-5B | 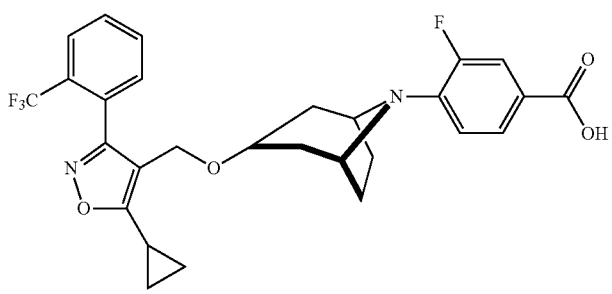 | MS m/z 531.2 (M + 1) |

| Ex | Physical Data MS (m/z), ¹H NMR |
|---|---|
| 25-6A 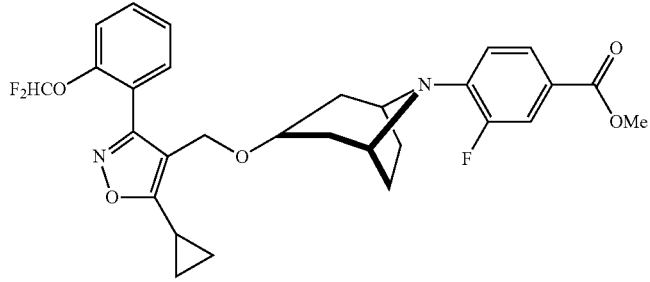 | MS m/z 543.2 (M + 1) |
| 25-6B 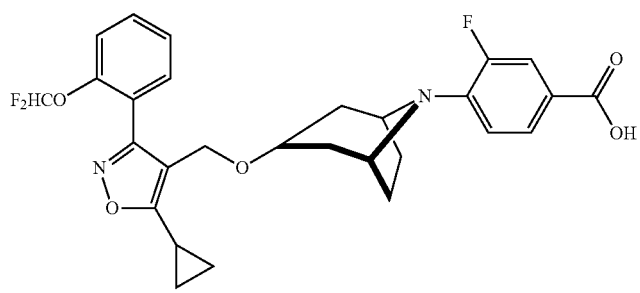 | MS m/z 529.2 (M + 1) |

EXAMPLE 26

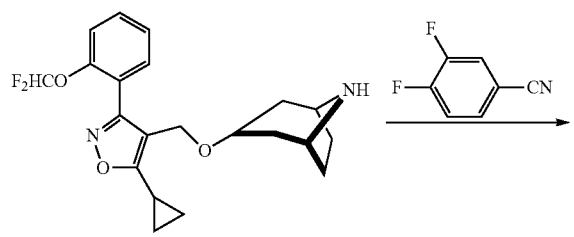

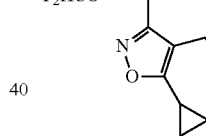

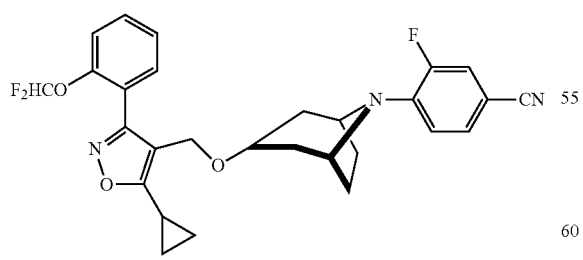

26-A

↓ NaN₃ NH₄Cl NMP

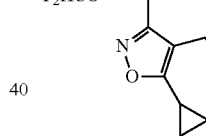

26-B 4-(3-((5-cyclopropyl-3-(2-(difluoromethoxy)phenyl)isoxazol-4-yl)methoxy)-8-azabicyclo[3.2.1]octan-8-yl)-3-fluorobenzonitrile (26-A) was prepared from 4-((8-azabicyclo[3.2.1]octan-3-yloxy)methyl)-5-cyclopropyl-3-(2-(difluoromethoxy)phenyl)isoxazole and 3,4-difluorobenzonitrile according to the procedure described for the preparation of example 23.

5-cyclopropyl-3-(2-(difluoromethoxy)phenyl)-4-(((8-(2-fluoro-4-(2H-tetrazol-5-yl)phenyl)-8-azabicyclo[3.2.1]octan-3-yl)oxy)methyl)isoxazole (26-B). 4-(3-((5-cyclopropyl-3-(2-(difluoromethoxy)phenyl)isoxazol-4-yl)methoxy)-8-azabicyclo[3.2.1]octan-8-yl)-3-fluorobenzonitrile (70 mg, 0.14 mmol) was dissolved in N,N-dimethylacetamide (2 ml), sodium azide (91 mg, 10 eq, 1.40 mmol) and ammonium chloride (75 mg, 10 eq, 1.40 mmol) were added, and the mixture was stirred at 120° C. overnight. Upon cooling to room temperature, the reaction mixture was diluted with ethyl acetate (30 mL) and washed with brine (2×20 mL). The combined organics were separated, dried (MgSO₄), and evaporated in vacuo. The product was purified by mass directed reverse phase HPLC to give a white solid.

| Ex | | Physical Data MS (m/z), ¹H NMR |
|---|---|---|
| 26A | 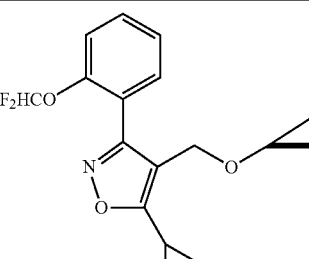 | MS m/z 510.2 (M + 1) |
| 26B | | MS m/z 553.2 (M + 1) |
EXAMPLE 27
Example 27 was prepared from example 25-6B according to the procedure previously described for the preparation of example 5.
| Ex | | Physical Data MS (m/z), ¹H NMR |
|---|---|---|
| 27 | | MS m/z 528.2 (M + 1) |
EXAMPLE 28
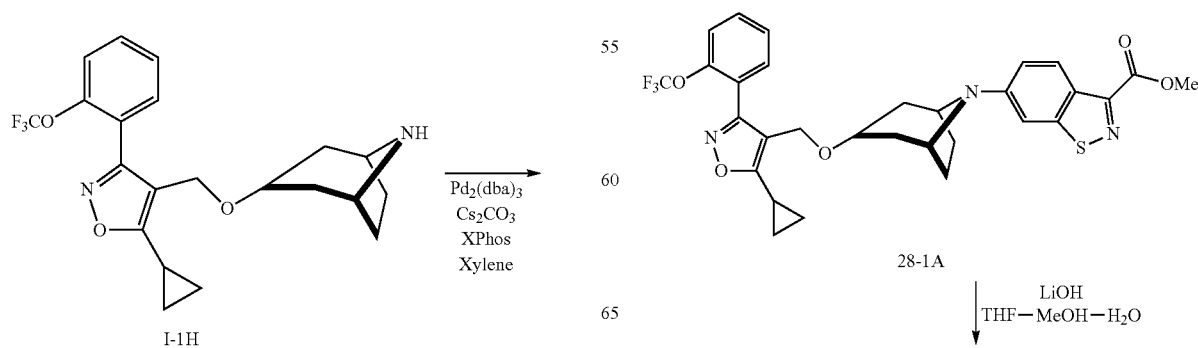
-continued -continued

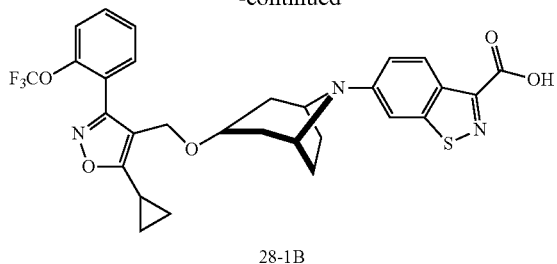

28-1B

Methyl 6-(3-((5-cyclopropyl-3-(2-(trifluoromethoxy)phenyl)isoxazol-4-yl)methoxy)-8-azabicyclo[3.2.1]octan-8-yl)benzo[d]isothiazole-3-carboxylate (28-1A). A microwave vial was charged with methyl 6-bromobenzo[d]isothiazole-3-carboxylate (WO07056582, 85 mg, 0.31 mmol), cesium carbonate (220 mg, 0.68 mmol), tris(dibenzylideneacetone)dipalladium(0) (13 mg, 0.014 mmol), 2-dicyclohexylphosphino-2',4',6'-triisopropylbiphenyl (XPhos) (14 mg, 0.028 mmol), and degassed xylene (1.5 mL). The mixture was degassed for 10 minutes and then 4-((8-azabicyclo[3.2.1]octan-3-yloxy)methyl)-5-cyclopropyl-3-(2-(trifluoromethoxy)phenyl)isoxazole (I-1H) (115 mg, 0.28 mmol) in xylene (1 mL) was added. The reaction flask was evacuated and backfilled with argon three times and then heated at 120° C. for 12 hours. The reaction mixture was cooled to rt, diluted with ethyl acetate and filtered through a CELITE® pad, the filtrate concentrated, and chromatographed on silica using linear gradient, 20-80%, EtOAc in Hexanes) to give the desired ester as a yellow solid. MS m/z 600.2 (M+1), 622.2. (M+23).

6-(3-((5-Cyclopropyl-3-(2-(trifluoromethoxy)phenyl)isoxazol-4-yl)methoxy)-8-azabicyclo[3.2.1]octan-8-yl)benzo[d]isothiazole-3-carboxylic acid (28-1B). Methyl 6-(3-((5-cyclopropyl-3-(2-(trifluoromethoxy)phenyl)isoxazol-4-yl)methoxy)-8-azabicyclo[3.2.1]octan-8-yl)benzo[d]isothiazole-3-carboxylate (37 mg, 0.062 mg) in a 3:2:1 THF-MeOH—H$_2$O solution (1 mL) was treated with a 6N LiOH solution (85 μL, 0.49 mmol) at rt for 12 hours. After this time the organic was removed in vacuo and the residue was diluted with water (1 mL.) and cooled in ice. 3N NaOH was added dropwise until pH 7. The solid that separated was collected by filtration, washed with additional water and dried in vacuo to afford the 6-(3-((5-cyclopropyl-3-(2-(trifluoromethoxy)phenyl)isoxazol-4-yl)methoxy)-8-azabicyclo[3.2.1]octan-8-yl)benzo[d]isothiazole-3-carboxylic acid as off white solid. $^1$H NMR (400 MHz, DMSO) δ 8.31 (d, J=8.0 Hz, 1H), 7.68-7.62 (m, 2H), 7.57-7.52 (m, 2H), 7.18 (bs, 1H), 6.90 (d, J=9.2 Hz, 1H), 4.31 (s, 2H), 4.18 (bs, 2H), 3.42 (m, 1H), 1.88-1.84 (m, 2H), 1.80 (1.78 (m, 4H), 1.53-1.49 (m, 2H), 1.15-1.03 (m, 5H). MS m/z 586.2 (M+1).

Examples 28-2 through Examples 28-26 were prepared from the corresponding nortropine intermediates according to the procedures described for Example 28-1.

| Ex | | Physical Data MS (m/z), $^1$H NMR |
|---|---|---|
| 28-1B | | $^1$H NMR (400 MHz, DMSO) δ 8.31 (d, J = 8.0 Hz, 1H), 7.68-7.62 (m, 2H), 7.57-7.52 (m, 2H), 7.18 (bs, 1H), 6.90 (d, J = 9.2 Hz, 1H), 4.31 (s, 2H), 4.18 (bs, 2H), 3.42 (m, 1H), 1.88-1.84 (m, 2H), 1.80 (1.78 (m, 4H), 1.53-1.49 (m, 2H), 1.15-1.03 (m, 5H), MS m/z 586.2 (M + 1). |
| 28-2 | | MS m/z 569.2 (M + 1) |
| 28-3 | | MS m/z 580.2 (M + 1) |

-continued
| Ex | | Physical Data MS (m/z), ¹H NMR |
|---|---|---|
| 28-4 | 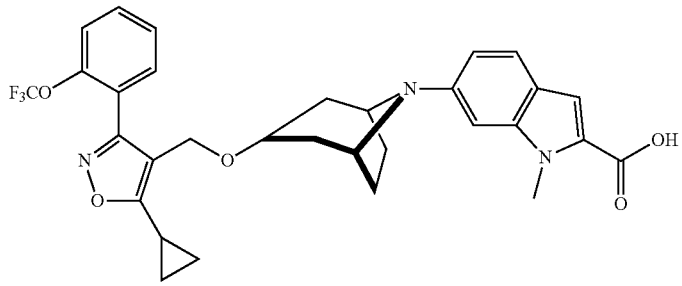 | MS m/z 582.2 (M + 1); ¹H NMR (DMSO-d$_6$, 400 MHz) δ 12.41 (s, 1H), 7.71-7.62 (m, 2H), 7.60-7.51 (m, 2H), 7.42 (d, J = 8.8 Hz, 1H), 7.05 (s, 1H), 6.72 (dd, J = 8.8, 2.0 Hz, 1H), 6.65 (s, 1H), 4.31 (s, 2H), 4.18 (bs, 2H), 3.90 (s, 3H), 3.41 (t, J = 4.4 Hz, 1H), 2.38-2.30 (m, 1H), 1.94-1.91 (m, 2H), 1.82-1.75 (m, 4H), 1.49 (d, J = 14.4 Hz, 2H), 1.16-1.06 (m, 4H). |
| 28-5 | 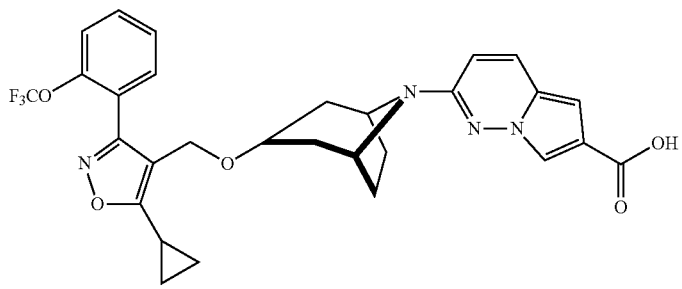 | MS m/z 582.2 (M + 1) |
| 28-6 | 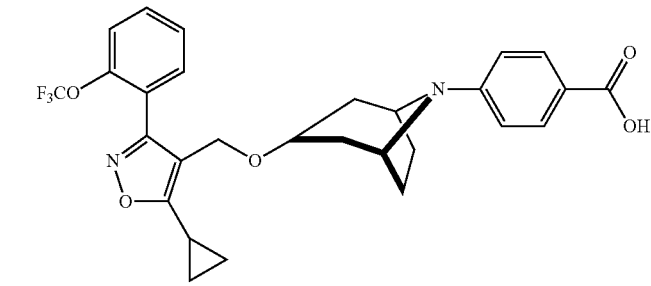 | MS m/z 529.2 (M + 1). ¹H NMR (MeOH-d$_4$, 400 MHz) δ 7.82 (d, J = 9.2 Hz, 2H), 7.66-7.57 (m, 2H), 7.52-7.48 (m, 2H), 6.74 (d, J = 9.2 Hz, 2H), 4.36 (s, 2H), 4.18 (bs, 2H), 3.46 (t, J = 4.4 Hz, 1H), 2.29-2.23 (m, 1H), 1.98-1.80 (m, 6H), 1.62 (d, J = 14.4 Hz, 2H), 1.17-1.13 (m, 4H). |
| 28-7 | 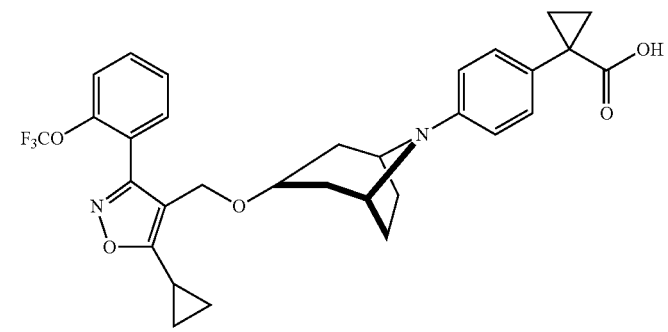 | MS m/z 569.2 (M + 1); ¹H NMR (MeOH-d$_4$, 400 MHz) δ 7.68 (app dt, J = 7.9, 2.0 Hz, 1H), 7.61 (app dt, J = 8.0, 2.0 Hz, 1H), 7.48 (app t, J = 8.0 Hz, 2H), 7.19 (app d, J = 9.0 Hz, 2H), 6.78 (app d, J = 9.0 Hz, 2H), 4.40 (s, 2H), 4.04 (br s, 2H), 3.38 (app t, J = 4.4 Hz, 1H), 2.27-2.21 (m, 1H), 2.04 (app dt, J = 11.6, 1.3 Hz, 2H), 1.98-1.84 (m, 4H), 1.55-1.48 (m, 4H), 1.10-1.04 (m, 6H). |
| 28-8 | 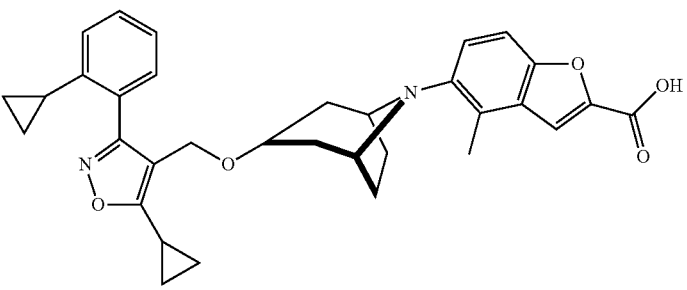 | MS m/z 539.2 (M + 1) |

| Ex | | Physical Data MS (m/z), ¹H NMR |
|---|---|---|
| 28-9 | 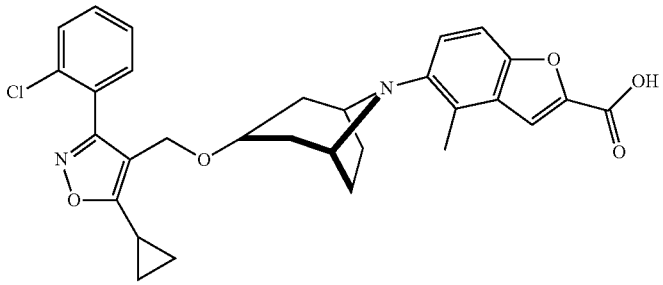 | MS m/z 533.2/535.2 (M + 1, Cl$_{35}$/Cl$_{37}$ isotope pattern) |
| 28-10 | 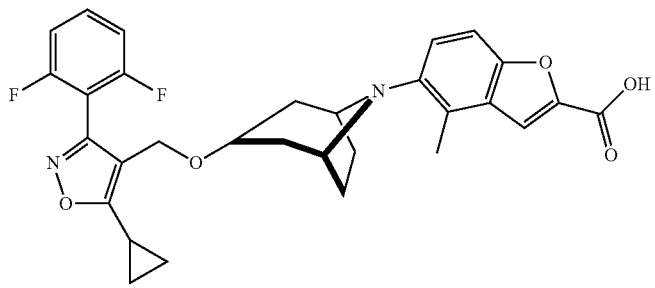 | MS m/z 535.2 (M + 1) |
| 28-11 | 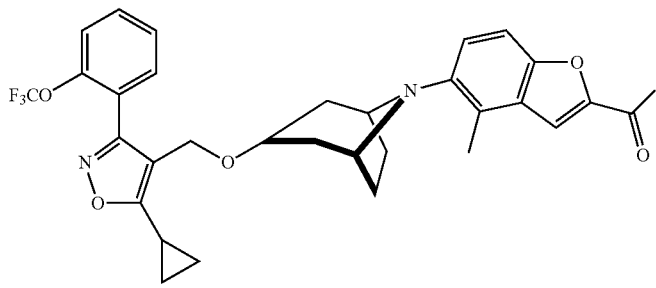 | Elemental Analysis (C$_{31}$H$_{29}$F$_3$N$_2$O$_6$): C 63.91, H 5.02, N 4.81; Found: C 63.51, H 5.07, N 4.92, MS m/z 583.2 (M + 1); ¹H NMR (MeOH-d$_4$, 400 MHz) δ 7.62 (app dt, J = 8.0, 2.0 Hz, 1H), 7.60 (app dt, J = 8.0, 2.0 Hz, 1H), 7.54 (d, J = 1.6 Hz, 1H), 7.49 (app t, J = 8.0 Hz, 2H), 7.24 (d, J = 9.2 Hz, 1H), 7.04 (d, J = 9.2 Hz, 1H), 4.40 (s, 2H), 3.67-3.62 (m, 3H), 2.59 (s, 3H), 2.31-2.27 (m, 1H), 2.08 (app dt, J = 14.6, 1.8 Hz, 2H), 2.00-1.74 (m, 6H), 1.15-1.08 (m, 4H). |
| 28-12 | 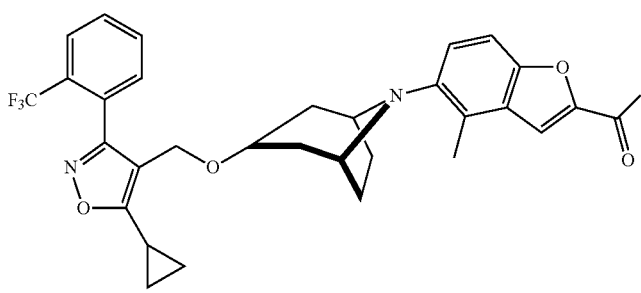 | MS m/z 567.2 (M + 1); ¹H NMR (MeOH-d$_4$, 400 MHz) δ 7.92 (dd, J = 8.4, 1.2 Hz, 1H), 7.80 (d, J = 1.2 Hz, 1H), 7.72 (app dt, J = 7.6, 1.0 Hz, 1H), 7.72 (app t, J = 7.6 Hz, 1H), 7.64-7.52 (m, 3H), 4.42 (bs, 4H), 3.78 (t, J = 4.7 Hz, 1H), 2.78 (s, 3H), 2.48 (app d, J = 15.6 Hz, 2H), 2.33-2.29 (m, 1H), 2.29-2.20 (m, 4H), 2.08 (app dd, J = 10.4, 5.1 Hz, 2H), 1.22-1.16 (m, 4H). |
| 28-13 | 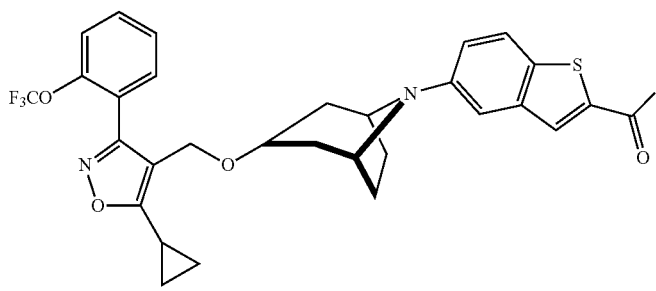 | MS m/z 585.2 (M + 1); ¹H NMR (MeOH-d$_4$, 400 MHz) δ 8.00 (d, J = 1.2 Hz, 1H), 7.92 (d, J = 9.0 Hz, 1H), 7.64 (s, 1H), 7.60-7.52 (m, 2H), 7.45 (app t, J = 8.5 Hz, 2H), 7.38 (dd, J = 8.8, 1.2 Hz, 1H), 4.42 (s, 2H), 4.38 (br s, 2H), 3.58 (t, J = 4.4 Hz, 1H), 2.35-2.30 (m, 1H), 2.08 (app dt, J = 14.6, 1.8 Hz, 2H), 2.10-1.85 (m, 6H), 1.18-1.12 (m, 4H). |

-continued
| Ex | | Physical Data MS (m/z), ¹H NMR |
|---|---|---|
| 28-14 | 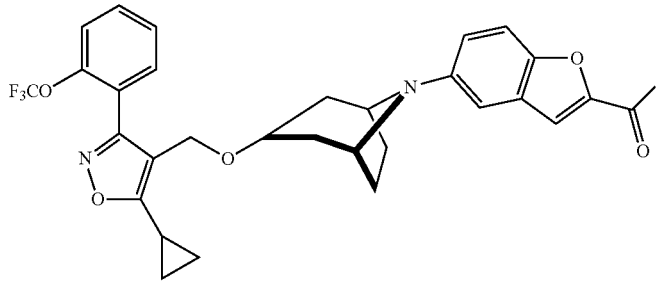 | MS m/z 569.2 (M + 1); ¹H NMR (MeOH-d₄, 400 MHz) δ 7.82 (br s, 1H), 7.74 (d, J = 8.9 Hz, 1H), 7.62-7.43 (m, 6H), 4.43-4.38 (br s, 4H), 3.68 (t, J = 4.4 Hz, 1H), 2.38-2.29 (m, 3H), 2.21-2.10 (m, 2H), 2.08 (app d, J = 13.6 Hz, 2H), 2.00 (app dd, J = 10.2, 4.9 Hz, 2H), 1.19-1.14 (m, 4H). |
| 28-15 | 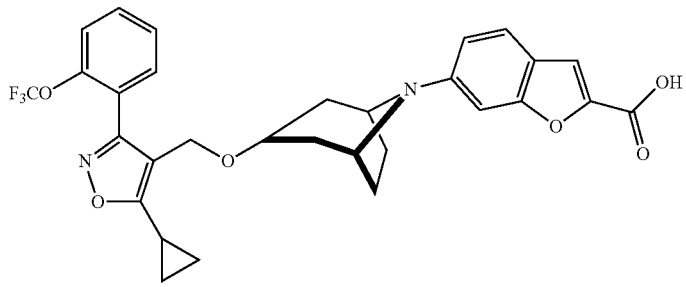 | MS m/z 569.2 (M + 1) |
| 28-16 | 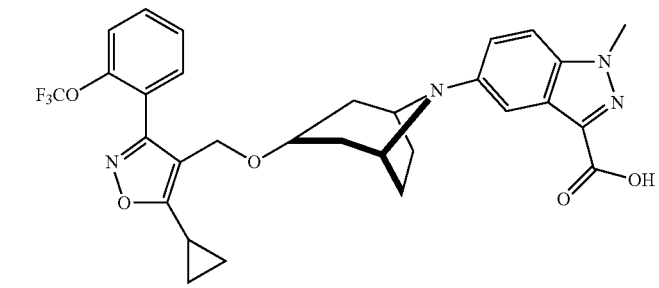 | MS m/z 583.2 (M + 1) |
| 28-17 | 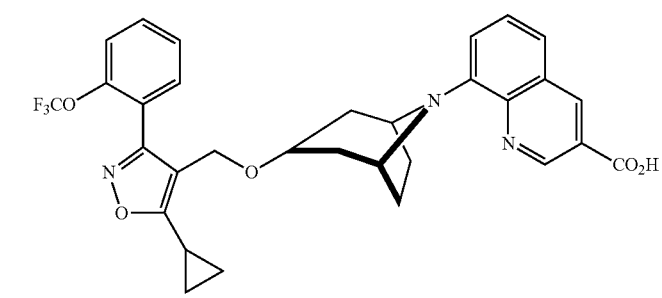 | MS m/z 580.2 (M + 1) |
| 28-18 | 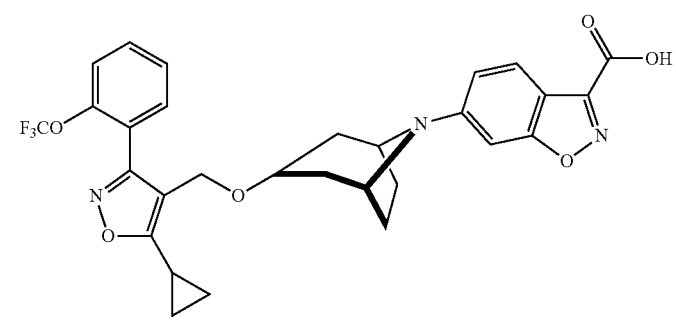 | MS m/z 570.2 (M + 1); ¹H NMR (MeOH-d₄, 400 MHz) δ 7.92 (d, J = 9.0 Hz, 1H), 7.67-7.61 (m, 2H), 7.54 (app t, J = 8.0 Hz, 2H), 6.92 (d, J = 8.2 Hz, 1H), 6.78 (app d, J = 1.2 Hz, 1H), 4.40 (s, 2H), 4.28 (br s, 2H), 3.44 (t, J = 4.0 Hz, 1H), 2.38-2.33 (m, 1H), 2.18-1.92 (m, 6H), 1.70 (app d, J = 14.0 Hz, 2H), 1.20-1.13 (m, 4H). |

| Ex | | Physical Data MS (m/z), ¹H NMR |
|---|---|---|
| 28-19 | 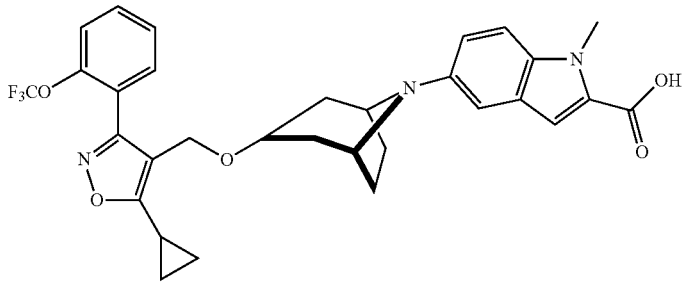 | MS m/z 582.2 (M + 1) |
| 28-20 | 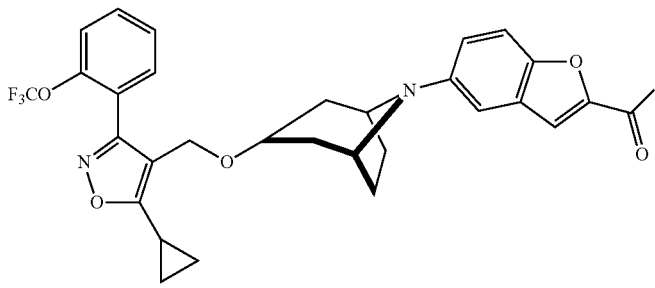 | MS m/z 553.2 (M + 1); ¹H NMR (MeOH-d₄, 400 MHz) δ 7.88-7.83 (m, 2H), 7.70-7.63 (m, 3H), 7.58 (s, 1H), 7.48 (app d, J = 7.8 Hz, 1H), 7.42 (app d, J = 7.8 Hz, 1H), 4.52 (bs, 2H), 4.38 (s, 2H), 3.62 (t, J = 4.4 Hz, 1H), 2.38-2.30 (m, 3H), 2.18-2.10 (m, 4H), 1.97 (app dd, J = 10.0, 5.1 Hz, 2H), 1.18-1.10 (m, 4H). |
| 28-21 | 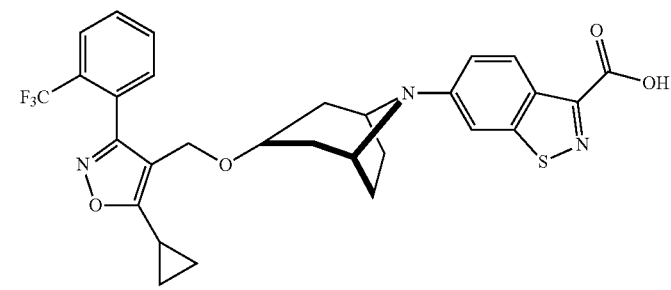 | ¹H NMR (400 MHz, CDCl₃) δ 8.59 (d, J = 8.8 Hz, 1H), 7.80-7.78 (m, 1H), 7.63-7.57 (m, 2H), 7.45-7.43 (m, 1H), 6.94-6.92 (m, 2H), 4.17 (s, 3H), 3.37 (bs, 1H), 2.12-2.05 (m, 1H), 1.99-1.93 (m, 4H), 1.63 (bs, 1H), 1.60 (bs, 1H), 1.30-1.08 (m, 4H), 1.13-1.08 (m, 2H), 0.88-0.83 (m, 2H), MS m/z 570.2 (M + 1). |
| 28-22 | 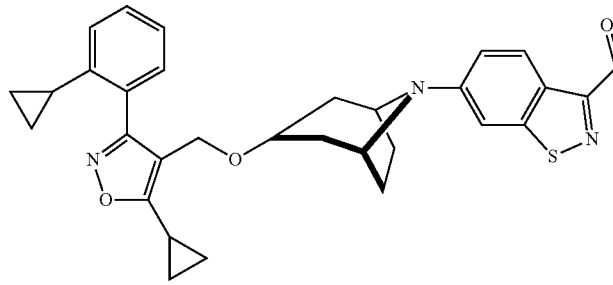 | ¹H NMR (400 MHz, DMSO) δ 8.32 (d, J = 8.8 Hz, 1H), 7.38 (dt, J = 6.8 and 2.4 Hz, 1H), 7.28-7.23 (m, 3H), 7.01 (bs, 1H), 6.95 (d, J = 8.0 Hz, 1H), 4.25 (s, 2H), 4.22 (bs, 2H), 3.40-3.37 (m, 2H), 1.86-1.76 (m, 7H), 1.57 (bs, 1H), 1.53 (bs, 1H), 1.14-1.06 (m, 5H), 0.88-0.84 (m, 2H), 068-0.64 (m, 2H), MS m/z 542.2 (M + 1). |
| 28-23 | 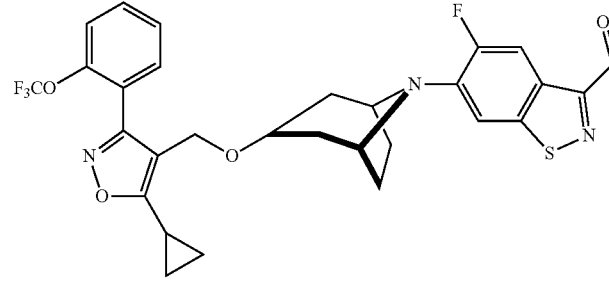 | ¹H NMR (400 MHz, DMSO) δ 8.11 (d, J$_{H-F}$ = 14.8 Hz, 1H), 7.70 (d, J$_{H-F}$ = 8.4 Hz, 1H), 7.68-7.66 (m, 1H),7.65-7.62 (m, 1H), 7.57-7.52 (m, 2H), 4.32 (s, 2H), 4.20 (bs, 2H), 3.49 (m, 1H), 2.34-2.32 (m, 1H), 1.94-1.90 (m, 2H), 1.79-1.77 (m, 5H), 1.66 (bs, 1H), 1.62 (bs, 1H), 1.14-1.11 (m, 2H), 1.08-1.07 (m, 2H). MS m/z 604.2 (M + 1). |

| Ex | | Physical Data MS (m/z), ¹H NMR |
|---|---|---|
| 28-24 | 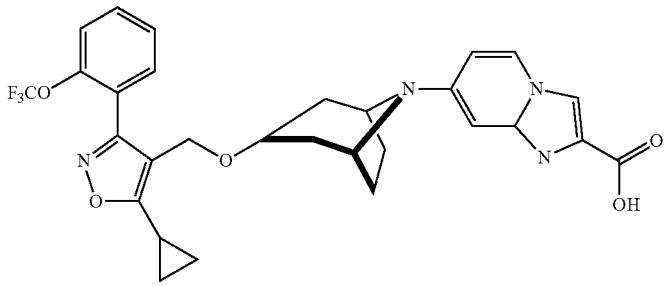 | MS m/z 569.2 (M + 1) |
| 28-25 | 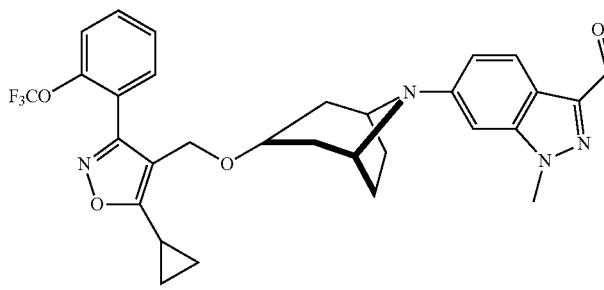 | ¹H NMR (400 MHz, CDCl₃) δ 7.91 (d, J = 9.2 Hz, 1H), 7.49-7.43 (m, 2H), 7.33-7.30 (m, 2H), 6.82 (d, J = 9.2 Hz, 1H), 6.36 (bs, 1H), 4.24 (bs, 2H), 4.10 (bs, 2H), 3.95 (s, 3H), 3.36 (m, 1H), 2.08-2.03 (m, 1H), 1.96-1.82 (m, 6H), 1.52-1.48 (m, 2H), 1.18-1.14 (m, 2H), 1.06-1.01 (m, 2H). MS m/z 583.2 (M + 1). |
| 28-26 | 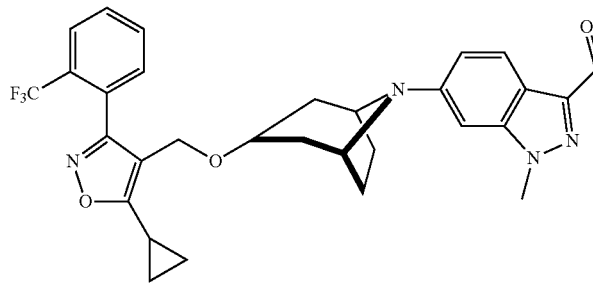 | ¹H NMR (400 MHz, CDCl₃) δ 7.98 (d, J = 8.8 Hz, 1H), 7.81 (d, J = 7.2 Hz, 1H), 7.64-7.59 (m, 2H), 7.45 (d, J = 7.2 Hz, 1H), 6.86 (d, J = 8.8 Hz, 1H), 6.41 (s, 1H), 4.17 (bs, 4H), 4.01 (s, 3H), 3.98 (m, 1H), 2.12-2.07 (m, 1H), 2.03-1.94 (m, 6H), 1.62-1.59 (m, 2H), 1.26-1.23 (m, 2H), 1.12-1.01 (m, 2H). MS m/z 567.2 (M + 1). |

EXAMPLE 29

The following examples were prepared from the corresponding azabicyclo[3.2.1]octane intermediates and the corresponding benzothiazole derivatives following the analogous procedures described in Example 1.

| Ex | | Physical Data MS (m/z), ¹H NMR |
|---|---|---|
| 29-1 | 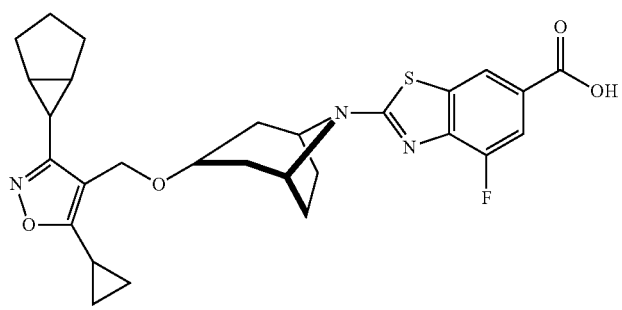 | MS m/z 524.3 (M + 1); 1H-NMR (400 MHz, CDCl₃) δ 8.14 (d, J = 1.5 Hz, 1H), 7.76 (dd, J = 11.1, 1.5 Hz, 1H), 4.44 (s, 1H), 4.38 (2H), 3.70 (m, 1H), 2.25 (m, 4H), 2.09 (m, 2H), 2.01 (m, 2H), 1.96-1.77 (m, 7H), 1.68 (m, 1H), 1.56 (m, 1H), 1.22 (m, 2H), 1.08 (m, 2H), 1.00 (m, 2H); MS m/z 524.3 (M + 1) |

-continued

| Ex | | Physical Data MS (m/z), ¹H NMR |
|---|---|---|
| 29-2 | 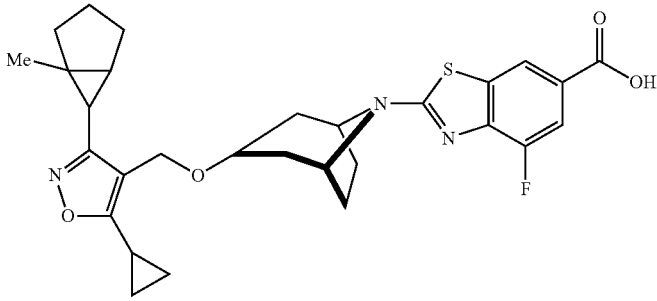 | MS m/z 538.3 (M + 1); 1H-NMR |
| 29-3 | 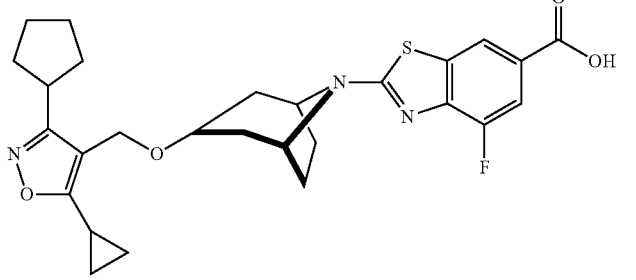 | MS m/z 512.3 (M + 1); 1H-NMR (400 MHz, CDCl$_3$) δ 8.13 (d, J = 1.2 Hz, 1H), 7.76 (dd, J = 11.2, 1.3 Hz, 1H), 4.43 (s, 1H), 4.35 (s, 2H), 3.69 (m, 1H), 3.08 (m, 1H), 2.24 (m, 4H), 2.10-1.93 (m, 7H), 1.87-1.78 (m, 4H), 1.66 (m, 2H), 1.25 (m, 1H), 1.11 (m, 2H), 1.02 (m, 2H); MS m/z 512.3 (M + 1) |
| 29-4 | 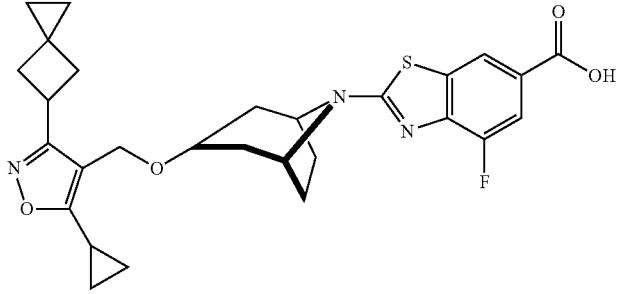 | MS m/z 524.2 (M + 1); 1H-NMR (400 MHz, CDCl$_3$) δ 8.14 (d, J = 1.4 Hz, 1H), 7.76 (dd, J = 11.2, 1.4 Hz, 1H), 4.43 (s, 1H), 4.31 (s, 2H), 3.69 (m, 3H), 2.63 (m, 2H), 2.37 (m, 2H), 2.23 (m, 4H), 2.08 (m, 2H), 2.01 (m, 1H), 1.97 (m, 2H), 1.12 (m, 2H), 1.03 (m, 2H), 0.54 (m, 2H), 0.44 (m, 2H); MS m/z 524.2 (M + 1) |
| 29-5 | 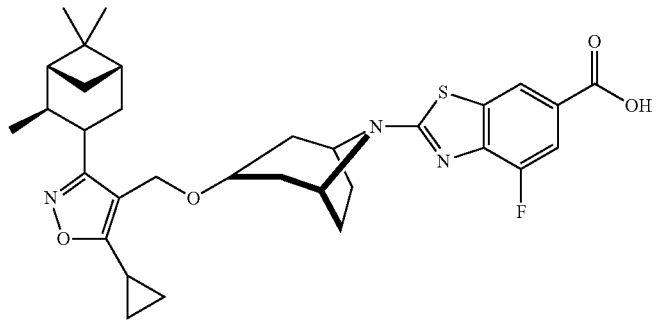 | MS m/z 580.3 (M + 1); 1H-NMR (400 MHz, CDCl$_3$) δ 8.13 (s, 1H), 7.75 (m, J = 11.1 Hz, 1H), 4.43 (s, 1H), 4.42 (s, 2H), 3.69 (m, 1H), 3.18 (m, 1H), 2.68 (m, 1H), 2.40 (m, 2H), 2.24 (m, 4H), 2.08 (m, 2H), 2.02-1.90 (m, 7H), 1.26 (s, 3H), 1.17 (m, 1H), 1.13 (m, 5H), 1.04 (m, 5H); MS m/z 580.2 (M + 1) |
| 29-6 | 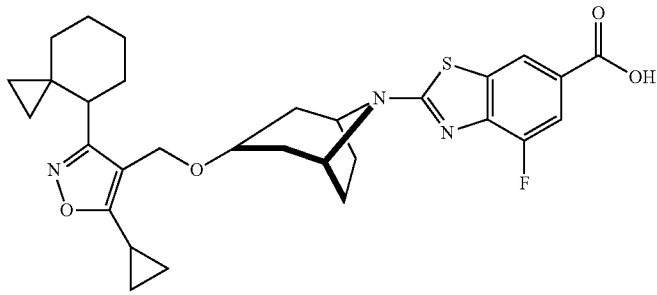 | ¹H NMR (400 MHz, CDCl$_3$) δ 8.12 (d, J = 1.2 Hz, 1H) 7.76 (dd, J = 9.2, 1.2 Hz, 1H), 4.44 (bs 1H), 434-4.26 (m, 2H), 3.68 (t, J = 4.4 Hz, 1H), 2.76 (m, 1H), 2.26-2.21 (m, 2H), 2.10-2.08 (m, 2H) 2.04-1.91 (m, 2H), 2.04-1.91 (m, 4H), 1.88-1.76 (m, 2H), 1.62-1.59 (m, 2H), 1.50-1.42 (m, 4H), 1.13-1.09 (m, 3H), 1.03-1.00 (m, 3), 0.49-0.47 (m, 1H), 0.28-0.12 (m, 2H). MS m/z 552.2 (M + 1) |

| Ex | | Physical Data<br>MS (m/z), $^1$H NMR |
|---|---|---|
| 29-7 | 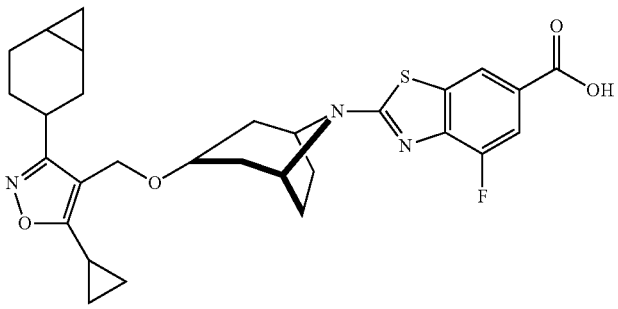 | MS m/z 538.2 (M + 1); $^1$H NMR (400 MHz, DMSO) δ 8.17 (s, 1H), 7.58 (dd, J = 11.6, 1.2 Hz, 1H), 4.38-4.35 (m, 4H), 3.72 (bs, 1H), 2.33-1.86 (m, 14H), 1.65-1.61 (m, 1H), 1.54-1.48 (m, 1H) 1.26-1.18 (m, 1H), 1.04-1.00 (m, 6H), 0.63-0.57 (m, 1H), 0.11-0.07 (m, 1H). MS m/z 538.2 (M + 1). |

EXAMPLE 30

The following compounds were prepared from the corresponding nortropine intermediates according to the procedures described previously for the preparation of Example 1, Example 2 or Example 18.

| Ex | | Physical Data<br>MS (m/z), $^1$H NMR |
|---|---|---|
| 30-1 | 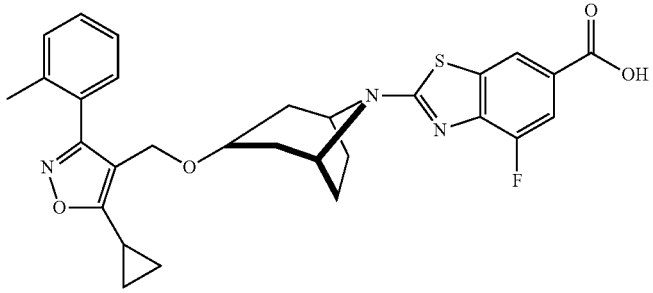 | MS m/z 534.2 (M + 1); $^1$H NMR (DMSO-d$_6$, 400 MHz) δ 8.21 (d, J = 1.6 Hz, 1H), 7.58 (dd, J = 11.6, 1.6 Hz, 1H), 7.43-7.29 (m, 4H), 4.37-4.23 (m, 4H), 3.56 (t, J = 4.2 Hz, 1H), 2.40-2.29 (m, 1H), 2.22 (s, 3H), 2.05-1.79 (m, 8H), 1.20-1.06 (m, 4H). |
| 30-2 | 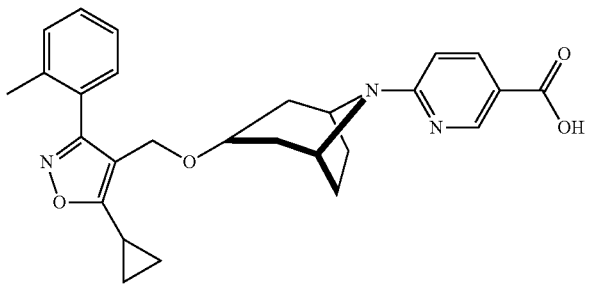 | MS m/z 460.3 (M + 1); $^1$H NMR (DMSO-d$_6$, 400 MHz) δ 12.45 (bs, 1H), 8.60 (d, J = 2.4 Hz, 1H), 7.87 (dd, J = 8.8, 2.4 Hz, 1H), 7.42-7.28 (m, 4H), 6.68 (d, J = 8.8 Hz, 1H), 4.45 (bs, 2H), 4.21 (s, 2H), 3.47 (t, J = 4.0 Hz, 1H), 2.38-2.28 (m, 1H), 2.21 (s, 3H), 1.92-1.78 (m, 6H), 1.66 (d, J = 14.8 Hz, 2H), 1.21-1.04 (m, 4H). |
| 30-3 | 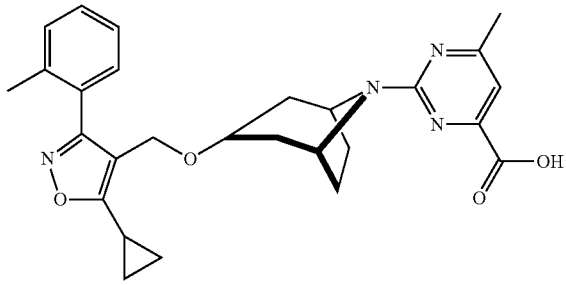 | MS m/z 475.3 (M + 1); |

-continued
| Ex | | Physical Data MS (m/z), ¹H NMR |
|---|---|---|
| 30-4 | 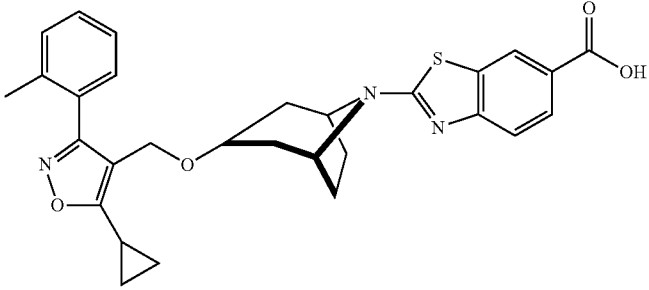 | MS m/z 516.1 (M + 1) |
| 30-5 | 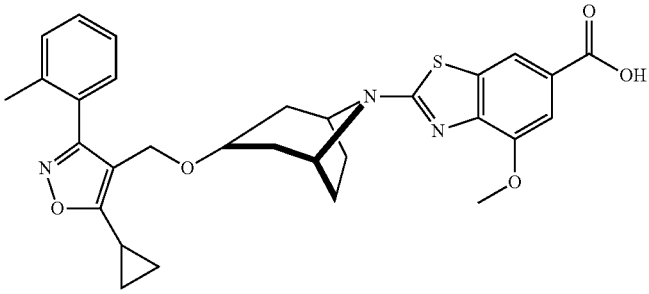 | MS m/z 546.1 (M + 1); ¹H NMR (DMSO-d$_6$, 400 MHz) δ 7.42-7.28 (m, 5H), 6.96 (s, 1H), 4.54 (bs, 2H), 4.21 (s, 2H), 3.49 (t, J = 4.0 Hz, 1H), 2.38-2.28 (m, 4H), 2.22 (s, 3H), 1.88-1.68 (m, 8H), 1.24-1.05 (m, 4H). |
| 30-6 | 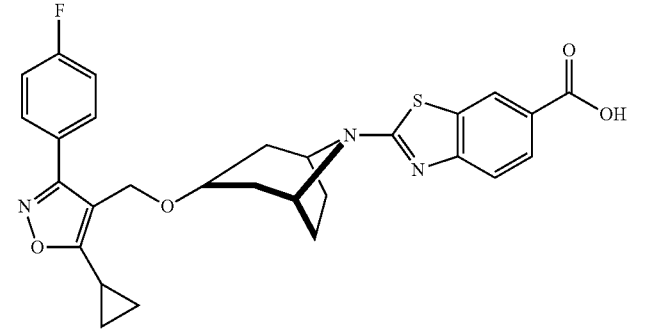 | MS m/z 520.1 (M + 1); ¹H NMR (DMSO-d$_6$, 400 MHz) δ 12.71 (s, 1H), 8.36 (d, J = 1.6 Hz, 1H), 7.86-7.78 (m, 3H), 7.47 (d, J = 8.4 Hz, 1H), 7.42-7.36 (m, 2H), 4.46 (s, 2H), 4.31 (bs, 2H), 3.73 (t, J = 4.0 Hz, 1H), 2.38-2.32 (m, 1H), 2.14-1.91 (m, 8H), 1.16-1.03 (m, 4H). |
| 30-7 | 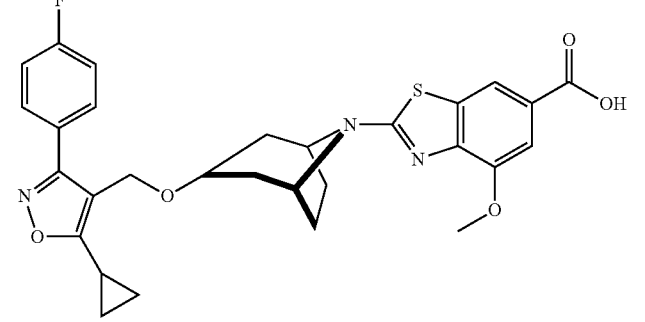 | MS m/z 550.1 (M + 1) |
| 30-8 | 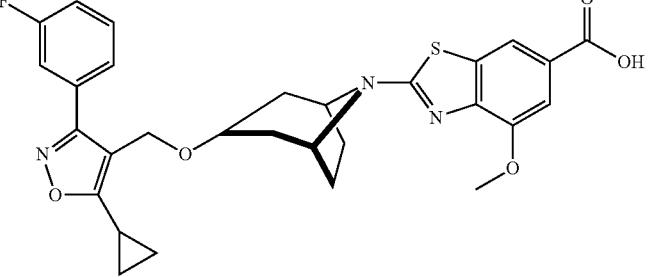 | MS m/z 550.1 (M + 1) |

-continued
| Ex | | Physical Data MS (m/z), ¹H NMR |
|---|---|---|
| 30-9 | 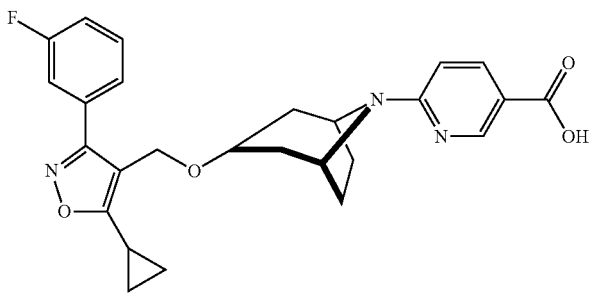 | MS m/z 464.2 (M + 1); ¹H NMR (DMSO-d₆, 400 MHz) δ 12.46 (s, 1H), 8.62 (d, J = 2.4 Hz, 1H), 7.90 (d, J = 8.8, 2.4 Hz, 1H), 7.63-7.56 (m, 3H), 7.43-7.37 (m, 1H), 6.72 (d, J = 8.8 Hz, 1H), 4.53 (bs, 2H), 4.47 (s, 2H), 3.68-3.64 (m, 1H), 2.40-2.30 (m, 1H), 2.08-1.82 (m, 8H), 1.14-1.04 (m, 4H). |
| 30-10 | 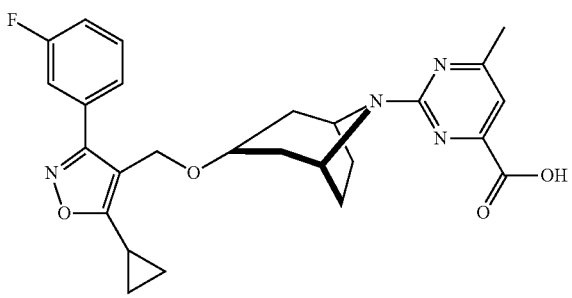 | MS m/z 479.1 (M + 1) |
| 30-11 | 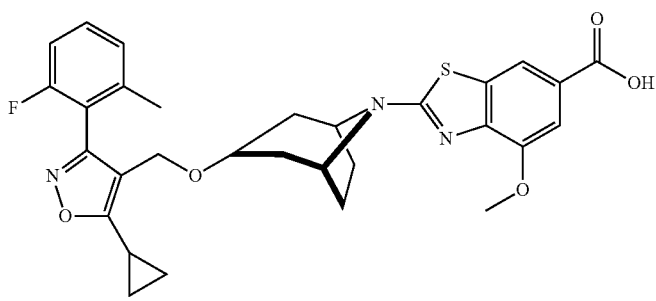 | MS m/z 564.1 (M + 1); ¹H NMR (DMSO-d₆, 400 MHz) δ 12.76 (s, 1H), 7.98 (d, J = 1.6 Hz, 1H), 7.49-7.43 (m, 1H), 7.37 (d, J = 1.6 Hz, 1H), 7.24-7.17 (m, 2H), 4.22 (s, 2H), 4.18 (bs, 2H), 3.89 (s, 3H), 3.50 (t, J = 4.0 Hz, 1H), 2.38-2.31 (m, 1H), 2.16 (s, 3H), 1.99-1.91 (m, 2H), 1.84-1.75 (m, 4H), 1.71 (d, J = 14.4 Hz, 2H), 1.19-1.07 (m, 4H). |
| 30-12 | 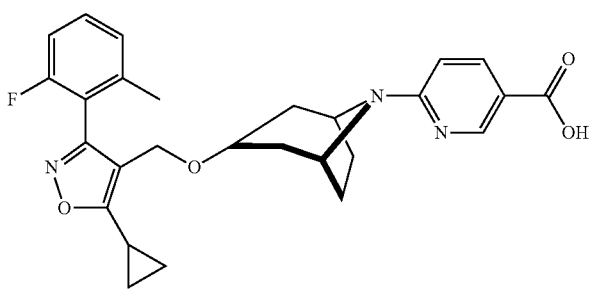 | MS m/z 478.1 (M + 1) |
| 30-13 | 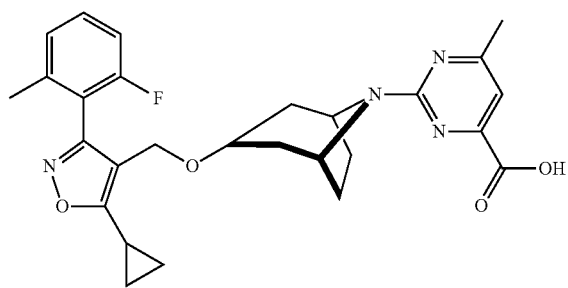 | MS m/z 493.1 (M + 1) |

| Ex | | Physical Data MS (m/z), ¹H NMR |
|---|---|---|
| 30-14 | 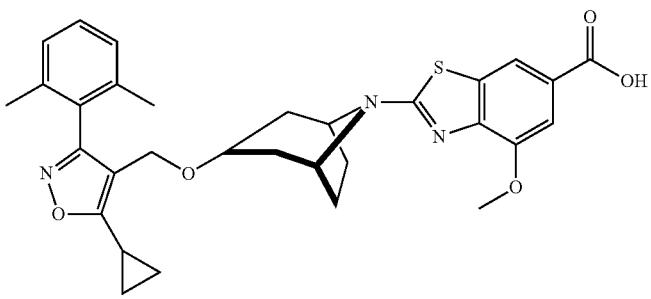 | MS m/z 560.2 (M + 1); ¹H NMR (DMSO-d₆, 400 MHz) δ 12.70 (s, 1H), 7.96 (d, J = 1.6 Hz, 1H), 7.35 (d, 1.6 Hz, 1H), 7.29-7.25 (m, 1H), 7.14 (d, J = 8.0 Hz, 2H), 4.18 (bs, 2H), 4.10 (s, 2H), 3.87 (s, 3H), 3.47 (t, J = 4.4 Hz, 1H), 2.36-2.29 (m, 1H), 2.03 (s, 6H), 2.00-1.91 (m, 2H), 1.89-1.80 (m, 4H), 1.74 (d, J = 14.4 Hz, 2H), 1.15-1.06 (m, 4H). |
| 30-15 | 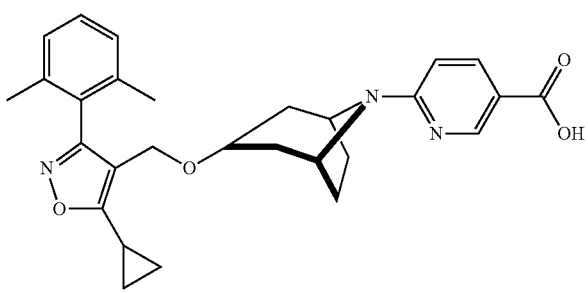 | MS m/z 474.2 (M + 1) |
| 30-16 | 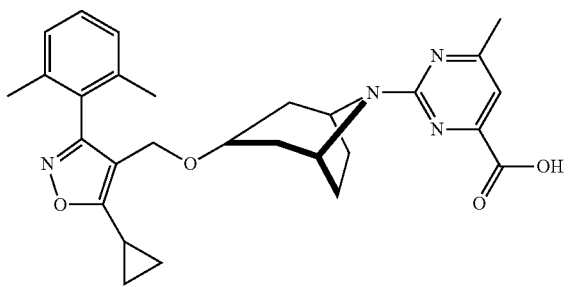 | MS m/z 489.2 (M + 1); ¹H NMR (DMSO-d₆, 400 MHz) δ 7.27 (t, J = 8.0 Hz, 1H), 7.14 (d, J = 7.6 Hz, 2H), 6.95 (s, 1H), 4.52 (bs, 2H), 4.09 (s, 2H), 3.42 (t, J = 4.0 Hz, 1H), 2.36-2.29 (m, 4H), 2.04 (s, 6H), 1.83-1.65 (m, 8H), 1.16-1.06 (m, 4H). |
| 30-17 | 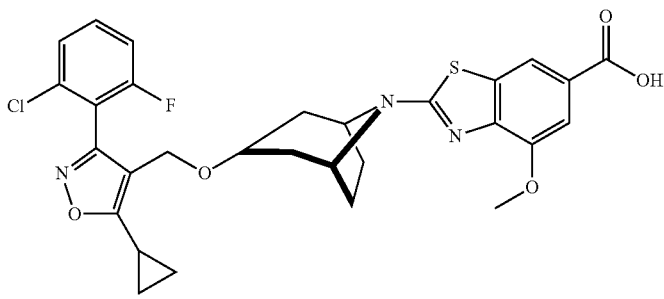 | MS m/z 584.1, 586.1 (M + 1, Cl₃₅/Cl₃₇ isotope pattern) |
| 30-18 | 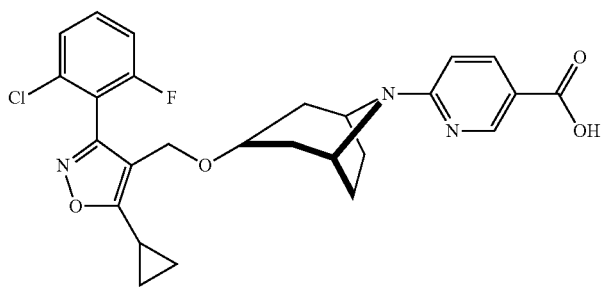 | MS m/z 498.1, 500.1 (M + 1, Cl₃₅/Cl₃₇ isotope pattern); ¹H NMR (DMSO-d₆, 400 MHz) δ 12.41 (s, 1H), 8.58 (d, J = 1.6 Hz, 1H), 7.89-7.85 (m, 1H), 7.64-7.60 (m, 1H), 7.52 (d, J = 5.2 Hz, 1H), 7.42 (t, J = 6.0 Hz, 1H), 6.66 (d, J = 6.0 Hz, 1H), 4.42 (bs, 2H), 4.28 (s, 2H), 3.47-3.42 (m, 1H), 2.39-2.31 (m, 1H), 1.77-1.67 (m, 6H), 1.58 (d, J = 9.6 Hz, 2H), 1.20-1.07 (m, 4H). |

| Ex | | Physical Data MS (m/z), ¹H NMR |
|---|---|---|
| 30-19 | 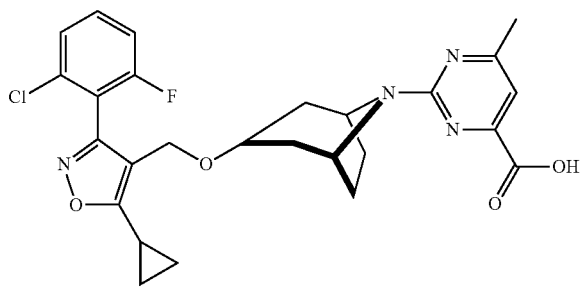 | MS m/z 513.2, 515.2 (M + 1, Cl$_{35}$/Cl$_{37}$ isotope pattern) |
| 30-20 | 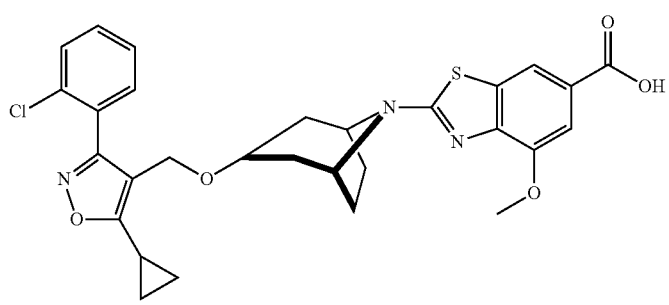 | MS m/z 566.2, 568.1 (M + 1, Cl$_{35}$/Cl$_{37}$ isotope pattern) ¹H NMR (DMSO-d$_6$, 400 MHz) δ 12.68 (s, 1H), 7.98 (d, J = 1.6 Hz, 1H), 7.65-7.64 (m, 1H), 7.59-7.54 (m, 1H), 7.51-7.47 (m, 2H), 7.37 (d, J = 1.6 Hz, 1H), 4.32 (s, 2H), 4.18 (bs, 2H), 3.89 (s, 3H), 3.52 (t, J = 4.4 Hz, 1H), 2.38-2.31 (m, 1H), 2.00-1.78 (m, 6H), 1.70 (d, J = 14.8 Hz, 2H), 1.17-1.06 (m, 4H). |
| 30-21 | 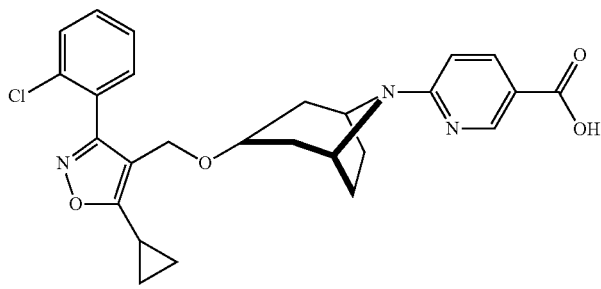 | MS m/z 480.1, 482.1 (M + 1, Cl$_{35}$/Cl$_{37}$ isotope pattern) |
| 30-22 | 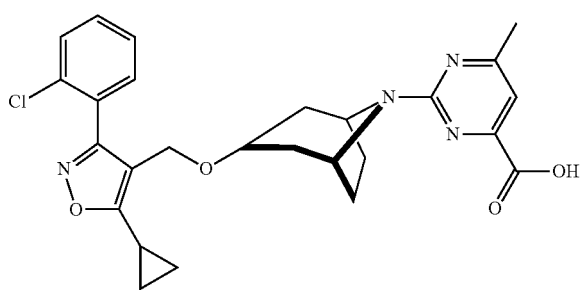 | MS m/z 495.1, 497.1 (M + 1, Cl$_{35}$/Cl$_{37}$ isotope pattern) |
| 30-23 | 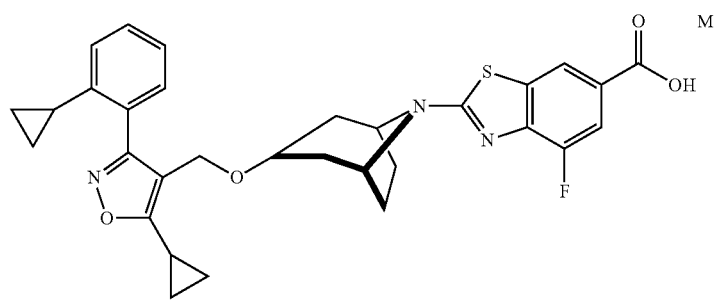 | MS m/z 560.2 (M + 1) |

| Ex | | Physical Data MS (m/z), ¹H NMR |
|---|---|---|
| 30-24 | 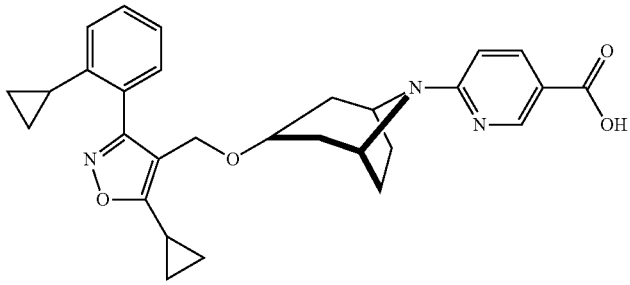 | MS m/z 486.2 (M + 1); ¹H NMR (DMSO-d₆, 400 MHz) δ 12.44 (s, 1H), 8.59 (d, J = 2.0 Hz, 1H), 7.87 (dd, J = 8.8, 2.4 Hz, 1H), 7.42-7.37 (m, 1H), 7.29-7.22 (m, 2H), 6.96 (d, J = 7.6 Hz, 1H), 6.67 (d, J = 8.8 Hz, 1H), 4.43 (bs, 2H), 4.27 (s, 2H), 3.46 (t, J = 4.4 Hz, 1H), 2.36-2.28 (m, 1H), 1.86-1.74 (m, 7H), 1.63 (d, J = 14.4 Hz, 2H), 1.16-1.06 (m, 4H), 0.90-0.83 (m, 2H), 0.69-0.65 (m, 2H). |
| 30-25 | 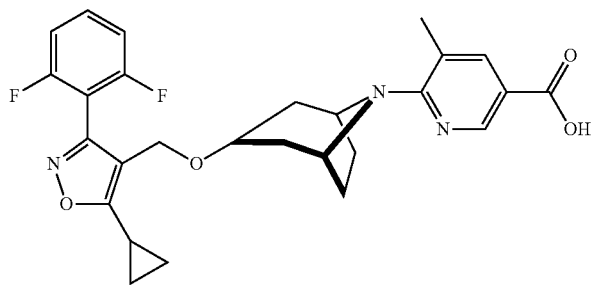 | MS m/z 496.2 (M + 1) |
| 30-26 | 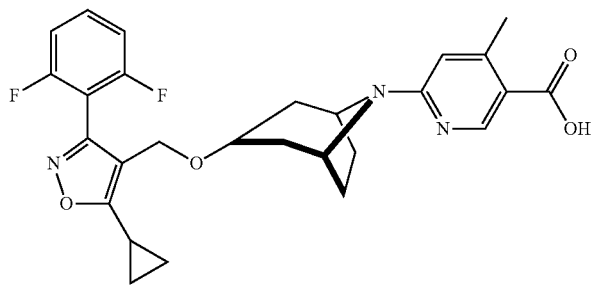 | MS m/z 496.3 (M + 1) |
| 30-27 | 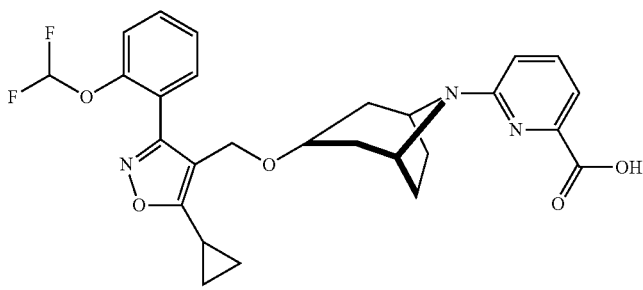 | MS m/z 512.2 (M + 1) |
| 30-28 | 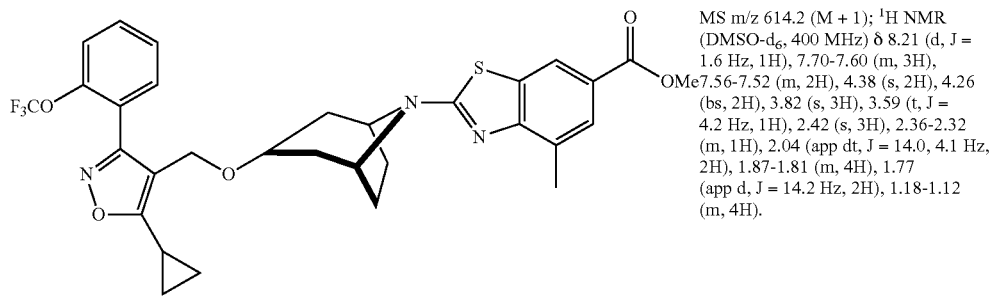 | MS m/z 614.2 (M + 1); ¹H NMR (DMSO-d₆, 400 MHz) δ 8.21 (d, J = 1.6 Hz, 1H), 7.70-7.60 (m, 3H), 7.56-7.52 (m, 2H), 4.38 (s, 2H), 4.26 (bs, 2H), 3.82 (s, 3H), 3.59 (t, J = 4.2 Hz, 1H), 2.42 (s, 3H), 2.36-2.32 (m, 1H), 2.04 (app dt, J = 14.0, 4.1 Hz, 2H), 1.87-1.81 (m, 4H), 1.77 (app d, J = 14.2 Hz, 2H), 1.18-1.12 (m, 4H). |

-continued
| Ex | | Physical Data MS (m/z), ¹H NMR |
|---|---|---|
| 30-29 | 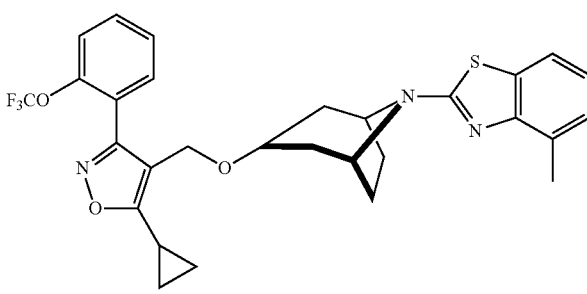 | MS m/z 600.2 (M + 1); ¹H NMR (DMSO-d₆, 400 MHz) δ 8.08 (d, J = 1.5 Hz, 1H), 7.64-7.58 (m, 3H), 7.46-7.42 (m, 2H), 4.31 (s, 2H), 4.18 (broad s, 2H), 3.44 (t, J = 4.2 Hz, 1H), 2.39 (s, 3H), 2.32-2.25 (m, 1H), 1.95 (app dt, J = 13.8, 4.0 Hz, 2H), 1.78-1.72 (m, 4H), 1.63 (d, J = 14.2, 2H), 1.09-1.04 (m, 4H). |
| 30-30 | 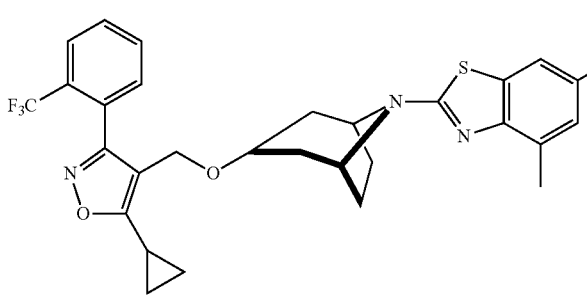 | MS m/z 598.1 (M + 1) |
| 30-31 | 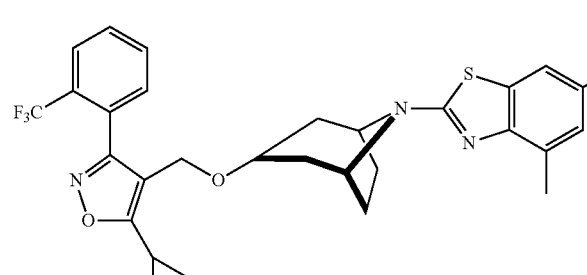 | MS m/z 584.2 (M + 1) |
| 30-32 | 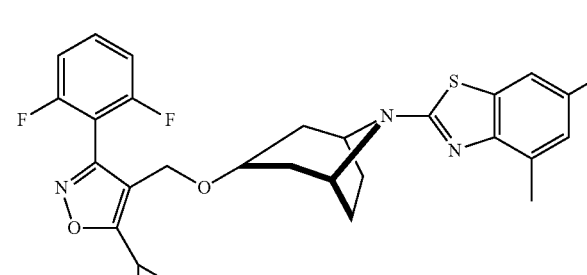 | MS m/z 566.1 (M + 1); ¹H NMR (DMSO-d₆, 400 MHz) δ 8.21 (d, J = 1.1 Hz, 1H), 7.68 (d, J = 1.1 Hz, 1H), 7.65 (app q, J = 7.2 Hz, 1H), 7.37-7.30 (m, 2H), 4.36 (s, 2H), 4.24 (br s, 2H), 3.83 (s, 3H), 3.54 (t, J = 4.0 Hz, 1H), 2.44 (s, 3H), 2.38-2.36 (m, 1H), 1.97 (app dt, J = 14.2, 4.0 Hz, 2H), 1.83-1.74 (m, 4H), 1.72 (app d, J = 14.6, 2H), 1.08-1.05 (m, 4H). |
| 30-33 | 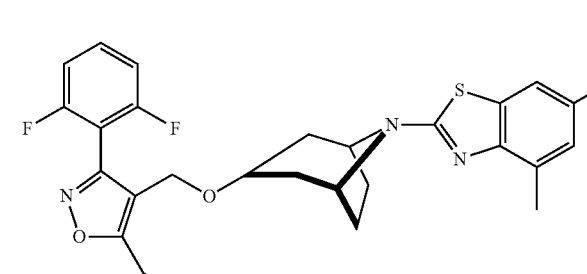 | MS m/z 552.2 (M + 1); ¹H NMR (DMSO-d₆, 400 MHz) δ 12.50 (br s, 1H, OH), 8.19 (d, J = 1.1 Hz, 1H), 7.74-7.69 (m, 2H), 7.33-7.28 (m, 2H), 4.32 (s, 2H), 4.22 (br s, 2H), 3.48 (t, J = 4.0 Hz, 1H), 2.43 (s, 3H), 2.35-2.33 (m, 1H), 1.99 (app dt, J = 14.2, 4.0 Hz, 2H), 1.88-1.77 (m, 4H), 1.74 (app d, J = 14.6 Hz, 2H), 1.18-1.09 (m, 4H). |

-continued
| Ex | | Physical Data MS (m/z), ¹H NMR |
|---|---|---|
| 30-34 | 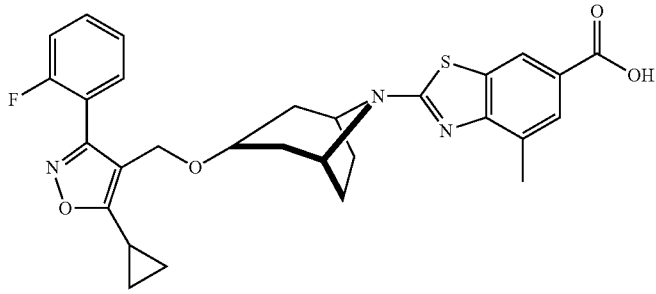 | MS m/z 534.2 (M + 1) |
| 30-35 | 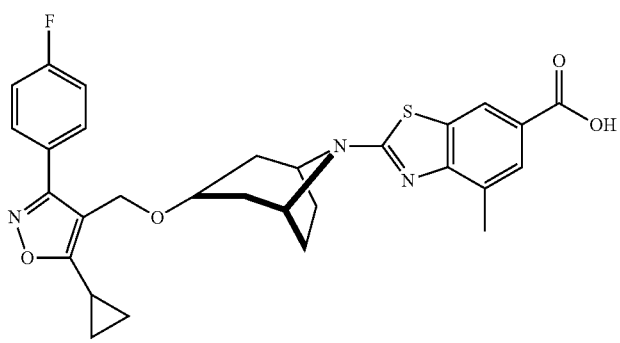 | MS m/z 534.2 (M + 1); ¹H NMR (MeOH-d$_4$, 400 MHz) δ 7.81-7.74 (m, 4H), 7.22 (app t, J = 8.2 Hz, 2H), 4.46 (br s, 2H), 4.37 (s, 2H), 3.75 (t, J = 4.0 Hz, 1H), 2.50 (s, 3H), 2.29-1.98 (m, 7H), 1.95 (app d, J =14.4 Hz, 2H), 1.16-1.12 (m, 4H). |
| 30-36 | 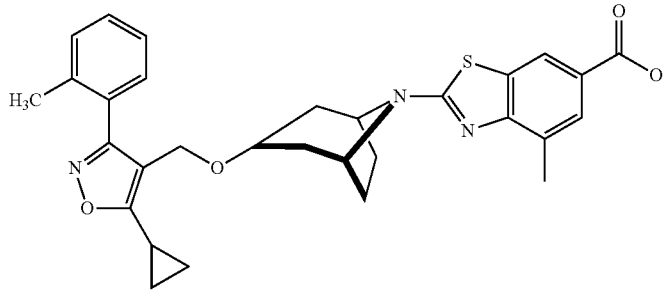 | MS m/z 530.2 (M + 1); ¹H NMR (MeOH-d$_4$, 400 MHz) δ 8.08 (d, J = 1.6 Hz, 1H), 7.78 (d, J = 1.7 Hz, 1H), 7.38-7.24 (m, 4H), 4.28 (br s, 2H), 4.26 (s, 2H), 3.58 (t, J = 3.8 Hz, 1H), 2.58 (s, 3H), 2.29-2.21 (m, 1H), 2.24 (s, 3H), 2.01 (app dt, J = 14.2, 4.0 Hz, 2H), 2.06-1.87 (m, 4H), 1.82 (app d, J = 14.2 Hz, 2H), 1.09-1.07 (m, 4H). |
| 30-37 | 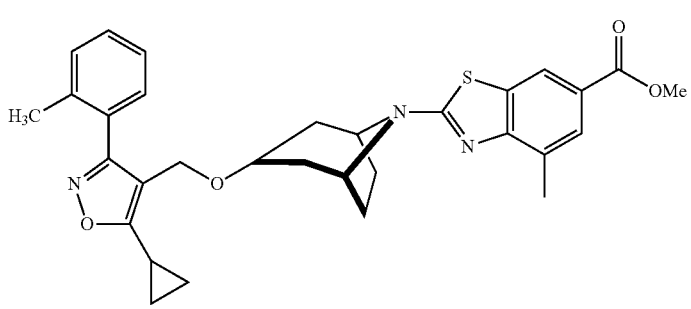 | MS m/z 544.2 (M + 1) |
| 30-38 | 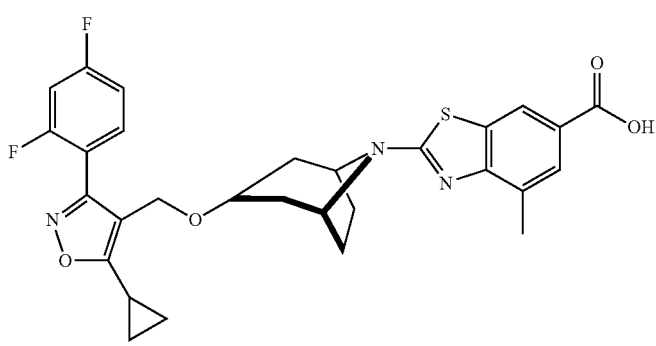 | MS m/z 552.2 (M + 1) |

-continued
| Ex | | Physical Data MS (m/z), ¹H NMR |
|---|---|---|
| 30-39 | 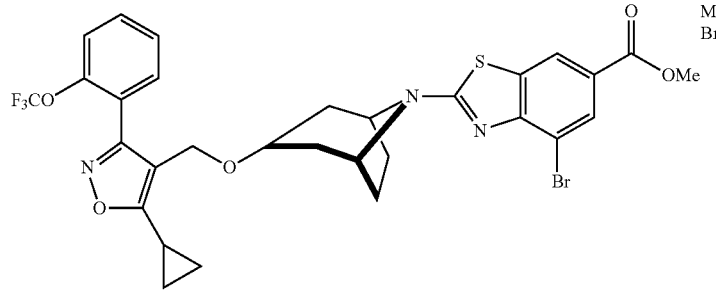 | MS m/z 678.1/680.1 (M + 1, Br$_{79}$/Br$_{81}$ isotope pattern). |
| 30-40 | 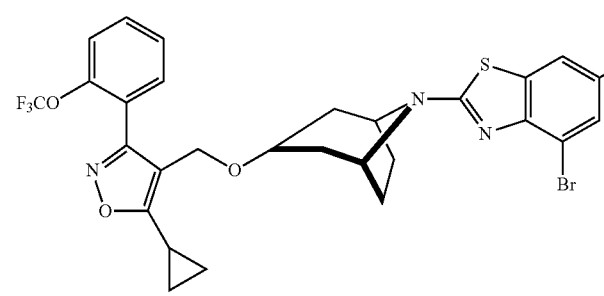 | MS m/z 664.1/666.1 (M + 1, Br$_{79}$/Br$_{81}$ isotope pattern).; ¹H NMR (MeOH-d$_4$, 400 MHz) δ 8.23 (d, J = 1.6 Hz, 1H), 7.92 (d, J = 1.6 Hz, 1H), 7.68-7.59 (m, 2H), 7.56-7.46 (m, 2H), 4.38 (s, 2H), 4.19 (broad s, 2H), 3.54 (t, J = 4.4 Hz, 1H), 2.38-2.32 (m, 1H), 1.99 (app dt, J = 14.0, 4.0 Hz, 2H), 1.90-1.84 (m, 4H), 1.73 (d, J = 14.0 Hz, 2H), 1.18-1.07 (m, 4H). |
| 30-41 | 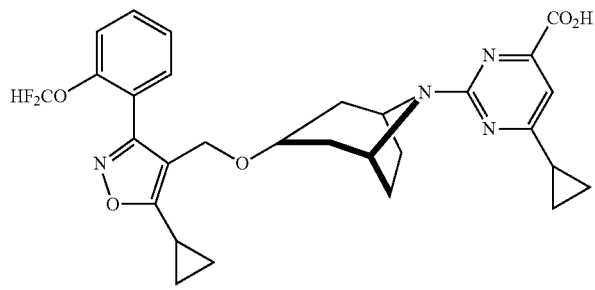 | MS m/z 553.2 (M + 1) |
| 30-42 | 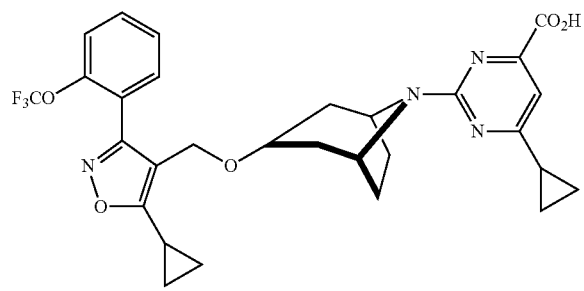 | MS m/z 571.2 (M + 1); ¹H NMR (MeOH-d$_4$, 400 MHz) δ 7.62 (dt, J = 8.0, 1.6 Hz, 1H), 7.59 (dd, J = 8.0, 1.6 Hz, 1H), 7.49 (app t, J =7.2 Hz, 2H), 6.91 (br s, 1H), 4.48 (bs, 2H), 4.37 (s, 2H), 3.54 (t, J = 4.2 Hz, 1H), 2.28-2.26 (m, 1H), 1.94-1.72 (m, 6H), 1.69 (d, J = 14.0 Hz, 2H), 1.07-1.00 (m, 4H). |
| 30-43 | 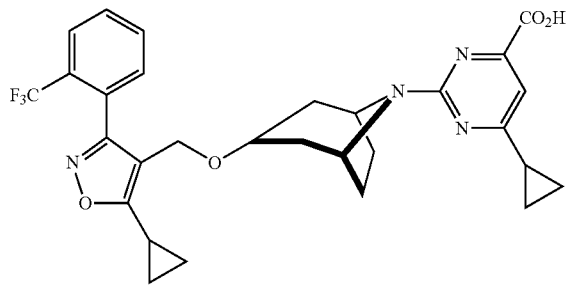 | MS m/z 555.2 (M + 1) |

-continued

| Ex | | Physical Data MS (m/z), ¹H NMR |
|---|---|---|
| 30-44 | 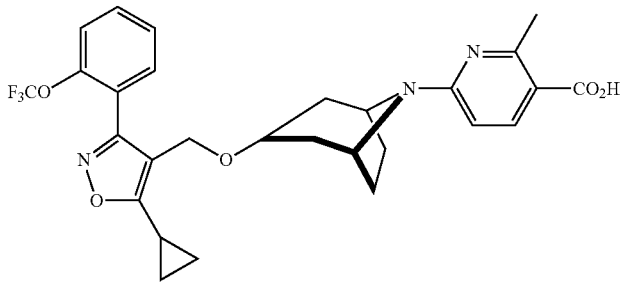 | MS m/z 544.2 (M + 1); ¹H NMR (MeOH-d₄, 400 MHz) δ 8.00 (d, J = 9.1 Hz, 1H), 7.63 (app dt, J = 8.0, 1.6 Hz, 1H), 7.58 (dd, J = 8.0, 1.6 Hz, 1H), 7.50 (app t, J = 8.0 Hz, 2H), 6.42 (d, J =9.1 Hz, 1H), 4.45 (bs, 2H), 4.37 (s, 2H), 3.50 (t, J = 4.4 Hz, 1H), 2.61 (s, 3H), 2.28-2.23 (m, 1H), 1.97-1.88 (m, 4H), 1.81 (app dd, J = 8.8, 4.8 Hz, 2H), 1.70 (d, J = 14.4 Hz, 2H), 1.18-1.13 (m, 4H). |
| 30-45 | 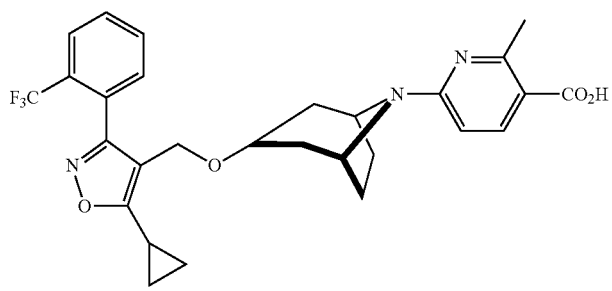 | MS m/z 528.2 (M + 1); ¹H NMR (MeOH-d₄, 400 MHz) δ 7.98 (d, J = 9.1 Hz, 1H), 7.86 (app dd, J = 7.2, 1.2 Hz, 1H), 7.75 (app t, J = 7.2 Hz, 1H), 7.72 (app t, J = 7.2 Hz, 1H), 7.52 (d, J = 7.2 Hz, 1H), 6.49 (d, J = 9.2 Hz, 1H), 4.46 (bs, 2H), 4.26 (s, 2H), 3.46 (t, J = 4.8 Hz, 1H), 2.61 (s, 3H), 2.27-2.23 (m, 1H), 1.98-1.88 (m, 4H), 1.82 (app dd, J = 8.8, 4.8 Hz, 2H), 1.70 (d, J = 14.4 Hz, 2H), 1.18-1.14 (m, 4H). |
| 30-46 | 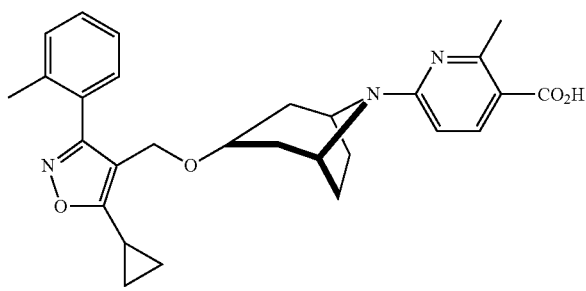 | MS m/z 474.2 (M + 1) |
| 30-47 | 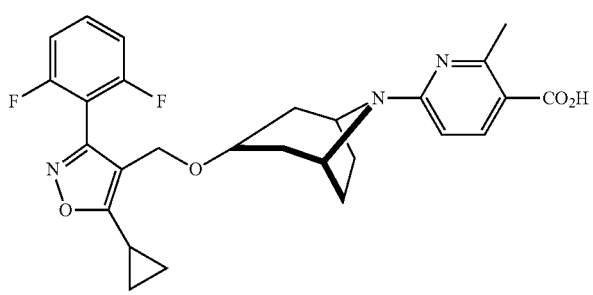 | MS m/z 496.2 (M + 1) |
| 30-48 | 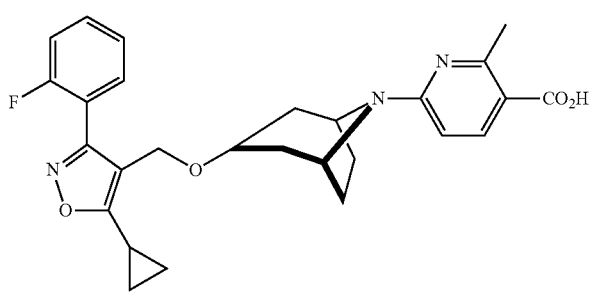 | MS m/z 478.2 (M + 1); ¹H NMR (MeOH-d₄, 400 MHz) δ 8.00 (d, J = 9.2 Hz, 1H), 7.59-7.53 (m, 2H), 7.33 (app dt, J = 7.6, 1.2 Hz, 1H), 7.29 (app dt, J = 8.2, 1.2 Hz, 1H), 6.48 (d, J = 9.2 Hz, 1H), 4.47 (bs, 2H), 4.42 (s, 2H), 3.54 (t, J = 4.8 Hz, 1H), 2.62 (s, 3H), 2.31-2.24 (m, 1H), 1.94-1.90 (m, 4H), 1.81 (app dd, J = 8.8, 5.2 Hz, 2H), 1.72 (d, J = 14.4 Hz, 2H), 1.18-1.10 (m, 4H). |

| Ex | | Physical Data MS (m/z), $^1$H NMR |
|---|---|---|
| 30-49 | 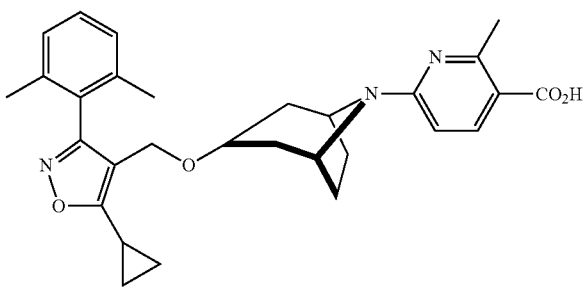 | MS m/z 488.2 (M + 1) |
| 30-50 | 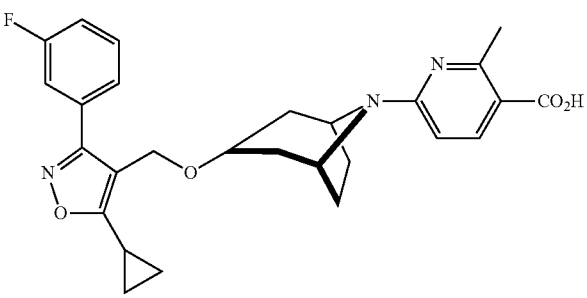 | MS m/z 478.2 (M + 1) |
| 30-51 | 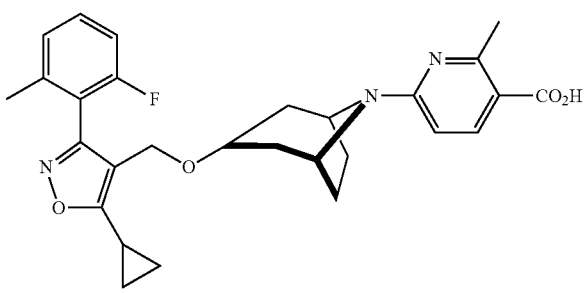 | MS m/z 492.2 (M + 1); $^1$H NMR (MeOH-$d_4$, 400 MHz) δ 7.94 (d, J = 8.8 Hz, 1H), 7.30 (ddd, J = 14.4, 6.8, 6.0 Hz, 1H), 7.58 (d, J = 7.6 Hz, 1H), 6.97 (app t, J = 8.8 Hz, 1H), 6.37 (d, J = 8.8 Hz, 1H), 4.36 (bs, 2H), 4.16 (s, 2H), 3.36 (t, J = 4.4 Hz, 1H), 2.53 (s, 3H), 2.20-2.13 (m, 1H), 2.22 (s, 3H), 1.87-1.71 (m, 6H), 1.61 (d, J = 14.4 Hz, 2H), 1.09-1.04 (m, 4H). |
| 30-52 | 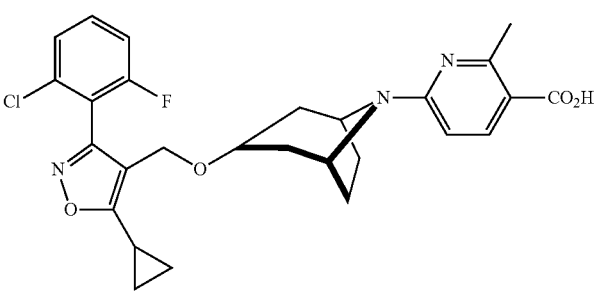 | MS m/z 512.2/514.2 (M + 1, $Cl_{35}/Cl_{37}$ isotope pattern) |
| 30-53 | 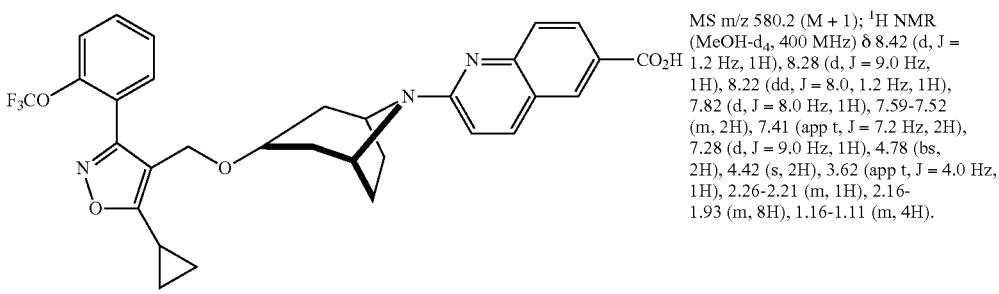 | MS m/z 580.2 (M + 1); $^1$H NMR (MeOH-$d_4$, 400 MHz) δ 8.42 (d, J = 1.2 Hz, 1H), 8.28 (d, J = 9.0 Hz, 1H), 8.22 (dd, J = 8.0, 1.2 Hz, 1H), 7.82 (d, J = 8.0 Hz, 1H), 7.59-7.52 (m, 2H), 7.41 (app t, J = 7.2 Hz, 2H), 7.28 (d, J = 9.0 Hz, 1H), 4.78 (bs, 2H), 4.42 (s, 2H), 3.62 (app t, J = 4.0 Hz, 1H), 2.26-2.21 (m, 1H), 2.16-1.93 (m, 8H), 1.16-1.11 (m, 4H). |

-continued

| Ex | | Physical Data<br>MS (m/z), $^1$H NMR |
|---|---|---|
| 30-54 | 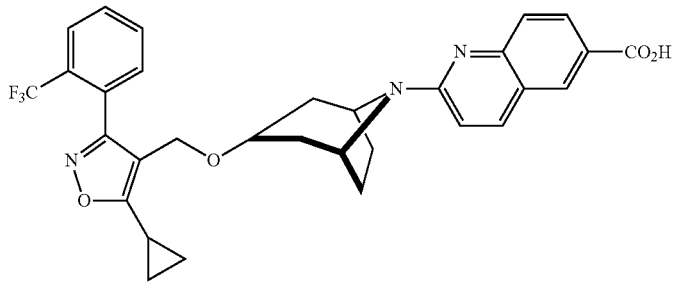 | MS m/z 564.2 (M + 1); $^1$H NMR (MeOH-d$_4$, 400 MHz) δ 8.52 (d, J = 1.2 Hz, 1H), 8.37 (d, J = 9.0 Hz, 1H), 8.32 (dd, J = 8.0, 1.2 Hz, 1H), 7.83 (app t, J = 7.2 Hz, 2H), 7.74-7.63 (m, 2H), 7.46 (d, J = 8.0 Hz, 1H), 7.38 (d, J = 9.0 Hz, 1H), 4.78 (bs, 2H), 4.34 (s, 2H), 3.59 (app t, J = 4.0 Hz, 1H), 2.29-2.23 (m, 1H), 2.19-1.94 (m, 8H), 1.18-1.12 (m, 4H). |
| 30-55 | 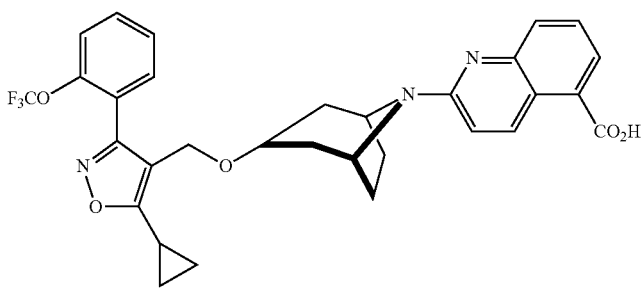 | MS m/z 580.2 (M + 1) |
| 30-56 | 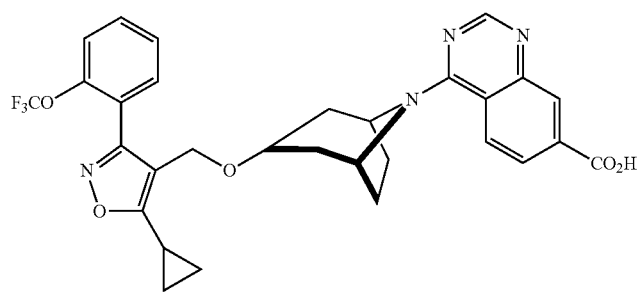 | MS m/z 581.2 (M + 1); $^1$H NMR (MeOH-d$_4$, 400 MHz) δ 8.50 (s, 1H), 8.20-8.14 (m, 3H), 7.58-7.50 (m, 2H), 7.42 (app t, J = 6.4 Hz, 2H), 4.72 (s, 2H, partially obscured by water in MeOH-d$_4$), 4.31 (s, 2H), 3.61 (app t, J = 4.0 Hz, 1H), 2.30-1.90 (m, 7H), 1.79-1.71 (m, 2H), 1.10-1.04 (m, 4H). |
| 30-57 | 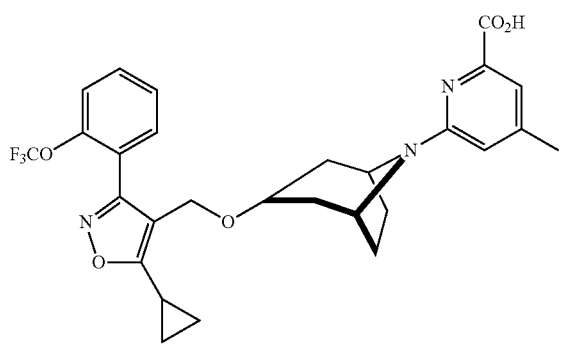 | MS m/z 528.2 (M + 1); $^1$H NMR (MeOH-d$_4$, 400 MHz) δ 7.88 (d, J = 9.0 Hz, 1H), 7.75 (app t, J = 7.6 Hz, 1H), 7.72 (app t, J = 7.6 Hz, 1H), 7.53 (app d, J = 9.0 Hz, 1H), 7.32 (s, 1H), 7.15 (s, 1H), 4.60 (br s, 2H), 4.38 (s, 2H), 3.58 (app t, J = 4.4 Hz, 1H), 2.40 (s, 3H), 2.28-2.22 (m, 1H), 2.08 (app d, J = 10.6 Hz, 2H), 2.02-1.95 (m, 4H), 1.84 (app d, J = 14.2 Hz, 2H), 1.18-1.13 (m, 4H). |
| 30-58 | 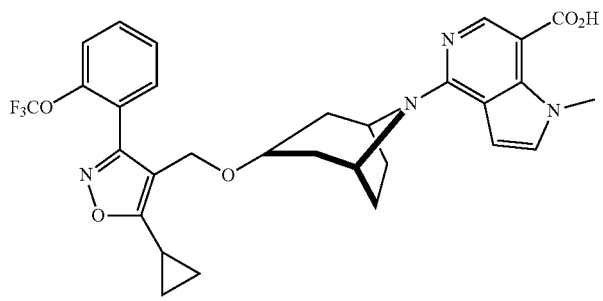 | MS m/z 583.2 (M + 1); $^1$H NMR (MeOH-d$_4$, 400 MHz) δ 7.64 (app dt, J = 7.6, 1.5 Hz, 1H), 7.60 (dd, J = 7.8, 1.5 Hz, 1H), 7.56 (app d, J = 9.0 Hz, 1H), 7.52 (app t, J = 6.6 Hz, 2H), 7.34 (d, J = 6.5 Hz, 1H), 6.93 (d, J = 6.5 Hz, 1H), 4.78 (br s, 2H), 4.42 (s, 2H), 4.00 (s, 3H), 3.62 (app t, J = 4.0 Hz, 1H), 2.38-2.30 (m, 1H), 2.18-1.96 (m, 6H), 1.92 (app d, J = 14.2 Hz, 2H), 1.18-1.14 (m, 4H). |

-continued
| Ex | | Physical Data MS (m/z), ¹H NMR |
|---|---|---|
| 30-59 | 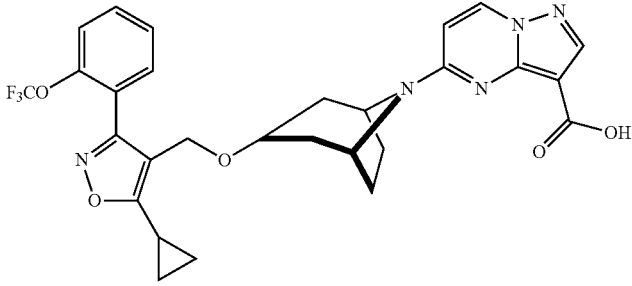 | MS m/z 570.2 (M + 1); ¹H NMR (MeOH-d₄, 400 MHz) δ 8.10 (br s, 1H), 7.81 (d, J = 8.6 Hz, 1H), 7.62-7.56 (m, 2H), 7.52 (app t, J = 7.6 Hz, 2H), 7.18 (d, J = 8.6 Hz, 1H), 4.42 (br s, 2H), 4.37 (s, 2H), 3.51 (app t, J = 4.4 Hz, 1H), 2.34-2.28 (m, 1H), 2.08 (app d, J = 10.4 Hz, 2H), 2.06-1.94 (m, 4H), 1.78 (app d, J = 14.2 Hz, 2H), 1.22-1.16 (m, 4H). |
| 30-60 | 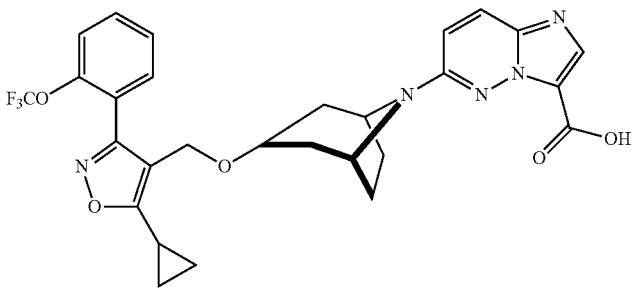 | MS m/z 570.2 (M + 1) |
| 30-61 | 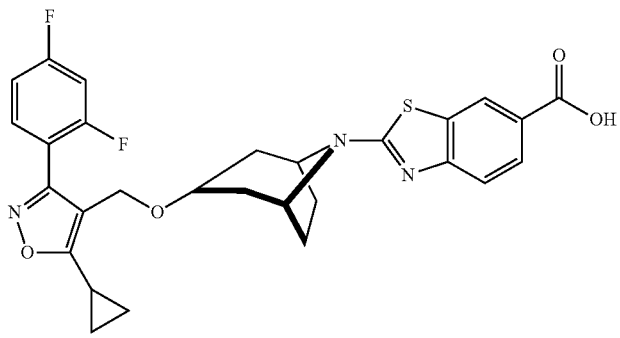 | ¹H NMR (400 MHz, CDCl₃) δ 8.32 (d, J = 1.6 Hz, 1H), 8.02 (dd, J = 8.8 and 2.0 Hz, 1H), 7.56-7.51 (m, 2H), 7.02-6.92 (m, 2H), 4.36 (d, J = 1.2 2H), 4.30 (bs, 1H), 3.59-3.57 (m, 1H), 2.17-2.06 (m, 3H), 2.02-1.98 (m, 4H), 1.85 (bs, 1H), 1.79 (bs, 1H), 1.25 (bs, 1H), 1.22-1.20 (m, 2H), 1.13-1.09 (m, 2H). MS m/z 538.1 (M + 1) |
| 30-62 | 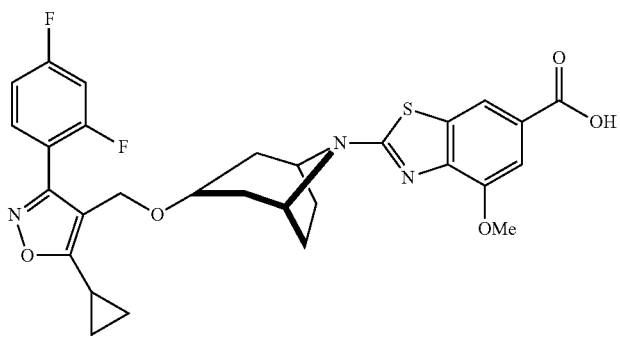 | ¹H NMR (400 MHz, CDCl₃) δ 8.00 (bs, 1H), 7.54-7.50 (m, 2H), 7.01-6.92 (m, 2H), 4.36 (bs, 2H), 4.02 (s, 3H), 3.57 (m, 1H), 2.17-2.15 (m, 3H), 1.98-1.96 (m, 4H), 1.82 (bs, 1H), 1.78 (bs, 1H), 1.25 (m, 1H), 1.21-1.20 (m, 2H), 1.12-1.09 (m, 2H). MS m/z 538.1 (M + 1). |

| Ex | | Physical Data MS (m/z), ¹H NMR |
|---|---|---|
| 30-63 | 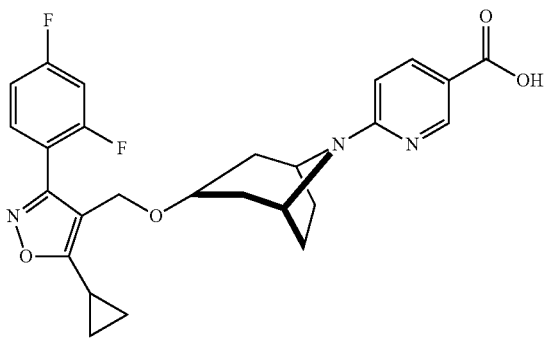 | MS m/z 482.2 (M + 1). |
| 30-64 | 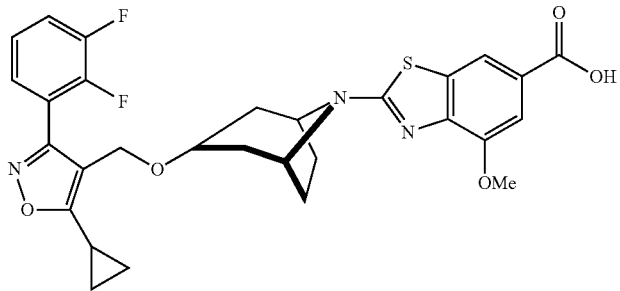 | ¹H NMR (400 MHz, CDCl₃) δ 8.01 (d, J = 1.6 Hz, 1H), 7.52 (d, J = 1.2 Hz, 1H), 7.32-7.28 (m, 2H), 7.21-7.15 (m, 1H), 4.38 (bs, 3H), 4.02 (s, 3H), 3.58 (m, 1H), 2.17-2.06 (m, 3H), 1.98-1.92 (m, 4H), 1.81 (bs, 1H), 1.78 (bs, 1H), 1.24-1.20 (m, 2H), 1.14-1.09 (m, 2H). MS m/z 568.2 (M + 1). |
| 30-65 | 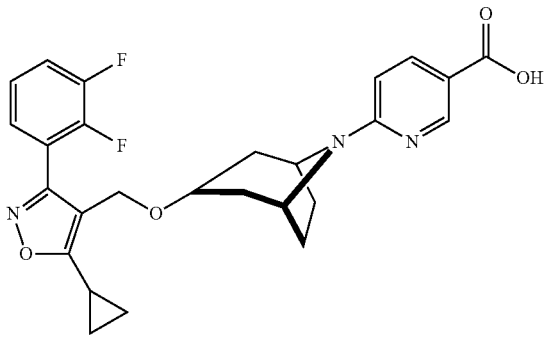 | MS m/z 482.2 (M + 1). |
| 30-66 | 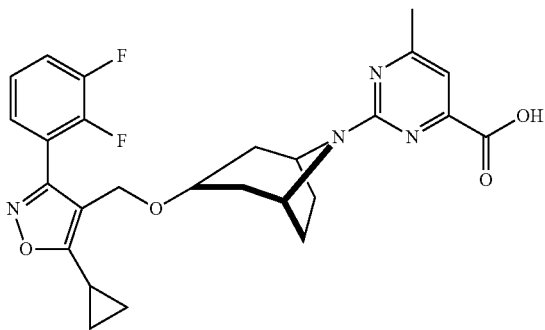 | ¹H NMR (400 MHz, DMSO) δ 7.67-7.60 (m, 1H), 7.43-7.34 (m, 2H), 6.75 (s, 1H), 4.41 (bs, 2H), 4.37 (bs, 2H), 3.51 (bs, 1H), 2.37-2.30 (m, 4H), 1.83-1.80 (m, 1H), 1.75-1.70 (m, 6H), 1.63 (bs, 1H), 1.59 (bs, 1H), 1.16-1.11 (m, 2H), 1.09-1.05 (m, 2H). MS m/z 497.2 (M + 1). |

| Ex | | Physical Data MS (m/z), ¹H NMR |
|---|---|---|
| 30-67 | 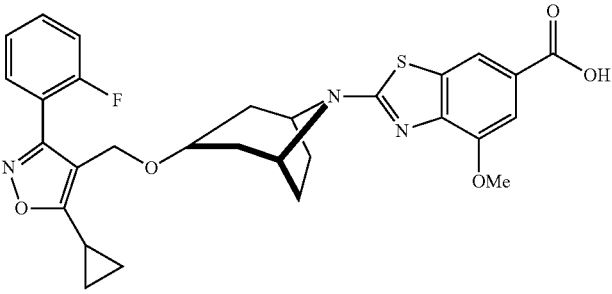 | ¹H NMR (400 MHz, CDCl₃) δ 8.00 (d, J = 1.2 Hz, 1H), 7.55-7.50 (m, 2H), 7.49-7.43 (m, 1H), 7.24-7.16 (m, 2H), 4.37 (bs, 2H), 4.34 (bs, 1H), 4.02 (s, 3H), 3.58 (m, 1H), 2.14-2.08 (m, 3H), 1.98-1.90 (1H, 5H), 1.80 (bs, 1H), 1.77 (bs, 1H), 1.24-1.20 (m, 2H), 1.13-1.08 (m, 2H). MS m/z 550.2 (M + 1). |
| 30-68 | 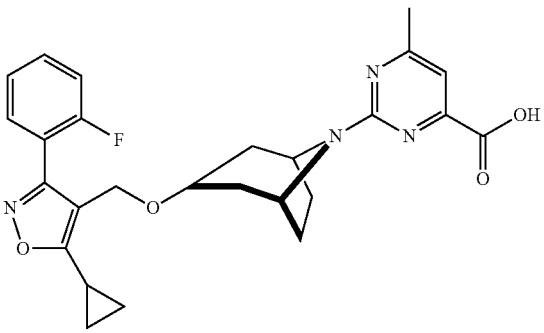 | MS m/z 479.2 (M + 1). |
| 30-69 | 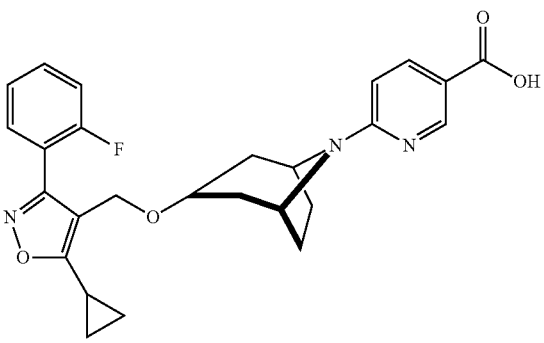 | ¹H NMR (400 MHz, CDCl₃) δ 8.82 (d, J = 2.4 Hz, 1H), 7.98 (dd, J = 9.2 and 2.4 Hz, 1H), 7.53 (dt, J = 7.6 and 2.0 Hz, 1H), 7.48-7.42 (m, 1H), 7.23 (dd, J = 7.6 and 1.2 Hz, 1H), 7.20-7.16 (m, 1H), 6.43 (d, J = 8.8 Hz, 1H), 4.36 (bs, 3H), 3.51 (m, 1H), 2.15-2.08 (m, 1H), 2.05-1.98 (m, 2H), 1.94-1.87 (m, 5H), 1.75 (bs, 1H), 1.71 (bs, 1H), 1.24-1.20 (m, 2H), 1.12-1.07 (m, 2H). MS m/z 464.2 (M + 1). |
| 30-70 | 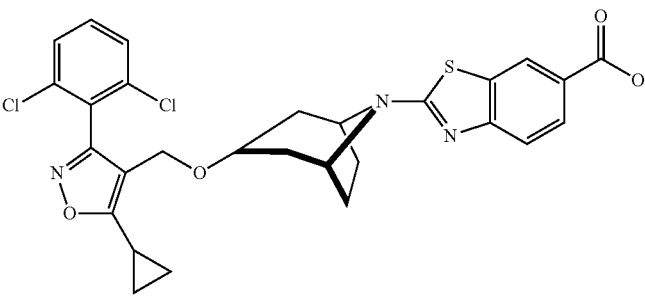 | ¹H NMR (400 MHz, CDCl₃) δ 8.32 (bs, 1H), 8.03-8.01 (m, 1H), 7.52-7.50 (m, 1H), 7.43-7.41 (m, 2H), 7.36-7.34 (m, 1H), 4.27 (bs, 4H), 3.52 (m, 1H), 2.11-2.09 (m, 3H), 1.99-1.94 (m, 5H), 1.80 (bs, 1H), 1.76 (bs, 1H), 1.27-1.24 (m, 2H), 1.14-1.11 (m, 2H). MS m/z 570.1 and 572.1 (M + 1). |
| 30-71 | 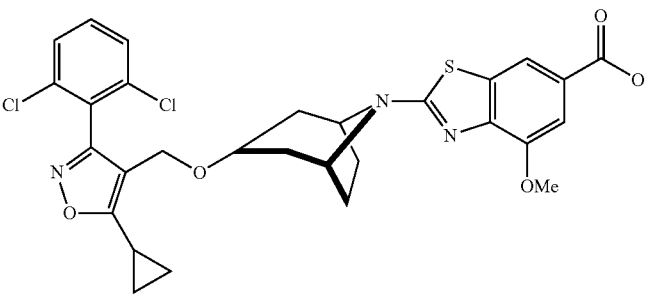 | ¹H NMR (400 MHz, CDCl₃) δ 8.00 (d, J = 1.6 Hz, 1H), 7.51 (d, J = 1.6 Hz, 1H), 7.43 (d, J = 1.6 Hz, 1H), 7.40 (bs, 1H), 7.36-7.32 (m, 1H), 4.33 (bs, 1H), 4.26 (s, 2H), 4.02 (s, 3H), 3.52 (m, 1H), 2.13-2.04 (m, 3H), 1.96-1.89 (m, 5H), 1.78 (bs, 1H), 1.75 (bs, 1H), 1.27-1.24 (m, 2H), 1.15-1.10 (m, 2H). MS m/z 600.1 and 602.1 (M + 1). |

-continued
| Ex | | Physical Data MS (m/z), ¹H NMR |
|---|---|---|
| 30-72 | 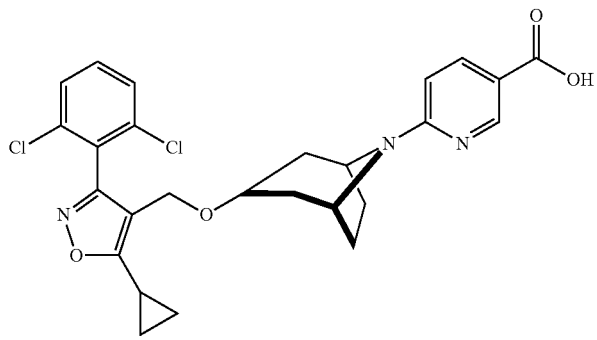 | ¹H NMR (400 MHz, CDCl₃) δ 8.82 (d, J = 2.4 Hz, 1H), 7.98 (dd, J = 8.8 and 2.4 Hz, 1H), 7.42 (d, J = 1.6 Hz, 1H), 7.40 (bs, 1H), 7.35-7.31 (m, 1H), 6.42 (d, J = 9.2 Hz, 1H), 4.25 (bs, 3H), 3.48 (m, 1H), 2.15-2.08 (m, 1H), 1.94-1.92 (m, 2H), 1.90-1.86 (m, 5H), 1.73 (bs, 1H), 1.69 (bs, 1H), 1.27-1.24 (m, 2H), 1.14-1.09 (m, 2H). MS m/z 514.2 and 5.16 (M + 1). |
| 30-73 | 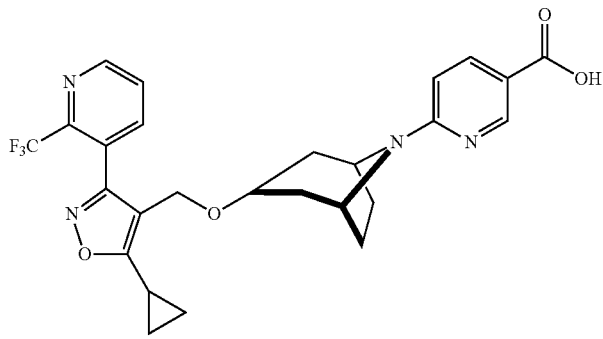 | MS m/z 515.2 (M + 1) |
| 30-74 | 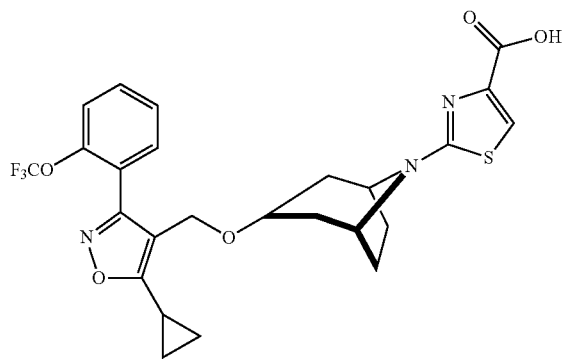 | MS m/z 536.2 (M + 1) |
| 30-75 | 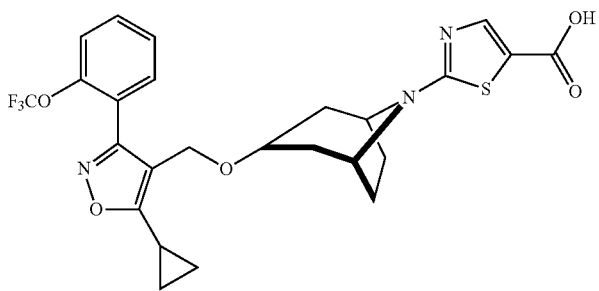 | ¹H NMR (400 MHz, CDCl₃) δ 7.75 (s, 1H), 7.53-7.46 (m, 2H), 7.38-7.34 (m, 2H), 4.27 (s, 2H), 4.03 9bs, 1H), 3.44 (bs, 1H), 2.11-2.05 (m, 1H), 1.96-1.80 (m, 8H), 1.63 (bs, 1H), 1.60 (bs, 1H), 1.24-1.18 (m, 2H), 1.11 91.06 (m, 2H). MS m/z 536.1 (M + 1) |

| Ex | Physical Data MS (m/z), ¹H NMR |
|---|---|
| 30-76 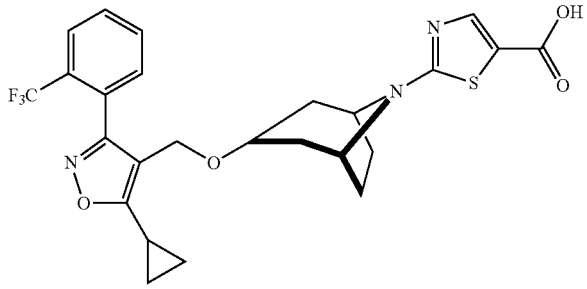 | MS m/z 520.1 (M + 1) |

EXAMPLE 31

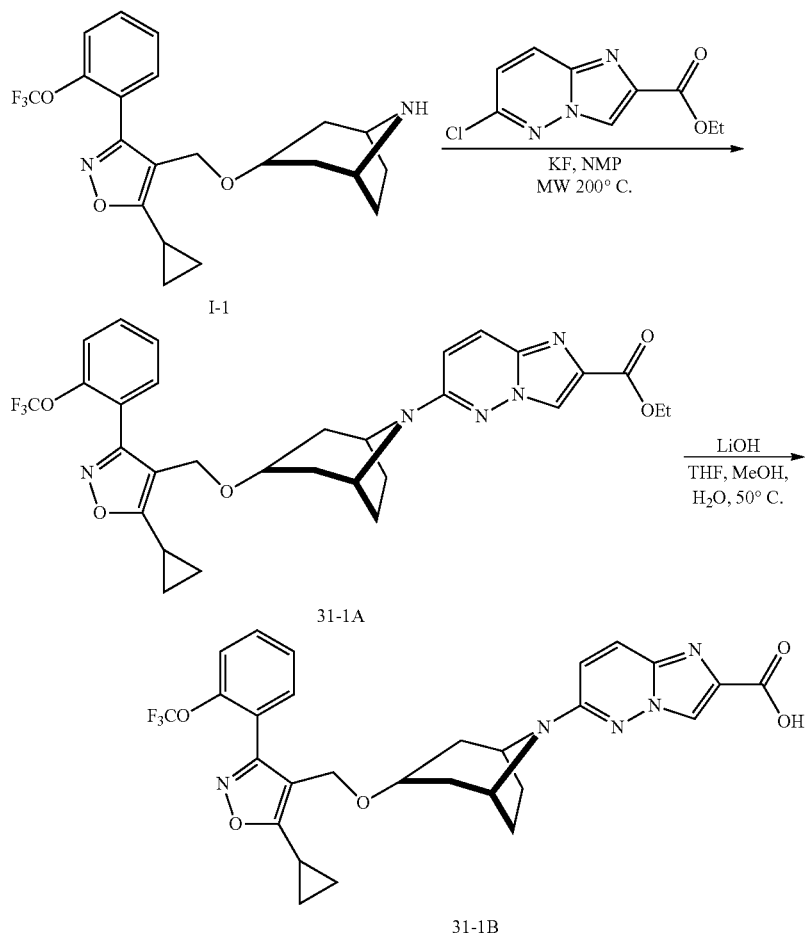

Ethyl 6-(3-((5-cyclopropyl-3-(2-(trifluoromethoxy)phenyl)isoxazol-4-yl)methoxy)-8-azabicyclo[3.2.1]octan-8-yl)imidazo[1,2-b]pyridazine-2-carboxylate (31-1ᵃ). To a suspension of commercially available ethyl 6-chloroimidazo[1,2-b]pyridazine-2-carboxylate (Il Farmaco, 1997, 52, 4, 213) (66 mg, 0.255 mmol) in NMP (2.5 mL) was added 4-((8-azabicyclo[3.2.1]octan-3-yloxy)methyl)-5-cyclopropyl-3-(2-(trifluoromethoxy)phenyl)isoxazole (I-1) (120 mg, 0.29 mmol) and potassium fluoride (51 mg, 0.88 mmol). The mixture was heated at 200° C. for 30 minutes under microwave irradiation. The mixture was poured into water and extracted with ethyl acetate twice. The combined organic layers were washed with brine, dried over sodium sulfate, filtered and concentrated. The crude product was purified using mass-triggered reverse phase HPLC using gradient of 40 to 60% acetonitrile/water with 0.05% TFA as modifier to yield ethyl 6-(3-((5-cyclopropyl-3-(2-(trifluoromethoxy)phenyl)isoxazol-4-yl)methoxy)-8-azabicyclo[3.2.1]octan-8-yl)imidazo[1,2-b]pyridazine-2-carboxylate as TFA salt. ¹H NMR (400 MHz, CDCl₃) δ 8.17 (s, 1H), 7.67 (d, J=10.0 Hz, 1H), 7.54

(dd, J=7.6 and 2.0 Hz, 1H), 7.51 (dd, J=7.6 and 0.8 Hz, 1H), 7.40-7.37 (m, 2H), 6.72 (d, J=10.0 Hz, 1H), 4.43 (q, J=7.2 Hz, 4H), 4.32 (bs, 2H), 4.28 (bs, 2H), 3.48 (m, 1H), 2.14-2.07 (m, 1H), 2.05-1.86 (m, 6H), 1.69 (bs, 1H), 1.65 (bs, 1H), 1.42 (t, J=7.2 Hz, 3H), 1.25-1.20 (m, 2H), 1.13-1.08 (m, 2H). MS m/z 598.2 (M+1).

6-(3-((5-Cyclopropyl-3-(2-(trifluoromethoxy)phenyl)isoxazol-4-yl)methoxy)-8-azabicyclo[3.2.1]octan-8-yl)imidazo[1,2-b]pyridazine-2-carboxylic acid (31-1B) was prepared from ethyl 6-(3-((5-cyclopropyl-3-(2-(trifluoromethoxy)phenyl)isoxazol-4-yl)methoxy)-8-azabicyclo[3.2.1]octan-8-yl)imidazo[1,2-b]pyridazine-2-carboxylate (31-A) using the analogous procedure as described for Example 1B. MS m/z 570.1 (M+11).

Examples 31-2 through 31-6 were prepared from the corresponding, nortropine intermediates according to the procedures described for Example 31-1.

| Ex | | Physical Data MS (m/z), ¹H NMR |
| --- | --- | --- |
| 31-1 | 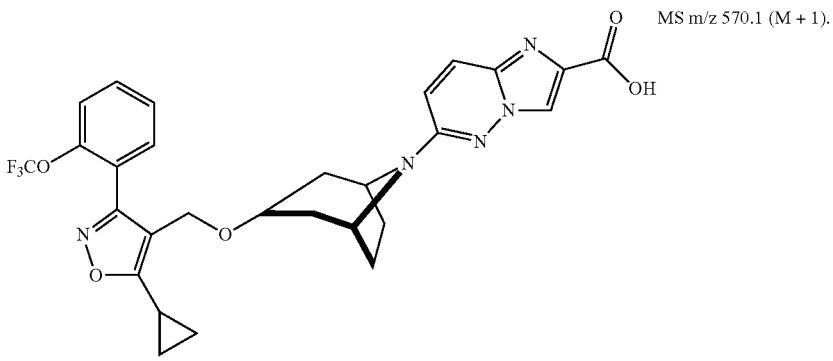 | MS m/z 570.1 (M + 1). |
| 31-2 | 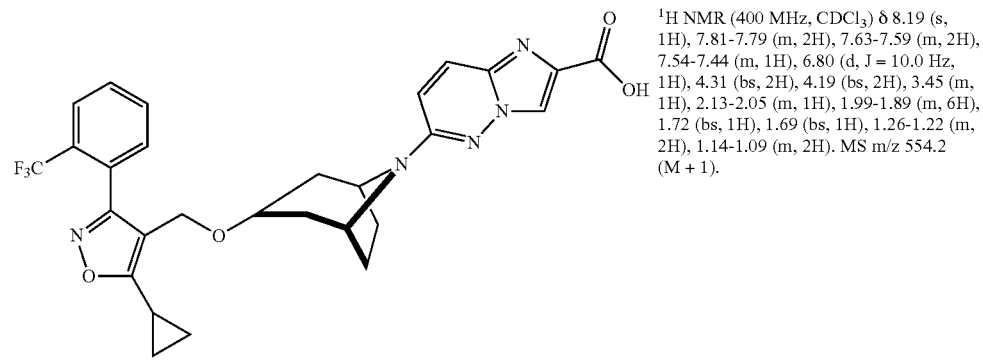 | ¹H NMR (400 MHz, CDCl₃) δ 8.19 (s, 1H), 7.81-7.79 (m, 2H), 7.63-7.59 (m, 2H), 7.54-7.44 (m, 1H), 6.80 (d, J = 10.0 Hz, 1H), 4.31 (bs, 2H), 4.19 (bs, 2H), 3.45 (m, 1H), 2.13-2.05 (m, 1H), 1.99-1.89 (m, 6H), 1.72 (bs, 1H), 1.69 (bs, 1H), 1.26-1.22 (m, 2H), 1.14-1.09 (m, 2H). MS m/z 554.2 (M + 1). |
| 31-3 | 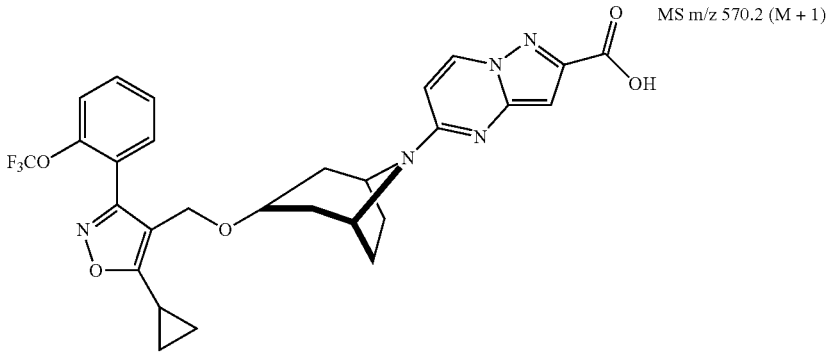 | MS m/z 570.2 (M + 1) |

| Ex | Physical Data MS (m/z), $^1$H NMR |
|---|---|
| 31-4 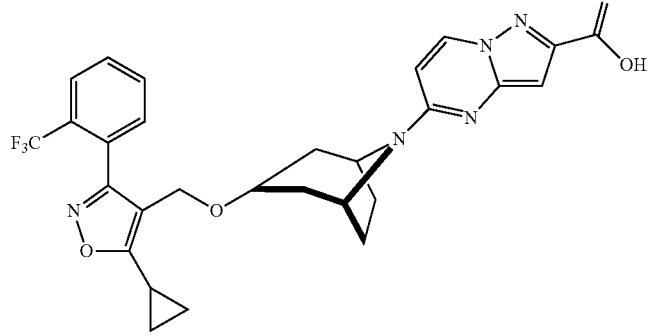 | MS m/z 554.2 (M + 1) |
| 31-5 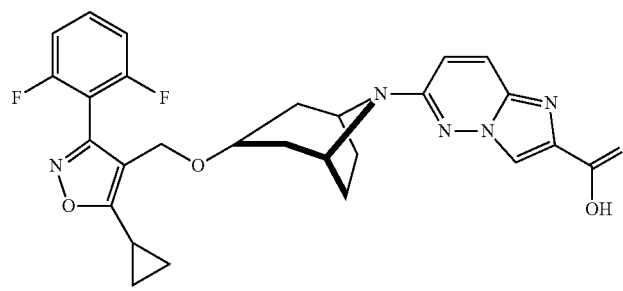 | MS m/z 522.2 (M + 1) $^1$H NMR (DMSO-$d_6$, 400 MHz) δ 8.25 (s, 1H), 7.80 (d, J = 10.0 Hz, 1H), 7.69-7.62 (m, 1H), 7.34-7.28 (m, 2H), 7.11 (d, J = 10.0 Hz, 1H), 4.30 (app bs, 4H), 3.46 (t, J = 4.4 Hz, 1H), 2.38-2.28 (m, 1H), 1.92-1.85 (m, 2H), 1.75-1.71 (m, 4H), 1.56 (d, J = 14.4 Hz, 2H), 1.15-1.05 (m, 4H). |
| 31-6 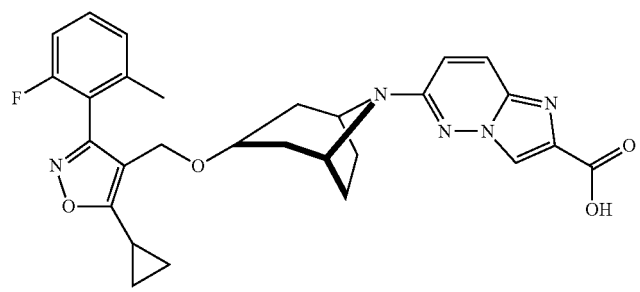 | MS m/z 518.2 (M + 1) |
EXAMPLE 32
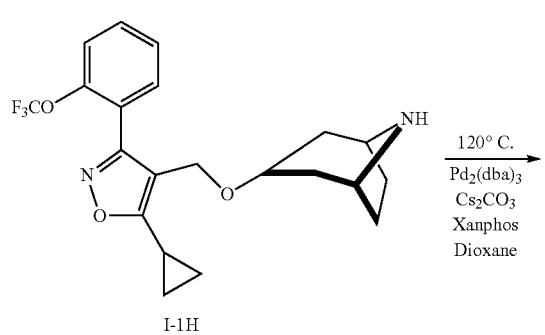
I-1H
$\xrightarrow{\begin{array}{c}120° \text{ C.}\\ \text{Pd}_2(\text{dba})_3\\ \text{Cs}_2\text{CO}_3\\ \text{Xanphos}\\ \text{Dioxane}\end{array}}$
-continued
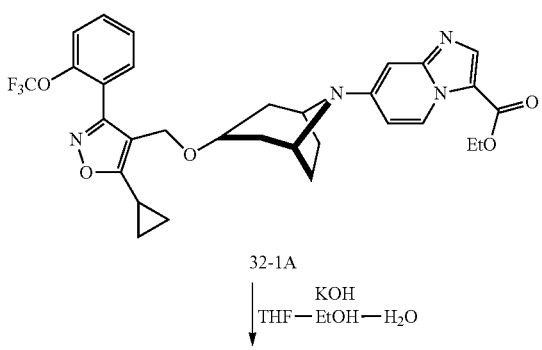
32-1A
$\downarrow \begin{array}{c}\text{KOH}\\ \text{THF—EtOH—H}_2\text{O}\end{array}$

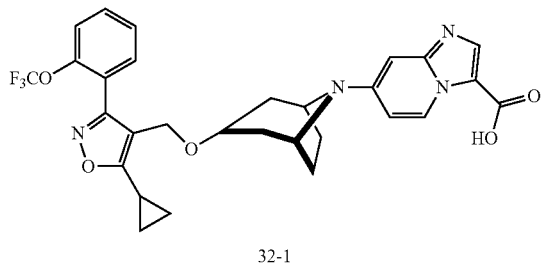

32-1

Ethyl 7-(3-((5-cyclopropyl-3-(2-(trifluoromethoxy)phenyl)isoxazol-4-yl)methoxy)-8-azabicyclo[3.2.1]octan-8-yl)imidazo[1,2-a]pyridine-3-carboxylate (32-1A). A sealable vessel was charged with ethyl 7-bromoimidazo[1,2-a]pyridine-3-carboxylate (67 mg, 0.25 mmol), 4-((8-azabicyclo[3.2.1]octan-3-yloxy)methyl)-5-cyclopropyl-3-(2-(trifluoromethoxy)phenyl)isoxazole (I-1H) cesium carbonate (122 mg, 0.38 mmol), 1,4-dioxane (2 mL). The mixture was degassed (argon bubble, 10 min) and then tris(dibenzylideneacetone)dipalladium(0) (11 mg, 0.012 mmol), 4,5-bis(diphenylphosphino)-9,9-dimethylxanthene (14 mg, 0.025 mmol) were added. The reaction flask was evacuated and backfilled with Ar three successive times, and then heated to 120° C. for 12 hours. The reaction mixture was cooled to RT, diluted with ethyl acetate (8 mL) and filtered through a CELITE® pad, the filtrate was washed with water (7 mL), dried over magnesium sulfate, concentrated, and chromatographed on silica using linear gradient, 0-100%, EtOAc in Hexanes) to give the desired product as a waxy solid.

7-(3-((5-cyclopropyl-3-(2-(trifluoromethoxy)phenyl)isoxazol-4-yl)methoxy)-8-azabicyclo[3.2.1]octan-8-yl)imidazo[1,2-a]pyridine-3-carboxylic acid (32-1). The ethyl ester, (32-A) was dissolved in THF (1 mL), EtOH (1 mL) and treated with KOH solution (1 N, 0.6 mL, 0.6 mmoles) and heated to 65° C. for 1 hour followed by cooling to RT and adjustment of the PH with HCl (1 N, 0.6 mL, 0.6 mmol) until PH 5. At this time the reaction mixture was extracted with ethyl acetate (3×5 mL) and the organic extracts were dried with magnesium sulfate, concentrated in vacuo, and the residue purified by reverse phase chromatography using acetonitrile and water that was TFA modified (0.5%) to give the desired solid as its TFA-salt.

Example 32-2 was prepared from the corresponding nortropine intermediate according to the procedures described for the 32-1.

| Ex | | Physical Data MS (m/z), $^1$H NMR |
|---|---|---|
| 32-1 | 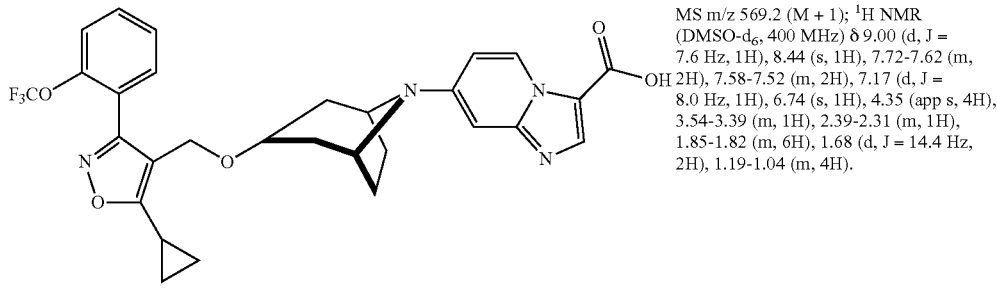 | MS m/z 569.2 (M + 1); $^1$H NMR (DMSO-d$_6$, 400 MHz) δ 9.00 (d, J = 7.6 Hz, 1H), 8.44 (s, 1H), 7.72-7.62 (m, 2H), 7.58-7.52 (m, 2H), 7.17 (d, J = 8.0 Hz, 1H), 6.74 (s, 1H), 4.35 (app s, 4H), 3.54-3.39 (m, 1H), 2.39-2.31 (m, 1H), 1.85-1.82 (m, 6H), 1.68 (d, J = 14.4 Hz, 2H), 1.19-1.04 (m, 4H). |
| 32-2 | 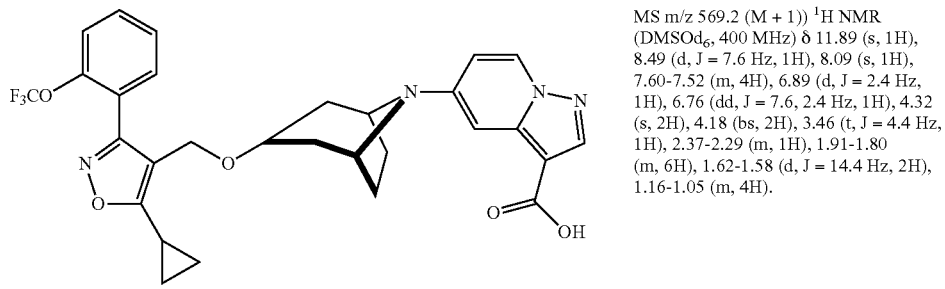 | MS m/z 569.2 (M + 1)) $^1$H NMR (DMSOd$_6$, 400 MHz) δ 11.89 (s, 1H), 8.49 (d, J = 7.6 Hz, 1H), 8.09 (s, 1H), 7.60-7.52 (m, 4H), 6.89 (d, J = 2.4 Hz, 1H), 6.76 (dd, J = 7.6, 2.4 Hz, 1H), 4.32 (s, 2H), 4.18 (bs, 2H), 3.46 (t, J = 4.4 Hz, 1H), 2.37-2.29 (m, 1H), 1.91-1.80 (m, 6H), 1.62-1.58 (d, J = 14.4 Hz, 2H), 1.16-1.05 (m, 4H). |

EXAMPLE 33

The following examples were prepared according to the procedures described in Kittelmann, M. et al., *Adv. Synth. Catal.* 2003, 345, 825-829.

| Ex | | Physical Data<br>MS (m/z), ¹H NMR |
|---|---|---|
| 33-1 | 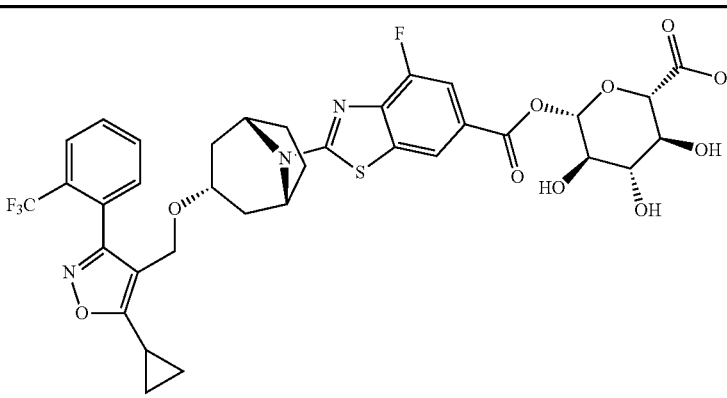 | MS m/z 764.3 (M + 1); MS m/z 764.3 (M + 1); ¹H NMR (DMSO $d_6$, 600 MHz); δ 12.87 (br s, 1H), 8.31 (d, J = 1.2 Hz, 1H), 7.91 (app t, J = 8.0 Hz, 1H), 7.76 (app t, J = 8.0 Hz, 1H), 7.71 (d, J = 9.3 Hz, 1H), 7.61 (d, J = 8.0 Hz, 1H), 5.58 (d, J = 7.3 Hz, 1H), 4.25 (s, 4H), 3.83 (d, J = 8.7 Hz, 1H), 3.52 (app t, J = 4.0 Hz, 1H), 3.43-3.31 (m, 4H), 2.36-2.32 (m, 1H), 1.96 (dt, J = 14.0, 4.0 Hz, 2H), 1.85-1.73 (m, 6H), 1.18-1.04 (m, 4H). |
| 33-2 | 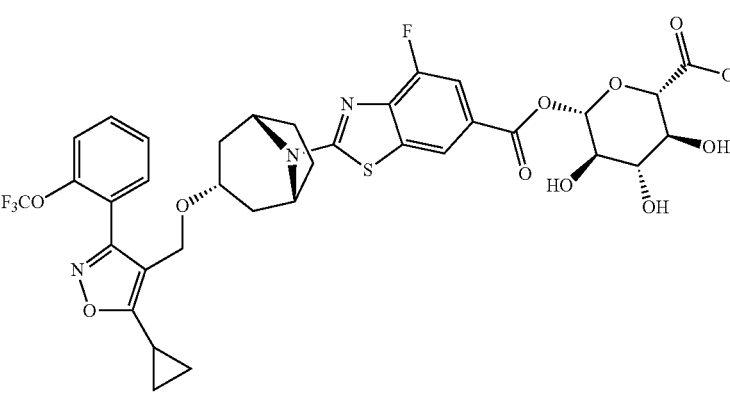 | MS m/z 780.2 (M + 1); |
| 33-3 | 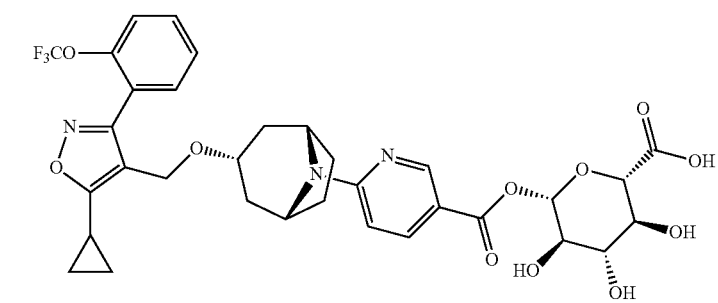 [SMILES: O=C(O[C@@H]1O[C@H](C(=O)O)[C@@H](O)[C@H](O)[C@H]1O)c1ccc(N2[C@@H]3CC[C@H]2C[C@@H](OCc2c(-c4ccccc4OC(F)(F)F)noc2C2CC2)C3)nc1] | MS m/z 706.3 (M + 1); |

Assay Description

Human GST-FXR LBD Co-activator interaction Assay. The FXR HTRF assay is a biochemical assay measuring the interaction between FXR and a coactivator protein (SRC1). The ligand-induced interaction with a coactivator protein is a critical step in transcriptional activation by FXR. Thus, this is an assay designed to measure FXR agonist activity of compounds.

Recombinant human Farnesoid X Receptor (FXR) ligand binding domain (amino acids 193-472) fused to glutathione S-transferase (GST) purified protein (GST-FXR LBD) was purchased (Invitrogen). The ligand-dependent interaction between GST-FXR LBD and a peptide derived from Steroid Receptor Coactivator-1 (SRC-1) was monitored by Fluorescence Resonance Energy Transfer (FRET). GST-FXR LBD was mixed with a biotin-labeled SRC-1 peptide (Biotin-CPSSHSSLTERHKILHRLLQEG -SPS-CONH2 (SEQ ID NO: 1), American Peptide) in assay buffer (50 mM Tris HCl, pH 7.4,50 mM NaCl,1 mM TCEP and 0.2% bovine serum albumen) and plated in 384 black Proxi plates (Greiner Bio-One). Test compounds (in DMSO solution) and detection reagents (anti-GST-Cryptate labeled antibody and Streptavidin-XL665 conjugate; CisBio) were added in assay buffer containing 50 mM KF. Plates are incubated at room temperature in the dark for 2.5 hours before reading on an Envision (PerkinElmer) at 665 nm and 590 nm The HTRF assay results were calculated from the 665 nm/590 nm ratio (ratio=(A665 nm/A590 nm)×10$^4$) and expressed in Delta F %=(Ratiosample−Rationegative)/Rationegative×100.

A negative control (without Streptavidin-XL665) was run with each assay and represented the background fluorescence. A reference FXR agonist, GW4064, was included in each experiment as positive control. The efficacy of each test compound was compared to that of GW4064. At each concentration, the relative activity of the test compound was expressed as Response %=($R_{sample}$−$R_{DMSO}$)/($R_{positive}$−$R_{DMSO}$), where $R_{sample}$ is the HTRF response (expressed in Delta F %) for the test compound, $R_{positive}$ is the maximal response for GW4064 at saturating concentrations, and $R_{DMSO}$ is the response for DMSO control. The $EC_{50}$ values were calculated using GraphPad Prism (GraphPad Software) using non-linear regression curve fit (log(agonist) vs. response—variable slope (four parameters)).

Table 1 summarizes $EC_{50}$ values for the compounds of the invention in human GST-FXR LBD co-activator interaction assay.

| Example | FXR Co-activator interaction assay ($EC_{50}$, uM) |
|---|---|
| 1-1A | 0.014 |
| 1-1B | 0.00019 |
| 1-2A | 0.028 |
| 1-2B | 0.00025 |
| 2-1B | 0.00017 |
| 2-2B | 0.003 |
| 3A | 0.020 |
| 3B | 0.00074 |
| 4 | 0.022 |
| 5-1 | 0.0076 |
| 5-2 | 0.0038 |
| 5-3 | 0.020 |
| 6-1A | 0.063 |
| 6-1B | 0.00067 |
| 6-2A | 0.051 |
| 6-2B | 0.00036 |
| 6-3A | 0.012 |
| 6-3B | 0.00027 |
| 6-4 | 0.00018 |
| 6-5A | 0.0038 |
| 6-5B | 0.0056 |
| 6-6A | 0.014 |
| 6-6B | 0.0003 |
| 6-7A | 0.014 |
| 6-7B | 0.00058 |
| 7B | 0.016 |
| 8-1 | 0.004 |
| 8-2 | 0.0024 |
| 8-3 | 0.018 |
| 8-4 | 0.0089 |
| 8-5B | 0.11 |
| 8-6B | 0.10 |
| 8-7B | 0.13 |
| 9-1 | 0.005 |
| 9-2 | 0.011 |
| 10B | 0.098 |
| 11 | 0.030 |
| 12-1 | 0.025 |
| 12-2 | 0.040 |
| 12-3 | 0.04 |
| 13-1B | 0.0013 |
| 13-2B | 0.00053 |
| 13-3B | 0.00067 |
| 14 | 0.035 |
| 15-1B | 0.0006 |
| 15-2 | 0.0005 |
| 15-3 | 0.017 |
| 15-4 | 0.0008 |
| 16-1 | 0.0006 |
| 16-2 | 0.0004 |
| 16-3 | 0.0012 |
| 16-4 | 0.009 |
| 17A | 0.032 |
| 17B | 0.005 |
| 18-1 | 0.009 |
| 18-2B | 0.007 |
| 18-3A | 0.008 |
| 18-3B | 0.004 |
| 18-4A | 0.02 |
| 18-4B | 0.01 |
| 18-5A | 0.02 |
| 18-5B | 0.003 |
| 18-6A | 0.05 |
| 18-6B | 0.005 |
| 18-7A | 0.018 |
| 18-7B | 0.002 |
| 18-8B | 0.009 |
| 19-1A | 0.18 |
| 19-1B | 0.04 |
| 19-2A | 0.08 |
| 19-2B | 0.02 |
| 19-3A | 0.09 |
| 19-3B | 0.01 |
| 19-4A | 0.07 |
| 19-4B | 0.005 |
| 19-5A | 0.20 |
| 19-5B | 0.009 |
| 19-6A | 0.05 |
| 19-6B | 0.007 |
| 19-7A | 0.01 |
| 19-7B | 0.003 |
| 20A | 0.17 |
| 20B | 0.33 |
| 21-1A | 0.30 |
| 21-1B | 0.26 |
| 21-2A | 0.12 |
| 21-2B | 0.01 |
| 21-3A | 0.18 |
| 21-3B | 0.009 |
| 21-4A | 0.25 |
| 21-4B | 0.02 |
| 21-5A | 0.11 |
| 21-5B | 0.01 |
| 21-6A | 0.06 |
| 21-6B | 0.016 |
| 22-1A | 0.53 |
| 22-1B | 0.02 |
| 22-2A | 0.06 |
| 22-2B | 0.009 |
| 22-3 | 0.01 |
| 22-4A | 0.02 |
| 22-4B | 0.009 |
| 22-5 | 0.027 |
| 22-6A | 0.056 |
| 22-6B | 0.16 |
| 22-7A | 0.01 |
| 22-7B | 0.005 |
| 22-8 | 0.005 |
| 22-9A | 1.03 |
| 22-9B | 0.017 |
| 22-10A | 0.36 |
| 22-10B | 0.008 |
| 22-11A | 0.11 |
| 22-11B | 0.01 |
| 22-12 | 0.004 |
| 22-13A | 0.08 |
| 22-13B | 0.009 |
| 22-14A | 0.07 |
| 22-14B | 0.013 |
| 22-15A | 0.13 |
| 22-15B | 0.028 |
| 22-16A | 0.16 |
| 22-16B | 0.01 |
| 22-17A | 0.065 |
| 22-17B | 0.003 |
| 22-18A | 0.043 |

| Example | FXR Co-activator interaction assay (EC$_{50}$, uM) |
| --- | --- |
| 22-18B | 0.018 |
| 22-19 | 0.057 |
| 22-20 | 0.025 |
| 22-21 | 0.029 |
| 23A | 0.006 |
| 23B | 0.004 |
| 24-1A | 0.04 |
| 24-1B | 0.008 |
| 25-1A | 0.028 |
| 25-1B | 0.003 |
| 25-2A | 0.42 |
| 25-2B | 0.005 |
| 25-3A | 0.08 |
| 25-3B | 0.0009 |
| 25-4A | 0.04 |
| 25-4B | 0.002 |
| 25-5A | 0.28 |
| 25-5B | 0.001 |
| 25-6A | 0.009 |
| 25-6B | 0.003 |
| 26B | 0.0003 |
| 27 | 0.002 |
| 28-1B | 0.0006 |
| 28-2 | 0.016 |
| 28-3 | 0.0008 |
| 28-4 | 0.002 |
| 28-5 | 0.006 |
| 28-6 | 0.0017 |
| 28-7 | 0.021 |
| 28-8 | 0.0104 |
| 28-9 | 0.0003 |
| 28-10 | 0.0009 |
| 28-11 | 0.0013 |
| 28-12 | 0.0028 |
| 28-13 | 0.0074 |
| 28-14 | 0.0046 |
| 28-15 | 0.0034 |
| 28-16 | 0.063 |
| 28-17 | 0.0098 |
| 28-18 | 0.0082 |
| 28-19 | 0.0015 |
| 28-20 | 0.0012 |
| 28-21 | 0.0022 |
| 28-22 | 0.0002 |
| 28-23 | 0.0005 |
| 28-24 | 0.024 |
| 28-25 | 0.0011 |
| 28-26 | 0.0012 |
| 29-1 | 0.014 |
| 29-2 | 0.008 |
| 29-3 | 0.011 |
| 29-4 | 0.011 |
| 29-5 | 0.006 |
| 29-6 | 0.002 |
| 29-7 | 0.005 |
| 30-1 | 0.0003 |
| 30-2 | 0.010 |
| 30-3 | 0.015 |
| 30-4 | 0.0007 |
| 30-5 | 0.0004 |
| 30-6 | 0.042 |
| 30-7 | 0.018 |
| 30-8 | 0.021 |
| 30-9 | 0.34 |
| 30-10 | 0.48 |
| 30-11 | 0.0003 |
| 30-12 | 0.005 |
| 30-13 | 0.006 |
| 30-14 | 0.0012 |
| 30-15 | 0.009 |
| 30-16 | 0.024 |
| 30-17 | 0.0007 |
| 30-18 | 0.006 |
| 30-19 | 0.023 |
| 30-20 | 0.00074 |
| 30-21 | 0.003 |
| 30-22 | 0.019 |
| 30-23 | 0.0004 |
| 30-24 | 0.004 |
| 30-25 | 0.003 |
| 30-26 | 0.007 |
| 30-27 | 0.007 |
| 30-28 | 0.012 |
| 30-29 | 0.0005 |
| 30-30 | 0.120 |
| 30-31 | 0.007 |
| 30-32 | 0.149 |
| 30-33 | 0.0007 |
| 30-34 | 0.0018 |
| 30-35 | 0.046 |
| 30-36 | 0.0011 |
| 30-37 | 0.14 |
| 30-38 | 0.0018 |
| 30-39 | 0.036 |
| 30-40 | 0.0007 |
| 30-41 | 0.004 |
| 30-42 | 0.003 |
| 30-43 | 0.0046 |
| 30-44 | 0.008 |
| 30-45 | 0.018 |
| 30-46 | 0.22 |
| 30-47 | 0.12 |
| 30-48 | 0.034 |
| 30-49 | 0.14 |
| 30-50 | 0.70 |
| 30-51 | 0.052 |
| 30-52 | 0.026 |
| 30-53 | 0.001 |
| 30-54 | 0.016 |
| 30-55 | 0.001 |
| 30-56 | 0.0057 |
| 30-57 | 0.032 |
| 30-58 | 0.21 |
| 30-59 | 0.092 |
| 30-60 | 0.094 |
| 30-61 | 0.002 |
| 30-62 | 0.0006 |
| 30-63 | 0.057 |
| 30-64 | 0.007 |
| 30-65 | 0.086 |
| 30-66 | 0.22 |
| 30-67 | 0.0005 |
| 30-68 | 0.013 |
| 30-69 | 0.021 |
| 30-70 | 0.0002 |
| 30-71 | 0.0003 |
| 30-72 | 0.0014 |
| 30-73 | 0.074 |
| 30-74 | 0.003 |
| 30-75 | 0.017 |
| 30-76 | 0.016 |
| 31-1 | 0.012 |
| 31-2 | 0.013 |
| 31-3 | 0.002 |
| 31-4 | 0.004 |
| 31-5 | 0.010 |
| 31-6 | 0.009 |
| 32-1 | 0.003 |
| 32-2 | 0.004 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound having Formula I:

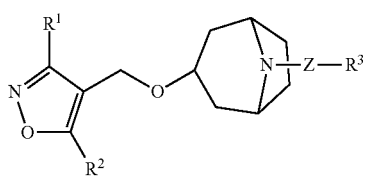

(I)

or a stereoisomer, enantiomer, a pharmaceutically acceptable salt, an amino acid conjugate or an acyl glucuronide conjugate thereof;

Z is phenyl, pyridyl, pyrimidinyl, pyrazinyl, pyridazinyl, thiazolyl, benzothiazolyl, benzo[d]isothiazolyl, imidazo[1,2-a]pyridinyl, quinolinyl, 1H-indolyl, pyrrolo[1,2-b]pyridazinyl, benzofuranyl, benzo[b]thiophenyl, 1H-indazolyl, benzo[d]isoxazolyl, quinazolinyl, 1H-pyrrolo[3,2-c]pyridinyl, pyrazolo[1,5-a]pyrimidinyl, imidazo[1,2-b]pyridazinyl, or pyrazolo[1,5-a]pyridinyl; each of which is optionally substituted with 1-2 $R^6$ radicals selected from the group consisting of halogen, $C_{1-6}$ alkyl, halo$C_{1-6}$ alkyl, $C_{1-6}$ alkoxy, halo$C_{1-6}$ alkoxy and cyclopropyl;

$R^1$ is phenyl, pyridyl, bicyclo[3.1.0]hexanyl, spiro[2.3]hexanyl, bicyclo[3.1.1]heptanyl, spiro[2.5]octanyl, bicyclo[4.1.0]heptanyl, bicyclo[3.1.0]hexan-6-yl, spiro[2.3]hexan-5-yl, bicyclo[3.1.1]heptan-3-yl, spiro[2.5]octan-4-yl, bicyclo[4.1.0]heptan-3-yl, cyclohexyl or cyclopentyl, each of which is optionally substituted with 1-3$R^{1a}$; or $R^1$ is cyclopropyl optionally substituted with 1-2 $R^{1a}$ or phenyl;

$R^{1a}$ is halogen, $C_{1-6}$ alkyl, halo$C_{1-6}$ alkyl, $C_{1-6}$ alkoxy, halo$C_{1-6}$ alkoxy or cyclopropyl;

$R^2$ is $C_{1-3}$ alkyl, halo$C_{1-3}$ alkyl or cyclopropyl optionally substituted with $C_{1-3}$ alkyl or halo$C_{1-3}$ alkyl;

$R^3$ is —X—$CO_2R^4$, hydroxy$C_{1-6}$ alkyl, $CONR^4R^5$, $CONR(CR_2)_{1-4}CO_2R^4$, $CONR(CR_2)_{1-4}SO_3R^5$ or tetrazolyl; wherein X is a bond, $C_{1-2}$ alkylene or cyclopropyl; and R, $R^4$ and $R^5$ are independently hydrogen or $C_{1-6}$ alkyl.

2. The compound of claim 1, wherein $R^2$ is cyclopropyl.

3. The compound of claim 1, wherein said compound is selected from the group consisting of:

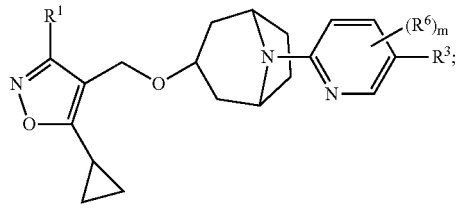

I-A

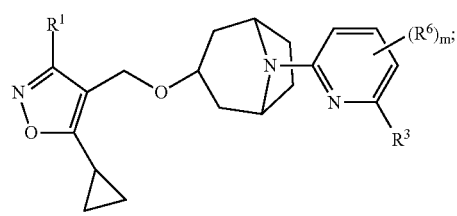

I-B

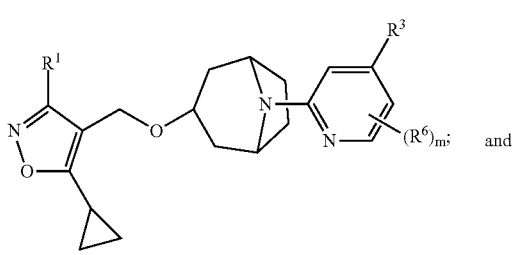

I-C and

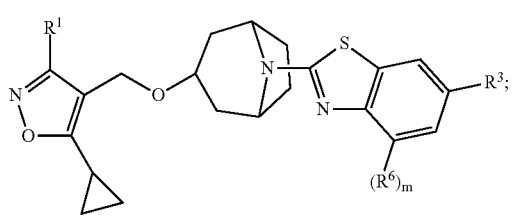

I-D or a stereoisomer, enantiomer, a pharmaceutically acceptable salt, an amino acid conjugate or an acyl glucuronide conjugate thereof; and m is 0-1.

4. The compound of claim 1, wherein said compound is selected from the group consisting of:

I-E
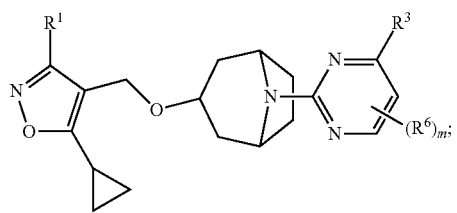
I-F
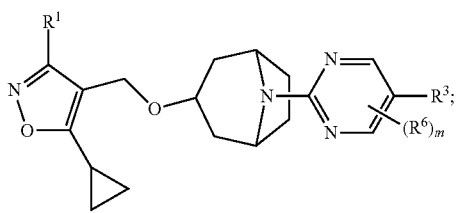
I-G
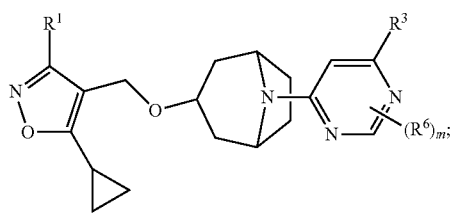
I-H
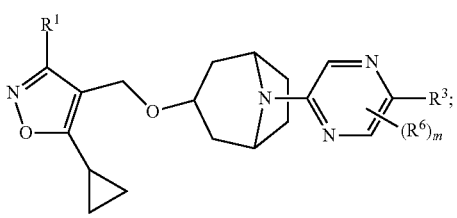
I-I
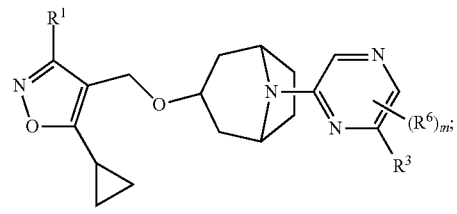
I-J
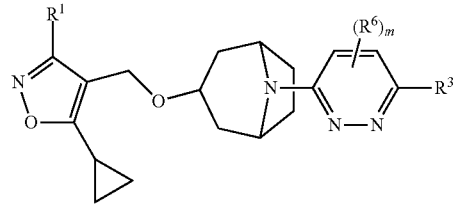
I-K
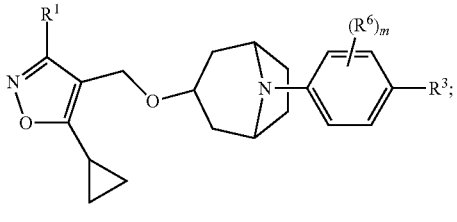
I-L
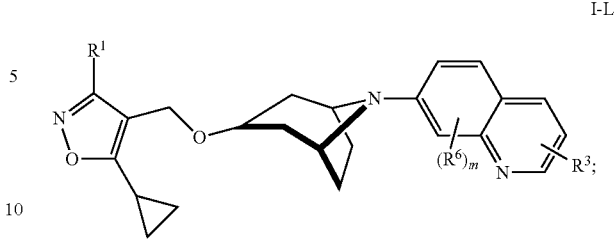
I-M
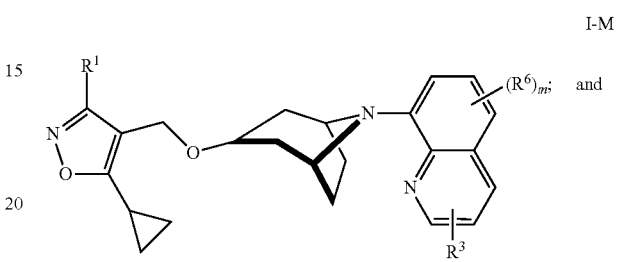
I-N
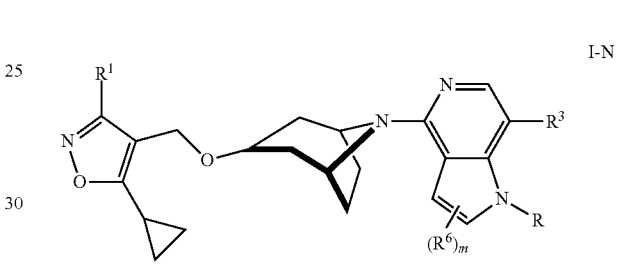
or a stereoisomer, enantiomer, a pharmaceutically acceptable salt, an amino acid conjugate or an acyl glucuronide conjugate thereof; and
m is 0-1.
5. The compound of claim 1, wherein said compound is selected from the group consisting of:
I-O
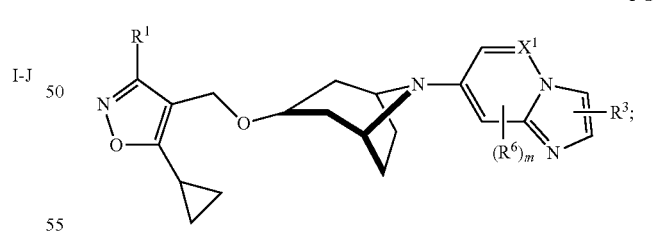
I-P
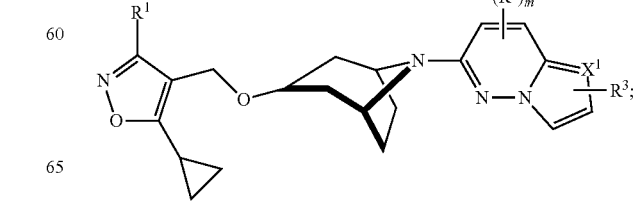

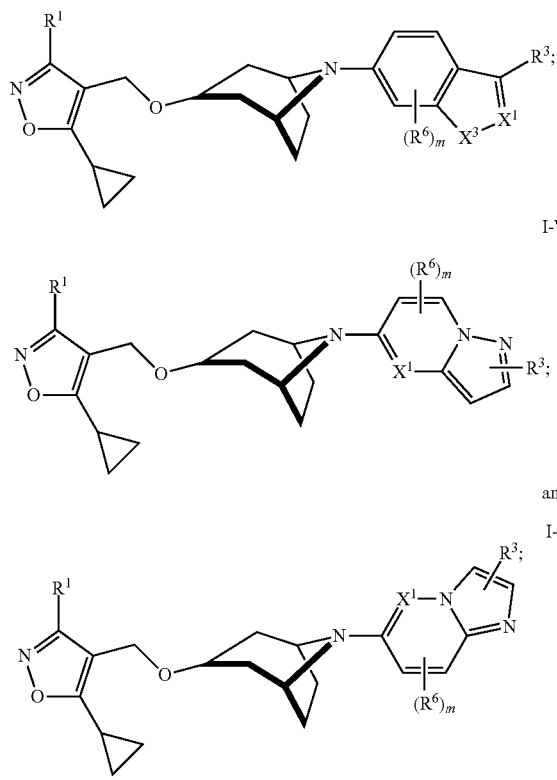

or a stereoisomer, enantiomer, a pharmaceutically acceptable salt, an amino acid conjugate or an acyl glucuronide conjugate thereof, wherein:
$X^1$ and $X^2$ are independently N, CH or $CR^6$;
$X^3$ is O or S;
and
m is 0-1.

6. The compound of claim 1, wherein $R^1$ is phenyl substituted with 1-3$R^{1a}$; and
$R^{1a}$ is halogen, $C_{1-6}$ alkyl, haloC$_{1-6}$ alkyl, $C_{1-6}$ alkoxy, haloC$_{1-6}$ alkoxy.

7. The compound of claim 1, wherein $R^3$ is —X—$CO_2R^4$; X is a bond and $R^4$ is hydrogen or $C_{1-6}$ alkyl.

8. The compound of claim 1, wherein $R^6$ is methyl, methoxy, fluoro or trifluoromethoxy.

9. The compound of claim 1, wherein said compound is selected from the group consisting of
methyl 2-[3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylate;
methyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylate;
2-[3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid;
methyl 2-[3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazole-6-carboxylate;
methyl 2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazole-6-carboxylate;
2-[3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazole-6-carboxylic acid;
2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazole-6-carboxylic acid;
Methyl 2-(3-((5-cyclopropyl-3-(2-(trifluoromethoxy)phenyl) isoxazol-4-yl)methoxy)-8-azabicyclo[3.2.1]octan-8-yl)-4-methoxybenzo[d]thiazole-6-carboxylate;
2-[3-({5-cyclopropyl-3-[2-(trifluoromethoxy)phenyl]-1,2-oxazol-4-yl}methoxy)-8-azabicyclo[3.2.1]octan-8-yl]-4-methoxy-1,3-benzothiazole-6-carboxylic acid;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-methoxy-1,3-benzothiazole-6-carboxylic acid;
methyl 2-(3-((5-cyclopropyl-3-(2-(trifluoromethyl)phenyl)isoxazol-4-yl)methoxy)-8-azabicyclo[3.2.1]octan-8-yl)-4-methoxybenzo[d]thiazole-6-carboxylate;
2-[3-({5-cyclopropyl-3-[2-(trifluoromethyl)phenyl]-1,2-oxazol-4-yl}methoxy)-8-azabicyclo[3.2.1]octan-8-yl]-4-methoxy-1,3-benzothiazole-6-carboxylic acid;
2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-methoxy-1,3-benzothiazole-6-carboxylic acid;
ethyl 2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylate;
ethyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylate;
2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylic acid;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylic acid;
2-{2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazol-6-yl}propan-2-ol;
2-{2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazol-6-yl}propan-2-ol;
2-[3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxamide;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxamide;
6-[3-({5-cyclopropyl-3-[2-(trifluoromethoxy)phenyl]-1,2-oxazol-4-yl}methoxy)-8-azabicyclo[3.2.1]octan-8-yl]pyridine-3-carboxamide;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-3-carboxamide;
2-[3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxamide;

2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxamide;

ethyl 2-[3-({5-cyclopropyl-3-[2-(trifluoromethyl)phenyl]-1,2-oxazol-4-yl}methoxy)-8-azabicyclo[3.2.1]octan-8-yl]-1,3-benzothiazole-6-carboxylate;

ethyl 2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-1,3-benzothiazole-6-carboxylate;

2-[3-({5-cyclopropyl-3-[2-(trifluoromethyl)phenyl]-1,2-oxazol-4-yl}methoxy)-8-azabicyclo[3.2.1]octan-8-yl]-1,3-benzothiazole-6-carboxylic acid;

2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-1,3-benzothiazole-6-carboxylic acid;

ethyl 2-[3-({5-cyclopropyl-3-[2-(difluoromethoxy)phenyl]-1,2-oxazol-4-yl}methoxy)-8-azabicyclo[3.2.1]octan-8-yl]-1,3-benzothiazole-6-carboxylate;

ethyl 2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-1,3-benzothiazole-6-carboxylate;

2-[3-({5-cyclopropyl-3-[2-(difluoromethoxy)phenyl]-1,2-oxazol-4-yl}methoxy)-8-azabicyclo[3.2.1]octan-8-yl]-1,3-benzothiazole-6-carboxylic acid;

2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-1,3-benzothiazole-6-carboxylic acid;

methyl 2-[3-({5-cyclopropyl-3-[2-(difluoromethoxy)phenyl]-1,2-oxazol-4-yl}methoxy)-8-azabicyclo[3.2.1]octan-8-yl]-4-fluoro-1,3-benzothiazole-6-carboxylate;

methyl 2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-4-fluoro-1,3-benzothiazole-6-carboxylate;

2-[3-({5-cyclopropyl-3-[2-(difluoromethoxy)phenyl]-1,2-oxazol-4-yl}methoxy)-8-azabicyclo[3.2.1]octan-8-yl]-4-fluoro-1,3-benzothiazole-6-carboxylic acid;

2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-4-fluoro-1,3-benzothiazole-6-carboxylic acid;

2-[3-({5-cyclopropyl-3-[2-(difluoromethoxy)phenyl]-1,2-oxazol-4-yl}methoxy)-8-azabicyclo[3.2.1]octan-8-yl]-4-methoxy-1,3-benzothiazole-6-carboxylic acid;

2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-4-methoxy-1,3-benzothiazole-6-carboxylic acid;

ethyl 2-[3-{[5-cyclopropyl-3-(2,6-difluorophenyl)-1,2-oxazol-4-yl]methoxy}-8-azabicyclo[3.2.1]octan-8-yl]-1,3-benzothiazole-6-carboxylate;

ethyl 2-[(1R,3r,5S)-3-{[5-cyclopropyl-3-(2,6-difluorophenyl)-1,2-oxazol-4-yl]methoxy}-8-azabicyclo[3.2.1]octan-8-yl]-1,3-benzothiazole-6-carboxylate;

2-[3-{[5-cyclopropyl-3-(2,6-difluorophenyl)-1,2-oxazol-4-yl]methoxy}-8-azabicyclo[3.2.1]octan-8-yl]-1,3-benzothiazole-6-carboxylic acid;

2-[(1R,3r,5S)-3-{[5-cyclopropyl-3-(2,6-difluorophenyl)-1,2-oxazol-4-yl]methoxy}-8-azabicyclo[3.2.1]octan-8-yl]-1,3-benzothiazole-6-carboxylic acid;

methyl 2-[3-{[5-cyclopropyl-3-(2,6-difluorophenyl)-1,2-oxazol-4-yl]methoxy}-8-azabicyclo[3.2.1]octan-8-yl]-4-methoxy-1,3-benzothiazole-6-carboxylate;

methyl 2-[(1R,3r,5S)-3-{[5-cyclopropyl-3-(2,6-difluorophenyl)-1,2-oxazol-4-yl]methoxy}-8-azabicyclo[3.2.1]octan-8-yl]-4-methoxy-1,3-benzothiazole-6-carboxylate;

2-[3-{[5-cyclopropyl-3-(2,6-difluorophenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(2,6-difluorophenyl)-1,2-oxazol-4-yl]methoxy}-8-azabicyclo[3.2.1]octan-8-yl]-4-methoxy-1,3-benzothiazole-6-carboxylic acid;

methyl 2-[3-{[5-cyclopropyl-3-(2,6-difluorophenyl)-1,2-oxazol-4-yl]methoxy}-8-azabicyclo[3.2.1]octan-8-yl]-4-fluoro-1,3-benzothiazole-6-carboxylate;

methyl 2-[(1R,3r,5S)-3-{[5-cyclopropyl-3-(2,6-difluorophenyl)-1,2-oxazol-4-yl]methoxy}-8-azabicyclo[3.2.1]octan-8-yl]-4-fluoro-1,3-benzothiazole-6-carboxylate;

2-[3-{[5-cyclopropyl-3-(2,6-difluorophenyl)-1,2-oxazol-4-yl]methoxy}-8-azabicyclo[3.2.1]octan-8-yl]-4-fluoro-1,3-benzothiazole-6-carboxylic acid;

2-[(1R,3r,5S)-3-{[5-cyclopropyl-3-(2,6-difluorophenyl)-1,2-oxazol-4-yl]methoxy}-8-azabicyclo[3.2.1]octan-8-yl]-4-fluoro-1,3-benzothiazole-6-carboxylic acid;

Ethyl 2-(3-((5-cyclopropyl-3-((trans)-2-(trifluoromethyl)cyclohexyl)isoxazol-4-yl)methoxy)-8-azabicyclo[3.2.1]octan-8-yl)benzo[d]thiazole-6-carboxylate;

2-[3-({5-cyclopropyl-3-[2-(trifluoromethyl)cyclohexyl]-1,2-oxazol-4-yl}methoxy)-8-azabicyclo[3.2.1]octan-8-yl]-1,3-benzothiazole-6-carboxylic acid;

2-[(1R,3r,5S)-3-({5-cyclopropyl-3-[(1S,2S)-2-(trifluoromethyl)cyclohexyl]-1,2-oxazol-4-yl}methoxy)-8-azabicyclo[3.2.1]octan-8-yl]-1,3-benzothiazole-6-carboxylic acid;

2-[3-({5-cyclopropyl-3-[2-(trifluoromethyl)cyclohexyl]-1,2-oxazol-4-yl}methoxy)-8-azabicyclo[3.2.1]octan-8-yl]-4-fluoro-1,3-benzothiazole-6-carboxylic acid;

2-[(1R,3r,5S)-3-({5-cyclopropyl-3-[(1S,2S)-2-(trifluoromethyl)cyclohexyl]-1,2-oxazol-4-yl}methoxy)-8-azabicyclo[3.2.1]octan-8-yl]-4-fluoro-1,3-benzothiazole-6-carboxylic acid;

2-[3-({5-cyclopropyl-3-[2-(trifluoromethyl)cyclohexyl]-1,2-oxazol-4-yl}methoxy)-8-azabicyclo [3.2.1]octan-8-yl]-4-methoxy-1,3-benzothiazole-6-carboxylic acid;

2-[(1R,3r,5S)-3-({5-cyclopropyl-3-[(1S,2S)-2-(trifluoromethyl)cyclohexyl]-1,2-oxazol-4-yl}methoxy)-8-azabicyclo[3.2.1]octan-8-yl]-4-methoxy-1,3-benzothiazole-6-carboxylic acid;

2-[3-{[5-cyclopropyl-3-(4,4-dimethylcyclohexyl)-1,2-oxazol-4-yl]methoxy}-8-azabicyclo[3.2.1]octan-8-yl]-1,3-benzothiazole-6-carboxylic acid;

2-[(1R,3r,5S)-3-{[5-cyclopropyl-3-(4,4-dimethylcyclohexyl)-1,2-oxazol-4-yl]methoxy}-8-azabicyclo[3.2.1]octan-8-yl]-1,3-benzothiazole-6-carboxylic acid;

2-[3-{[5-cyclopropyl-3-(4,4-dimethylcyclohexyl)-1,2-oxazol-4-yl]methoxy}-8-azabicyclo[3.2.1]octan-8-yl]-4-fluoro-1,3-benzothiazole-6-carboxylic acid;

2-[(1R,3r,5S)-3-{[5-cyclopropyl-3-(4,4-dimethylcyclohexyl)-1,2-oxazol-4-yl]methoxy}-8-azabicyclo[3.2.1]octan-8-yl]-4-fluoro-1,3-benzothiazole-6-carboxylic acid;

methyl 5-(3-((5-cyclopropyl-3-(2-(trifluoromethyl)cyclohexyl)isoxazol-4-yl)methoxy)-8-azabicyclo[3.2.1]octan-8-yl)pyrazine-2-carboxylate;

methyl 5-[(1R,3r,5S)-(3-((5-cyclopropyl-3-((1S,2S)-2-(trifluoromethyl)cyclohexyl)isoxazol-4yl)methoxy)-8-azabicyclo[3.2.1]octan-8yl)]pyrazine-2-carboxylate;

5-[3-({5-cyclopropyl-3-[2-(trifluoromethyl)cyclohexyl]-1,2-oxazol-4-yl}methoxy)-8-azabicyclo[3.2.1]octan-8-yl]pyrazine-2-carboxylic acid;

5-[(1R,3r,5S)-3-({5-cyclopropyl-3-[(1S,2S)-2-(trifluoromethy)cyclohexyl]-1,2-oxazol-4-yl}methoxy)-8-azabicyclo[3.2.1]octan-8-yl]pyrazine-2-carboxylic acid;

methyl 2-(3-((5-cyclopropyl-3-(2-(trifluoromethyl)cyclohexyl)isoxazol-4-yl)methoxy)-8-azabicyclo[3.2.1]octan-8-yl)-4-methylpyrimidine-5-carboxylate;

methyl 2-[(1R,3r,5S]-(34(5-cyclopropyl-3-((1S,2S)-2-(trifluoromethyl)cyclohexyl)isoxazol-4-yl)methoxy)-8-azabicyclo[3.2.1]octan-8-yl)]-4-methylpyrimidine-5-carboxylate;

2-[3-({5-cyclopropyl-3-[2-(trifluoromethyl)cyclohexyl]-1,2-oxazol-4-yl}methoxy)-8-azabicyclo[3.2.1]octan-8-yl]-6-methylpyrimidine-4-carboxylic acid;

2-[(1R,3r,5S)-3-({5-cyclopropyl-3-[(1S,2S)-2-(trifluoromethyl)cyclohexyl]-1,2-oxazol-4-yl}methoxy)-8-azabicyclo[3.2.1]octan-8-yl]-6-methylpyrimidine-4-carboxylic acid;

methyl 2-(3-((3-cyclohexyl-5-cyclopropylisoxazol-4-yl)methoxy)-8-azabicyclo[3.2.1]octan-8-yl)-6-methylpyrimidine-4-carboxylate;

2-(3-((3-cyclohexyl-5-cyclopropylisoxazol-4-yl)methoxy)-8-azabicyclo[3.2.1]octan-8-yl)-6-methylpyrimidine-4-carboxylic acid;

2-[3-[(3-cyclohexyl-5-cyclopropyl-1,2-oxazol-4-yl)methoxy]-8-azabicyclo[3.2.1]octan-8-yl]-4-fluoro-1,3-benzothiazole-6-carboxylic acid;

2-[(1R,3r,5S)-3-[(3-cyclohexyl-5-cyclopropyl-1,2-oxazol-4-yl)methoxy]-8-azabicyclo[3.2.1]octan-8-yl]-4-fluoro-1,3-benzothiazole-6-carboxylic acid;

2-[3-[(3-cyclohexyl-5-cyclopropyl-1,2-oxazol-4-yl)methoxy]-8-azabicyclo[3.2.1]octan-8-yl]-4-methoxy-1,3-benzothiazole-6-carboxylic acid 2-[(1R,3r,5S)-3-[(3-cyclohexyl-5-cyclopropyl-1,2-oxazol-4-yl)methoxy]-8-azabicyclo[3.2.1]octan-8-yl]-4-methoxy-1,3-benzothiazole-6-carboxylic acid Ethyl 2-(3-((5-cyclopropyl-3-(2-phenylcyclopropyl)isoxazol-4-yl)methoxy)-8-azabicyclo[3.2.1]octan-8-yl)benzo[d]thiazole-6-carboxylate;

2-[3-({5-cyclopropyl-3-[2-phenylcyclopropyl]-1,2-oxazol-4-yl}methoxy)-8-azabicyclo[3.2.1]octan-8-yl]-1,3-benzothiazole-6-carboxylic acid;

2-[(1R,3r,5S)-3-({5-cyclopropyl-3-[(1S,2S)-2-phenylcyclopropyl]-1,2-oxazol-4-yl}methoxy)-8-azabicyclo[3.2.1]octan-8-yl]-1,3-benzothiazole-6-carboxylic acid;

2-[3-({5-cyclopropyl-3-[2-(trifluoromethyl)cyclopropyl]-1,2-oxazol-4-yl}methoxy)-8-azabicyclo [3.2.1]octan-8-yl]-4-fluoro-1,3-benzothiazole-6-carboxylic acid;

2-[(1R,3r,5S)-3-({5-cyclopropyl-3-[(1S,2S)-2-(trifluoromethyl)cyclopropyl]-1,2-oxazol-4-yl}methoxy)-8-azabicyclo[3.2.1]octan-8-yl]-4-fluoro-1,3-benzothiazole-6-carboxylic acid;

2-[3-({5-cyclopropyl-3-[2-methylcyclopropyl]-1,2-oxazol-4-yl}methoxy)-8-azabicyclo[3.2.1]octan-8-yl]-4-fluoro-1,3-benzothiazole-6-carboxylic acid;

2-[(1R,3r,5S)-3-({5-cyclopropyl-3-[(1S,2S)-2-methylcyclopropyl]-1,2-oxazol-4-yl}methoxy)-8-azabicyclo[3.2.1]octan-8-yl]-4-fluoro-1,3-benzothiazole-6-carboxylic acid;

2-[3-[(3,5-dicyclopropyl-1,2-oxazol-4-yl)methoxy]-8-azabicyclo[3.2.1]octan-8-yl]-4-fluoro-1,3-benzothiazole-6-carboxylic acid;

2-[(1R,3r,5S)-3-[(3,5-dicyclopropyl-1,2-oxazol-4-yl)methoxy]-8-azabicyclo[3.2.1]octan-8-yl]-4-fluoro-1,3-benzothiazole-6-carboxylic acid;

2-[3-[(3,5-dicyclopropyl-1,2-oxazol-4-yl)methoxy]-8-azabicyclo[3.2.1]octan-8-yl]-4-methoxy-1,3-benzothiazole-6-carboxylic acid;

2-[(1R,3r,5S)-3-[(3,5-dicyclopropyl-1,2-oxazol-4-yl)methoxy]-8-azabicyclo[3.2.1]octan-8-yl]-4-methoxy-1,3-benzothiazole-6-carboxylic acid;

Ethyl 2-(3-((5-cyclopropyl-3-(spiro[2.5]octan-6-yl)isoxazol-4-yl)methoxy)-8-azabicyclo[3.2.1]octan-8-yl)benzo[d]thiazole-6-carboxylate;

2-[3-[(5-cyclopropyl-3-{spiro[2.5]octan-6-yl}-1,2-oxazol-4-yl)methoxy]-8-azabicyclo[3.2.1]octan-8-yl]-1,3-benzothiazole-6-carboxylic acid;

2-[(1R,3r,5S)-3-[(5-cyclopropyl-3-{spiro[2.5]octan-6-yl}-1,2-oxazol-4-yl)methoxy]-8-azabicyclo[3.2.1]octan-8-yl]-1,3-benzothiazole-6-carboxylic acid;

Methyl 2-(3-((5-cyclopropyl-3-(spiro[2.5]octan-6-yl)isoxazol-4-yl )methoxy)-8-azabicyclo[3.2.1]octan-8-yl)-4-fluorobenzo[d]thiazole-6-carboxylate;

2-[3-[(5-cyclopropyl-3-{spiro[2.5]octan-6-yl}-1,2-oxazol-4-yl)methoxy]-8-azabicyclo[3.2.1]octan-8-yl]-4-fluoro-1,3-benzothiazole-6-carboxylic acid;

2-[(1R,3r,5S)-3-[(5-cyclopropyl-3-{spiro[2.5]octan-6-yl}-1,2-oxazol-4-yl)methoxy]-8-azabicyclo[3.2.1]octan-8-yl]-4-fluoro-1,3-benzothiazole-6-carboxylic acid;

Methyl 2-(3-((5-cyclopropyl-3-(spiro[2.5]octan-6-yl)isoxazol-4-yl)methoxy)-8-azabicyclo[3.2.1]octan-8-yl)-4-methoxybenzo[d]thiazole-6-carboxylate;

2-[3-[(5-cyclopropyl-3-{spiro[2.5]octan-6-yl}-1,2-oxazol-4-yl)methoxy]-8-azabicyclo[3.2.1]octan-8-yl]-4-methoxy-1,3-benzothiazole-6-carboxylic acid;

2-[(1R,3r,5S)-3-[(5-cyclopropyl-3-{spiro[2.5]octan-6-yl}-1,2-oxazol-4-yl)methoxy]-8-azabicyclo[3.2.1]octan-8-yl]-4-methoxy-1,3-benzothiazole-6-carboxylic acid;

2-[3-[(5-cyclopropyl-3-{spiro[2.5]octan-6-yl}-1,2-oxazol-4-yl)methoxy]-8-azabicyclo[3.2.1]octan-8-yl]-6-methylpyrimidine-4-carboxylic acid;

2-[(1R,3r,5S)-3-[(5-cyclopropyl-3-{spiro[2.5]octan-6-yl}-1,2-oxazol-4-yl)methoxy]-8-azabicyclo[3.2.1]octan-8-yl]-6-methylpyrimidine-4-carboxylic acid;

2-({2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazol-6-yl}formamido)acetic acid;

2-({2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazol-6-yl}formamido)acetic acid;

2-({2-[3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)acetic acid;

2-({2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)acetic acid;

2-({6-[3-({5-cyclopropyl-3-[2-(trifluoromethoxy)phenyl]-1,2-oxazol-4-yl}methoxy)-8-azabicyclo[3.2.1]octan-8-yl]pyridin-3-yl}formamido)acetic acid;

2-({6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridin-3-yl}formamido)acetic acid;

2-({2-[3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazol-6-yl}formamido)acetic acid;
2-({2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazol-6-yl}formamido)acetic acid;
2-({2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazol-6-yl}formamido)ethane-1-sulfonic acid;
2-({2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazol-6-yl}formamido)ethane-1-sulfonic acid;
2-({2-[3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)ethane-1-sulfonic acid;
2-({2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)ethane-1-sulfonic acid;
2-({2-[3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazol-6-yl}formamido)ethane-1-sulfonic acid;
2-({2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazol-6-yl 1formamido)ethane-1-sulfonic acid;
2-({6-[3-({5-cyclopropyl-3-[2-(trifluoromethoxy)phenyl]-1,2-oxazol-4-yl}methoxy)-8-azabicyclo[3.2.1]octan-8-yl]pyridin-3-yl}formamido)ethane-1-sulfonic acid;
2-({6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridin-3-yl}formamido)ethane-1-sulfonic acid;
methyl 5-bromo-6-[3-({5-cyclopropyl-3-[2-(trifluoromethoxy)phenyl]-1,2-oxazol-4-yl}methoxy)-8-azabicyclo[3.2.1]octan-8-yl]pyridine-3-carboxylate;
methyl 5-bromo-6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-3-carboxylate;
Methyl 5-cyclopropyl-6-(3-((5-cyclopropyl-3-(2-(trifluoromethoxy)phenyl)isoxazol-4-yl)methoxy)-8-azabicyclo[3.2.1]octan-8-yl)nicotinate;
Methyl 5-cyclopropyl-6-((1R,3r,5S)-3-((5-cyclopropyl-3-(2-(trifluoromethoxy)phenyl)isoxazol-4-yl)methoxy)-8-azabicyclo[3.2.1]octan-8-yl)nicotinate;
5-cyclopropyl-6-[3-({5-cyclopropyl-3-[2-(trifluoromethoxy)phenyl]-1,2-oxazol-4-yl}methoxy)-8-azabicyclo[3.2.1]octan-8-yl]pyridine-3-carboxylic acid;
5-cyclopropyl-6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-3-carboxylic acid;
methyl 6-[3-({5-cyclopropyl-3-[2-(trifluoromethoxy)phenyl]-1,2-oxazol-4-yl}methoxy)-8-azabicyclo[3.2.1]octan-8-yl]pyridine-3-carboxylate;
methyl 6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-3-carboxylate;
6-[3-({5-cyclopropyl-3-[2-(trifluoromethoxy)phenyl]-1,2-oxazol-4-yl}methoxy)-8-azabicyclo[3.2.1]octan-8-yl]pyridine-3-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-3-carboxylic acid;
methyl 2-[3-({5-cyclopropyl-3-[2-(trifluoromethoxy)phenyl]-1,2-oxazol-4-yl}methoxy)-8-azabicyclo[3.2.1]octan-8-yl]pyrimidine-5-carboxylate;
methyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrimidine-5-carboxylate;
2-[3-({5-cyclopropyl-3-[2-(trifluoromethoxy)phenyl]-1,2-oxazol-4-yl}methoxy)-8-azabicyclo[3.2.1]octan-8-yl]pyrimidine-5-carboxylic acid;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrimidine-5-carboxylic acid;
methyl 5-[3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylate;
methyl 5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylate;
5-[3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylic acid;
5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylic acid;
methyl 6-[3-({5-cyclopropyl-3-[2-(trifluoromethyl)phenyl]-1,2-oxazol-4-yl}methoxy)-8-azabicyclo[3.2.1]octan-8-yl]pyridine-3-carboxylate;
methyl 6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-3-carboxylate;
6-[3-({5-cyclopropyl-3-[2-(trifluoromethyl)phenyl]-1,2-oxazol-4-yl}methoxy)-8-azabicyclo[3.2.1]octan-8-yl]pyridine-3-carboxylic acid;
6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-3-carboxylic acid;
methyl 2-[3-({5-cyclopropyl-3-[2-(trifluoromethoxy)phenyl]-1,2-oxazol-4-yl}methoxy)-8-azabicyclo[3.2.1]octan-8-yl]-6-methylpyrimidine-4-carboxylate;
methyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-6-methylpyrimidine-4-carboxylate;
2-[3-({5-cyclopropyl-3-[2-(trifluoromethoxy)phenyl]-1,2-oxazol-4-yl}methoxy)-8-azabicyclo[3.2.1]octan-8-yl]-6-methylpyrimidine-4-carboxylic acid;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-6-methylpyrimidine-4-carboxylic acid;
methyl 2-(3-((5-cyclopropyl-3-(2-(trifluoromethyl)phenyl)isoxazol-4-yl)methoxy)-8-azabicyclo[3.2.1]octan-8-yl)-6-methylpyrimidine-4-carboxylate;
2-[3-({5-cyclopropyl-3-[2-(trifluoromethyl)phenyl]-1,2-oxazol-4-yl}methoxy)-8-azabicyclo[3.2.1]octan-8-yl]-6-methylpyrimidine-4-carboxylic acid;
2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-6-methylpyrimidine-4-carboxylic acid;
methyl 2-{6-[3-({5-cyclopropyl-3-[2-(trifluoromethoxy)phenyl]-1,2-oxazol-4-yl}methoxy)-8-azabicyclo[3.2.1]octan-8-yl]pyridin-3-yl}acetate;

methyl 2-{6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridin-3-yl}acetate;
2-{6-[3-({5-cyclopropyl-3-[2-(trifluoromethoxy)phenyl]-1,2-oxazol-4-yl}methoxy)-8-azabicyclo[3.2.1]octan-8-yl]pyridin-3-yl}acetic acid;
2-{6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridin-3-yl}acetic acid;
methyl 2-[3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyrimidine-5-carboxylate;
methyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyrimidine-5-carboxylate;
2-[3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyrimidine-5-carboxylic acid;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyrimidine-5-carboxylic acid;
methyl 6-[3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyridine-3-carboxylate;
methyl 6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyridine-3-carboxylate;
6-[3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyridine-3-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-(trifluoromethyl)pyridine-3-carboxylic acid;
methyl 6-[3-({5-cyclopropyl-3-[2-(trifluoromethoxy)phenyl]-1,2-oxazol-4-yl}methoxy)-8-azabicyclo[3.2.1]octan-8-yl]-4-methylpyridine-3-carboxylate;
methyl 6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-methylpyridine-3-carboxylate;
6-[3-({5-cyclopropyl-3-[2-(trifluoromethoxy)phenyl]-1,2-oxazol-4-yl}methoxy)-8-azabicyclo[3.2.1]octan-8-yl]-4-methylpyridine-3-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-methylpyridine-3-carboxylic acid;
methyl 6-[3-({5-cyclopropyl-3-[2-(trifluoromethoxy)phenyl]-1,2-oxazol-4-yl}methoxy)-8-azabicyclo[3.2.1]octan-8-yl]-5-methylpyridine-3-carboxylate;
methyl 6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-5-methylpyridine-3-carboxylate;
6-[3-({5-cyclopropyl-3-[2-(trifluoromethoxy)phenyl]-1,2-oxazol-4-yl}methoxy)-8-azabicyclo[3.2.1]octan-8-yl]-5-methylpyridine-3-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-5-methylpyridine-3-carboxylic acid;
methyl 6-[3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylate;
methyl 6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylate;
6-[3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylic acid;
methyl 2-[3-({5-cyclopropyl-3-[2-(trifluoromethoxy)phenyl]-1,2-oxazol-4-yl}methoxy)-8-azabicyclo[3.2.1]octan-8-yl]pyrimidine-4-carboxylate;
methyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrimidine-4-carboxylate;
2-[3-({5-cyclopropyl-3-[2-(trifluoromethoxy)phenyl]-1,2-oxazol-4-yl}methoxy)-8-azabicyclo[3.2.1]octan-8-yl]pyrimidine-4-carboxylic acid;
2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrimidine-4-carboxylic acid;
methyl 6-[3-({5-cyclopropyl-3-[2-(trifluoromethoxy)phenyl]-1,2-oxazol-4-yl}methoxy)-8-azabicyclo[3.2.1]octan-8-yl]pyridine-2-carboxylate;
methyl 6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-2-carboxylate;
6-[3-({5-cyclopropyl-3-[2-(trifluoromethoxy)phenyl]-1,2-oxazol-4-yl}methoxy)-8-azabicyclo[3.2.1]octan-8-yl]pyridine-2-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyridine-2-carboxylic acid;
methyl 2-[3-({5-cyclopropyl-3-[2-(trifluoromethyl)phenyl]-1,2-oxazol-4-yl}methoxy)-8-azabicyclo[3.2.1]octan-8-yl]pyridine-4-carboxylate;
methyl 2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-4-carboxylate;
2-[3-({5-cyclopropyl-3-[2-(trifluoromethyl)phenyl]-1,2-oxazol-4-yl}methoxy)-8-azabicyclo[3.2.1]octan-8-yl]pyridine-4-carboxylic acid;
2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-4-carboxylic acid;
methyl 6-[3-({5-cyclopropyl-3-[2-(trifluoromethyl)phenyl]-1,2-oxazol-4-yl}methoxy)-8-azabicyclo[3.2.1]octan-8-yl]-2-methylpyridine-4-carboxylate;
methyl 6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-2-methylpyridine-4-carboxylate;
2-[3-({5-cyclopropyl-3-[2-(trifluoromethyl)phenyl]-1,2-oxazol-4-yl}methoxy)-8-azabicyclo[3.2.1]octan-8-yl]-6-methylpyridine-4-carboxylic acid;
2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-6-methylpyridine-4-carboxylic acid;
methyl 2-[3-({5-cyclopropyl-3-[2-(trifluoromethyl)phenyl]-1,2-oxazol-4-yl}methoxy)-8-azabicyclo[3.2.1]octan-8-yl]pyrimidine-5-carboxylate;
methyl 2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyrimidine-5-carboxylate;
2-[3-({5-cyclopropyl-3-[2-(trifluoromethyl)phenyl]-1,2-oxazol-4-yl}methoxy)-8-azabicyclo[3.2.1]octan-8-yl]pyrimidine-5-carboxylic acid;

2-[(1R,3r,5S)-3-({5-cyclopropyl-3-[2-(trifluoromethyl) phenyl]-1,2-oxazol-4-yl}methoxy)-8-azabicyclo[3.2.1] octan-8-yl]pyrimidine-5-carboxylic acid;
methyl 5-[3-({5-cyclopropyl-3-[2-(trifluoromethyl)phenyl]-1,2-oxazol-4-yl}methoxy)-8-azabicyclo[3.2.1]octan-8-yl]pyrazine-2-carboxylate;
methyl 5-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyrazine-2-carboxylate;
5-[3-({5-cyclopropyl-3-[2-(trifluoromethyl)phenyl]-1,2-oxazol-4-yl}methoxy)-8-azabicyclo[3.2.1]octan-8-yl]pyrazine-2-carboxylic acid;
5-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyrazine-2-carboxylic acid;
methyl 6-[3-({5-cyclopropyl-3-[2-(trifluoromethyl)phenyl]-1,2-oxazol-4-yl}methoxy)-8-azabicyclo[3.2.1]octan-8-yl]-4-(trifluoromethyl)pyridine-3-carboxylate;
methyl 6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-(trifluoromethyl)pyridine-3-carboxylate;
6-[3-({5-cyclopropyl-3-[2-(trifluoromethyl)phenyl]-1,2-oxazol-4-yl}methoxy)-8-azabicyclo[3.2.1]octan-8-yl]-4-(trifluoromethyl)pyridine-3-carboxylic acid;
6-[(1R,3r,5S)-3-({5-cyclopropyl-3-[2-(trifluoromethyl) phenyl]-1,2-oxazol-4-yl}methoxy)-8-azabicyclo[3.2.1] octan-8-yl]-4-(trifluoromethyl)pyridine-3-carboxylic acid;
methyl 2-[3-({5-cyclopropyl-3-[2-(trifluoromethyl)phenyl]-1,2-oxazol-4-yl}methoxy)-8-azabicyclo[3.2.1]octan-8-yl]pyrimidine-4-carboxylate;
methyl 2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyrimidine-4-carboxylate;
2-[3-({5-cyclopropyl-3-[2-(trifluoromethyl)phenyl]-1,2-oxazol-4-yl}methoxy)-8-azabicyclo[3.2.1]octan-8-yl]pyrimidine-4-carboxylic acid;
2-[(1R,3r,5S)-3-({5-cyclopropyl-3-[2-(trifluoromethyl) phenyl]-1,2-oxazol-4-yl}methoxy)-8-azabicyclo[3.2.1] octan-8-yl]pyrimidine-4-carboxylic acid;
methyl 6-[3-({5-cyclopropyl-3-[2-(trifluoromethyl)phenyl]-1,2-oxazol-4-yl}methoxy)-8-azabicyclo[3.2.1]octan-8-yl]pyridine-2-carboxylate;
methyl 6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyridine-2-carboxylate;
6-[3-({5-cyclopropyl-3-[2-(trifluoromethyl)phenyl]-1,2-oxazol-4-yl}methoxy)-8-azabicyclo[3.2.1]octan-8-yl]pyridine-2-carboxylic acid;
6-[(1R,3r,5S)-3-({5-cyclopropyl-3-[2-(trifluoromethyl) phenyl]-1,2-oxazol-4-yl}methoxy)-8-azabicyclo[3.2.1] octan-8-yl]pyridine-2-carboxylic acid;
methyl 6-[3-({5-cyclopropyl-3-[2-(difluoromethoxy)phenyl]-1,2-oxazol-4-yl}methoxy)-8-azabicyclo[3.2.1]octan-8-yl]-4-(trifluoromethyl)pyridine-3-carboxylate;
methyl 6-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-4-(trifluoromethyl)pyridine-3-carboxylate;
6-[3-({5-cyclopropyl-3-[2-(difluoromethoxy)phenyl]-1,2-oxazol-4-yl}methoxy)-8-azabicyclo[3.2.1]octan-8-yl]-4-(trifluoromethyl)pyridine-3-carboxylic acid;
6-[(1R,3r,5S)-3-({5-cyclopropyl-3-[2-(difluoromethoxy) phenyl]-1,2-oxazol-4-yl}methoxy)-8-azabicyclo[3.2.1] octan-8-yl]-4-(trifluoromethyl)pyridine-3-carboxylic acid;
methyl 2-[3-({5-cyclopropyl-3-[2-(difluoromethoxy)phenyl]-1,2-oxazol-4-yl}methoxy)-8-azabicyclo[3.2.1]octan-8-yl]pyrimidine-4-carboxylate;
methyl 2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyrimidine-4-carboxylate;
2-[3-({5-cyclopropyl-3-[2-(difluoromethoxy)phenyl]-1,2-oxazol-4-yl}methoxy)-8-azabicyclo[3.2.1]octan-8-yl]pyrimidine-4-carboxylic acid;
2-[(1R,3r,5S)-3-({5-cyclopropyl-3-[2-(difluoromethoxy) phenyl]-1,2-oxazol-4-yl}methoxy)-8-azabicyclo[3.2.1] octan-8-yl]pyrimidine-4-carboxylic acid;
methyl 6-[3-({5-cyclopropyl-3-[2-(difluoromethoxy)phenyl]-1,2-oxazol-4-yl}methoxy)-8-azabicyclo[3.2.1]octan-8-yl]pyridine-2-carboxylate;
methyl 6-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyridine-2-carboxylate;
methyl 6-[3-({5-cyclopropyl-3-[2-(difluoromethoxy)phenyl]-1,2-oxazol-4-yl}methoxy)-8-azabicyclo[3.2.1]octan-8-yl]-4-methylpyridine-3-carboxylate;
methyl 6-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-4-methylpyridine-3-carboxylate;
6-[3-({5-cyclopropyl-3-[2-(difluoromethoxy)phenyl]-1,2-oxazol-4-yl}methoxy)-8-azabicyclo[3.2.1]octan-8-yl]-4-methylpyridine-3-carboxylic acid;
6-[(1R,3r,5S)-3-({5-cyclopropyl-3-[2-(difluoromethoxy) phenyl]-1,2-oxazol-4-yl}methoxy)-8-azabicyclo[3.2.1] octan-8-yl]-4-methylpyridine-3-carboxylic acid;
methyl 2-[3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxylate;
methyl 2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxylate;
methyl 4-chloro-6-[3-({5-cyclopropyl-3-[2-(difluoromethoxy)phenyl]-1,2-oxazol-4-yl}methoxy)-8-azabicyclo[3.2.1]octan-8-yl]pyridine-3-carboxylate;
methyl 4-chloro-6-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyridine-3-carboxylate;
4-chloro-6-[3-({5-cyclopropyl-3-[2-(difluoromethoxy) phenyl]-1,2-oxazol-4-yl}methoxy)-8-azabicyclo[3.2.1] octan-8-yl]pyridine-3-carboxylic acid;
4-chloro-6-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyridine-3-carboxylic acid;
methyl 6-[3-({5-cyclopropyl-3-[2-(difluoromethoxy)phenyl]-1,2-oxazol-4-yl}methoxy)-8-azabicyclo[3.2.1]octan-8-yl]-5-methylpyridine-3-carboxylate;
methyl 6-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-5-methylpyridine-3-carboxylate;
6-[3-({5-cyclopropyl-3-[2-(difluoromethoxy)phenyl]-1,2-oxazol-4-yl}methoxy)-8-azabicyclo[3.2.1]octan-8-yl]-5-methylpyridine-3-carboxylic acid;
6-[(1R,3r,5S)-3-({5-cyclopropyl-3-[2-(difluoromethoxy) phenyl]-1,2-oxazol-4-yl}methoxy)-8-azabicyclo[3.2.1] octan-8-yl]-5-methylpyridine-3-carboxylic acid;
2-[3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxylic acid;

2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-6-methylpyrimidine-4-carboxylic acid;

methyl 6-[3-({5-cyclopropyl-3-[2-(difluoromethoxy)phenyl]-1,2-oxazol-4-yl}methoxy)-8-azabicyclo[3.2.1]octan-8-yl]pyridazine-3-carboxylate;

methyl 6-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyridazine-3-carboxylate;

6-[3-({5-cyclopropyl-3-[2-(difluoromethoxy)phenyl]-1,2-oxazol-4-yl}methoxy)-8-azabicyclo[3.2.1]octan-8-yl]pyridazine-3-carboxylic acid;

6-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyridazine-3-carboxylic acid;

methyl 2-[3-({5-cyclopropyl-3-[2-(difluoromethoxy)phenyl]-1,2-oxazol-4-yl}methoxy)-8-azabicyclo[3.2.1]octan-8-yl]pyrimidine-5-carboxylate;

methyl 2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyrimidine-5-carboxylate;

2-[3-({5-cyclopropyl-3-[2-(difluoromethoxy)phenyl]-1,2-oxazol-4-yl}methoxy)-8-azabicyclo[3.2.1]octan-8-yl]pyrimidine-5-carboxylic acid;

2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyrimidine-5-carboxylic acid;

methyl 5-[3-({5-cyclopropyl-3-[2-(difluoromethoxy)phenyl]-1,2-oxazol-4-yl}methoxy)-8-azabicyclo[3.2.1]octan-8-yl]pyrazine-2-carboxylate;

methyl 5-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyrazine-2-carboxylate;

5-[3-({5-cyclopropyl-3-[2-(difluoromethoxy)phenyl]-1,2-oxazol-4-yl}methoxy)-8-azabicyclo[3.2.1]octan-8-yl]pyrazine-2-carboxylic acid;

5-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyrazine-2-carboxylic acid;

6-[3-({5-cyclopropyl-3-[2-(difluoromethoxy)phenyl]-1,2-oxazol-4-yl}methoxy)-8-azabicyclo[3.2.1]octan-8-yl]pyridine-3-carboxylic acid;

6-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyridine-3-carboxylic acid;

methyl 6-[3-{[5-cyclopropyl-3-(2,6-difluorophenyl)-1,2-oxazol-4-yl]methoxy}-8-azabicyclo[3.2.1]octan-8-yl]pyridine-3-carboxylate;

methyl 6-[(1R,3r,5S)-3-{[5-cyclopropyl-3-(2,6-difluorophenyl)-1,2-oxazol-4-yl]methoxy}-8-azabicyclo[3.2.1]octan-8-yl]pyridine-3-carboxylate;

6-[3-{[5-cyclopropyl-3-(2,6-difluorophenyl)-1,2-oxazol-4-yl]methoxy}-8-azabicyclo[3.2.1]octan-8-yl]pyridine-3-carboxylic acid;

6-[(1R,3r,5S)-3-{[5-cyclopropyl-3-(2,6-difluorophenyl)-1,2-oxazol-4-yl]methoxy}-8-azabicyclo[3.2.1]octan-8-yl]pyridine-3-carboxylic acid;

methyl 2-[3-{[5-cyclopropyl-3-(2,6-difluorophenyl)-1,2-oxazol-4-yl]methoxy}-8-azabicyclo[3.2.1]octan-8-yl]pyrimidine-5-carboxylate;

methyl 2-[(1R,3r,5S)-3-{[5-cyclopropyl-3-(2,6-difluorophenyl)-1,2-oxazol-4-yl]methoxy}-8-azabicyclo[3.2.1]octan-8-yl]pyrimidine-5-carboxylate;

2-[3-{[5-cyclopropyl-3-(2,6-difluorophenyl)-1,2-oxazol-4-yl]methoxy}-8-azabicyclo[3.2.1]octan-8-yl]pyrimidine-5-carboxylic acid;

2-[(1R,3r,5S)-3-{[5-cyclopropyl-3-(2,6-difluorophenyl)-1,2-oxazol-4-yl]methoxy}-8-azabicyclo[3.2.1]octan-8-yl]pyrimidine-5-carboxylic acid;

methyl 5-[3-{[5-cyclopropyl-3-(2,6-difluorophenyl)-1,2-oxazol-4-yl]methoxy}-8-azabicyclo[3.2.1]octan-8-yl]pyrazine-2-carboxylate;

methyl 5-[(1R,3r,5S)-3-{[5-cyclopropyl-3-(2,6-difluorophenyl)-1,2-oxazol-4-yl]methoxy}-8-azabicyclo[3.2.1]octan-8-yl]pyrazine-2-carboxylate;

5-[3-{[5-cyclopropyl-3-(2,6-difluorophenyl)-1,2-oxazol-4-yl]methoxy}-8-azabicyclo[3.2.1]octan-8-yl]pyrazine-2-carboxylic acid;

5-[(1R,3r,5S)-3-{[5-cyclopropyl-3-(2,6-difluorophenyl)-1,2-oxazol-4-yl]methoxy}-8-azabicyclo[3.2.1]octan-8-yl]pyrazine-2-carboxylic acid;

methyl 6-[3-{[5-cyclopropyl-3-(2,6-difluorophenyl)-1,2-oxazol-4-yl]methoxy}-8-azabicyclo[3.2.1]octan-8-yl]-4-(trifluoromethyl)pyridine-3-carboxylate;

methyl 6-[(1R,3r,5S)-3-{[5-cyclopropyl-3-(2,6-difluorophenyl)-1,2-oxazol-4-yl]methoxy}-8-azabicyclo[3.2.1]octan-8-yl]-4-(trifluoromethyl)pyridine-3-carboxylate;

6-[3-{[5-cyclopropyl-3-(2,6-difluorophenyl)-1,2-oxazol-4-yl]methoxy}-8-azabicyclo[3.2.1]octan-8-yl]-4-(trifluoromethyl)pyridine-3-carboxylic acid;

6-[(1R,3r,5S)-3-{[5-cyclopropyl-3-(2,6-difluorophenyl)-1,2-oxazol-4-yl]methoxy}-8-azabicyclo[3.2.1]octan-8-yl]-4-(trifluoromethyl)pyridine-3-carboxylic acid;

methyl 5-cyclopropyl-6-[3-{[5-cyclopropyl-3-(2,6-difluorophenyl)-1,2-oxazol-4-yl]methoxy}-8-azabicyclo[3.2.1]octan-8-yl]pyridine-3-carboxylate;

methyl 5-cyclopropyl-6-[(1R,3r,5S)-3-{[5-cyclopropyl-3-(2,6-difluorophenyl)-1,2-oxazol-4-yl]methoxy}-8-azabicyclo[3.2.1]octan-8-yl]pyridine-3-carboxylate;

5-cyclopropyl-6-[3-{[5-cyclopropyl-3-(2,6-difluorophenyl)-1,2-oxazol-4-yl]methoxy}-8-azabicyclo[3.2.1]octan-8-yl]pyridine-3-carboxylic acid;

5-cyclopropyl-6-[(1R,3r,5S)-3-{[5-cyclopropyl-3-(2,6-difluorophenyl)-1,2-oxazol-4-yl]methoxy}-8-azabicyclo[3.2.1]octan-8-yl]pyridine-3-carboxylic acid;

methyl 2-[3-{[5-cyclopropyl-3-(2,6-difluorophenyl)-1,2-oxazol-4-yl]methoxy}-8-azabicyclo[3.2.1]octan-8-yl]-6-methylpyrimidine-4-carboxylate;

methyl 2-[(1R,3r,5S)-3-{[5-cyclopropyl-3-(2,6-difluorophenyl)-1,2-oxazol-4-yl]methoxy}-8-azabicyclo[3.2.1]octan-8-yl]-6-methylpyrimidine-4-carboxylate;

2-[3-{[5-cyclopropyl-3-(2,6-difluorophenyl)-1,2-oxazol-4-yl]methoxy}-8-azabicyclo[3.2.1]octan-8-yl]-6-methylpyrimidine-4-carboxylic acid;

2-[(1R,3r,5S)-3-{[5-cyclopropyl-3-(2,6-difluorophenyl)-1,2-oxazol-4-yl]methoxy}-8-azabicyclo[3.2.1]octan-8-yl]-6-methylpyrimidine-4-carboxylic acid;

methyl 2-chloro-6-[3-{[5-cyclopropyl-3-(2,6-difluorophenyl)-1,2-oxazol-4-yl]methoxy}-8-azabicyclo[3.2.1]octan-8-yl]pyrimidine-4-carboxylate;

methyl 2-chloro-6-[(1R,3r,5S)-3-{[5-cyclopropyl-3-(2,6-difluorophenyl)-1,2-oxazol-4-yl]methoxy}-8-azabicyclo[3.2.1]octan-8-yl]pyrimidine-4-carboxylate;

methyl 6-chloro-2-[3-{[5-cyclopropyl-3-(2,6-difluorophenyl)-1,2-oxazol-4-yl]methoxy}-8-azabicyclo[3.2.1]octan-8-yl]pyrimidine-4-carboxylate;

methyl 6-chloro-2-[(1R,3r,5S)-3-{[5-cyclopropyl-3-(2,6-difluorophenyl)-1,2-oxazol-4-yl]methoxy}-8-azabicyclo[3.2.1]octan-8-yl]pyrimidine-4-carboxylate;

methyl 5-bromo-6-[3-{[5-cyclopropyl-3-(2,6-difluorophenyl)-1,2-oxazol-4-yl]methoxy}-8-azabicyclo[3.2.1]octan-8-yl]pyridine-3-carboxylate;

methyl 5-bromo-6-[(1R,3r,5S)-3-{[5-cyclopropyl-3-(2,6-difluorophenyl)-1,2-oxazol-4-yl]methoxy}-8-azabicyclo[3.2.1]octan-8-yl]pyridine-3-carboxylate;
methyl 4-[3-({5-cyclopropyl-3-[2-(trifluoromethoxy)phenyl]-1,2-oxazol-4-yl}methoxy)-8-azabicyclo[3.2.1]octan-8-yl]-3-fluorobenzoate;
methyl 4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-3-fluorobenzoate;
4-[3-({5-cyclopropyl-3-[2-(trifluoromethoxy)phenyl]-1,2-oxazol-4-yl}methoxy)-8-azabicyclo[3.2.1]octan-8-yl]-3-fluorobenzoic acid;
4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-3-fluorobenzoic acid;
methyl 4-[3-({5-cyclopropyl-3-[2-(trifluoromethoxy)phenyl]-1,2-oxazol-4-yl}methoxy)-8-azabicyclo[3.2.1]octan-8-yl]-3,5-difluorobenzoate;
methyl 4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-3,5-difluorobenzoate;
4-[3-({5-cyclopropyl-3-[2-(trifluoromethoxy)phenyl]-1,2-oxazol-4-yl}methoxy)-8-azabicyclo[3.2.1]octan-8-yl]-3,5-difluorobenzoic acid;
4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-3,5-difluorobenzoic acid;
methyl 4-[3-({5-cyclopropyl-3-[2-(difluoromethoxy)phenyl]-1,2-oxazol-4-yl}methoxy)-8-azabicyclo[3.2.1]octan-8-yl]-3,5-difluorobenzoate;
methyl 4-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-3,5-difluorobenzoate;
4-[3-({5-cyclopropyl-3-[2-(difluoromethoxy)phenyl]-1,2-oxazol-4-yl}methoxy)-8-azabicyclo[3.2.1]octan-8-yl]-3,5-difluorobenzoic acid;
4-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-3,5-difluorobenzoic acid;
methyl 4-[3-({5-cyclopropyl-3-[2-(trifluoromethyl)phenyl]-1,2-oxazol-4-yl}methoxy)-8-azabicyclo[3.2.1]octan-8-yl]-3,5-difluorobenzoate;
methyl 4-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-3,5-difluorobenzoate;
4-[3-({5-cyclopropyl-3-[2-(trifluoromethyl)phenyl]-1,2-oxazol-4-yl}methoxy)-8-azabicyclo[3.2.1]octan-8-yl]-3,5-difluorobenzoic acid;
4-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-3,5-difluorobenzoic acid;
methyl 4-[3-{[5-cyclopropyl-3-(2,6-difluorophenyl)-1,2-oxazol-4-yl]methoxy}-8-azabicyclo[3.2.1]octan-8-yl]-3-fluorobenzoate;
methyl 4-[(1R,3r,5S)-3-{[5-cyclopropyl-3-(2,6-difluorophenyl)-1,2-oxazol-4-yl]methoxy}-8-azabicyclo[3.2.1]octan-8-yl]-3-fluorobenzoate;
4-[3-{[5-cyclopropyl-3-(2,6-difluorophenyl)-1,2-oxazol-4-yl]methoxy}-8-azabicyclo[3.2.1]octan-8-yl]-3-fluorobenzoic acid;
4-[(1R,3r,5S)-3-{[5-cyclopropyl-3-(2,6-difluorophenyl)-1,2-oxazol-4-yl]methoxy}-8-azabicyclo[3.2.1]octan-8-yl]-3-fluorobenzoic acid;
methyl 4-[3-{[5-cyclopropyl-3-(2,6-difluorophenyl)-1,2-oxazol-4-yl]methoxy}-8-azabicyclo[3.2.1]octan-8-yl]-3,5-difluorobenzoate;
methyl 4-[(1R,3r,5S)-3-{[5-cyclopropyl-3-(2,6-difluorophenyl)-1,2-oxazol-4-yl]methoxy}-8-azabicyclo[3.2.1]octan-8-yl]-3,5-difluorobenzoate;
4-[3-{[5-cyclopropyl-3-(2,6-difluorophenyl)-1,2-oxazol-4-yl]methoxy}-8-azabicyclo[3.2.1]octan-8-yl]-3,5-difluorobenzoic acid;
4-[(1R,3r,5S)-3-{[5-cyclopropyl-3-(2,6-difluorophenyl)-1,2-oxazol-4-yl]methoxy}-8-azabicyclo[3.2.1]octan-8-yl]-3,5-difluorobenzoic acid;
methyl 4-[3-({5-cyclopropyl-3-[2-(trifluoromethyl)phenyl]-1,2-oxazol-4-yl}methoxy)-8-azabicyclo[3.2.1]octan-8-yl]-3-fluorobenzoate;
methyl 4-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-3-fluorobenzoate;
4-[3-({5-cyclopropyl-3-[2-(trifluoromethyl)phenyl]-1,2-oxazol-4-yl}methoxy)-8-azabicyclo[3.2.1]octan-8-yl]-3-fluorobenzoic acid;
4-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-3-fluorobenzoic acid;
methyl 4-[3-({5-cyclopropyl-3-[2-(difluoromethoxy)phenyl]-1,2-oxazol-4-yl}methoxy)-8-azabicyclo[3.2.1]octan-8-yl]-3-fluorobenzoate;
methyl 4-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-3-fluorobenzoate;
4-[3-({5-cyclopropyl-3-[2-(difluoromethoxy)phenyl]-1,2-oxazol-4-yl}methoxy)-8-azabicyclo[3.2.1]octan-8-yl]-3-fluorobenzoic acid;
4-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-3-fluorobenzoic acid;
4-(3-((5-cyclopropyl-3-(2-(difluoromethoxy)phenyl)isoxazol-4-yl)methoxy)-8-azabicyclo[3.2.1]octan-8-yl)-3-fluorobenzonitrile;
3-({5-cyclopropyl-3-[2-(difluoromethoxy)phenyl]-1,2-oxazol-4-yl}methoxy)-8-[2-fluoro-4-(5H-1,2,3,4-tetrazol-5-yl)phenyl]-8-azabicyclo[3.2.1]octane;
(1R,3r,5S)-3-({5-cyclopropyl-3-[2-(difluoromethoxy)phenyl]-1,2-oxazol-4-yl}methoxy)-8-[2-fluoro-4-(5H-1,2,3,4-tetrazol-5-yl)phenyl]-8-azabicyclo[3.2.1]octane;
4-[3-({5-cyclopropyl-3-[2-(difluoromethoxy)phenyl]-1,2-oxazol-4-yl}methoxy)-8-azabicyclo[3.2.1]octan-8-yl]-3-fluorobenzamide;
4-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]-3-fluorobenzamide;
methyl 6-(3-((5-cyclopropyl-3-(2-(trifluoromethoxy)phenyl)isoxazol-4-yl)methoxy)-8-azabicyclo[3.2.1]octan-8-yl)benzo[d]isothiazole-3-carboxylate;
6-[3-({5-cyclopropyl-3-[2-(trifluoromethoxy)phenyl]-1,2-oxazol-4-yl}methoxy)-8-azabicyclo[3.2.1]octan-8-yl]-1,2-benzothiazole-3-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,2-benzothiazole-3-carboxylic acid;
6-[3-({5-cyclopropyl-3-[2-(trifluoromethoxy)phenyl]-1,2-oxazol-4-yl}methoxy)-8-azabicyclo[3.2.1]octan-8-yl]-1,2-benzothiazole-3-carboxylic acid;
6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,2-benzothiazole-3-carboxylic acid;
6-[3-({5-cyclopropyl-3-[2-(trifluoromethoxy)phenyl]-1,2-oxazol-4-yl}methoxy)-8-azabicyclo[3.2.1]octan-8-yl]imidazo[1,2-a]pyridine-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]imidazo[1,2-a]pyridine-3-carboxylic acid;

7-[3-({5-cyclopropyl-3-[2-(trifluoromethoxy)phenyl]-1,2-oxazol-4-yl}methoxy)-8-azabicyclo[3.2.1]octan-8-yl]quinoline-3-carboxylic acid;

7-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]quinoline-3-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-1-methyl-1H-indole-2-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-methyl-1H-indole-2-carboxylic acid;

2-[3-({5-cyclopropyl-3-[2-(trifluoromethoxy)phenyl]-1,2-oxazol-4-yl}methoxy)-8-azabicyclo[3.2.1]octan-8-yl]pyrrolo[1,2-b]pyridazine-6-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrrolo[1,2-b]pyridazine-6-carboxylic acid;

4-[3-({5-cyclopropyl-3-[2-(trifluoromethoxy)phenyl]-1,2-oxazol-4-yl}methoxy)-8-azabicyclo[3.2.1]octan-8-yl]benzoic acid;

4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]benzoic acid;

1-{4-[3-({5-cyclopropyl-3-[2-(trifluoromethoxy)phenyl]-1,2-oxazol-4-yl}methoxy)-8-azabicyclo[3.2.1]octan-8-yl]phenyl}cyclopropane-1-carboxylic acid;

1-{4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]phenyl}cyclopropane-1-carboxylic acid;

5-[3-{[5-cyclopropyl-3-(2-cyclopropylphenyl)-1,2-oxazol-4-yl]methoxy}-8-azabicyclo[3.2.1]octan-8-yl]-4-methyl-1-benzofuran-2-carboxylic acid;

5-[(1R,3r,5S)-3-{[5-cyclopropyl-3-(2-cyclopropylphenyl)-1,2-oxazol-4-yl]methoxy}-8-azabicyclo[3.2.1]octan-8-yl]-4-methyl-1-benzofuran-2-carboxylic acid;

5-[3-{[3-(2-chlorophenyl)-5-cyclopropyl-1,2-oxazol-4-yl]methoxy}-8-azabicyclo[3.2.1]octan-8-yl]-4-methyl-1-benzofuran-2-carboxylic acid;

5-[(1R,3r,5S)-3-{[3-(2-chlorophenyl)-5-cyclopropyl-1,2-oxazol-4-yl]methoxy}-8-azabicyclo[3.2.1]octan-8-yl]-4-methyl-1-benzofuran-2-carboxylic acid;

5-[3-{[5-cyclopropyl-3-(2,6-difluorophenyl)-1,2-oxazol-4-yl]methoxy}-8-azabicyclo[3.2.1]octan-8-yl]-4-methyl-1-benzofuran-2-carboxylic acid;

5-[(1R,3r,5S)-3-{[5-cyclopropyl-3-(2,6-difluorophenyl)-1,2-oxazol-4-yl]methoxy}-8-azabicyclo[3.2.1]octan-8-yl]-4-methyl-1-benzofuran-2-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]-4-methyl-1-benzofuran-2-carboxylic acid;

5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-methyl-1-benzofuran-2-carboxylic acid;

5-[3-({5-cyclopropyl-3-[2-(trifluoromethyl)phenyl]-1,2-oxazol-4-yl}methoxy)-8-azabicyclo[3.2.1]octan-8-yl]-4-methyl-1-benzofuran-2-carboxylic acid;

5-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-methyl-1-benzofuran-2-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]-1-benzothiophene-2-carboxylic acid;

5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-benzothiophene-2-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]-1-benzofuran-2-carboxylic acid;

5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-benzofuran-2-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-1-benzofuran-2-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-benzofuran-2-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]-1-methyl-1H-indazole-3-carboxylic acid;

5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-methyl-1H-indazole-3-carboxylic acid;

8-[3-({5-cyclopropyl-3-[2-(trifluoromethoxy)phenyl]-1,2-oxazol-4-yl}methoxy)-8-azabicyclo[3.2.1]octan-8-yl]quinoline-3-carboxylic acid;

8-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]quinoline-3-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-1,2-benzoxazole-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,2-benzoxazole-3-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]-1-methyl-1H-indole-2-carboxylic acid;

5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-methyl-1H-indole-2-carboxylic acid;

5-[3-({5-cyclopropyl-3-[2-(trifluoromethyl)phenyl]-1,2-oxazol-4-yl}methoxy)-8-azabicyclo[3.2.1]octan-8-yl]-1-benzofuran-2-carboxylic acid;

5-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-1-benzofuran-2-carboxylic acid;

6-[3-({5-cyclopropyl-3-[2-(trifluoromethyl)phenyl]-1,2-oxazol-4-yl}methoxy)-8-azabicyclo[3.2.1]octan-8-yl]-1,2-benzothiazole-3-carboxylic acid;

6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-1,2-benzothiazole-3-carboxylic acid;

6-[3-{[5-cyclopropyl-3-(2-cyclopropylphenyl)-1,2-oxazol-4-yl]methoxy}-8-azabicyclo[3.2.1]octan-8-yl]-1,2-benzothiazole-3-carboxylic acid;

6-[(1R,3r,5S)-3-{[5-cyclopropyl-3-(2-cyclopropylphenyl)-1,2-oxazol-4-yl]methoxy}-8-azabicyclo[3.2.1]octan-8-yl]-1,2-benzothiazole-3-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-5-fluoro-1,2-benzothiazole-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-5-fluoro-1,2-benzothiazole-3-carboxylic acid;

7-[3-({5-cyclopropyl-3-[2-(trifluoromethoxy)phenyl]-1,2-oxazol-4-yl}methoxy)-8-azabicyclo[3.2.1]octan-8-yl]imidazo[1,2-a]pyridine-2-carboxylic acid;

7-[(1R,3r,5S)-3-({5-cyclopropyl-3-[2-(trifluoromethoxy) phenyl]-1,2-oxazol-4-yl}methoxy)-8-azabicyclo[3.2.1] octan-8-yl]imidazo[1,2-a]pyridine-2-carboxylic acid;

6-[3-({5-cyclopropyl-3-[2-(trifluoromethoxy)phenyl]-1, 2-oxazol-4-yl}methoxy)-8-azabicyclo[3.2.1]octan-8-yl]-1-methyl-1H-indazole-3-carboxylic acid;

6-[(1R,3r,5S)-3-({5-cyclopropyl-3-[2-(trifluoromethoxy) phenyl]-1,2-oxazol-4-yl}methoxy)-8-azabicyclo[3.2.1] octan-8-yl]-1-methyl-1H-indazole-3-carboxylic acid;2-[3-({3-[bicyclo[3.1.0]hexan-6-yl]-5-cyclopropyl-1,2-oxazol-4-yl}methoxy)-8-azabicyclo[3.2.1]octan-8-yl]-4-fluoro-1,3-benzothiazole-6-carboxylic acid;

2-[(1R,3r,5S)-3-({3-[(1R,5S)-bicyclo[3.1.0]hexan-6-yl]-5-cyclopropyl-1,2-oxazol-4-yl}methoxy)-8-azabicyclo [3.2.1]octan-8-yl]-4-fluoro-1,3-benzothiazole-6-carboxylic acid;

2-[3-({5-cyclopropyl-3-[1-methylbicyclo[3.1.0]hexan-6-yl]-1,2-oxazol-4-yl}methoxy)-8-azabicyclo[3.2.1]octan-8-yl]-4-fluoro-1,3-benzothiazole-6-carboxylic acid;

2-[(1R,3r,5S)-3-({5-cyclopropyl-3-[(1R,5R,6S)-1-methylbicyclo[3.1.0]hexan-6-yl]-1,2-oxazol-4-yl}methoxy)-8-azabicyclo[3.2.1]octan-8-yl]-4-fluoro-1,3-benzothiazole-6-carboxylic acid;

2-[3-[(3-cyclopentyl-5-cyclopropyl-1,2-oxazol-4-yl)methoxy]-8-azabicyclo[3.2.1]octan-8-yl]-4-fluoro-1,3-benzothiazole-6-carboxylic acid;

2-[(1R,3r,5S)-3-[(3-cyclopentyl-5-cyclopropyl-1,2-oxazol-4-yl)methoxy]-8-azabicyclo[3.2.1]octan-8-yl]-4-fluoro-1,3-benzothiazole-6-carboxylic acid;

2-[3-[(5-cyclopropyl-3-{spiro[2.3]hexan-5-yl}-1,2-oxazol-4-yl)methoxy]-8-azabicyclo[3.2.1]octan-8-yl]-4-fluoro-1,3-benzothiazole-6-carboxylic acid;

2-[(1R,3r,5S)-3-[(5-cyclopropyl-3-{spiro[2.3]hexan-5-yl}-1,2-oxazol-4-yl)methoxy]-8-azabicyclo[3.2.1]octan-8-yl]-4-fluoro-1,3-benzothiazole-6-carboxylic acid;

2-[3-({5-cyclopropyl-3-[2,6,6-trimethylbicyclo[3.1.1] heptan-3-yl]-1,2-oxazol-4-yl}methoxy)-8-azabicyclo [3.2.1]octan-8-yl]-4-fluoro-1,3-benzothiazole-6-carboxylic acid;

2-[(1R,3r,5S)-3-({5-cyclopropyl-3-[(1R,2S,3S,5S)-2,6,6-trimethylbicyclo[3.1.1]heptan-3-yl]-1,2-oxazol-4-yl}methoxy)-8-azabicyclo[3.2.1]octan-8-yl]-4-fluoro-1,3-benzothiazole-6-carboxylic acid;

2-[3-[(5-cyclopropyl-3-{spiro[2.5]octan-4-yl}-1,2-oxazol-4-yl)methoxy]-8-azabicyclo[3.2.1]octan-8-yl]-4-fluoro-1,3-benzothiazole-6-carboxylic acid;

2-[(1R,3r,5S)-3-[(5-cyclopropyl-3-{spiro[2.5]octan-4-yl}-1,2-oxazol-4-yl)methoxy]-8-azabicyclo[3.2.1]octan-8-yl]-4-fluoro-1,3-benzothiazole-6-carboxylic acid;

2-[3-({3-[bicyclo[4.1.0]heptan-3-yl]-5-cyclopropyl-1,2-oxazol-4-yl}methoxy)-8-azabicyclo[3.2.1]octan-8-yl]-4-fluoro-1,3-benzothiazole-6-carboxylic acid;

2-[(1R,3r,5S)-3-({3-[(1S,3S,6S)-bicyclo[4.1.0]heptan-3-yl]-5-cyclopropyl-1,2-oxazol-4-yl}methoxy)-8-azabicyclo[3.2.1]octan-8-yl]-4-fluoro-1,3-benzothiazole-6-carboxylic acid;

2-[3-{[5-cyclopropyl-3-(2-methylphenyl)-1,2-oxazol-4-yl]methoxy}-8-azabicyclo[3.2.1]octan-8-yl]-4-fluoro-1,3-benzothiazole-6-carboxylic acid;

2-[(1R,3r,5S)-3-{[5-cyclopropyl-3-(2-methylphenyl)-1,2-oxazol-4-yl]methoxy}-8-azabicyclo[3.2.1]octan-8-yl]-4-fluoro-1,3-benzothiazole-6-carboxylic acid;

6-[3-{[5-cyclopropyl-3-(2-methylphenyl)-1,2-oxazol-4-yl]methoxy}-8-azabicyclo[3.2.1]octan-8-yl]pyridine-3-carboxylic acid;

6-[(1R,3r,5S)-3-{[5-cyclopropyl-3-(2-methylphenyl)-1,2-oxazol-4-yl]methoxy}-8-azabicyclo[3.2.1]octan-8-yl] pyridine-3-carboxylic acid;

2-[3-{[5-cyclopropyl-3-(2-methylphenyl)-1,2-oxazol-4-yl]methoxy}-8-azabicyclo[3.2.1]octan-8-yl]-6-methylpyrimidine-4-carboxylic acid;

2-[(1R,3r,5S)-3-{[5-cyclopropyl-3-(2-methylphenyl)-1,2-oxazol-4-yl]methoxy}-8-azabicyclo[3.2.1]octan-8-yl]-6-methylpyrimidine-4-carboxylic acid;

2-[3-{[5-cyclopropyl-3-(2-methylphenyl)-1,2-oxazol-4-yl]methoxy}-8-azabicyclo[3.2.1]octan-8-yl]-1,3-benzothiazole-6-carboxylic acid;

2-[(1R,3r,5S)-3-{[5-cyclopropyl-3-(2-methylphenyl)-1,2-oxazol-4-yl]methoxy}-8-azabicyclo[3.2.1]octan-8-yl]-1,3-benzothiazole-6-carboxylic acid;

2-[3-{[5-cyclopropyl-3-(2-methylphenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(2-methylphenyl)-1,2-oxazol-4-yl]methoxy}-8-azabicyclo[3.2.1]octan-8-yl]-4-methoxy-1,3-benzothiazole-6-carboxylic acid;

2-[3-{[5-cyclopropyl-3-(4-fluorophenyl)-1,2-oxazol-4-yl]methoxy}-8-azabicyclo[3.2.1]octan-8-yl]-1,3-benzothiazole-6-carboxylic acid;

2-[(1R,3r,5S)-3-{[5-cyclopropyl-3-(4-fluorophenyl)-1,2-oxazol-4-yl]nethoxyl -8-azabicyclo[3.2.1]octan-8-yl]-1,3-benzothiazole-6-carboxylic acid;

2-[3-{[5-cyclopropyl-3-(4-fluorophenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(4-fluorophenyl)-1,2-oxazol-4-yl]nethoxyl -8-azabicyclo[3.2.1]octan-8-yl]-4-methoxy-1,3-benzothiazole-6-carboxylic acid;

2-[3-{[5-cyclopropyl-3-(3-fluorophenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(3-fluorophenyl)-1,2-oxazol-4-yl]methoxy}-8-azabicyclo[3.2.1]octan-8-yl]-4-methoxy-1,3-benzothiazole-6-carboxylic acid;

6-[3-{[5-cyclopropyl-3-(3-fluorophenyl)-1,2-oxazol-4-yl]methoxy}-8-azabicyclo[3.2.1]octan-8-yl]pyridine-3-carboxylic acid;

6-[(1R,3r,5S)-3-{[5-cyclopropyl-3-(3-fluorophenyl)-1,2-oxazol-4-yl]methoxy}-8-azabicyclo[3.2.1]octan-8-yl] pyridine-3-carboxylic acid;

2-[3-{[5-cyclopropyl-3-(3-fluorophenyl)-1,2-oxazol-4-yl]methoxy}-8-azabicyclo[3.2.1]octan-8-yl]-6-methylpyrimidine-4-carboxylic acid;

2-[(1R,3r,5S)-3-{[5-cyclopropyl-3-(3-fluorophenyl)-1,2-oxazol-4-yl]methoxy}-8-azabicyclo[3.2.1]octan-8-yl]-6-methylpyrimidine-4-carboxylic acid;

2-[3-{[5-cyclopropyl-3-(2-fluoro-6-methylphenyl)-1,2-oxazol-4-yl]nethoxyl -8-azabicyclo[3.2.1]octan-8-yl]-4-methoxy-1,3-benzothiazole-6-carboxylic acid;

2-[(1R,3r,5S)-3-{[5-cyclopropyl-3-(2-fluoro-6-methylphenyl)-1,2-oxazol-4-yl]methoxy}-8-azabicyclo [3.2.1]octan-8-yl]-4-methoxy-1,3-benzothiazole-6-carboxylic acid;

6-[3-{[5-cyclopropyl-3-(2-fluoro-6-methylphenyl)-1,2-oxazol-4-yl]methoxy}-8-azabicyclo[3.2.1]octan-8-yl] pyridine-3-carboxylic acid;

6-[(1R,3r,5S)-3-{[5-cyclopropyl-3-(2-fluoro-6-methylphenyl)-1,2-oxazol-4-yl]methoxy}-8-azabicyclo [3.2.1]octan-8-yl]pyridine-3-carboxylic acid;

2-[3-{[5-cyclopropyl-3-(2-fluoro-6-methylphenyl)-1,2-oxazol-4-yl]methoxy}-8-azabicyclo[3.2.1]octan-8-yl]-6-methylpyrimidine-4-carboxylic acid;

2-[(1R,3r,5S)-3-{[5-cyclopropyl-3-(2-fluoro-6-methylphenyl)-1,2-oxazol-4-yl]methoxy}-8-azabicyclo[3.2.1]octan-8-yl]-6-methylpyrimidine-4-carboxylic acid;

2-[3-{[5-cyclopropyl-3-(2,6-dimethylphenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(2,6-dimethylphenyl)-1,2-oxazol-4-yl]methoxy}-8-azabicyclo[3.2.1]octan-8-yl]-4-methoxy-1,3-benzothiazole-6-carboxylic acid;

6-[3-{[5-cyclopropyl-3-(2,6-dimethylphenyl)-1,2-oxazol-4-yl]methoxy}-8-azabicyclo[3.2.1]octan-8-yl]pyridine-3-carboxylic acid;

6-[(1R,3r,5S)-3-{[5-cyclopropyl-3-(2,6-dimethylphenyl)-1,2-oxazol-4-yl]methoxy}-8-azabicyclo[3.2.1]octan-8-yl]pyridine-3-carboxylic acid;

2-[3-{[5-cyclopropyl-3-(2,6-dimethylphenyl)-1,2-oxazol-4-yl]methoxy}-8-azabicyclo[3.2.1]octan-8-yl]-6-methylpyrimidine-4-carboxylic acid;

2-[(1R,3r,5S)-3-{[5-cyclopropyl-3-(2,6-dimethylphenyl)-1,2-oxazol-4-yl]methoxy}-8-azabicyclo[3.2.1]octan-8-yl]-6-methylpyrimidine-4-carboxylic acid;

2-[3-{[3-(2-chloro-6-fluorophenyl)-5-cyclopropyl-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[3-(2-chloro-6-fluorophenyl)-5-cyclopropyl-1,2-oxazol-4-yl]methoxy}-8-azabicyclo[3.2.1]octan-8-yl]-4-methoxy-1,3-benzothiazole-6-carboxylic acid;

6-[3-{[3-(2-chloro-6-fluorophenyl)-5-cyclopropyl-1,2-oxazol-4-yl]methoxy}-8-azabicyclo[3.2.1]octan-8-yl]pyridine-3-carboxylic acid;

6-[(1R,3r,5S)-3-{[3-(2-chloro-6-fluorophenyl)-5-cyclopropyl-1,2-oxazol-4-yl]methoxy}-8-azabicyclo[3.2.1]octan-8-yl]pyridine-3-carboxylic acid;

2-[3-{[3-(2-chloro-6-fluorophenyl)-5-cyclopropyl-1,2-oxazol-4-yl]methoxy}-8-azabicyclo[3.2.1]octan-8-yl]-6-methylpyrimidine-4-carboxylic acid;

2-[(1R,3r,5S)-3-{[3-(2-chloro-6-fluorophenyl)-5-cyclopropyl-1,2-oxazol-4-yl]methoxy}-8-azabicyclo[3.2.1]octan-8-yl]-6-methylpyrimidine-4-carboxylic acid;

2-[3-{[3-(2-chlorophenyl)-5-cyclopropyl-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[3-(2-chlorophenyl)-5-cyclopropyl-1,2-oxazol-4-yl]methoxy}-8-azabicyclo[3.2.1]octan-8-yl]-4-methoxy-1,3-benzothiazole-6-carboxylic acid;

6-[3-{[3-(2-chlorophenyl)-5-cyclopropyl-1,2-oxazol-4-yl]methoxy}-8-azabicyclo[3.2.1]octan-8-yl]pyridine-3-carboxylic acid;

6-[(1R,3r,5S)-3-{[3-(2-chlorophenyl)-5-cyclopropyl-1,2-oxazol-4-yl]methoxy}-8-azabicyclo[3.2.1]octan-8-yl]pyridine-3-carboxylic acid;

2-[3-{[3-(2-chlorophenyl)-5-cyclopropyl-1,2-oxazol-4-yl]methoxy}-8-azabicyclo[3.2.1]octan-8-yl]-6-methylpyrimidine-4-carboxylic acid;

2-[(1R,3r,5S)-3-{[3-(2-chlorophenyl)-5-cyclopropyl-1,2-oxazol-4-yl]methoxy}-8-azabicyclo[3.2.1]octan-8-yl]-6-methylpyrimidine-4-carboxylic acid;

2-[3-{[5-cyclopropyl-3-(2-cyclopropylphenyl)-1,2-oxazol-4-yl]methoxy}-8-azabicyclo[3.2.1]octan-8-yl]-4-fluoro-1,3-benzothiazole-6-carboxylic acid;

2-[(1R,3r,5S)-3-{[5-cyclopropyl-3-(2-cyclopropylphenyl)-1,2-oxazol-4-yl]methoxy}-8-azabicyclo[3.2.1]octan-8-yl]-4-fluoro-1,3-benzothiazole-6-carboxylic acid;

6-[3-{[5-cyclopropyl-3-(2-cyclopropylphenyl)-1,2-oxazol-4-yl]methoxy}-8-azabicyclo[3.2.1]octan-8-yl]pyridine-3-carboxylic acid;

6-[(1R,3r,5S)-3-{[5-cyclopropyl-3-(2-cyclopropylphenyl)-1,2-oxazol-4-yl]methoxy}-8-azabicyclo[3.2.1]octan-8-yl]pyridine-3-carboxylic acid;

6-[3-{[5-cyclopropyl-3-(2,6-difluorophenyl)-1,2-oxazol-4-yl]methoxy}-8-azabicyclo[3.2.1]octan-8-yl]-5-methylpyridine-3-carboxylic acid;

6-[(1R,3r,5S)-3-{[5-cyclopropyl-3-(2,6-difluorophenyl)-1,2-oxazol-4-yl]methoxy}-8-azabicyclo[3.2.1]octan-8-yl]-5-methylpyridine-3-carboxylic acid;

6-[3-{[5-cyclopropyl-3-(2,6-difluorophenyl)-1,2-oxazol-4-yl]methoxy}-8-azabicyclo[3.2.1]octan-8-yl]-4-methylpyridine-3-carboxylic acid;

6-[(1R,3r,5S)-3-{[5-cyclopropyl-3-(2,6-difluorophenyl)-1,2-oxazol-4-yl]methoxy}-8-azabicyclo[3.2.1]octan-8-yl]-4-methylpyridine-3-carboxylic acid;

6-[3-({5-cyclopropyl-3-[2-(difluoromethoxy)phenyl]-1,2-oxazol-4-yl}methoxy)-8-azabicyclo[3.2.1]octan-8-yl]pyridine-2-carboxylic acid;

6-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyridine-2-carboxylic acid;

methyl 2-[3-({5-cyclopropyl-3-[2-(trifluoromethoxy)phenyl]-1,2-oxazol-4-yl}methoxy)-8-azabicyclo[3.2.1]octan-8-yl]-4-methyl-1,3-benzothiazole-6-carboxylate;

methyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-methyl-1,3-benzothiazole-6-carboxylate;

2-[3-({5-cyclopropyl-3-[2-(trifluoromethoxy)phenyl]-1,2-oxazol-4-yl}methoxy)-8-azabicyclo[3.2.1]octan-8-yl]-4-methyl-1,3-benzothiazole-6-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-methyl-1,3-benzothiazole-6-carboxylic acid;

methyl 2-[3-({5-cyclopropyl-3-[2-(trifluoromethyl)phenyl]-1,2-oxazol-4-yl}methoxy)-8-azabicyclo[3.2.1]octan-8-yl]-4-methyl-1,3-benzothiazole-6-carboxylate;

methyl 2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-methyl-1,3-benzothiazole-6-carboxylate;

2-[3-({5-cyclopropyl-3-[2-(trifluoromethyl)phenyl]-1,2-oxazol-4-yl}methoxy)-8-azabicyclo[3.2.1]octan-8-yl]-4-methyl-1,3-benzothiazole-6-carboxylic acid;

2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-methyl-1,3-benzothiazole-6-carboxylic acid;

methyl 2-[3-{[5-cyclopropyl-3-(2,6-difluorophenyl)-1,2-oxazol-4-yl]methoxy}-8-azabicyclo[3.2.1]octan-8-yl]-4-methyl-1,3-benzothiazole-6-carboxylate;

methyl 2-[(1R,3r,5S)-3-{[5-cyclopropyl-3-(2,6-difluorophenyl)-1,2-oxazol-4-yl]methoxy}-8-azabicyclo[3.2.1]octan-8-yl]-4-methyl-1,3-benzothiazole-6-carboxylate;

2-[3-{[5-cyclopropyl-3-(2,6-difluorophenyl)-1,2-oxazol-4-yl]methoxy}-8-azabicyclo[3.2.1]octan-8-yl]-4-methyl-1,3-benzothiazole-6-carboxylic acid;

2-[(1R,3r,5S)-3-{[5-cyclopropyl-3-(2,6-difluorophenyl)-1,2-oxazol-4-yl]methoxy}-8-azabicyclo[3.2.1]octan-8-yl]-4-methyl-1,3-benzothiazole-6-carboxylic acid;

2-[3-{[5-cyclopropyl-3-(2-fluorophenyl)-1,2-oxazol-4-yl]methoxy}-8-azabicyclo[3.2.1]octan-8-yl]-4-methyl-1,3-benzothiazole-6-carboxylic acid;

2-[(1R,3r,5S)-3-{[5-cyclopropyl-3-(2-fluorophenyl)-1,2-oxazol-4-yl]methoxy}-8-azabicyclo[3.2.1]octan-8-yl]-4-methyl-1,3-benzothiazole-6-carboxylic acid;

2-[3-{[5-cyclopropyl-3-(4-fluorophenyl)-1,2-oxazol-4-yl]methoxy}-8-azabicyclo[3.2.1]octan-8-yl]-4-methyl-1,3-benzothiazole-6-carboxylic acid;

2-[(1R,3r,5S)-3-{[5-cyclopropyl-3-(4-fluorophenyl)-1,2-oxazol-4-yl]methoxy}-8-azabicyclo[3.2.1]octan-8-yl]-4-methyl-1,3-benzothiazole-6-carboxylic acid;

2-[3-{[5-cyclopropyl-3-(2-methylphenyl)-1,2-oxazol-4-yl]methoxy}-8-azabicyclo[3.2.1]octan-8-yl]-4-methyl-1,3-benzothiazole-6-carboxylic acid;

2-[(1R,3r,5S)-3-{[5-cyclopropyl-3-(2-methylphenyl)-1,2-oxazol-4-yl]methoxy}-8-azabicyclo[3.2.1]octan-8-yl]-4-methyl-1,3-benzothiazole-6-carboxylic acid;

methyl 2-[3-{[5-cyclopropyl-3-(2-methylphenyl)-1,2-oxazol-4-yl]methoxy}-8-azabicyclo[3.2.1]octan-8-yl]-4-methyl-1,3-benzothiazole-6-carboxylate;

methyl 2-[(1R,3r,5S)-3-{[5-cyclopropyl-3-(2-methylphenyl)-1,2-oxazol-4-yl]methoxy}-8-azabicyclo[3.2.1]octan-8-yl]-4-methyl-1,3-benzothiazole-6-carboxylate;

2-[3-{[5-cyclopropyl-3-(2,4-difluorophenyl)-1,2-oxazol-4-yl]methoxy}-8-azabicyclo[3.2.1]octan-8-yl]-4-methyl-1,3-benzothiazole-6-carboxylic acid;

2-[(1R,3r,5S)-3-{[5-cyclopropyl-3-(2,4-difluorophenyl)-1,2-oxazol-4-yl]methoxy}-8-azabicyclo[3.2.1]octan-8-yl]-4-methyl-1,3-benzothiazole-6-carboxylic acid;

methyl 4-bromo-2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylate;

methyl 4-bromo-2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylate;

4-bromo-2-[3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylic acid;

4-bromo-2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-benzothiazole-6-carboxylic acid;

6-cyclopropyl-2-[3-({5-cyclopropyl-3-[2-(difluoromethoxy)phenyl]-1,2-oxazol-4-yl}methoxy)-8-azabicyclo[3.2.1]octan-8-yl]pyrimidine-4-carboxylic acid;

6-cyclopropyl-2-[(1R,3r,5S)-3-({5-cyclopropyl-3-[2-(difluoromethoxy)phenyl]-1,2-oxazol-4-yl}methoxy)-8-azabicyclo[3.2.1]octan-8-yl]pyrimidine-4-carboxylic acid;

6-cyclopropyl-243-({5-cyclopropyl-3-[2-(trifluoromethoxy)phenyl]-1,2-oxazol-4-yl}methoxy)-8-azabicyclo[3.2.1]octan-8-yl]pyrimidine-4-carboxylic acid;

6-cyclopropyl-2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrimidine-4-carboxylic acid;

6-cyclopropyl-2-[3-({5-cyclopropyl-3-[2-(trifluoromethyl)phenyl]-1,2-oxazol-4-yl}methoxy)-8-azabicyclo[3.2.1]octan-8-yl]pyrimidine-4-carboxylic acid;

6-cyclopropyl-2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyrimidine-4-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]-2-methylpyridine-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-2-methylpyridine-3-carboxylic acid;

6-[3-({5-cyclopropyl-3-[2-(trifluoromethyl)phenyl]-1,2-oxazol-4-yl}methoxy)-8-azabicyclo[3.2.1]octan-8-yl]-2-methylpyridine-3-carboxylic acid;

6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-2-methylpyridine-3-carboxylic acid;

6-[3-{[5-cyclopropyl-3-(2-methylphenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(2-methylphenyl)-1,2-oxazol-4-yl]methoxy}-8-azabicyclo[3.2.1]octan-8-yl]-2-methylpyridine-3-carboxylic acid;

6-[3-{[5-cyclopropyl-3-(2,6-difluorophenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(2,6-difluorophenyl)-1,2-oxazol-4-yl]methoxy}-8-azabicyclo[3.2.1]octan-8-yl]-2-methylpyridine-3-carboxylic acid;

6-[3-{[5-cyclopropyl-3-(2-fluorophenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(2-fluorophenyl)-1,2-oxazol-4-yl]methoxy}-8-azabicyclo[3.2.1]octan-8-yl]-2-methylpyridine-3-carboxylic acid;

6-[3-{[5-cyclopropyl-3-(2,6-dimethylphenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(2,6-dimethylphenyl)-1,2-oxazol-4-yl]methoxy}-8-azabicyclo[3.2.1]octan-8-yl]-2-methylpyridine-3-carboxylic acid;

6-[3-{[5-cyclopropyl-3-(3-fluorophenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(3-fluorophenyl)-1,2-oxazol-4-yl]methoxy}-8-azabicyclo[3.2.1]octan-8-yl]-2-methylpyridine-3-carboxylic acid;

6-[3-{[5-cyclopropyl-3-(2-fluoro-6-methylphenyl)-1,2-oxazol-4-yl]methoxy}-8-azabicyclo[3.2.1]octan-8-yl]-2-methylpyridine-3-carboxylic acid;

6-[(1R,3r,5S)-3-{[5-cyclopropyl-3-(2-fluoro-6-methylphenyl)-1,2-oxazol-4-yl]methoxy}-8-azabicyclo[3.2.1]octan-8-yl]-2-methylpyridine-3-carboxylic acid;

6-[3-{[3-(2-chloro-6-fluorophenyl)-5-cyclopropyl-1,2-oxazol-4-yl]methoxy}-8-azabicyclo[3.2.1]octan-8-yl]-2-methylpyridine-3-carboxylic acid;

6-[(1R,3r,5S)-3-{[3-(2-chloro-6-fluorophenyl)-5-cyclopropyl-1,2-oxazol-4-yl]methoxy}-8-azabicyclo[3.2.1]octan-8-yl]-2-methylpyridine-3-carboxylic acid;

2-[3-({5-cyclopropyl-3-[2-(trifluoromethoxy)phenyl]-1,2-oxazol-4-yl}methoxy)-8-azabicyclo[3.2.1]octan-8-yl]quinoline-6-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]quinoline-6-carboxylic acid;

2-[3-({5-cyclopropyl-3-[2-(trifluoromethyl)phenyl]-1,2-oxazol-4-yl}methoxy)-8-azabicyclo[3.2.1]octan-8-yl]quinoline-6-carboxylic acid;

2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]quinoline-6-carboxylic acid;

2-[3-({5-cyclopropyl-3-[2-(trifluoromethoxy)phenyl]-1,2-oxazol-4-yl}methoxy)-8-azabicyclo[3.2.1]octan-8-yl]quinoline-5-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]quinoline-5-carboxylic acid;

4-[3-({5-cyclopropyl-3-[2-(trifluoromethoxy)phenyl]-1,2-oxazol-4-yl}methoxy)-8-azabicyclo[3.2.1]octan-8-yl]quinazoline-7-carboxylic acid;

4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]quinazoline-7-carboxylic acid;

6-[3-({5-cyclopropyl-3-[2-(trifluoromethyl)phenyl]-1,2-oxazol-4-yl}methoxy)-8-azabicyclo[3.2.1]octan-8-yl]-4-methylpyridine-2-carboxylic acid;

6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-methylpyridine-2-carboxylic acid;

4-[3-({5-cyclopropyl-3-[2-(trifluoromethoxy)phenyl]-1,2-oxazol-4-yl}methoxy)-8-azabicyclo[3.2.1]octan-8-yl]-1-methyl-1H-pyrrolo[3,2-c]pyridine-7-carboxylic acid;

4-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1-methyl-1H-pyrrolo[3,2-c]pyridine-7-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]pyrazolo[1,5-a]pyrimidine-3-carboxylic acid;

5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazolo[1,5-a]pyrimidine-3-carboxylic acid;

6-[3-({5-cyclopropyl-3-[2-(trifluoromethoxy)phenyl]-1,2-oxazol-4-yl}methoxy)-8-azabicyclo[3.2.1]octan-8-yl]imidazo[1,2-b]pyridazine-3-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]imidazo[1,2-b]pyridazine-3-carboxylic acid;

2-[3-{[5-cyclopropyl-3-(2,4-difluorophenyl)-1,2-oxazol-4-yl]methoxy}-8-azabicyclo[3.2.1]octan-8-yl]-1,3-benzothiazole-6-carboxylic acid;

2-[(1R,3r,5S)-3-{[5-cyclopropyl-3-(2,4-difluorophenyl)-1,2-oxazol-4-yl]methoxy}-8-azabicyclo[3.2.1]octan-8-yl]-1,3-benzothiazole-6-carboxylic acid;

2-[3-{[5-cyclopropyl-3-(2,4-difluorophenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(2,4-difluorophenyl)-1,2-oxazol-4-yl]methoxy}-8-azabicyclo[3.2.1]octan-8-yl]-4-methoxy-1,3-benzothiazole-6-carboxylic acid;

6-[3-{[5-cyclopropyl-3-(2,4-difluorophenyl)-1,2-oxazol-4-yl]methoxy}-8-azabicyclo[3.2.1]octan-8-yl]pyridine-3-carboxylic acid;

6-[(1R,3r,5S)-3-{[5-cyclopropyl-3-(2,4-difluorophenyl)-1,2-oxazol-4-yl]methoxy}-8-azabicyclo[3.2.1]octan-8-yl]pyridine-3-carboxylic acid;

2-[3-{[5-cyclopropyl-3-(2,3-difluorophenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(2,3-difluorophenyl)-1,2-oxazol-4-yl]methoxy}-8-azabicyclo[3.2.1]octan-8-yl]-4-methoxy-1,3-benzothiazole-6-carboxylic acid;

6-[3-{[5-cyclopropyl-3-(2,3-difluorophenyl)-1,2-oxazol-4-yl]methoxy}-8-azabicyclo[3.2.1]octan-8-yl]pyridine-3-carboxylic acid;

6-[(1R,3r,5S)-3-{[5-cyclopropyl-3-(2,3-difluorophenyl)-1,2-oxazol-4-yl]methoxy}-8-azabicyclo[3.2.1]octan-8-yl]pyridine-3-carboxylic acid;

2-[3-{[5-cyclopropyl-3-(2,3-difluorophenyl)-1,2-oxazol-4-yl]methoxy}-8-azabicyclo[3.2.1]octan-8-yl]-6-methylpyrimidine-4-carboxylic acid;

2-[(1R,3r,5S)-3-{[5-cyclopropyl-3-(2,3-difluorophenyl)-1,2-oxazol-4-yl]methoxy}-8-azabicyclo[3.2.1]octan-8-yl]-6-methylpyrimidine-4-carboxylic acid;

2-[3-{[5-cyclopropyl-3-(2-fluorophenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(2-fluorophenyl)-1,2-oxazol-4-yl]methoxy}-8-azabicyclo[3.2.1]octan-8-yl]-4-methoxy-1,3-benzothiazole-6-carboxylic acid;

2-[3-{[5-cyclopropyl-3-(2-fluorophenyl)-1,2-oxazol-4-yl]methoxy}-8-azabicyclo[3.2.1]octan-8-yl]-6-methylpyrimidine-4-carboxylic acid;

2-[(1R,3r,5S)-3-{[5-cyclopropyl-3-(2-fluorophenyl)-1,2-oxazol-4-yl]methoxy}-8-azabicyclo[3.2.1]octan-8-yl]-6-methylpyrimidine-4-carboxylic acid;

6-[3-{[5-cyclopropyl-3-(2-fluorophenyl)-1,2-oxazol-4-yl]methoxy}-8-azabicyclo[3.2.1]octan-8-yl]pyridine-3-carboxylic acid;

6-[(1R,3r,5S)-3-{[5-cyclopropyl-3-(2-fluorophenyl)-1,2-oxazol-4-yl]methoxy}-8-azabicyclo[3.2.1]octan-8-yl]pyridine-3-carboxylic acid;

2-[3-{[5-cyclopropyl-3-(2,6-dichlorophenyl)-1,2-oxazol-4-yl]methoxy}-8-azabicyclo[3.2.1]octan-8-yl]-1,3-benzothiazole-6-carboxylic acid;

2-[(1R,3r,5S)-3-{[5-cyclopropyl-3-(2,6-dichlorophenyl)-1,2-oxazol-4-yl]nethoxyl -8-azabicyclo[3.2.1]octan-8-yl]-1,3-benzothiazole-6-carboxylic acid;

2-[3-{[5-cyclopropyl-3-(2,6-dichlorophenyl)-1,2-oxazol-4-yl]methoxy}-8-azabicyclo[3.2.1]octan-8-yl]-4-methoxy-1,3-benzothiazole-6-carboxylic acid;

2-[(1R,3r,5S)-3-{[5-cyclopropyl-3-(2,6-dichlorophenyl)-1,2-oxazol-4-yl]nethoxyl -8-azabicyclo[3.2.1]octan-8-yl]-4-methoxy-1,3-benzothiazole-6-carboxylic acid;

6-[3-{[5-cyclopropyl-3-(2,6-dichlorophenyl)-1,2-oxazol-4-yl]methoxy}-8-azabicyclo[3.2.1]octan-8-yl]pyridine-3-carboxylic acid;

6-[(1R,3r,5S)-3-{[5-cyclopropyl-3-(2,6-dichlorophenyl)-1,2-oxazol-4-yl]nethoxyl -8-azabicyclo[3.2.1]octan-8-yl]pyridine-3-carboxylic acid;

6-[3-({5-cyclopropyl-3-[2-(trifluoromethyl)pyridin-3-yl]-1,2-oxazol-4-yl}methoxy)-8-azabicyclo[3.2.1]octan-8-yl]pyridine-3-carboxylic acid;

6-[(1R,3r,5S)-3-({5-cyclopropyl-3-(trifluoromethyl)pyridin-3-yl]-1,2-oxazol-4-yl}methoxy)-8-azabicyclo[3.2.1]octan-8-yl]pyridine-3-carboxylic acid;

2-[3-({5-cyclopropyl-3-[2-(trifluoromethoxy)phenyl]-1,2-oxazol-4-yl}methoxy)-8-azabicyclo[3.2.1]octan-8-yl]-1,3-thiazole-4-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-thiazole-4-carboxylic acid;

2-[3-({5-cyclopropyl-3-[2-(trifluoromethoxy)phenyl]-1,2-oxazol-4-yl}methoxy)-8-azabicyclo[3.2.1]octan-8-yl]-1,3-thiazole-5-carboxylic acid;

2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-1,3-thiazole-5-carboxylic acid;

2-[3-({5-cyclopropyl-3-[2-(trifluoromethyl)phenyl]-1,2-oxazol-4-yl}methoxy)-8-azabicyclo[3.2.1]octan-8-yl]-1,3-thiazole-5-carboxylic acid;

2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-1,3-thiazole-5-carboxylic acid;

6-[3-({5-cyclopropyl-3-[2-(trifluoromethoxy)phenyl]-1,2-oxazol-4-yl}methoxy)-8-azabicyclo[b 3.2.1]octan-8-yl]imidazo[1,2-b]pyridazine-2-carboxylic acid;

6-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]imidazo[1,2-b]pyridazine-2-carboxylic acid;

6-[3-({5-cyclopropyl-3-[2-(trifluoromethyl)phenyl]-1,2-oxazol-4-yl}methoxy)-8-azabicyclo[3.2.1]octan-8-yl]imidazo[1,2-b]pyridazine-2-carboxylic acid;

6-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]imidazo[1,2-b]pyridazine-2-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]pyrazolo[1,5-a]pyrimidine-2-carboxylic acid;

5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazolo[1,5-a]pyrimidine-2-carboxylic acid;

5-[3-({5-cyclopropyl-3-[2-(trifluoromethyl)phenyl]-1,2-oxazol-4-yl}methoxy)-8-azabicyclo[3.2.1]octan-8-yl]pyrazolo[1,5-a]pyrimidine-2-carboxylic acid;

5-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]pyrazolo[1,5-a]pyrimidine-2-carboxylic acid;

6-[3-{[5-cyclopropyl-3-(2,6-difluorophenyl)-1,2-oxazol-4-yl]methoxy}-8-azabicyclo[3.2.1]octan-8-yl]imidazo[1,2-b]pyridazine-2-carboxylic acid;

6-[(1R,3r,5S)-3-{[5-cyclopropyl-3-(2,6-difluorophenyl)-1,2-oxazol-4-yl]methoxy}-8-azabicyclo[3.2.1]octan-8-yl]imidazo[1,2-b]pyridazine-2-carboxylic acid;

6-[3-{[5-cyclopropyl-3-(2-fluoro-6-methylphenyl)-1,2-oxazol-4-yl]methoxy}-8-azabicyclo[3.2.1]octan-8-yl]imidazo[1,2-b]pyridazine-2-carboxylic acid;

6-[(1R,3r,5S)-3-{[5-cyclopropyl-3-(2-fluoro-6-methylphenyl)-1,2-oxazol-4-yl]methoxy}-8-azabicyclo[3.2.1]octan-8-yl]imidazo[1,2-b]pyridazine-2-carboxylic acid;

7-[3-({5-cyclopropyl-3-[2-(trifluoromethoxy)phenyl]-1,2-oxazol-4-yl}methoxy)-8-azabicyclo[3.2.1]octan-8-yl]imidazo[1,2-a]pyridine-3-carboxylic acid;

7-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]imidazo[1,2-a]pyridine-3-carboxylic acid;

5-[3-({5-cyclopropyl-3-[2-(trifluoromethoxy)phenyl]-1,2-oxazol-4-yl}methoxy)-8-azabicyclo[3.2.1]octan-8-yl]pyrazolo[1,5-a]pyridine-3-carboxylic acid;

5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazolo[1,5-a]pyridine-3-carboxylic acid;

6-((2-(3-((5-cyclopropyl-3-(2-(trifluoromethyl)phenyl)isoxazol-4-yl)methoxy)-8-azabicyclo[3.2.1]octan-8-yl)-4-fluorobenzo[d]thiazole-6-carbonypoxy)-3,4,5-trihydroxytetrahydro-2H-pyran-2-carboxylic acid;

(2S,3S,4S,5R,6S)-6-((2-((1R,3S,5S)-3-((5-cyclopropyl-3-(2-(trifluoromethyl)phenyl)isoxazol-4-yl)methoxy)-8-azabicyclo[3.2.1]octan-8-yl)-4-fluorobenzo[d]thiazole-6-carbonypoxy)-3,4,5-trihydroxytetrahydro-2H-pyran-2-carboxylic acid;

6-((2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carbonyl)oxy)-3,4,5-trihydroxytetrahydro-2H-pyran-2-carboxylic acid;

(2S,3S,4 S,5R,6S)-6-((2-((1R,3S,5S)-3-((5-cyclopropyl-3-(2-(trifluoromethoxy)phenyl)isoxazol-4-yl)methoxy)-8-azabicyclo[3.2.1]ctan-8-yl)-4-fluorobenzo[d]thiazole-6-carbonyl)oxy)-3,4,5-trihydroxytetrahydro-2H-pyran-2-carboxylic acid;

6-((6-3-((5-cyclopropyl-3-(2-(trifluoromethoxy)phenyl)isoxazol-4-yl)methoxy)-8-azabicyclo[3.2.1]octan-8-yl)nicotinoyl)oxy)-3,4,5-trihydroxytetrahydro-2H-pyran-2-carboxylic acid; and (2S,3S,4S,5R,6S)-6-((6-((1R,3S,5S)-3-((5-cyclopropyl-3-(2-(trifluoromethoxy)phenyl)isoxazol-4-yl)methoxy)-8-azabicyclo[3.2.1]octan-8-yl)nicotinoyl)oxy)-3,4,5-trihydroxytetrahydro-2H-pyran-2-carboxylic acid; or a stereoisomer, enantiomer, a pharmaceutically acceptable salt, an amino acid conjugate or an acyl glucuronide conjugate thereof.

10. The compound of claim 1, wherein said compound is a glycine, taurine or acyl glucuronide conjugate of said compound.

11. A pharmaceutical composition comprising a therapeutically effective amount of the compound of claim 1 and a pharmaceutically acceptable carrier.

12. A combination comprising a therapeutically effective amount of the compound according to claim 1 or a pharmaceutically acceptable salt thereof, and a second therapeutic agent.

13. A method for treating a condition mediated by FXR in a subject suffering therefrom, comprising administering to the subject a therapeutically effective amount of the compound of claim 1, or a pharmaceutically acceptable salt thereof, and optionally in combination with a second therapeutic agent.

14. A compound having Formula II

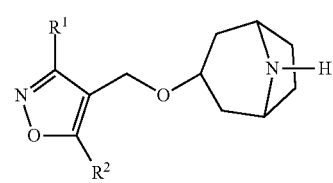

wherein $R^1$ and $R^2$ are as defined in claim 1; or a pharmaceutically acceptable salt thereof.

15. The compound of claim 14, wherein $R^2$ is cyclopropyl.

16. A process for preparing the compound of claim 1, comprising providing a compound of Formula II:

(II)

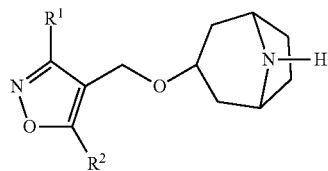

to react with a compound of Y—Z—R³;
wherein Y is a leaving group; and
R¹, R², R³ and Z are as defined in claim 1;
and optionally, converting the compound according to claim 1, wherein the substituents are as defined in claim 1, into another compound of Formula I as defined in claim 1; and
recovering the compound of Formula I in free form or as a salt; and optionally converting the compound of Formula I obtained in free form into a desired salt, or an obtained salt into the free form.

17. The process of claim 16, wherein Y is chloro or bromo.

18. The method of claim 13, wherein said condition is cholestasis, intrahepatic cholestasis, estrogen-induced cholestasis, drug-induced cholestasis, cholestasis of pregnancy, parenteral nutrition-associated cholestasis, primary biliary cirrhosis (PBC), primary sclerosing cholangitis (PSC), progressive familiar cholestasis (PFIC), non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, liver fibrosis, dyslipidemia, atherosclerosis, diabetes, diabetic nephropathy, colitis, newborn jaundice, kernicterus, veno-occlusive disease, portal hypertension, metabolic syndrome, hypercholesterolemia, intestinal bacterial overgrowth, or erectile dysfunction.

19. The method of claim 13, wherein said condition is primary biliary cirrhosis (PBC).

20. A compound having Formula I:

(I)

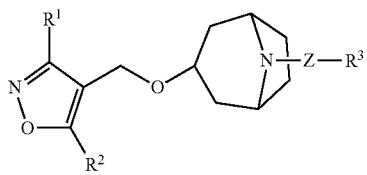

or a stereoisomer, enantiomer, a pharmaceutically acceptable salt or an amino acid conjugate thereof;
wherein Z is phenylene, $C_{5-7}$ cycloalkylene or 5-10 membered monocyclic or bicyclic heteroaryl containing 1-2 heteroatoms selected from the group consisting of N, O and S; each of which is optionally substituted with 1-2 $R^6$ radicals selected from the group consisting of halogen, $C_{1-6}$ alkyl, halo$C_{1-6}$ alkyl, $C_{1-6}$ alkoxy, halo$C_{1-6}$ alkoxy and cyclopropyl;
R¹ is phenyl, pyridyl, bicyclo[3.1.0]hexanyl, spiro[2.3]hexanyl, bicyclo[3.1.1]heptanyl, spiro[2.5]octanyl, bicyclo[4.1.0]heptanyl, bicyclo[3.1.0]hexan-6-yl, spiro[2.3]hexan-5-yl, bicyclo[3.1.1]heptan-3-yl, spiro[2.5]octan-4-yl, bicyclo[4.1.0]heptan-3-yl, cyclohexyl or cyclopentyl, each of which is optionally substituted with 1-3 $R^{1a}$; or R¹ is cyclopropyl optionally substituted with 1-2 $R^{1a}$ or phenyl;
$R^{1a}$ is halogen, $C_{1-6}$ alkyl, halo$C_{1-6}$ alkyl, $C_{1-6}$ alkoxy, halo$C_{1-6}$ alkoxy or cyclopropyl;
R² is $C_{1-3}$ alkyl, halo$C_{1-3}$ alkyl or cyclopropyl optionally substituted with $C_{1-3}$ alkyl or halo$C_{1-3}$ alkyl;
R³ is —X—CO₂R⁴, hydroxy$C_{1-6}$alkyl, CONR⁴R⁵, CONR(CR₂)₁₋₄CO₂R⁴, CONR(CR₂)₁₋₄SO₃R⁵ or tetrazolyl; wherein X is a bond, $C_{1-2}$ alkylene or cyclopropyl; and R, R⁴ and R⁵ are independently hydrogen or $C_{1-6}$ alkyl.

21. The compound of claim 20, wherein said compound is selected from the group consisting of:

I-T

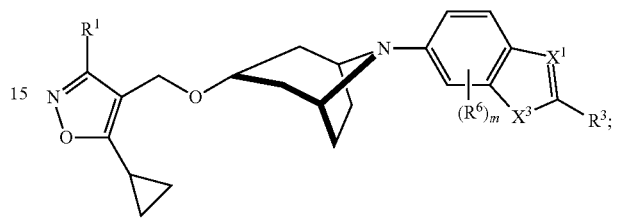

I-U

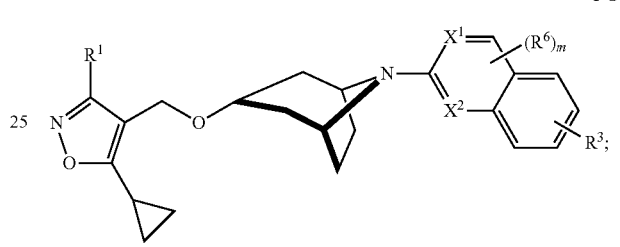

I-V

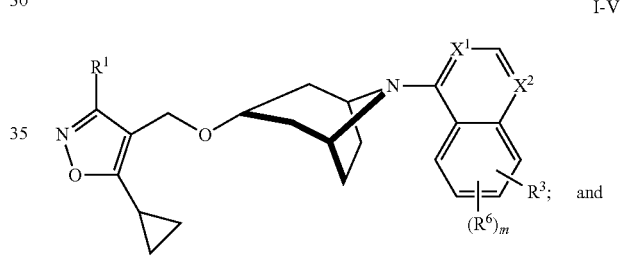

and

I-Y

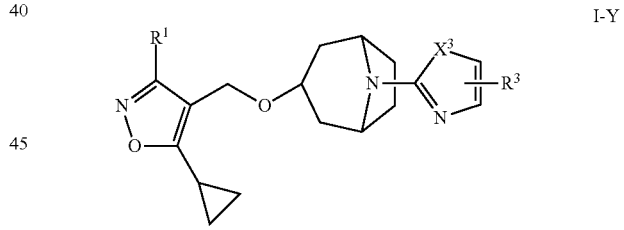

or a stereoisomer, enantiomer, a pharmaceutically acceptable salt or an amino acid conjugate thereof, wherein:
X¹ and X² are independently N, CH or CR⁶;
X³ is O or S;
and
m is 0-1.

22. The compound of claim 1, wherein said compound is selected from the group consisting of:
methyl 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylate;
methyl 2-[(1R,3r,5S)-3-({5-cyclopropyl-3-[2-(trifluoromethyl)phenyl]-1,2-oxazol-4-yl}methoxy)-8-azabicyclo[3.2.1]octan-8-yl]-4-fluoro-1,3-benzothiazole-6-carboxylate;
methyl 6-[(1R,3r,5S)-3-({5-cyclopropyl-3-[2-(trifluoromethoxy)phenyl]-1,2-oxazol-4-yl}methoxy)-8- azabicyclo[3.2.1]octan-8-yl]pyridine-3-carboxylate; and methyl-5-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]pyrazine-2-carboxylate; or a pharmaceutically acceptable salt thereof.

23. The compound of claim 1, wherein said compound is 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid; or a pharmaceutically acceptable salt thereof.

24. The compound of claim 1, wherein said compound is

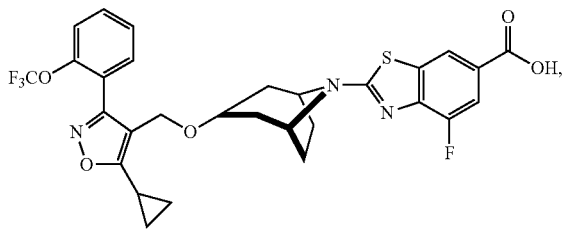

or a pharmaceutically acceptable salt thereof.

25. The compound of claim 1, wherein said compound is

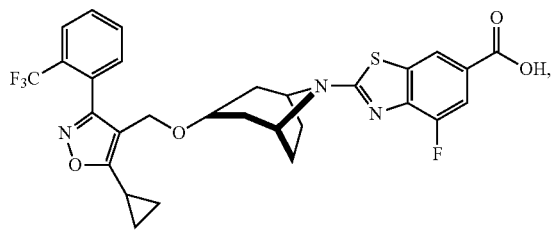

or a pharmaceutically acceptable salt thereof.

26. The compound of claim 1, wherein said compound is

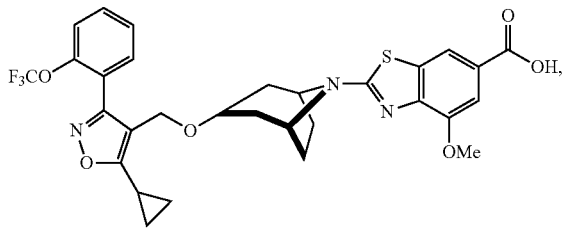

or a pharmaceutically acceptable salt thereof.

27. The compound of claim 1, wherein said compound is

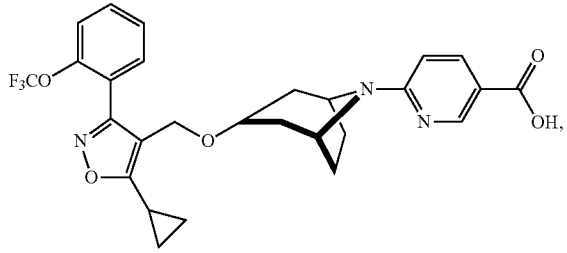

or a pharmaceutically acceptable salt thereof.

28. The compound of claim 1, wherein said compound is

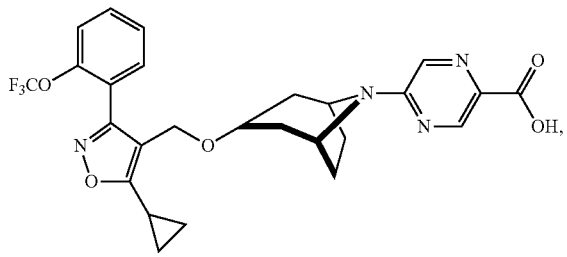

or a pharmaceutically acceptable salt thereof.

29. The compound of claim 1, wherein said compound is

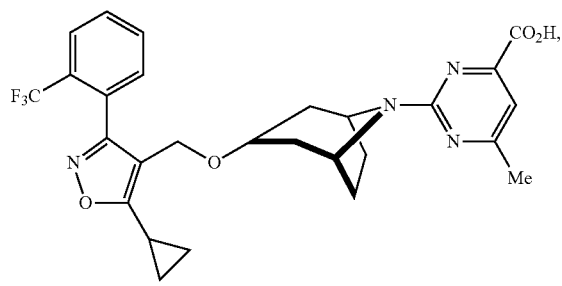

or a pharmaceutically acceptable salt thereof.

* * * * *

SEQUENCE LISTING

<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: peptide derived from Steroid Receptor Coactivator-1

<400> SEQUENCE: 1

```
Cys Pro Ser Ser His Ser Ser Leu Thr Glu Arg His Lys Ile Leu His
 1               5                  10                  15

Arg Leu Leu Gln Glu Gly Ser Pro Ser
             20                  25
```